(12) United States Patent
Quan et al.

(10) Patent No.: US 9,914,740 B2
(45) Date of Patent: Mar. 13, 2018

(54) TRICYCLIC PYRIDO-CARBOXAMIDE DERIVATIVES AS ROCK INHIBITORS

(71) Applicant: BRISTOL-MYERS SQUIBB COMPANY, Princeton, NJ (US)

(72) Inventors: Mimi L. Quan, Yardley, PA (US); Zilun Hu, Jamison, PA (US); Cailan Wang, New Hope, PA (US); Sharanabasappa Patil, Bangalore (IN)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 14/900,238

(22) PCT Filed: Jul. 1, 2014

(86) PCT No.: PCT/US2014/044988
§ 371 (c)(1),
(2) Date: Dec. 21, 2015

(87) PCT Pub. No.: WO2015/002915
PCT Pub. Date: Jan. 8, 2015

(65) Prior Publication Data
US 2016/0152628 A1 Jun. 2, 2016

Related U.S. Application Data

(60) Provisional application No. 61/842,098, filed on Jul. 2, 2013.

(51) Int. Cl.
C07D 491/052 (2006.01)
C07D 519/00 (2006.01)
C07D 471/04 (2006.01)
C07D 491/048 (2006.01)
C07D 498/04 (2006.01)

(52) U.S. Cl.
CPC ....... *C07D 491/052* (2013.01); *C07D 471/04* (2013.01); *C07D 491/048* (2013.01); *C07D 498/04* (2013.01); *C07D 519/00* (2013.01)

(58) Field of Classification Search
None
See application file for complete search history.

(56) References Cited

U.S. PATENT DOCUMENTS

| | | |
|---|---|---|
| 3,963,735 A | 6/1976 | Farkas et al. |
| 6,187,797 B1 | 2/2001 | Pruitt et al. |
| 7,259,155 B2 | 8/2007 | Sakai et al. |
| 7,351,727 B2 | 4/2008 | Weinstein |
| 2002/0177594 A1 | 11/2002 | Curtin et al. |
| 2004/0116425 A1 | 6/2004 | Li et al. |
| 2005/0065189 A1 | 3/2005 | Lange et al. |
| 2008/0275062 A1 | 11/2008 | Drewry et al. |
| 2009/0036654 A1 | 2/2009 | Jacobs et al. |
| 2009/0163545 A1 | 6/2009 | Goldfarb |
| 2010/0273781 A1 | 10/2010 | Ginn et al. |
| 2010/0273828 A1 | 10/2010 | Mack et al. |

FOREIGN PATENT DOCUMENTS

| | | |
|---|---|---|
| AR | 049472 A1 | 8/2006 |
| CN | 1580056 A | 2/2005 |
| DE | 24 53 083 | 5/1975 |
| DE | 3703435 A1 | 8/1988 |
| EP | 0432040 A1 | 6/1991 |
| GB | 2 023 590 A | 1/1980 |
| JP | 2002-53566 A | 2/2002 |
| WO | WO1982/02385 A1 | 7/1982 |
| WO | WO1996/37493 A1 | 11/1996 |
| WO | WO1998/28282 A2 | 7/1998 |
| WO | WO1999/21555 A2 | 5/1999 |
| WO | WO1999/52906 A1 | 10/1999 |
| WO | WO2001/07423 A1 | 2/2001 |
| WO | WO2001/68648 A1 | 9/2001 |
| WO | WO2001/81304 A1 | 11/2001 |

(Continued)

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*

Bandarage, Upul K. etal., "Convenient synthesis of N-(4-(2-aminopyridin-4-yl)thiazol-2-yl)-2-phenylacetamides", Tetrahedron Letters, vol. 47, pp. 8079-8081 (2006).

Feng, Yangbo et al., "Discovery of Substituted 4-(Pyrazol-4-yl)-phenylbenzodioxane-2-carboxamides as Potent and Highly Selective Rho Kinase (ROCK-II) Inhibitors", J. Med. Chemistry, vol. 51, pp. 6642-6645 (2008).

Hargrave, Karl et al., "N-(4-Substituted-thiazolyl)oxamic Acid Derivatives, a New Series of Potent, Orally Active Antiallergy Agents", J.Med. Chemistry, vol. 26(8), pp. 1158-1163 (1983).

(Continued)

*Primary Examiner* — Dennis Heyer
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

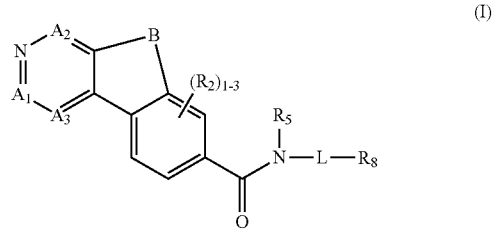

4 Claims, No Drawings

(56) References Cited

FOREIGN PATENT DOCUMENTS

| WO | WO2002/14291 A1 | 2/2002 |
|---|---|---|
| WO | WO2002/14311 A2 | 2/2002 |
| WO | WO2002/46129 A2 | 6/2002 |
| WO | WO2002/051442 A1 | 7/2002 |
| WO | WO2002/062775 A1 | 8/2002 |
| WO | WO2002/064586 A2 | 8/2002 |
| WO | WO2002/076957 A1 | 10/2002 |
| WO | WO2002/087589 A1 | 11/2002 |
| WO | WO2002/100433 A1 | 12/2002 |
| WO | WO2003/029249 A1 | 4/2003 |
| WO | WO2003/048140 A1 | 6/2003 |
| WO | WO2003/062215 A1 | 7/2003 |
| WO | WO2003/062233 A1 | 7/2003 |
| WO | WO2003/097047 A1 | 11/2003 |
| WO | WO2004/009017 A2 | 1/2004 |
| WO | WO2004/014370 A2 | 2/2004 |
| WO | WO2004/016592 A1 | 2/2004 |
| WO | WO2004/041813 A1 | 5/2004 |
| WO | WO2004/058255 A1 | 7/2004 |
| WO | WO2004/069226 A1 | 8/2004 |
| WO | WO2004/071509 A1 | 8/2004 |
| WO | WO2004/092115 A2 | 10/2004 |
| WO | WO2004/094375 A2 | 11/2004 |
| WO | WO2005/026137 A2 | 3/2005 |
| WO | WO2005/041879 A2 | 5/2005 |
| WO | WO2005/044194 A2 | 5/2005 |
| WO | WO2005/075435 A1 | 8/2005 |
| WO | WO2005/077345 A1 | 8/2005 |
| WO | WO2005/077373 A2 | 8/2005 |
| WO | WO2005/077900 A1 | 8/2005 |
| WO | WO2006/104141 A1 | 10/2006 |
| WO | WO2006/117211 A2 | 11/2006 |
| WO | WO2006/122011 A2 | 11/2006 |
| WO | WO2007/062222 A1 | 5/2007 |
| WO | WO2007/075896 A2 | 7/2007 |
| WO | WO2007/087427 A2 | 8/2007 |
| WO | WO2007/116106 A1 | 10/2007 |
| WO | WO2007/133622 A1 | 11/2007 |
| WO | WO2008/014199 A2 | 1/2008 |
| WO | WO2008/039645 A1 | 4/2008 |
| WO | WO2008/078674 A1 | 7/2008 |
| WO | WO2008/122787 A1 | 10/2008 |
| WO | WO2008/124000 A2 | 10/2008 |
| WO | WO2009/002933 A1 | 12/2008 |
| WO | WO2009/026701 A1 | 3/2009 |
| WO | WO2009/027392 A1 | 3/2009 |
| WO | WO2009/044250 A1 | 4/2009 |
| WO | WO2009/057827 A1 | 5/2009 |
| WO | WO2009/061652 A1 | 5/2009 |
| WO | WO2009/067607 A2 | 5/2009 |
| WO | WO2009/081222 A1 | 7/2009 |
| WO | WO2009/099195 A1 | 8/2009 |
| WO | WO2009/114552 A1 | 9/2009 |
| WO | WO2009/140519 A1 | 11/2009 |
| WO | WO2010/028193 A1 | 3/2010 |
| WO | WO2010/029300 A1 | 3/2010 |
| WO | WO2010/036821 A1 | 4/2010 |
| WO | WO2010/070068 A2 | 6/2010 |
| WO | WO2010/075376 A2 | 7/2010 |
| WO | WO2010080474 * | 7/2010 |
| WO | WO/2010/101849 A1 | 9/2010 |
| WO | WO2010/144404 A2 | 12/2010 |
| WO | WO2011/025838 A1 | 3/2011 |
| WO | WO2011/062766 A2 | 5/2011 |
| WO | WO2011/075684 A1 | 6/2011 |
| WO | WO2011/129095 A1 | 10/2011 |
| WO | WO2011/130740 A2 | 10/2011 |
| WO | WO2011/159857 A1 | 12/2011 |
| WO | WO2012/054367 A1 | 4/2012 |
| WO | WO2013/134036 A1 | 9/2013 |
| WO | WO2013/134336 * | 9/2013 |
| WO | WO2015/002915 A1 | 1/2015 |
| WO | WO2015/002926 A1 | 1/2015 |

OTHER PUBLICATIONS

Hay, Michael et al., "4-Pyridylanilinothiazoles that selectively target von Hippel-Lindau deficient Renal Cell Carcinoma cells by inducing autophagic cell death", J. Med. Chemistry, vol. 53(2), pp. 787-797 (2010).

Kahnt, F.W. et al., "On Adrenocortical Steroid Biosynthesis In Vitro", Acta Endocrinologica, vol. 70, pp. 315-330 (1972).

Krohnke, Fritz et al., "Examples for the King reaction", Chemische Berichte, vol. 92, pp. 22-36 (1959).

Lu, Yan-Chang et al., "4-Fluoro-N-[4-(pyridine-4-yl)thiazol-2-yl]benzamide", Acta Crystallographica Section E: Structure Reports Online, E62(11), pp. 5330-5331 (2006).

Vadivelan, S. et al., "Pharmacophore modeling and virtual screening studies to design some potential histone deacetylase inhibitors as new leads", J. of Molecular Graphics and Modelling, vol. 26, pp. 935-946 (2008).

Van Biesen, Wim "Rho/rho-kinase and C-reactive protein relationship in hypertension and atherosclerosis", Nephrology Dialysis Transplantation, vol. 21(4), pp. 1130-1131 (2005).

Wada, Carol K. et al., "α-Keto Amides as Inhibitors of Histone Deacetylase", Bioorganic & Medicinal Chemistry Letters, vol. 13, pp. 3331-3335 (2003).

Weinstein, David S. et al., Azaxanthene Based Selective Glucocorticoid Receptor Modulators: Design, Synthesis, and Pharmacological Evaluation of (S)-4-(5-(1-((1,3,4-Thiadiazol-2-yl)-amino)-2-methyl-1-oxopropan-2-yl)-5H-chromeno[2,3-b]pyridine-2-yl)-2-fluoro-N,N-dimethylbenzamide (BMS-776532) and Its Methylene Homologue (BMS-791826).

* cited by examiner

TRICYCLIC PYRIDO-CARBOXAMIDE DERIVATIVES AS ROCK INHIBITORS

CROSS REFERENCE TO RELATED APPLICATIONS

This application is a national phase application under 35 U.S.C. § 371 of International Patent Application No. PCT/US2014/044988, filed Jul. 1, 2014, which is entitled to priority pursuant to 35 U.S.C. § 119(e) to U.S. provisional patent application No. 61/842,098, filed on Jul. 2, 2013, which are incorporated herein in their entirety.

FIELD OF THE INVENTION

The present invention relates to novel tricyclic carboxamide derivatives, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the RhoA/ROCK signaling pathway plays an important role in signal transduction initiated by several vasoactive factors, for example angiotensin II (Yamakawa, T. et al., *Hypertension*, 35:313-318 (2000)), urotensin II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.*, 18:67-74 (2005)), cancer (Rattan, R. et al., *J. Neurosci. Res.*, 83:243-255 (2006); Lepley, D. et al., *Cancer Res.*, 65:3788-

3795 (2005)), fibrotic diseases (Jiang, C. et al., *Int. J. Mol. Sci.*, 13:8293-8307 (2012); Zhou, L. et al., *Am. J. Nephrol.*, 34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the US, with coronary heart disease accounting for ~1 in 6 deaths overall in the US. Contributing to these numbers, it was found that ~33.5% of the adult US population was hypertensive, and it was estimated that in 2010 ~6.6 million US adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, U.S. Publication No. 2008/0275062 A1), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel tricyclic carboxamide derivatives including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

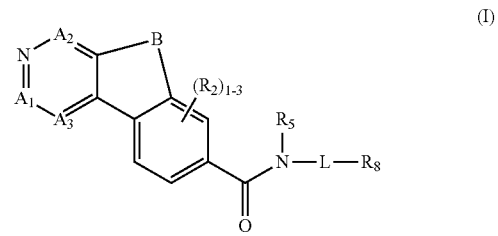

or stereoisomers, tautomers, pharmaceutically acceptable salts, solvates, or prodrugs thereof, wherein
$A_1$, $A_2$, and $A_3$ are independently selected from N and $CR_1$; provided no more than one $A_1$, $A_2$, and $A_3$ is N;
B is independently selected from —$(CR_3R_4)_mCR_3R_4$—, —$(CR_3R_4)_mO(CR_3R_4)_n$—, —$(CR_3R_4)_m$, $NR_a(CR_3R_4)_n$—, —$(CR_3R_4)_mS(O)_p(CR_3R_4)_n$—, —$(CR_3R_4)_mC(O)(CR_3R_4)_n$—, —$(CR_3R_4)_mC(O)O$ $(CR_3R_4)_n$—, —$(CR_3R_4)_mC(O)NR_a(CR_3R_4)_n$—, —$(CR_3R_4)_mOC(O)(CR_3R_4)_n$—, —$(CR_3R_4)_m$, $NR_aC(O)$ $(CR_3R_4)_n$—, —$(CR_3R_4)_m$, $NR_aS(O)_p(CR_3R_4)_n$—, and —$(CR_3R_4)_mS(O)_pNR_a(CR_3R_4)_n$—;
L is independently selected from —$(CR_6R_7)_q$, —$(CR_6R_7)_sNR_5(CR_6R_7)_q$—, —$(CR_6R_7)_sO(CR_6R_7)_q$—, and —$(CR_6R_7)_sC(O)(CR_6R_7)_q$—;
$R_1$ and $R_2$ are independently selected from H, F, Cl, Br, CN, $NR_aR_a$, —$OC_{1-4}$ alkyl substituted with 0-3 $R_e$, $C_{1-4}$ alkyl substituted with 0-3 $R_c$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)$ $NR_aR_a$, —$(CH_2)_rC(=O)(CH_2)_rNR_aR_a$, $(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_3$ and R$_4$ are independently selected from H, F, OH, CN, NR$_a$R$_a$, C$_{1-4}$ alkyl substituted with 0-3 R$_e$, C$_{1-4}$ alkenyl substituted with 0-3 R$_e$, and C$_{1-4}$ alkynyl substituted with 0-3 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, (CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_5$ is independently selected from H and C$_{1-4}$ alkyl optionally substituted with F, Cl, Br, CN, —OR$_b$, —S(O)$_p$R$_c$, —C(=O)R$_b$, —NR$_a$R$_a$, —C(=O)NR$_a$R$_a$, —C(=O)(CH$_2$)$_r$NR$_a$R$_a$, CN, —NR$_a$C(=O)R$_b$, —NR$_a$C(=O)OR$_b$, —OC(=O)NR$_a$R$_a$, —NR$_a$C(=O)NR$_a$R$_a$, —C(=O)OR$_b$, —S(O)$_p$NR$_a$R$_a$, —NR$_a$S(O)$_p$NR$_a$R$_a$, and —NR$_a$S(O)$_p$R$_c$, —(CH$_2$)$_r$—C$_{3-10}$ carbocyclyl substituted with 0-5 R$_e$, and —(CH$_2$)$_r$-heterocyclyl substituted with 0-5 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

alternatively, R$_6$ and R$_7$ together with the carbon atom to which they are both attached form a cycloalkyl or heterocyclyl, each substituted with 0-5 R$_e$; alternatively, when q is 2 or 3, two adjacent R$_6$ groups form a cycloalkyl or heterocyclyl, each substituted with 0-5 R$_e$;

R$_8$ is selected from C$_{3-10}$ carbocyclyl and heterocyclyl, each substituted with 0-5 R$_9$;

R$_9$ is independently selected from F, Cl, Br, C$_{1-4}$alkyl substituted with 0-5 R$_e$, C$_{2-4}$alkenyl substituted with 0-5 R$_e$, C$_{2-4}$alkynyl substituted with 0-5 R$_e$, =O, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, C$_{1-6}$ alkyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, Br, and OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O)C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

m and n, at each occurrence, are independently selected from zero, 1, and 2; provided m+n≤2;

p, at each occurrence, is independently selected from zero, 1, and 2;

q, at each occurrence, is independently selected from zero, 1, 2, and 3;

r, at each occurrence, is independently selected from zero, 1, 2, 3, and 4;

s, at each occurrence, is independently selected from 1, and 2; provided when s and q are in the same term, s+q≤3;

provided when A$_1$ is CR$_1$, A$_3$ is N, and B is —CH$_2$C(O)NH—, R$_1$ is not —NH— substituted phenyl.

In another aspect, the present invention provides compounds of Formula (II):

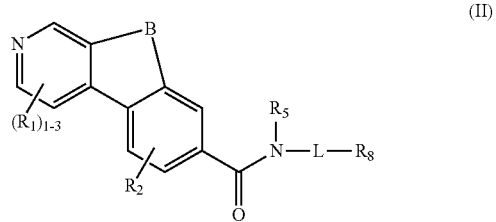

(II)

or stereoisomers, tautomers, pharmaceutically acceptable salts, solvates, or prodrugs thereof, wherein B is independently selected from —(CR$_3$R$_4$)$_m$O(CR$_3$R$_4$)$_n$—, —(CR$_3$R$_4$)$_m$NRa(CR$_3$R$_4$)$_n$—, —(CR$_3$R$_4$)$_m$S(O)$_p$(CR$_3$R$_4$)$_n$—, —(CR$_3$R$_4$)$_m$C(O)O(CR$_3$R$_4$)$_n$—, —(CR$_3$R$_4$)$_m$C(O)NRa(CR$_3$R$_4$)$_n$—, —(CR$_3$R$_4$)$_m$OC(O)(CR$_3$R$_4$)$_n$—, and —(CR$_3$R$_4$)$_m$,NRaC(O)(CR$_3$R$_4$)$_n$—;

other variables are as defined in Formula (I) above.

In another aspect, the present invention provides compounds of Formula (III):

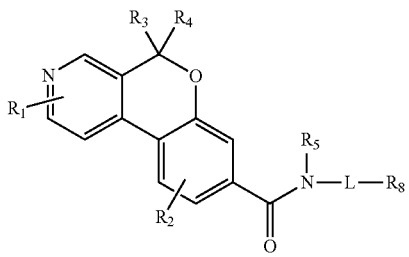

(III)

or stereoisomers, tautomers, pharmaceutically acceptable salts, solvates, or prodrugs thereof, wherein L is independently selected from $-(CR_6R_7)_q-$, $-(CR_6R_7)_sNR_5-$, $-(CR_6R_7)_sO-$, and $-(CR_6R_7)_sC(O)-$;

$R_1$ and $R_2$ are independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_3$ and $R_4$ are independently selected from H, F, OH, CN, and $C_{1-4}$ alkyl substituted with 0-3 $R_e$, $C_{1-4}$ alkenyl substituted with 0-3 $R_e$, and $C_{1-4}$ alkynyl substituted with 0-3 $R_e$;

$R_5$ is independently selected from H and $C_{1-4}$ alkyl optionally substituted with F, Cl, Br, CN, $-OR_b$, $-S(O)_pR_c$, $-C(=O)R_b$, $-NR_aR_a$, $-C(=O)NR_aR_a$, $-C(=O)(CH_2)_rNR_aR_a$, CN, $-NR_aC(=O)R_b$, $-NR_aC(=O)OR_b$, $-OC(=O)NR_aR_a$, $-NR_aC(=O)NR_aR_a$, $-C(=O)OR_b$, $-S(O)_pNR_aR_a$, $-NR_aS(O)_pNR_aR_a$, and $-NR_aS(O)_pR_c$, $-(CH_2)_r-C_{3-10}$ carbocyclyl substituted with 0-5 $R_e$, and $-(CH_2)_r$-heterocyclyl substituted with 0-5 $R_e$;

$R_6$ and $R_7$ are independently selected from H, $C_{1-4}$alkyl substituted with 0-4 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

alternatively, $R_6$ and $R_7$ together with the carbon atom to which they are both attached form a cycloalkyl or heterocyclyl, each substituted with 0-5 $R_e$; alternatively, when q is 2 or 3, two adjacent $R_6$ groups form a cycloalkyl or heterocyclyl, each substituted with 0-5 $R_e$;

$R_8$ is selected from aryl, $C_{3-6}$cycloalkyl, and heterocyclyl, each substituted with 0-5 $R_9$;

$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_rOC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, $C_{1-6}$ alkyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, $-(CH_2)_r-C_{3-10}$ carbocyclyl, $-(CH_2)_r$-heterocyclyl, F, Cl, Br, CN, $NO_2$, =O, $CO_2H$, $CO_2C_{1-6}$ alkyl, $-(CH_2)_rOC_{1-5}$ alkyl, $-(CH_2)_rOH$, $-(CH_2)_rNR_fR_f$, $-(CH_2)_rNR_fR_fC(=O)C_{1-4}$alkyl, $-C(=O)NR_fR_f$, $-C(=O)R_f$, $S(O)_pNR_fR_f$, $-NR_fR_fS(O)_pC_{1-4}$alkyl, and $S(O)_pC_{1-4}$alkyl;

$R_f$ at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from zero, 1, 2, and 3;

r, at each occurrence, is independently selected from zero, 1, 2, 3, and 4; and s, at each occurrence, is independently selected from 1 and 2.

In another aspect, the present invention provides compounds of Formula (IV):

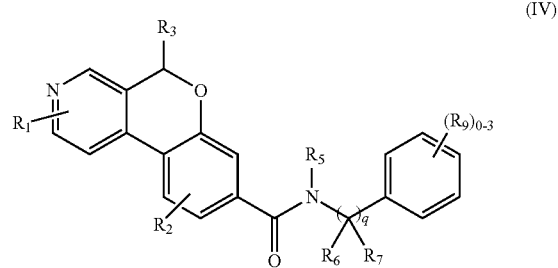

(IV)

or stereoisomers, tautomers, pharmaceutically acceptable salts, solvates, or prodrugs thereof, wherein $R_1$ and $R_2$ are independently selected from H, F, Cl, Br, OH, CN, $NR_aR_a$, $-OC_{1-4}$ alkyl substituted with 0-3 $R_e$, and $C_{1-4}$ alkyl substituted with 0-3 $R_e$;

$R_3$ is independently selected from H and $C_{1-4}$ alkyl substituted with 0-3 $R_e$, $C_{1-4}$ alkenyl substituted with 0-3 $R_e$, and $C_{1-4}$ alkynyl substituted with 0-3 $R_e$;

$R_5$ is independently selected from H and $C_{1-4}$ alkyl optionally substituted with F, Cl, Br, CN, $-OR_b$, $-S(O)_pR_c$, $-C(=O)R_b$, $-NR_aR_a$, $-C(=O)NR_aR_a$, $-C(=O)(CH_2)_rNR_aR_a$, CN, $-NR_aC(=O)R_b$, $-NR_aC(=O)OR_b$, $-OC(=O)NR_aR_a$, $-NR_aC(=O)NR_aR_a$, $-C(=O)OR_b$, $-S(O)_pNR_aR_a$, $-NR_aS(O)_pNR_aR_a$, and —NR$_a$S(O)$_p$R$_c$, —(CH$_2$)$_r$—C$_{3-10}$ carbocyclyl substituted with 0-5 R$_e$, and —(CH$_2$)$_r$-heterocyclyl substituted with 0-5 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

alternatively, R$_6$ and R$_7$ together with the carbon atom to which they are both attached form a cycloalkyl or heterocyclyl, each substituted with 0-5 R$_e$; alternatively, when q is 2 or 3, two adjacent R$_6$ groups form a cycloalkyl or heterocyclyl, each substituted with 0-5 R$_e$;

R$_9$ is independently selected from F, Cl, Br, C$_{1-4}$alkyl substituted with 0-5 R$_e$, C$_{2-4}$alkenyl substituted with 0-5 R$_e$, C$_{2-4}$alkynyl substituted with 0-5 R$_e$, =O, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, C$_{1-6}$ alkyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, Br, and OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O)C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from 1 and 2; and r, at each occurrence, is independently selected from zero, 1, 2, 3, and 4.

In another aspect, the present invention provides compounds of Formula (IV), or stereoisomers, tautomers, pharmaceutically acceptable salts, solvates, or prodrugs thereof, wherein R$_1$ and R$_2$ are H;

R$_3$ is independently selected from H and Me;

R$_5$ is H;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

alternatively, R$_6$ and R$_7$ together with the carbon atom to which they are both attached form a cycloalkyl or heterocyclyl, each substituted with 0-5 R$_e$; alternatively, when q is 2 or 3, two adjacent R$_6$ groups form a cycloalkyl or heterocyclyl, each substituted with 0-5 R$_e$;

R$_9$ is independently selected from F, Cl, Br, C$_{1-4}$alkyl substituted with 0-5 R$_e$, C$_{2-4}$alkenyl substituted with 0-5 R$_e$, C$_{2-4}$alkynyl substituted with 0-5 R$_e$, =O, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, C$_{1-6}$ alkyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, Br, and OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O)C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from 1 and 2;

r, at each occurrence, is independently selected from zero, 1, 2, 3, and 4;

other variables are as defined in Formula (IV) above.

In another aspect, the present invention provides compounds of Formula (IV), or stereoisomers, tautomers, pharmaceutically acceptable salts, solvates, or prodrugs thereof, wherein $R_6$ and $R_7$ are independently selected from H and $C_{1-4}$alkyl substituted with 0-4 $R_e$;

$R_9$ is independently selected from F, Cl, Br, $C_{1-4}$alkyl substituted with 0-5 $R_e$, $C_{2-4}$alkenyl substituted with 0-5 $R_e$, =O, nitro, —$(CHR_d)_rS(O)_pR_c$, —$(CHR_d)_r$ $S(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC$ (=O)$R_b$, —$(CHR_d)_rNR_aC$(=O)$NR_aR_a$, —$(CHR_d)_rC$ (=O)$OR_b$, —$(CHR_d)_rC$(=O)$R_b$, —$(CHR_d)_r$ OC(=O) $R_b$, —$(CHR_d)_rC$(=O)$NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, $C_{1-6}$ alkyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, —$(CH_2)_r$—$C_{3-10}$ carbocyclyl, —$(CH_2)_r$-heterocyclyl, F, Cl, Br, CN, $NO_2$, =O, $CO_2H$, $CO_2C_{1-6}$ alkyl, —$(CH_2)_rOC_{1-5}$ alkyl, —$(CH_2)_rOH$, —$(CH_2)_rNR_fR_f$, —$(CH_2)_rNR_fR_fC$(=O)$C_{1-4}$alkyl, —C(=O)$NR_fR_f$, —C(=O)$R_f$, $S(O)_pNR_fR_f$, —$NR_fR_fS$ $(O)_pC_{1-4}$alkyl, and $S(O)_pC_{1-4}$alkyl;

$R_f$, at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from 1 and 2;

r, at each occurrence, is independently selected from zero, 1, 2, 3, and 4;

other variables are as defined in Formula (IV) above.

In another aspect, the present invention provides compounds of Formula (V):

(V)

or stereoisomers, tautomers, pharmaceutically acceptable salts, solvates, or prodrugs thereof, wherein L is independently selected from —$(CR_6R_7)_q$—, —$(CR_6R_7)_sNR_5$—, —$(CR_6R_7)_sO$—, and —$(CR_6R_7)_sC(O)$—;

$R_1$ and $R_2$ are independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_3$ and $R_4$ are independently selected from H, F, OH, CN, and $C_{1-4}$ alkyl substituted with 0-3 $R_e$, $C_{1-4}$ alkenyl substituted with 0-3 $R_e$, and $C_{1-4}$ alkynyl substituted with 0-3 $R_e$;

$R_5$ is independently selected from H and $C_{1-4}$ alkyl optionally substituted with F, Cl, Br, CN, —$OR_b$, —$S(O)_pR_c$, —C(=O)$R_b$, —$NR_aR_a$, —C(=O)$NR_aR_a$, —C(=O) $(CH_2)_rNR_aR_a$, CN, —$NR_aC$(=O)$R_b$, —$NR_aC$(=O) $OR_b$, —OC(=O)$NR_aR_a$, —$NR_aC$(=O)$NR_aR_a$, —C(=O)$OR_b$, —$S(O)_pNR_aR_a$, —$NR_aS(O)_pNR_aR_a$, and —$NR_aS(O)_pR_c$, —$(CH_2)_r$—$C_{3-10}$ carbocyclyl substituted with 0-5 $R_e$, and —$(CH_2)_r$-heterocyclyl substituted with 0-5 $R_e$;

$R_6$ and $R_7$ are independently selected from H, $C_{1-4}$alkyl substituted with 0-4 $R_e$, —$(CH_2)_rOR_b$, —$(CH_2)_rS(O)_pR_c$, —$(CH_2)_rC$(=O)$R_b$, —$(CH_2)_rNR_aR_a$, —$(CH_2)_rC$(=O) $(CH_2)_rNR_aR_a$, —$(CH_2)_rNR_aC$(=O)$R_b$, —$(CH_2)_rNR_aC$ (=O)$OR_b$, —$(CH_2)_rOC$(=O)$NR_aR_a$, —$(CH_2)_rNR_aC$ (=O)$NR_aR_a$, —$(CH_2)_rC$(=O)$OR_b$, —$(CH_2)_rS(O)_p$ $NR_aR_a$, —$(CH_2)_rNR_aS(O)_pNR_aR_a$, —$(CH_2)_rNR_a$ $S(O)_pR_c$, $(CH_2)_r$—$C_{3-6}$ carbocyclyl substituted with 0-3 $R_e$, and —$(CH_2)_r$-heterocyclyl substituted with 0-3 $R_e$;

alternatively, $R_6$ and $R_7$ together with the carbon atom to which they are both attached form a cycloalkyl or heterocyclyl, each substituted with 0-5 $R_e$; alternatively, when q is 2 or 3, two adjacent $R_6$ groups form a cycloalkyl or heterocyclyl, each substituted with 0-5 $R_e$;

$R_8$ is selected from aryl, $C_{3-6}$cycloalkyl, and heterocyclyl, each substituted with 0-5 $R_9$;

$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC$(=O)$R_b$, —$(CHR_d)_rNR_aC$(=O)$NR_aR_a$, —$(CHR_d)_rC$(=O)$OR_b$, —$(CHR_d)_rC$(=O)$R_b$, —$(CHR_d)_r$ OC(=O)$R_b$, —$(CHR_d)_rC$(=O)$NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, C$_{1-6}$ alkyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, Br, and OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O)C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from zero, 1, 2, and 3;

r, at each occurrence, is independently selected from zero, 1, 2, 3, and 4; and s, at each occurrence, is independently selected from 1 and 2.

In another aspect, the present invention provides compounds of Formula (VI):

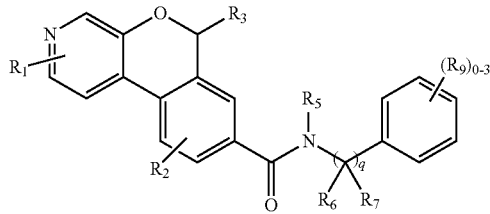

(VI)

or stereoisomers, tautomers, pharmaceutically acceptable salts, solvates, or prodrugs thereof, wherein R$_1$ and R$_2$ are independently selected from H, F, Cl, Br, OH, CN, NR$_a$R$_a$, —OC$_{1-4}$ alkyl substituted with 0-3 R$_e$, and C$_{1-4}$ alkyl substituted with 0-3 R$_e$;

R$_3$ is independently selected from H and C$_{1-4}$ alkyl substituted with 0-3 R$_e$, C$_{1-4}$ alkenyl substituted with 0-3 R$_e$, and C$_{1-4}$ alkynyl substituted with 0-3 R$_e$;

R$_5$ is independently selected from H and C$_{1-4}$ alkyl optionally substituted with F, Cl, Br, CN, —OR$_b$, —S(O)$_p$R$_c$, —C(=O)R$_b$, —NR$_a$R$_a$, —C(=O)NR$_a$R$_a$, —C(=O)(CH$_2$)$_r$NR$_a$R$_a$, CN, —NR$_a$C(=O)R$_b$, —NR$_a$C(=O)OR$_b$, —OC(=O)NR$_a$R$_a$, —NR$_a$C(=O)NR$_a$R$_a$, —C(=O)OR$_b$, —S(O)$_p$NR$_a$R$_a$, —NR$_a$S(O)$_p$NR$_a$R$_a$, and —NR$_a$S(O)$_p$R$_c$, —(CH$_2$)$_r$—C$_{3-10}$ carbocyclyl substituted with 0-5 R$_e$, and —(CH$_2$)$_r$-heterocyclyl substituted with 0-5 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_s$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

alternatively, R$_6$ and R$_7$ together with the carbon atom to which they are both attached form a cycloalkyl or heterocyclyl, each substituted with 0-5 R$_e$; alternatively, when q is 2 or 3, two adjacent R$_6$ groups form a cycloalkyl or heterocyclyl, each substituted with 0-5 R$_e$;

R$_9$ is independently selected from F, Cl, Br, C$_{1-4}$alkyl substituted with 0-5 R$_e$, C$_{2-4}$alkenyl substituted with 0-5 R$_e$, C$_{2-4}$alkynyl substituted with 0-5 R$_e$, =O, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, C$_{1-6}$ alkyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, Br, and OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O)C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from 1 and 2; and r, at each occurrence, is independently selected from zero, 1, 2, 3, and 4.

In another aspect, the present invention provides compounds of Formula (VII):

(VII)

or stereoisomers, tautomers, pharmaceutically acceptable salts, solvates, or prodrugs thereof, wherein L is independently selected from $-(CR_6R_7)_q-$, $-(CR_6R_7)_sNR_5-$, $-(CR_6R_7)_sO-$, and $-(CR_6R_7)_sC(O)-$;

$R_1$ and $R_2$ are independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_5$ is independently selected from H and $C_{1-4}$ alkyl optionally substituted with F, Cl, Br, CN, $-OR_b$, $-S(O)_pR_c$, $-C(=O)R_b$, $-NR_aR_a$, $-C(=O)NR_aR_a$, $-C(=O)(CH_2)_rNR_aR_a$, CN, $-NR_aC(=O)R_b$, $-NR_aC(=O)OR_b$, $-OC(=O)NR_aR_a$, $-NR_aC(=O)NR_aR_a$, $-C(=O)OR_b$, $-S(O)_pNR_aR_a$, $-NR_aS(O)_pNR_aR_a$, and $-NR_aS(O)_pR_c$, $-(CH_2)_r-C_{3-10}$ carbocyclyl substituted with 0-5 $R_e$, and $-(CH_2)_r$-heterocyclyl substituted with 0-5 $R_e$;

$R_6$ and $R_7$ are independently selected from H, $C_{1-4}$alkyl substituted with 0-4 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$carbocyclyl substituted with 0-3 $R_e$, and $-(CH_2)_r$-heterocyclyl substituted with 0-3 $R_e$;

alternatively, $R_6$ and $R_7$ together with the carbon atom to which they are both attached form a cycloalkyl or heterocyclyl, each substituted with 0-5 $R_e$; alternatively, when q is 2 or 3, two adjacent $R_6$ groups form a cycloalkyl or heterocyclyl, each substituted with 0-5 $R_e$;

$R_8$ is selected from aryl, $C_{3-6}$cycloalkyl, and heterocyclyl, each substituted with 0-5 $R_9$;

$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_r$ $OC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, $C_{1-6}$ alkyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, $-(CH_2)_r-C_{3-10}$ carbocyclyl, $-(CH_2)_r$-heterocyclyl, F, Cl, Br, CN, $NO_2$, =O, $CO_2H$, $CO_2C_{1-6}$ alkyl, $-(CH_2)_rOC_{1-5}$ alkyl, $-(CH_2)_rOH$, $-(CH_2)_rNR_fR_f$, $-(CH_2)_rNR_fR_fC(=O)C_{1-4}$alkyl, $-C(=O)NR_fR_f$, $-C(=O)R_f$, $S(O)_pNR_fR_f$, $-NR_fR_fS(O)_pC_{1-4}$alkyl, and $S(O)_pC_{1-4}$alkyl;

$R_f$, at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from zero, 1, 2, and 3;

r, at each occurrence, is independently selected from zero, 1, 2, 3, and 4; and s, at each occurrence, is independently selected from 1, and 2.

In another aspect, the present invention provides compounds of Formula (VIII):

(VIII)

or stereoisomers, tautomers, pharmaceutically acceptable salts, solvates, or prodrugs thereof, wherein L is independently selected from $-(CR_6R_7)_q-$, $-(CR_6R_7)_sNR_5-$, $-(CR_6R_7)_sO-$, and $-(CR_6R_7)_sC(O)-$;

$R_1$ and $R_2$ are independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$, $R_5$ is independently selected from H and $C_{1-4}$ alkyl optionally substituted with F, Cl, Br, CN, $-OR_b$, $-S(O)_pR_c$, $-C(=O)R_b$, $-NR_aR_a$, $-C(=O)NR_aR_a$, $-C(=O)(CH_2)_rNR_aR_a$, CN, $-NR_aC(=O)R_b$, $-NR_aC(=O)$ $OR_b$, $-OC(=O)NR_aR_a$, $-NR_aC(=O)NR_aR_a$, $-C(=O)OR_b$, $-S(O)_pNR_aR_a$, $-NR_aS(O)_pNR_aR_a$, and $-NR_aS(O)_pR_c$, $-(CH_2)_r-C_{3-10}$ carbocyclyl substituted with 0-5 $R_e$, and $-(CH_2)_r$-heterocyclyl substituted with 0-5 $R_e$;

$R_6$ and $R_7$ are independently selected from H, $C_{1-4}$alkyl substituted with 0-4 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

alternatively, $R_6$ and $R_7$ together with the carbon atom to which they are both attached form a cycloalkyl or heterocyclyl, each substituted with 0-5 $R_e$; alternatively, when q is 2 or 3, two adjacent $R_6$ groups form a cycloalkyl or heterocyclyl, each substituted with 0-5 $R_e$;

$R_8$ is selected from aryl, $C_{3-6}$cycloalkyl, and heterocyclyl, each substituted with 0-5 $R_9$;

$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_rOC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, $C_{1-6}$ alkyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, $-(CH_2)_r-C_{3-10}$ carbocyclyl, $-(CH_2)_r$-heterocyclyl, F, Cl, Br, CN, $NO_2$, =O, $CO_2H$, $CO_2C_{1-6}$ alkyl, $-(CH_2)_rOC_{1-5}$ alkyl, $-(CH_2)_rOH$, $-(CH_2)_rNR_fR_f$, $-(CH_2)_rNR_fR_fC(=O)C_{1-4}$alkyl, $-C(=O)NR_fR_f$, $-C(=O)R_f$, $S(O)_pNR_fR_f$, $-NR_fR_fS(O)_pC_{1-4}$alkyl, and $S(O)_pC_{1-4}$alkyl;

$R_f$, at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from zero, 1, 2, and 3;

r, at each occurrence, is independently selected from zero, 1, 2, 3, and 4; and s, at each occurrence is independently selected from 1, and 2.

In another aspect, the present invention provides compounds of Formula (IX):

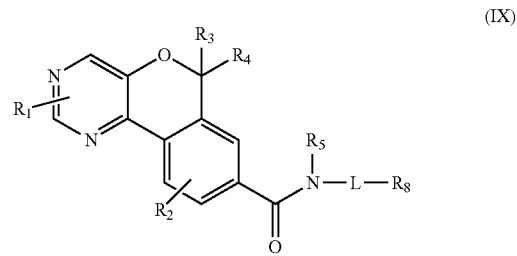

(IX)

or stereoisomers, tautomers, pharmaceutically acceptable salts, solvates, or prodrugs thereof, wherein L is independently selected from $-(CR_6R_7)_q$, $-(CR_6R_7)_sNR_5-$, $-(CR_6R_7)_sO-$, and $-(CR_6R_7)_sC(O)-$;

$R_1$ and $R_2$ are independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$, $R_3$ and $R_4$ are independently selected from H, F, and $C_{1-4}$ alkyl substituted with 0-3 $R_e$, $C_{1-4}$ alkenyl substituted with 0-3 $R_e$, and $C_{1-4}$ alkynyl substituted with 0-3 $R_e$;

$R_5$ is independently selected from H and $C_{1-4}$ alkyl optionally substituted with F, Cl, Br, CN, $-OR_b$, $-S(O)_pR_c$, $-C(=O)R_b$, $-NR_aR_a$, $-C(=O)NR_aR_a$, $-C(=O)(CH_2)_rNR_aR_a$, CN, $-NR_aC(=O)R_b$, $-NR_aC(=O)OR_b$, $-OC(=O)NR_aR_a$, $-NR_aC(=O)NR_aR_a$, $-C(=O)OR_b$, $-S(O)_pNR_aR_a$, $-NR_aS(O)_pNR_aR_a$, $-NR_aS(O)_pR_c$, $-(CH_2)_r-C_{3-10}$ carbocyclyl substituted with 0-5 $R_e$, and $-(CH_2)_r$-heterocyclyl substituted with 0-5 $R_e$;

$R_6$ and $R_7$ are independently selected from H, $C_{1-4}$alkyl substituted with 0-4 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

alternatively, $R_6$ and $R_7$ together with the carbon atom to which they are both attached form a cycloalkyl or heterocyclyl, each substituted with 0-5 $R_e$; alternatively, when q is 2 or 3, two adjacent $R_6$ groups form a cycloalkyl or heterocyclyl, each substituted with 0-5 $R_e$;

$R_8$ is selected from aryl, $C_{3-6}$cycloalkyl, and heterocyclyl, each substituted with 0-5 $R_9$;

$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, C$_{1-6}$ alkyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, Br, and OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O)C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from zero, 1, 2, and 3;

r, at each occurrence, is independently selected from zero, 1, 2, 3, and 4; and s, at each occurrence, is independently selected from 1, and 2.

In another aspect, the present invention provides compounds of Formula (IX), or stereoisomers, tautomers, pharmaceutically acceptable salts, solvates, or prodrugs thereof, wherein L is —(CR$_6$R$_7$)$_q$;

R$_1$ and R$_2$ are H;

R$_3$ and R$_4$ are independently selected from H, F, and C$_{1-4}$alkyl substituted with 0-3 R$_e$;

R$_5$ is H;

R$_6$ and R$_7$ are independently selected from H and C$_{1-4}$alkyl substituted with 0-3 R$_e$;

R$_8$ is selected from aryl and heterocyclyl, each substituted with 0-5 R$_9$; and R$_9$ is independently selected from F, Cl, Br, CN, C$_{1-4}$alkyl, OH, OC$_{1-4}$ alkyl, —C(=O)OC$_{1-4}$ alkyl, —C(=O)NH$_2$, —C(=O)NHC$_{1-4}$ alkyl, —C(=O)NHC$_{3-6}$ cycloalkyl, C$_{3-6}$cycloalkyl, heterocyclyl, aryl, and heteroaryl;

other variables are as defined in Formula (IX) above.

In another aspect, the present invention provides compounds of Formula (I), or stereoisomers, tautomers, pharmaceutically acceptable salts, solvates, or prodrugs thereof, wherein A$_1$ and A$_2$ are CR$_1$;

A$_3$ is independently selected from N and CR$_1$;

B is independently selected from —O—, —CR$_3$R$_4$O—, —OCR$_3$R$_4$—, —NR$_a$—, —C(O)O—, —OC(O)—, —C(O)NR$_a$—, —NR$_a$C(O)—, and —S—;

L is independently selected from —(CR$_6$R$_7$)$_q$—, —(CR$_6$R$_7$)$_s$NR$_5$(CR$_6$R$_7$)$_q$—, —(CR$_6$R$_7$)$_s$O(CR$_6$R$_7$)$_q$—, and —(CR$_6$R$_7$)$_s$C(O)(CR$_6$R$_7$)$_q$—;

R$_1$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, (CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_2$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, and —(CH$_2$)$_r$OR$_b$, R$_3$ and R$_4$ are independently selected from H, F, OH, CN, NR$_a$R$_a$, C$_{1-4}$ alkyl substituted with 0-3 R$_e$, C$_{1-4}$ alkenyl substituted with 0-3 R$_e$, and C$_{1-4}$ alkynyl substituted with 0-3 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, (CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_5$ is independently selected from H and C$_{1-4}$ alkyl optionally substituted with F, Cl, Br, CN, —OR$_b$, —S(O)$_p$R$_c$, —C(=O)R$_b$, —NR$_a$R$_a$, —C(=O)NR$_a$R$_a$, —C(=O)(CH$_2$)$_r$NR$_a$R$_a$, CN, —NR$_a$C(=O)R$_b$, —NR$_a$C(=O)OR$_b$, —OC(=O)NR$_a$R$_a$, —NR$_a$C(=O)NR$_a$R$_a$, —C(=O)OR$_b$, —S(O)$_p$NR$_a$R$_a$, —NR$_a$S(O)$_p$NR$_a$R$_a$, and —NR$_a$S(O)$_p$R$_c$, —(CH$_2$)$_r$—C$_{3-10}$ carbocyclyl substituted with 0-5 R$_e$, and —(CH$_2$)$_r$-heterocyclyl substituted with 0-5 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

alternatively, R$_6$ and R$_7$ together with the carbon atom to which they are both attached form a cycloalkyl or heterocyclyl, each substituted with 0-5 R$_e$; alternatively, when q is 2 or 3, two adjacent R$_6$ groups form a cycloalkyl or heterocyclyl, each substituted with 0-5 R$_e$;

R$_8$ is selected from C$_{3-10}$ carbocyclyl and heterocyclyl, each substituted with 0-5 R$_9$;

R$_9$ is independently selected from F, Cl, Br, C$_{1-4}$alkyl substituted with 0-5 R$_e$, C$_{2-4}$alkenyl substituted with 0-5 R$_e$, C$_{2-4}$alkynyl substituted with 0-5 R$_e$, =O, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;
alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, C$_{1-6}$ alkyl substituted with 0-5 R$_e$, C$_{2-6}$alkenyl substituted with 0-5 R$_e$, C$_{2-6}$alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, Br, and OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O)C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from zero, 1, 2, and 3;

r, at each occurrence, is independently selected from zero, 1, 2, 3, and 4;

s, at each occurrence, is independently selected from 1, and 2; provided when s and q are in the same term, s+q≤3.

In another aspect, the present invention provides compounds of Formula (II), or stereoisomers, tautomers, pharmaceutically acceptable salts, solvates, or prodrugs thereof, wherein B is independently selected from —O— and —NR$_a$—;
L is —(CR$_6$R$_7$)$_q$—;
R$_1$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, and —(CH$_2$)$_r$OR$_b$;
R$_2$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, and —(CH$_2$)$_r$OR$_b$,
R$_5$ is independently selected from H and C$_{1-4}$ alkyl;
R$_6$ and R$_7$ are independently selected from H, C$_{1-4}$alkyl substituted with 0-4 R$_e$, and —(CH$_2$)$_r$C(=O)OR$_b$, R$_8$ is selected from phenyl, C$_{3-6}$ cycloalkyl and heterocyclyl, each substituted with 0-5 R$_9$;

R$_9$ is independently selected from F, Cl, C$_{1-4}$alkyl substituted with 0-5 R$_e$, —NR$_a$S(O)$_p$C$_{1-4}$ alkyl, —OR$_b$, and —CN;

R$_a$, at each occurrence, is independently selected from H, C$_{1-6}$ alkyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_b$, at each occurrence, is independently selected from H and C$_{1-6}$ alkyl substituted with 0-5 R$_e$;

R$_c$, at each occurrence, is independently selected from C$_{1-6}$ alkyl (optionally substituted with F, Cl, Br, and OH), F, Cl, Br, CN, NO$_2$, —(CH$_2$)$_r$OC$_{1-5}$ alkyl, and —(CH$_2$)$_r$OH;

p, at each occurrence, is independently selected from zero, 1, and 2;

q, at each occurrence, is independently selected from zero, 1, 2, and 3; and r, at each occurrence, is independently selected from zero, 1, 2, 3, and 4.

In another aspect, the present invention provides compounds of Formula (III), or stereoisomers, tautomers, pharmaceutically acceptable salts, solvates, or prodrugs thereof, wherein L is independently selected from —(CR$_6$R$_7$)$_q$—, —(CR$_6$R$_7$)$_s$NR$_5$—, —(CR$_6$R$_7$)$_s$O—, and —(CR$_6$R$_7$)$_s$C(O)—;

R$_1$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, —(CH$_2$)$_r$OR$_b$, —NR$_a$C(=O)R$_b$, and —NR$_a$C(=O)OR$_b$, R$_2$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, and —(CH$_2$)$_r$OR$_b$, R$_3$ and R$_4$ are independently selected from H, F, OH, CN, and C$_{1-4}$ alkyl substituted with 0-3 R$_e$, C$_{1-4}$ alkenyl substituted with 0-3 R$_e$, and C$_{1-4}$ alkynyl substituted with 0-3 R$_e$;

R$_5$ is independently selected from H and C$_{1-4}$ alkyl optionally substituted with F, Cl, Br, CN, —OR$_b$, —S(O)$_p$R$_c$, —C(=O)R$_b$, —NR$_a$R$_a$, —C(=O)NR$_a$R$_a$, —C(=O)(CH$_2$)$_r$NR$_a$R$_a$, CN, —NR$_a$C(=O)R$_b$, —NR$_a$C(=O)OR$_b$, —OC(=O)NR$_a$R$_a$, —NR$_a$C(=O)NR$_a$R$_a$, —C(=O)OR$_b$, —S(O)$_p$NR$_a$R$_a$, —NR$_a$S(O)$_p$NR$_a$R$_a$, and —NR$_a$S(O)$_p$R$_c$, —(CH$_2$)$_r$—C$_{3-10}$ carbocyclyl substituted with 0-5 R$_e$, and —(CH$_2$)$_r$-heterocyclyl substituted with 0-5 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

alternatively, R$_6$ and R$_7$ together with the carbon atom to which they are both attached form a cycloalkyl or heterocyclyl, each substituted with 0-5 R$_e$; alternatively, when q is 2 or 3, two adjacent R$_6$ groups form a cycloalkyl or heterocyclyl, each substituted with 0-5 R$_e$;

R$_8$ is selected from aryl, C$_{3-6}$cycloalkyl, and heterocyclyl, each substituted with 0-5 R$_9$;

R$_9$ is independently selected from F, Cl, Br, C$_{1-4}$alkyl substituted with 0-5 R$_e$, C$_{2-4}$alkenyl substituted with 0-5 R$_e$, C$_{2-4}$alkynyl substituted with 0-5 R$_e$, =O, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;
alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, C$_{1-6}$ alkyl substituted with 0-5 R$_e$, C$_{2-6}$alkenyl substituted with 0-5 R$_e$, C$_{2-6}$alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, Br, and OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O)C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from zero, 1, 2, and 3;

r, at each occurrence, is independently selected from zero, 1, 2, 3, and 4; and s, at each occurrence, is independently selected from 1 and 2.

In another aspect, the present invention provides compounds of Formula (IV), or stereoisomers, tautomers, pharmaceutically acceptable salts, solvates, or prodrugs thereof, wherein R$_1$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, —(CH$_2$)$_r$OR$_b$, —NR$_a$C(=O)R$_b$, and —NR$_a$C(=O)OR$_b$;

R$_2$ is independently selected from H, F, Cl, Br, CN, and NR$_a$R$_a$;

R$_3$ is independently selected from H and C$_{1-4}$ alkyl substituted with 0-3 R$_e$, C$_{1-4}$ alkenyl substituted with 0-3 R$_e$, and C$_{1-4}$ alkynyl substituted with 0-3 R$_e$;

R$_5$ is independently selected from H and C$_{1-4}$ alkyl optionally substituted with F, Cl, Br, CN, —OR$_b$, —S(O)$_p$R$_c$, —C(=O)R$_b$, —NR$_a$R$_a$, —C(=O)NR$_a$R$_a$, —C(=O) (CH$_2$)$_r$NR$_a$R$_a$, CN, —NR$_a$C(=O)R$_b$, —NR$_a$C(=O)OR$_b$, —OC(=O)NR$_a$R$_a$, —NR$_a$C(=O)NR$_a$R$_a$, —C(=O)OR$_b$, —S(O)$_p$NR$_a$R$_a$, —NR$_a$S(O)$_p$NR$_a$R$_a$, and —NR$_a$S(O)$_p$R$_c$, —(CH$_2$)$_r$—C$_{3-10}$ carbocyclyl substituted with 0-5 R$_e$, and —(CH$_2$)$_r$-heterocyclyl substituted with 0-5 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

alternatively, R$_6$ and R$_7$ together with the carbon atom to which they are both attached form a cycloalkyl or heterocyclyl, each substituted with 0-5 R$_e$; alternatively, when q is 2 or 3, two adjacent R$_6$ groups form a cycloalkyl or heterocyclyl, each substituted with 0-5 R$_e$;

R$_9$ is independently selected from F, Cl, Br, C$_{1-4}$alkyl substituted with 0-5 R$_e$, C$_{2-4}$alkenyl substituted with 0-5 R$_e$, C$_{2-4}$alkynyl substituted with 0-5 R$_e$, =O, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, C$_{1-6}$ alkyl substituted with 0-5 R$_e$, C$_{2-6}$alkenyl substituted with 0-5 R$_e$, C$_{2-6}$alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, Br, and OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O)C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from 1 and 2; and r, at each occurrence, is independently selected from zero, 1, 2, 3, and 4.

In another aspect, the present invention provides compounds of Formula (IV), or stereoisomers, tautomers, pharmaceutically acceptable salts, solvates, or prodrugs thereof, wherein $R_1$ and $R_2$ are H;

$R_3$ is independently selected from H and Me;

$R_5$ is H;

$R_6$ and $R_7$ are independently selected from H, $C_{1-4}$alkyl substituted with 0-4 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

alternatively, $R_6$ and $R_7$ together with the carbon atom to which they are both attached form a cycloalkyl or heterocyclyl, each substituted with 0-5 $R_e$; alternatively, when q is 2 or 3, two adjacent $R_6$ groups form a cycloalkyl or heterocyclyl, each substituted with 0-5 $R_e$;

$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_rC(=O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, $C_{1-6}$ alkyl substituted with 0-5 $R_e$, $C_{2-6}$alkenyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, —$(CH_2)_r$—$C_{3-10}$ carbocyclyl, —$(CH_2)_r$-heterocyclyl, F, Cl, Br, CN, $NO_2$, =O, $CO_2H$, $CO_2C_{1-6}$ alkyl, —$(CH_2)_rOC_{1-5}$ alkyl, —$(CH_2)_rOH$, —$(CH_2)_rNR_fR_f$, —$(CH_2)_rNR_fR_fC(=O)C_{1-4}$alkyl, —$C(=O)NR_fR_f$, —$C(=O)R_f$, $S(O)_pNR_fR_f$, —$NR_fR_fS(O)_pC_{1-4}$alkyl, and $S(O)_pC_{1-4}$alkyl;

$R_f$, at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from 1 and 2;

r, at each occurrence, is independently selected from zero, 1, 2, 3, and 4; and other variables are as defined in Formula (IV) above.

In another aspect, the present invention provides compounds of Formula (IV), or stereoisomers, tautomers, pharmaceutically acceptable salts, solvates, or prodrugs thereof, wherein $R_6$ and $R_7$ are independently selected from H and $C_{1-4}$alkyl substituted with 0-4 $R_e$;

$R_9$ is independently selected from F, Cl, Br, $C_{1-4}$alkyl substituted with 0-5 $R_e$, $C_{2-4}$alkenyl substituted with 0-5 $R_e$, =O, nitro, —$(CHR_d)_rS(O)_pR_c$, —$(CHR_d)_r$ $S(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_rC(=O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, $C_{1-6}$ alkyl substituted with 0-5 $R_e$, $C_{2-6}$alkenyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, —$(CH_2)_r$—$C_{3-10}$ carbocyclyl, —$(CH_2)_r$-heterocyclyl, F, Cl, Br, CN, $NO_2$, =O, $CO_2H$, $CO_2C_{1-6}$ alkyl, —$(CH_2)_rOC_{1-5}$ alkyl, —$(CH_2)_rOH$, —$(CH_2)_rNR_fR_f$, —$(CH_2)_rNR_fR_fC(=O)C_{1-4}$alkyl, —$C(=O)NR_fR_f$, —$C(=O)R_f$, $S(O)_pNR_fR_f$, —$NR_fR_fS(O)_pC_{1-4}$alkyl, and $S(O)_pC_{1-4}$alkyl;

$R_f$, at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from 1 and 2;

r, at each occurrence, is independently selected from zero, 1, 2, 3, and 4; and other variables are as defined in Formula (IV) above.

In another aspect, the present invention provides compounds of Formula (V), or stereoisomers, tautomers, pharmaceutically acceptable salts, solvates, or prodrugs thereof, wherein L is independently selected from $-(CR_6R_7)_q-$, $-(CR_6R_7)_sNR_5-$, $-(CR_6R_7)_sO-$, and $-(CR_6R_7)_sC(O)-$;

$R_1$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, $-(CH_2)_rOR_b$, $-NR_aC(=O)R_b$, and $-NR_aC(=O)OR_b$;

$R_2$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_3$ and $R_4$ are independently selected from H, F, Cl, Br, OH, CN, $C_{1-4}$ alkyl substituted with 0-3 $R_e$, and $C_{3-6}$ carbocyclyl substituted with 0-3 $R_e$, $C_{1-4}$ alkenyl substituted with 0-3 $R_e$, and $C_{1-4}$ alkynyl substituted with 0-3 $R_e$;

$R_5$ is independently selected from H and $C_{1-4}$ alkyl optionally substituted with F, Cl, Br, CN, $-OR_b$, $-S(O)_pR_c$, $-C(=O)R_b$, $-NR_aR_a$, $-C(=O)NR_aR_a$, $-C(=O)(CH_2)_rNR_aR_a$, CN, $-NR_aC(=O)R_b$, $-NR_aC(=O)OR_b$, $-OC(=O)NR_aR_a$, $-NR_aC(=O)NR_aR_a$, $-C(=O)OR_b$, $-S(O)_pNR_aR_a$, $-NR_aS(O)_pNR_aR_a$, and $-NR_aS(O)_pR_c$, $-(CH_2)_r-C_{3-10}$ carbocyclyl substituted with 0-5 $R_e$, and $-(CH_2)_r$-heterocyclyl substituted with 0-5 $R_e$;

$R_6$ and $R_7$ are independently selected from H, $C_{1-4}$alkyl substituted with 0-4 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

alternatively, $R_6$ and $R_7$ together with the carbon atom to which they are both attached form a cycloalkyl or heterocyclyl, each substituted with 0-5 $R_e$; alternatively, when q is 2 or 3, two adjacent $R_6$ groups form a cycloalkyl or heterocyclyl, each substituted with 0-5 $R_e$;

$R_8$ is selected from aryl, $C_{3-6}$cycloalkyl, and heterocyclyl, each substituted with 0-5 $R_9$;

$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_rOC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, $C_{1-6}$ alkyl substituted with 0-5 $R_e$, $C_{2-6}$alkenyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, $-(CH_2)_r-C_{3-10}$ carbocyclyl, $-(CH_2)_r$-heterocyclyl, F, Cl, Br, CN, $NO_2$, =O, $CO_2H$, $CO_2C_{1-6}$ alkyl, $-(CH_2)_rOC_{1-5}$ alkyl, $-(CH_2)_rOH$, $-(CH_2)_rNR_fR_f$, $-(CH_2)_rNR_fR_fC(=O)C_{1-4}$alkyl, $-C(=O)NR_fR_f$, $-C(=O)R_f$, $S(O)_pNR_fR_f$, $-NR_fR_fS(O)_pC_{1-4}$alkyl, and $S(O)_pC_{1-4}$alkyl;

$R_f$, at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from zero, 1, 2, and 3;

r, at each occurrence, is independently selected from zero, 1, 2, 3, and 4; and s, at each occurrence, is independently selected from 1 and 2.

In another aspect, the present invention provides compounds of Formula (VIa):

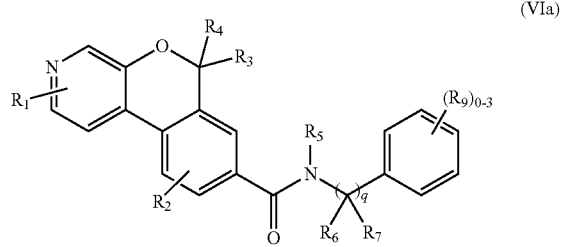

or stereoisomers, tautomers, pharmaceutically acceptable salts, solvates, or prodrugs thereof, wherein $R_1$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, $-(CH_2)_rOR_b$, $-NHC(=O)R_b$, and $-NHC(=O)OR_b$;

$R_2$ is independently selected from H, F, Cl, Br, OH, CN, and $NR_aR_a$;

$R_3$ and $R_4$ are independently selected from H, $C_{1-4}$ alkyl substituted with 0-3 $R_e$, and $-(CH_2)_r-C_{3-6}$ carbocyclyl substituted with 0-3 $R_e$;

$R_5$ is independently selected from H and $C_{1-4}$ alkyl optionally substituted with F, Cl, Br, CN, $-OR_b$, $-S(O)_pR_c$, $-C(=O)R_b$, $-NR_aR_a$, $-C(=O)NR_aR_a$, $-C(=O)$ $-(CH_2)_rNR_aR_a$, CN, $-NR_aC(=O)R_b$, $-NR_aC(=O)OR_b$, $-OC(=O)NR_aR_a$, $-NR_aC(=O)NR_aR_a$, $-C(=O)OR_b$, $-S(O)_pNR_aR_a$, $-NR_aS(O)_pNR_aR_a$, and $-NR_aS(O)_pR_c$, $-(CH_2)_r-C_{3-10}$ carbocyclyl substituted with 0-5 $R_e$, and $-(CH_2)_r$-heterocyclyl substituted with 0-5 $R_e$;

$R_6$ and $R_7$ are independently selected from H, $C_{1-4}$alkyl substituted with 0-4 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

alternatively, $R_6$ and $R_7$ together with the carbon atom to which they are both attached form a cycloalkyl or heterocyclyl, each substituted with 0-5 $R_e$; alternatively, when q is 2 or 3, two adjacent $R_6$ groups form a cycloalkyl or heterocyclyl, each substituted with 0-5 $R_e$;

$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_rOC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, $C_{1-6}$ alkyl substituted with 0-5 $R_e$, $C_{2-6}$alkenyl substituted with 0-5 $R_e$, $C_{2-6}$alkynyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, $-(CH_2)_r-C_{3-10}$ carbocyclyl, $-(CH_2)_r$-heterocyclyl, F, Cl, Br, CN, $NO_2$, =O, $CO_2H$, $CO_2C_{1-6}$ alkyl, $-(CH_2)_rOC_{1-5}$ alkyl, $-(CH_2)_rOH$, $-(CH_2)_rNR_fR_f$, $-(CH_2)_rNR_fR_fC(=O)C_{1-4}$alkyl, $-C(=O)NR_fR_f$, $-C(=O)R_f$, $S(O)_pNR_fR_f$, $-NR_fR_fS(O)_pC_{1-4}$alkyl, and $S(O)_pC_{1-4}$alkyl;

$R_f$, at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from 1 and 2; and r, at each occurrence, is independently selected from zero, 1, 2, 3, and 4.

In another aspect, the present invention provides compounds of Formula (X):

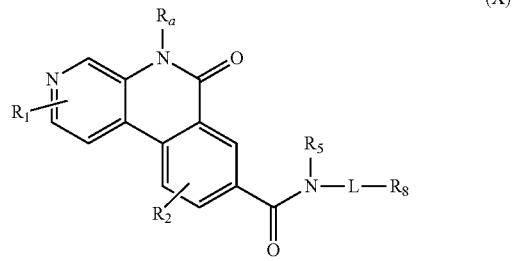

(X)

or stereoisomers, tautomers, pharmaceutically acceptable salts, solvates, or prodrugs thereof, wherein L is $-(CR_6R_7)_9$;

$R_1$ and $R_2$ are independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_5$ is independently selected from H and $C_{1-4}$ alkyl;

$R_6$ and $R_7$ are independently selected from H and $C_{1-4}$alkyl substituted with 0-4 $R_e$;

$R_8$ is aryl substituted with 0-5 $R_9$;

$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_rOC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$ alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, $-(CH_2)_r-C_{3-10}$ carbocyclyl, $-(CH_2)_r$-heterocyclyl, F, Cl, Br, CN, $NO_2$, =O, $CO_2H$, $CO_2C_{1-6}$ alkyl, $-(CH_2)_rOC_{1-5}$ alkyl, $-(CH_2)_rOH$, $-(CH_2)_rNR_fR_f$, $-(CH_2)_rNR_fR_fC(=O)C_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, and C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from zero, 1, 2, and 3; and r, at each occurrence, is independently selected from zero, 1, 2, 3, and 4.

In another aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the exemplified examples or a stereoisomer, a tautomer, a pharmaceutically acceptable salt, or a solvate thereof.

In another embodiment, the present invention provides a group of compounds having ROCK2 IC$_{50}$ values≤10 μM.

In another embodiment, the present invention provides a group of compounds having ROCK2 IC$_{50}$ values≤1 μM.

In another embodiment, the present invention provides a group of compounds having ROCK2 IC$_{50}$ values≤0.1 μM.

In another embodiment, the present invention provides a group of compounds having ROCK2 IC$_{50}$ values≤0.05 μM.

In another embodiment, the present invention provides a group of compounds having ROCK2 IC$_{50}$ values≤0.01 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a patient that has not yet presented with a clinical disease state, whereas secondary prevention is defined as preventing a second occurrence of the same or similar clinical disease state. In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood.

Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2H$" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH Ethanol
GMF glass microfiber filter
Grubbs (II) (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate
LAH lithium aluminum hydride
LG leaving group
LiOH lithium hydroxide
MeOH Methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ Ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
i-PrOH or IPA isopropanol
PS polystyrene
PyBOP benzotriazol-1-yl-oxytripyrrolidinophosphonium hexafluorophosphate
SEM-Cl 2-(trimethysilyl)ethoxymethyl chloride
SiO$_2$ silica oxide
SnCl$_2$ tin(II) chloride
TBAF tetra-n-butylammonium fluoride
TBAI tetra-n-butylammonium iodide
TEA triethylamine
TFA trifluoroacetic acid
THF tetrahydrofuran
TMSCHN$_2$ trimethylsilyldiazomethane
T$_3$P propane phosphonic acid anhydride
TRIS tris (hydroxymethyl)aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 µL assay containing 20 mM HEPES, pH 7.5, 20 mM MgCl$_2$, 0.015% Brij-35, 4 mM DTT, 5 µM ATP and 1.5 µM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC$_{50}$; i.e., the concentration of compound required to inhibit 50% of kinase activity.

Representative Examples were tested in the ROCK assay described above and found having ROCK inhibitory activity. A range of ROCK inhibitory activity (IC$_{50}$ values) of ≤50 µM (50000 nM) was observed. Table A below lists the ROCK2 IC$_{50}$ values measured for the following Examples.

TABLE A

| Example No. | ROCK2 IC$_{50}$ (nM) |
| --- | --- |
| I-1 | 0.51 |
| I-2 | 9.59 |
| I-3 | 5.52 |
| I-4 | 49.1 |
| I-5 | 238 |
| I-6 | 17.0 |
| I-7 | 367 |
| I-8 | 5490 |
| I-9 | 486 |
| I-10 | 30.4 |
| I-11 | 242 |
| I-12 | 664 |
| I-13 | 979 |
| I-14 | 149 |
| I-15 | 7440 |
| I-16 | 3920 |
| I-17 | 165 |
| I-18 | 37.2 |
| I-19 | 75.0 |
| I-20 | 199 |
| I-21 | 177 |
| I-22 | 29.4 |
| I-23 | 158 |
| I-24 | 50.7 |
| I-25 | 41.3 |
| I-26 | 300 |
| I-27 | 6.32 |
| I-28 | 59.8 |
| I-29 | 1640 |
| I-30 | 349 |
| I-31 | 2100 |
| I-32 | 55.5 |
| I-33 | 291 |
| I-34 | 1040 |
| I-35 | 602 |
| I-36 | 282 |
| I-37 | 198 |

TABLE A-continued

| Example No. | ROCK2 IC$_{50}$ (nM) |
|---|---|
| I-38 | 404 |
| I-39 | 1370 |
| I-40 | 7090 |
| I-41 | 38.0 |
| I-42 | 537 |
| I-43 | 643 |
| I-44 | 1790 |
| I-45 | 258 |
| I-46 | 233 |
| I-47 | 55.5 |
| I-48 | 3170 |
| I-49 | 717 |
| I-50 | 38.1 |
| I-51 | 3.23 |
| I-52 | 1640 |
| I-53 | 318 |
| I-54 | 137 |
| I-55 | 174 |
| I-56 | 19.9 |
| I-57 | 4910 |
| I-58 | 95.9 |
| I-59 | 113 |
| I-60 | 36.7 |
| I-61 | 98.3 |
| I-62 | 7610 |
| I-63 | 63.2 |
| I-64 | 2150 |
| I-65 | 198 |
| I-66 | 92.3 |
| I-67 | 54.5 |
| I-68 | 37.6 |
| I-69 | 75.5 |
| I-70 | 0.81 |
| I-71 | 12.3 |
| I-72 | 224 |
| I-73 | 5980 |
| I-74 | 24.8 |
| I-75 | 159 |
| I-76 | 493 |
| I-77 | 17.5 |
| I-78 | 4440 |
| I-79 | 184 |
| I-80 | 81.4 |
| I-81 | 4180 |
| I-82 | 2410 |
| I-83 | 7.69 |
| I-84 | 4.95 |
| I-85 | 25.2 |
| I-86 | 471 |
| I-87 | 4340 |
| I-88 | 4080 |
| I-89 | 5650 |
| I-90 | 49.7 |
| I-91 | 607 |
| I-92 | 682 |
| I-93 | 315 |
| I-94 | 260 |
| I-95 | 31.9 |
| I-96 | 2970 |
| I-97 | 2210 |
| I-98 | 1200 |
| I-99 | 657 |
| I-100 | 695 |
| I-101 | 1320 |
| I-102 | 1170 |
| I-103 | 1620 |
| I-104 | 4460 |
| I-105 | 62.1 |
| I-106 | 10.6 |
| I-107 | 429 |
| I-108 | 8.54 |
| I-109 | 131 |
| I-110 | 218 |
| I-111 | 3.62 |
| I-112 | 615 |
| I-113 | 1340 |
| I-114 | 106 |
| I-115 | 3210 |
| I-116 | 1080 |
| I-117 | 368 |
| I-118 | 15.1 |
| I-119 | 845 |
| I-120 | 2280 |
| I-121 | 973 |
| I-122 | 2780 |
| I-123 | 688 |
| I-124 | 7.28 |
| I-125 | 9.52 |
| I-126 | 16.8 |
| I-127 | 27.7 |
| I-128 | 141 |
| I-129 | 6310 |
| I-130 | 170 |
| I-131 | 411 |
| I-132 | 3780 |
| I-133 | 1990 |
| I-134 | 5320 |
| I-135 | 1980 |
| I-136 | 6580 |
| I-137 | 4470 |
| I-138 | 176 |
| I-139 | 24.5 |
| I-140 | 1620 |
| I-141 | 6270 |
| I-142 | 550 |
| I-143 | 5090 |
| I-144 | 9920 |
| I-145 | 3420 |
| I-146 | 106 |
| I-147 | 835 |
| I-148 | 640 |
| I-149 | 593 |
| I-150 | 589 |
| I-151 | 458 |
| I-152 | 8190 |
| I-153 | 7070 |
| I-154 | 378 |
| I-155 | 8640 |
| I-156 | 1210 |
| I-157 | 810 |
| I-158 | 6.18 |
| I-159 | 194 |
| I-160 | 3.68 |
| I-161 | 875 |
| I-162 | 22.4 |
| I-163 | 32.5 |
| I-164 | 14.0 |
| I-165 | 5.14 |
| I-166 | 1490 |
| II-1 | 15.5 |
| II-2 | 16.2 |
| II-3 | 25.4 |
| II-4 | 55.1 |
| II-5 | 458 |
| II-6 | 9070 |
| II-7 | 51.2 |
| II-8 | 6070 |
| II-9 | 42.6 |
| II-10 | 6930 |
| II-11 | 541 |
| II-12 | 516 |
| II-13 | 382 |
| II-14 | 36.0 |
| II-15 | 756 |
| II-16 | 35.2 |
| III-1 | 2.51 |
| III-2 | 25.5 |
| III-3 | 1.70 |
| III-4 | 2.24 |
| III-5 | 2.54 |
| III-6 | 281 |
| III-7 | 120 |
| III-8 | 33.8 |
| III-9 | 497 |
| III-10 | 684 |
| III-11 | 583 |

TABLE A-continued

| Example No. | ROCK2 IC$_{50}$ (nM) |
|---|---|
| III-12 | 429 |
| III-13 | 2.58 |
| III-14 | 18.8 |
| III-15 | 191 |
| III-16 | 66.9 |
| III-17 | 377 |
| III-18 | 18.2 |
| III-19 | 15.5 |
| IV-1 | 107 |
| IV-2 | 72.5 |
| IV-3 | 321 |
| IV-4 | 276 |
| IV-5 | 1590 |
| IV-6 | 44.5 |
| IV-7 | 111 |
| IV-8 | 1220 |
| IV-9 | 12.4 |
| IV-10 | 30.2 |
| IV-11 | 108 |
| IV-12 | 12.8 |
| IV-13 | 35.2 |
| IV-14 | 77.9 |
| IV-15 | 74.3 |
| IV-16 | 371 |
| IV-17 | 52.5 |
| IV-18 | 370 |
| IV-19 | 187 |
| V-1 | 30.2 |
| V-2 | 169 |
| V-3 | 23.1 |
| V-4 | 664 |
| V-5 | 4.71 |
| V-6 | 15.9 |
| V-7 | 24.3 |
| V-8 | 42.4 |
| V-9 | 8.97 |
| V-10 | 53.9 |
| V-11 | 80.3 |
| V-12 | 3.90 |
| VI-1 | 1.05 |
| VI-2 | 2.78 |
| VI-3 | 6.23 |
| VI-4 | 6.36 |
| VI-5 | 2.80 |
| VI-6 | 1.32 |
| VI-7 | 0.35 |
| VI-8 | 19.9 |
| VI-9 | 11.4 |
| VI-10 | 7.31 |
| VI-11 | 5.66 |
| VI-12 | 56.0 |
| VII-1 | 1.29 |
| VII-2 | 2.87 |
| VII-3 | 2.25 |
| VII-4 | 3.73 |
| VII-5 | 0.80 |
| VII-6 | 1.34 |
| VII-7 | 1.50 |
| VII-8 | 2.54 |
| VII-9 | 0.78 |
| VII-10 | 12.6 |
| VII-11 | 1.14 |
| VII-12 | 1.82 |
| VIII-1 | 0.59 |
| VIII-2 | 4.09 |
| VIII-3 | 1.99 |
| VIII-4 | 0.34 |
| VIII-5 | 0.85 |
| VIII-6 | 0.85 |
| VIII-7 | 0.85 |
| VIII-8 | 0.85 |
| VIII-9 | 2.55 |
| VIII-10 | 6.35 |
| VIII-11 | 2.54 |
| VIII-12 | 0.85 |
| VIII-13 | 0.85 |
| VIII-14 | 0.79 |
| VIII-15 | 0.56 |
| VIII-16 | 0.60 |
| VIII-17 | 13.8 |
| VIII-18 | 5.16 |
| VIII-19 | 4.10 |
| VIII-20 | 14.3 |
| VIII-21 | 11.2 |
| VIII-22 | 18.8 |
| VIII-23 | 0.72 |
| VIII-24 | 12.4 |
| VIII-25 | 4.18 |
| VIII-26 | 13.1 |
| VIII-27 | 11.9 |
| VIII-28 | 4.74 |
| VIII-29 | 41.5 |
| VIII-30 | 13.2 |
| VIII-31 | 11.0 |
| VIII-32 | 12.8 |
| VIII-33 | 4.38 |
| VIII-34 | 4.37 |
| VIII-35 | 18.6 |
| VIII-36 | 1.70 |
| VIII-37 | 9.03 |
| IX-1 | 9.66 |
| IX-2 | 3.74 |
| IX-3 | 2.39 |
| IX-4 | 20.9 |
| IX-5 | 18.7 |
| IX-6 | 17.7 |
| IX-7 | 231 |
| IX-8 | 27.6 |
| IX-9 | 46.3 |
| X-1 | 90.2 |
| X-2 | 138 |
| X-3 | 13.3 |
| X-4 | 2.71 |
| X-5 | 104 |
| XI-1 | 452 |
| XI-2 | 19.3 |
| XI-3 | 25.2 |
| XI-4 | 10.3 |
| XI-1 | 452 |
| XI-2 | 19.3 |
| XI-3 | 25.2 |
| XI-4 | 10.3 |
| XI-5 | 33.1 |
| XI-6 | 637 |
| XI-7 | 17.1 |
| XI-8 | 61.4 |
| XI-9 | 122.6 |
| XI-10 | 73.8 |
| XI-11 | 93.1 |
| XI-12 | 12.6 |
| XI-13 | 9.03 |
| XI-14 | 32.6 |
| XI-15 | 1112 |
| XI-16 | 0.52 |
| XI-17 | 0.18 |
| XI-18 | 176 |
| XI-19 | 3.79 |
| XI-20 | 1.81 |
| XI-21 | 0.65 |
| XI-22 | 7.34 |
| XI-23 | 2.95 |
| XI-24 | 20.4 |
| XI-25 | 4.69 |
| XI-26 | 9.28 |
| XI-27 | 3.94 |
| XI-28 | 239 |
| XI-29 | 362 |
| XI-30 | 15.9 |
| XI-31 | 1.44 |
| XI-32 | 935 |
| XI-33 | 51.7 |
| XI-34 | 472 |
| XI-35 | 229 |
| XI-36 | 265 |
| XI-37 | 494 |
| XI-38 | 130 |

TABLE A-continued

| Example No. | ROCK2 IC$_{50}$ (nM) |
| --- | --- |
| XII-1 | 1480 |
| XII-2 | 1750 |
| XII-3 | 957 |
| XII-4 | 782 |
| XII-5 | 49.3 |
| XII-6 | 620 |
| XIII-1 | 68.9 |
| XIII-2 | 882 |
| XIII-3 | 337 |
| XIII-4 | 781 |
| XIII-5 | 792 |
| XIII-6 | 47.9 |
| XIII-7 | 583 |
| XIII-8 | 68.9 |
| XIII-9 | 1840 |
| XIII-10 | 175 |
| XIV-1 | 3.91 |
| XIV-2 | 16.3 |
| XIV-3 | 13.7 |
| XIV-4 | 1.29 |
| XIV-5 | 89.6 |
| XIV-6 | 6.98 |
| XIV-7 | 13.7 |
| XIV-8 | 13.5 |
| XIV-9 | 2.32 |
| XIV-10 | 12.2 |
| XIV-11 | 7.16 |
| XIV-12 | 1020 |
| XIV-13 | 43.2 |
| XIV-14 | 48.8 |
| XIV-15 | 33.6 |
| XIV-16 | 3.69 |
| XIV-17 | 15.2 |
| XIV-18 | 45.9 |
| XIV-19 | 80.8 |
| XIV-20 | 1.01 |
| XIV-21 | 15.0 |
| XIV-22 | 27.7 |
| XIV-23 | 8.09 |
| XIV-24 | 25.3 |
| XIV-25 | 38.8 |
| XIV-26 | 144 |
| XIV-27 | 34.2 |
| XIV-28 | 46.6 |
| XIV-29 | 1490 |
| XIV-30 | 213 |
| XIV31 | 1.16 |
| XIV-32 | 5.70 |
| XIV-33 | 7.43 |
| XIV-34 | 66.3 |
| XIV-35 | 33.1 |
| XIV-36 | 2.66 |
| XIV-37 | 297 |
| XV-1 | 2.85 |
| XV-2 | 49.4 |
| XV-3 | 44.2 |
| XV-4 | 49.2 |
| XV-5 | 460 |
| XV-6 | 552 |
| XV-7 | 1140 |
| XV-8 | 606 |
| XV-9 | 161 |
| XV-10 | 77.8 |
| XV-11 | 965 |
| XV-12 | 28.6 |
| XV-13 | 81.0 |
| XV-14 | 26.4 |
| XV-15 | 224 |
| XV-16 | 1070 |
| XVI-1 | 20.3 |
| XVI-2 | 36.9 |
| XVI-3 | 7.40 |
| XVI-4 | 2230 |
| XVI-5 | 61.5 |
| XVI-6 | 34.3 |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

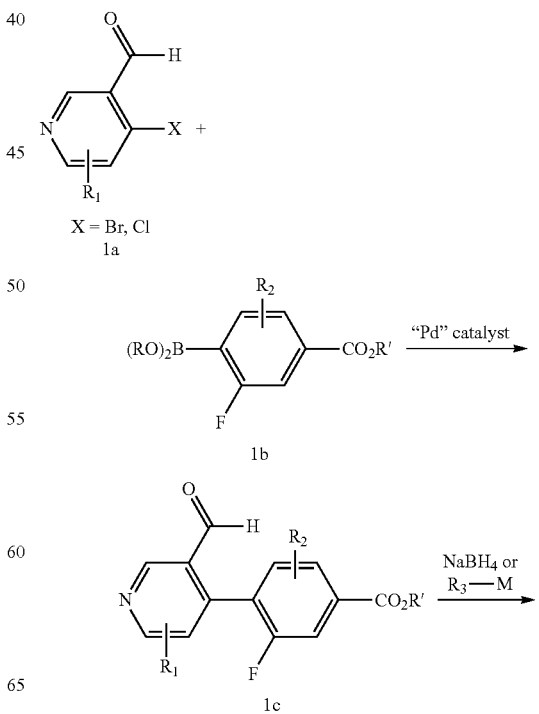

Scheme 1

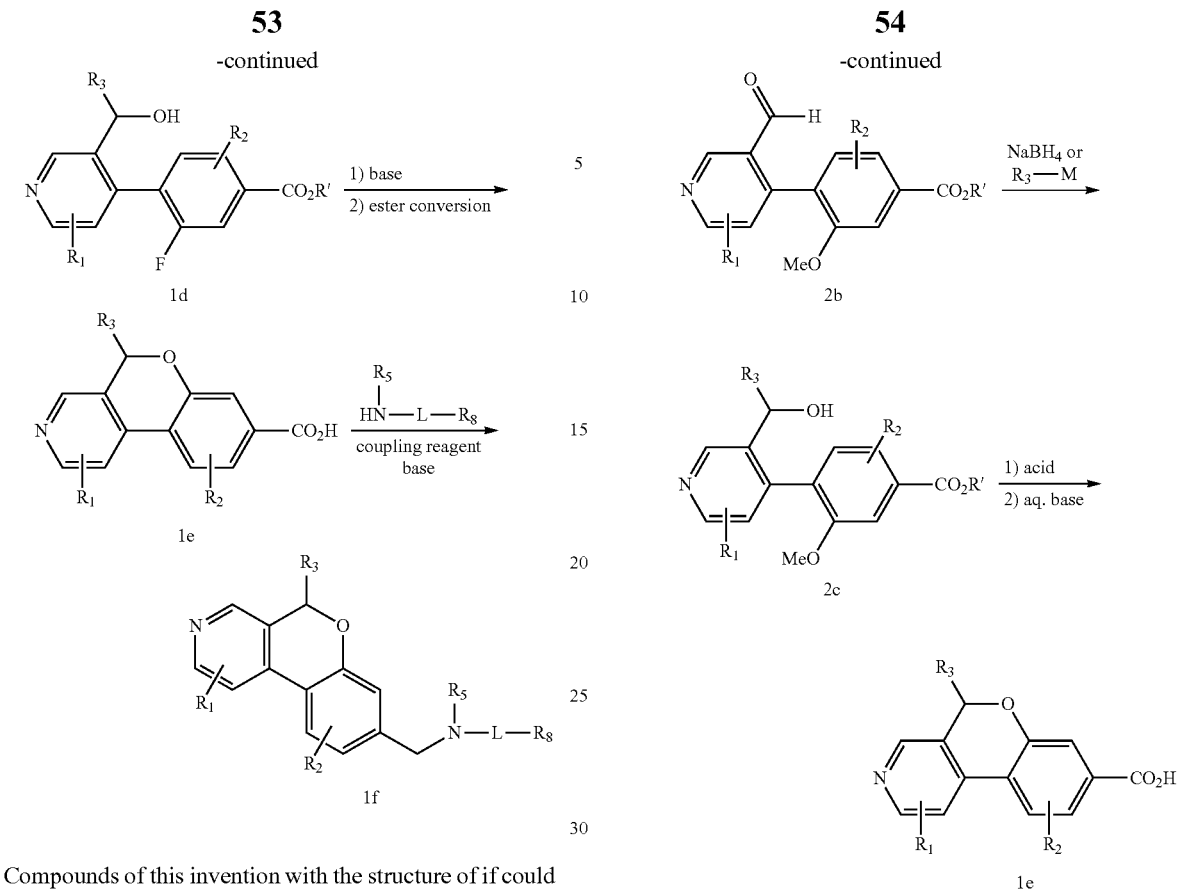

Compounds of this invention with the structure of 1f could be prepared as shown in Scheme 1. Suzuki-Miyaura coupling between 4-halopyridine derivative 1a and fluorophenyl boronic acid or boronate 1b, in the presence of a base such as $K_3PO_4$, and a Pd catalyst such as $PdCl_2(dppf)$, affords intermediate 1c. Aldehyde 1c is either reduced using a reducing reagent such as $NaBH_4$, or treated with an alkyl metal reagent such as a Grignard's reagent, to afford alcohol 1d. Ring closure of 1d by treatment with a base, such as NaH, $Cs_2CO_3$, etc, followed by aqueous basic workup to afford the tricyclic acid common intermediate 1e. Amide formation affords target 1f by coupling intermediate 1e with an appropriate amine in the presence of a coupling reagent, such as HATU or EDC, and a base such as DIEA.

Alternatively, the common intermediate 1e can be prepared as shown in Scheme 2. Suzuki-Miyaura coupling between 4-halopyridine derivative 1a and methoxyphenyl boronic acid or boronate 2a, in the presence of a base such as $K_3PO_4$, and a Pd catalyst such as $PdCl_2(dppf)$, affords intermediate 2b. Aldehyde 2b is either reduced using a reducing reagent such as $NaBH_4$, or treated with an alkyl metal reagent such as a Grignard's reagent, to afford alcohol 2c. Ring closure of 2c by treatment with a strong acid, such as HBr, followed by aqueous basic workup to afford the tricyclic acid 1e.

Scheme 2

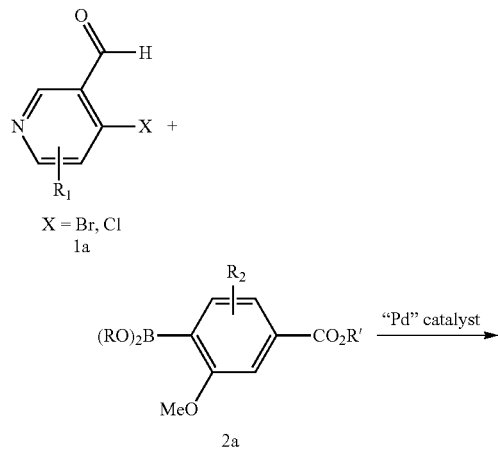

Scheme 3

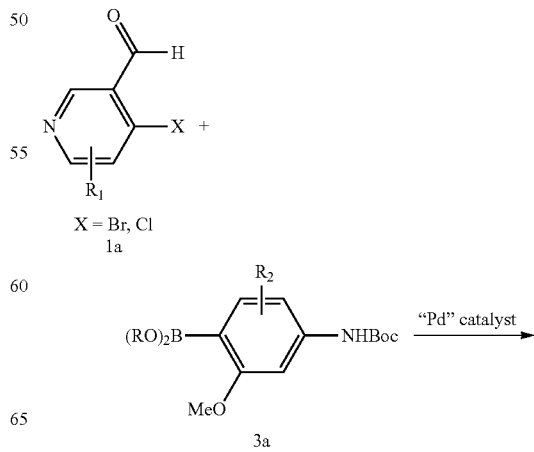

-continued

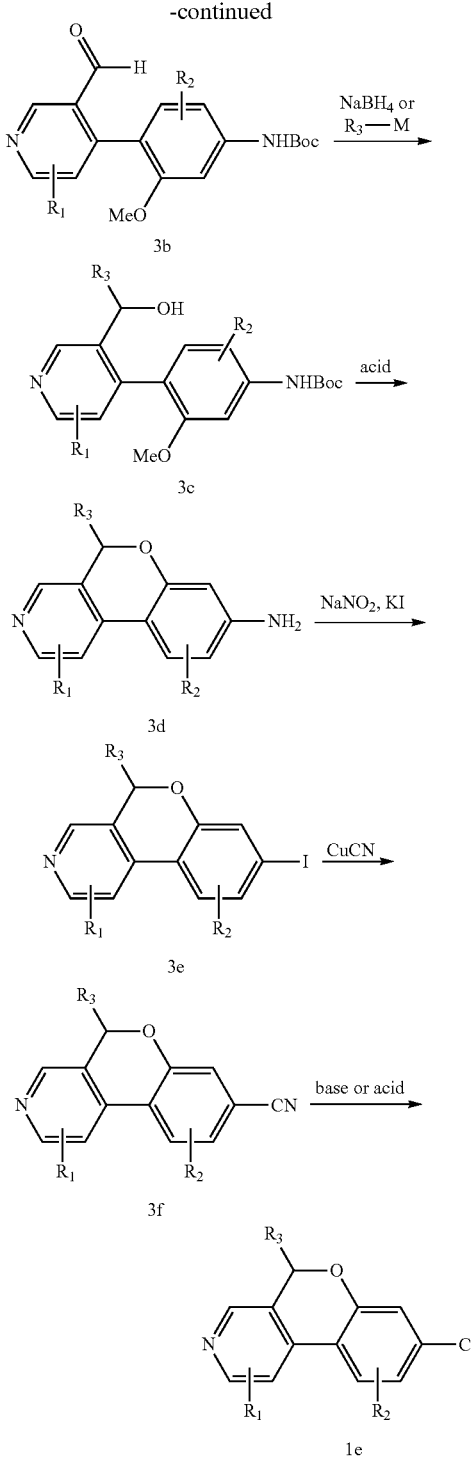

iodide in 3e, followed by cyanization provides 3f. The cyano group is hydrolyzed to the acid by treating 3f with an aqueous base such NaOH, or an aqueous acid such as HCl, to give the tricyclic acid 1e.

Scheme 4

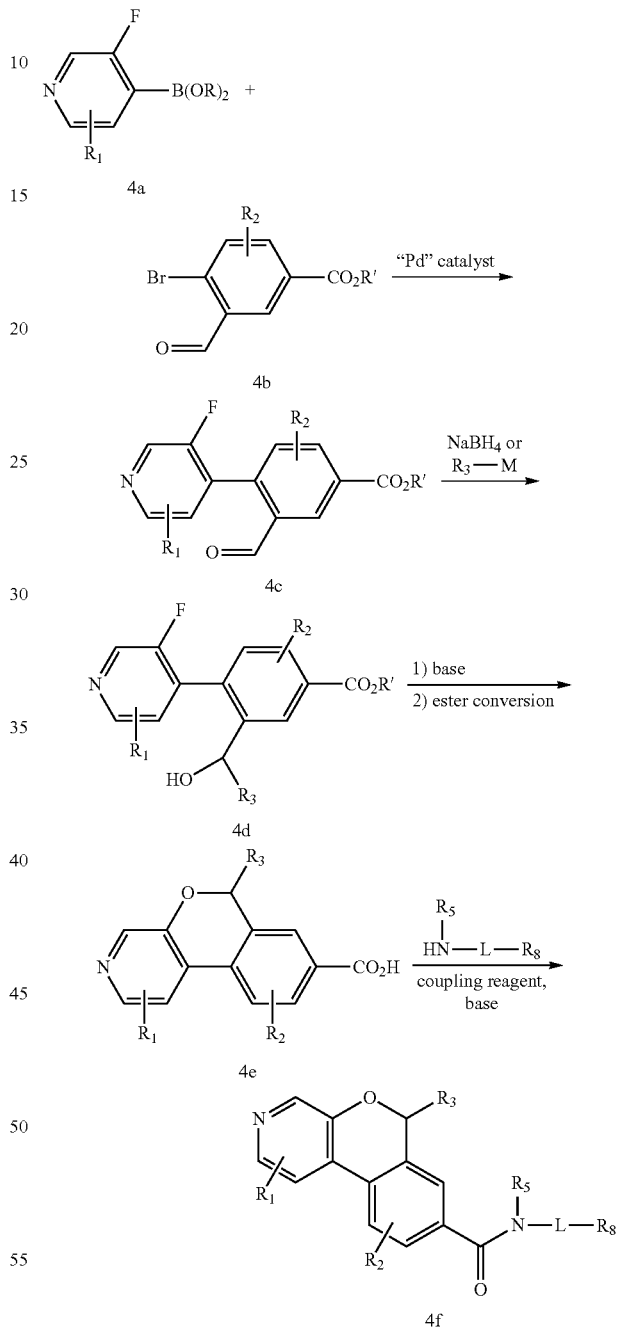

Alternatively, intermediate 1e can be prepared as shown in Scheme 3. Suzuki-Miyaura coupling between 4-halopyridine derivative 1a and methoxy aniline boronic acid or boronate 3a, in the presence of a base such as $K_3PO_4$, and a Pd catalyst such as $PdCl_2(dppf)$, affords intermediate 3b. Aldehyde 3b is either reduced using a reducing reagent such as $NaBH_4$, or treated with an alkyl metal reagent such as a Grignard's reagent, to afford alcohol 3c. Ring closure of 3c by treatment with a strong acid, such as HBr, to afford tricyclic aniline 3d. Conversion of the amino group of 3c to Compounds of this invention with the structure of 4f could be prepared as shown in Scheme 4. Suzuki-Miyaura coupling between 4-pyridine boronic acid or boronate derivative 4a and bromobenzaldehyde derivative 4b, or other appropriate Suzuki coupling partners, in the presence of a base such as $K_3PO_4$, and a Pd catalyst such as $PdCl_2$(dppf), affords intermediate 4c. Aldehyde 4c is either reduced using a reducing reagent such as $NaBH_4$, or treated with an alkyl metal reagent such as a Grignard's reagent, to afford alcohol 4d. Ring closure of 4d by treatment with a base, such as NaH, $Cs_2CO_3$, etc, followed by aqueous basic workup to afford the tricyclic acid common intermediate 4e. Amide formation affords target 4f by coupling intermediate 4e with an appropriate amine in the presence of a coupling reagent, such as HATU or EDC, and a base such as DIEA.

Scheme 5

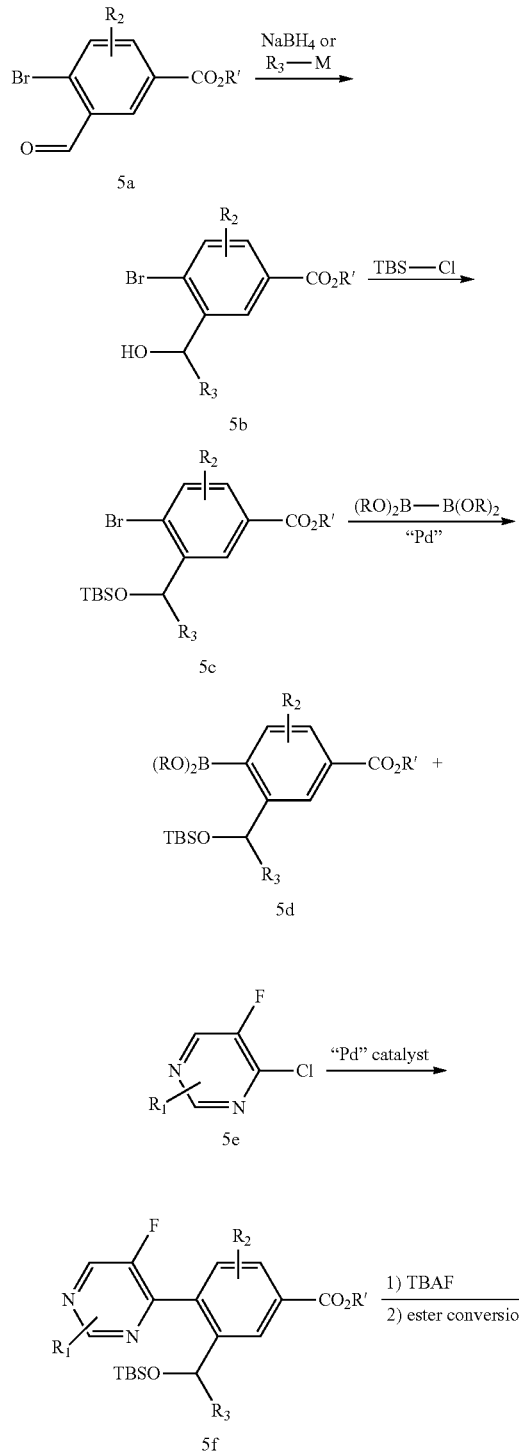

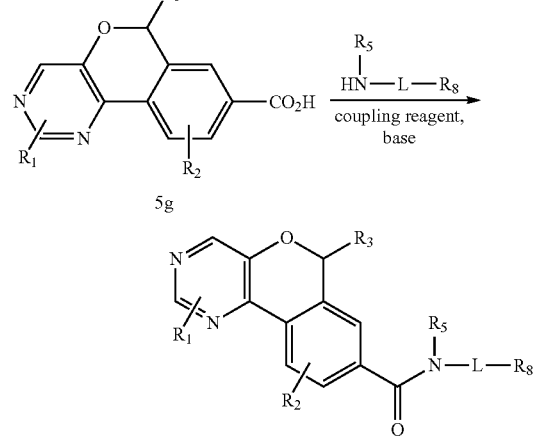

Compounds of this invention with the structure of 5h could be prepared as shown in Scheme 5. Aldehyde 5a is either reduced using a reducing reagent such as $NaBH_4$, or treated with an alkyl metal reagent such as a Grignard's reagent, to afford alcohol 5b. The alcohol is protected using a protecting group such as TBS to give 5c, which is then converted to boronic acid or boronate 5d under Miyaura condition. Suzuki-Miyaura coupling between 5d and chloropyrimidine derivative 5e, in the presence of a base such as $K_3PO_4$, and a Pd catalyst such as $Pd(PPh_3)_4$, affords intermediate 5f. Removal of the TBS protecting group and closure of the ring by treating 5f with TBAF followed by ester conversion by treating with an aqueous base such as LiOH, affords common intermediate 5g. Amide formation affords target 5h by coupling intermediate 5g with an appropriate amine in the presence of a coupling reagent, such as HATU or EDC, and a base such as DIEA.

Scheme 6

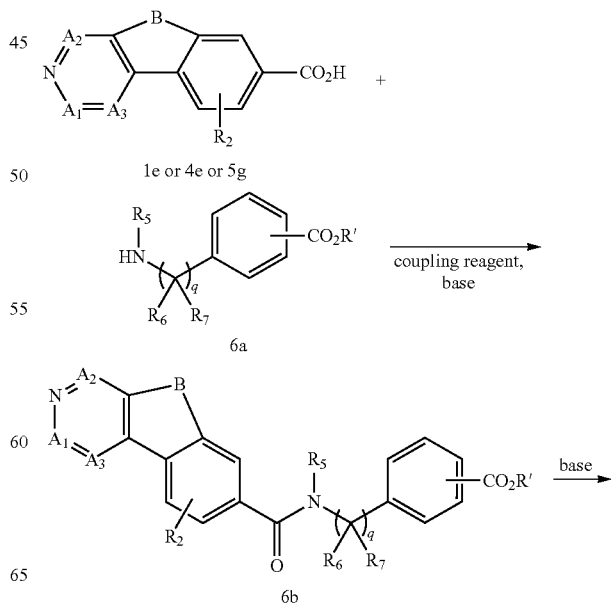

-continued

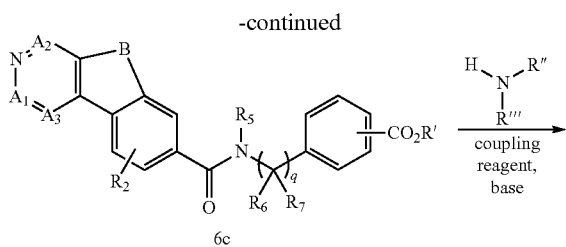

6c

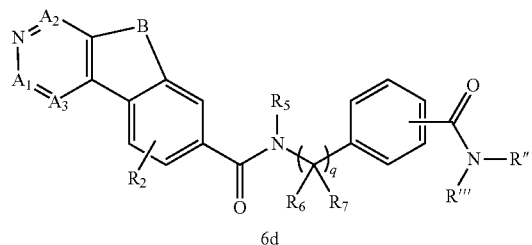

6d

Compounds of this invention with the structure of 6d could be prepared as shown in Scheme 6. Amide formation provides compound 6b by coupling intermediate 1e or 4e or 5g with amino ester 6a in the presence of a coupling reagent, such as HATU or EDC, and a base such as DIEA. Ester 6b is converted to acid 6c when treated with a base such as LiOH. Target 6d is afforded by coupling 6c with an appropriate amine using a coupling reagent, such as HATU or EDC, and a base such as DIEA.

Compounds of this invention with the structure of 7d could be prepared as shown in Scheme 7. Amide formation of intermediate 1e, or 4e, or 5g with 7a provides intermediate 7b. Suzuki-Miyaura coupling between 7b and an appropriate aromatic boronic acid or boronate derivative, in the presence of a base such as $K_3PO_4$, and a Pd catalyst such as $PdCl_2(dppf)$, affords 7d. Alternatively, 7b can be converted to boronic acid or boronate 7c. Then 7c can couple with aromatic halides following Suzuki-Miyaura coupling condition to afford target 7d.

Scheme 8

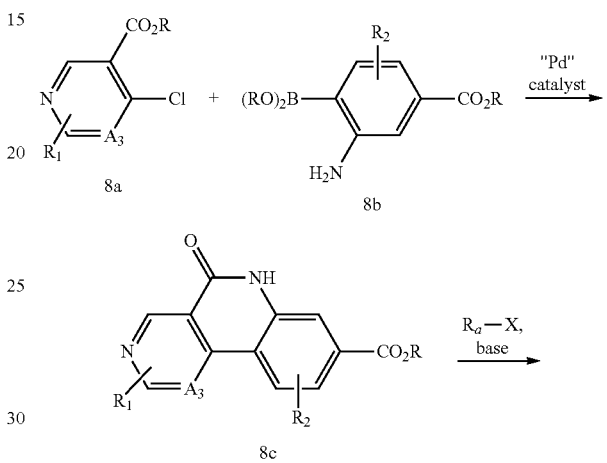

Scheme 7

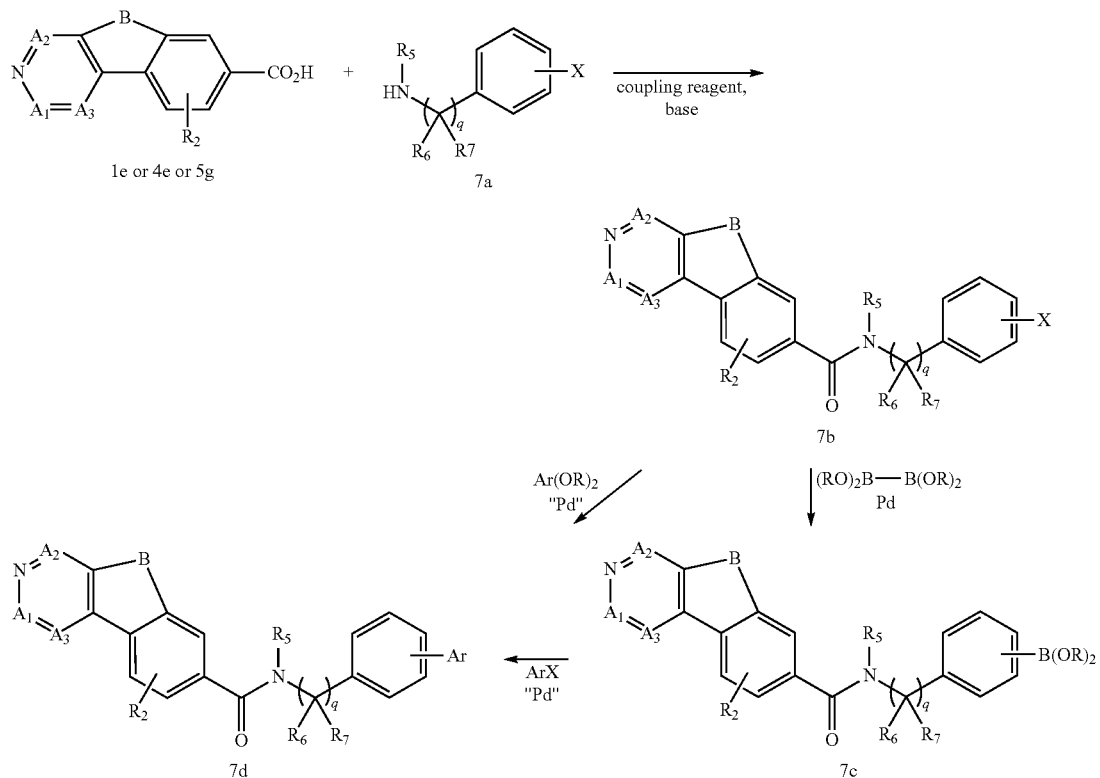

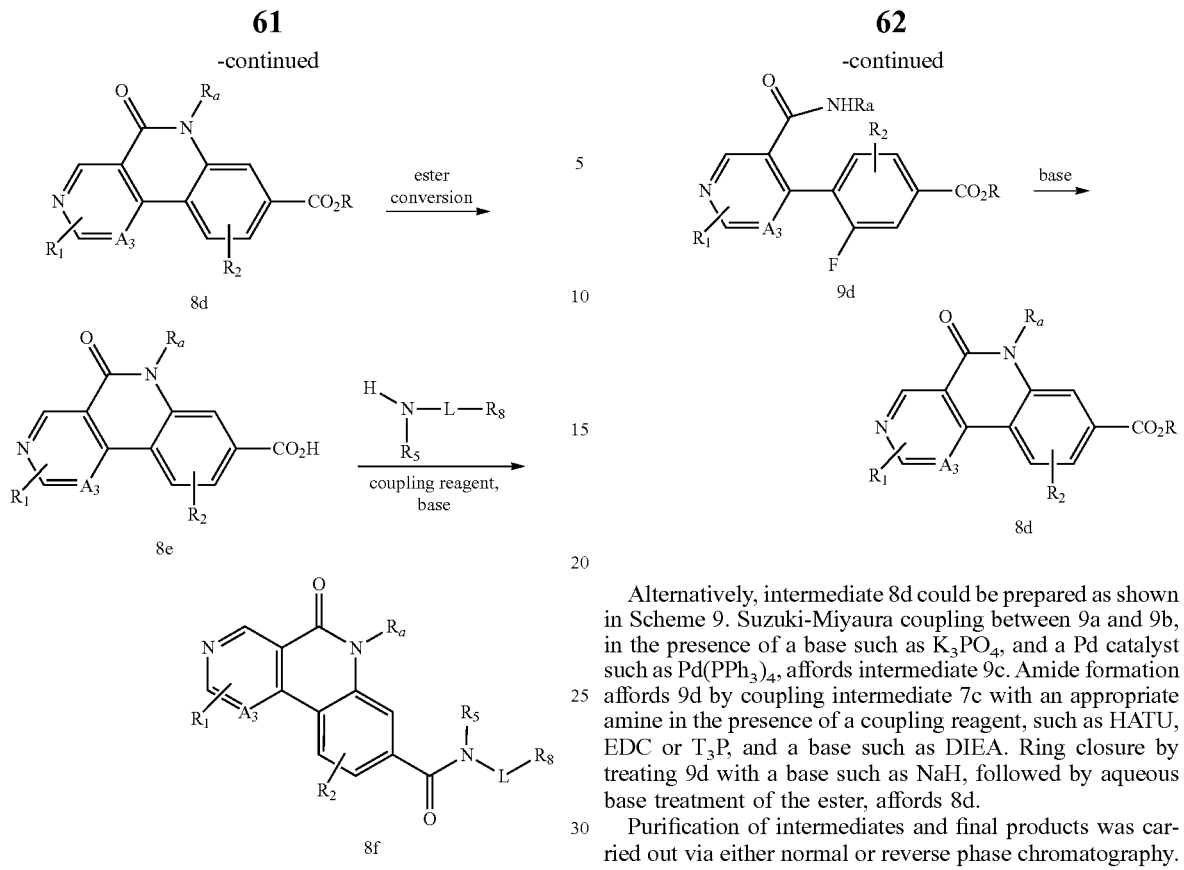

Compounds of this invention with the structure of 8f could be prepared as shown in Scheme 8. Suzuki-Miyaura coupling between 8a and 8b, in the presence of a base such as $K_3PO_4$, and a Pd catalyst such as $Pd(PPh_3)_4$, affords intermediate 8c. Substitution of the lactam by treating 8c with an appropriate alkylating reagent at the presence of a base such as NaH, affords 8d. Ester conversion by treatment with an aqueous base such as LiOH, affords common intermediate 8e. Amide formation affords target 8f by coupling intermediate 8e with an appropriate amine in the presence of a coupling reagent, such as HATU or EDC, and a base such as DIEA.

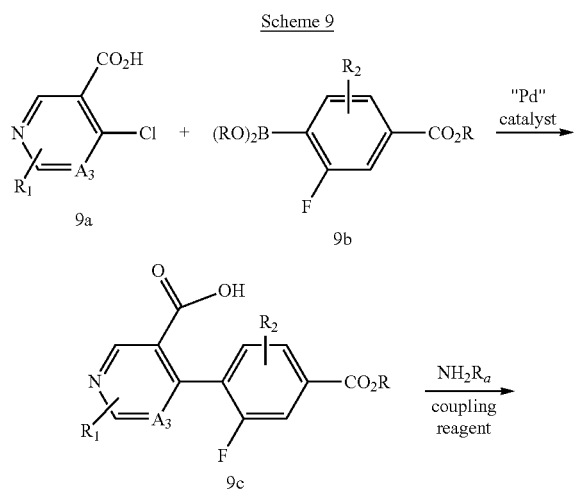

Alternatively, intermediate 8d could be prepared as shown in Scheme 9. Suzuki-Miyaura coupling between 9a and 9b, in the presence of a base such as $K_3PO_4$, and a Pd catalyst such as $Pd(PPh_3)_4$, affords intermediate 9c. Amide formation affords 9d by coupling intermediate 7c with an appropriate amine in the presence of a coupling reagent, such as HATU, EDC or $T_3P$, and a base such as DIEA. Ring closure by treating 9d with a base such as NaH, followed by aqueous base treatment of the ester, affords 8d.

Purification of intermediates and final products was carried out via either normal or reverse phase chromatography. Normal phase chromatography was carried out using pre-packed $SiO_2$ cartridges eluting with either gradients of hexanes and EtOAc or DCM and MeOH, or DCM and EtOAc unless otherwise indicated. Reverse phase preparative HPLC was carried out using C18 columns eluting with gradients of Solvent A (90% $H_2O$, 10% MeOH, 0.1% TFA) and Solvent B (10% $H_2O$, 90% MeOH, 0.1% TFA, UV 220 nm) or with gradients of Solvent A (90% $H_2O$, 10% ACN, 0.1% TFA) and Solvent B (10% $H_2O$, 90% ACN, 0.1% TFA, UV 220 nm) or with gradients of Solvent A (98% $H_2O$, 2% ACN, 0.05% TFA) and Solvent B (98% ACN, 2% $H_2O$, 0.05% TFA, UV 220 nm) (or) SunFire Prep C18 OBD 5μ 30×100 mm, 25 min gradient from 0-100% B. A=$H_2O$/ACN/TFA 90:10:0.1. B=ACN/$H_2O$/TFA 90:10:0.1 (or) Waters XBridge C18, 19×200 mm, 5-μm particles; Guard Column: Waters XBridge C18, 19×10 mm, 5-μm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min or with gradients of Solvent A (5:95 acetonitrile:water with 0.1% formic acid) and Solvent B (95:5 acetonitrile:water with 0.1% formic acid).

Unless otherwise stated, analysis of final products was carried out by reverse phase analytical HPLC.

Method A: SunFire C18 column (3.5 μm C18, 3.0×150 mm) Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method B: XBridge Phenyl column (3.5 μm C18, 3.0×150 mm) Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method C: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient 0.5 min hold at 0% B, 0-100% B over 4 minutes, then a 0.5-minute hold at 100% B; Flow: 1 mL/min.

Method C-1: Waters BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 40° C.; Gradient 0.5 min hold at 0% B, 0-100% B over 4 minutes, then a 0.5-minute hold at 100% B; Flow: 1 mL/min.

Method D: Waters BEH C18, 2.1×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Method E: Waters BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes; Flow: 1.11 mL/min.

Method F: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.11 mL/min.

Method G: SunFire C18 column (3.5 μm, 4.6×150 mm) Gradient elution (1.0 mL/min) from 10-100% Solvent B over 18 min and then 100% Solvent B for 5 min was used. Solvent A is (95% water, 5% acetonitrile, 0.05% TFA) and Solvent B is (5% water, 95% acetonitrile, 0.05% TFA, UV 220 nm).

Method H: XBridge Phenyl column (3.5 μm, 4.6×150 mm) Gradient elution (1.0 mL/min) from 10-100% Solvent B over 18 min and then 100% Solvent B for 5 min was used. Solvent A is (95% water, 5% acetonitrile, 0.05% TFA) and Solvent B is (5% water, 95% acetonitrile, 0.05% TFA, UV 220 nm).

Method I: SunFire C18 column (3.5 μm, 4.6×150 mm) Gradient elution (1.0 mL/min) from 10-100% Solvent B over 12 min and then 100% Solvent B for 3 min was used. Solvent A is (95% water, 5% acetonitrile, 0.05% TFA) and Solvent B is (5% water, 95% acetonitrile, 0.05% TFA, UV 220 nm).

Method J: XBridge Phenyl column (3.5 μm, 4.6×150 mm) Gradient elution (1.0 mL/min) from 10-100% Solvent B over 12 min and then 100% Solvent B for 3 min was used. Solvent A is (95% water, 5% acetonitrile, 0.05% TFA) and Solvent B is (5% water, 95% acetonitrile, 0.05% TFA, UV 220 nm).

Method K: SunFire C18 column (3.5 μm, 4.6×150 mm) Gradient elution (1.0 mL/min) from 0-50% Solvent B over 15 min, 50-100% Solvent B over 3 min, and then 100% Solvent B for 5 min was used. Solvent A is (95% water, 5% acetonitrile, 0.05% TFA) and Solvent B is (5% water, 95% acetonitrile, 0.05% TFA, UV 220 nm).

Method L: XBridge Phenyl column (3.5 μm, 4.6×150 mm) Gradient elution (1.0 mL/min) from 0-50% Solvent B over 15 min, 50-100% Solvent B over 3 min, and then 100% Solvent B for 5 min was used. Solvent A is (95% water, 5% acetonitrile, 0.05% TFA) and Solvent B is (5% water, 95% acetonitrile, 0.05% TFA, UV 220 nm).

Method M: Ascentis Express C18 (2.7 μm, 4.6×50 mm) Gradient elution (4.0 mL/min) from 0-100% Solvent B over 4 min. Solvent A is (95% water, 5% acetonitrile, 0.1% TFA) and Solvent B is (5% water, 95% acetonitrile, 0.1% TFA, UV 220 nm).

Method N: Ascentis Express C18 (2.7 μm, 4.6×50 mm) Gradient elution (4.0 mL/min) from 0-100% Solvent B over 4 min. Solvent A is (95% water, 5% acetonitrile, 10 mM NH$_4$OAc) and Solvent B is (5% water, 95% acetonitrile, 10 mM NH$_4$OAc, UV 220 nm).

INTERMEDIATE 1

5H-Chromeno[3,4-c]pyridine-8-carboxylic acid

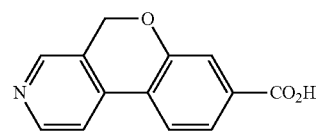 [SMILES: O=C(O)c1ccc2c(c1)OCc1cnccc1-2]

INTERMEDIATE 1a tert-Butyl (4-bromo-3-methoxyphenyl)carbamate

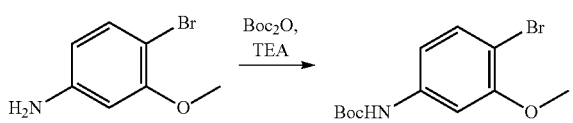

To a stirred solution of 4-bromo-3-methoxyaniline (50 g, 247 mmol) in THF (1.5 L) were added Boc$_2$O (69 mL, 297 mmol) and TEA (45 mL, 322 mmol). The reaction mixture was refluxed for 12 h. The solvent was removed and the residue was taken in ethyl acetate. It was washed with water and brine, and then dried over sodium sulfate and concentrated. The crude mixture was purified by normal phase chromatography to give Intermediate 1a as white solid (60.0 g, 78%). LC-MS (ESI) m/z: 302.0 [M+H]$^-$; $^1$H NMR (400 MHz, DMSO-d$_6$) δ 9.48 (s, 1H), 7.40 (d, J=8.4 Hz, 1H), 7.37 (d, J=2.0 Hz, 1H), 6.96 (dd, J=8.4, 2.0 Hz, 1H), 3.79 (s, 3H), 1.48 (s, 9H).

INTERMEDIATE 1b tert-Butyl (3-methoxy-4-(4,4,5,5-tetramethyl-1,3,2-dioxaborolan-2-yl)phenyl)carbamate

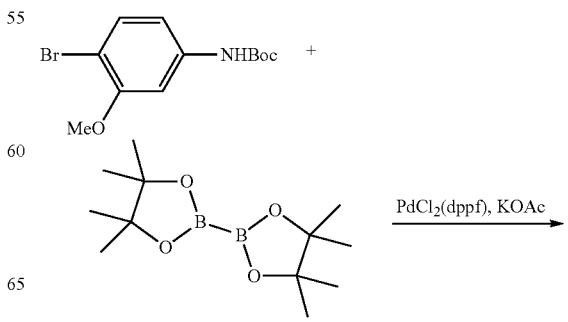

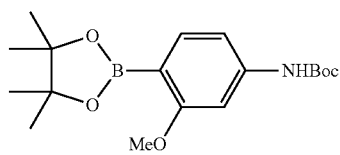

To a stirred solution of 1a (25 g, 83 mmol) in DMF (750 mL) were added KOAc (24.36 g, 248 mmol), 4,4,4',4',5,5,5',5'-octamethyl-2,2'-bi(1,3,2-dioxaborolane) (31.5 g, 124 mmol) and PdCl$_2$(dppf)-CH$_2$Cl$_2$ adduct (6.76 g, 8.27 mmol). The reaction was heated at 100° C. for 12 h. The DMF was removed and the residue was taken in ethyl acetate. It was washed with water and brine, dried over sodium sulfate and concentrated. The crude mixture was purified by normal phase chromatography to provide Intermediate 1b as white solid (15.0 g, 48%). $^1$H NMR (400 MHz, DMSO-d$_6$) δ 9.45 (s, 1H), 7.41 (d, J=8.0 Hz, 1H), 7.17 (d, J=1.6 Hz, 1H), 7.00 (dd, J=8.0, 1.6 Hz, 1H), 3.68 (s, 3H), 1.48 (s, 9H), 1.24 (s, 12H).

INTERMEDIATE 1c tert-Butyl (4-(3-formylpyridin-4-yl)-3-methoxyphenyl)carbamate

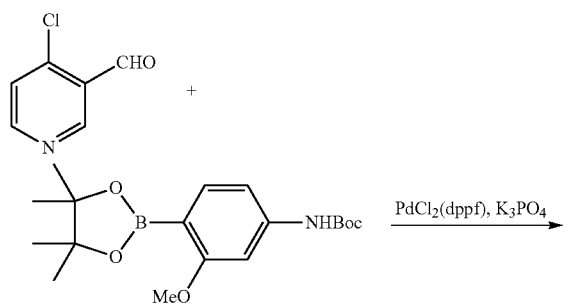

To a stirred solution of 1b (15.54 g, 44.5 mmol) in 1,4-dioxane (450 mL) and H$_2$O (75 mL) were added 4-chloronicotinaldehyde (6.0 g, 42.4 mmol), K$_3$PO$_4$ (36.0 g, 170 mmol), and PdCl$_2$(dppf)-CH$_2$Cl$_2$ adduct (2.77 g, 3.39 mmol). The reaction mixture was heated at 100° C. for 1 h under nitrogen. The reaction mixture was extracted with ethyl acetate. The combined organic layer was washed with water and brine, dried over sodium sulfate and then concentrated. Purification by normal phase chromatography provided Intermediate 1c as yellow solid (12.0 g, 84%). LC-MS (ESI) m/z: 329.2 [M+H]$^+$; $^1$H NMR (400 MHz, DMSO-d$_6$) δ 9.75 (d, J=0.4 Hz, 1H), 9.63 (s, 1H), 8.89 (s, 1H), 8.79 (d, J=6.8 Hz, 1H), 7.43-7.40 (m, 2H), 7.29 (d, J=11.2 Hz, 1H), 7.20 (dd, J=11.2, 2.4 Hz, 1H), 3.67 (s, 3H), 1.50 (s, 9H).

INTERMEDIATE 1d tert-Butyl (4-(3-(hydroxymethyl)pyridin-4-yl)-3-methoxyphenyl)carbamate

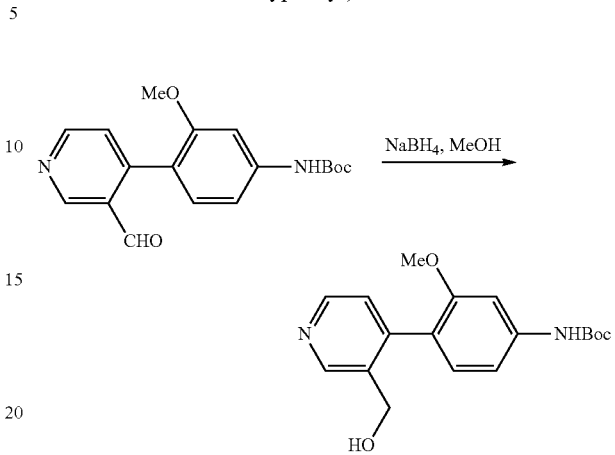

To a stirred solution of 1c (30 g, 91 mmol) in MeOH (500 mL) was added NaBH$_4$ (4.15 g, 110 mmol) at 0° C. under N$_2$. The reaction was stirred at rt for 1 h. The reaction was quenched with water (150 mL) and methanol was removed. The residue was extracted with ethyl acetate (2×200 mL). The combined organic phase was washed with water and brine, dried over sodium sulfate and concentrated. The crude solid was further washed with hot 50% ethyl acetate in petroleum ether (50 mL) to provide Intermediate 1d as off-white solid (30 g, 98%). LC-MS (ESI) m/z: 329.2 [M–H]$^-$; $^1$H NMR (400 MHz, DMSO-d$_6$) δ 9.45 (s, 1H), 8.67 (d, J=0.4 Hz, 1H), 8.43 (d, J=6.4 Hz, 1H), 7.38 (d, J=1.6 Hz, 1H), 7.12-7.03 (m, 3H), 5.14 (t, J=7.2 Hz, 1H), 4.03 (d, J=7.6 Hz, 1H), 3.68 (s, 3H), 1.50 (s, 9H).

INTERMEDIATE 1e

5H-Chromeno[3,4-c]pyridin-8-amine

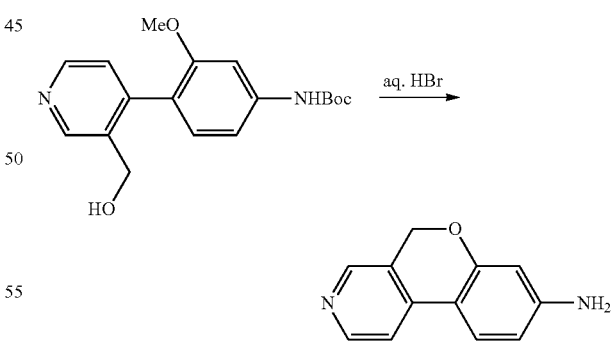

A suspension of 1d (30 g, 91 mmol) in HBr (63% in water, 8.0 mL, 91 mmol) was heated at 100° C. overnight. The reaction mixture was concentrated. The residue was dissolved in water and it was basified with sodium hydroxide solution and then extracted with DCM (2×300 mL). The combined organic layer was washed with water and brine, dried over sodium sulfate and concentrated. The crude solid was washed with 20% of ethyl acetate in petroleum ether and then dried to give Intermediate 1e as yellow solid (15 g, 83%). LC-MS (ESI) m/z: 199.1 [M+H]+; 1H NMR (400 MHz, DMSO-d6) δ 8.40 (d, J=6.8 Hz, 1H), 8.31 (m, 1H), 7.57 (d, J=11.2 Hz, 1H), 7.50 (d, J=6.8 Hz, 1H), 6.33 (dd, J=11.2, 2.8 Hz, 1H), 6.14 (d, J=2.8 Hz, 1H), 5.72 (s, 2H), 5.06 (s, 2H).

INTERMEDIATE 1f

8-Iodo-5H-chromeno[3,4-c]pyridine

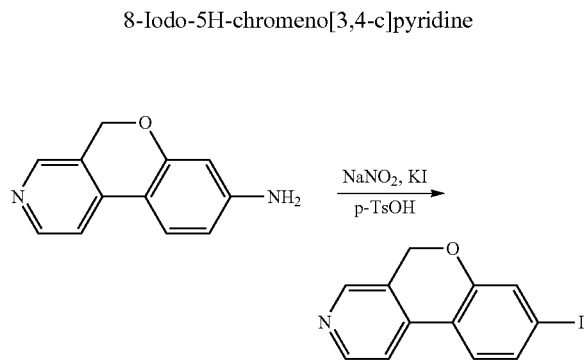

To a stirred solution of 1e (15 g, 76 mmol) in acetonitrile (150 mL) was added p-toluenesulfonic acid monohydrate (43.2 g, 227 mmol) at rt. After stirred for 10 min, an aqueous solution of NaNO2 (13.05 g, 189 mmol) and KI (25.1 g, 151 mmol) was added slowly. After the addition was completed, the reaction was stirred at rt for 1 h. The reaction was basified with saturated sodium carbonate solution and then it was extracted with EtOAc (2×50 mL). The combined organic layer was washed with saturated sodium thiosulfate solution, water and brine, dried over sodium sulfate and concentrated. Purification by normal phase chromatography provided if as off-white solid (17.5 g, 74%). LC-MS (ESI) m/z: 310.0 [M+H]+; 1H NMR (400 MHz, DMSO-d6) δ 8.59 (d, J=5.2 Hz, 1H), 8.50 (s, 1H), 7.81 (d, J=5.2 Hz, 1H), 7.76 (d, J=8.4 Hz, 1H), 7.50 (dd, J=8.0, 1.6 Hz, 1H), 7.44 (s, 1H), 5.23 (s, 1H).

INTERMEDIATE 1g

5H-Chromeno[3,4-c]pyridine-8-carbonitrile

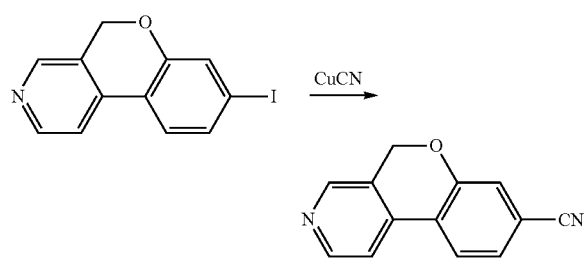

To a stirred solution of 1f (17 g, 55.0 mmol) in dry DMF (160 mL) was added CuCN (7.39 g, 82 mmol) as a single portion at rt under nitrogen. The reaction was heated at 150° C. overnight. The reaction was cooled to rt and then quenched with saturated aqueous ammonia solution (500 mL). The solid formed was collected by filtration and it was washed with water and then dried to afford 1g (9.0 g, 78%). LC-MS (ESI) m/z: 209.2 [M+H]+; 1H NMR (400 MHz, DMSO-d6) δ 8.65 (d, J=4.8 Hz, 1H), 8.56 (s, 1H), 8.18 (d, J=8.0 Hz, 1H), 8.18 (d, J=4.8 Hz, 1H), 7.59-7.56 (m, 2H), 5.32 (s, 2H).

INTERMEDIATE 1

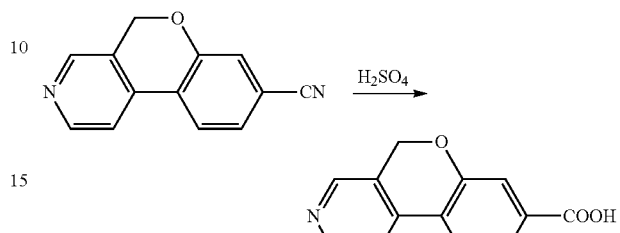

To a stirred solution of 1g (8.5 g, 40.8 mmol) in H2O (80 mL) was added H2SO4 (80 mL) as a single lot and the reaction was heated at 80° C. overnight. The reaction mixture was diluted with water (200 mL). The solid formed was collected by filtration, washed with water and dried. The crude solid was triturated with methanol at 50° C. and then cooled to rt. The solid was filtered and dried to give Intermediate 1 as light yellow solid (8.2 g, 86%). LC-MS (ESI) m/z: 228.1 [M+H]+; 1H NMR (400 MHz, DMSO-d6) δ 8.78 (d, J=5.6 Hz, 1H), 8.71 (s, 1H), 8.22-8.18 (m, 2H), 7.70 (dd, J=8.0, 1.6 Hz, 1H), 7.53 (d, J=1.6 Hz, 1H), 5.37 (s, 2H).

INTERMEDIATE 2

6H-Isochromeno[3,4-c]pyridine-8-carboxylic acid

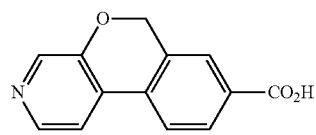

INTERMEDIATE 2a

Methyl 4-(3-fluoropyridin-4-yl)-3-formylbenzoate

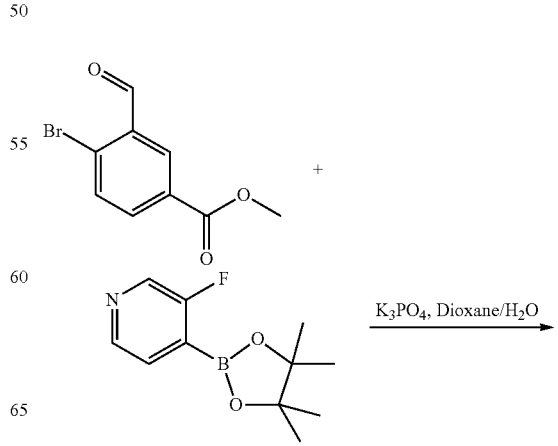

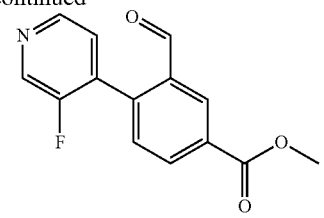

To a solution of methyl 4-bromo-3-formylbenzoate (500 mg, 2.057 mmol) in dioxane (15 mL) were added 3-fluoro-4-(4,4,5,5-tetramethyl-1,3,2-dioxaborolan-2-yl)pyridine (551 mg, 2.469 mmol), K₃PO₄ (6.17 mL, 6.17 mmol), and XPhos-G2-PreCat (81 mg, 0.103 mmol) at rt. The reaction was stirred under argon at 80° C. for 2 h. The reaction mixture was diluted with EtOAc, washed with H₂O and brine. The organic phase was dried over sodium sulfate, filtered and concentrated. The crude product was purified by normal phase chromatography to provide Intermediate 2a as pale solid (362 mg, 68%). LCMS (ESI) m/z: 260.0 [M+H]⁺; ¹H NMR (400 MHz, CDCl₃) δ 9.96 (d, J=2.4 Hz, 1H), 8.68 (d, J=1.5 Hz, 1H), 8.60 (d, J=1.3 Hz, 1H), 8.57 (dd, J=4.8, 0.9 Hz, 1H), 8.36 (dd, J=7.9, 1.8 Hz, 1H), 7.51 (d, J=8.1 Hz, 1H), 7.31 (dd, J=6.1, 5.0 Hz, 1H), 4.00 (s, 3H); ¹⁹F NMR (376 MHz, CDCl₃) δ −129.71 (s, 1F).

INTERMEDIATE 2b

Methyl 4-(3-fluoropyridin-4-yl)-3-(hydroxymethyl)benzoate

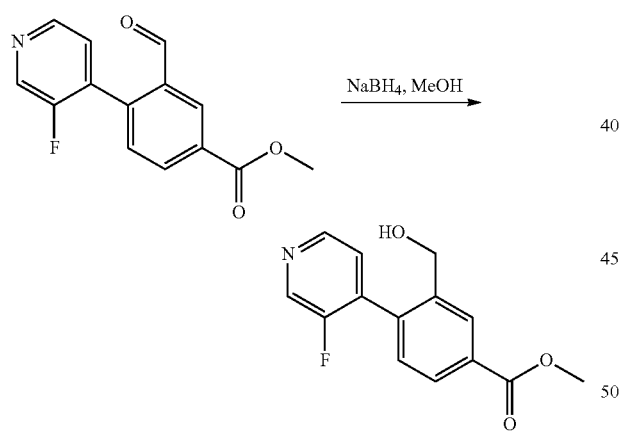

To a solution of Intermediate 2a (1.57g, 6.06 mmol) in MeOH (15 mL) was added NaBH₄ (0.229 g, 6.06 mmol) at 0° C. The reaction was stirred under argon at 0° C. for 30 min. LCMS showed the reaction was completed. The reaction mixture was diluted with EtOAc, washed with H₂O and brine. The organic layer was dried over sodium sulfate, filtered and concentrated. The crude product was purified by normal phase chromatography to give Intermediate 2b as clear colorless oil (0.82 g, 52%). LCMS (ESI) m/z: 262.0 [M+H]⁺; ¹H NMR (400 MHz, CDCl₃) δ 8.57 (d, J=1.3 Hz, 1H), 8.51 (dd, J=4.8, 0.9 Hz, 1H), 8.33 (d, J=1.1 Hz, 1H), 8.07 (dd, J=7.9, 1.8 Hz, 1H), 7.35 (d, J=7.9 Hz, 1H), 7.30 (dd, J=6.1, 5.0 Hz, 1H), 4.60 (d, J=5.1 Hz, 2H), 3.97 (s, 3H), 1.98 (t, J=5.6 Hz, 1H).

INTERMEDIATE 2

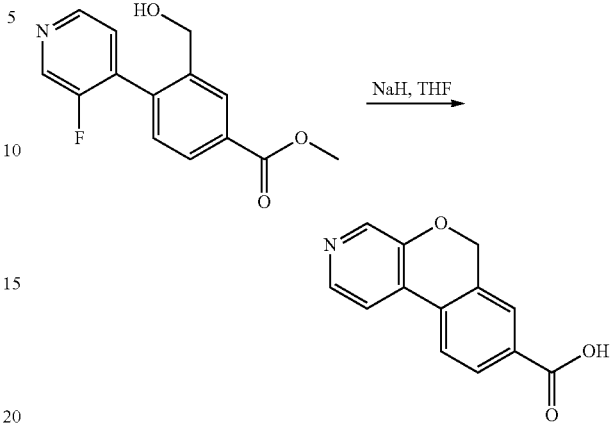

To a solution of Intermediate 2b (0.82 g, 3.14 mmol) in THF (10 mL) was added NaH (0.251 g, 6.28 mmol) at 0° C. The reaction was stirred under argon at 0° C. for 1 hr. Then it was stirred at rt overnight. Water (5 mL) was added carefully to quench the reaction and stirred for another hour at RT. The solvent was removed. The crude product was purified by reverse phase chromatography to provide Intermediate 2 as light brown solid (770 mg, 77%). LCMS (ESI) m/z: 228.0 [M+H]⁺; ¹H NMR (400 MHz, DMSO-d₆) δ 8.27 (s, 1H), 8.24 (d, J=5.1 Hz, 1H), 7.92-7.87 (m, 1H), 7.85-7.80 (m, 2H), 7.75 (d, J=0.9 Hz, 1H), 5.24 (s, 2H).

INTERMEDIATE 3

6H-Isochromeno[3,4-c]pyridine-8-carboxylic acid

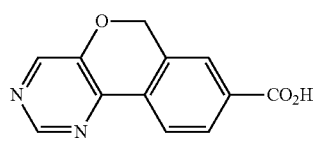 [SMILES: O=C(O)c1ccc2c(c1)COc1cncnc1-2]

INTERMEDIATE 3a

Methyl 4-bromo-3-(hydroxymethyl)benzoate

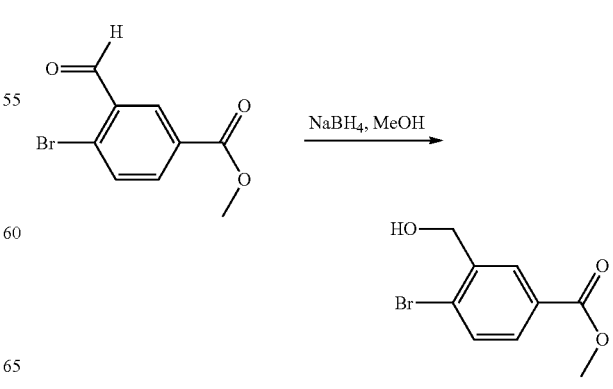

To a solution of methyl 4-bromo-3-formylbenzoate (1.53 g, 6.29 mmol) in MeOH (20 mL) was added NaBH$_4$ (0.238 g, 6.29 mmol) at 0° C. The reaction was stirred under argon at 0° C. for 30 min. LCMS showed the reaction was completed. The reaction mixture was diluted with EtOAc, washed with H$_2$O and brine. The organic phase was dried over sodium sulfate, filtered and concentrated to give Intermediate 3a as clear colorless oil (1.50 g, 97%). LCMS (ESI) m/z: 244.9/246.9 [M+H]$^+$; $^1$H NMR (400 MHz, CDCl$_3$) δ 8.17 (d, J=2.0 Hz, 1H), 7.82 (dd, J=8.4, 2.2 Hz, 1H), 7.62 (d, J=8.4 Hz, 1H), 4.79 (s, 2H), 3.93 (s, 3H).

INTERMEDIATE 3b

Methyl 4-bromo-3-(((tert-butyldimethylsilyl)oxy)methyl)benzoate

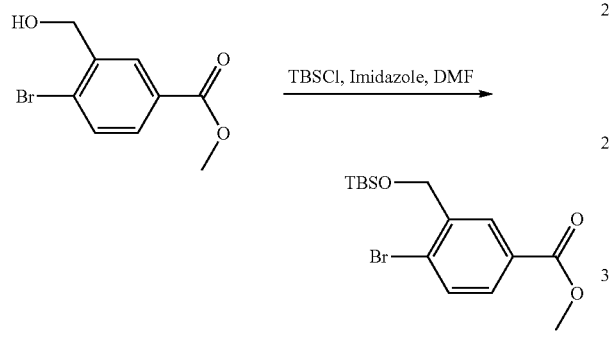

To a solution of Intermediate 3a (1.49 g, 6.08 mmol) in DMF (10 mL) were added imidazole (0.621 g, 9.12 mmol) and TBS-Cl (1.100 g, 7.30 mmol) at 0° C. The reaction was stirred under argon at rt overnight. The reaction mixture was diluted with EtOAc, washed with H$_2$O and brine. The organic phase was dried over sodium sulfate, filtered and concentrated. The crude product was purified by normal phase chromatography to give 3b (1.89 g, 87%). LCMS (ESI) m/z: 359.0/360.9 [M+H]$^+$; $^1$H NMR (400 MHz, CDCl$_3$) δ 8.26-8.21 (m, 1H), 7.79 (dd, J=8.4, 2.2 Hz, 1H), 7.58 (d, J=8.1 Hz, 1H), 4.76 (s, 2H), 3.93 (s, 3H), 1.00 (s, 9H), 0.16 (s, 6H).

INTERMEDIATE 3c

Methyl 3-(((tert-butyldimethylsilyl)oxy)methyl)-4-(4,4,5,5-tetramethyl-1,3,2-dioxaborolan-2-yl)benzoate

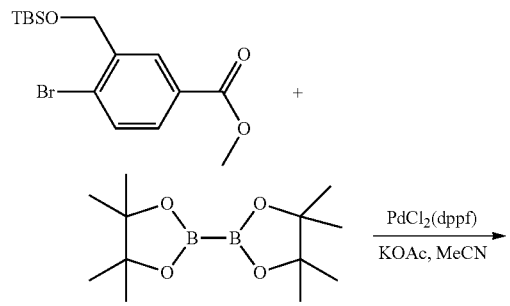

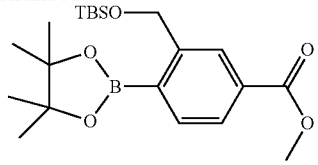

To a solution of Intermediate 3b (1.41 g, 3.92 mmol) in acetonitrile (15 mL) were added 4,4,4',4',5,5,5',5'-octamethyl-2,2'-bi(1,3,2-dioxaborolane) (1.196 g, 4.71 mmol), KOAc (0.770 g, 7.85 mmol), and PdCl$_2$(dppf) (0.144 g, 0.196 mmol) at rt. The reaction was stirred under argon at 90° C. for 5 h. The solvent was removed. The crude product was purified by normal phase chromatography to afford Intermediate 3c as clear colorless oil (1.18 g, 74%). LCMS (ESI) m/z: 407.1 [M+H]$^+$; $^1$H NMR (400 MHz, CDCl$_3$) δ 8.14 (d, J=0.9 Hz, 1H), 7.79-7.74 (m, 1H), 7.74-7.68 (m, 1H), 4.91 (s, 2H), 3.81 (s, 3H), 1.24 (s, 12H), 0.86 (s, 9H), 0.00 (s, 6H).

INTERMEDIATE 3d

Methyl 3-(((tert-butyldimethylsilyl)oxy)methyl)-4-(5-fluoropyrimidin-4-yl)benzoate

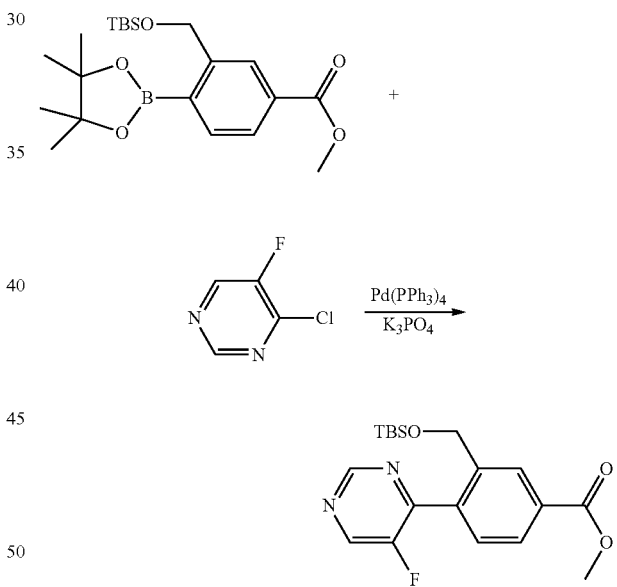

To a solution of Intermediate 3c (285 mg, 0.701 mmol) in dioxane (2 mL) were added 4-chloro-5-fluoropyrimidine (93 mg, 0.701 mmol), K$_3$PO$_4$ (447 mg, 2.104 mmol) and Pd(Ph$_3$P)$_4$ (81 mg, 0.070 mmol) at rt. The reaction mixture was stirred under argon at 90° C. for 3 h. The reaction mixture was diluted with EtOAc, washed with H$_2$O and brine. The organic phase was dried over sodium sulfate, filtered and concentrated. The crude product was purified by normal phase chromatography to give Intermediate 3d as clear colorless oil (225 mg, 85%). LCMS (ESI) m/z: 377.1 [M+H]$^+$; $^1$H NMR (400 MHz, CDCl$_3$) δ 9.14 (d, J=2.9 Hz, 1H), 8.71 (d, J=2.0 Hz, 1H), 8.33 (d, J=1.1 Hz, 1H), 8.09 (dd, J=7.9, 1.8 Hz, 1H), 7.55 (dd, J=8.0, 1.4 Hz, 1H), 4.87 (s, 2H), 3.99 (s, 3H), 0.85 (s, 9H), 0.00 (s, 6H).

INTERMEDIATE 3e

Methyl 6H-isochromeno[4,3-d]pyrimidine-8-carboxylate

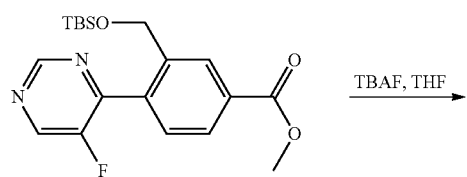

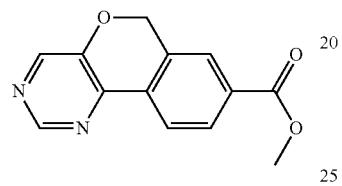

To a solution of Intermediate 3d (225 mg, 0.598 mmol) in THF (3 mL) was added TBAF (1 M in THF, 2.99 ml, 2.99 mmol) at rt. The reaction was stirred under argon at rt for 30 min. LCMS showed the reaction was completed. The solvent was removed. The crude product was purified by normal phase chromatography to afford Intermediate 3e as white solid (142 mg, 98%). LCMS (ESI) m/z: 243.1 [M+H]$^+$; $^1$H NMR (400 MHz, CDCl$_3$) δ 8.91 (s, 1H), 8.44 (s, 1H), 8.33 (d, J=8.1 Hz, 1H), 8.14 (dd, J=8.0, 1.7 Hz, 1H), 7.87 (d, J=0.9 Hz, 1H), 5.37 (s, 2H), 3.97 (s, 3H).

INTERMEDIATE 3

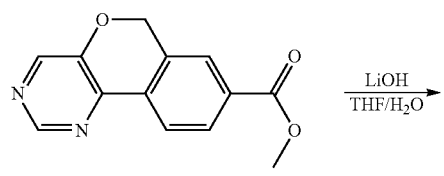

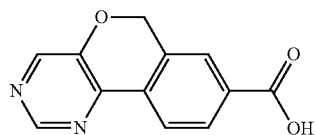

To a solution of Intermediate 3e (142 mg, 0.586 mmol) in THF (6 mL) and H$_2$O (2 mL) was added LiOH (70.2 mg, 2.93 mmol) at RT. The reaction was stirred under argon at rt for 2 h. The solvent was removed to give Intermediate 3 as white solid (134 mg, 100%). LCMS (ESI) m/z: 229.1 [M+H]$^+$; $^1$H NMR (400 MHz, DMSO-d$_6$) δ 8.82 (s, 1H), 8.46 (s, 1H), 8.04 (d, J=8.1 Hz, 1H), 7.95 (d, J=8.1 Hz, 1H), 7.77 (d, J=1.0 Hz, 1H), 5.39 (s, 2H)

INTERMEDIATE 4

5-Methyl-5H-chromeno[3,4-c]pyridine-8-carboxylic acid, TFA salt

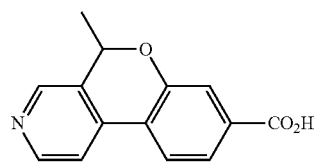 [SMILES: CC1Oc2cc(C(=O)O)ccc2-c2ccncc21]

INTERMEDIATE 4a

Methyl 3-fluoro-4-(3-formylpyridin-4-yl)benzoate

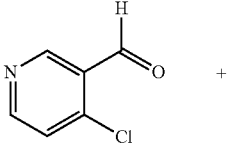

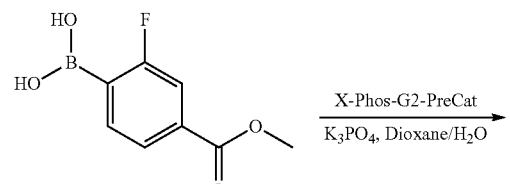

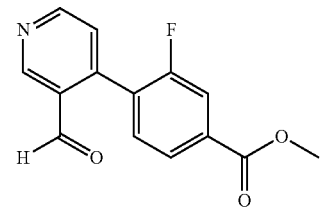

To a solution of (2-fluoro-4-(methoxycarbonyl)phenyl) boronic acid (441 mg, 2.225 mmol) in dioxane (6 mL) and H$_2$O (1.6 mL) were added 4-chloronicotinaldehyde (300 mg, 2.119 mmol), K$_3$PO$_4$ (990 mg, 4.66 mmol), and XPhos-G2-PreCat (66.8 mg, 0.085 mmol) at rt. The reaction was heated at 140° C. with microwave for 10 min. The reaction was diluted with EtOAc and the organic layer was separated and concentrated. Purification by normal phase chromatography gave Intermediate 4a as tan oil (320 mg, 58.2%). LC-MS (ESI) m/z: 260.0[M+H]$^+$; $^1$H NMR (400 MHz, DMSO-d$_6$) δ 9.99 (d, J=2.2 Hz, 1H), 9.13 (s, 1H), 8.94 (d, J=5.1 Hz, 1H), 7.94 (dd, J=7.9, 1.5 Hz, 1H), 7.84 (dd, J=10.3, 1.5 Hz, 1H), 7.68 (t, J=7.6 Hz, 1H), 7.59 (d, J=5.1 Hz, 1H), 3.92 (s, 3H).

INTERMEDIATE 4b

Methyl 3-fluoro-4-(3-(1-hydroxyethyl)pyridin-4-yl)benzoate

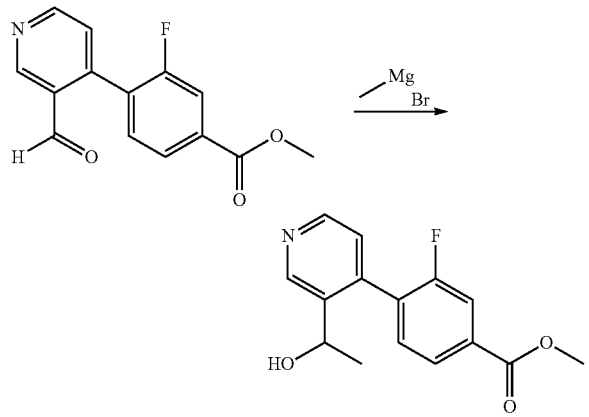

To a solution of 4a (320 mg, 1.234 mmol) in THF (10 mL) was added methyl magnesium bromide (0.970 mL, 1.358 mmol, 1.4 M in toluene/THF) dropwise over 30 min. The resulted mixture was stirred at rt for 20 min. The reaction was cooled to 0° C. and quenched with sat. NH$_4$Cl solution. The reaction mixture was extracted with EtOAc. The organic layer was concentrated and then purified by normal phase chromatography to give Intermediate 4b as oil (258 mg, 68.3%). LC-MS (ESI) m/z: 276.0[M+H]$^+$; $^1$H NMR (400 MHz, CDCl$_3$) δ 8.89 (s, 1H), 8.48 (d, J=5.1 Hz, 1H), 7.90 (dd, J=7.9, 1.3 Hz, 1H), 7.81 (dd, J=9.9, 1.3 Hz, 1H), 7.31 (t, J=7.5 Hz, 1H), 7.08 (d, J=5.1 Hz, 1H), 4.81 (q, J=5.9 Hz, 1H), 3.95 (s, 3H), 1.39 (d, J=6.2 Hz, 3H).

INTERMEDIATE 4

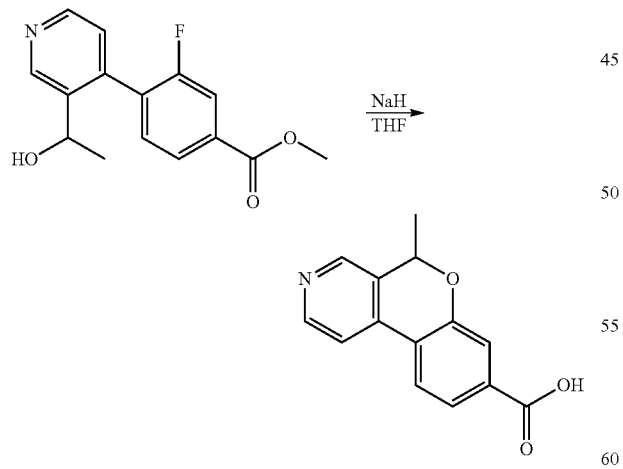

To a solution of Intermediate 4b (258 mg, 0.937 mmol) in THF (5 mL) was added NaH (75.0 mg, 1.874 mmol) at 0° C. The reaction was stirred under argon at 0° C. for 1 h and then at rt for 2 h. Water was added carefully to quench the reaction. The pH was adjusted to ~8 with 4 N HCl. The solvent was removed. Purification by reverse phase chromatography provided Intermediate 4 as white solid (195 mg, 55.6%). LC-MS (ESI) m/z: 242.0 M+H]$^+$; $^1$H NMR (400 MHz, CD$_3$OD) δ 8.91-8.63 (m, 1H), 8.38 (d, J=6.2 Hz, 1H), 8.16 (d, J=8.1 Hz, 1H), 7.81 (dd, J=8.3, 1.7 Hz, 1H), 7.67 (d, J=1.5 Hz, 1H), 5.60 (q, J=6.5 Hz, 1H), 1.74 (d, J=6.6 Hz, 3H).

INTERMEDIATE 5

N-(3-(4,4,5,5-Tetramethyl-1,3,2-dioxaborolan-2-yl)benzyl)-5H-chromeno[3,4-c]pyridine-8-carboxamide

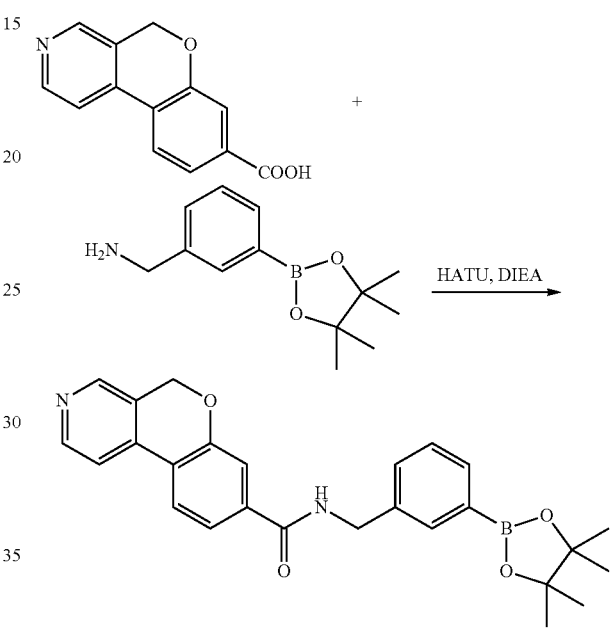

To a suspension of Intermediate 1 (792 mg, 3.49 mmol) in DMF (12 mL) were added (3-(4,4,5,5-tetramethyl-1,3,2-dioxaborolan-2-yl)phenyl)methanamine, HCl salt (940 mg, 3.49 mmol), DIEA (2.436 mL, 13.95 mmol) and HATU (1856 mg, 4.88 mmol) at rt. The reaction was stirred under argon at rt overnight. The reaction was diluted with EtOAc. The organic phase was washed with water and brine, dried over Na$_2$SO$_4$ and concentrated. Purification by normal phase chromatography gave Intermediate 5 as white solid (910 mg, 41%). LC-MS (ESI) m/z: 443.2[M+H]$^+$.

INTERMEDIATE 6

6-Methyl-6H-isochromeno[3,4-c]pyridine-8-carboxylic acid

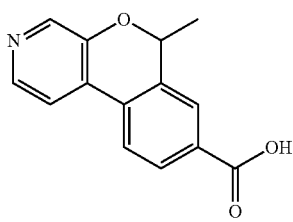 [SMILES: CC1Oc2cnccc2-c2ccc(C(=O)O)cc21]

INTERMEDIATE 6a

Methyl 4-(3-fluoropyridin-4-yl)-3-(1-hydroxyethyl)benzoate

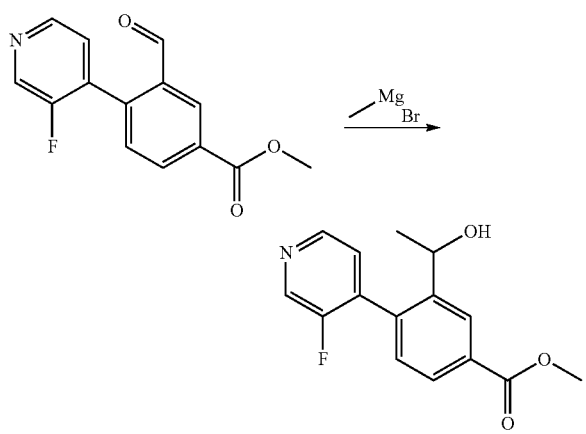

To a solution of Intermediate 2a (368 mg, 1.420 mmol) in THF (14 mL) was added methyl magnesium bromide (1.014 mL, 1.420 mmol, 1.4 M in toluene/THF) dropwise over 40 min. The resulted reaction mixture was stirred at rt for 30 min. It was then cooled to 0° C. and quenched with sat. NH$_4$Cl solution. The reaction mixture was extracted with EtOAc (3×). Organic phase was dried over Na$_2$SO$_4$ and concentrated. Purification by normal phase chromatography gave Intermediate 6a as oil (280 mg, 72%). LC-MS (ESI) m/z: 276.0[M+H]$^+$; $^1$H NMR (400 MHz, CD$_3$OD) δ 8.57 (d, J=1.1 Hz, 1H), 8.49 (d, J=4.8 Hz, 1H), 8.40 (d, J=1.8 Hz, 1H), 8.00 (dd, J=8.1, 1.8 Hz, 1H), 7.42 (dd, J=6.2, 5.3 Hz, 1H), 7.32 (d, J=8.1 Hz, 1H), 4.72 (q, J=6.2 Hz, 1H), 3.95 (s, 3H), 1.31 (d, J=6.4 Hz, 3H).

INTERMEDIATE 6

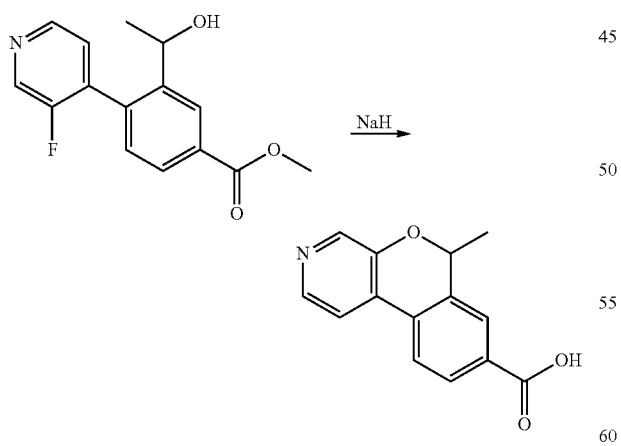

To a solution of methyl 4-(3-fluoropyridin-4-yl)-3-(1-hydroxyethyl)benzoate (280 mg, 1.017 mmol) in THF (5 mL) was added NaH (60%, 102 mg, 2.54 mmol) at 0° C. The reaction was stirred under argon at 0° C. for 20 min and then at rt overnight. Water was added carefully to quench the reaction and then 4 N HCl was added to adjust the pH to ~8. The solvent was removed. Purification by reverse phase chromatography provided Intermediate 6 as white solid (195 mg, 51%). LC-MS (ESI) m/z: 242.0[M+H]$^+$.

INTERMEDIATE 7

6-Ethyl-6H-isochromeno[3,4-c]pyridine-8-carboxylic acid

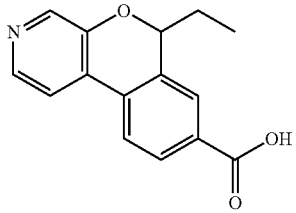 [SMILES: CCC1Oc2cnccc2-c2ccc(C(=O)O)cc21]

Intermediate 7 was prepared by following a similar procedure as described in Intermediate 6 by replacing methyl magnesium bromide with ethyl magnesium bromide in step 6a. LC-MS (ESI) m/z: 256.0[M+H]$^+$; $^1$H NMR (400 MHz, DMSO-d$_6$) δ 8.45 (s, 1H), 8.36 (d, J=5.1 Hz, 1H), 8.15 (d, J=8.1 Hz, 1H), 8.07-7.98 (m, 2H), 7.91 (s, 1H), 5.47 (dd, J=8.6, 4.8 Hz, 1H), 1.91-1.61 (m, 2H), 0.98 (t, J=7.4 Hz, 3H).

INTERMEDIATE 8

6-cyclopropyl-6H-isochromeno[3,4-c]pyridine-8-carboxylic acid

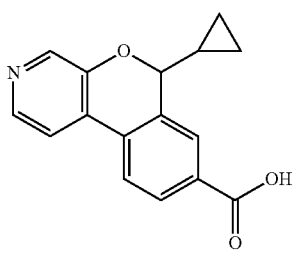 [SMILES: O=C(O)c1ccc2c(c1)C(C1CC1)Oc1cnccc1-2]

Intermediate 8 was prepared by following a similar procedure as described in Intermediate 6 by replacing methyl magnesium bromide with cyclopropyl magnesium bromide in step 6a. LC-MS (ESI) m/z: 268.0[M+H]$^+$.

INTERMEDIATE 9

Methyl 5-(aminomethyl)-2-fluorobenzoate

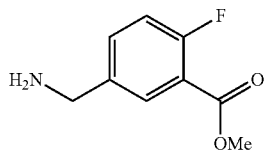 [SMILES: COC(=O)c1cc(CN)ccc1F]

INTERMEDIATE 9a

Methyl 5-(azidomethyl)-2-fluorobenzoate

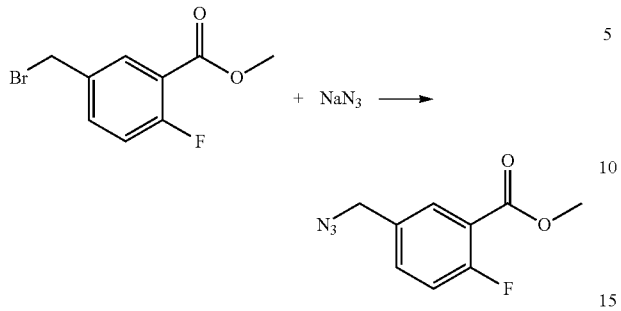

To a solution of methyl 5-(bromomethyl)-2-fluorobenzoate (500 mg, 2.024 mmol) in DMF (4 mL) was added NaN$_3$ (395 mg, 6.07 mmol) at rt. The reaction was stirred under argon at 60° C. overnight. The reaction mixture was diluted with EtOAc, washed with H$_2$O and brine. The organic phase was dried over sodium sulfate, filtered and concentrated. Purification by normal phase chromatography afforded Intermediate 9a as colorless oil (415 mg, 98%). LC-MS (ESI) m/z: 210.0[M+H]$^+$; $^1$H NMR (400 MHz, CDCl$_3$) δ 7.91 (dd, J=6.8, 2.2 Hz, 1H), 7.49 (ddd, J=8.5, 4.5, 2.4 Hz, 1H), 7.17 (dd, J=10.3, 8.6 Hz, 1H), 4.38 (s, 2H), 3.95 (s, 3H).

INTERMEDIATE 9

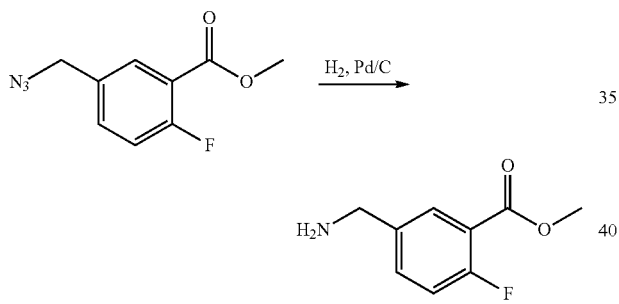

To a solution of Intermediate 9a (415 mg, 1.984 mmol) in MeOH (10 mL) was added catalytic amount of 5% Pd/C. The reaction was stirred under a hydrogen balloon at rt for 5 h. The catalyst was filtered off and the solvent was removed to afford Intermediate 9 as white solid (342 mg, 94%). LC-MS (ESI) m/z: 184.0[M+H]$^+$.

INTERMEDIATE 10

6-Allyl-6H-isochromeno[3,4-c]pyridine-8-carboxylic acid

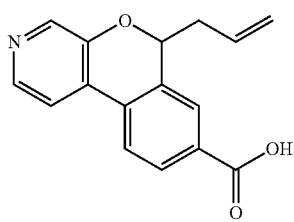 [SMILES: C=CCC1Oc2cnccc2-c2ccc(C(=O)O)cc21]

Intermediate 10 was prepared by following a similar procedure as described in Intermediate 6 by replacing methyl magnesium bromide with allyl magnesium bromide in step 6a. LC-MS (ESI) m/z: 268.0[M+H]$^+$.

INTERMEDIATE 11

1-(6-Methoxypyridin-2-yl)ethanamine HCl salt

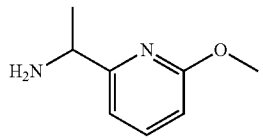

INTERMEDIATE 11A (R)-N-((6-Methoxypyridin-2-yl)methylene)-2-methylpropane-2-sulfinamide

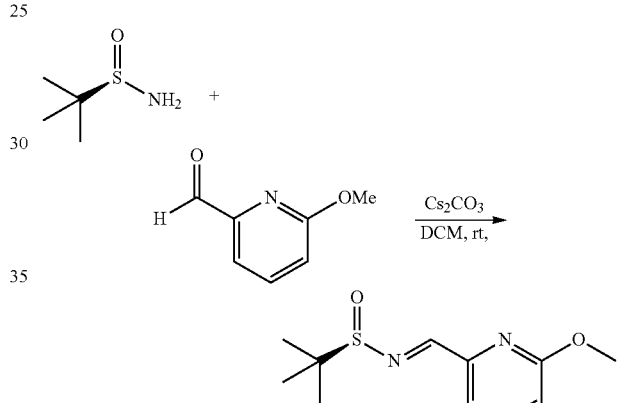

To a stirred suspension of (R)-2-methylpropane-2-sulfinamide (1.0 g, 8.3 mmol) and Cs$_2$CO$_3$ (4.0 g, 12 mmol) in DCM (15 mL), was added a solution of 6-methoxypicolinaldehyde in DCM (1.1 mL, 9.1 mmol, in 3 mL DCM) dropwise. The solution was then stirred at rt for 5 h. The solid was filtered off, and the solvent was removed. The crude product was purified by normal phase chromatography to afford Intermediate 11A (1.9 g, 96%) as a clear colorless oil. LC-MS (ESI) m/z: 241.0 [M+H]$^+$; $^1$H NMR (400 MHz, CDCl$_3$) δ 8.59 (s, 1H), 7.72-7.58 (m, 2H), 6.85 (dd, J=7.9, 1.1 Hz, 1H), 3.99 (s, 3H), 1.29 (s, 9H).

INTERMEDIATE 11B (R)-N-(1-(6-Methoxypyridin-2-yl)ethyl)-2-methylpropane-2-sulfinamide

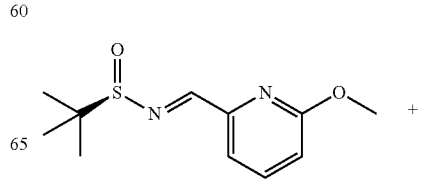

-continued

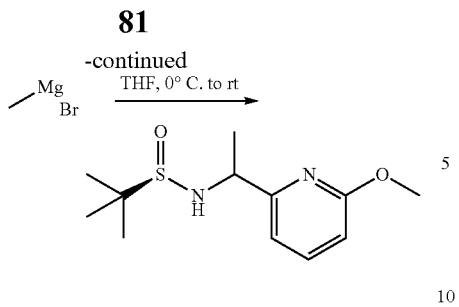

To a solution of Intermediate 11A (0.65 g, 2.7 mmol) in THF (6 mL), was added methylmagnesium bromide (1.4 M in toluene/THF, 2.9 mL, 4.1 mmol) at 0° C. The reaction was stirred under argon from 0° C. to rt for 2 h. It was cooled to 0° C., and NH₄Cl solution was carefully added. The reaction mixture was diluted with EtOAc, washed with H₂O and brine. The organic phase was dried over sodium sulfate, filtered and concentrated. The crude product was purified by normal phase chromatography to afford Intermediate 11B (0.58 g, 83%) as a mixture of two diastereomers as a clear colorless oil. LC-MS (ESI) m/z: 257.0 [M+H]⁺; ¹H NMR (400 MHz, CDCl₃) δ 7.53 (dt, J=8.3, 7.1 Hz, 2H), 6.86 (d, J=7.3 Hz, 1H), 6.82 (d, J=7.0 Hz, 1H), 6.62 (d, J=8.1 Hz, 2H), 4.83 (br. d, J=4.6 Hz, NH) 4.59-4.44 (m, 2H), 3.93 (s, 3H), 3.92 (s, 3H), 1.60 (d, J=6.8 Hz, 3H), 1.50 (d, J=6.6 Hz, 3H), 1.26 (s, 6H), 1.21 (s, 6H).

INTERMEDIATE 11

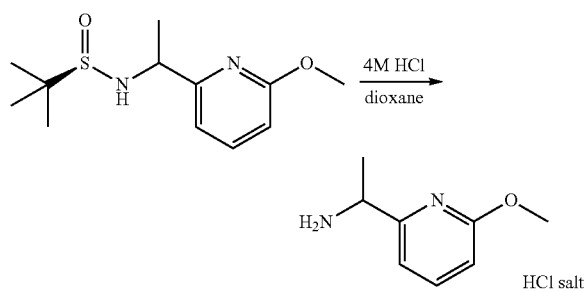

To a solution of Intermediate 11B (0.58, 2.3 mmol) in MeOH (5 mL), was added HCl (4 M in dioxane, 2.8 ml, 11 mmol) at rt. The reaction was stirred under argon at rt for 2 h. The solvent was removed to give Intermediate 11 (0.52 g, 100%) as white solid. LC-MS (ESI) m/z: 153.0 [M+H]⁺.

INTERMEDIATE 12

2-Acetamido-5H-chromeno[3,4-c]pyridine-8-carboxylic acid

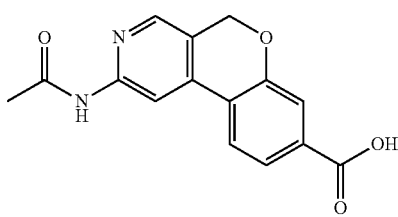 [SMILES: CC(=O)Nc1cc2c(cn1)COc1cc(C(=O)O)ccc1-2]

INTERMEDIATE 12A

5-Bromo-4-chloropyridin-2-amine

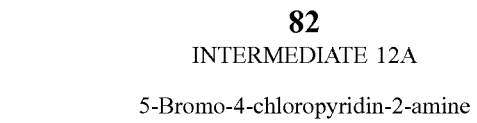

To a solution of 4-chloropyridin-2-amine (5.0 g, 39 mmol) in MeCN (200 mL) at 0° C. was added Br₂ (2.2 mL, 43 mmol) in portions over a period of 30 min. The reaction was warmed to rt and stirred overnight. The solid was filtered, washed with hexane (3×), and dried to afford Intermediate 12A (9.1 g, 81%) as an off-white solid. LC-MS (ESI) m/z: 206.9/208.9 [M+H]⁺; ¹H NMR (400 MHz, DMSO-d₆) δ 8.30 (s, 1H), 7.02 (s, 1H).

INTERMEDIATE 12B

N-(5-Bromo-4-chloropyridin-2-yl)acetamide

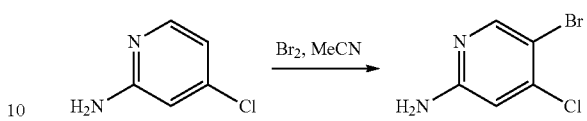

To a solution of Intermediate 12A (5.0 g, 17 mmol) in pyridine (40 mL) at 0° C., was added acetyl chloride (3.5 mL, 49 mmol) dropwise over 30 min. The reaction was allowed to warm to rt and stirred for 2 h. The reaction mixture was cooled to 0° C., and it was added acetyl chloride (6.2 mL, 87 mmol) dropwise. The reaction mixture was allowed to warm to rt and stirred for 2 h. It was diluted with DCM, and the solid was filtered off. The filtrate was concentrated. The residue was dissolved in EtOAc, washed with H₂O and brine. The organic phase was dried over sodium sulfate, filtered and concentrated. The crude product was purified by normal phase chromatography to afford Intermediate 12B (3.6 g, 82%) as an off-white solid. LC-MS (ESI) m/z: 248.9/250.9 [M+H]⁺; ¹H NMR (400 MHz, CDCl₃) δ 8.45 (s, 1H), 8.40-8.28 (m, 2H), 2.23 (s, 3H).

INTERMEDIATE 12C

N-(4-Chloro-5-vinylpyridin-2-yl)acetamide

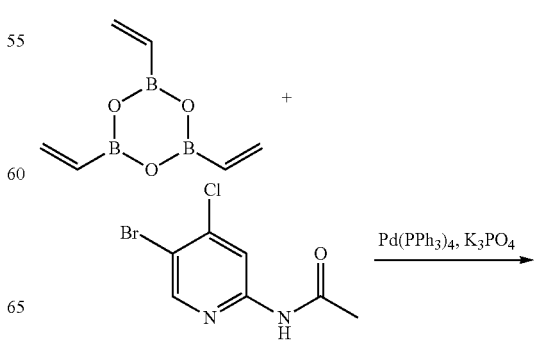

-continued

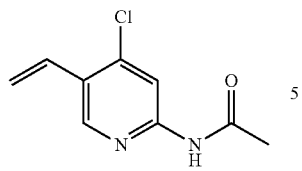

To a solution of Intermediate 12B (1.4 g, 5.4 mmol) in dioxane (12 mL) and water (2.2 mL), were added 2,4,6-trivinyl-1,3,5,2,4,6-trioxatriborinane pyridine complex (0.79 g, 4.9 mmol) and $K_3PO_4$ (2.3 g, 11 mmol). The reaction mixture was bubbled with argon for 10 min. Then $Pd(PPh_3)_4$ (0.44 g, 0.38 mmol) was added, and the mixture was again bubbled with argon for 5 min. The reaction was heated at 150° C. in a microwave reactor for 5 min. It was filtered through CELITE® and was washed with EtOAc (50 ml). The solvent was evaporated under reduced pressure. The residue was dissolved in EtOAc, washed with $H_2O$ and brine. The organic phase was dried over sodium sulfate, filtered and concentrated. The crude product was purified by normal phase chromatography to afford Intermediate 12C (0.73 g, 69%) as a yellowish solid. LC-MS (ESI) m/z: 197.0 $[M+H]^+$; $^1$H NMR (400 MHz, $CDCl_3$) δ 8.40 (s, 1H), 8.29 (s, 1H), 7.95 (br. s., 1H), 6.94 (dd, J=17.7, 11.6 Hz, 1H), 5.77 (dd, J=17.6, 0.7 Hz, 1H), 5.42 (dd, J=11.2, 0.9 Hz, 1H), 2.22 (s, 3H).

INTERMEDIATE 12D

N-(4-Chloro-5-formylpyridin-2-yl)acetamide

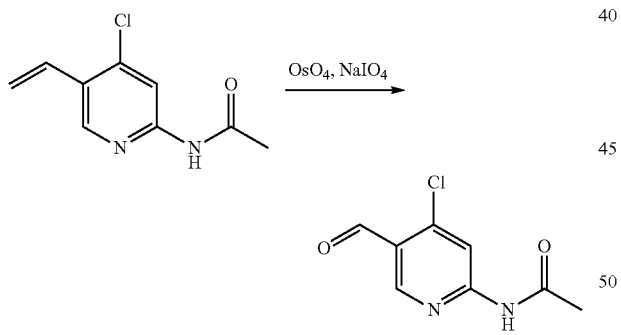

To a solution of Intermediate 12C (1.5 g, 7.8 mmol) and 2,6-lutidine (1.8 mL, 16 mmol) in dioxane (25 mL) and water (1.7 mL), was added sodium periodate (5.0 g, 23 mmol) at 0° C., followed by the addition of osmium tetroxide (2.5% in t-butanol, 2.4 mL, 0.21 mmol) over 10 min. The reaction was allowed to warm to rt and stirred overnight. The reaction mixture was diluted with EtOAc, washed with $H_2O$ and brine. The organic phase was dried over sodium sulfate, filtered and concentrated. The crude product was purified by normal phase chromatography to afford Intermediate 12D (1.0 g, 66%) as a white solid. LC-MS (ESI) m/z: 199.0 $[M+H]^+$; $^1$H NMR (400 MHz, $CDCl_3$) δ 10.38 (s, 1H), 8.76 (s, 1H), 8.39 (s, 1H), 8.19 (br. s., 1H), 2.27 (s, 3H).

INTERMEDIATE 12E

Methyl 4-(2-acetamido-5-formylpyridin-4-yl)-3-fluorobenzoate

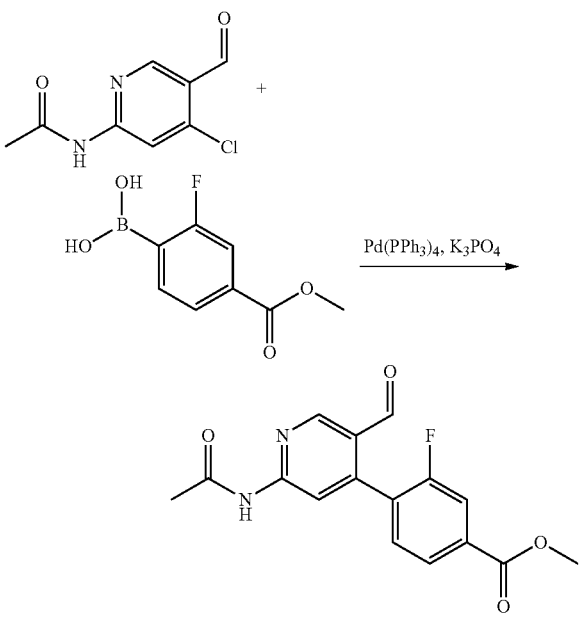

Intermediate 12D (0.92 g, 4.6 mmol), (2-fluoro-4-(methoxycarbonyl)phenyl)boronic acid (1.7 g, 8.3 mmol), $K_3PO_4$ (2.3 g, 11 mmol), dioxane (12 mL) and water (2 mL) were placed in a 20 mL microwave vial. The mixture was bubbled with argon for 10 min. $Pd(PPh_3)_4$ (0.32 g, 0.28 mmol) was added, and the mixture was again bubbled with argon for 7 min. The reaction was heated at 145° C. in a microwave reactor for 7 min. The reaction mixture was filtered through CELITE®, and was washed with EtOAc (55 ml). The solvent was removed under reduced pressure. The crude product was purified by normal phase chromatography to afford Intermediate 12E (1.4 g, 86%) as an off-white solid. LC-MS (ESI) m/z: 317.1 $[M+H]^+$; $^1$H NMR (400 MHz, $CDCl_3$) δ 9.87 (d, J=2.9 Hz, 1H), 8.89 (s, 1H), 8.28 (s, 1H), 8.24 (br. s., 1H), 7.98 (dd, J=7.9, 1.5 Hz, 1H), 7.86 (dd, J=10.0, 1.4 Hz, 1H), 7.47 (t, J=7.5 Hz, 1H), 3.99 (s, 3H), 2.28 (s, 3H).

INTERMEDIATE 12F

Methyl 4-(2-acetamido-5-(hydroxymethyl)pyridin-4-yl)-3-fluorobenzoate

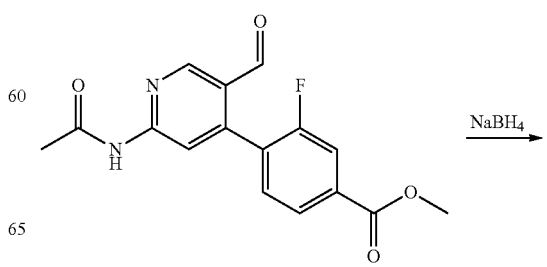

-continued

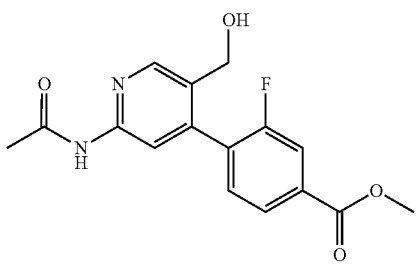

A suspension of Intermediate 12E (430 mg, 1.4 mmol) in ethanol (12 mL) was cooled to 0° C. To the reaction was added sodium borohydride (51 mg, 1.4 mmol) portionwise. The reaction mixture was stirred for 20 min at 0° C. Excess ethanol was removed under reduced pressure. Water was added to the mixture. The solid was filtered, washed with water, and dried to afford Intermediate 12F (380 mg, 87%) as a solid. LC-MS (ESI) m/z: 319.0 [M+H]$^+$; $^1$H NMR (400 MHz, DMSO-d$_6$) δ 10.64 (s, 1H), 8.46 (s, 1H), 7.99 (s, 1H), 7.90 (dd, J=7.9, 1.3 Hz, 1H), 7.83 (dd, J=10.3, 1.3 Hz, 1H), 7.58 (t, J=7.6 Hz, 1H), 5.16 (br. s., 1H), 4.32 (d, J=3.1 Hz, 2H), 3.91 (s, 3H), 2.10 (s, 3H).

INTERMEDIATE 12

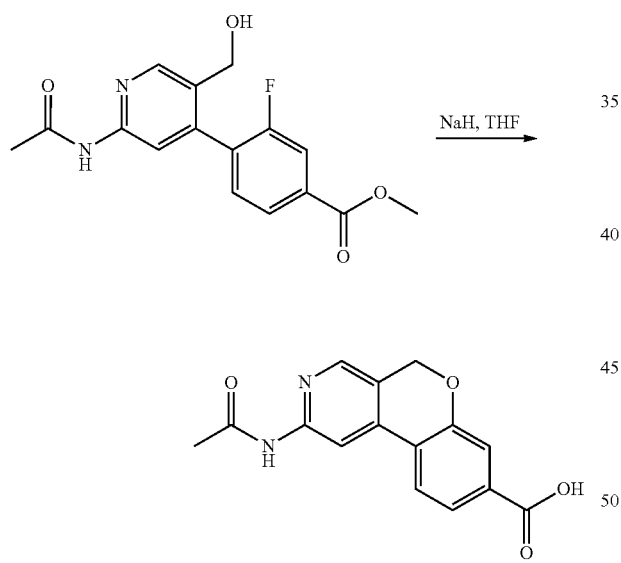

To a cooled a solution (−10° C.) of Intermediate 12F (370 mg, 1.2 mmol) in THF (10 mL) was added NaH (93 mg, 2.3 mmol) portionwise. The reaction was stirred at −10° C. for 50 min, then it was warmed to rt and stirred overnight. The reaction mixture was cooled to 0° C., and EtOAc was added. The reaction was quenched with aq. NH$_4$Cl. The two layers were separated. The aqueous layer was concentrated. The crude product was purified by reverse phase chromatography to afford Intermediate 12 (15 mg, 4.5%) as an off-white solid. LC-MS (ESI) m/z: 285.0 [M+H]$^+$.

INTERMEDIATE 13

2-Amino-5H-chromeno[3,4-c]pyridine-8-carboxylic acid

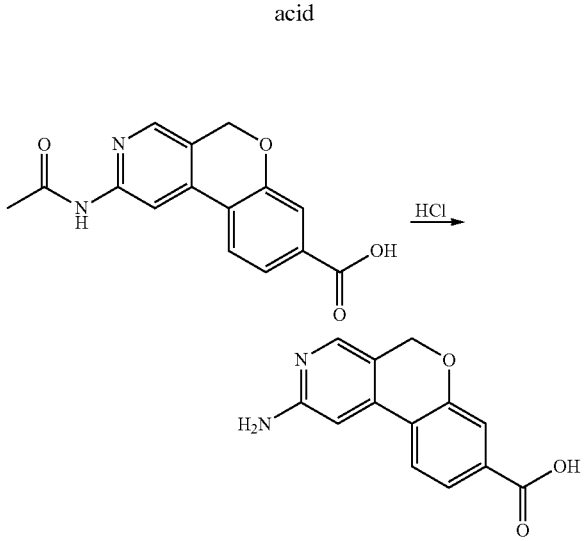

A suspension of Intermediate 12 (8.0 mg, 0.028 mmol) in concentrated HCl (160 μl, 2.0 mmol) in a sealed vial was heated at 100° C. for 70 min. The solvent was removed, and the residue was dried to afford Intermediate 13 (7.0 mg, 90%) as a yellow solid. LC-MS (ESI) m/z: 243.0 [M+H]$^+$.

INTERMEDIATE 14

2-Fluoro-6H-isochromeno[3,4-c]pyridine-8-carboxylic acid

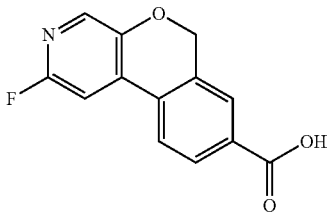 [SMILES: O=C(O)c1ccc2c(c1)COc1cnc(F)cc1-2]

INTERMEDIATE 14A

Methyl 4-bromo-3-(dibromomethyl)benzoate

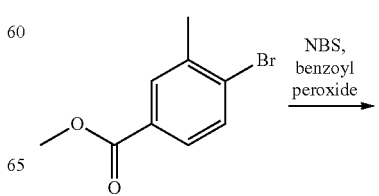

-continued

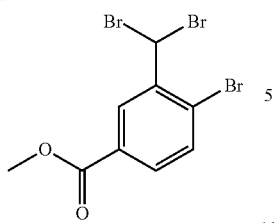

To a solution of methyl 4-bromo-3-methylbenzoate (5.8 g, 25 mmol) in CCl$_4$ (70 mL), was added NBS (15 g, 84 mmol), followed by addition of benzoyl peroxide (0.61 g, 2.5 mmol). The mixture was heated at reflux for 8 h. The mixture was cooled to rt, and was allowed to stir overnight. The solvent was removed under reduced pressure. Purification by normal phase chromatography afforded Intermediate 14A (9.7 g, 89%) as an off-white solid. LC-MS (ESI) m/z: 386.8/388.8 [M+H]$^+$; $^1$H NMR (400 MHz, CDCl$_3$) δ 8.68 (d, J=2.0 Hz, 1H), 7.83 (dd, J=8.4, 2.0 Hz, 1H), 7.61 (d, J=8.4 Hz, 1H), 7.09 (s, 1H), 3.97 (s, 3H).

INTERMEDIATE 14B

Methyl 4-bromo-3-formylbenzoate

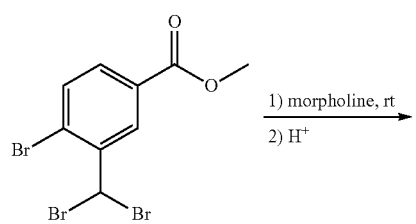

Intermediate 14A (9.7 g, 23 mmol) was suspended in morpholine (22 ml, 170 mmol), and the mixture was stirred at rt for 2 days. The reaction mixture was diluted with EtOAc, and was stirred at rt for 30 min. The solid was removed by filtration and washed with EtOAc. The filtrate was transferred to a separatory funnel and was washed with 5% aq. citric acid (3×), water and brine. The organic phase was dried over sodium sulfate, filtered and concentrated. The crude product was purified by normal phase chromatography to afford Intermediate 14B (5.6 g, 92%) as a white solid. LC-MS (ESI) m/z: 243.0/245.0 [M+H]$^+$; $^1$H NMR (400 MHz, CDCl$_3$) δ 10.39 (s, 1H), 8.54 (d, J=2.2 Hz, 1H), 8.10 (dd, J=8.4, 2.2 Hz, 1H), 7.76 (d, J=8.4 Hz, 1H), 3.96 (s, 3H).

INTERMEDIATE 14C (2-Formyl-4-(methoxycarbonyl)phenyl)boronic acid

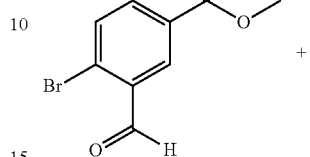

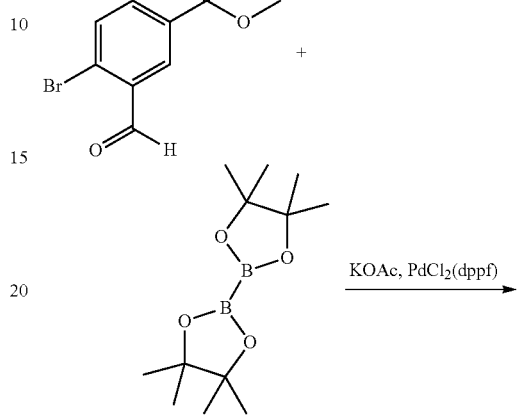

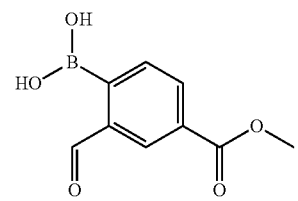

A mixture of Intermediate 12B (2.3 g, 9.5 mmol), 4,4,4',4',5,5,5',5'-octamethyl-2,2'-bi(1,3,2-dioxaborolane) (3.4 g, 13 mmol), PdCl$_2$(dppf).CH$_2$Cl$_2$ adduct (0.69 g, 0.95 mmol) and potassium acetate (2.8 g, 28 mmol) in dioxane (30 mL) was heated in an oil-bath at 95° C. for 2 h. The reaction was diluted with EtOAc, filtered through CELITE®. The solution was concentrated, and the crude product was purified by normal phase chromatography to afford Intermediate 14C (3.0 g, 91%) as a brown oil. LC-MS (ESI) m/z: 191.0 [M+H−18]$^+$; $^1$H NMR (400 MHz, DMSO-d$_6$) δ 10.18 (s, 1H), 8.43 (d, J=1.3 Hz, 1H), 8.35 (br. s., 2H), 8.16 (dd, J=7.6, 1.7 Hz, 1H), 7.72 (d, J=7.7 Hz, 1H), 3.91 (s, 3H).

INTERMEDIATE 14D

Methyl 4-(2,5-difluoropyridin-4-yl)-3-formylbenzoate

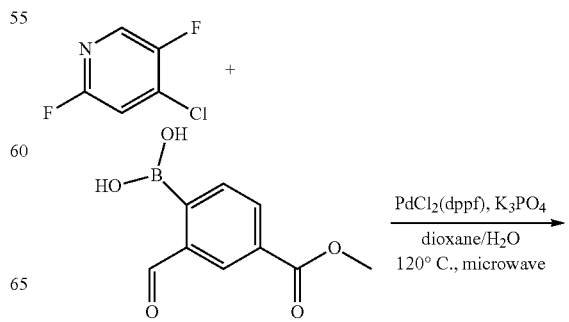

-continued

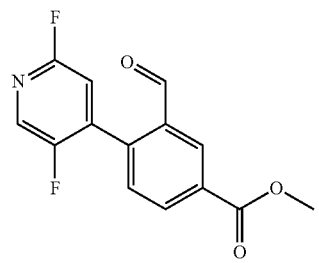

To a microwave vial containing solution of 4-chloro-2,5-difluoropyridine (0.40 g, 2.7 mmol) in dioxane (7 mL), were added Intermediate 14C (1100 mg, 3.2 mmol), K₃PO₄ (1.30 g, 6.2 mmol), water (1.4 mL) and PdCl$_2$(dppf)CH$_2$Cl$_2$ adduct (0.17 g, 0.21 mmol) at rt. The mixture was purged with nitrogen, and then was heated in a microwave reactor at 120° C. for 6 min. The reaction mixture was cooled to rt. The aqueous layer was removed with a pipette. The organic phase was concentrated and was purified by normal phase chromatography to afford Intermediate 14D (350 mg, 47%) as a tan solid. LC-MS (ESI) m/z: 278.0 [M+H]⁺.

INTERMEDIATE 14E

Methyl 4-(2,5-difluoropyridin-4-yl)-3-(hydroxymethyl)benzoate

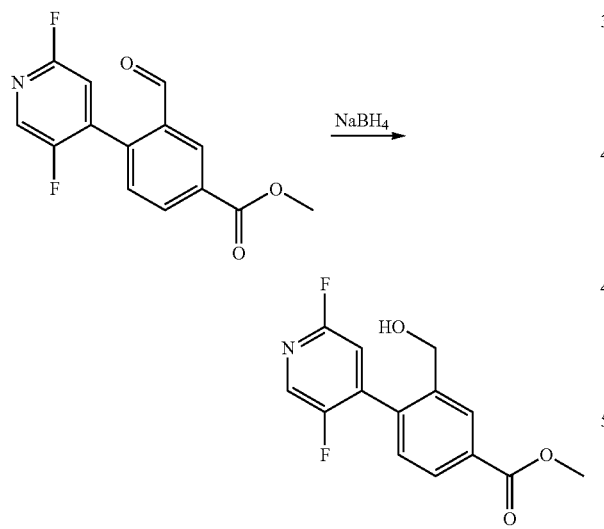

A suspension of Intermediate 14D (390 mg, 1.4 mmol) in ethanol (10 mL) was cooled to 0° C. Then sodium borohydride (64 mg, 1.7 mmol) was added portionwise. The reaction mixture was stirred for 20 min at 0° C. It was concentrated. The residue was dissolved in EtOAc (30 mL), and was washed with water and brine, dried over sodium sulfate, filtered and concentrated to afford Intermediate 14E (390 mg, 95%) as an oil. LC-MS (ESI) m/z: 280.0 [M+H]+; ¹H NMR (400 MHz, CD3OD) δ 8.31 (s, 1H), 8.20 (s, 1H), 8.05 (dd, J=7.9, 1.5 Hz, 1H), 7.43 (d, J=8.1 Hz, 1H), 7.16 (dd, J=4.6, 2.6 Hz, 1H), 4.53 (s, 2H), 3.96 (s, 3H).

INTERMEDIATE 14

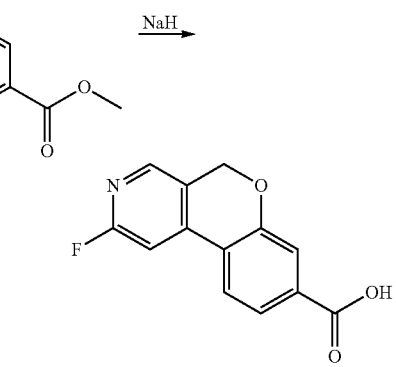

To a solution of Intermediate 14E (390 mg, 1.4 mmol) in THF (7 mL) was added NaH (180 mg, 4.6 mmol) at rt portionwise. The reaction mixture was stirred under argon at rt overnight. Water was added carefully to quench the reaction. Aqueous HCl (4 N) was added to adjust the pH to ~8. The solvent was removed. The residue was dissolved in MeOH-DMSO, filtered and purified by reverse phase chromatography to afford Intermediate 14 (50 mg, 6.0%) as an off-white solid. LC-MS (ESI) m/z: 246.0 [M+H]⁺.

INTERMEDIATE 15

2-Acetamido-6H-isochromeno[3,4-c]pyridine-8-carboxylic acid

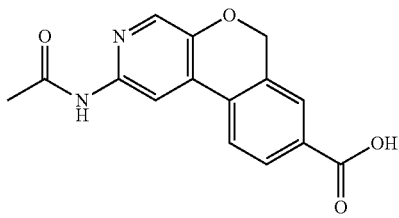 [SMILES: CC(=O)Nc1cc2c(cn1)OCc1cc(C(=O)O)ccc1-2]

INTERMEDIATE 15A

2-Bromo-5-fluoro-4-iodopyridine

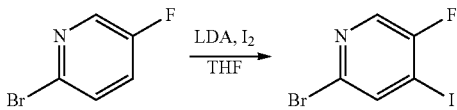 [SMILES: Fc1ccc(Br)nc1 ; Fc1cnc(Br)cc1I ; "THF"]

A solution of 2-bromo-5-fluoropyridine (2.0 g, 11 mmol) in THF (30 mL) was cooled to −78° C. LDA (2 M in THF, 6.3 mL, 13 mmol) was added slowly, and the mixture was stirred for 20 min. To this mixture was added a solution of iodine (3.5 g, 14 mmol) in THF (7 mL), dropwise. The reaction mixture was warmed up and stirred at 0° C. for 30 min. It was quenched with 10% aq. Na$_2$S$_2$O$_3$ solution and was extracted with ethyl acetate. The organic layer was washed with brine, dried over sodium sulfate, filtered and concentrated to afford Intermediate 15A (2.5 g, 72%) as a brown solid. LC-MS (ESI) m/z: 301.8/303.8 [M+H]$^+$; $^1$H NMR (400 MHz, CDCl$_3$) δ 8.14 (s, 1H), 7.92 (d, J=4.4 Hz, 1H).

INTERMEDIATE 15B

Methyl 4-(2-bromo-5-fluoropyridin-4-yl)-3-formylbenzoate

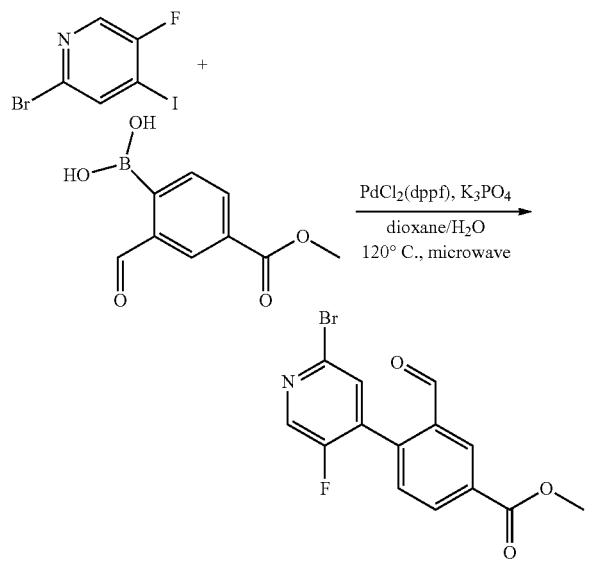

To a microwave vial containing a solution of Intermediate 15A (1.10 g, 3.3 mmol) in dioxane (10 mL), were added Intermediate 14C (0.90 g, 3.9 mmol), K$_3$PO$_4$ (1.60 g, 7.5 mmol), water (1.7 mL) and PdCl$_2$(dppf) CH$_2$Cl$_2$ adduct (0.21 g, 0.26 mmol). The mixture was purged with nitrogen, and then was heated with microwave at 120° C. for 5 min. The organic phase was separated and concentrated. Purification by normal phase chromatography afforded Intermediate 15B (0.62 g, 56%) as an off-white solid. LC-MS (ESI) m/z: 337.9/339.9 [M+H]$^+$; $^1$H NMR (400 MHz, CDCl$_3$) δ 10.00 (d, J=2.2 Hz, 1H), 8.67 (d, J=1.8 Hz, 1H), 8.43-8.28 (m, 2H), 7.54-7.41 (m, 2H), 4.02 (s, 3H).

INTERMEDIATE 15C

Methyl 4-(2-bromo-5-fluoropyridin-4-yl)-3-(hydroxymethyl)benzoate

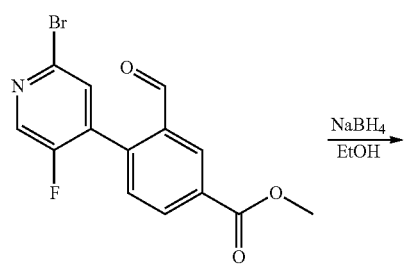

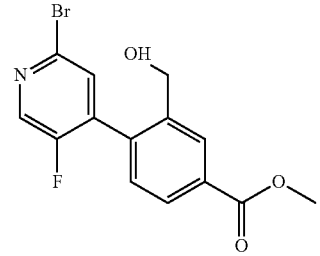

To a suspension of Intermediate 15B (610 mg, 1.8 mmol) in ethanol (10 mL) at 0° C., was added Sodium borohydride (69 mg, 1.8 mmol), portionwise. The reaction mixture was stirred at 0° C. for 20 min, and then was concentrated. The residue was dissolved in EtOAc, washed with water and brine, dried over sodium sulfate, filtered and concentrated to afford Intermediate 15C (610 mg, 67%) as a foam. LC-MS (ESI) m/z: 340.0/342.0 [M+H]$^+$; $^1$H NMR (400 MHz, CDCl$_3$) δ 8.27 (s, 1H), 8.24 (s, 1H), 8.03-7.96 (m, 1H), 7.42 (d, J=5.5 Hz, 1H), 8.25-7.20 (m, 1H), 4.54 (d, J=4.2 Hz, 2H), 3.93-3.87 (s, 3H).

INTERMEDIATE 15D

Methyl 2-bromo-6H-isochromeno[3,4-c]pyridine-8-carboxylate

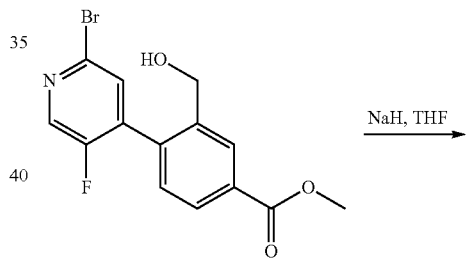

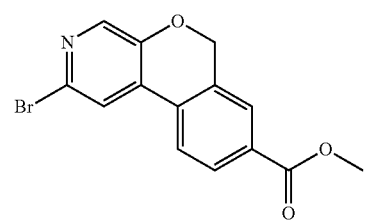

To a solution of Intermediate 15C (550 mg, 1.6 mmol) in THF (10 mL) at −10° C., was added NaH (110 mg, 2.8 mmol), portionwise. The reaction mixture was stirred at −10° C. for 50 min. It was quenched with aq. NH$_4$Cl and extracted with EtOAc. The organic layer was washed with brine, dried over sodium sulfate and purified by normal phase chromatography to afford Intermediate 15D (220 mg, 43%) as an off-white solid. LC-MS (ESI) m/z: 319.9/321.9 [M+H+MeOH]$^+$; $^1$H NMR (400 MHz, CDCl$_3$) δ 8.14 (s, 1H), 8.09 (dd, J=8.1, 1.5 Hz, 1H), 7.88 (d, J=0.7 Hz, 1H), 7.80-7.74 (m, 2H), 5.24 (s, 2H), 3.96 (s, 3H).

INTERMEDIATE 15E

Methyl 2-acetamido-6H-isochromeno[3,4-c]pyridine-8-carboxylate

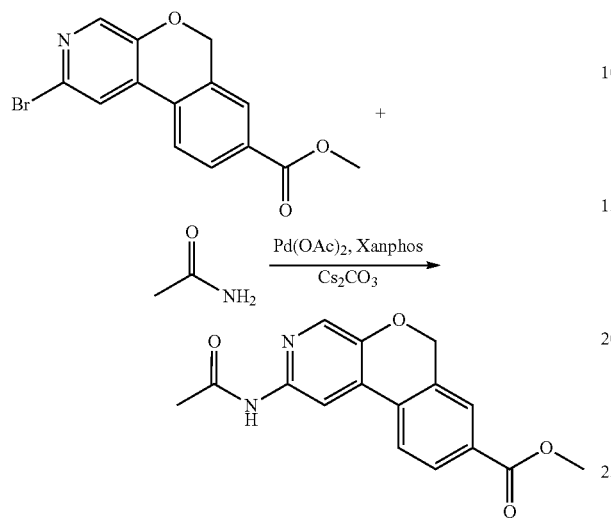

Intermediate 15D (22 mg, 0.70 mmol), Xantphos (41 mg, 0.070 mmol), Pd(OAc)$_2$ (7.9 mg, 0.035 mmol), Cs$_2$CO$_3$ (680 mg, 2.1 mmol), 1,4-dioxane (4 mL), and acetamide (62 mg, 1.1 mmol) were placed in a sealed vial. The mixture was degassed by flushing with argon for 20 min. It was heated at 70° C. for 4.5 h. The mixture was cooled, and was water (8 mL) added. After stirring for 10 min, the resultant precipitate was filtered, washed with ether, and suction-dried to afford Intermediate 15E (210 mg, 90%) as a tan solid. LC-MS (ESI) m/z: 299.1 [M+H]$^+$; $^1$H NMR (400 MHz, DMSO-d$_6$) δ 10.47 (s, 1H), 8.51 (s, 1H), 8.11 (s, 1H), 8.08-8.02 (m, 1H), 7.95 (d, J=1.3 Hz, 1H), 7.91 (d, J=8.1 Hz, 1H), 5.28 (s, 2H), 3.88 (s, 3H), 2.10 (s, 3H).

INTERMEDIATE 15

2-Acetamido-6H-isochromeno[3,4-c]pyridine-8-carboxylic acid

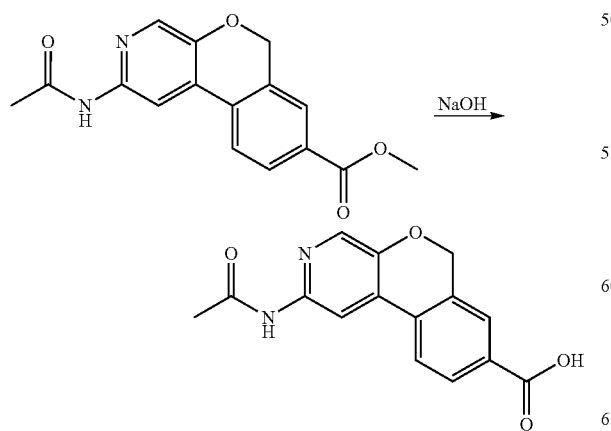

To a suspension of Intermediate 15E (8.7 mg, 0.020 mmol) in EtOH (1 mL), was added NaOH (1 N, 0.16 mL, 0.16 mmol) at rt. The reaction was stirred under argon at rt for 90 min, then HCl (3.7 N, 0.039 mL, 0.14 mmol) was added to adjust the pH to ~8. It was diluted with MeOH. The solid was collected by filtration and dried to afford Intermediate 15 (5.0 mg, 88%). LC-MS (ESI) m/z: 285.0 [M+H]$^+$.

INTERMEDIATE 16

2-Amino-6H-isochromeno[3,4-c]pyridine-8-carboxylic acid

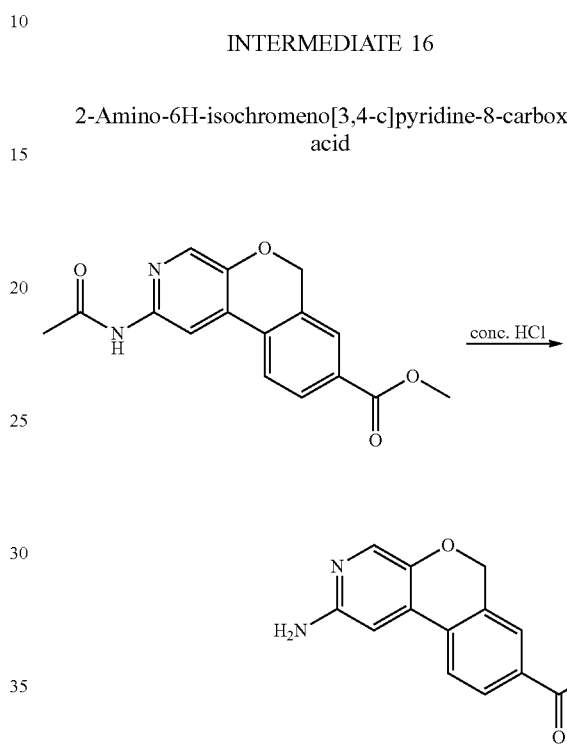

A suspension of Intermediate 15 (180 mg, 0.62 mmol) in concentrated HCl (23 µl, 28 mmol) in a sealed vial was heated 100° C. for 30 min. The reaction mixture was cooled to rt. It was diluted with water, and the solid was collected by filtration. The solid was washed with water and suction-dried to afford Intermediate 16 (130 mg, 77%) as a yellowish solid. LC-MS (ESI) m/z: 243.1 [M+H]$^+$; $^1$H NMR (400 MHz, DMSO-d$_6$) δ 8.12-8.07 (m, 1H), 8.03-7.95 (m, 2H), 7.89 (s, 1H), 7.48 (s, 1H), 5.28 (s, 2H).

INTERMEDIATE 17

6,6-Dimethyl-6H-isochromeno[3,4-c]pyridine-8-carboxylic acid

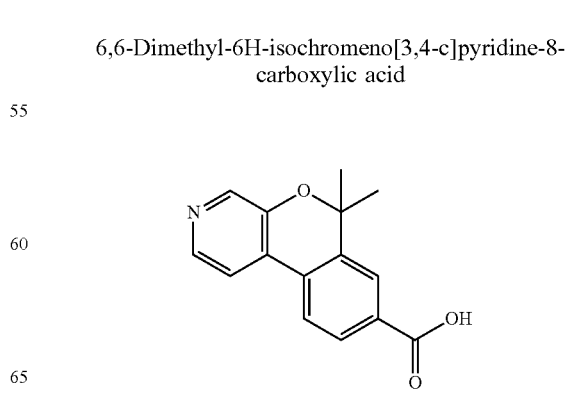

INTERMEDIATE 17A

Methyl 5-chloro-2-(3-fluoropyridin-4-yl)benzoate

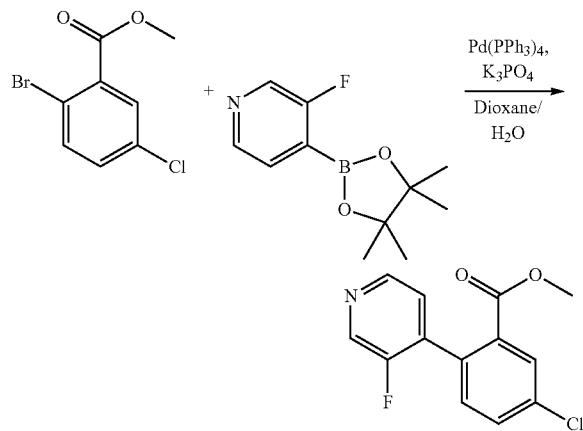

To a solution of methyl 2-bromo-5-chlorobenzoate (1.15g, 4.61 mmol) in dioxane (2 mL), were added 3-fluoro-4-(4,4,5,5-tetramethyl-1,3,2-dioxaborolan-2-yl)pyridine (1.234 g, 5.53 mmol), $K_3PO_4$ (2.446 g, 11.52 mmol) and $Pd(Ph_3P)_4$ (0.266 g, 0.230 mmol) at rt. The reaction was stirred under argon at 80° C. for 2 h. The reaction was cooled to rt. The reaction mixture was diluted with EtOAc, washed with $H_2O$ and brine. The organic phase was dried over sodium sulfate, filtered and concentrated. The crude product was purified by normal phase chromatography to afford Intermediate 17A as a clear colorless oil (0.50 g, 41%). LC-MS (ESI) m/z: 266.0 [M+H]$^+$; $^1$H NMR (400 MHz, CDCl$_3$) δ 8.53-8.44 (m, 2H), 8.04 (d, J=2.2 Hz, 1H), 7.60 (dd, J=8.1, 2.2 Hz, 1H), 7.28 (d, J=8.1 Hz, 1H), 7.22 (dd, J=6.3, 5.0 Hz, 1H), 3.74 (s, 3H).

INTERMEDIATE 17B 2-(5-Chloro-2-(3-fluoropyridin-4-yl)phenyl)propan-2-ol

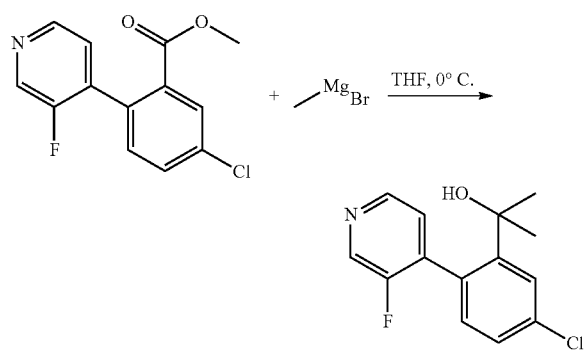

To a solution of Intermediate 17A (0.36 g, 1.4 mmol) in THF (10 mL), was added methylmagnesium bromide (3 M in ether, 1.0 mL, 3.0 mmol) at 0° C. The reaction was stirred under argon at 0° C. for 2 h. Aq. NH$_4$Cl was added to quench the reaction. The reaction mixture was diluted with EtOAc, washed with $H_2O$ and brine. The organic phase was dried over sodium sulfate, filtered and concentrated. The crude product was purified by normal phase chromatography to give Intermediate 17B as a white solid (259 mg, 72%). LC-MS (ESI) m/z: 266.0/268.0[M+H]$^+$; $^1$H NMR (400 MHz, CDCl$_3$) δ 8.41 (s, 1H), 8.36 (d, J=4.8 Hz, 1H), 7.59 (d, J=2.2 Hz, 1H), 7.28 (dd, J=8.3, 2.1 Hz, 1H), 7.19 (dd, J=6.2, 5.1 Hz, 1H), 6.96 (d, J=8.1 Hz, 1H), 2.03 (s, 1H), 1.53 (s, 3H), 1.46 (s, 3H).

INTERMEDIATE 17C

8-Chloro-6,6-dimethyl-6H-isochromeno[3,4-c]pyridine

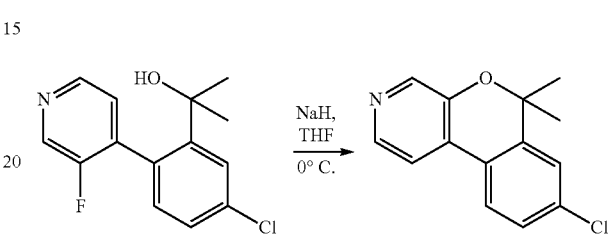

To a solution of Intermediate 17B (200 mg, 0.75 mmol) in THF (3 mL), was added NaH (90 mg, 2.3 mmol) at 0° C. The reaction was stirred under argon from 0° C. to rt overnight. The reaction was quenched with NH$_4$Cl solution. The reaction mixture was diluted with EtOAc, washed with $H_2O$ and brine. The organic phase was dried over sodium sulfate, filtered and concentrated. The crude product was purified by normal phase chromatography to give Intermediate 17C as a white solid (170 mg, 92%). LC-MS (ESI) m/z: 246.1 [M+H]$^+$; $^1$H NMR (400 MHz, CDCl$_3$) δ 8.32 (s, 1H), 8.27 (d, J=5.3 Hz, 1H), 7.69 (d, J=8.4 Hz, 1H), 7.51 (d, J=5.1 Hz, 1H), 7.37 (dd, J=8.4, 2.2 Hz, 1H), 7.26 (d, J=1.8 Hz, 1H), 1.65 (s, 6H).

INTERMEDIATE 17D 6,6-Dimethyl-6H-isochromeno[3,4-c]pyridine-8-carbonitrile

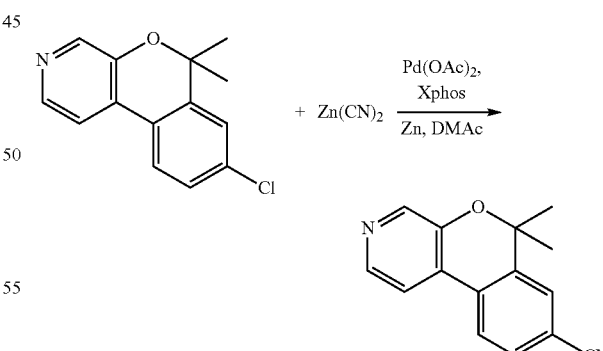

To a solution of Intermediate 17C (170 mg, 0.69 mmol) in DMAc (8 mL), were added Pd(OAc)$_2$ (7.8 mg, 0.035 mmol), XPhos (33 mg, 0.069 mmol), zinc powder (4.5 mg, 0.069 mmol), one drop of sulfuric acid and dicyanozinc (81 mg, 0.69 mmol) at rt. The reaction mixture was purged with argon before heated under argon at 120° C. for 5 h. The reaction was cooled to rt and then filtered. The crude product was purified by reverse phase chromatography to afford Intermediate 17D as a white solid (185 mg, 76%). LC-MS (ESI) m/z: 237.1 [M+H]+; 1H NMR (400 MHz, CDCl3/CD3OD mixture) δ 8.27 (s, 1H), 8.23 (d, J=5.5 Hz, 1H), 7.85 (d, J=8.1 Hz, 1H), 7.69 (d, J=5.3 Hz, 1H), 7.66 (dd, J=7.9, 1.5 Hz, 1H), 7.54 (d, J=1.5 Hz, 1H), 1.63 (d, J=3.5 Hz, 6H).

INTERMEDIATE 17

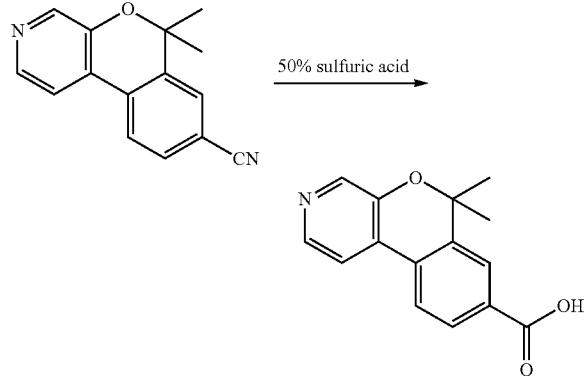

A solution of Intermediate 17D (100 mg, 0.42 mmol) in 50% H2SO4 solution was heated in a microwave reactor at 160° C. for 15 min. The reaction was diluted with water. The aqueous solution was purified by reverse phase chromatography to give Intermediate 17 as a white solid (92 mg, 85%). LC-MS (ESI) m/z: 256.1 [M+H]+; 1H NMR (400 MHz, DMSO-d6) δ 8.38 (s, 1H), 8.34 (d, J=5.3 Hz, 1H), 8.15 (d, J=7.9 Hz, 1H), 8.05-7.98 (m, 2H), 7.95 (d, J=1.3 Hz, 1H), 1.67 (s, 6H).

EXAMPLE I-1

(R)-N-(1-(3-Methoxyphenyl)ethyl)-5H-chromeno[3,4-c]pyridine-8-carboxamide

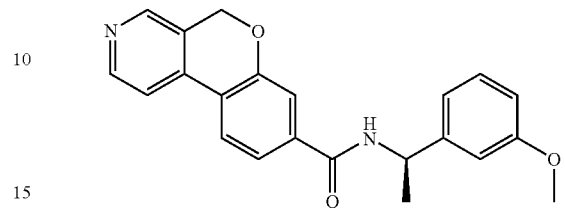

To a solution of Intermediate 1 (33 mg, 0.145 mmol) in DMF (1 mL) were added (R)-1-(3-methoxyphenyl)ethanamine (26.4 mg, 0.174 mmol), DIEA (0.178 mL, 1.017 mmol), and HATU (94 mg, 0.247 mmol) at RT. The reaction was stirred under argon at rt overnight. Purification by reverse phase chromatography afforded Example I-1 as white solid (25.2 mg, 47%). LC-MS (ESI) m/z: 361.1[M+H]+; 1H NMR (500 MHz, DMSO-d6) δ 8.86 (d, J=8.0 Hz, 1H), 8.61 (d, J=5.0 Hz, 1H), 8.53 (s, 1H), 8.07 (d, J=8.0 Hz, 1H), 7.86 (d, J=4.7 Hz, 1H), 7.63 (d, J=8.0 Hz, 1H), 7.54 (s, 1H), 7.24 (t, J=7.8 Hz, 1H), 6.96 (br. s., 2H), 6.80 (d, J=8.3 Hz, 1H), 5.27 (s, 2H), 5.13 (quin, J=6.9 Hz, 1H), 3.74 (s, 3H), 1.47 (d, J=6.9 Hz, 3H). Analytical HPLC RT E: 1.62 min, F: 1.30 min.

The compounds listed in Table I were prepared by following the similar procedure as described in Example I-1 via reactions of Intermediate 1 with the appropriate amines.

TABLE I

| Ex. No. | R | Name | LCMS (M+H)+ | HPLC Method, RT (min.) | 1H NMR (δ, NM) |
|---|---|---|---|---|---|
| I-2 | ![HN-CH2-C6H4-Cl (2-chlorobenzyl)] | N-(2-chlorobenzyl)-5H-chromeno[3,4-c]pyridine-8-carboxamide | 351.1 | E:1.18 F:1.52 | (500MHz, CD3OD) 8.53 (d, J = 5.2 Hz, 1H), 8.39 (s, 1H), 7.89 (d, J = 8.3 Hz, 1H), 7.70 (d, J = 5.2 Hz, 1H), 7.63-7.54 (m, 2H), 7.51 (d, J = 1.9 Hz, 1H), 7.44-7.33 (m, 2H), 7.29-7.15 (m, 2H), 5.22 (s, 2H), 4.67 (s, 2H) |
| I-3 | ![HN-CH(Me)-Ph (1-phenylethyl)] | N-(1-phenylethyl)-5H-chromeno[3,4-c]pyridine-8-carboxamide | 331.1 | A:5.12 B:5.59 | (400MHz, CD3OD) 8.78 (d, J = 6.2 Hz, 1H), 8.75 (s, 1H), 8.39 (d, J = 6.2 Hz, 1H), 8.17 (d, J = 8.4 Hz, 1H), 7.67 (dd, J = 8.3, 1.7 Hz, 1H), 7.56 (d, J = 1.8 Hz, 1H), 7.43-7.38 (m, 2H), 7.38-7.31 (m, 2H), 7.28-7.21 (m, 1H), 5.41 (s, 2H), 5.24 (q, J = 7.0 Hz, 1H), 1.58 (d, J = 7.0 Hz, 3H) |

TABLE I-continued

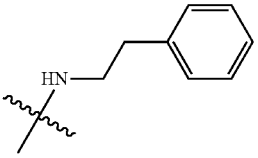 [SMILES: *NCCc1ccccc1]

| Ex. No. | R | Name | LCMS (M+H)+ | HPLC Method, RT (min.) | $^1$H NMR (δ, NM) |
|---|---|---|---|---|---|
| I-4 | 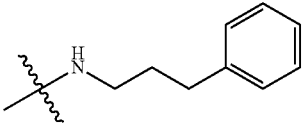 [SMILES: *NCCCc1ccccc1] | N-phenethyl-5H-chromeno[3,4-c]pyridine-8-carboxamide | 331.1 | A:4.92<br>B:5.49 | (400MHz, CD$_3$OD) 8.86-8.68 (m, 2H), 8.37 (d, J = 5.5 Hz, 1H), 8.16 (d, J = 8.1 Hz, 1H), 7.60 (d, J = 7.9 Hz, 1H), 7.48 (s, 1H), 7.36-7.11 (m, 5H), 5.40 (s, 2H), 3.61 (t, J = 7.3 Hz, 2H), 2.93 (t, J = 7.4 Hz, 2H) |
| I-5 | 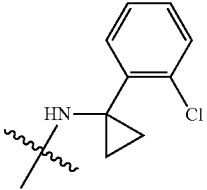 [SMILES: *NC1(c2ccccc2Cl)CC1] | N-(3-phenylpropyl)-5H-chromeno[3,4-c]pyridine-8-carboxamide | 345.0 | A:6.04<br>B:6.04 | (400MHz, CD$_3$OD) 8.83-8.66 (m, 2H), 8.38 (d, J = 5.7 Hz, 1H), 8.17 (d, J = 8.4 Hz, 1H), 7.63 (dd, J = 8.4, 1.5 Hz, 1H), 7.52 (d, J = 1.5 Hz, 1H), 7.31-7.08 (m, 5H), 5.41 (s, 2H), 3.45-3.38 (t, J = 7.5 Hz, 2H), 2.74-2.67 (t, J = 7.5 Hz, 2H), 1.95 (quin, J = 7.5 Hz, 2H) |
| I-6 | 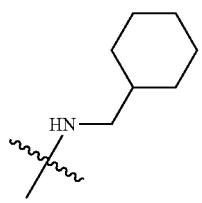 [SMILES: *NCC1CCCCC1] | N-(1-(2-chlorophenyl)cyclopropyl)-5H-chromeno[3,4-c]pyridine-8-carboxamide | 377.0 | A:5.45<br>B:6.20 | (400MHz, CD$_3$OD) 9.31 (s, 1H), 8.78 (d, J = 6.2 Hz, 1H), 8.75 (s, 1H), 8.39 (d, J = 6.2 Hz, 1H), 8.14 (d, J = 8.4 Hz, 1H), 7.81-7.75 (m, 1H), 7.58 (dd, J = 8.3, 1.7 Hz, 1H), 7.48 (d, J = 1.5 Hz, 1H), 7.41-7.37 (m, 1H), 7.30-7.25 (m, 2H), 5.40 (s, 2H), 1.37-1.29 (m, 2H), 1.29-1.21 (m, 2H) |
| I-7 | 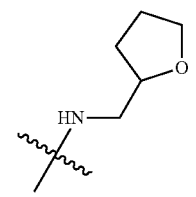 [SMILES: *NCC1CCCO1] | N-(cyclohexylmethyl)-5H-chromeno[3,4-c]pyridine-8-carboxamide | 323.3 | C:2.49<br>D:3.71 | (500MHz, DMSO-d6) 8.64 (d, J = 4.9 Hz, 2H), 8.55 (br. s., 1H), 8.08 (d, J = 8.2 Hz, 1H), 7.91 (d, J = 4.6 Hz, 1H), 7.61 (d, J = 8.2 Hz, 1H), 7.49 (s, 1H), 5.28 (s, 2H), 4.05-3.93 (m, 1H), 3.77 (d, J = 6.7 Hz, 1H), 3.68-3.59 (m, 1H), 3.55-3.31 (m, 7H),1.96-1.73 (m, 2H), 1.64-1.51 (m, 1H) |
| I-8 | | N-((tetrahydrofuran-2-yl)methyl)-5H-chromeno[3,4-c]pyridine-8-carboxamide | 311.2 | C:1.67<br>D:2.83 | (500MHz, DMSO-d$_6$) 8.64 (d, J = 4.9 Hz, 2H), 8.55 (br. s., 1H), 8.08 (d, J = 8.2 Hz, 1H), 7.91 (d, J = 4.6 Hz, 1H), 7.61 (d, J = 8.2 Hz, 1H), 7.49 (s, 1H), 5.28 (s, 2H), 4.04-3.93 (m, 1H), 3.77 (d, J = 6.7 Hz, 1H), 3.69-3.59 (m, 1H), 3.31 (d, J = 6.4 Hz, 3H), 1.97-1.70 (m, 2H), 1.65-1.49 (m, 1H) |

TABLE I-continued

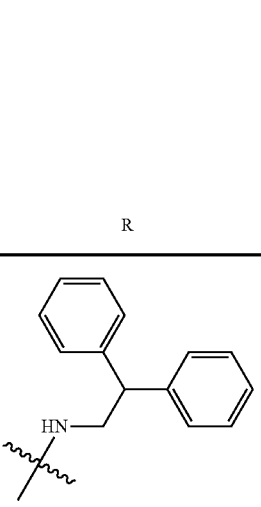

| Ex. No. | R | Name | LCMS (M+H)+ | HPLC Method, RT (min.) | ¹H NMR (δ, NM) |
|---|---|---|---|---|---|
| I-9 | 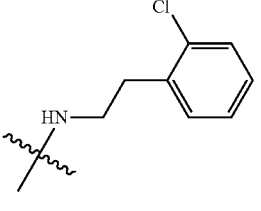 [SMILES: *NCCc1ccccc1Cl] | N-(2,2-diphenylethyl)-5H-chromeno[3,4-c]pyridine-8-carboxamide | 407.4 | C:2.80 D:3.92 | (500MHz, DMSO-$d_6$) 8.61 (br. s., 2H), 8.51 (br. s., 1H), 8.01 (d, J = 7.6 Hz, 1H), 7.84 (br. s., 1H), 7.45 (d, J = 7.9 Hz, 1H), 7.38-7.24 (m, 8H), 7.19 (br. s., 2H), 5.24 (br. s., 2H), 4.43 (br. s., 1H), 3.90 (br. s., 2H) |
| I-10 | 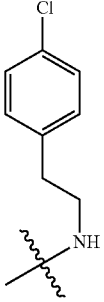 [SMILES: *NCCc1ccc(Cl)cc1] | N-(2-chlorophenethyl)-5H-chromeno[3,4-c]pyridine-8-carboxamide | 365.3 | C:2.53 D:3.70 | (500MHz, DMSO-$d_6$) 8.69 (br. s., 1H), 8.64 (br. s., 1H), 8.56 (br. s., 1H), 8.08 (d, J = 7.9 Hz, 1H), 7.92 (br. s., 1H), 7.56 (d, J = 8.2 Hz, 1H), 7.47-7.37 (m, 2H), 7.38-7.18 (m, 3H), 5.28 (br. s., 2H), 3.51 (br. s., 2H), 3.03-2.93 (m, 2H) |
| I-11 | 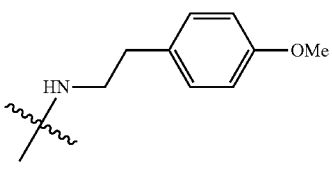 [SMILES: *NCCc1ccc(OC)cc1] | N-(4-chlorophenethyl)-5H-chromeno[3,4-c]pyridine-8-carboxamide | 365.3 | C:2.59 D:3.76 | (500MHz, DMSO-$d_6$) 8.63 (br. s., 2H), 8.54 (s, 1H), 8.06 (d, J = 7.6 Hz, 1H), 7.88 (d, J = 4.6 Hz, 1H), 7.55 (d, J = 7.9 Hz, 1H), 7.43 (s, 1H), 7.34 (d, J = 7.9 Hz, 2H), 7.27 (d, J = 7.6 Hz, 2H), 5.27 (s, 2H), 3.52-3.45 (m, 2H), 2.84 (t, J = 6.9 Hz, 2H) |
| I-12 | 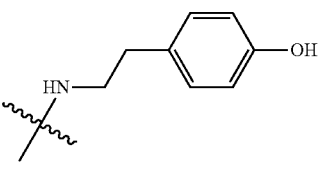 [SMILES: *NCCc1ccc(O)cc1] | N-(4-methoxyphenethyl)-5H-chromeno[3,4-c]pyridine-8-carboxamide | 361.3 | C:2.31 D:3.47 | (500MHz, DMSO-$d_6$) 8.62 (d, J = 4.0 Hz, 2H), 8.53 (s, 1H), 8.06 (d, J = 7.9 Hz, 1H), 7.87 (d, J = 5.2 Hz, 1H), 7.56 (d, J = 7.9 Hz, 1H), 7.45 (s, 1H), 7.15 (d, J = 8.2 Hz, 2H), 6.86 (d, J = 8.2 Hz, 2H), 5.27 (s, 2H), 3.71 (s, 3H), 3.51-3.41 (m, 2H), 2.78 (t, J = 7.2 Hz, 2H) |
| I-13 | | N-(4-hydroxyphenethyl)-5H-chromeno[3,4-c]pyridine-8-carboxamide | 347.3 | C:1.90 D:3.01 | (500MHz, DMSO-$d_6$) 8.68 (d, J = 5.2 Hz, 1H), 8.66-8.53 (m, 2H), 8.11 (d, J = 8.2 Hz, 1H), 8.01 (d, J = 5.2 Hz, 1H), 7.58 (d, J = 8.2 Hz, 1H), 7.46 (s, 1H), 7.02 (d, J = 7.9 Hz, 2H), 6.68 (d, J = 8.2 Hz, 2H), 5.30 (s, 2H), 3.41 (m, 2H), 2.72 (t, J = 7.2 Hz, 2H) |

TABLE I-continued

| Ex. No. | R | Name | LCMS (M+H)+ | HPLC Method, RT (min.) | 1H NMR (δ, NM) |
|---|---|---|---|---|---|
| I-14 | (2-phenoxyethyl-NH-) | N-(2-phenoxyethyl)-5H-chromeno[3,4-c]pyridine-8-carboxamide | 347.5 | C:2.32 D:3.45 | (500MHz, DMSO-d$_6$) 8.82 (br. s., 1H), 8.67 (br. s., 1H), 8.59 (br. s., 1H), 8.11 (d, J = 7.9 Hz, 1H), 7.98 (d, J = 4.9 Hz, 1H), 7.63 (d, J = 7.3 Hz, 1H), 7.52 (s, 1H), 7.29 (t, J = 7.6 Hz, 2H), 6.99-6.86 (m, 3H), 5.30 (s, 2H), 4.12 (t, J = 5.6 Hz, 2H), 3.64 (d, J = 5.8 Hz, 2H) |
| I-15 | (1-benzylpyrrolidin-3-yl-NH-) | N-(1-benzylpyrrolidin-3-yl)-5H-chromeno[3,4-c]pyridine-8-carboxamide | 386.4 | C:1.96 D:3.50 | (500MHz, DMSO-d6) 8.70 (br. s., 1H), 8.62 (d, J = 5.2 Hz, 1H), 8.53 (s, 1H), 8.08 (d, J = 8.2 Hz, 1H), 7.87 (d, J = 5.2 Hz, 1H), 7.59 (d, J = 7.9 Hz, 1H), 7.54-7.36 (m, 4H), 7.13 (br. s., 1H), 5.27 (s, 2H), 4.50 (br. s., 1H), 3.15-2.69 (m, 4H), 2.04 (br. s., 2H), 1.91 (s, 2H) |
| I-16 | (4-cyanobenzyl-NH-) | N-(4-cyanobenzyl)-5H-chromeno[3,4-c]pyridine-8-carboxamide | 342.3 | C:2.10 D:3.12 | (500MHz, DMSO-d$_6$) 9.25 (br. s., 1H), 8.63 (d, J = 4.9 Hz, 1H), 8.54 (s, 1H), 8.10 (d, J = 7.6 Hz, 1H), 7.89 (d, J = 5.5 Hz, 1H), 7.81 (d, J = 7.9 Hz, 2H), 7.65 (d, J = 7.9 Hz, 1H), 7.56-7.45 (m, 3H), 5.28 (s, 2H), 4.56 (d, J = 5.5 Hz, 2H) |
| I-17 | (furan-2-ylmethyl-NH-) | N-(furan-2-ylmethyl)-5H-chromeno[3,4-c]pyridine-8-carboxamide | 307.3 | C:1.96 D:3.06 | (500MHz, DMSO-d$_6$) 9.10 (br. s., 1H), 8.70 (d, J = 4.9 Hz, 1H), 8.62 (s, 1H), 8.13 (d, J = 8.2 Hz, 1H), 8.04 (d, J = 5.2 Hz, 1H), 7.65 (d, J = 7.9 Hz, 1H), 7.58 (s, 1H), 7.53 (s, 1H), 6.40 (br. s., 1H), 6.29 (br. s., 1H), 5.31 (s, 2H), 4.47 (d, J = 5.2 Hz, 2H) |
| I-18 | (thiophen-2-ylmethyl-NH-) | N-(thiophen-2-ylmethyl)-5H-chromeno[3,4-c]pyridine-8-carboxamide | 323.2 | C:2.14 D:3.24 | (500MHz, DMSO-d$_6$) 9.25 (br. s., 1H), 8.63 (d, J = 4.9 Hz, 1H), 8.55 (s, 1H), 8.09 (d, J = 8.2 Hz, 1H), 7.90 (d, J = 4.9 Hz, 1H), 7.62 (d, J = 8.2 Hz, 1H), 7.51 (s, 1H), 7.39 (d, J = 4.9 Hz, 1H), 7.02 (br. s., 1H), 6.99-6.93 (m, 1H), 5.28 (s, 2H), 4.63 (d, J = 5.5 Hz, 2H) |

TABLE I-continued

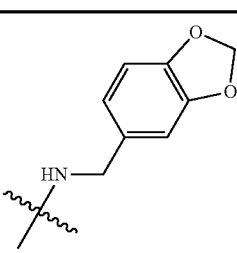

| Ex. No. | R | Name | LCMS (M+H)+ | HPLC Method, RT (min.) | ¹H NMR (δ, NM) |
|---|---|---|---|---|---|
| I-19 | 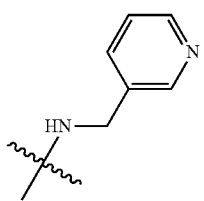 [SMILES: *NCc1cccnc1] | N-(benzo[d][1,3]dioxol-5-ylmethyl)-5H-chromeno[3,4-c]pyridine-8-carboxamide | 361.3 | C:2.19 D:3.30 | (500MHz, DMSO-$d_6$) 9.09 (br. s., 1H), 8.67 (d, J = 4.6 Hz, 1H), 8.59 (br. s., 1H), 8.12 (d, J = 8.2 Hz, 1H), 7.99 (d, J = 5.5 Hz, 1H), 7.64 (d, J = 8.2 Hz, 1H), 7.53 (s, 1H), 6.95-6.83 (m, 2H), 6.80 (d, J = 7.9 Hz, 1H), 5.98 (s, 2H), 5.30 (s, 2H), 4.38 (d, J = 5.5 Hz, 2H) |
| I-20 | 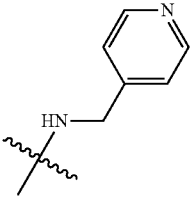 [SMILES: *NCc1ccncc1] | N-(pyridin-3-ylmethyl)-5H-chromeno[3,4-c]pyridine-8-carboxamide | 318.3 | C:1.68 D:2.81 | (500MHz, DMSO-$d_6$) 9.23 (br. s., 1H), 8.64 (d, J = 4.6 Hz, 1H), 8.60 (br. s., 1H), 8.55 (br. s., 1H), 8.51 (br. s., 1H), 8.10 (d, J = 8.2 Hz, 1H), 7.91 (d, J = 4.9 Hz, 1H), 7.84 (d, J = 7.3 Hz, 1H), 7.64 (d, J = 7.9 Hz, 1H), 7.53 (br. s., 1H), 7.46 (br. s., 1H), 5.28 (s, 2H), 4.52 (d, J = 5.2 Hz, 2H) |
| I-21 | 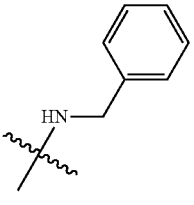 [SMILES: *NCc1ccccc1] | N-(pyridin-4-ylmethyl)-5H-chromeno[3,4-c]pyridine-8-carboxamide | 318.5 | C:1.64 D:2.63 | (500MHz, DMSO-$d_6$) 9.30 (br. s., 1H), 8.66 (br. s., 1H), 8.58 (br. s., 3H), 8.14 (d, J = 7.9 Hz, 1H), 7.93 (br. s., 1H), 7.69 (d, J = 7.6 Hz, 1H), 7.59 (br. s., 1H), 7.45 (br. s., 2H), 5.32 (br. s., 2H), 4.57 (br. s., 2H) |
| I-22 | 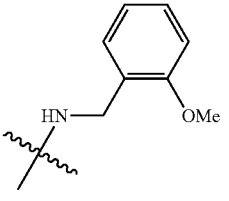 [SMILES: *NCc1ccccc1OC] | N-benzyl-5H-chromeno[3,4-c]pyridine-8-carboxamide | 317.5 | C:2.21 D:3.28 | (500MHz, DMSO-$d_6$) 9.14 (br. s., 1H), 8.61 (d, J = 4.9 Hz, 1H), 8.53 (s, 1H), 8.08 (d, J = 7.9 Hz, 1H), 7.87 (d, J=4.3 Hz, 1H), 7.65 (d, J = 7.9 Hz, 1H), 7.54 (s, 1H), 7.38-7.21 (m, 4H), 5.27 (s, 2H), 4.49 (d, J = 5.8 Hz, 2H) |
| I-23 | 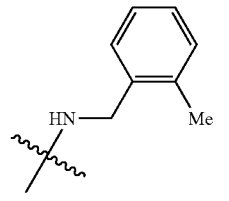 [SMILES: *NCc1ccccc1C] | N-(2-methoxybenzyl)-5H-chromeno[3,4-c]pyridine-8-carboxamide | 347.2 | C:2.86 C-1:2.86 | (500MHz, DMSO-$d_6$) 8.96 (br. s., 1H), 8.64 (d, J = 4.6 Hz, 1H), 8.55 (s, 1H), 8.10 (d, J = 8.2 Hz, 1H), 7.92 (d, J = 5.2 Hz, 1H), 7.66 (d, J = 8.2 Hz, 1H), 7.55 (s, 1H), 7.32-7.20 (m, 1H), 7.18 (d, J = 7.3 Hz, 1H), 7.00 (d, J = 7.9 Hz, 1H), 6.91 (t, J = 7.3 Hz, 1H), 5.28 (s, 2H), 4.45 (d, J = 5.5 Hz, 2H), 3.83 (s, 3H) |
| I-24 | | N-(2-methylbenzyl)-5H-chromeno[3,4-c]pyridine-8-carboxamide | 331.5 | C:2.37 D:3.48 | (500MHz, DMSO-$d_6$) 9.02 (br. s., 1H), 8.63 (d, J = 4.6 Hz, 1H), 8.55 (s, 1H), 8.09 (d, J = 8.2 Hz, 1H), 7.90 (d, J = 5.2 Hz, 1H), 7.66 (d, J = 7.3 Hz, 1H), 7.55 (s, 1H), 7.24 (d, J = 4.3 Hz, 1H), 7.16 (br. s., 3H), 5.28 (s, 2H), 4.46 (d, J = 5.8 Hz, 2H), 2.32 (s, 3H) |

TABLE I-continued

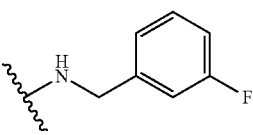 [SMILES: *NCc1cccc(F)c1]

| Ex. No. | R | Name | LCMS (M+H)+ | HPLC Method, RT (min.) | $^1$H NMR (δ, NM) |
|---|---|---|---|---|---|
| I-25 | 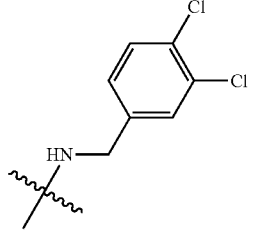 [SMILES: *NCc1ccc(Cl)c(Cl)c1] | N-(3-fluorobenzyl)-5H-chromeno[3,4-c]pyridine-8-carboxamide | 335.3 | C:2.34 D:3.42 | (500MHz, DMSO-$d_6$) 9.19 (br. s., 1H), 8.64 (d, J = 5.2 Hz, 1H), 8.56 (s, 1H), 8.10 (d, J = 7.9 Hz, 1H), 7.92 (d, J = 5.2 Hz, 1H), 7.65 (d, J = 7.9 Hz, 1H), 7.54 (s, 1H), 7.44-7.32 (m, 1H), 7.20-7.02 (m, 3H), 5.28 (s, 2H), 4.49 (d, J = 5.5 Hz, 2H) |
| I-26 | 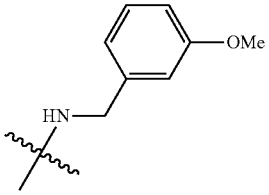 [SMILES: *NCc1cccc(OC)c1] | N-(3,4-dichlorobenzyl)-5H-chromeno[3,4-c]pyridine-8-carboxamide | 385.3 | C:2.69 D:3.88 | (500MHz, DMSO-$d_6$) 9.21 (br. s., 1H), 8.66 (br. s., 1H), 8.58 (br. s., 1H), 8.12 (d, J = 7.9 Hz, 1H), 7.96 (br. s., 1H), 7.69-7.50 (m, 4H), 7.32 (d, J = 8.2 Hz, 1H), 5.30 (s, 2H), 4.47 (d, J = 5.8 Hz, 2H) |
| I-27 | 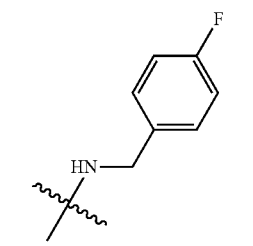 [SMILES: *NCc1ccc(F)cc1] | N-(3-methoxybenzyl)-5H-chromeno[3,4-c]pyridine-8-carboxamide | 347.3 | C:2.27 D:3.37 | (500MHz, DMSO-$d_6$) 9.14 (br. s., 1H), 8.67 (br. s., 1H), 8.59 (br. s., 1H), 8.12 (d, J = 7.9 Hz, 1H), 7.99 (d, J = 4.3 Hz, 1H), 7.66 (d, J = 8.2 Hz, 1H), 7.54 (s, 1H), 7.25 (t, J = 7.5 Hz, 1H), 6.88 (br. s., 2H), 6.82 (d, J = 6.7 Hz, 1H), 5.30 (s, 2H), 4.46 (d, J = 5.2 Hz, 2H), 3.73 (s, 3H) |
| I-28 | 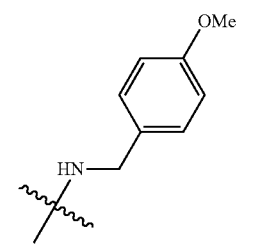 [SMILES: *NCc1ccc(OC)cc1] | N-(4-fluorobenzyl)-5H-chromeno[3,4-c]pyridine-8-carboxamide | 335.3 | C:2.20 D:3.32 | (500MHz, DMSO-$d_6$) 9.16 (br. s., 1H), 8.66 (d, J = 5.2 Hz, 1H), 8.58 (s, 1H), 8.11 (d, J = 8.2 Hz, 1H), 7.96 (d, J = 5.2 Hz, 1H), 7.65 (d, J = 8.2 Hz, 1H), 7.54 (s, 1H), 7.41-7.32 (m, 2H), 7.16 (t, J = 8.7 Hz, 2H), 5.29 (s, 2H), 4.46 (d, J = 5.8 Hz, 2H) |
| I-29 | | N-(4-methoxybenzyl)-5H-chromeno[3,4-c]pyridine-8-carboxamide | 347.3 | C:2.25 D:3.34 | (500MHz, DMSO-$d_6$) 9.10 (br. s., 1H), 8.69 (d, J = 4.6 Hz, 1H), 8.61 (br. s., 1H), 8.12 (d, J = 8.2 Hz, 1H), 8.01 (d, J = 4.6 Hz, 1H), 7.65 (d, J = 7.9 Hz, 1H), 7.53 (s, 1H), 7.25 (d, J = 8.5 Hz, 2H), 6.89 (d, J = 8.5 Hz, 2H), 5.30 (s, 2H), 4.41 (d, J = 5.5 Hz, 2H), 3.72 (s, 3H) |

TABLE I-continued

| Ex. No. | R | Name | LCMS (M+H)⁺ | HPLC Method, RT (min.) | ¹H NMR (δ, NM) |
|---|---|---|---|---|---|
| I-30 | 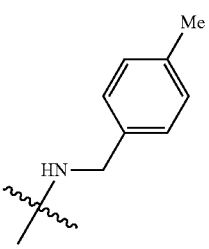 [SMILES: *NCc1ccc(C)cc1] | N-(4-methylbenzyl)-5H-chromeno[3,4-c]pyridine-8-carboxamide | 331.1 | C:2.44 D:3.58 | (500MHz, DMSO-d₆) 9.11 (br. s., 1H), 8.65 (br. s., 1H), 8.58 (br. s., 1H), 8.11 (d, J = 7.9 Hz, 1H), 7.96 (d, J = 5.2 Hz, 1H), 7.64 (d, J = 7.6 Hz, 1H), 7.53 (s, 1H), 7.21 (d, J = 7.9 Hz, 2H), 7.13 (d, J = 7.6 Hz, 2H), 5.29 (s, 2H), 4.43 (d, J = 5.8 Hz, 2H), 2.27 (s, 3H) |
| I-31 | 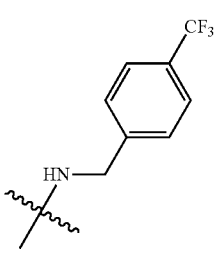 [SMILES: *NCc1ccc(C(F)(F)F)cc1] | N-(4-(trifluoromethyl)benzyl)-5H-chromeno[3,4-c]pyridine-8-carboxamide | 385.3 | C:2.61 D:3.74 | (500MHz, DMSO-d₆) 9.28 (br. s., 1H), 8.71 (br. s., 1H), 8.63 (br. s., 1H), 8.16 (d, J = 8.2 Hz, 1H), 8.06 (d, J = 4.9 Hz, 1H), 781-7.63 (m, 3H), 7.60-7.45 (m, 3H), 5.32 (s, 2H), 4.57 (d, J = 4.6 Hz, 2H) |
| I-32 | 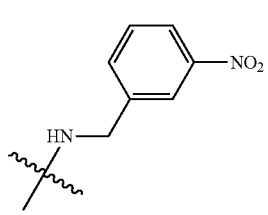 [SMILES: *NCc1cccc([N+](=O)[O-])c1] | N-(3-nitrobenzyl)-5H-chromeno[3,4-c]pyridine-8-carboxamide | 362.3 | C:2.24 D:3.31 | (500MHz, DMSO-d₆) 9.30 (br. s., 1H), 8.62 (d, J = 5.2 Hz, 1H), 8.53 (s, 1H), 8.19 (br. s., 1H), 8.11 (dd, J = 12.4, 8.1 Hz, 2H), 7.88 (d, J = 4.9 Hz, 1H), 7.80 (d, J = 7.6 Hz, 1H), 7.70-7.60 (m, 2H), 7.54 (s, 1H), 5.28 (s, 2H), 4.60 (d, J = 5.8 Hz, 2H) |
| I-33 | 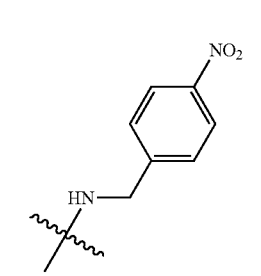 [SMILES: *NCc1ccc([N+](=O)[O-])cc1] | N-(4-nitrobenzyl)-5H-chromeno[3,4-c]pyridine-8-carboxamide | 362.7 | C:2.20 D:3.22 | (500MHz, DMSO-d₆) 9.30 (br. s., 1H), 8.62 (d, J = 4.9 Hz, 1H), 8.53 (s, 1H), 8.21 (d, J = 8.2 Hz, 2H), 8.10 (d, J = 8.2 Hz, 1H), 7.88 (d, J = 5.2 Hz, 1H), 7.65 (d, J = 7.9 Hz, 1H), 7.59 (d, J = 8.2 Hz, 2H), 7.54 (s, 1H), 5.28 (s, 2H), 4.60 (d, J = 5.5 Hz, 2H) |
| I-34 | 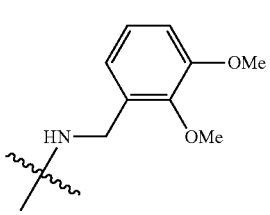 [SMILES: *NCc1cccc(OC)c1OC] | N-(2,3-dimethoxybenzyl)-5H-chromeno[3,4-c]pyridine-8-carboxamide | 377.6 | C:2.22 D:3.27 | (500MHz, DMSO-d₆) 9.01 (br. s., 1H), 8.61 (br. s., 1H), 8.53 (br. s., 1H), 8.08 (d, J = 8.2 Hz, 1H), 7.87 (d, J = 5.2 Hz, 1H), 7.65 (d, J = 8.2 Hz, 1H), 7.53 (s, 1H), 7.07-6.99 (m, 1H), 6.95 (d, J = 7.9 Hz, 1H), 6.85 (d, J = 7.6 Hz, 1H), 5.27 (s, 2H), 4.49 (d, J = 5.5 Hz, 2H), 3.80 (s, 3H), 3.77 (s, 3H) |

TABLE I-continued

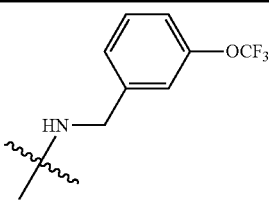

| Ex. No. | R | Name | LCMS (M+H)+ | HPLC Method, RT (min.) | $^1$H NMR (δ, NM) |
|---|---|---|---|---|---|
| I-35 | 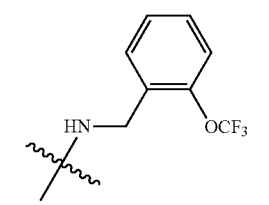 [SMILES: *NCc1ccccc1OC(F)(F)F] | N-(3-(trifluoromethoxy) benzyl)-5H-chromeno[3,4-c] pyridine-8-carboxamide | 401.3 | C:2.67 D:3.80 | (500MHz, DMSO-$d_6$) 9.22 (br. s., 1H), 8.62 (d, J = 4.9 Hz, 1H), 8.54 (s, 1H), 8.10 (d, J = 8.2 Hz, 1H), 7.88 (d, J = 5.2 Hz, 1H), 7.64 (d, J = 8.5 Hz, 1H), 7.53 (s, 1H), 7.48 (t, J = 7.8 Hz, 1H), 7.36 (d, J = 7.6 Hz, 1H), 7.30 (br. s., 1H), 7.25 (d, J = 7.9 Hz, 1H), 5.28 (s, 2H), 4.53 (d, J = 5.5 Hz, 2H) |
| I-36 | 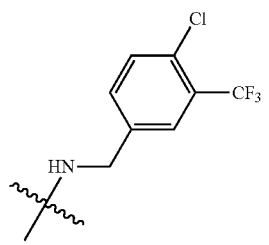 [SMILES: *NCc1ccc(Cl)c(C(F)(F)F)c1] | N-(2-(trifluoromethoxy) benzyl)-5H-chromeno[3,4-c] pyridine-8-carboxamide | 401.1 | C:3.21 C-1:3.19 | (500MHz, DMSO-$d_6$) 9.17 (br. s., 1H), 8.70 (d, J = 4.9 Hz, 1H), 8.62 (s, 1H), 8.15 (d, J = 7.9 Hz, 1H), 8.03 (d, J = 5.2 Hz, 1H), 7.67 (d, J = 7.9 Hz, 1H), 7.56 (s, 1H), 7.49-7.24 (m, 4H), 5.32 (s, 2H), 4.55 (d, J = 5.5 Hz, 2H) |
| I-37 | 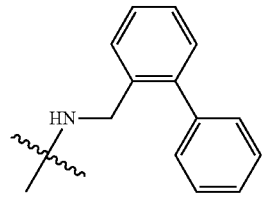 [SMILES: *NCc1ccccc1-c1ccccc1] | N-(4-chloro-3-(trifluoromethyl)benzyl)-5H-chromeno[3,4-c]pyridine-8-carboxamide | 419.5 | C:2.77 D:3.90 | (500MHz, DMSO-$d_6$) 9.24 (br. s., 1H), 8.63 (br. s., 1H), 8.55 (br. s., 1H), 8.10 (d, J = 7.9 Hz, 1H), 7.90 (d, J = 4.9 Hz, 1H), 7.81 (s, 1H), 7.74-7.67 (m, 1H), 7.63 (d, J = 7.9 Hz, 2H), 7.52 (s, 1H), 5.28 (s, 2H), 4.54 (d, J = 5.5 Hz, 2H) |
| I-38 | 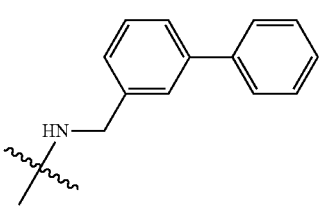 [SMILES: *NCc1cccc(-c2ccccc2)c1] | N-(biphenyl-2-ylmethyl)-5H-chromeno[3,4-c]pyridine-8-carboxamide | 393.6 | C:2.74 D:3.89 | (500MHz, DMSO-$d_6$) 9.04 (br. s., 1H), 8.65 (br. s., 1H), 8.57 (br. s., 1H), 8.10 (d, J = 7.9 Hz, 1H), 7.94 (br. s., 1H), 7.62 (d, J = 7.9 Hz, 1H), 7.55-7.30 (m, 8H), 7.24 (d, J = 7.0 Hz, 1H), 5.29 (br. s., 2H), 4.43 (d, J = 5.2 Hz, 2H) |
| I-39 | 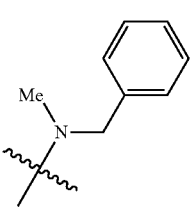 [SMILES: *N(C)Cc1ccccc1] | N-(biphenyl-3-ylmethyl)-5H-chromeno[3,4-c]pyridine-8-carboxamide | 393.4 | C:2.78 D:3.96 | (500MHz, DMSO-$d_6$) 9.18 (br. s., 1H), 8.61 (d, J = 4.9 Hz, 1H), 8.53 (s, 1H), 8.08 (d, J = 7.9 Hz, 1H), 7.86 (d, J = 4.9 Hz, 1H), 7.74-7.59 (m, 4H), 7.55 (br. s., 2H), 7.50-7.40 (m, 3H), 7.39-7.31 (m, 2H), 5.27 (s, 2H), 4.56 (d, J = 5.5 Hz, 2H) |
| I-40 |  | N-benzyl-N-methyl-5H-chromeno[3,4-c]pyridine-8-carboxamide | 331.5 | C:2.35 D:3.48 | (500MHz, DMSO-$d_6$) 8.66 (br. s., 1H), 8.59 (br. s., 1H), 8.08 (d, J = 13.1 Hz, 1H), 7.97 (d, J = 17.4 Hz, 1H), 7.45-7.05 (m, 7H), 5.29 (s, 2H), 4.44 (s, 2H), 2.79 (s, 3H) |

TABLE I-continued

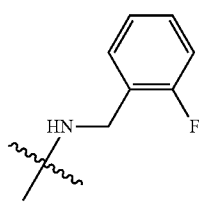 [SMILES: *NCc1ccccc1F]

| Ex. No. | R | Name | LCMS (M+H)+ | HPLC Method, RT (min.) | $^1$H NMR (δ, NM) |
|---|---|---|---|---|---|
| I-41 | 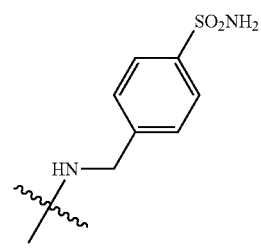 [SMILES: *NCc1ccc(S(N)(=O)=O)cc1] | N-(2-fluorobenzyl)-5H-chromeno[3,4-c]pyridine-8-carboxamide | 335.5 | C:2.28<br>D:3.30 | (500MHz, DMSO-d$_6$) 9.13 (br. s., 1H), 8.62 (d, J = 4.9 Hz, 1H), 8.53 (s, 1H), 8.08 (d, J = 8.2 Hz, 1H), 7.88 (d, J = 4.9 Hz, 1H), 7.64 (d, J = 7.9 Hz, 1H), 7.53 (s, 1H), 7.41-7.27 (m, 2H), 7.23-7.11 (m, 2H), 5.27 (s, 2H), 4.52 (d, J = 5.2 Hz, 2H) |
| I-42 | 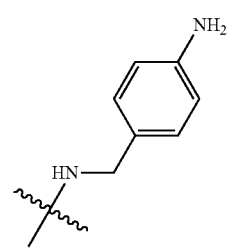 [SMILES: *NCc1ccc(N)cc1] | N-(4-sulfamoylbenzyl)-5H-chromeno[3,4-c]pyridine-8-carboxamide | 396.3 | C:1.70<br>D:2.64 | (500MHz, DMSO-d$_6$) 9.23 (br. s., 1H), 8.62 (d, J = 4.9 Hz, 1H), 8.53 (s, 1H), 8.09 (d, J = 7.9 Hz, 1H), 7.87 (d, J = 5.2 Hz, 1H), 7.78 (d, J = 7.9 Hz, 2H), 7.65 (d, J = 7.9 Hz, 1H), 7.57-7.43 (m, 3H), 7.31 (s, 2H), 5.27 (s, 2H), 4.54 (d, J = 5.2 Hz, 2H) |
| I-43 | 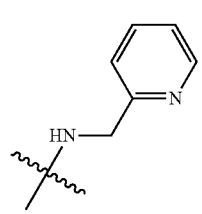 [SMILES: *NCc1ccccn1] | N-(4-aminobenzyl)-5H-chromeno[3,4-c]pyridine-8-carboxamide | 332.5 | C:1.75<br>D:2.63 | (500MHz, DMSO-d$_6$) 8.95 (br. s., 1H), 8.61 (d, J = 4.6 Hz, 1H), 8.52 (br. s., 1H), 8.06 (d, J = 7.6 Hz, 1H), 7.86 (d, J = 4.3 Hz, 1H), 7.62 (d, J = 7.9 Hz, 1H), 7.51 (br. s., 1H), 6.99 (d, J = 7.9 Hz, 2H), 6.53 (d, J = 8.2 Hz, 2H), 5.26 (br. s., 2H), 4.29 (br. s., 2H) |
| I-44 | 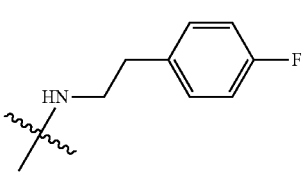 [SMILES: *NCCc1ccc(F)cc1] | N-(pyridin-2-ylmethyl)-5H-chromeno[3,4-c]pyridine-8-carboxamide | 318.3 | C:1.75<br>D:2.91 | (500MHz, DMSO-d$_6$) 9.23 (d, J = 4.6 Hz, 1H), 8.63 (t, J = 4.6 Hz, 1H), 8.59-8.48 (m, 2H), 8.16-8.08 (m, 1H), 7.91 (br. s., 1H), 7.79 (br. s., 1H), 7.67 (br. s., 1H), 7.57 (br. s., 1H), 7.36 (d, J = 6.7 Hz, 1H), 7.30 (br. s., 1H), 7.23 (br. s., 1H), 7.13 (d, J = 4.0 Hz, 1H), 7.03 (br. s., 1H), 5.28 (br, s 2H), 4.58 (br. s., 2H) |
| I-45 | | N-(4-fluorophenethyl)-5H-chromeno[3,4-c]pyridine-8-carboxamide | 349.2 | C:2.35<br>D:3.43 | (500MHz, DMSO-d$_6$) 8.67-8.57 (m, 2H), 8.52 (s, 1H), 8.05 (d, J = 8.2 Hz, 1H), 7.85 (d, J = 5.2 Hz, 1H), 7.55 (d, J = 7.9 Hz, 1H), 7.43 (s, 1H), 7.32-7.24 (m, 2H), 7.11 (t, J = 8.9 Hz, 2H), 5.26 (s, 2H), 3.52-3.44 (m, 2H), 2.84 (t, J = 7.0 Hz, 2H) |

TABLE I-continued

| Ex. No. | R | Name | LCMS (M+H)+ | HPLC Method, RT (min.) | 1H NMR (δ, NM) |
|---|---|---|---|---|---|
| I-46 | (2-(phenylamino)ethyl)amino | N-(2-(phenylamino)ethyl)-5H-chromeno[3,4-c]pyridine-8-carboxamide | 346.2 | C:2.21<br>D:3.21 | (500MHz, DMSO-d6) 8.70 (br. s., 1H), 8.61 (d, J = 4.9 Hz, 1H), 8.53 (s, 1H), 8.07 (d, J = 7.9 Hz, 1H), 7.86 (d, J = 5.2 Hz, 1H), 7.61 (d, J = 8.2 Hz, 1H), 7.50 (s, 1H), 7.08 (t, J = 7.5 Hz, 2H), 6.62 (d, J = 7.9 Hz, 2H), 6.53 (t, J = 6.9 Hz, 1H), 5.73 (br. s., 1H), 5.27 (s, 2H), 3.44 (br. s., 2H), 3.21 (d, J = 5.8 Hz, 2H) |
| I-47 | (2-(thiophen-2-yl)ethyl)amino | N-(2-(thiophen-2-yl)ethyl)-5H-chromeno[3,4-c]pyridine-8-carboxamide | 337.2 | C:2.23<br>D:3.27 | (500MHz, DMSO-d6) 8.72 (br. s., 1H), 8.61 (d, J = 5.2 Hz, 1H), 8.53 (s, 1H), 8.07 (d, J = 7.9 Hz, 1H), 7.58 (d, J = 7.9 Hz, 1H), 7.47 (s, 1H), 7.34 (d, J = 4.9 Hz, 1H), 6.96 (d, J = 3.4 Hz, 1H), 6.92 (br. s., 1H), 5.27 (s, 2H), 3.57-3.46 (m, 2H), 3.07 (t, J = 6.7 Hz, 2H) |
| I-48 | methyl(phenethyl)amino | N-methyl-N-phenethyl-5H-chromeno[3,4-c]pyridine-8-carboxamide | 345.2 | C:2.38<br>D:3.38 | (500MHz, DMSO-d6) 8.59 (d, J = 4.9 Hz, 1H), 8.51 (s, 1H), 8.08-7.90 (m, 1H), 7.83 (br. s., 1H), 7.42-7.15 (m, 4H), 7.02-6.82 (m,3H), 5.24 (s, 2H), 3.30 (br. s., 3H), 2.86 (m, 2H), 2.73 (m, 2H) |
| I-49 | (benzo[d]thiazol-2-ylmethyl)amino | N-(benzo[d]thiazol-2-ylmethyl)-5H-chromeno[3,4-c]pyridine-8-carboxamide | 374.1 | C:2.24<br>D:3.37 | (500MHz, DMSO-d6) 9.62 (t, J = 5.8 Hz, 1H), 8.63 (d, J = 5.2 Hz, 1H), 8.54 (s, 1H), 8.13 (d, J = 7.9 Hz, 1H), 8.06 (d, J = 7.6 Hz, 1H), 7.96 (d, J = 8.2 Hz, 1H), 7.89 (d, J = 4.9 Hz, 1H), 7.68 (dd, J = 8.1, 1.7 Hz, 1H), 7.57 (d, J = 1.8 Hz, 1H), 7.54-7.47 (m, 1H), 7.48-7.38 (m, 1H), 5.29 (s, 2H), 4.88 (d, J = 6.1 Hz, 2H) |
| I-50 | (4-hydroxybenzyl)amino | N-(4-hydroxybenzyl)-5H-chromeno[3,4-c]pyridine-8-carboxamide | 333.2 | C:1.80<br>D:2.70 | (500MHz, DMSO-d6) 9.28 (s, 1H), 9.08-8.96 (m, 1H), 8.61 (d, J = 4.9 Hz, 1H), 8.53 (s, 1H), 8.07 (d, J = 8.2 Hz, 1H), 7.87 (d, J=4.9 Hz, 1H), 7.63 (d, J = 7.9 Hz, 1H), 7.51 (s, 1H), 7.12 (d, J = 8.2 Hz, 2H), 6.71 (d, J = 8.2 Hz, 2H), 5.26 (s, 2H), 4.36 (d, J = 5.5 Hz, 2H) |

TABLE I-continued

| Ex. No. | R | Name | LCMS (M+H)+ | HPLC Method, RT (min.) | 1H NMR (δ, NM) |
|---|---|---|---|---|---|
| I-51 | (R)-HN-CH(Me)-Ph | (R)-N-(1-phenylethyl)-5H-chromeno[3,4-c]pyridine-8-carboxamide | 331.1 | A:5.04 B:6.08 | (400MHz, DMSO-d6) 8.93 (d, J = 7.9 Hz, 1H), 8.74 (d, J = 5.7 Hz, 1H), 8.67 (s, 1H), 8.19-8.09 (m, 2H), 7.67 (dd, J = 8.1, 1.8 Hz, 1H), 7.58 (d, J = 1.5 Hz, 1H), 7.45-7.36 (m, 2H), 7.36-7.29 (m, 2H), 7.27-7.19 (m, 1H), 5.33 (s, 2H), 5.16 (quin, J = 7.3 Hz, 1H), 1.48 (d, J = 7.0 Hz, 3H) |
| I-52 | (S)-HN-CH(Me)-Ph | (S)-N-(1-phenylethyl)-5H-chromeno[3,4-c]pyridine-8-carboxamide | 331.1 | A:5.12 B:5.59 | (400MHz, methanol-d4) 8.74 (d, J = 6.2 Hz, 1H), 8.70 (s, 1H), 8.30 (d, J = 5.9 Hz, 1H), 8.15 (d, J = 8.1 Hz, 1H), 7.66 (dd, J = 8.1, 1.8 Hz, 1H), 7.56 (d, J = 1.5 Hz, 1H), 7.45-7.38 (m, 2H), 7.34 (t, J = 7.6 Hz, 2H), 7.29-7.18 (m, 1H), 5.39 (s, 2H), 5.30-5.18 (m, 1H), 1.58 (d, J = 7.0 Hz, 3H) |
| I-53 | (S)-HN-CH(Me)-(2-Cl-Ph) | (S)-N-(1-(2-chlorophenyl)ethyl)-5H-chromeno[3,4-c]pyridine-8-carboxamide | 365.0 | A:5.56 B:6.22 | (400MHz, methanol-d4) 9.08 (d, J = 7.5 Hz, 1H), 8.74 (d, J = 5.9 Hz, 1H), 8.69 (s, 1H), 8.28 (d, J = 5.9 Hz, 1H), 8.16 (d, J = 8.1 Hz, 1H), 7.67 (dd, J = 8.3, 1.4 Hz, 1H), 7.58 (d, J = 1.3 Hz, 1H), 7.48 (d, J = 7.5 Hz, 1H), 7.41 (d, J = 7.9 Hz, 1H), 7.36-7.28 (m, 1H), 7.28-7.21 (m, 1H), 5.57 (t, J = 7.2 Hz, 1H), 5.39 (s, 2H), 1.56 (d, J = 7.0 Hz, 3H) |
| I-54 | HN-CH2-(3,5-diCl-Ph) | N-(3,5-dichlorobenzyl)-5H-chromeno[3,4-c]pyridine-8-carboxamide | 385.1 | C:2.74 C-1:2.30 | (500MHz, DMSO-d6) 9.26-9.14 (m, 1H), 8.61 (d, J = 5.2 Hz, 1H), 8.52 (s, 1H), 8.08 (d, J = 7.9 Hz, 1H), 7.86 (d, J = 4.9 Hz, 1H), 7.63 (d, J = 8.2 Hz, 1H), 7.52 (s, 1H), 7.48 (s, 1H), 7.36 (s, 2H), 5.27 (s, 2H), 4.47 (d, J = 5.5 Hz, 2H) |
| I-55 | HN-CH2-(4-Br-Ph) | N-(4-bromobenzyl)-5H-chromeno[3,4-c]pyridine-8-carboxamide | 395.1 | C:2.50 D:3.67 | (500MHz, DMSO-d6) 9.25-9.14 (m, 1H), 8.61 8.43 (m, 2H), 8.02 (d, J = 8.2 Hz, 1H), 7.82 (d, J = 5.2 Hz, 1H), 7.59 (d, J = 8.2 Hz, 1H), 7.53-7.42 (m, 3H), 7.26 (d, J = 7.9 Hz, 2H), 5.23 (s, 2H), 4.41 (d, J = 5.8 Hz, 2H) |

TABLE I-continued

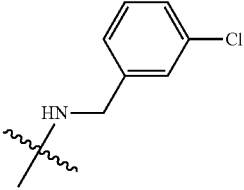 [SMILES: *NCc1cccc(Cl)c1]

| Ex. No. | R | Name | LCMS (M+H)+ | HPLC Method, RT (min.) | 1H NMR (δ, NM) |
|---|---|---|---|---|---|
| I-56 | 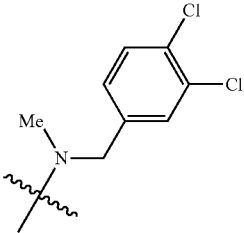 [SMILES: *N(C)Cc1ccc(Cl)c(Cl)c1] | N-(3-chlorobenzyl)-5H-chromeno[3,4-c]pyridine-8-carboxamide | 351.1 | C:2.45 D:3.59 | (500MHz, DMSO-$d_6$) 9.18 (br. s., 1H), 8.61 (d, J = 4.0 Hz, 1H), 8.53 (d, J = 2.1 Hz, 1H), 8.09 (dd, J = 7.8, 3.2 Hz, 1H), 7.87 (br. s., 1H), 7.64 (d, J = 6.1 Hz, 1H), 7.53 (br. s., 1H), 7.42-7.22 (m, 4H), 5.27 (d, J = 2.7 Hz, 2H), 4.48 (br. s., 2H) |
| I-57 | 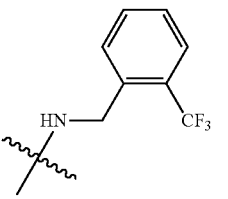 [SMILES: *NCc1ccccc1C(F)(F)F] | N-(3,4-dichlorobenzyl)-N-methyl-5H-chromeno[3,4-c]pyridine-8-carboxamide | 399.1 | C:2.79 D:3.88 | (500MHz, DMSO-$d_6$) 8.60 (br. s., 1H), 8.52 (br. s., 1H), 8.04 (br. s., 1H), 7.84 (br. s., 1H), 7.64 (d, J = 7.9 Hz, 2H), 7.48-7.00 (m, 3H), 5.27 (br. s., 2H), 4.66 (m, 2H), 2.89 (br. s., 3H) |
| I-58 | 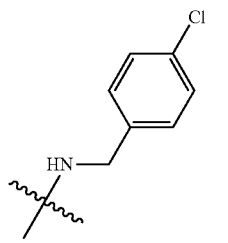 [SMILES: *NCc1ccc(Cl)cc1] | N-(2-(trifluoromethyl)benzyl)-5H-chromeno[3,4-c]pyridine-8-carboxamide | 385.2 | C:2.56 D:3.57 | (500MHz, DMSO-$d_6$) 9.23 (br. s., 1H), 8.58 (d, J = 4.9 Hz, 1H), 8.49 (s, 1H), 8.05 (d, J = 8.2 Hz, 1H), 7.84 (d, J = 4.9 Hz, 1H), 7.76-7.69 (m, 1H), 7.63 (d, J = 7.3 Hz, 2H), 7.54-7.43 (m, 3H), 5.24 (s, 2H), 4.64 (d, J = 5.2 Hz, 2H) |
| I-59 | 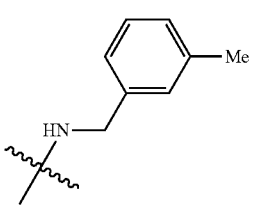 [SMILES: *NCc1cccc(C)c1] | N-(4-chlorobenzyl)-5H-chromeno[3,4-c]pyridine-8-carboxamide | 351.1 | C:2.45 D:3.58 | (500MHz, DMSO-$d_6$) 9.25-9.07 (m, 1H), 8.61 (d, J = 4.9 Hz, 1H), 8.53 (s, 1H), 8.08 (d, J = 8.2 Hz, 1H), 7.87 (d, J = 4.9 Hz, 1H), 7.63 (d, J = 7.3 Hz, 1H), 7.52 (s, 1H), 7.43-7.37 (m, 2H), 7.37-7.25 (m, 2H), 5.27 (s, 2H), 4.46 (d, J = 5.8 Hz, 2H) |
| I-60 | 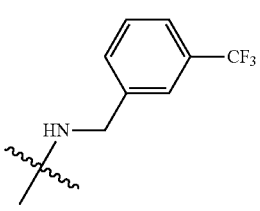 [SMILES: *NCc1cccc(C(F)(F)F)c1] | N-(3-methylbenzyl)-5H-chromeno[3,4-c]pyridine-8-carboxamide | 331.2 | C:2.38 D:3.53 | (500MHz, DMSO-$d_6$) 9.11 (br. s., 1H), 8.61 (d, J = 4.6 Hz, 1H), 8.53 (s, 1H), 8.08 (d, J = 7.6 Hz, 1H), 7.87 (d, J = 5.2 Hz, 1H), 7.65 (d, J = 7.9 Hz, 1H), 7.53 (s, 1H), 7.28-7.17 (m, 1H), 7.16-7.00 (m, 3H), 5.27 (s, 2H), 4.45 (d, J = 5.2 Hz, 2H), 2.29 (s, 3H) |
| I-61 | | N-(3-(trifluoromethyl)benzyl)-5H-chromeno[3,4-c]pyridine-8-carboxamide | 385.1 | C:3.25 C-1:3.27 | (500MHz, DMSO-$d_6$) 9.24 (br. s., 1H), 8.61 (d, J = 5.2 Hz, 1H), 8.53 (s, 1H), 8.09 (d, J = 7.9 Hz, 1H), 7.87 (d, J = 5.2 Hz, 1H), 7.71-7.56 (m, 5H), 7.53 (s, 1H), 5.27 (s, 2H), 4.57 (d, J = 5.2 Hz, 2H) |

TABLE I-continued

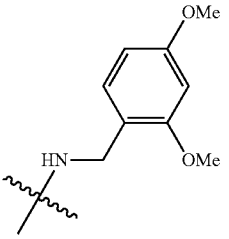 [SMILES: *NCc1ccc(OC)cc1OC]

| Ex. No. | R | Name | LCMS (M+H)+ | HPLC Method, RT (min.) | 1H NMR (δ, NM) |
|---|---|---|---|---|---|
| I-62 | 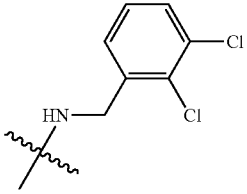 [SMILES: *NCc1cccc(Cl)c1Cl] | N-(2,4-dimethoxybenzyl)-5H-chromeno[3,4-c]pyridine-8-carboxamide | 377.2 | C:2.32 D:3.38 | (500MHz, DMSO-$d_6$) 8.86 (br. s., 1H), 8.60 (d, J = 5.2 Hz, 1H), 8.52 (s, 1H), 8.05 (d, J = 7.9 Hz, 1H), 7.85 (d, J = 5.2 Hz, 1H), 7.63 (d, J = 7.9 Hz, 1H), 7.51 (s, 1H), 7.09 (d, J = 8.2 Hz, 1H), 6.55 (s, 1H), 6.47 (d, J = 8.5 Hz, 1H), 5.26 (s, 2H), 4.36 (d, J = 5.2 Hz, 2H), 3.80 (s, 3H), 3.73 (s, 3H) |
| I-63 | 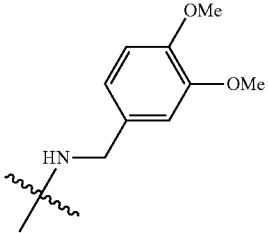 [SMILES: *NCc1ccc(OC)c(OC)c1] | N-(2,3-dichlorobenzyl)-5H-chromeno[3,4-c]pyridine-8-carboxamide | 385.1 | C:2.62 D:3.76 | (500MHz, DMSO-$d_6$) 9.21 (br. s., 1H), 8.60 (d, J = 5.2 Hz, 1H), 8.51 (s, 1H), 8.06 (d, J = 7.9 Hz, 1H), 7.85 (d, J = 4.6 Hz, 1H), 7.63 (d, J = 7.9 Hz, 1H), 7.58-7.47 (m, 2H), 7.39-7.29 (m, 2H), 5.26 (s, 2H), 4.55 (d, J = 5.5 Hz, 2H) |
| I-64 | 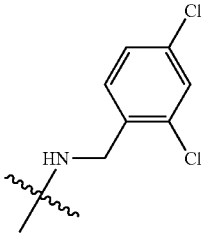 [SMILES: *NCc1ccc(Cl)cc1Cl] | N-(3,4-dimethoxybenzyl)-5H-chromeno[3,4-c]pyridine-8-carboxamide | 377.2 | C:2.04 D:3.09 | (500MHz, DMSO-$d_6$) 9.17-9.03 (m, 1H), 8.57 (d, J = 4.0 Hz, 1H), 8.48 (s, 1H), 8.02 (d, J = 6.4 Hz, 1H), 7.82 (d, J = 4.3 Hz, 1H), 7.58 (d, J = 7.9 Hz, 1H), 7.46 (s, 1H), 6.92 (br. s., 1H), 6.89-6.80 (m, 2H), 5.23 (s, 2H), 4.38 (d, J = 4.3 Hz, 2H), 3.71 (s, 3H), 3.69 (s, 3H) |
| I-65 | 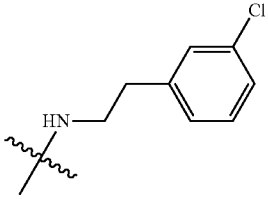 [SMILES: *NCCc1cccc(Cl)c1] | N-(2,4-dichlorobenzyl)-5H-chromeno[3,4-c]pyridine-8-carboxamide | 385.1 | C:2.68 D:3.87 | (500MHz, DMSO-$d_6$) 9.16 (br. s., 1H), 8.62 (d, J = 4.9 Hz, 1H), 8.53 (s, 1H), 8.09 (d, J = 7.9 Hz, 1H), 7.87 (d, J = 5.2 Hz, 1H), 7.70-7.60 (m, 2H), 7.55 (s, 1H), 7.47-7.29 (m, 2H), 5.28 (s, 2H), 4.51 (d, J = 5.2 Hz, 2H) |
| I-66 | | N-(3-chlorophenethyl)-5H-chromeno[3,4-c]pyridine-8-carboxamide | 365.1 | C:2.52 D:3.71 | (500MHz, DMSO-$d_6$) 8.69-8.59 (m, 2H), 8.52 (s, 1H), 8.06 (d, J = 7.9 Hz, 1H), 7.86 (d, J = 5.2 Hz, 1H), 7.55 (d, J = 7.3 Hz, 1H), 7.43 (s, 1H), 7.37-7.17 (m, 4H), 5.26 (s, 2H), 3.50 (m, 2H), 2.87 (t, J = 7.2 Hz, 2H) |

TABLE I-continued

| Ex. No. | R | Name | LCMS (M+H)+ | HPLC Method, RT (min.) | 1H NMR (δ, NM) |
|---|---|---|---|---|---|
| I-67 | HN–C(Me)(Me)–Ph | N-(2-phenylpropan-2-yl)-5H-chromeno[3,4-c]pyridine-8-carboxamide | 345.2 | C:2.48 D:3.54 | (500MHz, DMSO-$d_6$) 8.61 (d, J = 4.9 Hz, 1H), 8.53 (d, J = 4.0 Hz, 2H), 8.05 (d, J = 8.2 Hz, 1H), 7.87 (d, J = 5.2 Hz, 1H), 7.58 (d, J = 8.2 Hz, 1H), 7.51 (s, 1H), 7.38 (d, J = 7.3 Hz, 2H), 7.28 (t, J = 7.6 Hz, 2H), 7.22-7.10 (m, 1H), 5.27 (s, 2H), 1.67 (s, 6H) |
| I-68 | HN–CH2–C6H4–NH2 (2-amino) | N-(2-aminobenzyl)-5H-chromeno[3,4-c]pyridine-8-carboxamide | 332.4 | C:2.00 D:3.11 | (500MHz, DMSO-$d_6$) 9.02 (br. s., 1H), 8.61 (d, J = 4.6 Hz, 1H), 8.52 (s, 1H), 8.07 (d, J = 7.9 Hz, 1H), 7.86 (d, J = 4.9 Hz, 1H), 7.63 (d, J = 8.2 Hz, 1H), 7.51 (s, 1H), 7.03 (d, J = 7.3 Hz, 1H), 6.96 (t, J = 7.6 Hz, 1H), 6.62 (d, J = 7.9 Hz, 1H), 6.51 (t, J = 7.2 Hz, 1H), 5.26 (s, 2H), 5.12 (br. s., 2H), 4.32 (d, J = 5.8 Hz, 2H) |
| I-69 | HN–CH2–C6H4–OH (2-hydroxy) | N-(2-hydroxybenzyl)-5H-chromeno[3,4-c]pyridine-8-carboxamide | 333.1 | C:2.07 D:3.17 | (500MHz, DMSO-$d_6$) 9.78 (s, 1H), 9.17-8.93 (m, 1H), 8.57 (d, J = 4.3 Hz, 1H), 8.48 (s, 1H), 8.13-7.98 (m, 1H), 7.82 (d, J = 5.5 Hz, 1H), 7.60 (d, J = 7.9 Hz, 1H), 7.48 (s, 1H), 7.16-6.99 (m, 2H), 6.88-6.70 (m, 2H), 5.23 (s, 2H), 4.40 (d, J = 5.5 Hz, 2H) |
| I-70 | HN–CH2–C6H4–OH (3-hydroxy) | N-(3-hydroxybenzyl)-5H-chromeno[3,4-c]pyridine-8-carboxamide | 333.2 | C:2.54 D:2.89 | |
| I-71 | HN–CH(Me)–C6H4–Cl (2-Cl, R) | (R)-N-(1-(2-chlorophenyl)ethyl)-5H-chromeno[3,4-c]pyridine-8-carboxamide | 365.0 | A:5.60 B:6.20 | (400MHz, methanol-$d_4$) 9.06 (d, J = 6.6 Hz, 1H), 8.73 (d, J = 5.9 Hz, 1H), 8.68 (s, 1H), 8.27 (d, J = 5.9 Hz, 1H), 8.15 (d, J = 8.1 Hz, 1H), 7.67 (dd, J = 8.1, 1.8 Hz, 1H), 7.57 (d, J = 1.5 Hz, 1H), 7.48 (dd, J = 7.8, 1.7 Hz, 1H), 7.40 (dd, J = 7.9, 1.3 Hz, 1H), 7.35-7.19 (m, 2H), 5.57 (quin, J = 7.0 Hz, 1H), 5.38 (s, 2H), 1.56 (d, J = 7.0 Hz, 3H) |

TABLE I-continued

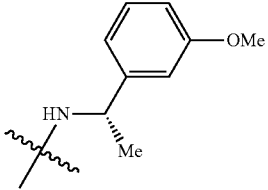 [SMILES: *N[C@@H](C)c1cccc(OC)c1]

| Ex. No. | R | Name | LCMS (M+H)+ | HPLC Method, RT (min.) | ¹H NMR (δ, NM) |
|---|---|---|---|---|---|
| I-72 | 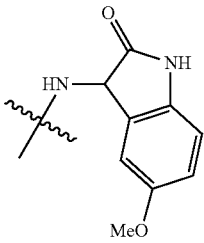 [SMILES: *NC1C(=O)Nc2ccc(OC)cc21] | (S)-N-(1-(3-methoxyphenyl)ethyl)-5H-chromeno[3,4-c]pyridine-8-carboxamide | 361.1 | E:1.30 F:1.63 | (500MHz, DMSO-$d_6$) 8.86 (d, J = 7.7 Hz, 1H), 8.66-8.59 (m, 1H), 8.53 (s, 1H), 8.07 (d, J = 8.0 Hz, 1H), 7.86 (d, J = 4.7 Hz, 1H), 7.63 (d, J = 8.0 Hz, 1H), 7.54 (s, 1H), 7.24 (t, J = 7.8 Hz, 1H), 6.96 (br. s., 2H), 6.80 (d, J = 8.3 Hz, 1H), 5.27 (s, 2H), 5.13 (quin, J = 6.9 Hz, 1H), 3.74 (s, 3H), 1.47 (d, J = 6.9 Hz, 3H) |
| I-73 | 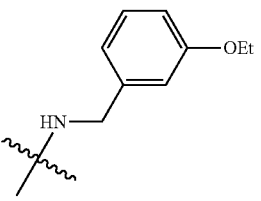 [SMILES: *NCc1cccc(OCC)c1] | N-(5-methoxy-2-oxoindolin-3-yl)-5H-chromeno[3,4-c]pyridine-8-carboxamide | 388.1 | E:1.09 F:1.32 | (500MHz, DMSO-$d_6$) 10.31 (br. s., 1H), 9.41 (d, J = 7.4 Hz, 1H), 8.69 (br. s., 1H), 8.61 (br. s., 1H), 8.15 (d, J = 8.0 Hz, 1H), 8.03 (br. s., 1H), 7.66 (d, J = 8.3 Hz, 1H), 7.55 (br. s., 1H), 6.82-6.72 (m, 3H), 5.31 (s., 2H), 5.21 (d, J = 7.2 Hz, 1H), 3.68 (s., 3H) |
| I-74 | 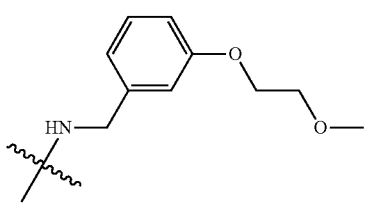 [SMILES: *NCc1cccc(OCCOC)c1] | N-(3-ethoxybenzyl)-5H-chromeno[3,4-c]pyridine-8-carboxamide | 361.1 | E:1.37 F:1.67 | (500MHz, DMSO-$d_6$) 9.10 (br. s., 1H), 8.61 (br. s., 1H), 8.53 (s, 1H), 8.08 (d, J = 8.0 Hz, 1H), 7.87 (br. s., 1H), 7.64 (d, J = 8.0 Hz, 1H), 7.53 (s, 1H), 7.23 (t, J = 7.7 Hz, 1H), 6.91-6.84 (m, 2H), 6.80 (d, J = 8.3 Hz, 1H), 5.27 (s, 2H), 4.45 (d, J = 5.2 Hz, 2H), 4.00 (q, J = 6.6 Hz, 2H), 1.31 (t, J = 6.9 Hz, 3H) |
| I-75 | 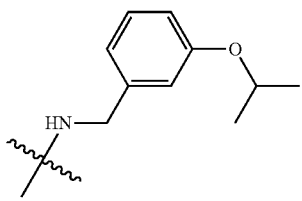 [SMILES: *NCc1cccc(OC(C)C)c1] | N-(3-(2-methoxyethoxy)benzyl)-5H-chromeno[3,4-c]pyridine-8-carboxamide | 391.1 | E:1.27 F:1.53 | (500MHz, DMSO-$d_6$) 9.10 (br. s., 1H), 8.61 (d, J = 2.8 Hz, 1H), 8.53 (s, 1H), 8.08 (d, J = 8.0 Hz, 1H), 7.87 (br. s., 1H), 7.65 (d, J = 8.0 Hz, 1H), 7.53 (s, 1H), 7.23 (t, J = 7.8 Hz, 1H), 6.88 (br. s., 2H), 6.82 (d, J = 8.3 Hz, 1H), 5.27 (s, 2H), 4.45 (d, J = 4.7 Hz, 2H), 4.06 (br. s., 2H), 3.64 (d, J = 2.8 Hz, 2H), 3.27 (s, 3H) |
| I-76 | | N-(3-isopropoxybenzyl)-5H-chromeno[3,4-c]pyridine-8-carboxamide | 375.1 | E:1.46 F:1.77 | (500MHz, DMSO-$d_6$) 9.09 (br. s., 1H), 8.61 (br. s., 1H), 8.53 (s, 1H), 8.08 (d, J = 8.0 Hz, 1H), 7.87 (br. s., 1H), 7.64 (d, J = 8.0 Hz, 1H), 7.53 (s, 1H), 7.22 (t, J = 7.8 Hz, 1H), 6.89-6.83 (m, 2H), 6.79 (d, J = 8.3 Hz, 1H), 5.27 (s, 2H), 4.64-4.52 (m, 1H), 4.44 (d, J = 5.0 Hz, 2H), 1.29-1.16 (m, 6H) |

TABLE I-continued

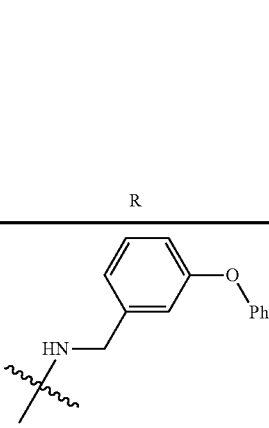

| Ex. No. | R | Name | LCMS (M+H)+ | HPLC Method, RT (min.) | 1H NMR (δ, NM) |
|---|---|---|---|---|---|
| I-77 | 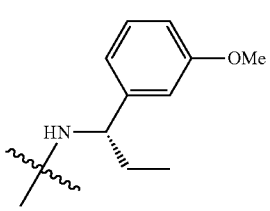 [SMILES: *N[C@@H](CC)c1cccc(OC)c1] | N-(3-phenoxybenzyl)-5H-chromeno[3,4-c]pyridine-8-carboxamide | 409.1 | E:1.62 F:1.92 | (500MHz, DMSO-d6) 9.12 (br. s., 1H), 8.61 (d, J = 2.5 Hz, 1H), 8.53 (s, 1H), 8.07 (d, J = 8.0 Hz, 1H), 7.87 (br. s., 1H), 7.61 (d, J = 8.0 Hz, 1H), 7.50 (s, 1H), 7.43-7.29 (m, 3H), 7.18-7.07 (m, 2H), 7.03-6.95 (m, 3H), 6.87 (d, J = 8.0 Hz, 1H), 5.27 (s, 2H), 4.47 (d, J = 5.0 Hz, 2H) |
| I-78 | 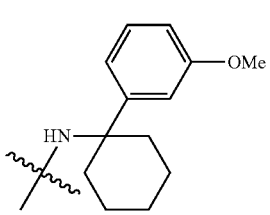 [SMILES: *NC1(c2cccc(OC)c2)CCCCC1] | (S)-N-(1-(3-methoxyphenyl)propyl)-5H-chromeno[3,4-c]pyridine-8-carboxamide | 375.1 | E:1.33 F:1.67 | (500MHz, DMSO-d6) 8.82 (d, J = 8.3 Hz, 1H), 8.71 (d, J = 4.7 Hz, 1H), 8.63 (s, 1H), 8.13 (d, J = 8.0 Hz, 1H), 8.05 (br. s., 1H), 7.64 (d, J = 8.0 Hz, 1H), 7.56 (s, 1H), 7.28-7.18 (m, 1H), 7.02-6.93 (m, 2H), 6.80 (d, J = 8.0 Hz, 1H), 5.32 (s, 2H), 4.88 (m, 1H), 3.74 (s, 3H), 1.92-1.73 (m, 2H), 0.90 (t, J = 7.0 Hz, 3H) |
| I-79 | 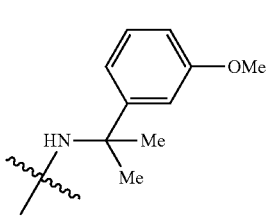 [SMILES: *NC(C)(C)c1cccc(OC)c1] | N-(1-(3-methoxyphenyl)cyclohexyl)-5H-chromeno[3,4-c]pyridine-8-carboxamide | 415.2 | E:1.58 F:1.96 | (500MHz, DMSO-d6) 8.21 (br. s., 1H), 8.06 (d, J = 7.7 Hz, 1H), 7.87 (br. s., 1H), 7.56 (d, J = 7.4 Hz, 1H), 7.49 (br. s., 1H), 7.21 (t, J = 7.4 Hz, 1H), 6.99 (d, J = 7.7 Hz, 1H), 6.94 (br. s., 1H), 6.76 (d, J = 8.0 Hz, 1H), 5.28 (br. s., 2H), 3.71 (br. s., 3H), 2.56 (d, J = 11.6 Hz, 2H), 1.73-1.52 (m, 7H), 1.32 (s, 1H) |
| I-80 | 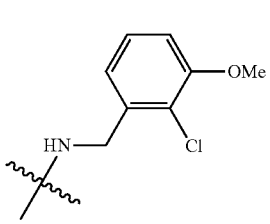 [SMILES: *NCc1cccc(OC)c1Cl] | N-(2-(3-methoxyphenyl)propan-2-yl)-5H-chromeno[3,4-c]pyridine-8-carboxamide | 375.1 | E:1.31 F:1.65 | (500MHz, DMSO-d6) 8.62 (d, J = 5.2 Hz, 1H), 8.52 (d, J = 8.5 Hz, 2H), 8.06 (d, J = 8.3 Hz, 1H), 7.87 (d, J = 5.2 Hz, 1H), 7.57 (dd, J = 8.3, 1.7 Hz, 1H), 7.50 (d, J = 1.4 Hz, 1H), 7.21 (t, J = 8.0 Hz, 1H), 6.95 (d, J = 8.0 Hz, 1H), 6.89 (t, J = 2.1 Hz, 1H), 6.76 (dd, J = 8.1, 2.3 Hz, 1H), 5.27 (s, 2H), 3.71 (s, 3H), 1.65 (s, 6H) |
| I-81 | | N-(2-chloro-3-methoxybenzyl)-5H-chromeno[3,4-c]pyridine-8-carboxamide | 381.0 | E:1.22 F:1.55 | (500MHz, DMSO-d6) 9.15 (t, J = 5.9 Hz, 1H), 8.63 (d, J = 5.2 Hz, 1H), 8.54 (s, 1H), 8.11 (d, J = 8.0 Hz, 1H), 7.89 (d, J = 5.2 Hz, 1H), 7.67 (dd, J = 8.0, 1.7 Hz, 1H), 7.56 (d, J = 1.7 Hz, 1H), 7.29 (t, J = 8.1 Hz, 1H), 7.07 (d, J = 7.4 Hz, 1H), 6.94 (d, J = 7.7 Hz, 1H), 5.29 (s, 2H), 4.54 (d, J = 5.8 Hz, 2H), 3.87 (s, 3H) |

TABLE I-continued

| Ex. No. | R | Name | LCMS (M+H)+ | HPLC Method, RT (min.) | 1H NMR (δ, NM) |
|---|---|---|---|---|---|
| I-82 | (1-(3-ethoxyphenyl)-4-methylcyclohexyl)amino | N-(1-(3-ethoxyphenyl)-4-methylcyclohexyl)-5H-chromeno[3,4-c]pyridine-8-carboxamide | 443.1 | E:1.81 F:2.19 | (500MHz, DMSO-$d_6$) 8.61 (d, J = 5.0 Hz, 1H), 8.52 (s, 1H), 8.23 (s, 1H), 8.03 (d, J = 8.3 Hz, 1H), 7.85 (d, J = 5.2 Hz, 1H), 7.51 (d, J = 8.3 Hz, 1H), 7.44 (s, 1H), 7.25-7.17 (m, 1H), 7.05 (d, J = 8.0 Hz, 1H), 6.99 (s, 1H), 6.75 (dd, J = 8.0, 1.9 Hz, 1H), 5.26 (s, 2H), 3.98 (q, J = 6.9 Hz, 2H), 2.36 (br. s., 2H), 2.11 (d, J = 9.1 Hz, 2H), 1.74 (br. s., 3H), 1.31 (t, J = 6.9 Hz, 3H), 1.14 (br. s., 2H), 0.92 (d, J = 6.1 Hz, 3H) |
| I-83 | (1-(3-ethoxyphenyl)ethyl)amino | N-(1-(3-ethoxyphenyl)ethyl)-5H-chromeno[3,4-c]pyridine-8-carboxamide | 375.1 | E:1.37 | (500MHz, DMSO-$d_6$) 8.87 (d, J = 8.0 Hz, 1H), 8.62 (d, J = 5.0 Hz, 1H), 8.53 (s, 1H), 8.07 (d, J = 8.0 Hz, 1H), 7.87 (d, J = 5.2 Hz, 1H), 7.63 (d, J = 8.0 Hz, 1H), 7.54 (s, 1H), 7.22 (t, J = 7.8 Hz, 1H), 6.98-6.90 (m, 2H), 6.78 (d, J = 8.3 Hz, 1H), 5.27 (s, 2H), 5.12 (quin, J = 7.2 Hz, 1H), 4.00 (q, J = 6.9 Hz, 2H), 1.46 (d, J = 7.2 Hz, 3H), 1.31 (t, J = 6.9 Hz, 3H) |
| I-84 | (3-sulfamoylbenzyl)amino | N-(3-sulfamoylbenzyl)-5H-chromeno[3,4-c]pyridine-8-carboxamide | 396.0 | E:0.91 F:1.14 | (500MHz, DMSO-$d_6$) 9.29 (br. s., 1H), 8.63 (br. s., 1H), 8.55 (s, 1H), 8.12 (d, J = 8.0 Hz, 1H), 7.89 (br. s., 1H), 7.80 (br. s., 1H), 7.76-7.63 (m, 2H), 7.56 (br. s., 3H), 7.39 (br. s., 2H), 5.29 (s, 2H), 4.57 (d, J = 4.7 Hz, 2H) |
| I-85 | (3-(N-ethylsulfamoyl)benzyl)amino | N-(3-(N-ethylsulfamoyl)benzyl)-5H-chromeno[3,4-c]pyridine-8-carboxamide | 424.0 | E:1.09 F:1.33 | (500MHz, DMSO-$d_6$) 9.28 (br. s., 1H), 8.63 (br. s., 1H), 8.55 (br. s., 1H), 8.12 (d, J = 8.0 Hz, 1H), 7.99-7.86 (m, 1H), 7.76 (br. s., 1H), 7.72-7.52 (m, 6H), 5.29 (br. s., 2H), 4.58 (br. s., 2H), 2.76 (d, J = 17.6 Hz, 2H), 0.97 (t, J = 7.0 Hz, 3H) |
| I-86 | (2-oxo-2-o-tolylethyl)amino | N-(2-oxo-2-o-tolylethyl)-5H-chromeno[3,4-c]pyridine-8-carboxamide | 359.2 | C:2.50 D:3.59 | (500MHz, DMSO-$d_6$) 9.03 (t, J = 5.5 Hz, 1H), 8.62 (d, J = 5.2 Hz, 1H), 8.53 (s, 1H), 8.09 (d, J = 7.9 Hz, 1H), 7.95-7.74 (m, 2H), 7.62 (dd, J = 8.2, 1.5 Hz, 1H), 7.51 (d, J = 1.5 Hz, 1H), 7.48-7.42 (m, 1H), 7.38-7.26 (m, 2H), 5.28 (s, 2H), 4.59 (d, J = 5.5 Hz, 2H), 2.42 (s, 3H) |

TABLE I-continued

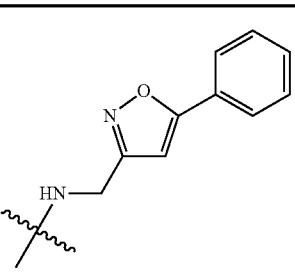

| Ex. No. | R | Name | LCMS (M+H)+ | HPLC Method, RT (min.) | 1H NMR (δ, NM) |
|---|---|---|---|---|---|
| I-87 | 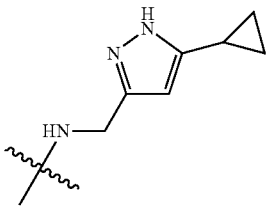 [SMILES: *NCc1cc(C2CC2)[nH]n1] | N-((5-phenylisoxazol-3-yl)methyl)-5H-chromeno[3,4-c]pyridine-8-carboxamide | 384.2 | C:2.58 D:3.71 | (500MHz, DMSO-d$_6$) 9.24 (t, J = 5.3 Hz, 1H), 8.62 (d, J = 5.2 Hz, 1H), 8.53 (s, 1H), 8.10 (d, J = 8.2 Hz, 1H), 7.87 (d, J = 5.8 Hz, 3H), 7.66 (d, J = 8.2 Hz, 1H), 7.58-7.43 (m, 4H), 6.97 (s, 1H), 5.28 (s, 2H), 4.58 (d, J = 5.8 Hz, 2H) |
| I-88 | 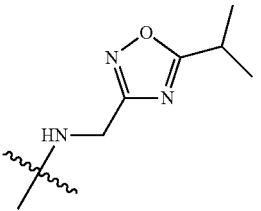 [SMILES: *NCc1noc(C(C)C)n1] | N-((5-cyclopropyl-1H-pyrazol-3-yl)methyl)-5H-chromeno[3,4-c]pyridine-8-carboxamide | 347.2 | C:2.08 D:3.27 | (500MHz, DMSO-d$_6$) 8.95 (br. s., 1H), 8.61 (d, J = 4.9 Hz, 1H), 8.52 (s, 1H), 8.06 (d, J = 7.9 Hz, 1H), 7.86 (d, J = 5.2 Hz, 1H), 7.62 (d, J = 7.9 Hz, 1H), 7.51 (s, 1H), 5.82 (s, 1H), 5.26 (s, 2H), 4.38 (d, J = 5.8 Hz, 2H), 1.87-1.77 (m, 1H), 0.85 (d, J = 6.1 Hz, 2H), 0.61 (d, J = 3.7 Hz, 2H) |
| I-89 | 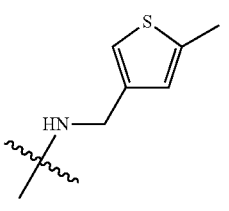 [SMILES: *NCc1csc(C)c1] | N-((5-isopropyl-1,2,4-oxadiazol-3-yl)methyl)-5H-chromeno[3,4-c]pyridine-8-carboxamide | 351.2 | C:2.22 D:3.30 | (500MHz, DMSO-d$_6$) 9.24 (t, J = 5.6 Hz, 1H), 8.62 (d, J = 5.2 Hz, 1H), 8.53 (s, 1H), 8.10 (d, J = 8.2 Hz, 1H), 7.87 (d, J = 4.9 Hz, 1H), 7.63 (dd, J = 8.2, 1.5 Hz, 1H), 7.52 (d, J = 1.5 Hz, 1H), 5.28 (s, 2H), 4.57 (d, J = 5.8 Hz, 2H), 3.29-3.20 (m, 1H), 1.31 (d, J = 7.0 Hz, 6H) |
| I-90 | 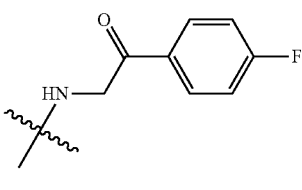 [SMILES: *NCC(=O)c1ccc(F)cc1] | N-((5-methylthiophen-3-yl)methyl)-5H-chromeno[3,4-c]pyridine-8-carboxamide | 337.2 | C:2.49 D:3.63 | (500MHz, DMSO-d$_6$) 9.02 (br. s., 1H), 8.61 (d, J = 4.6 Hz, 1H), 8.53 (s, 1H), 8.07 (d, J = 7.6 Hz, 1H), 7.86 (d, J = 4.6 Hz, 1H), 7.63 (d, J = 7.9 Hz, 1H), 7.52 (s, 1H), 7.04 (s, 1H), 6.77 (br. s., 1H), 5.20 (s, 2H), 4.37 (d, J = 5.5 Hz, 2H), 2.40 (s, 3H) |
| I-91 | | N-(2-(4-fluorophenyl)-2-oxoethyl)-5H-chromeno[3,4-c]pyridine-8-carboxamide | 363.2 | C:2.22 D:3.28 | (500MHz, DMSO-d$_6$) 8.98 (t, J = 5.6 Hz, 1H), 8.62 (d, J = 5.2 Hz, 1H), 8.54 (s, 1H), 8.18-8.05 (m, 3H), 7.88 (d, J = 5.2 Hz, 1H), 7.65 (dd, J = 8.2, 1.5 Hz, 1H), 7.53 (d, J = 1.5 Hz, 1H), 7.40 (t, J = 8.9 Hz, 2H), 5.29 (s, 2H), 4.78 (d, J = 5.5 Hz, 2H) |

TABLE I-continued

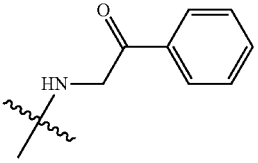 [SMILES: *NCC(=O)c1ccccc1]

| Ex. No. | R | Name | LCMS (M+H)+ | HPLC Method, RT (min.) | ¹H NMR (δ, NM) |
|---|---|---|---|---|---|
| I-92 | 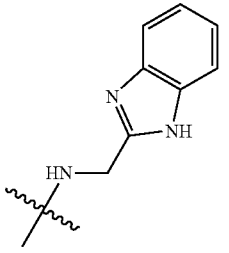 [SMILES: *NCc1nc2ccccc2[nH]1] | N-(2-oxo-2-phenylethyl)-5H-chromeno[3,4-c]pyridine-8-carboxamide | 345.2 | C:2.13 D:3.22 | (500MHz, DMSO-$d_6$) 8.98 (t, J = 5.5 Hz, 1H), 8.62 (d, J = 5.2 Hz, 1H), 8.54 (s, 1H), 8.11 (d, J = 8.2 Hz, 1H), 8.05 (d, J = 7.6 Hz, 2H), 7.88 (d, J = 5.2 Hz, 1H), 7.73-7.62 (m, 2H), 7.60-7.50 (m, 3H), 5.29 (s, 2H), 4.80 (d, J = 5.8 Hz, 2H) |
| I-93 | 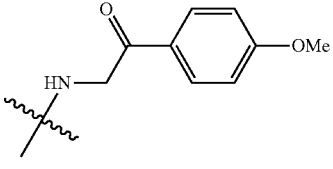 [SMILES: *NCC(=O)c1ccc(OC)cc1] | N-((1H-benzo[d]imidazol-2-yl)methyl)-5H-chromeno[3,4-c]pyridine-8-carboxamide | 357.2 | C:1.85 D:3.10 | (500MHz, DMSO-$d_6$) 12.26 (br. s., 1H), 9.28 (t, J = 5.6 Hz, 1H), 8.80-8.47 (m, 2H), 8.11 (d, J = 8.2 Hz, 1H), 7.88 (d, J = 5.2 Hz, 1H), 7.69 (d, J = 7.9 Hz, 1H), 7.60 (s, 1H), 7.55 (d, J = 7.6 Hz, 1H), 7.44 (d, J = 6.7 Hz, 1H), 7.14 (br. s., 2H), 5.28 (s, 2H), 4.70 (d, J = 5.5 Hz, 2H) |
| I-94 | 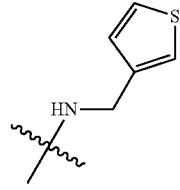 [SMILES: *NCc1ccsc1] | N-(2-(4-methoxyphenyl)-2-oxoethyl)-5H-chromeno[3,4-c]pyridine-8-carboxamide | 375.2 | C:2.18 D:3.28 | (500MHz, DMSO-$d_6$) 8.92 (t, J = 5.5 Hz, 1H), 8.62 (d, J = 4.9 Hz, 1H), 8.54 (s, 1H), 8.10 (d, J = 8.2 Hz, 1H), 8.03 (d, J = 8.5 Hz, 2H), 7.88 (d, J = 5.2 Hz, 1H), 7.65 (dd, J = 7.9, 1.5 Hz, 1H), 7.54 (d, J = 1.5 Hz, 1H), 7.08 (d, J = 8.9 Hz, 2H), 5.29 (s, 2H), 4.74 (d, J = 5.5 Hz, 2H), 3.86 (s, 3H) |
| I-95 | 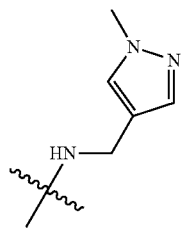 [SMILES: *NCc1cnn(C)c1] | N-(thiophen-3-ylmethyl)-5H-chromeno[3,4-c]pyridine-8-carboxamide | 323.1 | C:2.13 D:3.23 | (500MHz, DMSO-$d_6$) 9.15-8.99 (m, 1H), 8.61 (d, J = 5.2 Hz, 1H), 8.53 (s, 1H), 8.07 (d, J = 8.2 Hz, 1H), 7.87 (d, J = 5.2 Hz, 1H), 7.63 (d, J = 8.2 Hz, 1H), 7.52 (s, 1H), 7.48 (dd, J = 4.6, 3.1 Hz, 1H), 7.33 (br. s., 1H), 7.09 (d, J = 4.6 Hz, 1H), 5.27 (s, 2H), 4.47 (d, J = 6.1 Hz, 2H) |
| I-96 | | N-((1-methyl-1H-pyrazol-4-yl)methyl)-5H-chromeno[3,4-c]pyridine-8-carboxamide | 321.2 | C:1.62 D:2.59 | (500MHz, DMSO-$d_6$) 8.91 (t, J = 5.8 Hz, 1H), 8.61 (d, J = 5.2 Hz, 1H), 8.52 (s, 1H), 8.06 (d, J = 7.9 Hz, 1H), 7.86 (d, J = 5.2 Hz, 1H), 7.66-7.56 (m, 2H), 7.49 (s, 1H), 7.35 (s, 1H), 5.26 (s, 2H), 4.29 (d, J = 5.8 Hz, 2H), 3.78 (s, 3H) |

TABLE I-continued

| Ex. No. | R | Name | LCMS (M+H)⁺ | HPLC Method, RT (min.) | ¹H NMR (δ, NM) |
|---|---|---|---|---|---|
| I-97 | | N-((3-phenyl-1H-pyrazol-4-yl)methyl)-5H-chromeno[3,4-c]pyridine-8-carboxamide | 383.2 | C:2.03 D:3.18 | (500MHz, DMSO-d$_6$) 8.94 (br. s., 1H), 8.61 (d, J = 4.9 Hz, 1H), 8.52 (s, 1H), 8.05 (d, J = 7.9 Hz, 1H), 7.86 (d, J = 4.9 Hz, 1H), 7.66 (d, J = 7.3 Hz, 3H), 7.61 (d, J = 8.2 Hz, 1H), 7.53-7.42 (m, 3H), 7.40-7.31 (m, 1H), 5.26 (s, 2H), 4.49 (d, J = 4.9 Hz, 2H) |
| I-98 | | N-(2-(3-nitrophenyl)-2-oxoethyl)-5H-chromeno[3,4-c]pyridine-8-carboxamide | 390.2 | C:2.14 D:3.17 | (500MHz, DMSO-d$_6$) 9.10 (br. s., 1H), 8.71 (s, 1H), 8.62 (d, J = 4.9 Hz, 1H), 8.56-8.45 (m, 3H), 8.10 (d, J = 7.9 Hz, 1H), 7.91-7.84 (m, 2H), 7.65 (d, J = 7.9 Hz, 1H), 7.53 (s, 1H), 5.28 (s, 2H), 4.87 (d, J = 5.2 Hz, 2H) |
| I-99 | | N-(2-(4-bromophenyl)-2-oxoethyl)-5H-chromeno[3,4-c]pyridine-8-carboxamide | 423.1 | C:2.44 D:3.58 | (500MHz, DMSO-d$_6$) 8.99 (t, J = 5.5 Hz, 1H), 8.62 (d, J = 5.2 Hz, 1H), 8.54 (s, 1H), 8.10 (d, J = 8.2 Hz, 1H), 7.98 (d, J = 8.5 Hz, 2H), 7.88 (d, J = 5.2 Hz, 1H), 7.79 (d, J = 8.5 Hz, 2H), 7.64 (dd, J = 8.1, 1.7 Hz, 1H), 7.53 (d, J = 1.5 Hz, 1H), 5.28 (s, 2H), 4.77 (d, J = 5.5 Hz, 2H) |
| I-100 | | N-((5-methylisoxazol-3-yl)methyl)-5H-chromeno[3,4-c]pyridine-8-carboxamide | 322.2 | D:2.91 | (500MHz, DMSO-d$_6$) 9.16 (t, J = 5.8 Hz, 1H), 8.61 (d, J = 5.2 Hz, 1H), 8.53 (s, 1H), 8.08 (d, J = 8.2 Hz, 1H), 7.87 (d, J = 5.2 Hz, 1H), 7.62 (dd, J = 8.1, 1.7 Hz, 1H), 7.51 (d, J = 1.5 Hz, 1H), 6.17 (s, 1H), 5.27 (s, 2H), 4.46 (d, J = 6.1 Hz, 2H), 2.37 (s, 3H) |
| I-101 | | N-((5-phenyl-1H-imidazol-2-yl)methyl)-5H-chromeno[3,4-c]pyridine-8-carboxamide | 397.2 | C:2.05 | (500MHz, DMSO-d$_6$) 9.12-8.97 (m, 1H), 8.60 (d, J = 4.9 Hz, 1H), 8.52 (s, 1H), 8.02 (d, J = 7.9 Hz, 1H), 7.85 (d, J = 5.2 Hz, 1H), 7.54 (d, J = 8.2 Hz, 1H), 7.41 (s, 1H), 7.35-7.27 (m, 2H), 7.27-7.20 (m, 1H), 7.19-7.10 (m, 3H), 6.88 (s, 1H), 5.29 (s, 2H), 5.25 (s, 2H), 4.52 (d, J = 5.2 Hz, 2H) |

TABLE I-continued

| Ex. No. | R | Name | LCMS (M+H)+ | HPLC Method, RT (min.) | 1H NMR (δ, NM) |
|---|---|---|---|---|---|
| I-102 | (2-oxo-2-(pyridin-3-yl)ethyl)amino | N-(2-oxo-2-(pyridin-3-yl)ethyl)-5H-chromeno[3,4-c]pyridine-8-carboxamide | 346.2 | C:1.47 D:2.68 | (500MHz, DMSO-d$_6$) 9.21 (s, 1H), 9.05 (t, J = 5.3 Hz, 1H), 8.83 (d, J = 4.9 Hz, 1H), 8.62 (d, J = 4.9 Hz, 1H), 8.54 (s, 1H), 8.37 (d, J = 7.9 Hz, 1H), 8.11 (d, J = 7.9 Hz, 1H), 7.88 (d, J = 5.2 Hz, 1H), 7.69-7.58 (m, 2H), 7.53 (s, 1H), 5.29 (s, 2H), 4.81 (d, J = 5.5 Hz, 2H) |
| I-103 | (2-(4-chlorophenyl)-2-oxoethyl)amino | N-(2-(4-chlorophenyl)-2-oxoethyl)-5H-chromeno[3,4-c]pyridine-8-carboxamide | 379.2 | D:3.54 | (500MHz, DMSO-d$_6$) 9.00 (t, J = 5.5 Hz, 1H), 8.62 (d, J = 5.2 Hz, 1H), 8.54 (s, 1H), 8.10 (d, J = 8.2 Hz, 1H), 8.06 (d, J = 8.5 Hz, 2H), 7.88 (d, J = 5.2 Hz, 1H), 7.64 (d, J = 8.5 Hz, 3H), 7.53 (d, J = 1.5 Hz, 1H), 5.29 (s, 2H), 4.78 (d, J = 5.5 Hz, 2H) |
| I-104 | (2-(4-nitrophenyl)-2-oxoethyl)amino | N-(2-(4-nitrophenyl)-2-oxoethyl)-5H-chromeno[3,4-c]pyridine-8-carboxamide | 390.2 | D:3.23 | (500MHz, DMSO-d$_6$) 9.09 (t, J = 5.3 Hz, 1H), 8.61 (d, J = 5.2 Hz, 1H), 8.53 (s, 1H), 8.37 (d, J = 8.9 Hz, 2H), 8.26 (d, J = 8.9 Hz, 2H), 8.09 (d, J = 8.2 Hz, 1H), 7.87 (d, J = 5.5 Hz, 1H), 7.64 (dd, J = 8.1, 1.7 Hz, 1H), 7.52 (d, J = 1.5 Hz, 1H), 5.28 (s, 2H), 4.84 (d, J = 5.5 Hz, 2H) |
| I-105 | (3-(methylsulfonyl)benzyl)amino | N-(3-(methylsulfonyl)benzyl)-5H-chromeno[3,4-c]pyridine-8-carboxamide | 395.0 | E:1.02 F:1.23 | (500MHz, DMSO-d$_6$) 9.33 (br. s., 1H), 8.75 (br. s., 1H), 8.67 (br. s., 1H), 8.19 (d, J = 7.4 Hz, 1H), 8.11 (br. s., 1H), 7.94-7.80 (m, 2H), 7.76-7.54 (m, 4H), 5.35 (br. s., 2H), 4.61 (br. s., 2H), 3.23 (br. s., 3H) |
| I-106 | (1-(3,5-difluorophenyl)ethyl)amino | N-(1-(3,5-difluorophenyl)ethyl)-5H-chromeno[3,4-c]pyridine-8-carboxamide | 367.0 | E:1.35 F:1.66 | (500MHz, DMSO-d$_6$) 8.96 (d, J = 7.7 Hz, 1H), 8.73 (d, J = 5.5 Hz, 1H), 8.65 (s, 1H), 8.16 (d, J = 8.0 Hz, 1H), 8.08 (d, J = 5.5 Hz, 1H), 7.67 (dd, J = 8.0, 1.7 Hz, 1H), 7.59 (d, J = 1.7 Hz, 1H), 7.20-7.05 (m, 3H), 5.34 (s, 2H), 5.18 (t, J = 7.3 Hz, 1H), 1.49 (d, J = 7.2 Hz, 3H) |

TABLE I-continued

| Ex. No. | R | Name | LCMS (M+H)+ | HPLC Method, RT (min.) | 1H NMR (δ, NM) |
|---|---|---|---|---|---|
| I-107 | | N-(3-(morpholine-4-carbonyl)benzyl)-5H-chromeno[3,4-c]pyridine-8-carboxamide | 430.1 | E:1.04 F:1.22 | (500MHz, DMSO-d$_6$) 9.17 (t, J = 5.9 Hz, 1H), 8.61 (d, J = 5.0 Hz, 1H), 8.53 (s, 1H), 8.09 (d, J = 8.3 Hz, 1H), 7.87 (d, J = 5.2 Hz, 1H), 7.64 (dd, J = 8.3, 1.7 Hz, 1H), 7.53 (d, J = 1.7 Hz, 1H), 7.41 (d, J = 5.2 Hz, 2H), 7.35 (s, 1H), 7.28 (td, J = 4.4, 1.7 Hz, 1H), 5.27 (s, 2H), 4.52 (d, J = 5.8 Hz, 2H), 3.58 (br. s., 8H) |
| I-108 | | N-(2-chloro-4-fluorobenzyl)-5H-chromeno[3,4-c]pyridine-8-carboxamide | 369.0 | E:1.34 F:1.65 | (500MHz, DMSO-d$_6$) 9.12 (t, J = 5.6 Hz, 1H), 8.62 (d, J = 5.0 Hz, 1H), 8.53 (s, 1H), 8.09 (d, J = 8.0 Hz, 1H), 7.87 (d, J = 5.2 Hz, 1H), 7.65 (dd, J = 8.3, 1.7 Hz, 1H), 7.55 (d, J = 1.7 Hz, 1H), 7.49-7.38 (m, 2H), 7.22 (td, J = 8.5, 2.8 Hz, 1H), 5.28 (s, 2H), 4.51 (d, J = 5.5 Hz, 2H) |
| I-109 | | N-(2,4-difluoro-3-methoxybenzyl)-5H-chromeno[3,4-c]pyridine-8-carboxamide | 383.0 | E:1.27 F:1.56 | (500MHz, DMSO-d$_6$) 9.10 (t, J = 5.8 Hz, 1H), 8.60 (br. s., 1H), 8.08 (d, J = 8.3 Hz, 1H), 7.89 (br. s., 1H), 7.63 (dd, J = 8.1, 1.8 Hz, 1H), 7.52 (d, J = 1.7 Hz, 1H), 7.15-7.04 (m, 2H), 5.27 (s, 2H), 4.48 (d, J = 5.8 Hz, 2H), 3.92 (s, 3H) |
| I-110 | | N-(2,6-difluoro-3-methoxybenzyl)-5H-chromeno[3,4-c]pyridine-8-carboxamide | 383.0 | E:1.22 F:1.49 | (500MHz, DMSO-d$_6$) 8.98 (br. s., 1H), 8.61 (br. s., 1H), 8.52 (br. s., 1H), 8.05 (d, J = 7.7 Hz, 1H), 7.86 (br. s., 1H), 7.59 (d, J = 8.0 Hz, 1H), 7.48 (br. s., 1H), 7.19-7.09 (m, 1H), 7.08-6.96 (m, 1H), 5.25 (br. s., 2H), 4.51 (br. s., 2H), 3.82 (br. s., 3H) |
| I-111 | | (R)-N-(1-(3-ethoxyphenyl)ethyl)-5H-chromeno[3,4-c]pyridine-8-carboxamide | 375.1 | A:5.71 B:6.36 | (400MHz, methanol-d$_4$) 8.67-8.30 (m, 2H), 7.93 (d, J = 8.1 Hz, 1H), 7.77 (d, J = 3.7 Hz, 1H), 7.55 (dd, J = 8.1, 1.5 Hz, 1H), 7.46 (d, J = 1.5 Hz, 1H), 7.22 (t, J = 8.0 Hz, 1H), 7.02-6.91 (m, 2H), 6.83-6.72 (m, 1H), 5.2 (s, 2H), 5.20-5.13 (m, 1H), 4.01 (q, J = 6.9 Hz, 2H), 1.55 (d, J = 7.0 Hz, 3H), 1.36 (t, J = 6.9 Hz, 3H) |

TABLE I-continued

| Ex. No. | R | Name | LCMS (M+H)+ | HPLC Method, RT (min.) | 1H NMR (δ, NM) |
|---|---|---|---|---|---|
| I-112 | (S-configured 1-(3-ethoxyphenyl)ethyl amine substituent) | (S)-N-(1-(3-ethoxyphenyl)ethyl)-5H-chromeno[3,4-c]pyridine-8-carboxamide | 375.0 | A:5.65 B:6.34 | (400MHz, methanol-$d_4$) 8.51 (d, J = 5.3 Hz, 1H), 8.40 (s, 1H), 7.92 (d, J = 8.1 Hz, 1H), 7.75 (d, J = 5.3 Hz, 1H), 7.54 (dd, J = 8.0, 1.7 Hz, 1H), 7.45 (d, J = 1.5 Hz, 1H), 7.27-7.15 (m, 1H), 7.01-6.91 (m, 2H), 6.82-6.72 (m, 1H), 5.24-5.13 (m, 3H), 4.00 (q, J = 6.9 Hz, 2H), 1.54 (d, J = 7.0 Hz, 3H), 1.35 (t, J = 6.9 Hz, 3H) |
| I-113 | ((1H-1,2,4-triazol-3-yl)methylamino) | N-((1H-1,2,4-triazol-3-yl)methyl)-5H-chromeno[3,4-c]pyridine-8-carboxamide | 308.2 | C:1.24 | (500MHz, DMSO-$d_6$) 9.14 (br. s., 1H), 8.61 (d, J = 5.2 Hz, 1H), 8.53 (s, 1H), 8.18 (br. s., 1H), 8.08 (d, J = 7.9 Hz, 1H), 7.87 (d, J = 5.2 Hz, 1H), 7.64 (d, J = 7.9 Hz, 1H), 7.53 (s, 1H), 5.27 (s, 2H), 4.55 (d, J = 5.5 Hz, 2H) |
| I-114 | (thiazol-2-ylmethylamino) | N-(thiazol-2-ylmethyl)-5H-chromeno[3,4-c]pyridine-8-carboxamide | 324.5 | D:2.70 | (500MHz, DMSO-$d_6$) 9.49 (t, J = 6.0 Hz, 1H), 8.62 (d, J = 4.9 Hz, 1H), 8.54 (s, 1H), 8.11 (d, J = 8.2 Hz, 1H), 7.88 (d, J = 5.2 Hz, 1H), 7.74 (d, J = 3.4 Hz, 1H), 7.70-7.60 (m, 2H), 7.54 (d, J = 1.5 Hz, 1H), 5.28 (s, 2H), 4.76 (d, J = 5.8 Hz, 2H) |
| I-115 | (5-tert-butyl-2-carboxyfuran-3-yl)methylamino | 3-((5H-chromeno[3,4-c]pyridine-8-carboxamido)methyl)-5-tert-butylfuran-2-carboxylic acid | 324.5 | D:2.70 | (500MHz, DMSO-$d_6$) 8.61 (d, J = 5.2 Hz, 1H), 8.53 (s, 1H), 8.07 (d, J = 8.2 Hz, 1H), 7.87 (d, J = 5.2 Hz, 1H), 7.65 (d, J = 8.2 Hz, 1H), 7.54 (s, 1H), 6.19 (s, 1H), 5.27 (s, 2H), 4.60 (d, J = 5.2 Hz, 2H), 1.23 (s, 9H) |
| I-116 | ((1H-imidazol-2-yl)methylamino) | N-((1H-imidazol-2-yl)methyl)-5H-chromeno[3,4-c]pyridine-8-carboxamide | 307.2 | C:1.40 | (500MHz, DMSO-$d_6$) 9.09 (t, J = 5.5 Hz, 1H), 8.61 (d, J = 5.2 Hz, 1H), 8.53 (s, 1H), 8.08 (d, J = 7.9 Hz, 1H), 7.87 (d, J = 5.2 Hz, 1H), 7.65 (dd, J = 7.9, 1.5 Hz, 1H), 7.55 (d, J = 1.8 Hz, 1H), 6.94 (s, 2H), 5.27 (s, 2H), 4.50 (d, J = 5.8 Hz, 2H) |

TABLE I-continued

| Ex. No. | R | Name | LCMS (M+H)+ | HPLC Method, RT (min.) | 1H NMR (δ, NM) |
|---|---|---|---|---|---|
| I-117 | (oxazol-2-ylmethyl)amino | N-(oxazol-2-ylmethyl)-5H-chromeno[3,4-c]pyridine-8-carboxamide | 308.5 | C:1.66 | (500MHz, DMSO-$d_6$) 9.25 (t, J = 5.6 Hz, 1H), 8.62 (d, J = 5.2 Hz, 1H), 8.53 (s, 1H), 8.09 (d, J = 8.2 Hz, 1H), 8.05 (s, 1H), 7.87 (d, J = 5.2 Hz, 1H), 7.63 (d, J = 8.2 Hz, 1H), 7.52 (d, J = 1.2 Hz, 1H), 7.16 (s, 1H), 5.28 (s, 2H), 4.59 (d, J = 5.8 Hz, 2H) |
| I-118 | ((2-bromothiophen-3-yl)methyl)amino | N((2-bromothiophen-3-yl)methyl)-5H-chromeno[3,4-c]pyridine-8-carboxamide | 401.0 | D:3.57 | (500MHz, DMSO-$d_6$) 9.11 (br. s., 1H), 8.61 (d, J = 4.9 Hz, 1H), 8.53 (s, 1H), 8.08 (d, J = 7.9 Hz, 1H), 7.87 (d, J = 4.9 Hz, 1H), 7.63 (d, J=7.9 Hz, 1H), 7.58-7.45 (m, 2H), 7.00 (d, J = 5.5 Hz, 1H), 5.27 (s, 2H), 4.38 (d, J = 5.5 Hz, 2H) |
| I-119 | ((3,5-dimethylisoxazol-4-yl)methyl)amino | N-((3,5-dimethylisoxazol-4-yl)methyl)-5H-chromeno[3,4-c]pyridine-8-carboxamide | 336.2 | C:1.84 | (500MHz, DMSO-$d_6$) 8.89 (t, J = 5.3 Hz, 1H), 8.61 (d, J = 5.2 Hz, 1H), 8.52 (s, 1H), 8.06 (d, J = 8.2 Hz, 1H), 7.86 (d, J = 5.2 Hz, 1H), 7.59 (dd, J = 8.1, 1.7 Hz, 1H), 7.48 (d, J = 1.5 Hz, 1H), 5.26 (s, 2H), 4.21 (d, J = 5.5 Hz, 2H), 2.40 (s, 3H), 2.22 (s, 3H) |
| I-120 | ((6-oxo-1,6-dihydropyridin-3-yl)methyl)amino | N-((6-oxo-1,6-dihydropyridin-3-yl)methyl)-5H-chromeno[3,4-c]pyridine-8-carboxamide | 334.2 | C:1.69 | (500MHz, DMSO-$d_6$) 8.96 (t, J = 5.6 Hz, 1H), 8.61 (d, J = 5.2 Hz, 1H), 8.52 (s, 1H), 8.07 (d, J = 8.2 Hz, 1H), 7.86 (d, J = 5.2 Hz, 1H), 7.60 (dd, J = 7.9, 1.5 Hz, 1H), 7.49 (d, J = 1.5 Hz, 1H), 7.43 (dd, J = 9.5, 2.7 Hz, 1H), 7.29 (d, J = 1.8 Hz, 1H), 6.31 (d, J = 9.5 Hz, 1H), 5.26 (s, 2H), 4.19 (d, J = 5.8 Hz, 2H) |
| I-121 | (2-(3-fluorophenyl)-2-oxoethyl)amino | N-(2-(3-fluorophenyl)-2-oxoethyl)-5H-chromeno[3,4-c]pyridine-8-carboxamide | 363.2 | C:2.16 | (500MHz, DMSO-$d_6$) 9.01 (t, J = 5.6 Hz, 1H), 8.62 (d, J = 5.2 Hz, 1H), 8.54 (s, 1H), 8.11 (d, J = 7.9 Hz, 1H), 7.95-7.86 (m, 2H), 7.83 (d, J = 9.5 Hz, 1H), 7.69-7.60 (m, 2H), 7.58-7.48 (m, 2H), 5.29 (s, 2H), 4.79 (d, J = 5.8 Hz, 2H) |

TABLE I-continued

| Ex. No. | R | Name | LCMS (M+H)+ | HPLC Method, RT (min.) | 1H NMR (δ, NM) |
|---|---|---|---|---|---|
| I-122 | (5-phenyl-1,3,4-oxadiazol-2-yl)methyl attached via HN-CH2 | N-((5-phenyl-1,3,4-oxadiazol-2-yl)methyl)-5H-chromeno[3,4-c]pyridine-8-carboxamide | 385.2 | C:2.02 | (500MHz, DMSO-d6) 9.40 (t, J = 5.3 Hz, 1H), 8.62 (d, J = 5.2 Hz, 1H), 8.53 (s, 1H), 8.11 (d, J = 7.9 Hz, 1H), 8.02-7.96 (m, 2H), 7.87 (d, J = 5.2 Hz, 1H), 7.70-7.51 (m, 5H), 5.28 (s, 2H), 4.80 (d, J = 5.5 Hz, 2H) |
| I-123 | (1,2,4-oxadiazol-3-yl)methyl attached via HN-CH2 | N-((1,2,4-oxadiazol-3-yl)methyl)-5H-chromeno[3,4-c]pyridine-8-carboxamide | 309.2 | C:1.45 | (500MHz, DMSO-d6) 9.56 (s, 1H), 9.28 (t, J = 5.6 Hz, 1H), 8.62 (d, J = 5.2 Hz, 1H), 8.53 (s, 1H), 8.10 (d, J = 8.2 Hz, 1H), 7.87 (d, J = 5.2 Hz, 1H), 7.63 (d, J = 7.9 Hz, 1H), 7.51 (s, 1H), 5.28 (s, 2H), 4.64 (d, J = 5.5 Hz, 2H) |
| I-124 | 1-(3-fluorophenyl)ethyl attached via HN-CH(Me) | N-(1-(3-fluorophenyl)ethyl)-5H-chromeno[3,4-c]pyridine-8-carboxamide | 349.0 | E:1.30 F:1.59 | (500MHz, DMSO-d6) 8.96 (d, J = 7.7 Hz, 1H), 8.74 (d, J = 5.5 Hz, 1H), 8.66 (s, 1H), 8.16 (d, J = 8.0 Hz, 1H), 8.10 (d, J = 5.5 Hz, 1H), 7.68 (dd, J = 8.3, 1.7 Hz, 1H), 7.59 (d, J = 1.7 Hz, 1H), 7.39 (td, J = 8.0, 6.1 Hz, 1H), 7.30-7.19 (m, 2H), 7.07 (td, J = 8.5, 2.3 Hz, 1H), 5.34 (s, 2H), 5.19 (t, J = 7.3 Hz, 1H), 1.50 (d, J = 6.9 Hz, 3H) |
| I-125 | 2-fluoro-5-methoxybenzyl attached via HN-CH2 | N-(2-fluoro-5-methoxybenzyl)-5H-chromeno[3,4-c]pyridine-8-carboxamide | 365.2 | E:1.14 F:1.50 | (500MHz, DMSO-d6) 9.08 (t, J = 5.8 Hz, 1H), 8.62 (d, J = 5.2 Hz, 1H), 8.53 (s, 1H), 8.08 (d, J = 8.3 Hz, 1H), 7.87 (d, J = 5.2 Hz, 1H), 7.64 (dd, J = 8.3, 1.7 Hz, 1H), 7.53 (d, J = 1.7 Hz, 1H), 7.12 (t, J = 9.2 Hz, 1H), 6.90 (dd, J = 6.1, 3.0 Hz, 1H), 6.85 (dt, J = 8.9, 3.7 Hz, 1H), 5.27 (s, 2H), 4.48 (d, J = 5.8 Hz, 2H), 3.71 (s, 3H) |
| I-126 | 5-fluoro-2-methylbenzyl attached via HN-CH2 | N-(5-fluoro-2-methylbenzyl)-5H-chromeno[3,4-c]pyridine-8-carboxamide | 349.0 | E:1.22 F:1.60 | (500MHz, DMSO-d6) 9.06 (br. s., 1H), 8.72-8.49 (m, 2H), 8.10 (d, J = 8.0 Hz, 1H), 7.88 (d, J = 5.0 Hz, 1H), 7.67 (d, J = 8.0 Hz, 1H), 7.56 (s, 1H), 7.27-7.19 (m, 1H), 7.01 (t, J = 8.8 Hz, 2H), 5.29 (s, 2H), 4.45 (d, J = 5.2 Hz, 2H), 2.31 (s, 3H) |

TABLE I-continued

| Ex. No. | R | Name | LCMS (M+H)+ | HPLC Method, RT (min.) | 1H NMR (δ, NM) |
|---|---|---|---|---|---|
| I-127 | 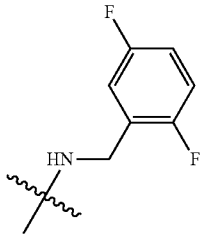 [SMILES: *NCc1cc(F)ccc1F] | N-(2,5-difluorobenzyl)-5H-chromeno[3,4-c]pyridine-8-carboxamide | 353.0 | E:1.14 F:1.52 | (500MHz, DMSO-d6) 9.15 (t, J = 5.8 Hz, 1H), 8.63 (d, J = 5.0 Hz, 1H), 8.55 (s, 1H), 8.10 (d, J = 8.3 Hz, 1H), 7.89 (d, J = 5.2 Hz, 1H), 7.66 (dd, J = 8.0, 1.7 Hz, 1H), 7.55 (d, J = 1.7 Hz, 1H), 7.34-7.23 (m, 1H), 7.22-7.12 (m, 2H), 5.29 (s, 2H), 4.52 (d, J = 5.8 Hz, 2H) |
| I-128 | 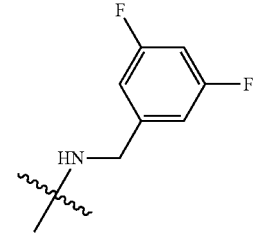 [SMILES: *NCc1cc(F)cc(F)c1] | N-(3,5-difluorobenzyl)-5H-chromeno[3,4-c]pyridine-8-carboxamide | 353.1 | E:1.18 F:1.55 | (500MHz, DMSO-d6) 9.19 (t, J = 5.8 Hz, 1H), 8.66 (d, J = 5.0 Hz, 1H), 8.58 (s, 1H), 8.12 (d, J = 8.0 Hz, 1H), 7.95 (s, 1H), 7.66 (d, J = 8.0 Hz, 1H), 7.55 (s, 1H), 7.15-7.00 (m, 3H), 5.30 (s, 2H), 4.50 (d, J = 6.1 Hz, 2H) |
| I-129 | 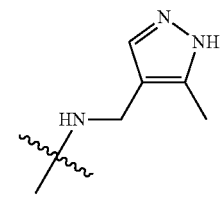 [SMILES: *NCc1cn[nH]c1C] | N-((5-methyl-1H-pyrazol-4-yl)methyl)-5H-chromeno[3,4-c]pyridine-8-carboxamide | 321.2 | C:1.42 D:2.64 | (500MHz, DMSO-d6) 8.79 (t, J = 5.2 Hz, 1H), 8.60 (d, J = 5.2 Hz, 1H), 8.52 (s, 1H), 8.05 (d, J = 8.2 Hz, 1H), 7.85 (d, J = 5.2 Hz, 1H), 7.60 (d, J = 8.2 Hz, 1H), 7.48 (s, 1H), 7.42 (br. s., 1H), 5.25 (s, 2H), 4.26 (d, J = 5.2 Hz, 2H), 2.20 (s, 3H) |
| I-130 | 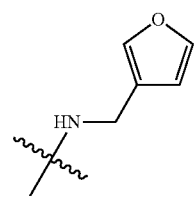 [SMILES: *NCc1ccoc1] | N-(furan-3-ylmethyl)-5H-chromeno[3,4-c]pyridine-8-carboxamide | 307.2 | C:1.76 D:3.03 | (500MHz, DMSO-d6) 8.95 (t, J = 5.8 Hz, 1H), 8.61 (d, J = 5.2 Hz, 1H), 8.52 (s, 1H), 8.07 (d, J = 8.2 Hz, 1H), 7.86 (d, J = 5.2 Hz, 1H), 7.64-7.57 (m, 3H), 7.50 (d, J = 1.5 Hz, 1H), 6.47 (s, 1H), 5.26 (s, 2H), 4.31 (d, J = 5.8 Hz, 2H) |
| I-131 | 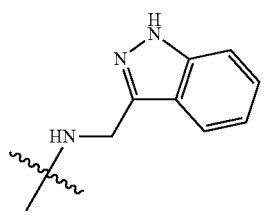 [SMILES: *NCc1n[nH]c2ccccc12] | N-((1H-indazol-3-yl)methyl)-5H-chromeno[3,4-c]pyridine-8-carboxamide | 357.2 | C:2.12 D:3.14 | (500MHz, DMSO-d6) 12.85 (br. s., 1H), 9.19 (br. s., 1H), 8.60 (d, J = 5.2 Hz, 1H), 8.51 (s, 1H), 8.05 (d, J = 7.9 Hz, 1H), 7.90-7.75 (m, 2H), 7.64 (d, J = 7.9 Hz, 1H), 7.56-7.44 (m, 2H), 7.32 (t, J = 7.2 Hz, 1H), 7.07 (t, J = 7.2 Hz, 1H), 5.25 (s, 2H), 4.83 (d, J = 5.8 Hz, 2H) |
| I-132 | 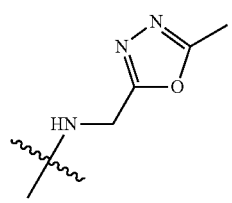 [SMILES: *NCc1nnc(C)o1] | N-((5-methyl-1,3,4-oxadiazol-2-yl)methyl)-5H-chromeno[3,4-c]pyridine-8-carboxamide | 323.2 | C:1.66 D:2.44 | (500MHz, DMSO-d6) 9.44-9.24 (m, 1H), 8.64 (d, J = 5.2 Hz, 1H), 8.56 (s, 1H), 8.12 (d, J = 8.2 Hz, 1H), 7.90 (d, J = 5.2 Hz, 1H), 7.66 (d, J = 8.2 Hz, 1H), 7.54 (s, 1H), 5.30 (s, 2H), 4.69 (d, J = 5.5 Hz, 2H), 2.52 (br. s., 3H) |

TABLE I-continued

| Ex. No. | R | Name | LCMS (M+H)+ | HPLC Method, RT (min.) | 1H NMR (δ, NM) |
|---|---|---|---|---|---|
| I-133 | | N-((4,5,6,7-tetrahydro-1H-indazol-3-yl)methyl)-5H-chromeno[3,4-c]pyridine-8-carboxamide | 361.3 | C:2.13 D:3.26 | (500MHz, DMSO-d$_6$) 8.84 (t, J = 5.2 Hz, 1H), 8.59 (d, J = 5.2 Hz, 1H), 8.50 (s, 1H), 8.04 (d, J = 8.2 Hz, 1H), 7.84 (d, J = 5.2 Hz, 1H), 7.61 (d, J = 7.9 Hz, 1H), 7.49 (s, 1H), 5.24 (s, 2H), 4.38 (d, J = 5.5 Hz, 2H), 2.52-2.49 (m, 2H), 2.36 (t, J = 5.8 Hz, 2H), 1.72-1.54 (m, 4H) |
| I-134 | | N-((5-(2-fluorophenyl)-1,3,4-oxadiazol-2-yl)methyl)-5H-chromeno[3,4-c]pyridine-8-carboxamide | 403.2 | C:2.17 D:3.13 | (500MHz, DMSO-d$_6$) 9.40 (t, J = 5.5 Hz, 1H), 8.62 (d, J = 5.2 Hz, 1H), 8.53 (s, 1H), 8.11 (d, J = 8.2 Hz, 1H), 8.00 (td, J = 7.6, 1.7 Hz, 1H), 7.88 (d, J = 5.2 Hz, 1H), 7.75-7.67 (m, 1H), 7.65 (dd, J = 8.1, 1.7 Hz, 1H), 7.53 (d, J = 1.5 Hz, 1H), 7.52-7.36 (m, 2H), 5.28 (s, 2H), 4.81 (d, J = 5.5 Hz, 2H) |
| I-135 | | N-(imidazo[1,2-a]pyridin-6-ylmethyl)-5H-chromeno[3,4-c]pyridine-8-carboxamide | 357.2 | C:1.79 D:2.73 | (500MHz, DMSO-d$_6$) 9.16 (t, J = 5.6 Hz, 1H), 8.61 (d, J = 5.2 Hz, 1H), 8.53 (s, 1H), 8.49 (s, 1H), 8.08 (d, J = 8.2 Hz, 1H), 7.96 (s, 1H), 7.87 (d, J = 5.2 Hz, 1H), 7.64 (dd, J = 8.2, 1.5 Hz, 1H), 7.57-7.49 (m, 3H), 7.23 (dd, J = 9.5, 1.5 Hz, 1H), 5.27 (s, 2H), 4.48 (d, J = 5.8 Hz, 2H) |
| I-136 | | N-((5-ethyl-1,3,4-oxadiazol-2-yl)methyl)-5H-chromeno[3,4-c]pyridine-8-carboxamide | 337.2 | C:1.79 D:2.67 | (500MHz, DMSO-d$_6$) 9.30 (t, J = 5.6 Hz, 1H), 8.62 (d, J = 5.2 Hz, 1H), 8.53 (s, 1H), 8.10 (d, J = 7.9 Hz, 1H), 7.87 (d, J = 5.2 Hz, 1H), 7.63 (dd, J = 8.2, 1.5 Hz, 1H), 7.51 (d, J = 1.5 Hz, 1H), 5.28 (s, 2H), 4.67 (d, J = 5.5 Hz, 2H), 2.84 (q, J = 7.6 Hz, 2H), 1.24 (t, J = 7.5 Hz, 3H) |
| I-137 | | N-((5-cyclopropylisoxazol-3-yl)methyl)-5H-chromeno[3,4-c]pyridine-8-carboxamide | 348.2 | C:2.19 D:3.14 | (500MHz, DMSO-d$_6$) 9.13 (br. s., 1H), 8.62 (d, J = 4.9 Hz, 1H), 8.53 (s, 1H), 8.08 (d, J = 7.9 Hz, 1H), 7.87 (d, J = 5.2 Hz, 1H), 7.62 (d, J = 7.6 Hz, 1H), 7.51 (br. s., 1H), 6.12 (s, 1H), 5.27 (s, 2H), 4.44 (d, J = 5.8 Hz, 2H), 2.11 (br. s., 1H), 1.08-0.98 (m, 2H), 0.90-0.77 (m, 2H) |

TABLE I-continued

| Ex. No. | R | Name | LCMS (M+H)+ | HPLC Method, RT (min.) | 1H NMR (δ, NM) |
|---|---|---|---|---|---|
| I-138 | 4-bromothiazol-2-yl (via CH2NH) | N((4-bromothiazol-2-yl)methyl)-5H-chromeno[3,4-c]pyridine-8-carboxamide | 402.1 404.1 | C:2.19 D:3.15 | (500MHz, DMSO-d6) 9.53 (t, J = 5.8 Hz, 1H), 8.62 (d, J = 5.2 Hz, 1H), 8.54 (s, 1H), 8.11 (d, J = 8.2 Hz, 1H), 7.88 (d, J = 5.2 Hz, 1H), 7.75 (s, 1H), 7.64 (dd, J = 7.9, 1.5 Hz, 1H), 7.53 (d, J = 1.5 Hz, 1H), 5.28 (s, 2H), 4.74 (d, J = 5.8 Hz, 2H) |
| I-139 | benzo[c][1,2,5]thiadiazol-4-yl (via CH2NH) | N-(benzo[c][1,2,5]thiadiazol-4-ylmethyl)-5H-chromeno[3,4-c]pyridine-8-carboxamide | 375.2 | C:2.33 D:3.34 | (500MHz, DMSO-d6) 9.28 (t, J = 5.6 Hz, 1H), 8.62 (d, J = 5.2 Hz, 1H), 8.54 (s, 1H), 8.10 (d, J = 8.2 Hz, 1H), 8.00 (d, J = 8.5 Hz, 1H), 7.88 (d, J = 5.2 Hz, 1H), 7.76-7.65 (m, 2H), 7.62-7.47 (m, 2H), 5.28 (s, 2H), 4.99 (d, J = 5.5 Hz, 2H) |
| I-140 | 1H-pyrazol-4-yl (via CH2NH) | N-((1H-pyrazol-4-yl)methyl)-5H-chromeno[3,4-c]pyridine-8-carboxamide | 307.2 | C:1.62 D:2.44 | (500MHz, DMSO-d6) 8.90 (t, J = 5.5 Hz, 1H), 8.61 (d, J = 5.2 Hz, 1H), 8.52 (s, 1H), 8.05 (d, J = 7.9 Hz, 1H), 7.86 (d, J = 5.2 Hz, 1H), 7.61 (dd, J = 8.2, 1.5 Hz, 2H), 7.49 (d, J = 1.5 Hz, 2H), 5.26 (s, 1H), 4.34 (d, J = 5.5 Hz, 1H) |
| I-141 | 5-(furan-2-yl)isoxazol-3-yl (via CH2NH) | N-((5-(furan-2-yl)isoxazol-3-yl)methyl)-5H-chromeno[3,4-c]pyridine-8-carboxamide | 374.1 | C:2.32 D:3.26 | (500MHz, DMSO-d6) 9.24 (t, J = 5.8 Hz, 1H), 8.62 (d, J = 5.2 Hz, 1H), 8.53 (s, 1H), 8.10 (d, J = 8.2 Hz, 1H), 7.92 (s, 1H), 7.87 (d, J = 5.2 Hz, 1H), 7.66-7.61 (m, 1H), 7.54 (d, J = 1.5 Hz, 1H), 7.14 (d, J = 3.4 Hz, 1H), 6.77-6.69 (m, 2H), 5.28 (s, 2H), 4.56 (d, J = 5.8 Hz, 2H) |
| I-142 | 3-(methoxymethyl)-1,2,4-oxadiazol-5-yl (via CH2NH) | N-((3-(methoxymethyl)-1,2,4-oxadiazol-5-yl)methyl)-5H-chromeno[3,4-c]pyridine-8-carboxamide | 353.2 | C:1.82 D:2.65 | (500MHz, DMSO-d6) 9.44 (t, J = 5.6 Hz, 1H), 8.62 (d, J = 5.2 Hz, 1H), 8.54 (s, 1H), 8.11 (d, J = 8.2 Hz, 1H), 7.88 (d, J = 5.2 Hz, 1H), 7.64 (dd, J = 7.9, 1.5 Hz, 1H), 7.53 (d, J = 1.2 Hz, 1H), 5.28 (s, 2H), 4.76 (d, J = 5.8 Hz, 2H), 4.53 (s, 2H), 3.33 (br. s., 3H) |

TABLE I-continued

| Ex. No. | R | Name | LCMS (M+H)+ | HPLC Method, RT (min.) | 1H NMR (δ, NM) |
|---|---|---|---|---|---|
| I-143 | (1-methyl-1H-pyrazol-3-yl)methyl, via HN-CH2 linker | N-((1-methyl-1H-pyrazol-3-yl)methyl)-5H-chromeno[3,4-c]pyridine-8-carboxamide | 321.1 | C:1.74 D:2.98 | (500MHz, DMSO-d$_6$) 8.99 (t, J = 5.8 Hz, 1H), 8.60 (d, J = 5.2 Hz, 1H), 8.52 (s, 1H), 8.06 (d, J = 8.2 Hz, 1H), 7.86 (d, J = 5.5 Hz, 1H), 7.62 (dd, J = 7.9, 1.5 Hz, 1H), 7.57 (d, J = 1.8 Hz, 1H), 7.50 (d, J = 1.5 Hz, 1H), 6.12 (d, J = 2.1 Hz, 1H), 5.26 (s, 2H), 4.40 (d, J = 5.8 Hz, 2H), 3.78 (s, 3H) |
| I-144 | (1,5-dimethyl-1H-pyrazol-3-yl)methyl, via HN-CH2 linker | N-((1,5-dimethyl-1H-pyrazol-3-yl)methyl)-5H-chromeno[3,4-c]pyridine-8-carboxamide | 335.1 | C:1.86 D:3.17 | (500MHz, DMSO-d$_6$) 8.94 (t, J = 5.6 Hz, 1H), 8.61 (d, J = 5.2 Hz, 1H), 8.52 (s, 1H), 8.05 (d, J = 7.9 Hz, 1H), 7.86 (d, J = 5.2 Hz, 1H), 7.62 (dd, J = 7.9, 1.5 Hz, 1H), 7.50 (d, J = 1.2 Hz, 1H), 5.93 (s, 1H), 5.26 (s, 2H), 4.33 (d, J = 5.5 Hz, 2H), 3.65 (s, 3H), 2.19 (s, 3H) |
| I-145 | 2,5-dimethyl-3-carboxyfuran-4-ylmethyl, via HN-CH2 linker | 4-((5H-chromeno[3,4-c]pyridine-8-carboxamido)methyl)-2,5-dimethylfuran-3-carboxylic acid | 379.2 | C:1.77 D:2.93 | (500MHz, DMSO-d$_6$) 8.75 (br. s., 1H), 8.60 (d, J = 4.9 Hz, 1H), 8.52 (s, 1H), 8.03 (d, J = 8.2 Hz, 1H), 7.84 (d, J = 5.5 Hz, 1H), 7.59-7.51 (m, 1H), 7.44 (s, 1H), 5.25 (s, 2H), 4.38 (d, J = 4.6 Hz, 2H), 2.45 (s, 3H), 2.23 (s, 3H) |
| I-146 | benzo[b]thiophen-3-ylmethyl, via HN-CH2 linker | N-(benzo[b]thiophen-3-ylmethyl)-5H-chromeno[3,4-c]pyridine-8-carboxamide | 373.1 | C:2.65 D:3.68 | (500MHz, DMSO-d$_6$) 9.14 (t, J = 5.5 Hz, 1H), 8.61 (d, J = 5.2 Hz, 1H), 8.52 (s, 1H), 8.07 (d, J = 7.9 Hz, 1H), 7.97 (dd, J = 16.9, 7.8 Hz, 2H), 7.86 (d, J = 5.2 Hz, 1H), 7.64 (d, J = 7.9 Hz, 1H), 7.59 (s, 1H), 7.53 (s, 1H), 7.48-7.34 (m, 2H), 5.26 (s, 2H), 4.73 (d, J = 5.5 Hz, 2H) |
| I-147 | 2-(3-chlorothiophen-2-yl)-2-oxoethyl, via HN-CH2 linker | N-(2-(3-chlorothiophen-2-yl)-2-oxoethyl)-5H-chromeno[3,4-c]pyridine-8-carboxamide | 385.1 | C:2.25 D:3.50 | (500MHz, DMSO-d$_6$) 9.04 (t, J = 5.5 Hz, 1H), 8.62 (d, J = 5.2 Hz, 1H), 8.54 (s, 1H), 8.16-8.08 (m, 2H), 7.88 (d, J = 5.2 Hz, 1H), 7.65 (dd, J = 8.1, 1.4 Hz, 1H), 7.53 (d, J = 1.2 Hz, 1H), 7.32 (d, J = 5.2 Hz, 1H), 5.29 (s, 2H), 4.70 (d, J = 5.5 Hz, 2H) |

TABLE I-continued

| Ex. No. | R | Name | LCMS (M+H)+ | HPLC Method, RT (min.) | 1H NMR (δ, NM) |
|---|---|---|---|---|---|
| I-148 | 5-chlorobenzo[b]thiophen-3-yl methylamine group | N-((5-chlorobenzo[b]thiophen-3-yl)methyl)-5H-chromeno[3,4-c]pyridine-8-carboxamide | 407.0 | C:2.79 D:4.09 | (500MHz, DMSO-d6) 9.18 (t, J = 5.6 Hz, 1H), 8.61 (d, J = 5.2 Hz, 1H), 8.52 (s, 1H), 8.12-8.06 (m, 2H), 8.03 (d, J = 8.5 Hz, 1H), 7.86 (d, J = 5.2 Hz, 1H), 7.71 (s, 1H), 7.63 (dd, J = 7.9, 1.5 Hz, 1H), 7.52 (d, J = 1.5 Hz, 1H), 7.41 (dd, J = 8.5, 2.1 Hz, 1H), 5.26 (s, 2H), 4.69 (d, J = 5.5 Hz, 2H) |
| I-149 | 4-bromo-1-ethyl-1H-pyrazol-3-yl methylamine group | N-((4-bromo-1-ethyl-1H-pyrazol-3-yl)methyl)-5H-chromeno[3,4-c]pyridine-8-carboxamide | 413.0 415.0 | C:2.15 D:3.44 | (500MHz, DMSO-d6) 8.91 (t, J = 5.3 Hz, 1H), 8.60 (d, J = 5.2 Hz, 1H), 8.52 (s, 1H), 8.05 (d, J = 8.2 Hz, 1H), 7.95 (s, 1H), 7.86 (d, J = 5.2 Hz, 1H), 7.62 (d, J = 7.9 Hz, 1H), 7.51 (s, 1H), 5.26 (s, 2H), 4.43 (d, J = 5.2 Hz, 2H), 4.08 (q, J = 7.3 Hz, 2H), 1.34 (t, J = 7.2 Hz, 3H) |
| I-150 | 4-bromo-1-methyl-1H-pyrazol-3-yl methylamine group | N-((4-bromo-1-methyl-1H-pyrazol-3-yl)methyl)-5H-chromeno[3,4-c]pyridine-8-carboxamide | 399.1 401.1 | C:1.98 D:3.28 | (500MHz, DMSO-d6) 8.97-8.86 (m, 1H), 8.61 (d, J = 4.9 Hz, 1H), 8.52 (s, 1H), 8.05 (d, J = 8.2 Hz, 1H), 7.89 (s, 1H), 7.86 (d, J = 5.2 Hz, 1H), 7.62 (dd, J = 7.9, 1.5 Hz, 1H), 7.51 (d, J = 1.5 Hz, 1H), 5.26 (s, 2H), 4.41 (d, J = 5.5 Hz, 2H), 3.79 (s, 3H) |
| I-151 | benzo[d]oxazol-2-yl methylamine group | N-(benzo[d]oxazol-2-ylmethyl)-5H-chromeno[3,4-c]pyridine-8-carboxamide | 358.1 | C:2.14 D:3.48 | (500MHz, DMSO-d6) 9.41 (t, J = 5.5 Hz, 1H), 8.62 (d, J = 5.2 Hz, 1H), 8.54 (s, 1H), 8.11 (d, J = 8.2 Hz, 1H), 7.88 (d, J = 5.2 Hz, 1H), 7.76-7.63 (m, 3H), 7.56 (d, J = 1.5 Hz, 1H), 7.43-7.30 (m, 2H), 5.28 (s, 2H), 4.78 (d, J = 5.5 Hz, 2H) |
| I-152 | 5-methyl-4H-1,2,4-triazol-3-yl methylamine group | N-((5-methyl-4H-1,2,4-triazol-3-yl)methyl)-5H-chromeno[3,4-c]pyridine-8-carboxamide | 322.1 | C:1.53 D:2.69 | (500MHz, DMSO-d6) 8.61 (d, J = 4.9 Hz, 1H), 8.52 (s, 1H), 8.07 (d, J = 8.2 Hz, 1H), 7.86 (d, J = 4.9 Hz, 1H), 7.64 (d, J = 8.2 Hz, 1H), 7.53 (s, 1H), 5.27 (s, 2H), 4.46 (br. s., 2H), 2.29 (br. s., 3H) |

TABLE I-continued

| Ex. No. | R | Name | LCMS (M+H)+ | HPLC Method, RT (min.) | 1H NMR (δ, NM) |
|---|---|---|---|---|---|
| I-153 | pyrazolo[1,5-a]pyridin-2-ylmethylamino | N-(pyrazolo[1,5-a]pyridin-2-ylmethyl)-5H-chromeno[3,4-c]pyridine-8-carboxamide | 357.1 | C:2.03 D:3.39 | (500MHz, DMSO-d$_6$) 9.18 (t, J = 5.8 Hz, 1H), 8.68-8.57 (m, 2H), 8.53 (s, 1H), 8.08 (d, J = 8.2 Hz, 1H), 7.86 (d, J = 5.2 Hz, 1H), 7.66 (dd, J = 7.9, 1.5 Hz, 1H), 7.61 (d, J = 8.9 Hz, 1H), 7.55 (d, J = 1.5 Hz, 1H), 7.25-7.11 (m, 1H), 6.82 (td, J = 6.9, 1.2 Hz, 1H), 6.50 (s, 1H), 5.27 (s, 2H), 4.65 (d, J = 5.8 Hz, 2H) |
| I-154 | (1H-indol-3-yl)methylamino | N-((1H-indol-3-yl)methyl)-5H-chromeno[3,4-c]pyridine-8-carboxamide | 356.1 | C:2.25 D:3.20 | (500MHz, DMSO-d$_6$) 10.91 (br. s., 1H), 8.91 (br. s., 1H), 8.59 (d, J = 4.9 Hz, 1H), 8.51 (s, 1H), 8.03 (d, J = 8.2 Hz, 1H), 7.84 (d, J = 4.9 Hz, 1H), 7.62 (t, J = 9.2 Hz, 2H), 7.50 (s, 1H), 7.35 (d, J = 7.9 Hz, 1H), 7.29 (br. s., 1H), 7.07 (t, J = 7.5 Hz, 1H), 7.00-6.92 (m, 1H), 5.24 (s, 2H), 4.62 (d, J = 5.5 Hz, 2H) |
| I-155 | (5-amino-1H-1,2,4-triazol-3-yl)methylamino | N-((5-amino-1H-1,2,4-triazol-3-yl)methyl)-5H-chromeno[3,4-c]pyridine-8-carboxamide | 323.1 | C:1.47 D:2.52 | (500MHz, DMSO-d$_6$) 8.60 (d, J = 5.2 Hz, 1H), 8.51 (s, 1H), 8.04 (d, J = 8.2 Hz, 1H), 7.93 (s, 1H), 7.85 (d, J = 4.9 Hz, 1H), 7.61 (d, J = 8.2 Hz, 1H), 7.50 (s, 1H), 5.25 (s, 2H), 4.29 (br. s., 2H) |
| I-156 | (5-phenyl-1H-imidazol-2-yl)methylamino | N-((5-phenyl-1H-imidazol-2-yl)methyl)-5H-chromeno[3,4-c]pyridine-8-carboxamide | 383.2 | C:2.19 D:3.33 | (400MHz, CD$_3$OD) 8.55 (d, J = 5.5 Hz, 1H), 8.44 (s, 1H), 7.99 (d, J = 8.0 Hz, 1H), 7.81 (d, J = 5.3 Hz, 1H), 7.71-7.61 (m, 3H), 7.55 (d, J = 1.8 Hz, 1H), 7.41-7.31 (m, 3H), 7.26-7.17 (m, 1H), 5.24 (s, 2H), 4.67 (s, 2H) |
| I-157 | (2,5-dimethylfuran-3-yl)methylamino | N-((2,5-dimethylfuran-3-yl)methyl)-5H-chromeno[3,4-c]pyridine-8-carboxamide | 335.2 | C:2.35 D:3.69 | (400MHz, CD$_3$OD) 8.54 (d, J = 5.3 Hz, 1H), 8.43 (s, 1H), 7.96 (d, J = 8.3 Hz, 1H), 7.79 (d, J = 5.3 Hz, 1H), 7.54 (dd, J = 8.0, 1.8 Hz, 1H), 7.43 (d, J = 1.8 Hz, 1H), 5.92 (s, 1H), 5.23 (s, 2H), 4.26 (s, 2H), 2.25 (s, 3H), 2.17 (d, J = 0.5 Hz, 3H) |

TABLE I-continued

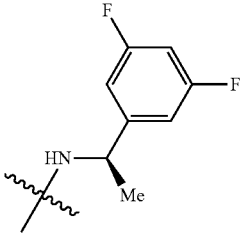 [SMILES: *N[C@H](C)c1cc(F)cc(F)c1]

| Ex. No. | R | Name | LCMS (M+H)+ | HPLC Method, RT (min.) | ¹H NMR (δ, NM) |
|---|---|---|---|---|---|
| I-158 | 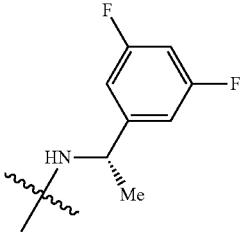 | (R)-N-(1-(3,5-difluorophenyl) ethyl)-5H-chromeno[3,4-c]pyridine-8-carboxamide | 367.0 | A:5.95 B:5.95 | (400MHz, CD$_3$OD) 8.6-8.46 (m, 2H), 7.92 (d, J = 8.1 Hz, 1H), 7.74 (d, J = 4.8 Hz, 1H), 7.55 (d, J = 8.1 Hz, 1H), 7.45 (s, 1H), 6.99 (d, J = 6.6 Hz, 2H), 6.87-6.56 (m, 1H), 5.20 (s, 2H), 1.55 (d, J = 7.0 Hz, 3H) |
| I-159 | 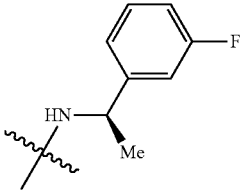 [SMILES: *N[C@H](C)c1cccc(F)c1] | (S)-N-(1-(3,5-difluorophenyl) ethyl)-5H-chromeno[3,4-c] pyridine-8-carboxamide | 367.1 | A:5.43 B:6.00 | (400MHz, CD$_3$OD) 8.54 (d, J = 3.3 Hz, 1H), 8.44 (br. s., 1H), 7.98 (d, J = 7.9 Hz, 1H), 7.80 (d, J = 5.3 Hz, 1H), 7.58 (dd, J = 8.0, 1.7 Hz, 1H), 7.49 (d, J = 1.5 Hz, 1H), 7.00 (dd, J = 8.4, 2.0 Hz, 2H), 6.88-6.73 (m, 1H), 5.23 (s, 2H), 1.56 (d, J = 7.3 Hz, 3H) |
| I-160 | 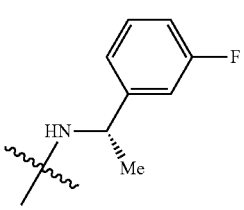 | (R)-N-(1-(3-fluorophenyl) ethyl)-5H-chromeno[3,4-c] pyridine-8-carboxamide | 349.0 | A:5.17 B:5.78 | (400MHz, CD$_3$OD) 8.51 (br. s., 1H), 8.41 (br. s., 1H), 7.95 (d, J = 8.1 Hz, 1H), 7.78 (d, J = 5.1 Hz, 1H), 7.55 (dd, J = 8.1, 1.8 Hz, 1H), 7.45 (d, J = 1.5 Hz, 1H), 7.31 (td, J = 8.0, 6.1 Hz, 1H), 7.18 (d, J = 7.9 Hz, 1H), 7.10 (dt, J = 10.2, 2.0 Hz, 1H), 6.99-6.87 (m, 1H), 5.25-5.13 (m, 3H), 1.53 (d, J = 7.3 Hz, 3H) |
| I-161 | | (S)-N-(1-(3-fluorophenyl) ethyl)-5H-chromeno[3,4-c] pyridine-8-carboxamide | 349.0 | A:5.17 B:5.79 | (400MHz, CD$_3$OD) 8.74-8.30 (m, 2H), 7.98 (d, J = 8.1 Hz, 1H), 7.82 (d, J = 3.3 Hz, 1H), 7.58 (d, J = 7.9 Hz, 1H), 7.49 (s, 1H), 7.40-7.28 (m, 1H), 7.21 (d, J = 7.7 Hz, 1H), 7.14 (d, J = 10.3 Hz, 1H), 7.02-6.92 (m, 1H), 5.28-5.18 (m, 3H), 1.57 (d, J = 7.0 Hz, 3H) |

TABLE I-continued

[Structure: 5H-chromeno[3,4-c]pyridine-8-carboxamide core with R group on the carbonyl]

| Ex. No. | R | Name | LCMS (M+H)+ | HPLC Method, RT (min.) | ¹H NMR (δ, NM) |
|---|---|---|---|---|---|
| I-162 | [(R)-HN-CH(Me)-(4-F-phenyl)] | (R)-N-(1-(4-fluorophenyl) ethyl)-5H-chromeno[3,4-c] pyridine-8-carboxamide | 349.0 | E:1.28 F:1.62 | (500MHz, DMSO-d₆) 8.91 (d, J = 7.7 Hz, 1H), 8.69 (d, J = 5.0 Hz, 1H), 8.61 (s, 1H), 8.12 (d, J = 8.0 Hz, 1H), 8.02 (d, J = 5.0 Hz, 1H), 7.64 (d, J = 8.0 Hz, 1H), 7.56 (s, 1H), 7.43 (t, J = 6.3 Hz, 2H), 7.15 (t, J = 8.4 Hz, 2H), 5.31 (s, 2H), 5.16 (t, J = 7.0 Hz, 1H), 1.48 (d, J = 6.9 Hz, 3H) |
| I-163 | [HN-CH₂-(3-NHSO₂Me-phenyl)] | N-(3-(methylsulfonamido) benzyl)-5H-chromeno[3,4-c] pyridine-8-carboxamide | 410.0 | E:0.90 F:1.17 | (500MHz, DMSO-d₆) 9.14 (t, J = 5.2 Hz, 1H), 8.62 (d, J = 4.7 Hz, 1H), 8.53 (s, 1H), 8.08 (d, J = 8.3 Hz, 1H), 7.87 (d, J = 5.0 Hz, 1H), 7.64 (d, J = 8.0 Hz, 1H), 7.53 (s, 1H), 7.36-7.23 (m, 1H), 7.17 (s, 1H), 7.09 (d, J = 8.0 Hz, 1H), 7.05 (d, J = 7.4 Hz, 1H), 5.27 (s, 2H), 4.46 (d, J = 5.5 Hz, 2H), 2.97 (s, 3H) |
| I-164 | [HN-CH(Ph)-CH₂-CH₂-OH] | N-(3-hydroxy-1-phenylpropyl)-5H-chromeno[3,4-c]pyridine-8-carboxamide | 361.1 | E:0.96 F:1.24 | (500MHz, DMSO-d₆) 8.85 (d, J = 8.0 Hz, 1H), 8.61 (d, J = 4.7 Hz, 1H), 8.53 (s, 1H), 8.07 (d, J = 7.7 Hz, 1H), 7.86 (d, J = 4.4 Hz, 1H), 7.61 (d, J = 8.0 Hz, 1H), 7.53 (s, 1H), 7.42-7.36 (m, 2H), 7.32 (t, J = 7.2 Hz, 2H), 7.25-7.18 (m, 1H), 5.27 (s, 2H), 5.15 (q, J = 7.1 Hz, 1H), 4.56 (br. s., 1H), 3.44 (dd, J = 13.9, 6.2 Hz, 2H), 2.13-1.98 (m, 1H), 1.97-1.83 (m, 1H) |
| I-165 (Enantiomer 1) | [HN-CH(Ph)-CH₂-CH₂-OH] | N-(3-hydroxy-1-phenylpropyl)-5H-chromeno[3,4-c]pyridine-8-carboxamide | 361.1 | A:4.05 B:4.40 | (400MHz, DMSO-d₆) 8.85 (d, J = 8.1 Hz, 1H), 8.62 (d, J = 5.1 Hz, 1H), 8.53 (s, 1H), 8.07 (d, J = 8.1 Hz, 1H), 7.86 (d, J = 5.3 Hz, 1H), 7.61 (dd, J = 8.1, 1.8 Hz, 1H), 7.53 (d, J = 1.5 Hz, 1H), 7.43-7.36 (m, 2H), 7.35-7.29 (m, 2H), 7.26-7.17 (m, 1H), 5.27 (s, 2H), 5.21-5.08 (m, 1H), 4.56 (t, J = 4.8 Hz, 1H), 3.53-3.36 (m, 2H), 2.13-1.99 (m, 1H), 1.91 (dt, J = 213.3, 6.8 Hz, 1H) |

TABLE I-continued

| Ex. No. | R | Name | LCMS (M+H)+ | HPLC Method, RT (min.) | 1H NMR (δ, NM) |
|---|---|---|---|---|---|
| I-166 (Enantiomer 2) | 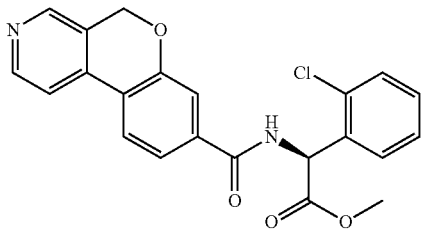 | N-(3-hydroxy-1-phenylpropyl)-5H-chromeno[3,4-c]pyridine-8-carboxamide | 361.1 | A:4.05 B:4.38 | (400MHz, DMSO-d6) 8.85 (d, J = 8.1 Hz, 1H), 8.62 (d, J = 5.1 Hz, 1H), 8.53 (s, 1H), 8.07 (d, J = 8.1 Hz, 1H), 7.87 (d, J = 5.3 Hz, 1H), 7.61 (dd, J = 8 .0 , 1.7 Hz, 1H), 7.53 (d, J = 1.5 Hz, 1H), 7.43-7.36 (m, 2H), 7.35-7.29 (m, 2H), 7.27-7.18 (m, 1H), 5.27 (s, 2H), 5.20-5.07 (m, 1H), 4.56 (t, J = 5.0 Hz, 1H), 3.53-3.37 (m, 2H), 2.14-1.99 (m, 1H), 1.90 (dq, J = 13.3, 6.6 Hz, 1H) |

EXAMPLE II-1

(S)-Methyl 2-(2-chlorophenyl)-2-(5H-chromeno[3,4-c]pyridine-8-carboxamido)acetate

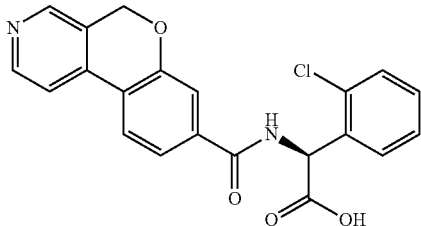 [SMILES: O=C(N[C@H](C(=O)O)c1ccccc1Cl)c1ccc2c(c1)OCc1cnccc1-2]

To a suspension of Intermediate 1 (40 mg, 0.176 mmol) in DCM (2 mL) were added (S)-methyl 2-amino-2-(2-chlorophenyl)acetate, HCl salt (49.9 mg, 0.211 mmol), DIEA (0.154 mL, 0.880 mmol), and T3P (50% in EtOAc, 0.293 mL, 0.493 mmol) at rt. The reaction was stirred under argon at rt for 3 h. Purification by reverse phase chromatography afforded Example II-1 (12 mg, 13%). LC-MS (ESI) m/z: 409.1 [M+H]+; 1H NMR (400 MHz, CD3OD) δ 8.78 (d, J=6.2 Hz, 1H), 8.74 (s, 1H), 8.38 (d, J=6.2 Hz, 1H), 8.17 (d, J=8.4 Hz, 1H), 7.68 (dd, J=8.3, 1.7 Hz, 1H), 7.57 (d, J=1.8 Hz, 1H), 7.53-7.46 (m, 2H), 7.40-7.36 (m, 2H), 6.18 (s, 1H), 5.41 (s, 2H), 3.80 (s, 3H); Analytical HPLC RT A: 5.34 min, B: 6.41 min.

EXAMPLE II-2

(S)-2-(2-Chlorophenyl)-2-(5H-chromeno[3,4-c]pyridine-8-carboxamido)acetic acid

To a solution of Example II-1 (130 mg, 0.249 mmol) in EtOH (5 mL) was added NaOH (1N, 1.740 mL, 1.740 mmol) at rt. The reaction was stirred under argon at RT for 1.5 h. To the reaction mixture was added HCl (4 N, 0.373 mL, 1.492 mmol) dropwise to adjust pH to ~4. Purification by reverse phase chromatography afforded Example II-2 as TFA salt (95 mg, 75% yield). LC-MS (ESI) m/z: 395.0 [M+H]+; 1H NMR (400 MHz, CD3OD) δ 8.84-8.67 (m, 2H), 8.39 (d, J=6.4 Hz, 1H), 8.15 (d, J=8.4 Hz, 1H), 7.66 (dd, J=8.1, 1.8 Hz, 1H), 7.58-7.45 (m, 3H), 7.41-7.30 (m, 2H), 6.14 (s, 1H), 5.40 (s, 2H), 2.03 (s, 1H); Analytical HPLC RT A: 4.40 min, B: 4.99 min.

EXAMPLE II-3

(S)-N-(1-(2-Chlorophenyl)-2-(methylamino)-2-oxoethyl)-5H-chromeno[3,4-c]pyridine-8-carboxamide

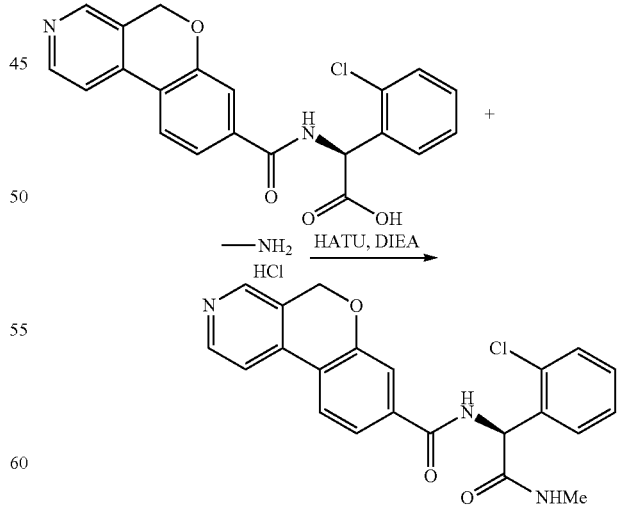

To a solution of Example II-2 (20 mg, 0.039 mmol) in DMF (1 mL) were added methanamine hydrochloride (31.8 mg, 0.472 mmol), DIEA (0.124 mL, 0.708 mmol), and HATU (26.9 mg, 0.071 mmol) at rt. The reaction was stirred under argon at rt overnight. Purification by reverse phase chromatography afforded Example II-3 (10.6 mg, 66%). LC-MS (ESI) m/z: 408.1[M+H]$^+$; $^1$H NMR (500 MHz, DMSO-d$_6$) δ 9.10 (d, J=7.7 Hz, 1H), 8.61 (d, J=5.2 Hz, 1H), 8.53 (s, 1H), 8.13 (d, J=4.7 Hz, 1H), 8.06 (d, J=8.0 Hz, 1H), 7.87 (d, J=5.2 Hz, 1H), 7.66 (dd, J=8.1, 1.5 Hz, 1H), 7.59 (d, J=1.4 Hz, 1H), 7.47 (dt, J=6.0, 2.9 Hz, 2H), 7.38-7.30 (m, 2H), 5.92 (d, J=7.7 Hz, 1H), 5.26 (s, 2H), 2.65 (d, J=4.7 Hz, 3H); Analytical HPLC RT E: 0.96 min, F: 1.32 min.

The compounds listed in Table II were prepared following the similar procedures as described in Examples II-1 to II-3.

TABLE II

| Ex. No. | R | Name | LCMS (M + H)$^+$ | HPLC Method, RT (min.) | $^1$H NMR (δ, ppm) |
|---|---|---|---|---|---|
| II-4 | (2-Cl-phenyl)-CH(NH-)-CO$_2$Me | (S)-methyl 2-(5H-chromeno[3,4-c]pyridine-8-carboxamido)-2-phenylacetate | 375.1 | A:4.90 B:5.47 | (400 MHz, CDCl$_3$) 8.63 (d, J = 5.1 Hz, 1H), 8.46 (s, 1H), 7.80 (d, J = 7.9 Hz, 1H), 7.65-7.32 (m, 8H), 7.21 (d, J = 6.6 Hz, 1H), 5.78 (d, J = 6.8 Hz, 1H), 5.20 (s, 2H), 3.79 (s, 3H) |
| II-5 | (2-Cl-phenyl)-CH(NH-)-CO$_2$-tBu | (S)-tert-butyl 2-(5H-chromeno[3,4-c]pyridine-8-carboxamido)-3-phenylpropanoate | 431.2 | A:6.50 B:6.90 | (400 MHz, CD$_3$OD) 8.55 (d, J = 5.3 Hz, 1H), 8.45 (d, J = 0.4 Hz, 1H), 7.97 (d, J = 8.1 Hz, 1H), 7.81 (d, J = 5.3 Hz, 1H), 7.48 (dd, J = 7.9, 1.8 Hz, 1H), 7.38 (d, J = 1.5 Hz, 1H), 7.33-7.26 (m, 4H), 7.25-7.16 (m, 1H), 5.24 (s, 2H), 1.44 (s, 9H) |
| II-6 | phenyl-CH$_2$-CH(NH-)-CO$_2$H | (R)-2-(5H-chromeno[3,4-c]pyridine-8-carboxamido)-3-phenylpropanoic acid | 375.1 | A:4.47 B:4.63 | (400 MHz, DMF-d$_7$) 8.87-8.75 (m, 3H), 8.21-8.11 (m, 2H), 7.70 (dd, J = 8.0, 1.7 Hz, 1H), 7.59 (d, J = 1.5 Hz, 1H), 7.46-7.39 (m, 2H), 7.36-7.28 (m, 2H), 7.26-7.17 (m, 1H), 5.42 (s, 2H), 4.89 (ddd, J = 10.5, 8.3, 4.4 Hz, 1H), 3.42-3.31 (m, 1H), 3.21 (dd, J = 13.9, 10.6 Hz, 1H) |
| II-7 | (2-Cl-phenyl)-CH(NH-)-CO$_2$H | (S)-2-(5H-chromeno[3,4-c]pyridine-8-carboxamido)-2-phenylacetic acid | 361.0 | E:0.98 F:0.98 | (500 MHz, CD$_3$OD) 8.60 (d, J = 5.5 Hz, 1H), 8.50 (s, 1H), 7.98-7.88 (m, 2H), 7.61 (dd, J = 8.3, 1.7 Hz, 1H), 7.53 (d, J = 1.4 Hz, 1H), 7.48 (d, J = 7.2 Hz, 2H), 7.41-7.29 (m, 3H), 5.27 (s, 2H) |
| II-8 | (2-Cl-phenyl)-CH(NH-)-CO$_2$-t-Bu | (R)-tert-butyl 2-(5H-chromeno[3,4-c]pyridine-8-carboxamido)-3-phenylpropanoate | 431.2 | E:1.56 F:1.92 | (500 MHz, CD$_3$OD) 8.64-8.47 (m, 2H), 7.95-7.87 (m, 2H), 7.49 (dd, J = 8.3, 1.7 Hz, 1H), 7.41 (d, J = 1.7 Hz, 1H), 7.31-7.17 (m, 6H), 5.26 (s, 2H), 4.79 (dd, J = 7.7, 6.3 Hz, 1H), 3.26-3.09 (m, 2H), 1.46-1.38 (s, 9H) |
| II-9 | (2-Cl-phenyl)-CH(NH-)-CONH$_2$ | (S)-N-(2-amino-2-oxo-1-phenylethyl)-5H-chromeno[3,4-c]pyridine-8-carboxamide | 360.1 | E:0.90 F:1.19 | (500 MHz, DMSO-d$_6$) 8.61 (d, J = 5.2 Hz, 1H), 8.53 (s, 1H), 8.06 (d, J = 8.3 Hz, 1H), 7.87 (d, J = 5.2 Hz, 1H), 7.70-7.63 (m, 2H), 7.56 (d, J = 1.7 Hz, 1H), 7.52 (d, J = 7.2 Hz, 2H), 7.39-7.33 (m, 2H), 7.31 (d, J = 7.2 Hz, 1H), 7.22 (s, 1H), 5.61 (d, J = 8.0 Hz, 1H), 5.27 (s, 2H) |

TABLE II-continued

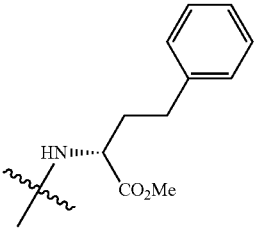 [SMILES: *N[C@H](CCc1ccccc1)C(=O)OC]

| Ex. No. | R | Name | LCMS (M + H)+ | HPLC Method, RT (min.) | 1H NMR (δ, ppm) |
|---|---|---|---|---|---|
| II-10 | 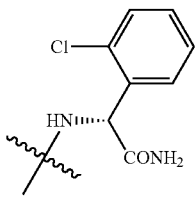 [SMILES: *N[C@@H](C(N)=O)c1ccccc1Cl] | (R)-methyl 2-(5H-chromeno[3,4-c]pyridine-8-carboxamido)-4-phenylbutanoate | 403.1 | A:5:87 B:6.10 | (400 MHz, CD3OD) 8.78 (d, J = 6.2 Hz, 1H), 8.74 (s, 1H), 8.38 (d, J = 6.2 Hz, 1H), 8.19 (d, J = 8.1 Hz, 1H), 7.68 (dd, J = 8.3, 1.7 Hz, 1H), 7.57 (d, J = 1.5 Hz, 1H), 7.33-7.15 (m, 5H), 5.42 (s, 2H), 4.63-4.55 (m, 1H), 3.75 (s, 3H), 2.87-2.69 (m, 2H), 2.33-2.11 (m, 2H) |
| II-11 | 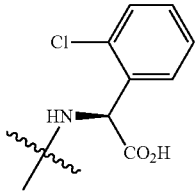 [SMILES: *N[C@H](C(=O)O)c1ccccc1Cl] | (R)-N-(1-amino-1-oxo-3-phenylpropan-2-yl)-5H-chromeno[3,4-c]pyridine-8-carboxamide | 374.1 | A:4:11 B:4.08 | (400 MHz, CD3OD) 8.73 (d, J = 5.9 Hz, 1H), 8.69 (s, 1H), 8.29 (d, J = 6.2 Hz, 1H), 8.12 (d, J = 8.1 Hz, 1H), 7.54 (dd, J = 8.1, 1.8 Hz, 1H), 7.44 (d, J = 1.5 Hz, 1H), 7.35-7.25 (m, 4H), 7.24-7.19 (m, 1H), 5.38 (s, 2H), 4.90-4.85 (m, 1H), 3.42-3.31 (m, 1H), 3.06 (dd, J = 14.0, 9.6 Hz, 1H) |
| II-12 | 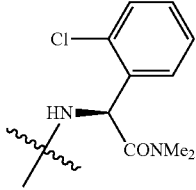 | (S)-2-(5H-chromeno[3,4-c]pyridine-8-carboxamido)-3-phenylpropanoic acid | 375.1 | E:1.04 F:1.04 | (500 MHz, DMSO-d6) 8.82 (d, J = 8.3 Hz, 1H), 8.66 (d, J = 5.2 Hz, 1H), 8.58 (s, 1H), 8.09 (d, J = 8.0 Hz, 1H), 7.95 (d, J = 5.5 Hz, 1H), 7.55 (dd, J = 8.3, 1.7 Hz, 1H), 7.44 (d, J = 1.4 Hz, 1H), 7.34-7.25 (m, 4H), 7.22-7.15 (m, 1H), 5.29 (s, 2H), 4.62 (ddd, J = 10.8, 8.2, 4.4 Hz, 1H), 3.20 (dd, J = 13.9, 4.3 Hz, 1H), 3.07 (dd, J = 13.8, 10.7 Hz, 1H)( |
| II-13 | 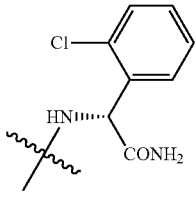 [SMILES: *N[C@@H](C(N)=O)c1ccccc1Cl] | (S)-N-(1-(2-chlorophenyl)-2-(dimethylamino)-2-oxoethyl)-5H-chromeno[3,4-c]pyridine-8-carboxamide | 422.1 | E:1.08 F:1.44 | (500 MHz, DMSO-d6) 9.25 (d, J = 8.0 Hz, 1H), 8.61 (d, J = 5.2 Hz, 1H), 8.53 (s, 1H), 8.06 (d, J = 8.0 Hz, 1H), 7.87 (d, J = 5.2 Hz, 1H), 7.68 (dd, J = 8.1, 1.5 Hz, 1H), 7.59 (d, J = 1.7 Hz, 1H), 7.51 (dd, J = 5.6, 3.7 Hz, 1H), 7.46-7.42 (m, 1H), 7.38 (dd, J = 5.8, 3.6 Hz, 2H), 6.28 (d, J = 7.7 Hz, 1H), 5.26 (s, 2H), 2.91 (d, J = 3.9 Hz, 6H) |
| II-14 | 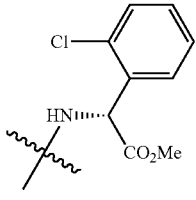 [SMILES: *N[C@@H](C(=O)OC)c1ccccc1Cl] | (S)-N-(2-amino-1-(2-chlorophenyl)-2-oxoethyl)-5H-chromeno[3,4-c]pyridine-8-carboxamide | 394.0 | A:3.79 B:4.24 | (400 MHz, CD3OD) 8.77 (d, J = 6.2 Hz, 1H), 8.73 (s, 1H), 8.37 (d, J = 6.2 Hz, 1H), 8.17 (d, J = 8.1 Hz, 1H), 7.70 (dd, J = 8.1, 1.8 Hz, 1H), 7.63-7.56 (m, 2H), 7.53-7.48 (m, 1H), 7.40-7.35 (m, 2H), 6.09 (s, 1H), 5.41 (s, 2H) |
| II-15 | 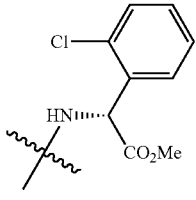 [SMILES: *N[C@@H](C(=O)OC)c1ccccc1Cl] | (R)-methyl 2-(2-chlorophenyl)-2-(5H-chromeno[3,4-c]pyridine-8-carboxamido)acetate | 409.0 | A:5.27 B:6.07 | (400 MHz, CD3OD) 8.78 (d, J = 6.2 Hz, 1H), 8.75 (s, 1H), 8.39 (d, J = 6.2 Hz, 1H), 8.18 (d, J = 8.1 Hz, 1H), 7.68 (dd, J = 8.1, 1.8 Hz, 1H), 7.58 (d, J = 1.5 Hz, 1H), 7.53-7.46 (m, 2H), 7.43-7.34 (m, 2H), 6.18 (s, 1H), 5.42 (s, 2H), 3.80 (s, 3H) |

TABLE II-continued

| Ex. No. | R | Name | LCMS (M + H)+ | HPLC Method, RT (min.) | 1H NMR (δ, ppm) |
|---|---|---|---|---|---|
| II-16 | (structure: 2-chlorophenyl with HN and CO2H) | (R)-2-(2-chlorophenyl)-2-(5H-chromeno[3,4-c]pyridine-8-carboxamido) acetic acid | 395.0 | A:4.40 B:4.90 | (400 MHz, CD3OD) 8.79-8.69 (m, 2H), 8.36 (d, J = 6.2 Hz, 1H), 8.14 (d, J = 8.1 Hz, 1H), 7.66 (dd, J = 8.1, 1.8 Hz, 1H), 7.57-7.46 (m, 3H), 7.41-7.30 (m, 2H), 6.13 (s, 1H), 5.39 (s, 2H) |

EXAMPLE III-1

Methyl 3-((5H-chromeno[3,4-c]pyridine-8-carboxamido)methyl)benzoate

EXAMPLE III-2

3-((5H-Chromeno[3,4-c]pyridine-8-carboxamido)methyl)benzoic acid

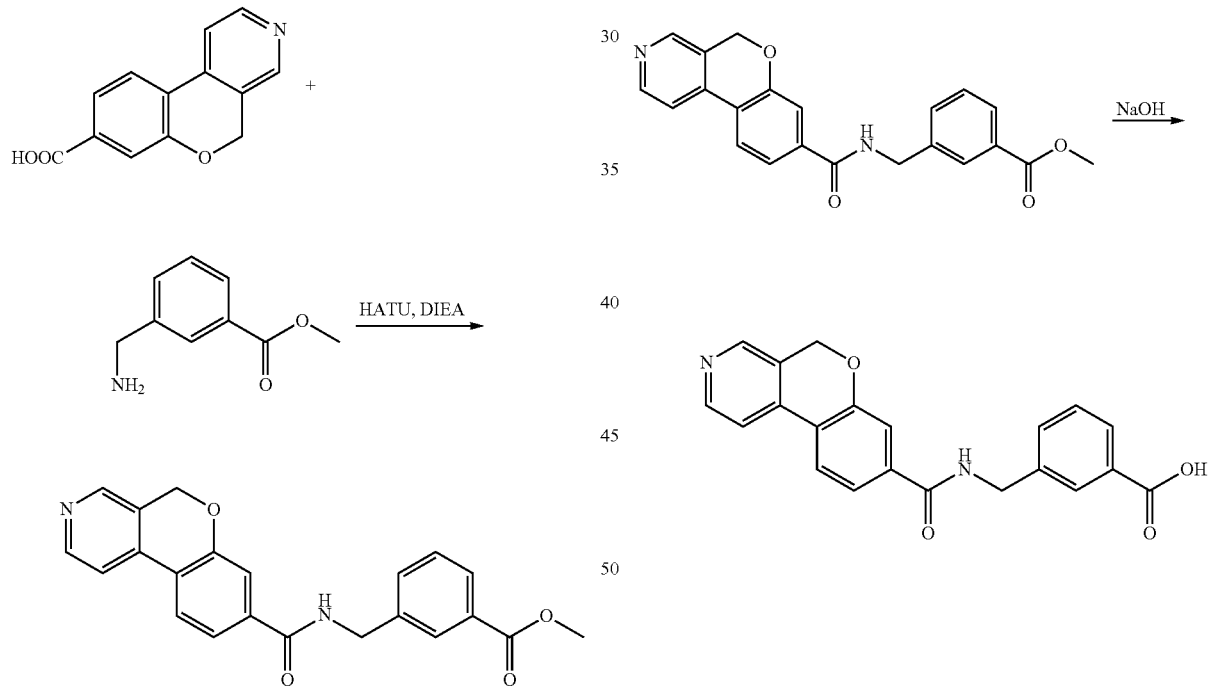

Example III-1 was prepared by following a similar procedure as described in Example I-1 by replacing (R)-1-(3-methoxyphenyl)ethanamine with methyl 3-(aminomethyl)benzoate, HCl salt. LC-MS (ESI) m/z: 375.1[M+H]+; 1H NMR (400 MHz, CD3OD) δ 8.79 (d, J=6.2 Hz, 1H), 8.76 (s, 1H), 8.41 (d, J=6.2 Hz, 1H), 8.20 (d, J=8.1 Hz, 1H), 8.07-8.02 (m, 1H), 7.94 (dt, J=7.8, 1.4 Hz, 1H), 7.71 (dd, J=8.3, 1.7 Hz, 1H), 7.63 (dd, J=7.7, 0.7 Hz, 1H), 7.60 (d, J=1.5 Hz, 1H), 7.51-7.44 (m, 1H), 5.43 (s, 2H), 4.68-4.63 (m, 2H), 3.91 (s, 3H); Analytical HPLC RT A: 4.70 min, B: 5.10 min.

To a suspension of Example III-1 (40 mg, 0.107 mmol) (estimated weight) in EtOH (3 mL) was added NaOH (1N, 0.855 mL, 0.855 mmol) at rt. After stirred under argon for 2.5 h, the reaction was neutralized with 6N HCl to pH ~8. Purification by reverse phase chromatography afforded Example III-2 as white solid (40 mg, 77%). LC-MS (ESI) m/z: 361.0[M+H]+; 1H NMR (400 MHz, CD3OD) δ 8.74 (d, J=6.2 Hz, 1H), 8.70 (s, 1H), 8.30 (d, J=5.9 Hz, 1H), 8.16 (d, J=8.4 Hz, 1H), 8.05 (s, 1H), 7.98-7.89 (m, 1H), 7.69 (dd, J=8.3, 1.7 Hz, 1H), 7.62 (d, J=8.1 Hz, 1H), 7.59 (d, J=1.5 Hz, 1H), 7.51-7.42 (m, 1H), 5.39 (s, 2H), 4.65 (d, J=4.4 Hz, 2H); Analytical HPLC RT A: 3.98 min, B: 4.14 min.

EXAMPLE III-3

N-(3-(Methylcarbamoyl)benzyl)-5H-chromeno[3,4-c]pyridine-8-carboxamide

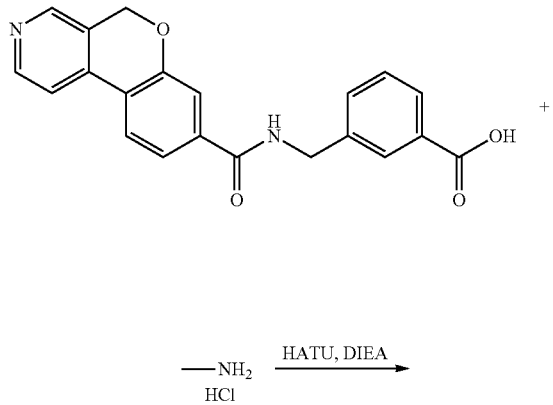

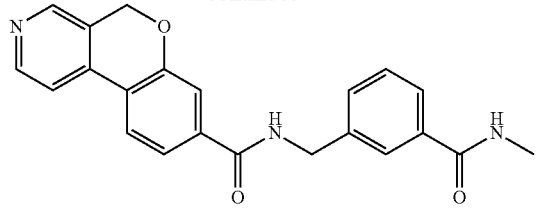

To a solution of Example III-2 (12 mg, 0.025 mmol) in DMF (1 mL) were added methanamine hydrochloride (17.08 mg, 0.253 mmol), DIEA (0.053 mL, 0.304 mmol), and HATU (17.31 mg, 0.046 mmol) at rt. The reaction was stirred under argon at rt for 3 h. Purification by reverse phase chromatography afforded Example III-3 as white solid (6.7 mg, 70%). LC-MS (ESI) m/z: 374.0[M+H]+; $^1$H NMR (500 MHz, DMSO-$d_6$) δ 9.20 (t, J=5.9 Hz, 1H), 8.71-8.39 (m, 3H), 8.09 (d, J=8.3 Hz, 1H), 7.88 (d, J=5.2 Hz, 1H), 7.79 (s, 1H), 7.70 (d, J=7.4 Hz, 1H), 7.65 (d, J=8.3 Hz, 1H), 7.54 (d, J=1.1 Hz, 1H), 7.49-7.44 (m, 1H), 7.43-7.35 (m, 1H), 5.27 (s, 2H), 4.52 (d, J=5.8 Hz, 2H), 2.77 (d, J=4.7 Hz, 3H); Analytical HPLC RT E: 0.93 min, F: 1.15 min.

The compounds listed in Table III were prepared by following the similar procedure as described in Examples III-1 to III-3.

TABLE III

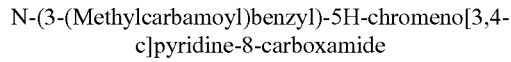

| Ex. No. | R | Name | LCMS (M + H)+ | HPLC Method, RT (min.) | $^1$H NMR (δ, ppm) |
|---|---|---|---|---|---|
| III-4 | 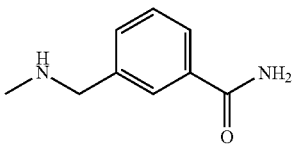 | N-(3-carbamoylbenzyl)-5H-chromeno[3,4-c]pyridine-8-carboxamide | 360.0 | E:0.90 F:1.10 | (500 MHz, DMSO-$d_6$) 9.19 (t, J = 5.9 Hz, 1H), 8.69-8.49 (m, 2H), 8.09 (d, J = 8.3 Hz, 1H), 7.98 (br. S., 1H), 7.88 (d, J = 5.0 Hz, 1H), 7.84 (s, 1H), 7.75 (d, J = 7.7 Hz, 1H), 7.65 (d, J = 8.3 Hz, 1H), 7.55 (s, 1H), 7.50-7.45 (m, 1H), 7.44-7.38 (m, 1H), 7.36 (br. S., 1H), 5.27 (s, 2H), 4.52 (d, J = 5.8 Hz, 2H) |
| III-5 | 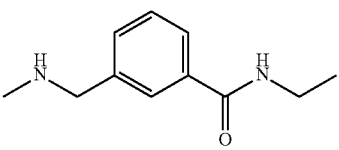 | N-(3-(ethylcarbamoyl)benzyl)-5H-chromeno[3,4-c]pyridine-8-carboxamide | 388.1 | A:3.72 B:4.50 | (400 MHz, DMSO-$d_6$) 9.22 (t, J = 5.9 Hz, 1H), 8.76 (d, J = 5.7 Hz, 1H), 8.69 (s, 1H), 8.44 (t, J = 5.3 Hz, 1H), 8.24-8.13 (m, 2H), 7.80 (s, 1H), 7.74-7.64 (m, 2H), 7.57 (d, J = 1.5 Hz, 1H), 7.52-7.34 (m, 2H), 5.35 (s, 2H), 4.53 (d, J = 5.9 Hz, 2H), 3.35-3.17 (m, 2H), 1.11 (t, J = 7.3 Hz, 3H) |
| III-6 | 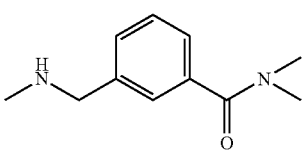 | N-(3-(dimethylcarbamoyl)benzyl)-5H-chromeno[3,4-c]pyridine-8-carboxamide | 388.1 | E:1.04 F:1.24 | (500 MHz, DMSO-$d_6$) 9.17 (t, J = 6.1 Hz, 1H), 8.62 (d, J = 5.2 Hz, 1H), 8.54 (s, 1H), 8.09 (d, J = 8.3 Hz, 1H), 7.88 (d, J = 5.2 Hz, 1H), 7.65 (dd, J = 8.3, 1.7 Hz, 1H), 7.54 (d, J = 1.7 Hz, 1H), 7.41-7.37 (m, 2H), 7.34 (s, 1H), 7.29-7.23 (m, 1H), 5.28 (s, 2H), 4.52 (d, J = 6.1 Hz, 2H), 2.97 (br. s., 3H), 2.89 (s, 3H) |
| III-7 | 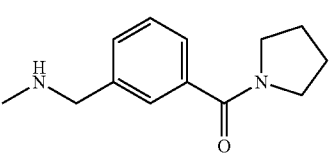 | N-(3-(pyrrolidine-1-carbonyl)benzyl)-5H-chromeno[3,4-c]pyridine-8-carboxamide | 414.1 | E:1.11 F:1.33 | $^1$H NMR (500 MHz, DMSO-$d_6$) δ 9.17 (t, J = 6.1 Hz, 1H), 8.62 (d, J = 5.2 Hz, 1H), 8.53 (s, 1H), 8.09 (d, J = 8.3 Hz, 1H), 7.87 (d, J = 5.2 Hz, 1H), 7.64 (dd, J = 8.0, 1.7 Hz, 1H), 7.53 (d, J = 1.4 Hz, 1H), 7.45 (s, 1H), 7.41-7.34 (m, 3H), 5.27 (s, 2H), 4.52 (d, J = 6.1 Hz, 2H), 3.45 (t, J = 6.9 Hz, 2H), 3.36 (t, J = 6.5 Hz, 2H), 1.93-1.71 (m, 4H) |

TABLE III-continued

| Ex. No. | R | Name | LCMS (M + H)+ | HPLC Method, RT (min.) | 1H NMR (δ, ppm) |
|---|---|---|---|---|---|
| III-8 | | N-(3-(azetidine-1-carbonyl)benzyl)-5H-chromeno[3,4-c]pyridine-8-carboxamide | 400.1 | E:1.06 F:1.26 | (500 MHz, DMSO-d$_6$) 9.19 (t, J = 5.9 Hz, 1H), 8.62 (d, J = 5.2 Hz, 1H), 8.53 (s, 1H), 8.09 (d, J = 8.3 Hz, 1H), 7.87 (d, J = 5.2 Hz, 1H), 7.65 (dd, J = 8.3, 1.7 Hz, 1H), 7.57 (s, 1H), 7.54 (d, J = 1.7 Hz, 1H), 7.49-7.43 (m, 2H), 7.43-7.36 (m, 1H), 5.28 (s, 2H), 4.52 (d, J = 5.8 Hz, 2H), 4.26 (t, J = 7.4 Hz, 2H), 4.02 (t, J = 7.6 Hz, 2H), 2.24 (quin, J = 7.8 Hz, 2H) |
| III-9 | | N-(3-(ethyl(methyl)carbamoyl)benzyl)-5H-chromeno[3,4-c]pyridine-8-carboxamide | 402.2 | E:1.11 F:1.32 | (500 MHz, DMSO-d6) 9.20 (br. s., 1H), 8.62 (br. s., 1H), 8.53 (br. s., 1H), 8.09 (d, J = 7.7 Hz, 1H), 7.87 (br. s., 1H), 7.64 (d, J = 8.0 Hz, 1H), 7.53 (br. s., 1H), 7.38 (br. s., 2H), 7.35-7.20 (m, 2H), 5.27 (br. s., 2H), 4.52 (br. s., 2H), 2.96-2.74 (m, 5H), 1.18-0.98 (m, 3H) |
| III-10 | | N-(3-((2-methoxyethyl)(methyl)carbamoyl)benzyl)-5H-chromeno[3,4-c]pyridine-8-carboxamide | 432.2 | E:1.07 F:1.28 | (500 MHz, DMSO-d$_6$) 9.20 (br. s., 1H), 8.62 (br. s., 1H), 8.53 (br. s., 1H), 8.09 (d, J = 7.4 Hz, 1H), 7.87 (br. s., 1H), 7.65 (d, J = 7.7 Hz, 1H), 7.54 (br. s., 1H), 7.38 (br. s., 2H), 7.30 (br. s., 1H), 7.25 (br. s., 1H), 5.27 (br. s., 2H), 4.51 (br. s., 2H), 3.66-3.49 (m, 2H), 3.33-3.22 (m, 3H), 3.10 (br. s.,2H), 2.93 (d, J = 17.1 Hz, 3H) |
| III-11 | | N-(3-(piperidine-1-carbonyl)benzyl)-5H-chromeno[3,4-c]pyridine-8-carboxamide | 428.1 | E:1.21 F:1.45 | (500 MHz, DMSO-d$_6$) 9.17 (t, J = 5.9 Hz, 1H), 8.62 (d, J = 5.0 Hz, 1H), 8.53 (s, 1H), 8.09 (d, J = 8.3 Hz, 1H), 7.87 (d, J = 5.2 Hz, 1H), 7.64 (dd, J = 8.3, 1.7 Hz, 1H), 7.53 (d, J = 1.7 Hz, 1H), 7.41-7.35 (m, 2H), 7.30 (s, 1H), 7.25-7.19 (m, 1H), 5.27 (s, 2H), 4.52 (d, J = 6.1 Hz, 2H), 3.56 (br. s., 2H), 3.35-3.18 (m, 2H), 1.59 (d, J = 4.1 Hz, 2H), 1.56-1.34 (m, 4H) |
| III-12 | | N-(3-(morpholine-4-carbonyl)benzyl)-5H-chromeno[3,4-c]pyridine-8-carboxamide | 430.1 | E:1.04 F:1.23 | (500 MHz, DMSO-d$_6$) 9.17 (t, J = 5.9 Hz, 1H), 8.61 (d, J = 5.0 Hz, 1H), 8.53 (s, 1H), 8.09 (d, J = 8.3 Hz, 1H), 7.87 (d, J = 5.2 Hz, 1H), 7.64 (dd, J = 8.3, 1.7 Hz, 1H), 7.53 (d, J = 1.7 Hz, 1H), 7.41 (d, J = 5.2 Hz, 2H), 7.35 (s, 1H), 7.28 (td, J = 4.4, 1.7 Hz, 1H), 5.27 (s, 2H), 4.52 (d, J = 5.8 Hz, 2H), 3.58 (br. s., 8H) |
| III-13 | | N-(3-(cyclopropylcarbamoyl)benzyl)-5H-chromeno[3,4-c]pyridine-8-carboxamide | 400.1 | E:1.05 F:1.27 | (500 MHz, DMSO-d$_6$) 9.19 (br. s., 1H), 8.62 (br. s., 1H), 8.53 (br. s., 1H), 8.45 (br. s., 1H), 8.09 (d, J = 8.0 Hz, 1H), 7.88 (br. s., 1H), 7.78 (br. s., 1H), 7.66 (dd, J = 16.1, 7.6 Hz, 2H), 7.54 (br. s., 1H), 7.45 (br. s., 1H), 7.42-7.36 (m, 1H), 5.27 (br. s., 2H), 4.52 (br. s., 2H), 2.83 (br. s., 1H), 0.68 (d, J = 2.2 Hz, 2H), 0.56 (br. s., 2H) |
| III-14 | | N-(3-(3-methoxyazetidine-1-carbonyl)benzyl)-5H-chromeno[3,4-c]pyridine-8-carboxamide | 430.1 | E:0.95 F:1.24 | (500 MHz, DMSO-d$_6$) 9.19 (t, J = 6.1 Hz, 1H), 8.62 (d, J = 5.0 Hz, 1H), 8.53 (s, 1H), 8.09 (d, J = 8.3 Hz, 1H), 7.87 (d, J = 5.2 Hz, 1H), 7.65 (dd, J = 8.0, 1.7 Hz, 1H), 7.59 (s, 1H), 7.54 (d, J = 1.7 Hz, 1H), 7.52-7.44 (m, 2H), 7.44-7.39 (m, 1H), 5.28 (s, 2H), 4.53 (d, J = 5.8 Hz, 2H), 4.39 (br. s., 1H), 4.26-4.18 (m, 2H), 4.09 (d, J = 8.3 Hz, 1H), 3.82 (d, J = 5.5 Hz, 1H), 3.20 (s, 3H) |

TABLE III-continued

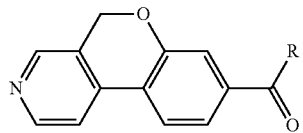

| Ex. No. | R | Name | LCMS (M + H)+ | HPLC Method, RT (min.) | 1H NMR (δ, ppm) |
|---|---|---|---|---|---|
| III-15 | ![R group] | (R)-N-(3-(3-hydroxypyrrolidine-1-carbonyl)benzyl)-5H-chromeno[3,4-c]pyridine-8-carboxamide | 430.1 | E:0.86 F:1.09 | (500 MHz, DMSO-d6) δ 9.18 (t, J = 6.1 Hz, 1H), 8.62 (d, J = 5.2 Hz, 1H), 8.53 (s, 1H), 8.09 (d, J = 8.0 Hz, 1H), 7.87 (d, J = 5.2 Hz, 1H), 7.65 (d, J = 8.0 Hz, 1H), 7.54 (s, 1H), 7.45 (br. s., 1H), 7.42-7.36 (m, 3H), 5.28 (s, 2H), 5.02-4.88 (m, 1H), 4.52 (d, J = 6.1 Hz, 2H), 4.37-4.17 (m, 1H), 3.61-3.45 (m, 3H), 1.99-1.71 (m, 2H) |
| III-16 | ![R group] | (S)-N-(3-(3-hydroxypyrrolidine-1-carbonyl)benzyl)-5H-chromeno[3,4-c]pyridine-8-carboxamide | 430.1 | E:0.86 F:1.09 | (500 MHz, DMSO-d6) 9.18 (t, J = 5.9 Hz, 1H), 8.62 (d, J = 5.2 Hz, 1H), 8.53 (s, 1H), 8.09 (d, J = 8.3 Hz, 1H), 7.87 (d, J = 5.0 Hz, 1H), 7.65 (d, J = 8.3 Hz, 1H), 7.54 (s, 1H), 7.45 (br. s., 1H), 7.42-7.35 (m, 3H), 5.28 (s, 2H), 5.03-4.89 (m, 1H), 4.52 (d, J = 6.1 Hz, 2H), 4.36-4.18 (m, 1H), 3.61-3.46 (m, 3H), 2.00-1.70 (m, 2H) |
| III-17 | ![R group] | (R)-N-(3-(3-methoxypyrrolidine-1-carbonyl)benzyl)-5H-chromeno[3,4-c]pyridine-8-carboxamide | 444.1 | E:0.96 F:1.25 | (500 MHz, DMSO-d6) 9.17 (t, J = 5.9 Hz, 1H), 8.61 (d, J = 5.0 Hz, 1H), 8.53 (s, 1H), 8.08 (d, J = 8.3 Hz, 1H), 7.86 (d, J = 5.2 Hz, 1H), 7.64 (d, J = 8.0 Hz, 1H), 7.53 (s, 1H), 7.45 (d, J = 6.3 Hz, 1H), 7.42-7.33 (m, 3H), 5.27 (s, 2H), 4.52 (d, J = 5.8 Hz, 2H), 4.05-3.86 (m, 1H), 3.62-3.42 (m, 4H), 3.26-3.10 (m, 3H), 2.03-1.81 (m, 2H) |
| III-18 | ![R group] | N-(3-(3-fluoroazetidine-1-carbonyl)benzyl)-5H-chromeno[3,4-c]pyridine-8-carboxamide | 418.0 | E:0.95 F:1.25 | (500 MHz, DMSO-d6) 9.19 (t, J = 6.1 Hz, 1H), 8.62 (d, J = 5.2 Hz, 1H), 8.53 (s, 1H), 8.09 (d, J = 8.3 Hz, 1H), 7.87 (d, J = 5.2 Hz, 1H), 7.65 (dd, J = 8.1, 1.8 Hz, 1H), 7.61 (s, 1H), 7.56-7.46 (m, 3H), 7.45-7.37 (m, 1H), 5.54-5.32 (m, 1H), 5.27 (s, 2H), 4.53 (d, J = 5.8 Hz, 3H), 4.46-3.99 (m, 3H) |
| III-19 | ![R group] | N-(3-(3,3-difluoroazetidine-1-carbonyl)benzyl)-5H-chromeno[3,4-c]pyridine-8-carboxamide | 436.1 | E:1.04 F:1.36 | (500 MHz, DMSO-d6) 9.20 (t, J = 5.9 Hz, 1H), 8.62 (d, J = 5.2 Hz, 1H), 8.54 (s, 1H), 8.10 (d, J = 8.3 Hz, 1H), 7.88 (d, J = 5.0 Hz, 1H), 7.71-7.61 (m, 2H), 7.59-7.49 (m, 3H), 7.48-7.40 (m, 1H), 5.28 (s, 2H), 4.85-4.64 (m, 2H), 4.54 (d, J = 5.8 Hz, 3H), 4.49 (br. s., 2H) |

EXAMPLE IV-1

Ethyl 2-(3-((5H-chromeno[3,4-c]pyridine-8-carboxamido)methyl)phenyl)thiazole-4-carboxylate

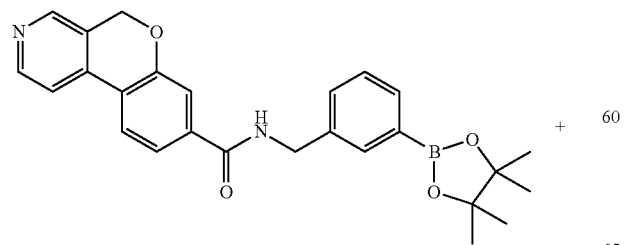

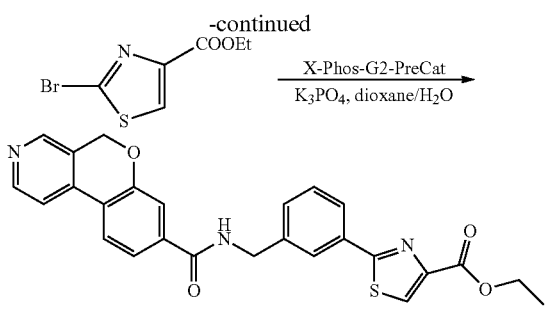

To a solution of Intermediate 5 (47 mg, 0.106 mmol) in dioxane (1.2 mL) and H$_2$O (0.324 mL) were added ethyl 2-bromothiazole-4-carboxylate (25.09 mg, 0.106 mmol), K$_3$PO$_4$ (56.4 mg, 0.266 mmol) and XPhos-G2-PreCat (4.19 mg, 5.31 μmol). The reaction was heated with microwave at 140° C. for 15 min. The solvent was removed. Purification by reverse phase chromatography afforded Example IV-1 as white solid (21 mg, 41%). LC-MS (ESI) m/z: 472.2[M+H]+; 1H NMR (500 MHz, DMSO-d6) δ 9.25 (br. s., 1H), 8.67-8.46 (m, 3H), 8.13-7.80 (m, 4H), 7.71-7.43 (m, 5H), 5.27 (br. s., 2H), 4.57 (br. s., 2H), 4.33 (br. s., 2H), 1.31 (br. s., 3H); Analytical HPLC RT E: 1.28 min, F: 1.59 min.

EXAMPLE IV-2

2-(3-((5H-Chromeno[3,4-c]pyridine-8-carboxamido)methyl)phenyl)thiazole-4-carboxylic acid

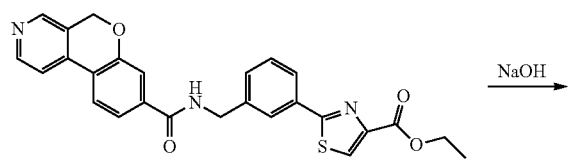

NaOH →

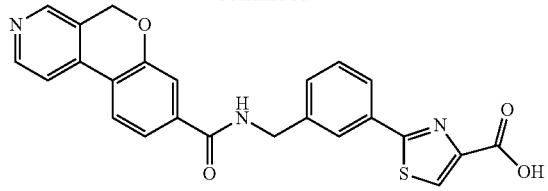

Example IV-2 was prepared by following a similar procedure as described in Example III-2. LC-MS (ESI) m/z: 444.0[M+H]+; 1H NMR (500 MHz, DMSO-d6) δ 9.25 (t, J=6.1 Hz, 1H), 8.63 (d, J=5.2 Hz, 1H), 8.54 (s, 1H), 8.49 (s, 1H), 8.10 (d, J=8.3 Hz, 1H), 7.97 (s, 1H), 7.89 (d, J=5.2 Hz, 1H), 7.86 (dt, J=6.7, 1.9 Hz, 1H), 7.66 (dd, J=8.0, 1.7 Hz, 1H), 7.55 (d, J=1.7 Hz, 1H), 7.49-53 (m, 2H), 5.28 (s, 2H), 4.58 (d, J=6.1 Hz, 2H); Analytical HPLC RT E: 1.13 min, F: 1.07 min.

The compounds listed in Table IV were prepared by following the similar procedures as described in Examples IV-1 and IV-2.

TABLE IV

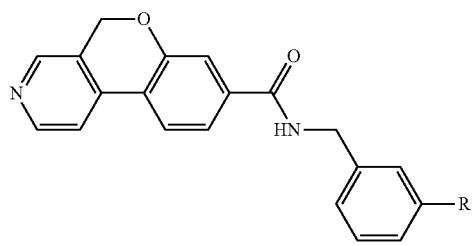

| Ex. No. | R | Name | LCMS (M + H)+ | HPLC Method, RT (min.) | 1H NMR (δ, ppm) |
|---|---|---|---|---|---|
| IV-3 | 1-methyl-1H-pyrazol-5-yl | N-(3-(1-methyl-1H-pyrazol-5-yl)benzyl)-5H-chromeno[3,4-c]pyridine-8-carboxamide | 397.2 | E:1.14 F:1.43 | (500 MHz, DMSO-d6) 9.19 (t, J = 5.9 Hz, 1H), 8.62 (d, J = 5.2 Hz, 1H), 8.53 (s, 1H), 8.08 (d, J = 8.3 Hz, 1H), 7.87 (d, J = 5.0 Hz, 1H), 7.65 (dd, J = 8.3, 1.7 Hz, 1H), 7.54 (d, J = 1.4 Hz, 1H), 7.50-7.44 (m, 3H), 7.43-7.36 (m, 2H), 6.38 (d, J = 1.9 Hz, 1H), 5.27 (s, 2H), 4.56 (d, J = 6.1 Hz, 2H), 3.84 (s, 3H) |
| IV-4 | 2-(azetidin-1-yl)pyrimidin-5-yl | N-(3-(2-(azetidin-1-yl)pyrimidin-5-yl)benzyl)-5H-chromeno[3,4-c]pyridine-8-carboxamide | 450.2 | E:1.10 F:1.53 | (500 MHz, DMSO-d6) 9.18 (t, J = 5.9 Hz, 1H), 8.71 (d, J = 5.5 Hz, 1H), 8.66-8.62 (m, 3H), 8.15 (d, J = 8.3 Hz, 1H), 8.06 (d, J = 5.5 Hz, 1H), 7.68 (d, J = 8.0 Hz, 1H), 7.57 (d, J = 2.5 Hz, 2H), 7.51 (d, J = 7.7 Hz, 1H), 7.41 (t, J = 7.7 Hz, 1H), 7.29 (d, J = 7.7 Hz, 1H), 5.32 (s, 2H), 4.54 (d, J = 5.8 Hz, 2H), 4.08 (t, J = 7.6 Hz, 4H), 2.33 (quin, J = 7.5 Hz, 2H) |
| IV-5 | 1-methyl-1H-pyrazol-4-yl | N-(3-(1-methyl-1H-pyrazol-4-yl)benzyl)-5H-chromeno[3,4-c]pyridine-8-carboxamide | 397.2 | E:1.17 F:1.43 | (500 MHz, DMSO-d6) 9.13 (t, J = 5.9 Hz, 1H), 8.61 (d, J = 5.0 Hz, 1H), 8.53 (s, 1H), 8.11-8.04 (m, 2H), 7.86 (d, J = 5.2 Hz, 1H), 7.81 (s, 1H), 7.65 (d, J = 8.3 Hz, 1H), 7.54 (s, 1H), 7.51 (s, 1H), 7.43 (d, J = 7.7 Hz, 1H), 7.31 (t, J = 7.6 Hz, 1H), 7.14 (d, J = 7.7 Hz, 1H), 5.27 (s, 2H), 4.50 (d, J = 5.8 Hz, 2H), 3.85 (s, 3H) |
| IV-6 | 1H-imidazol-4-yl | N-(3-(1H-imidazol-4-yl)benzyl)-5H-chromeno[3,4-c]pyridine-8-carboxamide | 383.1 | E:0.97 F:1.25 | (500 MHz, DMSO-d6) 9.21 (t, J = 5.9 Hz, 1H), 9.15 (s, 1H), 8.67 (d, J = 5.2 Hz, 1H), 8.59 (s, 1H), 8.15-8.09 (m, 2H), 7.97 (d, J = 5.2 Hz, 1H), 7.77 (s, 1H), 7.68 (t, J = 8.9 Hz, 2H), 7.57 (s, 1H), 7.50 (t, J = 7.7 Hz, 1H), 7.40 (d, J = 7.7 Hz, 1H), 5.30 (s, 2H), 4.55 (d, J = 5.8 Hz, 2H) |

TABLE IV-continued

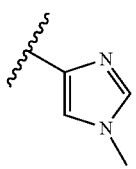

| Ex. No. | R | Name | LCMS (M + H)+ | HPLC Method, RT (min.) | ¹H NMR (δ, ppm) |
|---|---|---|---|---|---|
| IV-7 | 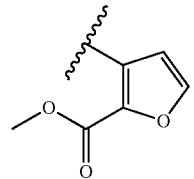 [SMILES: *c1ccoc1C(=O)OC] | N-(3-(1-methyl-1H-imidazol-4-yl)benzyl)-5H-chromeno[3,4-c]pyridine-8-carboxamide | 397.2 | E:0.98 F:1.33 | (500 MHz, DMSO-d₆) 9.21 (t, J = 5.8 Hz, 1H), 9.01 (s, 1H), 8.67 (d, J = 5.2 Hz, 1H), 8.59 (s, 1H), 8.12 (d, J = 8.3 Hz, 1H), 8.08 (s, 1H), 7.97 (d, J = 5.2 Hz, 1H), 7.71 (s, 1H), 7.66 (dd, J = 16.1, 7.8 Hz, 2H), 7.57 (s, 1H), 7.49 (t, J = 7.7 Hz, 1H), 7.39 (d, J = 7.7 Hz, 1H), 5.30 (s, 2H), 4.55 (d, J = 5.8 Hz, 2H), 3.87 (s, 3H) |
| IV-8 | 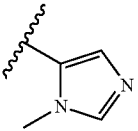 | methyl 3-(3-((5H-chromeno[3,4-c]pyridine-8-carboxamido)methyl)phenyl)furan-2-carboxylate | 441.1 | E:1.34 F:1.62 | (500 MHz, DMSO-d₆) 9.20 (t, J = 5.9 Hz, 1H), 8.70 (d, J = 5.5 Hz, 1H), 8.63 (s, 1H), 8.14 (d, J = 8.0 Hz, 1H), 8.05 (d, J = 5.5 Hz, 1H), 7.99 (d, J = 1.1 Hz, 1H), 7.67 (d, J = 8.0 Hz, 1H), 7.57 (d, J = 3.9 Hz, 2H), 7.49 (d, J = 7.7 Hz, 1H), 7.43-7.36 (m, 1H), 7.36-7.29 (m, 1H), 6.87 (d, J = 1.1 Hz, 1H), 5.32 (s, 2H), 4.53 (d, J = 6.1 Hz, 2H), 3.72 (s, 3H) |
| IV-9 | 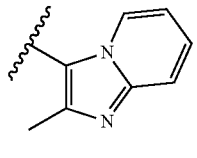 [SMILES: *c1c(C)nc2ccccn12] | N-(3-(1-methyl-1H-imidazol-5-yl)benzyl)-5H-chromeno[3,4-c]pyridine-8-carboxamide | 397.2 | E:0.98 F:1.31 | (500 MHz, DMSO-d₆) 9.17 (t, J = 5.8 Hz, 1H), 8.61 (d, J = 5.0 Hz, 1H), 8.53 (s, 1H), 8.08 (d, J = 8.0 Hz, 1H), 7.87 (d, J = 5.2 Hz, 1H), 7.69 (s, 1H), 7.65 (d, J = 8.3 Hz, 1H), 7.54 (s, 1H), 7.46-7.40 (m, 2H), 7.39-7.35 (m, 1H), 7.32 (d, J = 7.4 Hz, 1H), 7.02 (s, 1H), 5.27 (s, 2H), 4.54 (d, J = 5.8 Hz, 2H), 3.67 (s, 3H) |
| IV-10 | 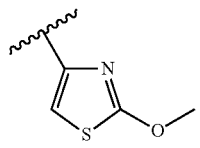 [SMILES: *c1csc(OC)n1] | N-(3-(2-methyl-imidazo[1,2-a]pyridin-3-yl)benzyl)-5H-chromeno[3,4-c]pyridine-8-carboxamide | 447.2 | E:1.04 F:1.49 | (500 MHz, DMSO-d₆) 9.19 (t, J = 5.9 Hz, 1H), 8.61 (d, J = 5.2 Hz, 1H), 8.53 (s, 1H), 8.28 (d, J = 6.9 Hz, 1H), 8.08 (d, J = 8.3 Hz, 1H), 7.86 (d, J = 5.2 Hz, 1H), 7.65 (d, J = 8.3 Hz, 1H), 7.58-7.48 (m, 4H), 7.42 (dd, J = 12.1, 7.7 Hz, 2H), 7.28-7.17 (m, 1H), 6.86 (t, J = 6.7 Hz, 1H), 5.27 (s, 2H), 4.59 (d, J = 5.8 Hz, 2H), 2.37 (s, 3H) |
| IV-11 | 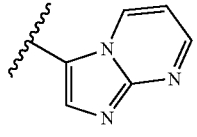 [SMILES: *c1cnc2ncccn12] | N-(3-(2-methoxy-thiazol-4-yl)benzyl)-5H-chromeno[3,4-c]pyridine-8-carboxamide | 430.2 | E:1.45 F:1.76 | (500 MHz, DMSO-d₆) 9.17 (t, J = 5.8 Hz, 1H), 8.61 (d, J = 5.0 Hz, 1H), 8.53 (s, 1H), 8.08 (d, J = 8.3 Hz, 1H), 7.87 (d, J = 5.2 Hz, 1H), 7.83 (s, 1H), 7.74 (d, J = 7.7 Hz, 1H), 7.65 (d, J = 8.3 Hz, 1H), 7.54 (s, 1H), 7.44 (s, 1H), 7.38 (t, J = 7.6 Hz, 1H), 7.28 (d, J = 7.7 Hz, 1H), 5.27 (s, 2H), 4.53 (d, J = 5.8 Hz, 2H), 4.09 (s, 3H) |
| IV-12 | 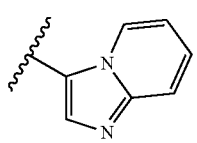 [SMILES: *c1cnc2ccccn12] | N-(3-(imidazo[1,2-a]pyrimidin-3-yl)benzyl)-5H-chromeno[3,4-c]pyridine-8-carboxamide | 434.1 | E:0.97 F:1.30 | (500 MHz, DMSO-d₆) 9.18 (t, J = 5.9 Hz, 1H), 9.05-9.00 (m, 1H), 8.64-8.57 (m, 2H), 8.53 (s, 1H), 8.08 (d, J = 8.0 Hz, 1H), 7.95 (s, 1H), 7.86 (d, J = 5.0 Hz, 1H), 7.68-7.63 (m, 2H), 7.61-7.57 (m, 1H), 7.56-7.50 (m, 2H), 7.41 (d, J = 7.7 Hz, 1H), 7.12 (dd, J = 6.9, 3.9 Hz, 1H), 5.27 (s, 2H), 4.59 (d, J = 5.8 Hz, 2H) |
| IV-13 | | N-(3-(imidazo[1,2-a]pyridin-3-yl)benzyl)-5H-chromeno[3,4-c]pyridine-8-carboxamide | 433.2 | E:1.02 F:1.47 | (500 MHz, DMSO-d₆) 9.18 (t, J = 5.9 Hz, 1H), 8.61 (d, J = 5.2 Hz, 1H), 8.57 (d, J = 7.2 Hz, 1H), 8.53 (s, 1H), 8.08 (d, J = 8.3 Hz, 1H), 7.86 (d, J = 5.2 Hz, 1H), 7.75 (s, 1H), 7.69-7.60 (m, 3H), 7.57-7.49 (m, 3H), 7.40 (d, J = 7.2 Hz, 1H), 7.33-7.28 (m, 1H), 6.97 (t, J = 6.7 Hz, 1H), 5.27 (s, 2H), 4.59 (d, J = 5.8 Hz, 2H) |

TABLE IV-continued

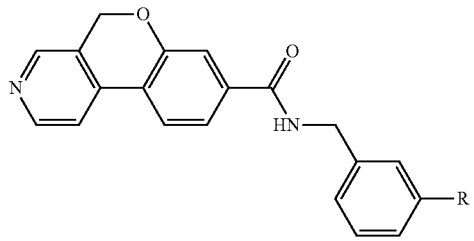

| Ex. No. | R | Name | LCMS (M + H)+ | HPLC Method, RT (min.) | ¹H NMR (δ, ppm) |
|---|---|---|---|---|---|
| IV-14 | 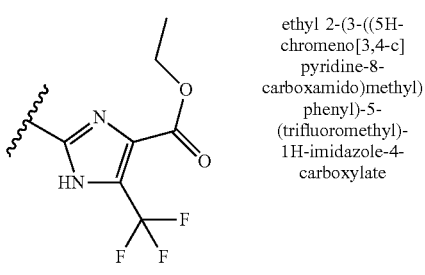 | N-(3-(2-(methyl-sulfonyl)pyrimidin-5-yl)benzyl)-5H-chromeno[3,4-c]pyridine-8-carboxamide | 473.2 | E:1.12 F:1.36 | (500 MHz, DMSO-$d_6$) 9.39 (s, 2H), 9.21 (t, J = 5.8 Hz, 1H), 8.66 (d, J = 5.0 Hz, 1H), 8.57 (s, 1H), 8.11 (d, J = 8.0 Hz, 1H), 7.95-7.92 (m, 1H), 7.87 (s, 1H), 7.80 (d, J = 7.7 Hz, 1H), 7.67 (d, J = 8.3 Hz, 1H), 7.60-7.54 (m, 2H), 7.52-7.48 (m, 1H), 5.29 (s, 2H), 4.60 (d, J = 6.1 Hz, 2H), 3.45 (s, 3H) |
| IV-15 | 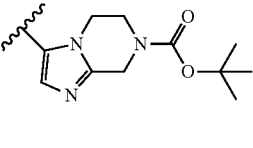 | ethyl 2-(3-((5H-chromeno[3,4-c]pyridine-8-carboxamido)methyl)phenyl)-5-(trifluoromethyl)-1H-imidazole-4-carboxylate | 523.1 | E:1.50 F:1.78 | (500 MHz, DMSO-$d_6$) 9.20 (br. s., 1H), 8.61 (d, J = 5.0 Hz, 1H), 8.53 (s, 1H), 8.13-8.07 (m, 2H), 8.02 (d, J = 7.4 Hz, 1H), 7.87 (d, J = 4.7 Hz, 1H), 7.66 (d, J = 8.0 Hz, 1H), 7.55 (s, 1H), 7.49-7.38 (m, 2H), 5.27 (s, 2H), 4.55 (d, J = 5.2 Hz, 2H), 4.35 (q, J = 6.9 Hz, 2H), 1.32 (t, J = 7.0 Hz, 3H) |
| IV-16 | 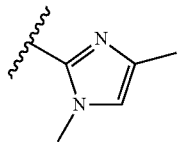 [SMILES: *c1nc(C)cn1C] | tert-butyl 3-(3-((5H-chromeno[3,4-c]pyridine-8-carboxamido)methyl)phenyl)-5,6-dihydroimidazo[1,2-a]pyrazine-7(8H)-carboxylate | 538.2 | E:1.15 F:1.56 | (500 MHz, DMSO-$d_6$) 9.16 (br. s., 1H), 8.61 (d, J = 5.0 Hz, 1H), 8.53 (s, 1H), 8.08 (d, J = 8.3 Hz, 1H), 7.86 (d, J = 4.4 Hz, 1H), 7.65 (d, J = 7.7 Hz, 1H), 7.54 (s, 1H), 7.46-7.35 (m, 3H), 7.31 (d, J = 7.2 Hz, 1H), 7.05 (s, 1H), 5.27 (s, 2H), 4.60 (br. s., 2H), 4.53 (d, J = 5.5 Hz, 2H), 4.02 (br. s., 2H), 3.73 (br. s., 2H), 1.44 (s, 9H) |
| IV-17 | 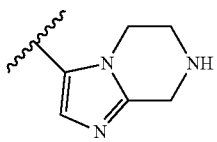 [SMILES: *c1cnc2n1CCNC2] | N-(3-(1,4-dimethyl-1H-imidazol-2-yl)benzyl)-5H-chromeno[3,4-c]pyridine-8-carboxamide | 411.1 | E:0.88 F:1.32 | (500 MHz, DMSO-$d_6$) 9.25-9.09 (m, 1H), 8.61 (d, J = 5.0 Hz, 1H), 8.53 (s, 1H), 8.08 (d, J = 8.0 Hz, 1H), 7.87 (d, J = 5.0 Hz, 1H), 7.65 (d, J = 8.0 Hz, 1H), 7.62 (s, 1H), 7.56-7.49 (m, 2H), 7.42 (t, J = 7.6 Hz, 1H), 7.35 (d, J = 7.4 Hz, 1H), 6.92 (s, 1H), 5.27 (s, 2H), 4.54 (d, J = 5.8 Hz, 2H), 3.66 (s, 3H), 2.10 (s, 3H) |
| IV-18 | 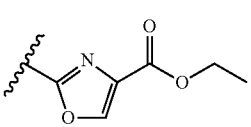 [SMILES: *c1nc(C(=O)OCC)co1] | N-(3-(5,6,7,8-tetra-hydroimidazo[1,2-a]pyrazin-3-yl)benzyl)-5H-chromeno[3,4-c]pyridine-8-carboxamide | 438.2 | E:0.78 F:1.11 | (500 MHz, DMSO-$d_6$) 9.19 (br. s., 1H), 8.62 (br. s., 1H), 8.53 (br. s., 1H), 8.08 (d, J = 7.7 Hz, 1H), 7.86 (br. s., 1H), 7.64 (d, J = 8.0 Hz, 1H), 7.53 (br. s., 1H), 7.48-7.42 (m, 2H), 7.39-7.34 (m, 2H), 7.15 (br. s., 1H), 5.27 (br. s., 2H), 4.53 (br. s., 2H), 4.28 (br. s., 2H), 4.11 (br. s., 2H), 3.5 (m., 2H) |
| IV-19 | | ethyl 2-(3-((5H-chromeno[3,4-c]pyridine-8-carbox-amido)methyl)phenyl)oxazole-4-carboxylate | 456.0 | E:1.34 F:1.66 | (500 MHz, DMSO-$d_6$) 9.26 (t, J = 6.1 Hz, 1H), 8.93 (s, 1H), 8.62 (d, J = 5.2 Hz, 1H), 8.53 (s, 1H), 8.09 (d, J = 8.3 Hz, 1H), 8.01 (s, 1H), 7.93-7.82 (m, 2H), 7.66 (dd, J = 8.1, 1.5 Hz, 1H), 7.59-7.48 (m, 3H), 5.28 (s, 2H), 4.57 (d, J = 6.1 Hz, 2H), 4.31 (q, J = 7.1 Hz, 2H), 1.30 (t, J = 7.2 Hz, 3H) |

EXAMPLE V-1

Methyl 3-((5-methyl-5H-chromeno[3,4-c]pyridine-8-carboxamido)methyl)benzoate

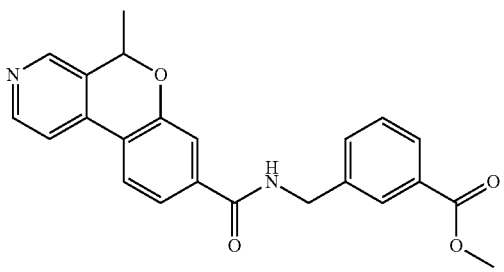 [SMILES: COC(=O)c1cccc(CNC(=O)c2ccc3c(c2)OC(C)c2cnccc2-3)c1]

Example V-1 was prepared by following the similar procedure as described in Example I-1 by replacing Intermediate 1 with Intermediate 4. LC-MS (ESI) m/z: 389.0 [M+H]$^+$; $^1$H NMR (400 MHz, CD$_3$OD) δ 8.57 (d, J=5.3 Hz, 1H), 8.46 (s, 1H), 8.08-8.00 (m, 2H), 7.98-7.91 (m, 1H), 7.85 (d, J=5.3 Hz, 1H), 7.68-7.55 (m, 2H), 7.54-7.42 (m, 2H), 5.49 (q, J=6.6 Hz, 1H), 4.64 (s, 2H), 3.91 (s, 3H), 1.65 (d, J=6.6 Hz, 3H); Analytical HPLC RT A: 4.94 min, B: 5.40 min.

EXAMPLE V-2

3-((5-Methyl-5H-chromeno[3,4-c]pyridine-8-carboxamido)methyl)benzoic acid

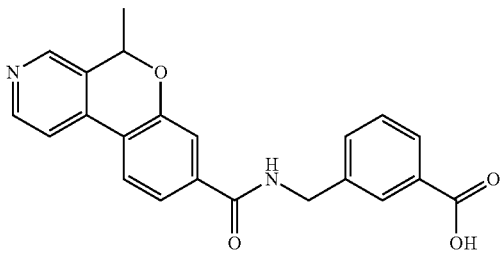 [SMILES: CC1Oc2cc(C(=O)NCc3cccc(C(=O)O)c3)ccc2-c2ccncc21]

Example V-2 was prepared by following the similar procedure as described in Example III-2 using Example V-1. LC-MS (ESI) m/z: 375.0[M+H]$^+$; $^1$H NMR (400 MHz, CD$_3$OD) δ 8.73 (d, J=5.9 Hz, 1H), 8.68 (s, 1H), 8.28 (d, J=6.2 Hz, 1H), 8.16 (d, J=8.1 Hz, 1H), 8.05 (s, 1H), 7.95 (dd, J=7.7, 1.3 Hz, 1H), 7.68 (dd, J=8.3, 1.7 Hz, 1H), 7.62 (d, J=7.7 Hz, 1H), 7.57 (d, J=1.8 Hz, 1H), 7.51-7.43 (m, 1H), 5.60 (q, J=6.6 Hz, 1H), 4.70-4.63 (m, 2H), 1.73 (d, J=6.6 Hz, 3H); Analytical HPLC RT A: 4.10 min, B: 4.35 min.

EXAMPLE V-3

N-(3-(2-Hydroxy-2-methylpropylcarbamoyl)benzyl)-5-methyl-5H-chromeno[3,4-c]pyridine-8-carboxamide

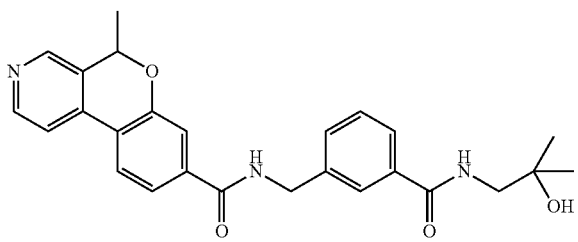 [SMILES: CC1Oc2cc(C(=O)NCc3cccc(C(=O)NCC(C)(C)O)c3)ccc2-c2ccncc21]

To a solution of V-2 (10 mg, 0.020 mmol) in DMF (1 mL) were added 1-amino-2-methylpropan-2-ol (9.13 mg, 0.102 mmol), DIEA (0.036 mL, 0.205 mmol) and HATU (14.01 mg, 0.037 mmol) at rt. The reaction was stirred under argon at rt for 1.5 h. Purification by reverse phase chromatography afforded Example V-3 as white solid (9.0 mg, 98%). LC-MS (ESI) m/z: 446.1[M+H]$^+$; $^1$H NMR (500 MHz, DMSO-d$_6$) δ 9.18 (br. s., 1H), 8.61 (d, J=4.7 Hz, 1H), 8.54 (s, 1H), 8.21 (br. s., 1H), 8.09 (d, J=8.0 Hz, 1H), 7.88 (d, J=5.0 Hz, 1H), 7.83 (s, 1H), 7.75 (d, J=7.4 Hz, 1H), 7.63 (d, J=8.0 Hz, 1H), 7.53 (s, 1H), 7.50-7.45 (m, 1H), 7.45-7.38 (m, 1H), 5.52 (q, J=6.2 Hz, 1H), 4.62-4.47 (m, 3H), 3.25 (d, J=5.8 Hz, 2H), 1.58 (d, J=6.3 Hz, 3H), 1.10 (s, 6H); Analytical HPLC RT E: 0.99 min, F: 1.27 min.

The compounds listed in Table V were prepared by following the similar procedures as described in Examples V-1 to V-3.

TABLE V

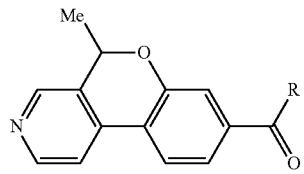

| Ex. No. | R | Name | LCMS (M + H)$^+$ | HPLC Method, RT (min.) | $^1$H NMR (δ, ppm) |
|---|---|---|---|---|---|
| V-4 |  | N-(1-(3,5-difluorophenyl)ethyl)-5-methyl-5H-chromeno[3,4-c]pyridine-8-carboxamide | 381.0 | E:1.36 F:1.61 | (500 MHz, DMSO-d$_6$) 8.93 (d, J = 7.4 Hz, 1H), 8.69 (d, J = 5.5 Hz, 1H), 8.62 (s, 1H), 8.14 (d, J = 8.3 Hz, 1H), 8.02 (d, J = 5.2 Hz, 1H), 7.64 (d, J = 8.0 Hz, 1H), 7.57 (d, J = 5.0 Hz, 1H), 7.16-7.05 (m, 3H), 5.56 (q, J = 6.6 Hz, 1H), (quin, J = 7.0 Hz, 1H), 1.61 (d, J = 6.6 Hz, 3H), 1.47 (d, J = 6.9 Hz, 3H) |

TABLE V-continued

| Ex. No. | R | Name | LCMS (M + H)+ | HPLC Method, RT (min.) | $^1$H NMR (δ, ppm) |
|---|---|---|---|---|---|
| V-5 | | N-((R)-1-(3-methoxyphenyl)ethyl)-5-methyl-5H-chromeno[3,4-c]pyridine-8-carboxamide | 375.1 | E:1.27 F:1.62 | (500 MHz, DMSO-d$_6$) 8.87 (d, J = 8.0 Hz, 1H), 8.68 (d, J = 5.0 Hz, 1H), 8.60 (s, 1H), 8.12 (d, J = 8.0 Hz, 1H), 8.00 (d, J = 5.2 Hz, 1H), 7.63 (d, J = 8.0 Hz, 1H), 7.55 (d, J = 4.4 Hz, 1H), 7.24 (t, J = 7.8 Hz, 1H), 6.97 (br. s., 2H), 6.80 (d, J = 8.0 Hz, 1H), 5.55 (q, J = 6.4 Hz, 1H), 5.13 (q, J = 7.2 Hz, 1H), 3.74 (s, 3H), 1.61 (q, J = 6.3 Hz, 3H), 1.47 (d, J = 6.9 Hz, 3H) |
| V-6 | | N-(3-(cyclopropylcarbamoyl)benzyl)-5-methyl-5H-chromeno[3,4-c]pyridine-8-carboxamide | 414.1 | E:1.05 F:1.35 | (500 MHz, DMSO-d$_6$) 9.19 (br. s., 1H), 8.69 (d, J = 4.7 Hz, 1H), 8.62 (s, 1H), 8.42 (br. s., 1H), 8.15 (d, J = 8.3 Hz, 1H), 8.04 (d, J = 5.0 Hz, 1H), 7.78 (s, 1H), 7.67 (dd, J = 15.1, 7.7 Hz, 2H), 7.55 (s, 1H), 7.49-7.44 (m, 1H), 7.43-7.35 (m, 1H), 5.56 (q, J = 6.4 Hz, 1H), 4.52 (d, J = 5.2 Hz, 2H), 2.83 (d, J = 3.0 Hz, 1H), 1.60 (d, J = 6.6 Hz, 3H), 0.68 (d, J = 6.9 Hz, 2H), 0.56 (br. s., 2H) |
| V-7 | | N-(3-(ethylcarbamoyl)benzyl)-5-methyl-5H-chromeno[3,4-c]pyridine-8-carboxamide | 402.1 | E:1.04 F:1.33 | (500 MHz, DMSO-d$_6$) 9.19 (br. s., 1H), 8.70 (d, J = 5.0 1H), 8.63 (s, 1H), 8.45 (br. s., 1H), 8.05 (d, J = 5.0 Hz, 1H), 8.00 (d, J = 8.0 Hz, 1H), 7.80 (s, 1H), 7.71 (d, J = 7.4 Hz, 1H), 7.66 (d, J = 8.0 Hz, 1H), 7.55 (s, 1H), 7.50-7.44 (m, 1H), 7.43-7.37 (m, 1H), 5.57 (q, J = 6.1 Hz, 1H), 4.53 (d, J = 5.2 Hz, 2H), 3.27 (quin, J = 6.4 Hz, 2H), 1.61 (d, J = 6.3 Hz, 3H), 1.11 (t, J = 7.0 Hz, 3H) |
| V-8 | | N-(3-carbamoylbenzyl)-5-methyl-5H-chromeno[3,4-c]pyridine-8-carboxamide | 374.1 | E:0.92 F:1.18 | (500 MHz, DMSO-d$_6$) 9.15 (br. S., 1H), 8.61 (d, J = 5.0 Hz, 1H), 8.54 (s, 1H), 8.09 (d, J = 8.0 Hz, 1H), 7.88 (d, J = 4.7 Hz, 1H), 7.84 (s, 1H), 7.75 (d, J = 7.4 Hz, 1H), 7.64 (d, J = 8.0 Hz, 1H), 7.53 (s, 1H), 7.50-7.45 (m, 1H), 7.44-7.37 (m, 1H), 7.33 (br. S., 1H), 5.52 (q, J = 6.2 Hz, 1H), 4.52 (d, J = 5.5 Hz, 2H), 1.59 (d, J = 6.3 Hz, 3H) |
| V-9 | | N-(3-(cyclopropylmethylcarbamoyl)benzyl)-5-methyl-5H-chromeno[3,4-c]pyridine-carboxamide | 428.1 | E:1.17 F:1.48 | (500 MHz, DMSO-d$_6$) 9.22-9.11 (m, 1H), 8.62 (d, J = 5.0 Hz, 1H), 8.54 (s, 2H), 8.09 (d, J = 8.3 Hz, 1H), 7.88 (d, J = 4.7 Hz, 1H), 7.82 (s, 1H), 7.73 (d, J = 7.4 Hz, 1H), 7.64 (d, J = 8.3 Hz, 1H), 7.53 (s, 1H), 7.50-7.44 (m, 1H), 7.44-7.38 (m, 1H), 5.52 (q, J = 6.5 Hz, 1H), 4.53 (d, J = 5.5 Hz, 2H), 3.13 (t, J = 6.1 Hz, 2H), 1.59 (d, J = 6.3 Hz, 3H), 1.03 (d, J = 6.1 Hz, 1H), 0.42 (d, J = 7.2 Hz, 2H), 0.22 (d, J = 4.1 Hz, 2H) |
| V-10 | | 5-methyl-N-(3-(methylcarbamoyl)benzyl)-5H-chromeno[3,4-c]pyridine-8-carboxamide | 388.1 | E:0.96 F:1.24 | (500 MHz, DMSO-d$_6$) 9.16 (br. s., 1H), 8.62 (d, J = 5.0 Hz, 1H), 8.54 (s, 1H), 8.41 (br. s., 1H), 8.09 (d, J = 8.0 Hz, 1H), 7.88 (d, J = 5.0 Hz, 1H), 7.80 (s, 1H), 7.70 (d, J = 7.4 Hz, 1H), 7.63 (d, J = 8.0 Hz, 1H), 7.53 (s, 1H), 7.49-7.44 (m, 1H), 7.43-7.37 (m, 1H), 5.52 (q, J = 6.3 Hz, 1H), 4.52 (d, J = 5.5 Hz, 2H), 2.77 (d, J = 1.9 Hz, 3H), 1.59 (d, J = 6.3 Hz, 3H) |
| V-11 | | 5-methyl-N-(3-(1-methylcyclopropylcarbamoyl)benzyl)-5H-chromeno[3,4-c]pyridine-8-carboxamide | 428.1 | E:1.14 F:1.43 | (500 MHz, DMSO-d$_6$) 9.14 (t, J = 5.9 Hz, 1H), 8.62 (d, J = 5.2 Hz, 2H), 8.54 (s, 1H), 8.09 (d, J = 8.3 Hz, 1H), 7.88 (d, J = 5.0 Hz, 1H), 7.78 (s, 1H), 7.68 (d, J = 7.7 Hz, 1H), 7.63 (dd, J = 8.3, 1.7 Hz, 1H), 7.53 (d, J = 1.9 Hz, 1H), 7.48-7.42 (m, 1H), 7.41-7.32 (m, 1H), 5.52 (q, J = 6.6 Hz, 1H), 4.51 (d, J = 6.1 Hz, 2H), 1.59 (d, J = 6.6 Hz, 3H), 1.35 (s, 3H), 0.76-0.70 (m, 2H), 0.62-0.56 (m, 2H) |

TABLE V-continued

| Ex. No. | R | Name | LCMS (M + H)⁺ | HPLC Method, RT (min.) | ¹H NMR (δ, ppm) |
|---|---|---|---|---|---|
| V-12 | (structure) | 5-methyl-N-(3-(((R)-tetrahydrofuran-2-yl)methylcarbamoyl)benzyl)-5H-chromeno[3,4-c]pyridine-8-carboxamide | 458.1 | E:1.05 F:1.36 | (500 MHz, DMSO-$d_6$) 9.16 (t, J = 6.1 Hz, 1H), 8.62 (d, J = 5.2 Hz, 1H), 8.54 (s, 1H), 8.49 (t, J = 5.8 Hz, 1H), 8.09 (d, J = 8.3 Hz, 1H), 7.89 (d, J = 5.0 Hz, 1H), 7.81 (s, 1H), 7.72 (d, J = 7.7 Hz, 1H), 7.63 (dd, J = 8.1, 1.8 Hz, 1H), 7.53 (d, J = 1.7 Hz, 1H), 7.50-7.45 (m, 1H), 7.44-7.36 (m, 1H), 5.52 (q, J = 6.6 Hz, 1H), 4.52 (d, J = 5.8 Hz, 2H), 3.96 (quin, J = 6.3 Hz, 1H), 3.76 (ddd, J = 8.2, 7.1, 6.2 Hz, 1H), 3.65-3.57 (m, 1H), 3.31-3.26 (m, 2H), 1.94-1.74 (m, 3H), 1.62-1.53 (m, 4H) |

EXAMPLE VI-1

(R)-N-(1-Phenylethyl)-6H-isochromeno[3,4-c]pyridine-8-carboxamide

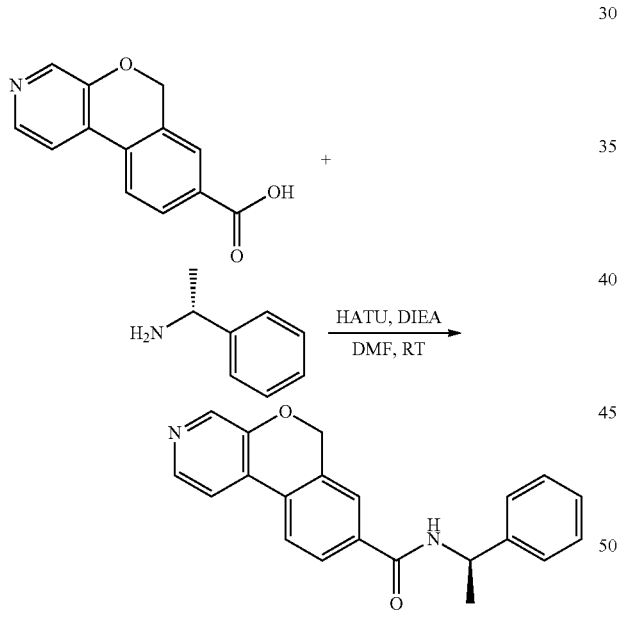

To a solution of Intermediate 3 (15 mg, 0.066 mmol) in DMF (1 mL) were added (R)-1-phenylethanamine (8.0 mg, 0.066 mmol), DIEA (0.058 mL, 0.330 mmol) and HATU (30.1 mg, 0.079 mmol) at rt. The reaction was stirred under argon at rt for 1 hr. Purification by reverse phase chromatography afforded Example VI-1 as white solid (9.4 mg 42%). LC-MS (ESI) m/z: 331.15 [M+H]⁺; ¹H NMR (500 MHz, DMSO-$d_6$) δ 8.93 (d, J=8.0 Hz, 1H), 8.33 (s, 1H), 8.30 (d, J=5.0 Hz, 1H), 8.06 (d, J=8.0 Hz, 1H), 7.96 (dd, J=8.3, 1.7 Hz, 1H), 7.92 (d, J=5.0 Hz, 1H), 7.84 (s, 1H), 7.40 (d, J=7.2 Hz, 2H), 7.33 (t, J=7.6 Hz, 2H), 7.25-7.20 (m, 1H), 5.31 (s, 2H), 5.18 (quin, J=7.3 Hz, 1H), 1.49 (d, J=6.9 Hz, 3H). Analytical HPLC RT E: 1.17 min; F: 1.53 min.

EXAMPLE VI-2

(S)-N-(2-Amino-1-phenylethyl)-6H-isochromeno[3,4-c]pyridine-8-carboxamide

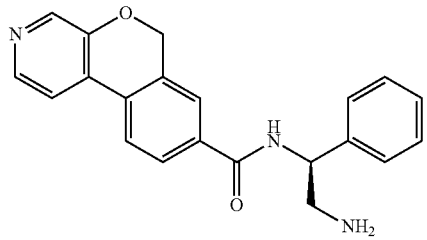 [SMILES: NC[C@@H](NC(=O)c1ccc2c(c1)COc1cnccc1-2)c1ccccc1]

EXAMPLE VI-2a (S)-2-((tert-Butoxycarbonyl)amino)-2-phenylethyl methanesulfonate

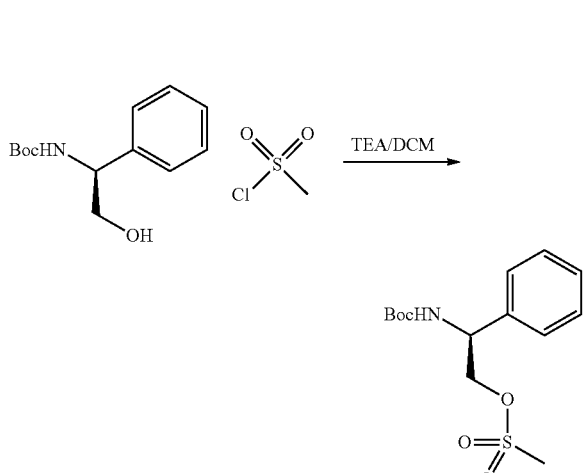

To a solution of (S)-tert-butyl (2-hydroxy-1-phenylethyl)carbamate (3.45 g, 14.54 mmol) in DCM (40 mL) were added TEA (3.04 mL, 21.81 mmol) and methanesulfonyl chloride (1.246 mL, 15.99 mmol) at −5° C. The reaction was stirred under argon at −5° C. for 2 h. The reaction mixture was diluted with DCM, washed with 1M HCl, sat NaHCO$_3$ and brine. The organic phase was dried over sodium sulfate, filtered and concentrated. After dried in vacuo, VI-2a was obtained as white solid (4.59g, 100%). LC-MS (ESI) m/z: 316.0 [M+H]$^+$; $^1$H NMR (400 MHz, CDCl$_3$) δ 7.43-7.36 (m, 2H), 7.36-7.29 (m, 3H), 5.14 (br. s., 1H), 5.02 (br. s., 1H), 4.55-4.34 (m, 2H), 2.89 (s, 3H), 1.45 (s, 9H).

EXAMPLE VI-2b (S)-tert-Butyl (2-azido-1-phenylethyl)carbamate

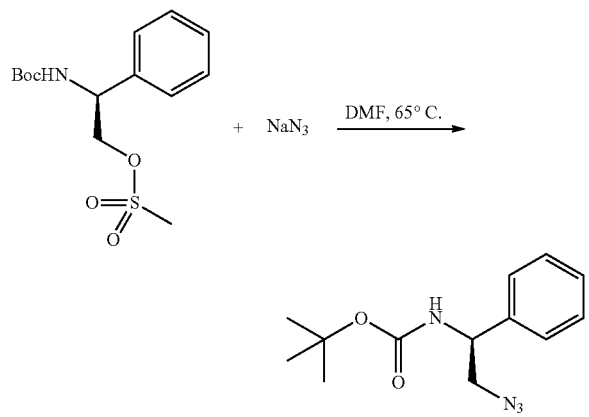

To a solution of VI-2a (4.59 g, 14.55 mmol) in DMF (20 mL) was added NaN$_3$ (1.892 g, 29.1 mmol) at rt. The reaction was stirred under argon at 65° C. for 3 h. The reaction was cooled to rt and diluted with water. The white precipitate formed was collected by filtration and was further washed with water, then was dried in vacuo to afford VI-2b as white solid (3.01 g, 79%). LC-MS (ESI) m/z: 263.1 [M+H]$^+$; $^1$H NMR (400 MHz, CDCl$_3$) δ 7.43-7.35 (m, 2H), 7.35-7.29 (m, 3H), 5.05 (br. s., 1H), 4.88 (br. s., 1H), 3.76-3.52 (m, 2H), 1.45 (s, 9H).

EXAMPLE VI-2c (S)-2-Azido-1-phenylethanamine, TFA salt

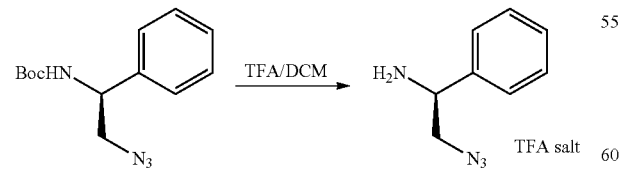

To a solution of VI-2b (295 mg, 1.125 mmol) in DCM (3 mL) was added TFA (1 mL) at rt. The reaction was stirred under argon at rt for 2 h. The solvent was removed and the resulted residue was dried in vacuo to give VI2-c as white solid (311 mg, 100%). LC-MS (ESI) m/z: 163.1 [M+H]$^+$.

EXAMPLE VI-2d (S)-N-(2-Azido-1-phenylethyl)-6H-isochromeno[3,4-c]pyridine-8-carboxamide, TFA salt

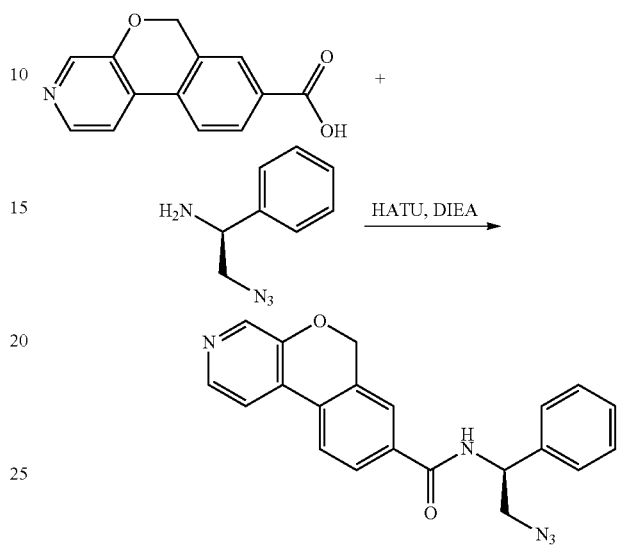

To a solution of Intermediate 2 (30 mg, 0.132 mmol) in DMF (1 mL) were added VI-2c (36.5 mg, 0.132 mmol), DIEA (0.115 mL, 0.660 mmol) and HATU (60.2 mg, 0.158 mmol) at rt. The reaction was stirred under argon at rt for 1.5 h. The crude product was purified by reverse phase chromatography to give VI-2d as white solid (22 mg, 34.3%). LC-MS (ESI) m/z: 372.1[M+H]$^+$; $^1$H NMR (400 MHz, CD$_3$OD) δ 8.54 (s, 1H), 8.47-8.43 (m, 1H), 8.42-8.37 (m, 1H), 8.19 (d, J=8.4 Hz, 1H), 8.02 (dd, J=8.1, 1.8 Hz, 1H), 7.83 (d, J=0.9 Hz, 1H), 7.48-7.43 (m, 2H), 7.41-7.35 (m, 2H), 7.34-7.28 (m, 1H), 5.51 (s, 2H), 5.41-5.29 (m, 1H), 3.83-3.65 (m, 2H).

EXAMPLE VI-2

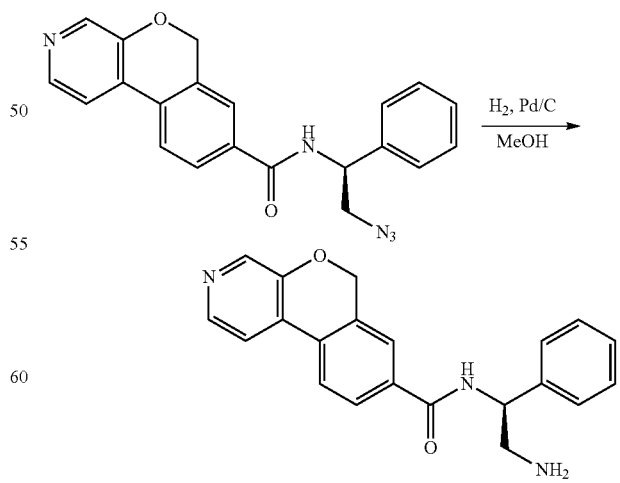

To a solution of VI-2d (22 mg, 0.045 mmol) in MeOH (3 mL) was added catalytic amount of 5% Pd/C. The reaction was stirred under a hydrogen balloon at rt for 2 h. The catalyst was filtered and the solvent was removed from the filtrate to afford Example VI-2 as white solid (13.3 mg, 82%). LC-MS (ESI) m/z: 346.1 [M+H]+; 1H NMR (400 MHz, CD3OD) δ 8.28 (s, 1H), 8.26 (d, J=5.1 Hz, 1H), 8.02 (s, 2H), 7.91-7.83 (m, 2H), 7.54-7.49 (m, 2H), 7.45 (t, J=7.5 Hz, 2H), 7.41-7.35 (m, 1H), 5.50 (dd, J=9.7, 4.6 Hz, 1H), 5.31 (s, 2H), 3.56-3.41 (m, 2H); Analytical HPLC RT A: 5.14 min, B: 5.67 min.

EXAMPLE VI-3

(±)-N-(1-(6-Methoxypyridin-2-yl)ethyl)-6H-isochromeno[3,4-c]pyridine-8-carboxamide

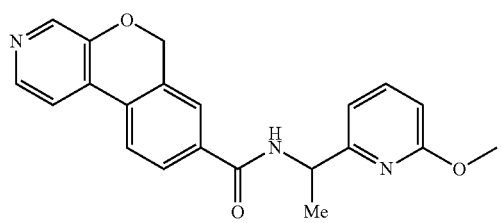 [SMILES: COc1cccc(C(C)NC(=O)c2ccc3c(c2)COc2cnccc2-3)n1]

EXAMPLE VI-3a (R,E)-N-((6-Methoxypyridin-2-yl)methylene)-2-methylpropane-2-sulfinamide

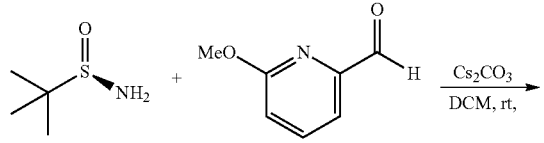

To a stirred suspension of (R)-2-methylpropane-2-sulfinamide (1.0g, 8.25 mmol) and Cs2CO3 (4.03 g, 12.38 mmol) in DCM (15 mL) was added a solution of 6-methoxypicolinaldehyde (1.092 mL, 9.08 mmol) in DCM (2 mL) dropwise. The solution was then stirred at rt for 5 h. The solid was filtered and solvent was removed. The crude product was purified by normal phase chromatography to provide VI-3a as clear colorless oil (1.91 g, 96%). LC-MS (ESI) m/z: 241.0 [M+H]+; 1H NMR (400 MHz, CDCl3) δ 8.59 (s, 1H), 7.72-7.58 (m, 2H), 6.85 (dd, J=7.9, 1.1 Hz, 1H), 3.99 (s, 3H), 1.29 (s, 9H).

EXAMPLE VI-3b (R)-N-(1-(6-Methoxypyridin-2-yl)ethyl)-2-methylpropane-2-sulfinamide

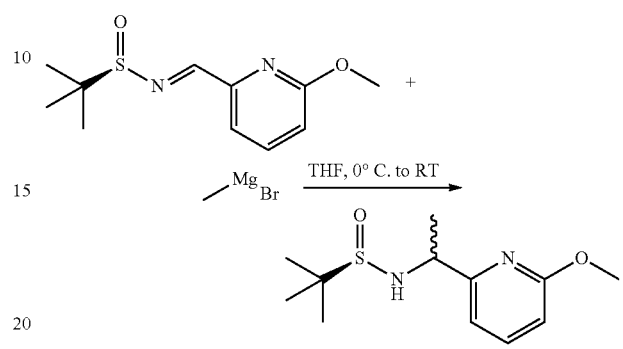

To a solution of VI-3a (650 mg, 2.70 mmol) in THF (6 mL) was added methylmagnesium bromide (1.4 M in toluene, 2.90 mL, 4.06 mmol) at 0° C. The reaction was stirred under argon at 0° C. for 2 h and then was warmed up to rt. After stirred for another 30 min, it was cooled to 0° C. and NH4Cl solution was carefully added. The reaction mixture was diluted with EtOAc, washed with H2O and brine. The organic phase was dried over sodium sulfate, filtered and concentrated. The crude product was purified by normal phase chromatography. Two close peaks of two diastereomers were collected and combined. After removal of solvent, VI-3b was obtained as clear colorless oil (578 mg, 83%). LC-MS (ESI) m/z: 257.0 [M+H]+; 1H NMR (400 MHz, CDCl3) δ 7.53 (dt, J=8.3, 7.1 Hz, 2H), 6.86 (d, J=7.3 Hz, 1H), 6.82 (d, J=7.0 Hz, 1H), 6.62 (d, J=8.1 Hz, 2H), 4.83 (br. d, J=4.6 Hz, NH) 4.59-4.44 (m, 2H), 3.93 (s, 3H), 3.92 (s, 3H), 1.60 (d, J=6.8 Hz, 3H), 1.50 (d, J=6.6 Hz, 3H), 1.26 (s, 6H), 1.21 (s, 6H).

EXAMPLE VI-3c 1-(6-Methoxypyridin-2-yl)ethanamine, 2HCl

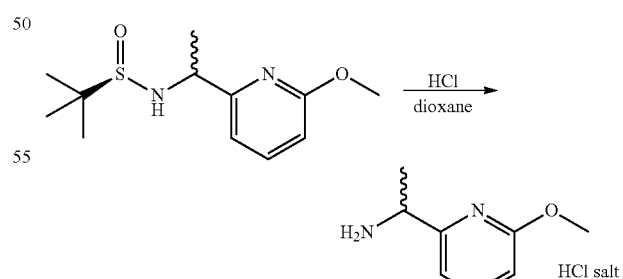

To a solution of VI-3b (578 mg, 2.255 mmol) in MeOH (5 mL) was added HCl (4 M in dioxane, 2.818 mL, 11.27 mmol) at RT. The reaction was stirred under argon at rt for 2 h. The solvent was removed to give VI-3c as white solid (520 mg, 100%). LC-MS (ESI) m/z: 153.0[M+H]+.

EXAMPLE VI-3

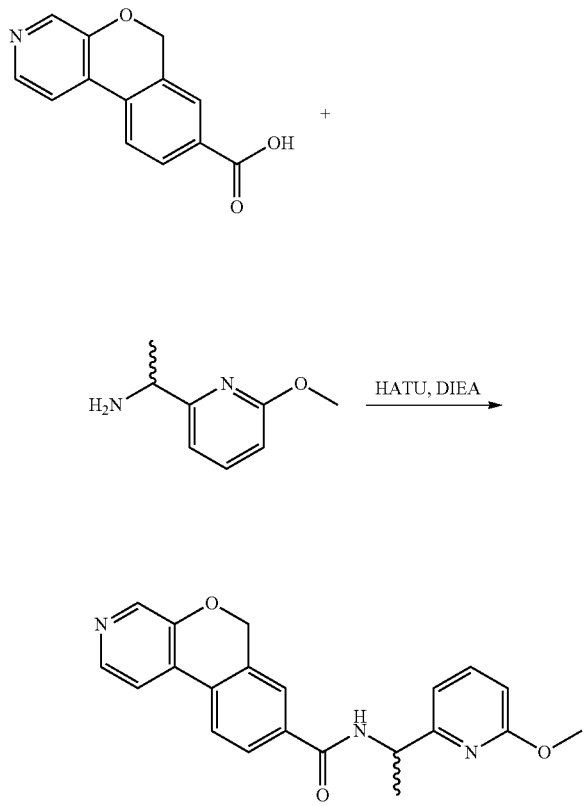

Example VI-3 was prepared by following a similar procedure as described in VI-1 by replacing (R)-1-phenylethanamine with VI-3c. LC-MS (ESI) m/z: 362.15[M+H]$^+$; $^1$H NMR (500 MHz, DMSO-d$_6$) δ 8.87 (d, J=8.0 Hz, 1H), 8.35 (s, 1H), 8.31 (d, J=5.0 Hz, 1H), 8.08 (d, J=8.0 Hz, 1H), 8.00 (dd, J=8.1, 1.8 Hz, 1H), 7.94 (d, J=5.2 Hz, 1H), 7.87 (d, J=1.1 Hz, 1H), 7.66 (dd, J=8.1, 7.6 Hz, 1H), 6.98 (d, J=7.4 Hz, 1H), 6.67 (d, J=8.3 Hz, 1H), 5.32 (s, 2H), 5.12 (quin, J=7.2 Hz, 1H), 3.87 (s, 3H), 1.52 (d, J=7.2 Hz, 3H); Analytical HPLC RT E: 1.12 min, F: 1.59 min.

EXAMPLE VI-4

N-((3S,4R)-4-Phenylpyrrolidin-3-yl)-6H-isochromeno[3,4-c]pyridine-8-carboxamide

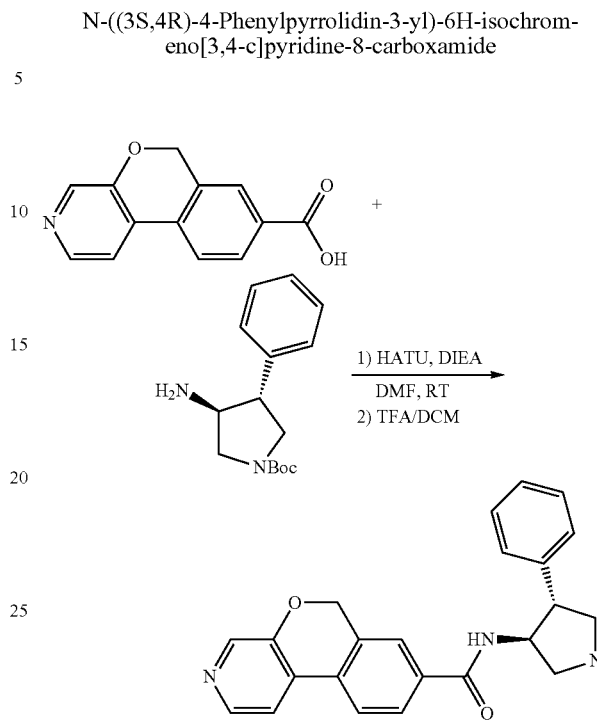

Amide coupling was carried out by following a similar procedure as described in Example VI-1 by replacing (R)-1-phenylethanamine with (3S,4R)-tert-butyl 3-amino-4-phenylpyrrolidine-1-carboxylate. Thus obtained intermediate was treated with TFA in DCM to provide Example VI-4 as white solid after reverse phase chromatography purification. LC-MS (ESI) m/z: 372.20 [M+H]$^+$; $^1$H NMR (500 MHz, DMSO-d$_6$) δ 8.80 (d, J=8.0 Hz, 1H), 8.35 (s, 1H), 8.31 (d, J=5.0 Hz, 1H), 8.07 (d, J=8.3 Hz, 1H), 7.95-7.87 (m, 2H), 7.78 (s, 1H), 7.41-7.37 (m, 2H), 7.36-7.31 (m, 2H), 7.28-7.22 (m, 1H), 5.31 (s, 2H), 4.61 (quin, J=7.7 Hz, 1H), 3.61-3.56 (m, 1H), 3.47 (dd, J=17.6, 9.4 Hz, 1H), 3.08 (t, J=10.3 Hz, 1H), 2.98 (dd, J=11.1, 7.6 Hz, 1H); Analytical HPLC RT E: 0.92 min, F: 1.20 min.

The compounds listed in Table VI were prepared by following the similar procedure as described in Example VI-1.

TABLE VI

| Ex. No. | R | Name | LCMS (M + H)$^+$ | HPLC Method, RT (min.) | $^1$H NMR (δ, ppm) |
|---|---|---|---|---|---|
| VI-5 | ![structure with NH, phenyl, Cl, methyl] | (R)-N-(1-(2-chlorophenyl)ethyl)-6H-isochromeno[3,4-c]pyridine-8-carboxamide | 364.90 | E:1.36 F:1.69 | (500 MHz, DMSO-d$_6$) 9.06 (d, J = 7.2 Hz, 1H), 8.34 (s, 1H), 8.30 (d, J = 4.7 Hz, 1H), 8.08 (d, J = 8.0 Hz, 1H), 7.98 (d, J = 8.0 Hz, 1H), 7.93 (d, J = 4.7 Hz, 1H), 7.85 (s, 1H), 7.55 (d, J = 7.7 Hz, 1H), 7.43 (d, J = 7.7 Hz, 1H), 7.34 (t, J = 7.4 Hz, 1H), 7.30-7.23 (m, 1H), 5.50-5.41 (m, 1H), 5.32 (s, 2H), 1.46 (d, J = 6.6 Hz, 3H) |

TABLE VI-continued

| Ex. No. | R | Name | LCMS (M + H)+ | HPLC Method, RT (min.) | 1H NMR (δ, ppm) |
|---|---|---|---|---|---|
| VI-6 | | N-(3-methoxy-benzyl)-6H-isochromeno[3,4-c]pyridine-8-carboxamide | 346.90 | E:1.15 F:1.49 | (500 MHz, DMSO-d6) 9.16 (br. s., 1H), 8.40 (br. s., 1H), 8.34 (br. s., 1H), 8.11 (d, J = 8.3 Hz, 1H), 8.04-7.94 (m, 2H), 7.86 (s, 1H), 7.25 (t, J = 7.7 Hz, 1H), 6.95-6.87 (m, 2H), 6.82 (d, J = 8.3 Hz, 1H), 5.34 (s, 2H), 4.47 (d, J = 5.0 Hz, 2H), 3.73 (s, 3H) |
| VI-7 | | (R)-N-(1-(3-methoxyphenyl)ethyl)-6H-iso-chromeno[3,4-c]pyridine-8-carboxamide | 361.20 | E:1.26 F:1.56 | (500 MHz, DMSO-d6) 8.89 (d, J = 8.0 Hz, 1H), 8.35 (s, 1H), 8.32 (d, J = 5.0 Hz, 1H), 8.08 (d, J = 8.3 Hz, 1H), 7.97 (dd, J = 8.0, 1.7 Hz, 1H), 7.93 (d, J = 5.2 Hz, 1H), 7.85 (d, J = 0.8 Hz, 1H), 7.26 (t, J = 8.0 Hz, 1H), 7.03-6.95 (m, 2H), 6.87-6.76 (m, 1H), 5.33 (s, 2H), 5.17 (quin, J = 7.3 Hz, 1H), 3.76 (s, 3H), 1.49 (d, J = 6.9 Hz, 3H) |
| VI-8 | | N-(4-chloro-2-fluorobenzyl)-6H-isochromeno[3,4-c]pyridine-8-carboxamide | 369.10 | E:1.29 F:1.66 | (500 MHz, DMSO-d6) 9.16 (t, J = 5.8 Hz, 1H), 8.34 (s, 1H), 8.30 (d, J = 6.0 Hz, 1H), 8.08 (d, J = 8.3 Hz, 1H), 7.96 (dd, J = 8.3, 1.7 Hz, 1H), 7.92 (d, J = 5.2 Hz, 1H), 7.84 (s, 1H), 7.46-7.37 (m, 2H), 7.28 (dd, J = 8.3, 1.9 Hz, 1H), 5.31 (s, 2H), 4.50 (d, J = 5.8 Hz, 2H) |
| VI-9 | | N-(3,5-difluoro-benzyl)-6H-isochromeno[3,4-c]pyridine-8-carboxamide | 353.15 | E:1.08 F:1.64 | (500 MHz, DMSO-d6) 9.23 (t, J = 5.9 Hz, 1H), 8.34 (s, 1H), 8.30 (d, J = 5.2 Hz, 1H), 8.09 (d, J = 8.3 Hz, 1H), 7.97 (dd, J = 8.3, 1.4 Hz, 1H), 7.92 (d, J = 5.2 Hz, 1H), 7.86 (s, 1H), 7.17-7.08 (m, 1H), 7.08-7.00 (m, 2H), 5.32 (s, 2H), 4.51 (d, J = 5.8 Hz, 2H) |
| VI-10 | | N-(3-(difluoro-methoxy)benzyl)-6H-isochromeno[3,4-c]pyridine-8-carboxamide | 383.15 | E:1.23 F:1.57 | (500 MHz, DMSO-d6) 9.21 (t, J = 5.9 Hz, 1H), 8.34 (s, 1H), 8.30 (d, J = 5.2 Hz, 1H), 8.08 (d, J = 8.3 Hz, 1H), 7.97 (dd, J = 8.3, 1.4 Hz, 1H), 7.93 (d, J = 5.0 Hz, 1H), 7.85 (s, 1H), 7.42-7.19 (m, 3H), 7.13 (s, 1H), 7.09-7.04 (m, 1H), 5.31 (s, 2H), 4.51 (d, J = 5.8 Hz, 2H) |
| VI-11 | | (R)-N-(1-(4-fluoro-phenyl)ethyl)-6H-isochromeno[3,4-c]pyridine-8-carboxamide | 349.20 | E:1.22 F:1.57 | (500 MHz, DMSO-d6) 8.93 (d, J = 8.0 Hz, 1H), 8.33 (s, 1H), 8.30 (d, J = 5.0 Hz, 1H), 8.06 (d, J = 8.3 Hz, 1H), 7.95 (dd, J = 8.1, 1.2 Hz, 1H), 7.92 (d, J = 5.0 Hz, 1H), 7.83 (s, 1H), 7.43 (dd, J = 8.5, 5.8 Hz, 2H), 7.15 (t, J = 8.8 Hz, 2H), 5.31 (s, 2H), 5.17 (quin, J = 7.2 Hz, 1H), 1.48 (d, J = 7.2 Hz, 3H) |
| VI-12 | | (S)-N-(1-hydroxy-3-phenylpropan-2-yl)-6H-isochromeno[3,4-c]pyridine-8-carboxamide | 361.20 | E:1.03 F:1.31 | (500 MHz, DMSO-d6) 8.36-8.27 (m, 3H), 8.04 (d, J = 8.0 Hz, 1H), 7.90 (d, J = 5.0 Hz, 1H), 7.86 (d, J = 8.0 Hz, 1H), 7.74 (s, 1H), 7.30-7.22 (m, 4H), 7.15 (br. s., 1H), 5.29 (s, 2H), 4.88 (t, J = 5.4 Hz, 1H), 4.17 (d, J = 5.5 Hz, 1H), 3.54-3.47 (m, 1H), 3.43 (dt, J = 10.7, 5.5 Hz, 1H), 2.96 (dd, J = 13.5, 5.0 Hz, 1H), 2.79 (dd, J = 13.2, 9.4 Hz, 1H) |

EXAMPLE VII-1

Methyl 3-((6H-isochromeno[3,4-c]pyridine-8-carboxamido)methyl)benzoate

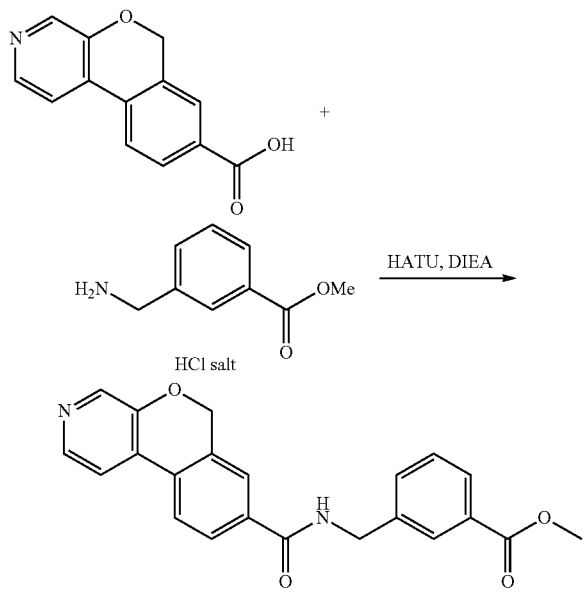

Example VII-1 was prepared by following a similar procedure as described in VI-1 by replacing (R)-1-phenylethanamine with methyl 3-(aminomethyl)benzoate, HCl salt. LC-MS (ESI) m/z: 375.20[M+H]+; 1H NMR (500 MHz, DMSO-d6) δ 9.25 (t, J=5.9 Hz, 1H), 8.40 (s, 1H), 8.35 (d, J=5.0 Hz, 1H), 8.11 (d, J=8.3 Hz, 1H), 8.01 (d, J=5.2 Hz, 1H), 7.98 (dd, J=8.0, 1.7 Hz, 1H), 7.94 (s, 1H), 7.88-7.83 (m, 2H), 7.62 (d, J=7.7 Hz, 1H), 7.53-7.47 (m, 1H), 5.35 (s, 2H), 4.56 (d, J=6.1 Hz, 2H), 3.85 (s, 3H). Analytical HPLC RT E: 1.19 min, F: 1.49 min.

EXAMPLE VII-2

3-((6H-Isochromeno[3,4-c]pyridine-8-carboxamido)methyl)benzoic acid

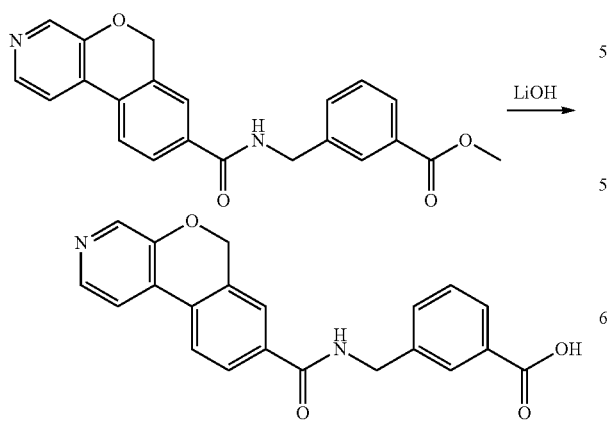

To a solution of Example VII-1 (220 mg, 0.588 mmol) in THF (5 mL) and H2O (2 mL) was added LiOH (42.2 mg, 1.763 mmol) at rt. The reaction was stirred under argon at rt for 4 h. The solvent was removed. Reverse phase purification gave VII-2 as white solid (200 mg, 94%). LC-MS (ESI) m/z: 361.12 [M+H]+; 1H NMR (500 MHz, DMSO-d6) δ 9.22 (t, J=5.9 Hz, 1H), 8.33 (s, 1H), 8.30 (d, J=5.2 Hz, 1H), 8.08 (d, J=8.3 Hz, 1H), 8.00-7.94 (m, 1H), 7.91 (d, J=3.9 Hz, 2H), 7.86 (s, 1H), 7.82 (d, J=7.7 Hz, 1H), 7.56 (d, J=7.7 Hz, 1H), 7.48-7.41 (m, 1H), 5.31 (s, 2H), 4.55 (d, J=5.8 Hz, 2H); Analytical HPLC RT E: 0.96 min, F: 0.96 min.

EXAMPLE VII-3

N-(3-((2-Hydroxy-2-methylpropyl)carbamoyl)benzyl)-6H-isochromeno[3,4-c]pyridine-8-carboxamide

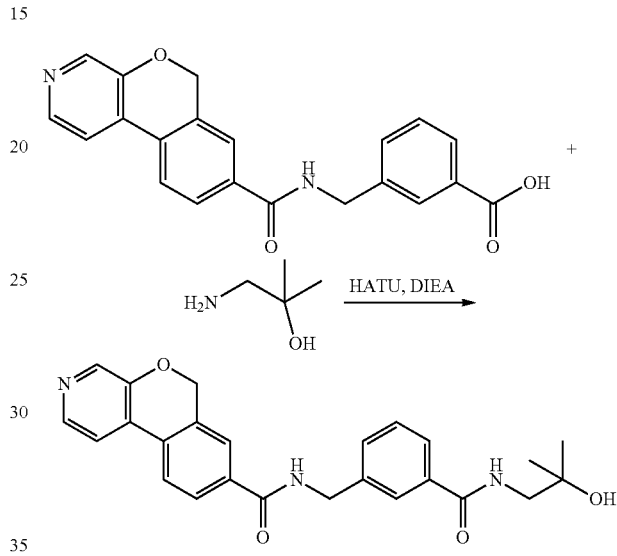

To a solution of VII-2 (30 mg, 0.083 mmol) in DMF (1.5 mL) were added 1-amino-2-methylpropan-2-ol (14.84 mg, 0.166 mmol), DIEA (0.044 mL, 0.250 mmol) and HATU (38.0 mg, 0.100 mmol) at rt. The reaction was stirred under argon at rt for 2 h. The crude product was purified by reverse phase chromatography to afford VII-3 as white solid (20.6 mg, 45%). LC-MS (ESI) m/z: 432.2 [M+H]+; 1H NMR (400 MHz, DMSO-d6) δ 9.22 (t, J=5.9 Hz, 1H), 8.45 (s, 1H), 8.38 (d, J=5.3 Hz, 1H), 8.20 (t, J=5.9 Hz, 1H), 8.14 (d, J=8.1 Hz, 1H), 8.09 (d, J=5.3 Hz, 1H), 8.00 (dd, J=8.1, 1.8 Hz, 1H), 7.87 (s, 1H), 7.83 (s, 1H), 7.75 (d, J=7.7 Hz, 1H), 7.52-7.47 (m, 1H), 7.46-7.40 (m, 1H), 5.37 (s, 2H), 4.55 (d, J=5.9 Hz, 2H), 3.25 (d, J=6.2 Hz, 2H), 1.10 (s, 6H); Analytical HPLC RT A: 3.56 min, B: 3.72 min.

EXAMPLE VII-4

N-(3-(Ethylcarbamoyl)-4-fluorobenzyl)-6H-isochromeno[3,4-c]pyridine-8-carboxamide

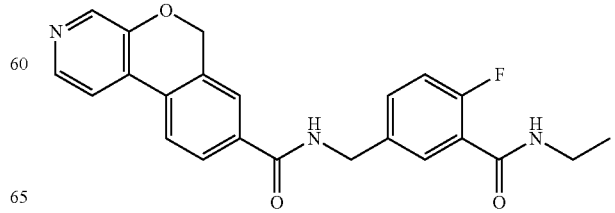

Example VII-4 was prepared by following a similar procedure as described in VII-1, VII-2 and VII-3 by replacing methyl 3-(aminomethyl)benzoate, HCl salt with Intermediate 9 in Example VII-1. LC-MS (ESI) m/z: 406.20 [M+H]+; 1H NMR (500 MHz, DMSO-d6) δ 9.19 (t, J=5.9 Hz, 1H), 8.33 (s, 1H), 8.30 (d, J=5.0 Hz, 1H), 8.27 (br. s., 1H), 8.07 (d, J=8.3 Hz, 1H), 7.96 (d, J=8.0 Hz, 1H), 7.91 (d, J=5.0 Hz, 1H), 7.84 (s, 1H), 7.57 (dd, J=6.9, 2.2 Hz, 1H), 7.49-7.42 (m, 1H), 7.23 (dd, J=10.3, 8.7 Hz, 1H), 5.31 (s, 2H), 4.49 (d, J=6.1 Hz, 2H), 3.28-3.23 (m, 2H), 1.10 (t, J=7.2 Hz, 3H); Analytical HPLC RT E: 1.06 min, F: 1.33 min.

The compounds listed in Table VII were prepared by following the similar procedure as described in example Examples VII-1 to VII-4.

TABLE VII

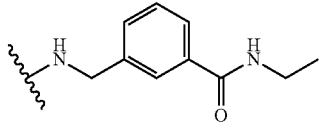 [SMILES: *NCc1cccc(C(=O)NCC)c1]

| Ex. No. | R | Name | LCMS (M + H)+ | HPLC Method, RT (min.) | 1H NMR (δ ppm) |
|---|---|---|---|---|---|
| VII-5 | 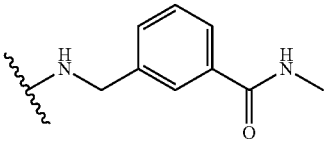 [SMILES: *NCc1cccc(C(=O)NC)c1] | N-(3-(ethylcarbamoyl)benzyl)-6H-isochromeno[3,4-c]pyridine-8-carboxamide | 388.1 | A:6.01 B:6.24 | (400 MHz, DMSO-d6) 9.20 (t, J = 5.9 Hz, 1H), 8.45 (s, 2H), 8.38 (d, J = 5.3 Hz, 1H), 8.14 (d, J = 8.1 Hz, 1H), 8.09 (d, J = 5.3 Hz, 1H), 8.00 (dd, J = 8.1, 1.8 Hz, 1H), 7.87 (d, J = 1.1 Hz, 1H), 7.81 (s, 1H), 7.71 (d, J = 7.7 Hz, 1H), 7.50-7.45 (m, 1H), 7.44-7.38 (m, 1H), 5.37 (s, 2H), 4.54 (d, J = 5.9 Hz, 2H), 3.34-3.22 (m, 2H), 1.11 (t, J = 7.2 Hz, 3H) |
| VII-6 | 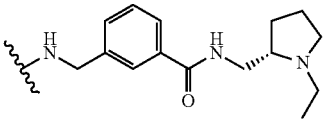 [SMILES: *NCc1cccc(C(=O)NC[C@@H]2CCCN2CC)c1] | N-(3-(methylcarbamoyl)benzyl)-6H-isochromeno[3,4-c]pyridine-8-carboxamide | 374.15 | E:0.89 F:1.18 | (500 MHz, DMSO-d6) 9.20 (t, J = 5.9 Hz, 1H), 8.42 (s, 2H), 8.36 (d, J = 5.2 Hz, 1H), 8.12 (d, J = 8.0 Hz, 1H), 8.04 (d, J = 5.2 Hz, 1H), 8.00 (s, 1H), 7.87 (s, 1H), 7.81 (s, 1H), 7.70 (d, J = 7.4 Hz, 1H), 7.50-7.45 (m, 1H), 7.42 (d, J = 7.4 Hz, 1H), 5.35 (s, 2H), 4.57-4.52 (m, 2H), 2.77 (d, J = 4.4 Hz, 3H) |
| VII-7 | 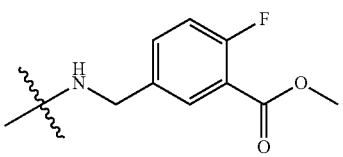 [SMILES: *NCc1ccc(F)c(C(=O)OC)c1] | (S)-N-(3-((1-ethylpyrrolidin-2-yl)methylcarbamoyl)benzyl)-6H-ischromeno[3,4-c]pyridine-8-carboxamide | 471.30 | E:0.91 F:1.15 | (500 MHz, DMSO-d6) 9.21 (br. s., 1H), 8.35 (s, 1H), 8.32 (br. s., 1H), 8.10 (d, J = 8.3 Hz, 1H), 7.99 (d, J = 8.3 Hz, 1H), 7.94 (br. s., 1H), 7.87 (s, 1H), 7.82 (br. s., 1H), 7.73 (d, J = 7.4 Hz, 1H), 7.51 (br. s., 1H), 7.46 (d, J = 7.2 Hz, 1H), 5.33 (s, 2H), 4.57 (d, J = 4.4 Hz, 2H), 3.76-2.98 (m, 7H), 1.69 (br. s., 4H), 1.27-0.92 (m, 3H) |
| VII-8 | 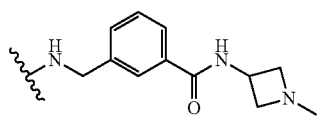 [SMILES: *NCc1cccc(C(=O)NC2CN(C)C2)c1] | methyl 5-((6H-isochromeno[3,4-c]pyridine-8-carboxamido)methyl)-2-fluorobenzoate | 393.0 | A:4.89 B:5.37 | (400 MHz, DMSO-d6) 9.24 (t, J = 5.9 Hz, 1H), 8.45 (s, 1H), 8.38 (d, J = 5.3 Hz, 1H), 8.14 (d, J = 8.1 Hz, 1H), 8.08 (d, J = 5.3 Hz, 1H), 7.98 (dd, J = 8.3, 1.7 Hz, 1H), 7.90-7.83 (m, 2H), 7.68-7.58 (m, 1H), 7.33 (dd, J = 11.0, 8.6 Hz, 1H), 5.37 (s, 2H), 4.52 (d, J = 5.7 Hz, 2H), 3.85 (s, 3H) |
| VII-9 | 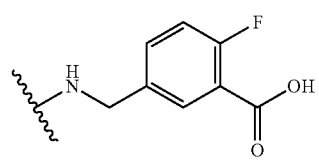 [SMILES: *NCc1ccc(F)c(C(=O)O)c1] | N-(3-(1-methylazetidin-3-ylcarbamoyl)benzyl)-6H-isochromeno[3,4-c]pyridine-8-carboxamide | 429.00 | E:0.85 F:0.99 | (500 MHz, DMSO-d6) 9.21 (t, J = 6.1 Hz, 1H), 8.89 (d, J = 6.6 Hz, 1H), 8.34 (s, 1H), 8.31 (d, J = 5.2 Hz, 1H), 8.09 (d, J = 8.3 Hz, 1H), 7.98 (dd, J = 8.1, 1.5 Hz, 1H), 7.92 (d, J = 5.2 Hz, 1H), 7.86 (s, 1H), 7.83 (s, 1H), 7.75 (d, J = 7.7 Hz, 1H), 7.54-7.50 (m, 1H), 7.48-7.43 (m, 1H), 5.32 (s, 2H), 4.56 (d, J = 5.8 Hz, 4H), 3.95-3.81 (m, 2H), 3.46 (br. S., 2H) |
| VII-10 |  | 5-((6H-isochromeno[3,4-c]pyridine-8-carboxamido)methyl)-2-fluorobenzoic acid | 379.15 | | (500 MHz, DMSO-d6) 9.22 (t, J = 5.9 Hz, 1H), 8.38 (s, 1H), 8.33 (d, J = 5.2 Hz, 1H), 8.10 (d, J = 8.3 Hz, 1H), 8.01-7.93 (m, 2H), 7.85 (d, J = 1.1 Hz, 1H), 7.83 (dd, J = 7.0, 2.3 Hz, 1H), 7.59 (ddd, J = 8.5, 4.7, 2.5 Hz, 1H), 7.28 (dd, J = 10.7, 8.5 Hz, 1H), 5.33 (s, 2H), 4.51 (d, J = 5.8 Hz, 2H) |

TABLE VII-continued

| Ex. No. | R | Name | LCMS (M + H)+ | HPLC Method, RT (min.) | 1H NMR (δ ppm) |
|---|---|---|---|---|---|
| VII-11 | | (R)-N-(3-(pyrrolidin-2-ylmethyl-carbamoyl)benzyl)-6H-isochromeno[3,4-c]pyridine-8-carboxamide | 443.25 | E:0.84 F:1.00 | (500 MHz, DMSO-$d_6$) 9.27 (t, J = 5.9 Hz, 1H), 9.02 (br. s., 1H), 8.81 (t, J = 5.6 Hz, 1H), 8.38 (s, 1H), 8.34 (d, J = 5.2 Hz, 1H), 8.12 (d, J = 8.3 Hz, 1H), 8.00 (d, J = 8.3 Hz, 1H), 7.97 (d, J = 5.0 Hz, 1H), 7.88 (s, 1H), 7.85 (s, 1H), 7.77 (d, J = 7.7 Hz, 1H), 7.58-7.52 (m, 1H), 7.51-7.45 (m, 1H), 5.34 (s, 2H), 4.57 (d, J = 6.1 Hz, 2H), 3.66-3.49 (m, 3H), 3.25 (ddd, J = 10.9, 7.3, 4.1 Hz, 1H), 3.19-3.10 (m, 1H), 2.11-2.02 (m, 1H), 1.98-1.82 (m, 2H), 1.68 (dq, J = 12.9, 8.4 Hz, 1H) |
| VII-12 | | N-(4-fluoro-3-(2-hydroxy-2-methyl-propylcarbamoyl)benzyl)-6H-isochromeno[3,4-c]pyridine-8-carboxamide | 450.25 | E:0.95 F:1.21 | (500 MHz, DMSO-$d_6$) 9.22 (br. s., 1H), 8.35 (br. s., 1H), 8.31 (br. s., 1H), 8.09 (d, J = 8.0 Hz, 1H), 8.01 (br. s., 1H), 7.97 (d, J = 7.7 Hz, 1H), 7.93 (br. s., 1H), 7.85 (br. s., 1H), 7.63 (br. s., 1H), 7.49 (br. s., 1H), 7.27 (t, J = 9.2 Hz, 1H), 5.32 (br. s., 2H), 4.58 (br. s., 1H), 4.51 (br. s., 2H), 3.25 (br. s., 2H), 1.13 (br. s., 6H) |

EXAMPLE VIII-1

Methyl 3-((6-ethyl-6H-isochromeno[3,4-c]pyridine-8-carboxamido)methyl)benzoate

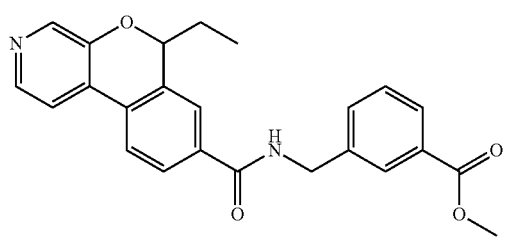 [SMILES: CCC1Oc2cnccc2-c2ccc(C(=O)NCc3cccc(C(=O)OC)c3)cc21]

Example VIII-1 was prepared by following the similar procedure as described in Example III-1 using Intermediate 7 to replace Intermediate 1. LC-MS (ESI) m/z: 40.3.1[M+H]+; 1H NMR (400 MHz, CD$_3$OD) δ 8.25 (s, 1H), 8.21 (d, J=5.1 Hz, 1H), 8.05 (s, 1H), 8.03-7.98 (m, 1H), 7.97-7.89 (m, 2H), 7.85 (d, J=5.1 Hz, 1H), 7.76 (s, 1H), 7.63 (d, J=7.7 Hz, 1H), 7.50-7.42 (m, 1H), 5.28 (dd, J=8.8, 4.6 Hz, 1H), 4.65 (s, 2H), 3.89 (s, 3H), 1.97-1.74 (m, 2H), 1.06 (t, J=7.4 Hz, 3H); Analytical HPLC RT A: 5.38 min, B: 5.91 min.

EXAMPLE VIII-2

3-((6-Ethyl-6H-isochromeno[3,4-c]pyridine-8-carboxamido)methyl)benzoic acid

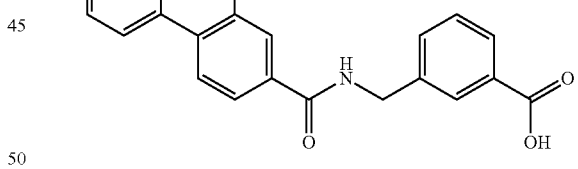

Example VIII-2 was prepared by following the similar procedure as described in Example III-2 using Example VIII-1 to replace Example III-1. LC-MS (ESI) m/z: 389.0 [M+H]+; 1H NMR (400 MHz, CD$_3$OD) δ 8.57 (s, 1H), 8.43 (s, 2H), 8.20 (d, J=8.4 Hz, 1H), 8.07-8.00 (m, 2H), 7.97-7.90 (m, 1H), 7.85 (d, J=1.8 Hz, 1H), 7.62 (dd, J=7.7, 0.4 Hz, 1H), 7.51-7.41 (m, 1H), 5.54 (dd, J=8.6, 4.6 Hz, 1H), 4.66 (s, 2H), 2.08-1.82 (m, 2H), 1.09 (t, J=7.3 Hz, 3H); Analytical HPLC RT A: 4.49 min, B: 4.86 min.

EXAMPLE VIII-3

6-Ethyl-N-(3-(2-hydroxy-2-methylpropylcarbamoyl)benzyl)-6H-isochromeno[3,4-c]pyridine-8-carboxamide

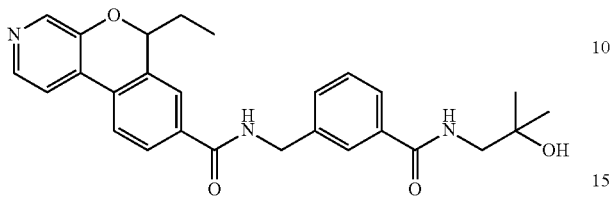

Example VIII-3 was prepared by following the similar procedure as described in Example III-3 using Example VIII-2 to replace Example III-2 to couple with 1-amino-2-methylpropan-2-ol. LC-MS (ESI) m/z: 460.1[M+H]$^+$; $^1$H NMR (500 MHz, DMSO-d$_6$) δ 9.21 (t, J=5.8 Hz, 1H), 8.33 (s, 1H), 8.28 (d, J=5.2 Hz, 1H), 8.24 (t, J=5.9 Hz, 1H), 8.09 (d, J=8.0 Hz, 1H), 7.97 (d, J=8.3 Hz, 1H), 7.92 (d, J=5.2 Hz, 1H), 7.83 (s, 2H), 7.75 (d, J=7.7 Hz, 1H), 7.52-7.46 (m, 1H), 7.46-7.39 (m, 1H), 5.35 (dd, J=8.7, 4.5 Hz, 1H), 4.58-4.53 (m, 2H), 3.24 (d, J=6.1 Hz, 2H), 1.85-1.69 (m, 2H), 1.09 (s, 6H), 0.98 (t, J=7.3 Hz, 3H); Analytical HPLC RT E: 1.08 min, F: 1.42 min.

The compounds listed in Table VIII were prepared by following the similar procedure as described in Example VII-1-3, by using Intermediates 6, 7, 8, 9 and 10.

TABLE VIII

| Ex. No. | R | Name | LCMS (M + H)+ | HPLC Method, RT (min.) | 1H NMR (δ, ppm) |
|---|---|---|---|---|---|
| VIII-4 | 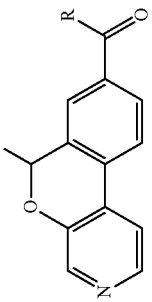 | methyl 3-((6-methyl-6H-isochromeno[3,4-c]pyridine-8-carboxamido)methyl)benzoate | 389.0 | A: 5.27<br>B: 5.62 | (400 MHz, CD$_3$OD) 8.21 (s, 1H), 8.19 (d, J = 5.1 Hz, 1H), 8.03 (s, 1H), 7.99-7.86 (m, 3H), 7.81 (d, J = 5.3 Hz, 1H), 7.78-7.72 (m, 1H), 7.61 (d, J = 7.7 Hz, 1H), 7.48-7.38 (m, 1H), 5.43 (q, J = 6.5 Hz, 1H), 4.64 (s, 2H), 3.88 (s, 3H), 1.60 (d, J = 6.6 Hz, 3H) |
| VIII-5 | 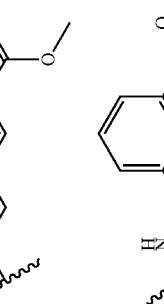 | 3-((6-methyl-6H-isochromeno[3,4-c]pyridine-8-carboxamido)methyl)benzoic acid | 375.0 | A: 4.32<br>B: 4.50 | (400 MHz, DMF-d$_7$) 9.24 (t, J = 5.8 Hz, 1H), 8.39 (s, 1H), 8.37 (d, J = 5.3 Hz, 1H), 8.20-8.06 (m, 4H), 8.05-7.98 (m, 2H), 7.93 (d, J = 7.9 Hz, 1H), 7.68 (d, J = 8.1 Hz, 1H), 7.56-7.45 (m, 1H), 5.59 (q, J = 6.5 Hz, 1H), 4.70 (d, J = 5.9 Hz, 2H), 1.64 (d, J = 6.6 Hz, 3H) |
| VIII-6 | 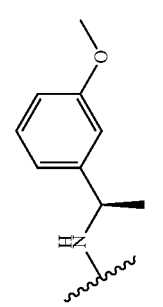 | N-((R)-1-(3-methoxyphenyl)ethyl)-6-methyl-6H-isochromeno[3,4-c]pyridine-8-carboxamide | 375.2 | A: 5.63<br>B: 6.02 | (400 MHz, DMSO-d$_6$) 8.94 (d, J = 7.3 Hz, 1H), 8.55 (s, 1H), 8.46 (d, J = 5.5 Hz, 1H), 8.25 (d, J = 5.5 Hz, 1H), 8.20 (d, J = 8.1 Hz, 1H), 8.02 (dt, J = 8.0, 2.3 Hz, 1H), 7.87 (br. s., 1H), 7.26 (t, J = 8.1 Hz, 1H), 7.04-6.94 (m, 2H), 6.85-6.76 (m, 1H), 5.77-5.62 (m, 1H), 5.18 (quin, J = 7.3 Hz, 1H), 3.76 (s, 3H), 1.61 (dd, J = 6.6, 2.4 Hz, 3H), 1.50 (d, J = 6.6 Hz, 3H) |
| VIII-7 | 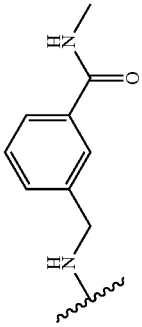 | 6-methyl-N-(3-(methylcarbamoyl)benzyl)-6H-isochromeno[3,4-c]pyridine-8-carboxamide | 388.1 | E: 0.90<br>F: 1.19 | (500 MHz, DMSO-d$_6$) 9.20 (br. s., 1H), 8.42 (br. s., 1H), 8.34 (s, 1H), 8.30 (d, J = 4.7 Hz, 1H), 8.10 (d, J = 8.0 Hz, 1H), 8.02-7.94 (m, 2H), 7.86 (s, 1H), 7.81 (s, 1H), 7.70 (d, J = 7.4 Hz, 1H), 7.53-7.45 (m, 1H), 7.45-7.37 (m, 1H), 5.54 (q, J = 6.2 Hz, 1H), 4.55 (br. s., 2H), 2.77 (d, J = 1.9 Hz, 3H), 1.59 (d, J = 6.3 Hz, 3H) |

TABLE VIII-continued

| Ex. No. | R' | R | Name | LCMS (M + H)+ | HPLC Method, RT (min.) | 1H NMR (δ, ppm) |
|---|---|---|---|---|---|---|
| VIII-8 | Me | N-(3-(ethylcarbamoyl)benzyl group | N-(3-(ethylcarbamoyl)benzyl)-6-methyl-6H-isochromeno[3,4-c]pyridine-8-carboxamide | 402.1 | E: 0.97<br>F: 1.27 | (500 MHz, DMSO-d6) 9.20 (br. s., 1H), 8.45 (br. s., 1H), 8.33 (s, 1H), 8.29 (d, J = 4.7 Hz, 1H), 8.10 (d, J = 8.0 Hz, 1H), 7.99 (d, J = 8.0 Hz, 1H), 7.94 (d, J = 6.3 Hz, 1H), 7.86 (s, 1H), 7.82 (s, 1H), 7.71 (d, J = 7.4 Hz, 1H), 7.50-7.44 (m, 1H), 7.44-7.35 (m, 1H), 5.54 (q, J = 6.1 Hz, 1H), 4.55 (br. s., 2H), 3.27 (quin, J = 6.6 Hz, 2H), 1.59 (d, J = 6.6 Hz, 3H), 1.11 (t, J = 7.0 Hz, 3H) |
| VIII-9 | Me | N-(3-(cyclopropylmethyl)carbamoyl)benzyl group | N-(3-(cyclopropylmethyl)carbamoyl)benzyl)-6-methyl-6H-isochromeno[3,4-c]pyridine-8-carboxamide | 428.1 | E: 1.08<br>F: 1.41 | (500 MHz, DMSO-d6) 8.98 (br. s., 1H), 8.12 (s, 1H), 8.08 (d, J = 4.1 Hz, 1H), 7.88 (d, J = 8.0 Hz, 1H), 7.77 (d, J = 8.0 Hz, 1H), 7.73 (br. s., 2H), 7.63 (d, J = 13.8 Hz, 2H), 7.51 (d, J = 7.4 Hz, 1H), 7.31-7.23 (m, 1H), 7.23-7.14 (m, 1H), 5.32 (q, J = 6.0 Hz, 1H), 4.34 (br. s., 2H), 2.91 (t, J = 5.6 Hz, 2H), 1.37 (d, J = 6.3 Hz, 3H), 0.85-0.72 (m, 1H), 0.20 (d, J = 7.2 Hz, 2H), 0.00 (d, J = 2.2 Hz, 2H) |
| VIII-10 | Me | 3-(1-methylcyclopropylcarbamoyl)benzyl group | 6-methyl-N-(3-(1-methylcyclopropylcarbamoyl)benzyl)-6H-isochromeno[3,4-c]pyridine-8-carboxamide | 428.1 | E: 1.14<br>F: 1.48 | (500 MHz, DMSO-d6) 9.19 (br. s., 1H), 8.63 (s, 1H), 8.35 (s, 1H), 8.31 (d, J = 4.1 Hz, 1H), 8.10 (d, J = 7.7 Hz, 1H), 8.03-7.97 (m, 2H), 7.86 (s, 1H), 7.79 (s, 1H), 7.68 (d, J = 7.7 Hz, 1H), 7.46 (d, J = 7.4 Hz, 1H), 7.42-7.34 (m, 1H), 5.55 (q, J = 6.1 Hz, 1H), 4.54 (br. s., 2H), 1.59 (d, J = 6.3 Hz, 3H), 1.35 (s, 3H), 0.72 (br. s., 2H), 0.59 (br. s., 2H) |
| VIII-11 | Me | (R)-1-(4-fluorophenyl)ethylamino group | N-((R)-1-(4-fluorophenyl)ethyl)-6-methyl-6H-isochromeno[3,4-c]pyridine-8-carboxamide | 363.0 | E: 1.37<br>F: 1.74 | (500 MHz, DMSO-d6) 8.91 (d, J = 7.7 Hz, 1H), 8.36 (s, 1H), 8.31 (d, J = 4.4 Hz, 1H), 8.09 (d, J = 8.0 Hz, 1H), 7.98 (d, J = 4.4 Hz, 2H), 7.82 (s, 1H), 7.44 (t, J = 6.3 Hz, 2H), 7.16 (t, J = 8.4 Hz, 2H), 5.56 (d, J = 6.3 Hz, 2H), 5.19 (t, J = 6.9 Hz, 1H), 1.58 (d, J = 6.3 Hz, 3H), 1.50 (d, J = 6.9 Hz, 3H) |

TABLE VIII-continued

| Ex. No. | R | R' | Name | LCMS (M + H)+ | HPLC Method, RT (min.) | 1H NMR (δ, ppm) |
|---|---|---|---|---|---|---|
| VIII-12 | 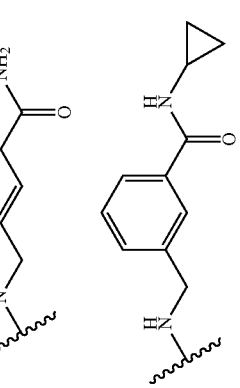 | Me | N-(3-carbamoylbenzyl)-6-methyl-6H-isochromeno[3,4-c]pyridine-8-carboxamide | 374.1 | E: 0.87<br>F: 1.12 | (500 MHz, DMSO-d6) 9.21 (br. s., 1H), 8.35 (s, 1H), 8.31 (br. s., 1H), 8.11 (d, J = 8.3 Hz, 1H), 8.01 (d, J = 8.3 Hz, 1H), 7.88 (br. s., 2H), 7.77 (d, J = 7.4 Hz, 1H), 7.50 (d, J = 7.4 Hz, 1H), 7.46-7.39 (m, 1H), 7.35 (br. s., 1H), 5.56 (d, J = 6.3 Hz, 1H), 4.57 (br. s., 2H), 1.60 (d, J = 6.3 Hz, 3H) |
| VIII-13 | 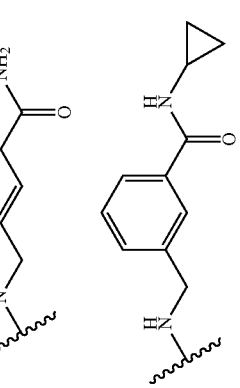 | Me | N-(3-(cyclopropylcarbamoyl)benzyl)-6-methyl-6H-isochromeno[3,4-c]pyridine-8-carboxamide | 414.1 | E: 0.97<br>F: 1.27 | (500 MHz, DMSO-d6) 9.19 (br. s., 1H), 8.42 (br. s., 1H), 8.33 (br. s., 1H), 8.29 (br. s., 1H), 8.09 (d, J = 8.0 Hz, 1H), 7.98 (d, J = 8.0 Hz, 1H), 7.85 (s, 1H), 7.79 (br. s., 1H), 7.68 (d, J = 7.4 Hz, 1H), 7.47 (d, J = 7.4 Hz, 1H), 7.43-7.37 (m, 1H), 5.54 (d, J = 6.1 Hz, 1H), 4.54 (br. s., 2H), 2.86-2.79 (m, 1H), 1.58 (d, J = 6.1 Hz, 3H), 0.72-0.64 (m, 2H), 0.56 (br. s., 2H) |
| VIII-14 | 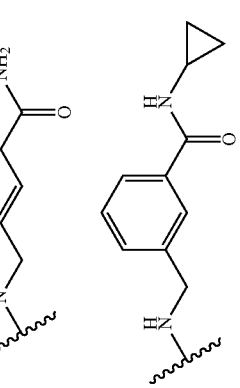 | Me | N-(3-(2-hydroxy-2-methylpropylcarbamoyl)benzyl)-6-methyl-6H-isochromeno[3,4-c]pyridine-8-carboxamide | 446.2 | E: 0.92<br>F: 1.19 | (500 MHz, DMSO-d6) 9.20 (t, J = 5.9 Hz, 1H), 8.33 (s, 1H), 8.29 (d, J = 5.0 Hz, 1H), 8.20 (t, J = 5.9 Hz, 1H), 8.09 (d, J = 8.3 Hz, 1H), 8.01-7.97 (m, 1H), 7.93 (d, J = 5.2 Hz, 1H), 7.85 (d, J = 9.9 Hz, 2H), 7.75 (d, J = 7.4 Hz, 1H), 7.52-7.47 (m, 1H), 7.45-7.40 (m, 1H), 5.53 (q, J = 6.5 Hz, 1H), 4.56 (dd, J = 5.6, 2.3 Hz, 2H), 3.25 (d, J = 6.3 Hz, 2H), 1.58 (d, J = 6.6 Hz, 3H), 1.10 (s, 6H) |
| VIII-15 | 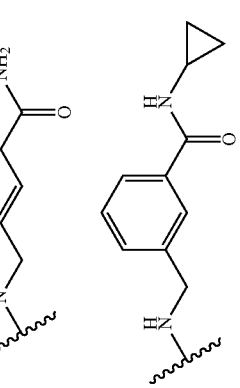 | Et | 6-ethyl-N-((R)-1-(3-methoxyphenyl)ethyl)-6H-isochromeno[3,4-c]pyridine-8-carboxamide | 389.1 | E: 1.43<br>F: 1.81 | (500 MHz, DMSO-d6) 8.89 (d, J = 7.7 Hz, 1H), 8.44 (s, 1H), 8.36 (d, J = 5.2 Hz, 1H), 8.13 (d, J = 8.3 Hz, 1H), 8.07 (d, J = 5.2 Hz, 1H), 8.01-7.96 (m, 1H), 7.83 (dd, J = 4.0, 1.5 Hz, 1H), 7.30-7.22 (m, 1H), 6.99-6.94 (m, 2H), 6.85-6.74 (m, 1H), 5.42 (dt, J = 8.5, 4.0 Hz, 1H), 5.16 (quin, J = 7.3 Hz, 1H), 3.73 (s, 3H), 1.88-1.70 (m, 2H), 1.49 (d, J = 6.9 Hz, 3H), 1.00 (td, J = 7.4, 1.5 Hz, 3H) |

TABLE VIII-continued

| Ex. No. | R' | R | Name | LCMS (M + H)+ | HPLC Method, RT (min.) | 1H NMR (δ, ppm) |
|---|---|---|---|---|---|---|
| VIII-16 | Me | (3-((S)-1-ethylpyrrolidin-2-yl)methyl-carbamoyl benzyl) structure | N-(3-(((S)-1-ethylpyrrolidin-2-yl)methylcarbamoyl)benzyl)-6-methyl-6H-isochromeno[3,4-c]pyridine-8-carboxamide | 485.2 | E: 0.92<br>F: 1.20 | (500 MHz, DMSO-d6) 9.20 (t, J = 5.9 Hz, 1H), 8.38-8.31 (m, 2H), 8.29 (d, J = 5.0 Hz, 1H), 8.09 (d, J = 8.0 Hz, 1H), 7.98 (dd, J = 8.0, 1.7 Hz, 1H), 7.92 (d, J = 5.0 Hz, 1H), 7.86 (d, J = 1.4 Hz, 1H), 7.80 (s, 1H), 7.71 (d, J = 7.7 Hz, 1H), 7.52-7.45 (m, 1H), 7.45-7.39 (m, 1H), 5.53 (q, J = 6.5 Hz, 1H), 4.55 (dd, J = 5.6, 2.9 Hz, 2H), 3.12-2.99 (m, 2H), 2.84 (dd, J = 11.6, 7.2 Hz, 1H), 2.66-2.56 (m, 1H), 2.29 (br. s., 1H), 2.14 (br. s., 1H), 1.91 (s, 1H), 1.82-1.73 (m, 1H), 1.67-1.53 (m, 6H), 1.03 (t, J = 7.2 Hz, 3H) |
| VIII-17 | Et | 2-fluoro-5-carboxybenzyl structure | 5-((6-ethyl-6H-isochromeno[3,4-c]pyridine-8-carboxamido)methyl)-2-fluorobenzoic acid | 407.1 | A: 4.50<br>B: 4.80 | (400 MHz, CD3OD) 8.59 (s, 1H), 8.50-8.42 (m, 2H), 8.21 (d, J = 8.4 Hz, 1H), 8.03 (dd, J = 8.1, 1.8 Hz, 1H), 7.97 (dd, J = 6.8, 2.4 Hz, 1H), 7.85 (d, J = 1.8 Hz, 1H), 7.62 (ddd, J = 8.5, 4.5, 2.4 Hz, 1H), 7.19 (dd, J = 10.7, 8.5 Hz, 1H), 5.56 (dd, J = 8.6, 4.6 Hz, 1H), 4.62 (s, 2H), 2.03-1.85 (m, 2H), 1.10 (t, J = 7.4 Hz, 3H) |
| VIII-18 | Et | 4-fluoro-3-(ethylcarbamoyl)benzyl structure | 6-ethyl-N-(3-(ethylcarbamoyl)-4-fluorobenzyl)-6H-isochromeno[3,4-c]pyridine-8-carboxamide | 434.1 | E: 1.19<br>F: 1.59 | (500 MHz, DMSO-d6) δ 9.22 (t, J = 5.8 Hz, 1H), 8.36 (s, 1H), 8.30 (d, J = 5.0 Hz, 2H), 8.11 (d, J = 8.3 Hz, 1H), 7.99-7.90 (m, 2H), 7.83 (s, 1H), 7.57 (d, J = 6.6 Hz, 1H), 7.46 (br. s., 1H), 7.24 (t, J = 9.4 Hz, 1H), 5.37 (dd, J = 8.7, 4.5 Hz, 1H), 4.49 (d, J = 5.5 Hz, 2H), 3.25 (quin, J = 6.8 Hz, 3H), 1.87-1.68 (m, 2H), 1.09 (t, J = 7.2 Hz, 3H), 0.98 (t, J = 7.2 Hz, 3H) |
| VIII-19 | Et | (R)-1-phenylethyl structure | 6-ethyl-N-((R)-1-phenylethyl)-6H-isochromeno[3,4-c]pyridine-8-carboxamide | 359.1 | E: 1.41<br>F: 1.85 | (500 MHz, DMSO-d6) 8.94 (d, J = 8.0 Hz, 1H), 8.45 (br. s., 1H), 8.36 (d, J = 4.1 Hz, 1H), 8.13 (d, J = 8.3 Hz, 1H), 8.08 (d, J = 4.7 Hz, 1H), 7.99 (d, J = 7.4 Hz, 1H), 7.83 (d, J = 6.1 Hz, 1H), 7.42-7.38 (m, 2H), 7.33 (t, J = 7.3 Hz, 2H), 7.27-7.18 (m, 1H), 5.41 (d, J = 4.4 Hz, 1H), 5.19 (quin, J = 7.2 Hz, 1H), 1.85-1.70 (m, 2H), 1.50 (d, J = 7.2 Hz, 3H), 0.99 (t, J = 7.2 Hz, 3H) |

TABLE VIII-continued

| Ex. No. | R' | R | Name | LCMS (M + H)+ | HPLC Method, RT (min.) | 1H NMR (δ, ppm) |
|---|---|---|---|---|---|---|
| VIII-20 | Et | 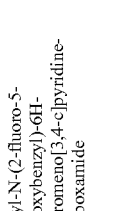 | 6-ethyl-N-(2-fluoro-5-methoxybenzyl)-6H-isochromeno[3,4-c]pyridine-8-carboxamide | 393.1 | E: 1.37 F: 1.80 | (500 MHz, DMSO-d6) 9.14 (t, J = 5.2 Hz, 1H), 8.44 (s, 1H), 8.36 (d, J = 4.7 Hz, 1H), 8.14 (d, J = 8.3 Hz, 1H), 8.07 (d, J = 5.0 Hz, 1H), 7.98 (d, J = 8.3 Hz, 1H), 7.85 (s, 1H), 7.12 (d, J = 9.9 Hz, 1H), 6.91 (d, J = 3.3 Hz, 1H), 6.89-6.81 (m, 1H), 5.42 (dd, J = 8 .4 , 4.3 Hz, 1H), 4.50 (br. s., 2H), 3.72 (s, 3H), 1.89-1.66 (m, 2H), 0.99 (t, J = 7.2 Hz, 3H) |
| VIII-21 | Et | 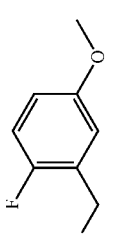 | N-(2-chloro-4-fluorobenzyl)-6-ethyl-6H-isochromeno[3,4-c]pyridine-8-carboxamide | 397.0 | E: 1.50 F: 1.95 | (500 MHz, DMSO-d6) 9.18 (t, J = 5.1 Hz, 1H), 8.45 (s, 1H), 8.36 (d, J = 4.4 Hz, 1H), 8.15 (d, J = 8.3 Hz, 1H), 8.07 (d, J = 5.0 Hz, 1H), 8.00 (d, J = 8.3 Hz, 1H), 7.86 (s, 1H), 7.51-7.40 (m, 2H), 7.22 (d, J = 8.5 Hz, 1H), 5.42 (dd, J = 8.3, 4.4 Hz, 1H), 4.54 (br. s., 2H), 1.90-1.69 (m, 2H), 0.99 (t, J = 7.2 Hz, 3H) |
| VIII-22 | Et | 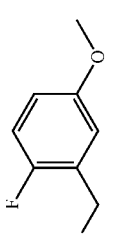 | N-(3-cyanobenzyl)-6-ethyl-6H-N isochromeno[3,4-c]pyridine-8-carboxamide | 370.1 | E: 1.18 F: 1.57 | (500 MHz, DMSO-d6) 9.23 (t, J = 5.4 Hz, 1H), 8.33 (s, 1H), 8.28 (d, J = 5.0 Hz, 1H), 8.10 (d, J = 8.0 Hz, 1H), 7.97 (d, J = 8.0 Hz, 1H), 7.92 (d, J = 4.7 Hz, 1H), 7.83 (s, 1H), 7.78 (s, 1H), 7.74 (d, J = 7.7 Hz, 1H), 7.69 (d, J = 7.7 Hz, 1H), 7.60-7.54 (m, 1H), 5.36 (dd, J = 8.1, 4.5 Hz, 1H), 4.55 (d, J = 5.2 Hz, 2H), 1.85-1.69 (m, 2H), 0.99 (t, J = 7.2 Hz, 3H) |
| VIII-23 | c-Propyl | 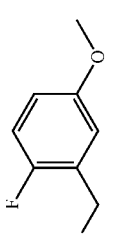 | 6-cyclopropyl-N-((R)-1-(3-methoxyphenyl)ethyl)-6H-isochromeno[3,4-c]pyridine-8-carboxamide | 401.1 | E: 1.36 F: 1.74 | (500 MHz, DMSO-d6) 8.94 (d, J = 7.4 Hz, 1H), 8.45 (s, 1H), 8.35 (d, J = 5.0 Hz, 1H), 8.14 (d, J = 8.3 Hz, 1H), 8.07 (d, J = 4.7 Hz, 1H), 8.05-7.99 (m, 1H), 7.91 (br. s., 1H), 7.25 (t, J = 8.0 Hz, 1H), 6.97 (br. s., 2H), 6.81 (d, J = 8.0 Hz, 1H), 5.16 (quin, J = 6.9 Hz, 1H), 4.78 (d, J = 9.1 Hz, 1H), 3.74 (s, 3H), 1.49 (d, J = 6.9 Hz, 3H), 1.31-1.21 (m, 1H), 0.60 (br. s., 2H), 0.54 (d, J = 3.0 Hz, 2H) |

TABLE VIII-continued

| Ex. No. | R' | R | Name | LCMS (M + H)+ | HPLC Method, RT (min.) | 1H NMR (δ, ppm) |
|---|---|---|---|---|---|---|
| VIII-24 | Et | 1-(2-chlorophenyl)cyclopropyl-NH- | N-(1-(2-chlorophenyl)cyclopropyl)-6-ethyl-6H-isochromeno[3,4-c]pyridine-8-carboxamide | 405.1 | E: 1.48<br>F: 1.92 | (500 MHz, DMSO-$d_6$) 9.16 (s, 1H), 8.48 (s, 1H), 8.37 (d, J = 5.0 Hz, 1H), 8.11 (d, J = 8.0 Hz, 2H), 7.89 (d, J = 8.0 Hz, 1H), 7.78-7.71 (m, 2H), 7.39 (d, J = 7.4 Hz, 1H), 7.33-7.22 (m, 2H), 5.39 (dd, J = 8.3, 4.4 Hz, 1H), 1.86-1.67 (m, 2H), 1.27 (d, J = 5.0 Hz, 2H), 1.16 (d, J = 5.8 Hz, 2H), 0.97 (t, J = 7.2 Hz, 3H) |
| VIII-25 | c-Propyl | (R)-1-phenylethyl-NH- | 6-cyclopropyl-N-((R)-1-phenylethyl)-6H-isochromeno[3,4-c]pyridine-8-carboxamide | 371.2 | E: 1.40<br>F: 1.84 | (500 MHz, DMSO-$d_6$) 8.94 (d, J = 7.7 Hz, 1H), 8.35 (s, 1H), 8.28 (br. s., 1H), 8.09 (d, J = 8.0 Hz, 1H), 8.05-7.97 (m, 1H), 7.95 (br. s., 1H), 7.90 (d, J = 4.4 Hz, 1H), 7.45-7.38 (m, 2H), 7.34 (t, J = 7.2 Hz, 2H), 7.27-7.19 (m, 1H), 5.19 (t, J = 7.0 Hz, 1H), 4.72 (d, J = 9.1 Hz, 1H), 1.50 (d, J = 6.6 Hz, 3H), 1.25 (br. s., 1H), 0.67-0.46 (m, 4H) |
| VIII-26 | c-Propyl | 2-fluoro-5-methoxybenzyl-NH- | 6-cyclopropyl-N-(2-fluoro-5-methoxybenzyl)-6H-isochromeno[3,4-c]pyridine-8-carboxamide | 405.2 | E: 1.36<br>F: 1.79 | (500 MHz, DMSO-$d_6$) 9.18 (br. s., 1H), 8.46 (s, 1H), 8.36 (br. s., 1H), 8.15 (d, J = 8.0 Hz, 1H), 8.08 (d, J = 3.3 Hz, 1H), 8.01 (d, J = 8.0 Hz, 1H), 7.95 (s, 1H), 7.13 (t, J = 9.2 Hz, 1H), 6.91 (d, J = 3.0 Hz, 1H), 6.88-6.81 (m, 1H), 4.78 (d, J = 9.1 Hz, 1H), 4.51 (br. s., 2H), 3.71 (s, 3H), 1.28 (d, J = 5.0 Hz, 1H), 0.67-0.51 (m, 4H) |
| VIII-27 | c-Propyl | 3-hydroxy-1-phenylpropyl-NH- | 6-cyclopropyl-N-(3-hydroxy-1-phenylpropyl)-6H-isochromeno[3,4-c]pyridine-8-carboxamide | 401.2 | E: 1.18<br>F: 1.58 | (500 MHz, DMSO-$d_6$) 8.96-8.84 (m, 1H), 8.35 (br. s., 1H), 8.28 (br. s., 1H), 8.09 (d, J = 7.7 Hz, 1H), 7.99 (d, J = 8.0 Hz, 1H), 7.94 (br. s., 1H), 7.87 (s, 1H), 7.42-7.36 (m, 2H), 7.33 (t, J = 7.3 Hz, 2H), 7.23 (d, J = 6.9 Hz, 1H), 5.17 (d, J = 6.9 Hz, 1H), 4.71 (d, J = 8.8 Hz, 1H), 4.62 (br. s., 1H), 3.51-3.40 (m, 2H), 2.12-1.87 (m, 2H), 1.25 (br. s., 1H), 0.66-0.48 (m, 4H) |

TABLE VIII-continued

| Ex. No. | R' | R | Name | LCMS (M + H)+ | HPLC Method, RT (min.) | 1H NMR (δ, ppm) |
|---|---|---|---|---|---|---|
| VIII-28 | c-Propyl | (4-fluoro-2-chlorobenzyl)aminomethyl | N-(2-chloro-4-fluorobenzyl)-6-cyclopropyl-6H-isochromeno[3,4-c]pyridine-8-carboxamide | 409.1 | E: 1.44  F: 1.83 | (500 MHz, DMSO-d6) 9.22 (br. s., 1H), 8.49 (s, 1H), 8.38 (d, J = 4.1 Hz, 1H), 8.18 (d, J = 8.0 Hz, 1H), 8.13 (d, J = 4.1 Hz, 1H), 8.04 (d, J = 8.0 Hz, 1H), 7.96 (s, 1H), 7.56-7.39 (m, 2H), 7.23 (t, J = 8.5 Hz, 1H), 4.80 (d, J = 9.1 Hz, 1H), 4.54 (br. s., 2H), 1.29 (d, J = 5.2 Hz, 1H), 0.70-0.46 (m, 4H) |
| VIII-29 | c-Propyl | (3-cyanobenzyl)aminomethyl | N-(3-cyanobenzyl)-6-cyclopropyl-6H-isochromeno[3,4-c]pyridine-8-carboxamide | 382.1 | E: 1.20  F: 1.55 | (500 MHz, DMSO-d6) 9.28 (br. s., 1H), 8.37 (s, 1H), 8.30 (d, J = 3.9 Hz, 1H), 8.13 (d, J = 8.0 Hz, 1H), 8.02 (d, J = 8.0 Hz, 1H), 7.95 (br. s., 2H), 7.80 (s, 1H), 7.76 (d, J = 7.4 Hz, 1H), 7.71 (d, J = 7.7 Hz, 1H), 7.63-7.55 (m, 1H), 4.74 (d, J = 9.1 Hz, 1H), 4.57 (br. s., 2H), 1.28 (d, J = 5.0 Hz, 1H), 0.68-0.51 (m, 4H) |
| VIII-30 | Et | (R)-1-(4-fluorophenyl)ethylamino | 6-ethyl-N-((R)-1-(4-fluorophenyl)ethyl)-6H-isochromeno[3,4-c]pyridine-8-carboxamide | 377.1 | E: 1.39  F: 1.77 | (500 MHz, DMSO-d6) 8.94 (d, J = 7.4 Hz, 1H), 8.45 (s, 1H), 8.36 (br. s., 1H), 8.13 (d, J = 8.0 Hz, 1H), 8.08 (br. s., 1H), 7.98 (d, J = 8.0 Hz, 1H), 7.82 (d, J = 5.0 Hz, 1H), 7.44 (t, J = 5.9 Hz, 2H), 7.16 (t, J = 8.3 Hz, 2H), 5.41 (d, J = 4.1 Hz, 1H), 5.18 (t, J = 7.0 Hz, 1H), 1.88-1.67 (m, 2H), 1.49 (d, J = 6.6 Hz, 3H), 0.99 (t, J = 7.0 Hz, 3H) |
| VIII-31 | c-Propyl | (R)-1-(4-fluorophenyl)ethylamino | 6-cyclopropyl-N-((R)-1-(4-fluorophenyl)ethyl)-6H-isochromeno[3,4-c]pyridine-8-carboxamide | 389.2 | E: 1.40  F: 1.76 | (500 MHz, DMSO-d6) 8.97 (d, J = 7.4 Hz, 1H), 8.46 (s, 1H), 8.36 (br. s., 1H), 8.14 (d, J = 8.0 Hz, 1H), 8.10 (d, J = 3.3 Hz, 1H), 8.02 (t, J = 6.3 Hz, 1H), 7.91 (br. s., 1H), 7.44 (t, J = 5.9 Hz, 2H), 7.16 (t, J = 8.3 Hz, 2H), 5.19 (t, J = 7.0 Hz, 1H), 4.78 (d, J = 8.8 Hz, 1H), 1.49 (d, J = 6.9 Hz, 3H), 1.26 (d, J = 6.6 Hz, 1H), 0.68-0.47 (m, 4H) |
| VIII-32 | Et | (2-chloro-6-fluorobenzyl)aminomethyl | N-(2-chloro-6-fluorobenzyl)-6-ethyl-6H-isochromeno[3,4-c]pyridine-8-carboxamide | 397.1 | E: 1.36  F: 1.77 | (500 MHz, DMSO-d6) 8.88 (br. s., 1H), 8.32 (s, 1H), 8.26 (br. s., 1H), 8.05 (d, J = 8.0 Hz, 1H), 7.96-7.87 (m, 2H), 7.77 (s, 1H), 7.45-7.32 (m, 2H), 7.26 (t, J = 8.7 Hz, 1H), 5.38-5.28 (m, 1H), 4.61 (br. s., 2H), 1.85-1.64 (m, 2H), 0.97 (t, J = 6.9 Hz, 3H) |

TABLE VIII-continued

| Ex. No. | R' | R | Name | LCMS (M + H)+ | HPLC Method, RT (min.) | 1H NMR (δ, ppm) |
|---|---|---|---|---|---|---|
| VIII-33 | c-Propyl | 2-chloro-6-fluorobenzyl (NH linker) | N-(2-chloro-6-fluorobenzyl)-6-cyclopropyl-6H-isochromeno[3,4-c]pyridine-8-carboxamide | 409.1 | E: 1.39 F: 1.77 | (500 MHz, DMSO-d6) 8.92 (br. s., 1H), 8.34 (s, 1H), 8.27 (d, J = 3.3 Hz, 1H), 8.06 (d, J = 8.3 Hz, 1H), 7.99-7.84 (m, 3H), 7.47-7.23 (m, 3H), 4.70 (d, J = 9.1 Hz, 1H), 4.61 (br. s., 2H), 1.25 (d, J = 5.2 Hz, 1H), 0.67-0.41 (m, 4H) |
| VIII-34 | Et | 3-hydroxy-1-phenylpropyl (NH linker) | 6-ethyl-N-(3-hydroxy-1-phenylpropyl)-6H-isochromeno[3,4-c]pyridine-8-carboxamide | 389.2 | E: 1.14 F: 1.47 | (500 MHz, DMSO-d6) 8.88 (d, J = 7.4 Hz, 1H), 8.33 (s, 1H), 8.27 (br. s., 1H), 8.08 (d, J = 8.0 Hz, 1H), 7.99-7.88 (m, 2H), 7.79 (br. s., 1H), 7.45-7.36 (m, 2H), 7.33 (t, J = 7.0 Hz, 2H), 7.26-7.16 (m, 1H), 5.35 (br. s., 1H), 5.17 (d, J = 7.2 Hz, 1H), 4.60 (br. s., 1H), 3.45 (m, 2H), 2.14-2.00 (m, 1H), 1.97-1.85 (m, 1H), 1.84-1.65 (m, 2H), 1.06-0.90 (m, 3H) |
| VIII-35 | c-Propyl | 1-(2-chlorophenyl)cyclopropyl (NH linker) | N-(1-(2-chlorophenyl)cyclopropyl)-6-cyclopropyl-6H-isochromeno[3,4-c]pyridine-8-carboxamide | 417.1 | E: 1.51 F: 1.90 | (500 MHz, DMSO-d6) 9.17 (s, 1H), 8.44 (s, 1H), 8.34 (d, J = 3.9 Hz, 1H), 8.09 (d, J = 8.0 Hz, 1H), 8.06 (d, J = 3.6 Hz, 1H), 7.94 (br. s., 1H), 7.84 (s, 1H), 7.75 (d, J = 7.2 Hz, 1H), 7.39 (d, J = 7.2 Hz, 1H), 7.28 (quin, J = 7.4 Hz, 2H), 4.71 (d, J = 9.1 Hz, 1H), 1.34-1.21 (m, 4H), 1.17 (br. s., 2H), 0.65-0.48 (m, 4H) |
| VIII-36 | allyl | (R)-1-phenylethyl (NH linker) | 6-allyl-N-((R)-1-phenylethyl)-6H-isochromeno[3,4-c]pyridine-8-carboxamide | 371.1 | A: 9.31 B: 10.13 | (400 MHz, CDCl3) 8.35 (s, 1H), 8.30 (d, J = 5.1 Hz, 1H), 7.83-7.72 (m, 2H), 7.63 (s, 1H), 7.56 (d, J = 5.1 Hz, 1H), 7.40 (q, J = 7.9 Hz, 3H), 7.35-7.28 (m, 1H), 6.43 (d, J = 7.5 Hz, 1H), 5.93-5.80 (m, 1H), 5.34 (dt, J = 14.4, 7.1 Hz, 2H), 5.16-5.04 (m, 2H), 2.67 (dt, J = 15.0, 7.7 Hz, 1H), 2.55-2.43 (m, 1H), 1.70 (s, 1H), 1.65 (d, J = 6.8 Hz, 3H) |

TABLE VIII-continued
| Ex. No. | R' | R | Name | LCMS (M + H)+ | HPLC Method, RT (min.) | 1H NMR (δ, ppm) |
|---|---|---|---|---|---|---|
| VIII-37 | 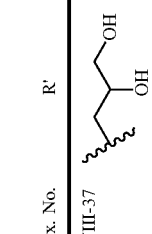 | 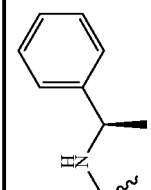 | 6-(2,3-dihydroxy-propyl)-N-((R)-1-phenylethyl)-6H-isochromeno [3,4-c]pyridine-8-carboxamide | 405.2 | E: 1.07 F: 1.26 | (500 MHz, DMSO-d6) 8.92 (br. s., 1H), 8.30 (d, J = 15.7 Hz, 2H), 8.07 (br. s., 1H), 8.01-7.90 (m, 2H), 7.81 (br. s., 1H), 7.40 (br. s., 2H), 7.33 (br. s., 2H), 7.23 (br. s., 1H), 5.68-5.54 (m, 1H), 5.19 (br. s., 1H), 5.02-4.34 (m, 2H), 3.79 (br. s., 1H), 3.30- 3.21 (m, 2H), 2.00-1.82 (m, 2H), 1.50 (br. s., 3H) |

EXAMPLE IX-1

(R)-N-(1-Phenylethyl)-6H-isochromeno[4,3-d]pyrimidine-8-carboxamide

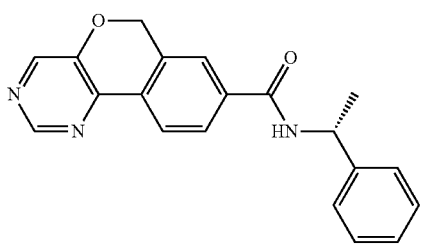 [SMILES: C[C@@H](NC(=O)c1ccc2c(c1)COc1cncnc1-2)c1ccccc1]

Example IX-1 was prepared by following a similar procedure as described in I-1 by replacing Intermediate 1 with Intermediate 3. LC-MS (ESI) m/z: 332.10 [M+H]$^+$; $^1$H NMR (500 MHz, DMSO-d$_6$) δ 8.99 (d, J=8.0 Hz, 1H), 8.89 (s, 1H), 8.55 (s, 1H), 8.21 (d, J=8.0 Hz, 1H), 8.00 (d, J=8.0 Hz, 1H), 7.84 (s, 1H), 7.43-7.38 (m, 2H), 7.33 (t, J=7.6 Hz, 2H), 7.26-7.21 (m, 1H), 5.46 (s, 2H), 5.18 (quin, J=7.2 Hz, 1H), 1.49 (d, J=7.2 Hz, 3H); Analytical HPLC RT E: 1.53 min, F: 1.58 min.

EXAMPLE IX-2

(S)-N-(2-Amino-1-phenylethyl)-6H-isochromeno[4,3-d]pyrimidine-8-carboxamide

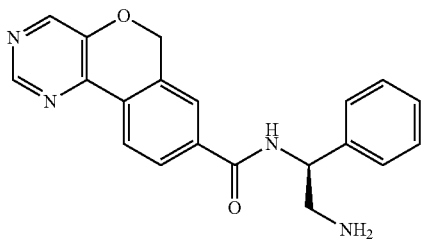

Example IX-2 was prepared by following a similar procedure as described in Example VI-2 by replacing Intermediate 2 with Intermediate 3 in VI-2d. LC-MS (ESI) m/z: 347.1[M+H]$^+$; $^1$H NMR (400 MHz, CD$_3$OD) δ 8.85 (s, 1H), 8.47 (s, 1H), 8.35 (d, J=8.1 Hz, 1H), 8.03 (dd, J=8.0, 1.7 Hz, 1H), 7.82 (s, 1H), 7.53-7.43 (m, 4H), 7.42-7.38 (m, 1H), 5.51 (dd, J=9.2, 5.7 Hz, 1H), 5.45 (s, 2H), 3.51-3.45 (m, 2H); Analytical HPLC RT A: 7.06 min, F: 7.41 min.

The compounds listed in Table IX were prepared by following the similar procedures as described in Examples IX-1 and IX-2.

TABLE IX

| Ex. No. | R | Name | LCMS (M + H)$^+$ | HPLC Method, RT (min.) | $^1$H NMR (δ, ppm) |
|---|---|---|---|---|---|
| IX-3 | 3-methoxyphenyl ethyl HN group | (R)-N-(1-(3-methoxyphenyl)ethyl)-6H-isochromeno[4,3-d]pyrimidine-8-carboxamide | 362.10 | A: 8.30 B: 7.24 | (400 MHz, DMSO-d$_6$) 8.93 (d, J = 8.1 Hz, 1H), 8.88 (s, 1H), 8.54 (s, 1H), 8.21 (d, J = 8.1 Hz, 1H), 7.99 (dd, J = 8.0, 1.7 Hz, 1H), 7.82 (d, J = 0.9 Hz, 1H), 7.24 (t, J = 8.1 Hz, 1H), 7.01-6.94 (m, 2H), 6.80 (ddd, J = 8.2, 2.5, 1.0 Hz, 1H), 5.46 (s, 2H), 5.15 (quin, J = 7.3 Hz, 1H), 3.74 (s, 3H), 1.48 (d, J = 7.0 Hz, 3H) |
| IX-4 | methyl benzoate HN group | methyl 3-((6H-isochromeno[4,3-d]pyrimidine-8-carboxamido)methyl)benzoate | 376.1 | A: 11.56 B: 10.29 | (400 MHz, DMSO-d$_6$) 9.28 (t, J = 5.9 Hz, 1H), 8.88 (s, 1H), 8.54 (s, 1H), 8.22 (d, J = 8.1 Hz, 1H), 8.01 (dd, J = 8.1, 1.5 Hz, 1H), 7.95 (s, 1H), 7.88-7.82 (m, 2H), 7.63 (d, J = 7.9 Hz, 1H), 7.53-7.47 (m, 1H), 5.46 (s, 2H), 4.56 (d, J = 5.9 Hz, 2H), 3.84 (s, 3H) |
| IX-5 | 2-fluoro-5-methoxyphenyl ethyl HN group | (±)-N-(1-(2-fluoro-5-methoxyphenyl)ethyl)-6H-isochromeno[4,3-d]pyrimidine-8-carboxamide | 380.10 | E: 1.60 F: 1.65 | (500 MHz, DMSO-d$_6$) 9.01 (d, J = 7.7 Hz, 1H), 8.89 (s, 1H), 8.55 (s, 1H), 8.22 (d, J = 8.3 Hz, 1H), 8.00 (d, J = 8.3 Hz, 1H), 7.83 (s, 1H), 7.10 (t, J = 9.4 Hz, 1H), 7.02 (dd, J = 5.8, 2.8 Hz, 1H), 6.87-6.79 (m, 1H), 5.47 (s, 2H), 5.37 (quin, J = 7.2 Hz, 1H), 3.71 (s, 3H), |

TABLE IX-continued

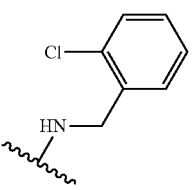 [SMILES: *NCc1ccccc1Cl]

| Ex. No. | R | Name | LCMS (M + H)+ | HPLC Method, RT (min.) | 1H NMR (δ, ppm) |
|---|---|---|---|---|---|
| | | | | | 1.46 (d, J = 6.9 Hz, 3H) |
| IX-6 | | N-(2-chlorobenzyl)-6H-isochromeno[4,3-d]pyrimidine-8-carboxamide | 352.10 | E: 1.59 F: 1.64 | (500 MHz, DMSO-d6) 9.21 (t, J = 5.5 Hz, 1H), 8.89 (s, 1H), 8.55 (s, 1H), 8.23 (d, J = 8.3 Hz, 1H), 8.04 (d, J = 8.3 Hz, 1H), 7.88 (s, 1H), 7.47 (d, J = 7.4 Hz, 1H), 7.42-7.37 (m, 1H), 7.36-7.28 (m, 2H), 5.47 (s, 2H), 4.56 (d, J = 5.5 Hz, 2H) |
| IX-7 | | N-((3S,4R)-4-phenylpyrrolidin-3-yl)-6H-isochromeno[4,3-d]pyrimidine-8-carboxamide | 373.20 | E: 1.15 F: 1.17 | (500 MHz, DMSO-d6) 8.97 (d, J = 8.0 Hz, 1H), 8.90 (s, 1H), 8.57 (s, 1H), 8.22 (d, J = 8.3 Hz, 1H), 7.93 (d, J = 8.0 Hz, 1H), 7.77 (s, 1H), 7.46-7.41 (m, 2H), 7.38 (t, J = 7.6 Hz, 2H), 7.33-7.27 (m, 1H), 5.46 (s, 2H), 4.79 (quin, J = 8.5 Hz, 1H), 3.81 (br. s., 1H), 3.72 (br. s., 1H), 3.68-3.60 (m, 1H), 3.18 (br. s., 1H) |
| IX-8 | | N-(3-(2-hydroxy-2-methylpropylcarbamoyl)benzyl)-6H-isochromeno[4,3-d]pyrimidine-8-carboxamide | 433.25 | E: 1.12 F: 1.14 | (500 MHz, DMSO-d6) 9.26 (t, J = 5.5 Hz, 1H), 8.89 (s, 1H), 8.55 (s, 1H), 8.28-8.19 (m, 2H), 8.01 (d, J = 8.0 Hz, 1H), 7.86 (s, 1H), 7.83 (s, 1H), 7.75 (d, J = 7.4 Hz, 1H), 7.51-7.46 (m, 1H), 7.45-7.39 (m, 1H), 5.46 (s, 2H), 4.60-4.51 (m, 3H), 3.24 (d, J = 5.8 Hz, 2H), 1.09 (s, 6H) |
| IX-9 | | 3-((6H-isochromeno[4,3-d]pyrimidine-8-carboxamido)methyl)benzoic acid | 362.15 | E: 1.16 F: 0.93 | (500 MHz, DMSO-d6) 9.30 (t, J = 5.6 Hz, 1H), 8.89 (s, 1H), 8.55 (s, 1H), 8.22 (d, J = 8.0 Hz, 1H), 8.01 (d, J = 8.0 Hz, 1H), 7.92 (s, 1H), 7.86 (s, 1H), 7.83 (d, J = 7.7 Hz, 1H), 7.59 (d, J = 7.7 Hz, 1H), 7.51-7.43 (m, 1H), 5.47 (s, 2H), 4.55 (d, J = 5.8 Hz, 2H) |

EXAMPLE X-1

(R)-N-(1-(4-Fluorophenyl)ethyl)-5-oxo-5H-chromeno[3,4-c]pyridine-8-carboxamide

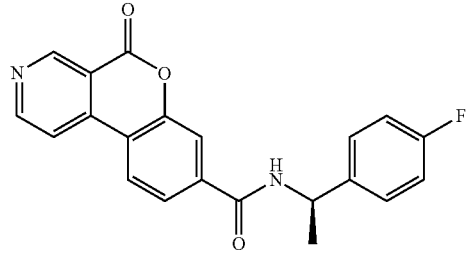 [SMILES: C[C@@H](NC(=O)c1ccc2c(c1)oc(=O)c1cnccc12)c1ccc(F)cc1]

EXAMPLE X-1a

Methyl 4-chloronicotinate

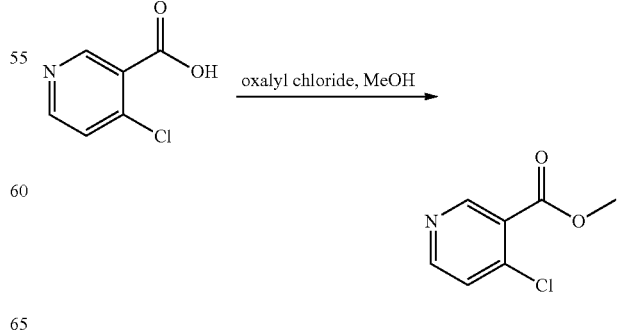

To a suspension of the 4-chloronicotinic acid (1.12g, 7.11 mmol) in DCM (10 mL) at rt was added oxalyl chloride (2M in DCM, 8.89 mL, 17.77 mmol) followed by addition of DMF (0.250 mL) dropwise. After stirred for 45 min at rt, the reaction was cooled to 0° C. and quenched with methanol. The crude oil was triturated with EtOAc, and the solid was collected by filtration, which was further washed with hexane and dried to afford X-a as white solid (1.2 g, 98%). LC-MS (ESI) m/z: 171.9[M+H]$^+$; $^1$H NMR (400 MHz, DMSO-d$_6$) δ 8.97 (s, 1H), 8.70 (d, J=5.5 Hz, 1H), 7.72 (d, J=5.5 Hz, 1H), 3.91 (s, 3H).

EXAMPLE X-1b

3-Methoxy-4-(4,4,5,5-tetramethyl-1,3,2-dioxaborolan-2-yl)benzonitrile

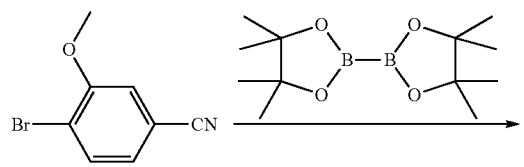

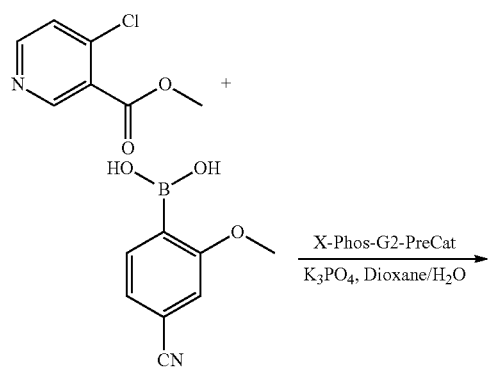

A mixture of 4-bromo-3-methoxybenzonitrile (1g, 4.72 mmol), 4,4,4',4',5,5,5',5'-octamethyl-2,2'-bi(1,3,2-dioxaborolane) (1.796 g, 7.07 mmol), K$_3$PO$_4$ (1.157 g, 11.79 mmol) and PdCl$_2$(dppf) CH$_2$Cl$_2$ adduct (0.207 g, 0.283 mmol) in dioxane (12 mL) was degassed and then heated at 90° C. for 3 h. The reaction was cooled to rt and was filtered through a pad of CELITE®. The solvent was removed. Normal phase chromatography afforded X-1b as brown oil (1.7 g, 5.76 mmol, 100%). LC-MS (ESI) of the boronic acid m/z: 178.0 [M+H]$^+$.

EXAMPLE X-1c

Methyl 4-(4-cyano-2-methoxyphenyl)nicotinate

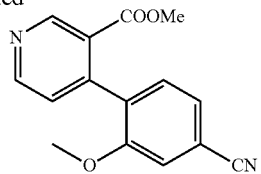

To a solution of X-1a (1.12g, 6.53 mmol) in dioxane (10 mL) and H$_2$O (2.5 mL) were added X-1b (1.733 g, 7.83 mmol), K$_3$PO$_4$ (3.05 g, 14.36 mmol) and XPhos-G2-PreCat (0.206 g, 0.261 mmol) at rt. The reaction was heated with microwave at 140° C. for 10 min. The solvent was removed. Normal phase chromatography afforded X-1c as pale solid (0.84 g, 48.0%) LC-MS (ESI) m/z: 269.0[M+H]$^+$; $^1$H NMR (400 MHz, CDCl$_3$) δ 9.14 (s, 1H), 8.80 (d, J=5.1 Hz, 1H), 7.45-7.37 (m, 1H), 7.35-7.30 (m, 1H), 7.22 (d, J=5.1 Hz, 1H), 7.16 (d, J=1.3 Hz, 1H), 3.77 (s, 3H), 3.75 (s, 3H).

EXAMPLE X-1d

5-Oxo-5H-chromeno[3,4-c]pyridine-8-carbonitrile

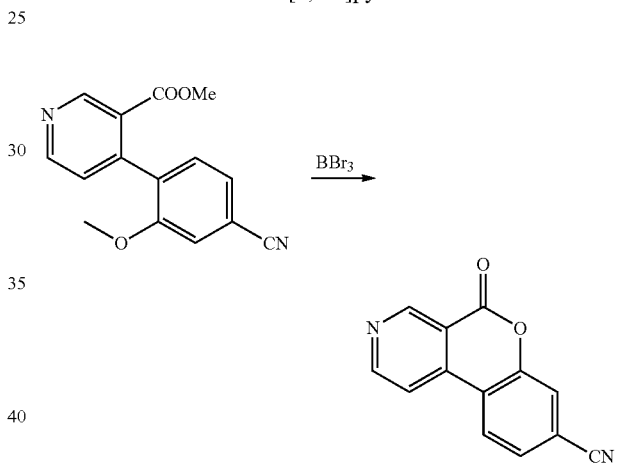

To a solution of X-1c (123 mg, 0.458 mmol) in DCM (3 mL) at 0° C. was added BBr$_3$ (1M in heptane, 2.751 mL, 2.75 mmol) dropwise. The solution was warmed to rt and stirred overnight. The solvent was removed. Purification by reverse phase chromatography afforded X-1d. LC-MS (ESI) m/z: 223.0[M+H]$^+$.

EXAMPLE X-1e

5-Oxo-5H-chromeno[3,4-c]pyridine-8-carboxylic acid

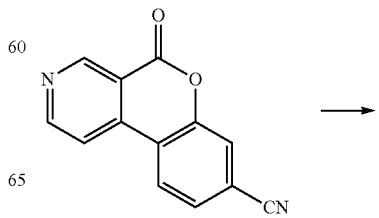

229

-continued

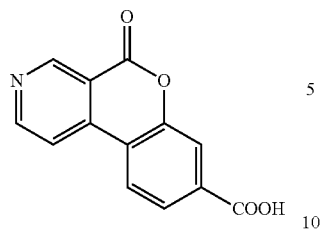

A suspension of X-1d (14 mg, 0.042 mmol) in HCl (aq. 7N, 0.297 ml, 2.082 mmol) was heated at 100° C. in a sealed vial for 8 h. The solvent was removed to afford X-1e as solid (10.4 mg, 90%). LC-MS (ESI) m/z: 242.0[M+H]+.

EXAMPLE X-1

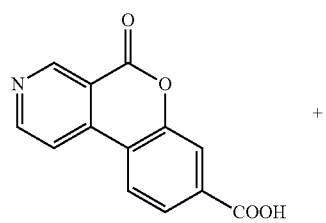

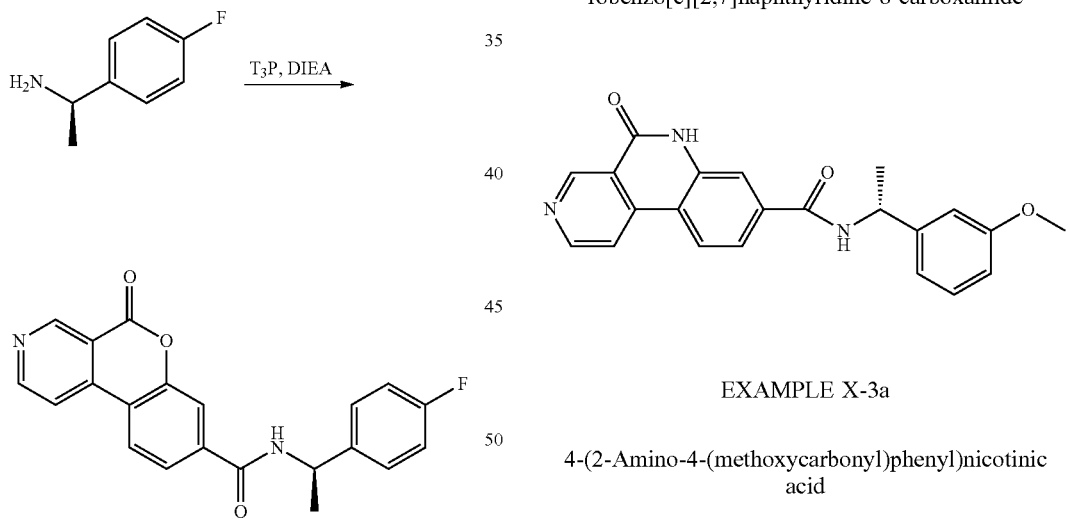

To a suspension of X-1e (10 mg, 0.036 mmol) in DCM (1 mL) were added (R)-1-(4-fluorophenyl)ethanamine, HCl salt (6.96 mg, 0.040 mmol), DIEA (0.044 mL, 0.252 mmol) and T$_3$P (0.060 mL, 0.101 mmol) at rt. The reaction was stirred under argon at rt for 1.5 h and then sat over weekend. Purification by reverse phase chromatography afforded Example X-1 as white solid (7.2 mg, 51%). LC-MS (ESI) m/z: 363.0[M+H]+; $^1$H NMR (500 MHz, DMSO-d$_6$) δ 9.39 (s, 1H), 9.11-9.02 (m, 2H), 8.55 (d, J=8.0 Hz, 1H), 8.43 (d, J=5.0 Hz, 1H), 7.98-7.92 (m, 2H), 7.45 (t, J=6.3 Hz, 2H), 7.16 (t, J=8.3 Hz, 2H), 5.20 (t, J=7.0 Hz, 1H), 1.51 (d, J=6.9 Hz, 3H); Analytical HPLC RT E: 1.50 min, F: 1.59 min.

230

EXAMPLE X-2

(R)-5-Oxo-N-(1-phenylethyl)-5H-chromeno[3,4-c]pyridine-8-carboxamide

Example X-2 was prepared by following the similar procedure as described in Example X-1. LC-MS (ESI) m/z: 345.0[M+H]+; $^1$H NMR (400 MHz, CD$_3$OD) δ 9.47 (s, 1H), 8.99 (d, J=5.5 Hz, 1H), 8.44 (d, J=8.1 Hz, 1H), 8.36 (d, J=5.5 Hz, 1H), 7.99-7.84 (m, 2H), 7.50-7.40 (m, 2H), 7.35 (t, J=7.7 Hz, 2H), 7.30-7.21 (m, 1H), 5.37-5.21 (m, 1H), 1.61 (d, J=7.0 Hz, 3H); Analytical HPLC RT A: 5.67 min, F: 5.48 min.

EXAMPLE X-3

(R)-N-(1-(3-Methoxyphenyl)ethyl)-5-oxo-5,6-dihydrobenzo[c][2,7]naphthyridine-8-carboxamide EXAMPLE X-3a 4-(2-Amino-4-(methoxycarbonyl)phenyl)nicotinic acid

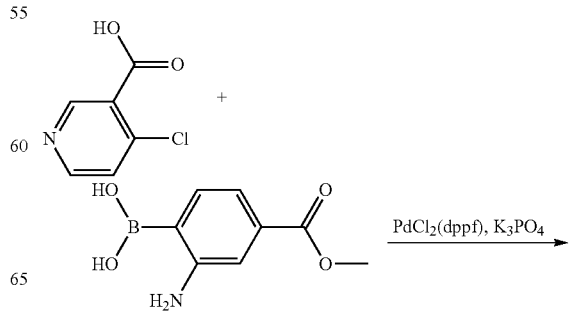

-continued

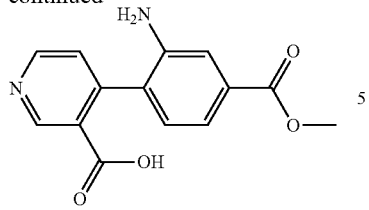

To a solution of 4-chloronicotinic acid (110 mg, 0.698 mmol) in dioxane (3 mL) were added (2-amino-4-(methoxycarbonyl)phenyl)boronic acid, HCl salt (194 mg, 0.838 mmol), $K_3PO_4$ (1.745 mL, 1.745 mmol) and $Pd(Ph_3P)_4$ (40.3 mg, 0.035 mmol) at rt. The reaction was heated with microwave at 150° C. for 15 min. The solvent was removed. Purified by reverse phase chromatography afforded X-3a as white solid (85 mg, 24%). LC-MS (ESI) m/z: 273.0[M+H]$^+$.

EXAMPLE X-3b

Methyl 5-oxo-5,6-dihydrobenzo[c][2,7]naphthyridine-8-carboxylate

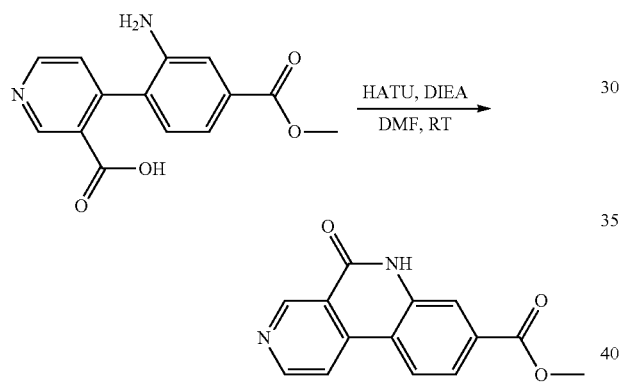

To a solution of X-3a (20 mg, 0.040 mmol) in DMF (1.5 mL) were added DIEA (0.035 mL, 0.200 mmol) and HATU (15.20 mg, 0.040 mmol) at rt. The reaction was stirred under argon at RT for 1.5 h. The crude product was purified by reverse phase chromatography to afford X-3b as light yellow solid (9 mg, 61%). LC-MS (ESI) m/z: 255.0[M+H]$^+$; $^1$H NMR (400 MHz, $CD_3OD$) δ 9.59 (s, 1H), 8.95 (d, J=5.9 Hz, 1H), 8.58 (d, J=5.9 Hz, 1H), 8.54 (d, J=8.6 Hz, 1H), 8.06 (d, J=1.3 Hz, 1H), 7.99 (dd, J=8.4, 1.5 Hz, 1H), 3.99 (s, 3H).

EXAMPLE X-3c

5-Oxo-5,6-dihydrobenzo[c][2,7]naphthyridine-8-carboxylic acid

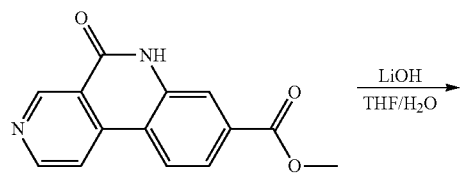

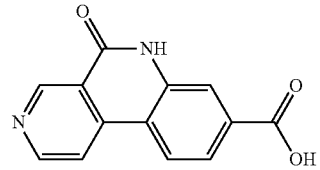

To a solution of X-3b (9 mg, 0.024 mmol) in THF (1.5 mL) and $H_2O$ (0.5 mL) was added LiOH (5.85 mg, 0.244 mmol) at rt. The reaction was stirred under argon for 2 h. the solvent was removed to afford X-3c as light yellow solid (5.87 mg, 100%). LC-MS (ESI) m/z: 241.1[M+H]$^+$.

EXAMPLE X-3

To a solution of X-3c (6 mg, 0.025 mmol) in DMF (1 mL) were added (R)-1-(3-methoxyphenyl)ethanamine (18.88 mg, 0.125 mmol), DIEA (0.044 mL, 0.250 mmol) and HATU (18.99 mg, 0.050 mmol). The reaction was stirred under argon at rt for 1 h. Purification by reverse phase chromatography afforded X-3 as white solid (2.5 mg, 26%). LC-MS (ESI) m/z: 374.20 [M+H]$^+$; $^1$H NMR (500 MHz, DMSO-$d_6$) δ 12.04 (s, 1H), 9.03 (d, J=8.0 Hz, 1H), 8.57 (d, J=8.3 Hz, 1H), 8.54 (br. s., 1H), 7.83 (s, 1H), 7.80 (dd, J=8.5, 1.4 Hz, 1H), 7.28-7.23 (m, 1H), 7.01-6.95 (m, 2H), 6.81 (dd, J=8.1, 1.8 Hz, 1H), 5.16 (quin, J=7.3 Hz, 1H), 3.75 (s, 3H), 1.48 (d, J=7.2 Hz, 3H); Analytical HPLC RT E: 1.12 min, F: 1.29 min.

EXAMPLE X-4

(R)-6-(2-(Dimethylamino)ethyl)-N-(1-(3-methoxyphenyl)ethyl)-5-oxo-5,6-dihydrobenzo[c][2,7]naphthyridine-8-carboxamide

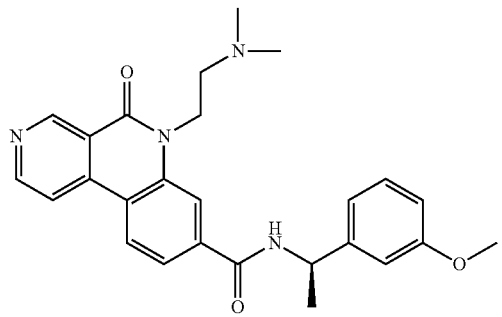 [SMILES: COc1cccc([C@@H](C)NC(=O)c2ccc3c4ccncc4c(=O)n(CCN(C)C)c3c2)c1]

EXAMPLE X-4a

Methyl 6-(2-(dimethylamino)ethyl)-5-oxo-5,6-dihydrobenzo[c][2,7]naphthyridine-8-carboxylate

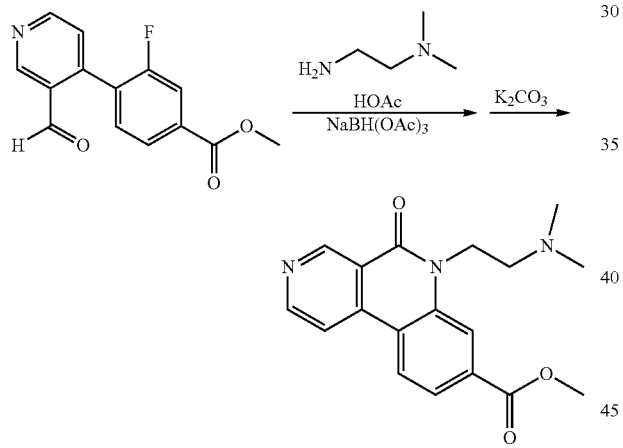

To a solution of Intermediate 4a (54 mg, 0.208 mmol) in DCE (1.5 mL) were added N1,N1-dimethylethane-1,2-diamine (0.046 mL, 0.417 mmol) and acetic acid (0.036 mL, 0.625 mmol). The reaction was stirred under argon at rt for 1 h. and followed by addition of sodium triacetoxyborohydride (93 mg, 0.417 mmol). After stirring at rt for 1.5 h, it was heated at 50° C. for 4 h, and then cooled to rt. To the reaction mixture was added potassium carbonate (17.27 mg, 0.125 mmol) and the mixture was stirred at rt for 1.5 h. LCMS showed the reaction was completed. The solvent was removed. The residue was dissolved in DMF/MeOH/water and purified by reverse phase chromatography to afford X-4a as TFA salt (42.8 mg, 37.1%). LCMS (ESI) m/z: 326.1 [M+H]$^+$.

EXAMPLE X-4b 6-(2-(Dimethylamino)ethyl)-5-oxo-5,6-dihydrobenzo[c][2,7]naphthyridine-8-carboxylic acid

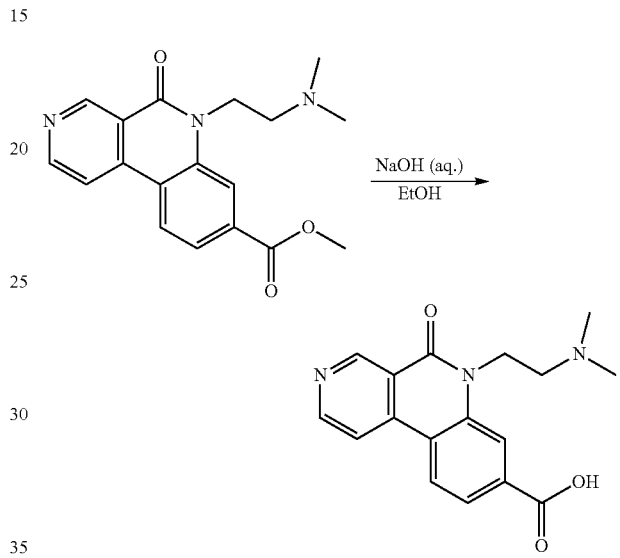

To a solution of X-4a (42.8 mg, 0.132 mmol) in EtOH (2 mL) was added NaOH (1N aq.) (0.527 mL, 0.527 mmol). The reaction was stirred under argon at rt for 2 h. To the reaction mixture was added HCl ((3.7N) (0.214 mL, 0.790 mmol) to adjust the PH~8. Purification by reverse phase chromatography afforded X-4b as TFA salt (41 mg, 57.7% yield). LC-MS (ESI) m/z: 312.1 [M+H]$^+$

EXAMPLE X-4

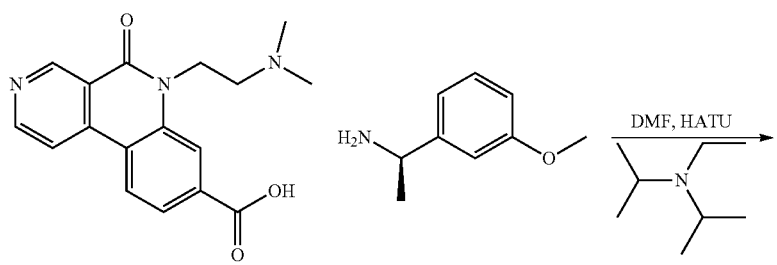

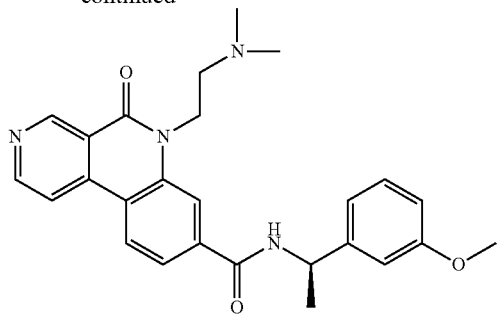

To a solution of X-4b (17 mg, 0.032 mmol) in DMF (1 mL) were added (R)-1-(3-methoxyphenyl)ethanamine hydrochloride (17.74 mg, 0.095 mmol), DIEA (0.055 mL, 0.315 mmol), and HATU (21.57 mg, 0.057 mmol) at rt. The reaction was stirred under argon at rt overnight. Purification by reverse phase chromatography afforded X-4 as TFA salt (3.0 mg, 4.22 μmol, 13.39% yield). LC-MS (ESI) m/z: 445.1[M+H]$^+$; $^1$H NMR (400 MHz, DMSO-d$_6$) δ 9.53 (s, 1H), 9.29 (br. s., 1H), 9.07 (d, J=7.9 Hz, 1H), 9.00 (d, J=5.7 Hz, 1H), 8.74 (d, J=8.6 Hz, 1H), 8.56 (d, J=5.7 Hz, 1H), 8.02-7.93 (m, 2H), 7.27 (t, J=8.1 Hz, 1H), 7.01 (d, J=4.2 Hz, 2H), 6.88-6.79 (m, 1H), 5.21 (t, J=7.3 Hz, 1H), 4.82 (t, J=5.8 Hz, 2H), 3.76 (s, 3H), 3.52 (d, J=5.3 Hz, 2H), 2.97 (d, J=4.2 Hz, 6H), 1.54 (d, J=7.0 Hz, 3H); Analytical HPLC RT A: 7.13 min, B: 7.88 min.

EXAMPLE X-5

(R)-6-Ethyl-5-oxo-N-(1-phenylethyl)-5,6-dihydrobenzo[c][2,7]naphthyridine-8-carboxamide

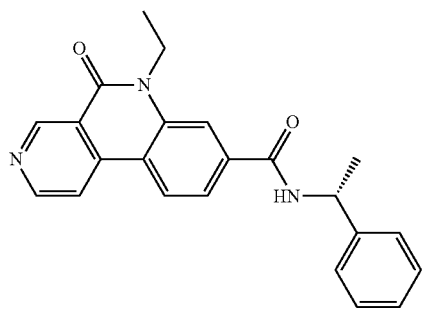 [SMILES: CCn1c(=O)c2cnccc2c2ccc(C(=O)N[C@H](C)c3ccccc3)cc21]

EXAMPLE X-5a 4-(2-Fluoro-4-(methoxycarbonyl)phenyl)nicotinic acid

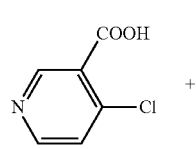

+

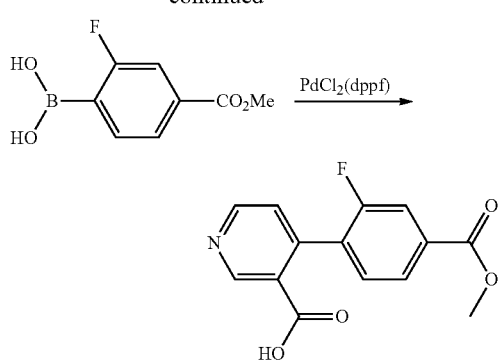

To a solution of 4-chloronicotinic acid (580 mg, 3.68 mmol) in dioxane (20 mL) and water (5 mL) were added (2-fluoro-4-(methoxycarbonyl)phenyl)boronic acid (802 mg, 4.05 mmol), K$_3$PO$_4$ (1954 mg, 9.20 mmol) and PdCl$_2$(dppf) (135 mg, 0.184 mmol) at rt. The reaction was stirred under argon at 90° C. for 2 h. The reaction mixture was diluted with EtOAc, washed with H$_2$O. Solvent was removed. Purification by reverse phase chromatography afforded X-5a as white solid (150 mg, 15%). LC-MS (ESI) m/z: 276.2 [M+H]$^+$; $^1$H NMR (400 MHz, DMSO-d$_6$) δ 13.34 (br. s., 1H), 9.07 (d, J=0.7 Hz, 1H), 8.85 (d, J=5.1 Hz, 1H), 7.89 (dd, J=7.9, 1.5 Hz, 1H), 7.75 (dd, J=10.6, 1.5 Hz, 1H), 7.60 (t, J=7.7 Hz, 1H), 7.49 (dd, J=5.1, 0.7 Hz, 1H), 3.90 (s, 3H).

EXAMPLE X-5b

Methyl 4-(3-(ethylcarbamoyl)pyridin-4-yl)-3-fluorobenzoate

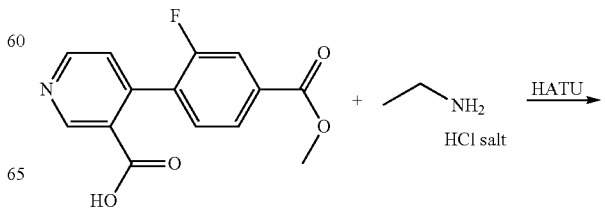

-continued

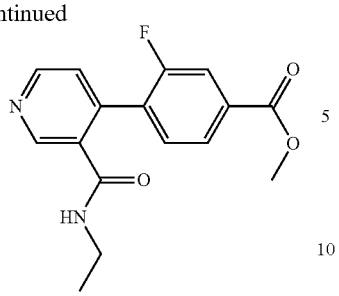

To a solution of X-5a (20 mg, 0.073 mmol) in DMF (1.5 mL) were added ethanamine, HCl (11.85 mg, 0.145 mmol), HATU (41.4 mg, 0.109 mmol) and DIEA (0.1 mL) at rt. The reaction was stirred under argon at rt for 1 hr. Purification by reverse phase chromatography afforded X-5b as white solid (29 mg, 96%). LC-MS (ESI) m/z: 303.1[M+H]+; 1H NMR (400 MHz, CDCl3) δ 9.06 (s, 1H), 8.83 (d, J=5.5 Hz, 1H), 7.98 (dd, J=7.9, 1.5 Hz, 1H), 7.86 (dd, J=10.5, 1.4 Hz, 1H), 7.78 (d, J=5.7 Hz, 1H), 7.50 (t, J=7.6 Hz, 1H), 6.75 (br. s., 1H), 3.97 (s, 3H), 3.44-3.32 (m, 2H), 1.14 (t, J=7.3 Hz, 3H).

EXAMPLE X-5c

Methyl 6-ethyl-5-oxo-5,6-dihydrobenzo[c][2,7]naphthyridine-8-carboxylate

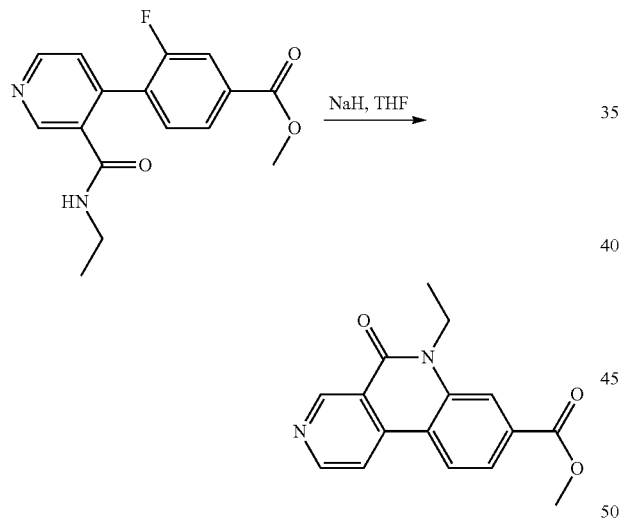

To a solution of X-5b (29 mg, 0.070 mmol) in THF (3 mL) was added NaH (13.93 mg, 0.348 mmol) at 0° C. The reaction was stirred under argon at 0° C. for 1 hr. The reaction was quenched by adding citric acid solution. The reaction mixture was diluted with EtOAc, washed with H2O and brine. The organic phase was dried over sodium sulfate, filtered and concentrated to give X-5c as white solid (17 mg, 86%). LC-MS (ESI) m/z: 283.1[M+H]+; 1H NMR (400 MHz, CDCl3) δ 9.76 (s, 1H), 8.94 (d, J=5.5 Hz, 1H), 8.35 (d, J=8.4 Hz, 1H), 8.15 (d, J=1.1 Hz, 1H), 8.06 (d, J=5.5 Hz, 1H), 7.99 (dd, J=8.3, 1.4 Hz, 1H), 4.51 (q, J=7.3 Hz, 2H), 4.02 (s, 3H), 1.46 (t, J=7.2 Hz, 3H).

EXAMPLE X-5d, Example X-5

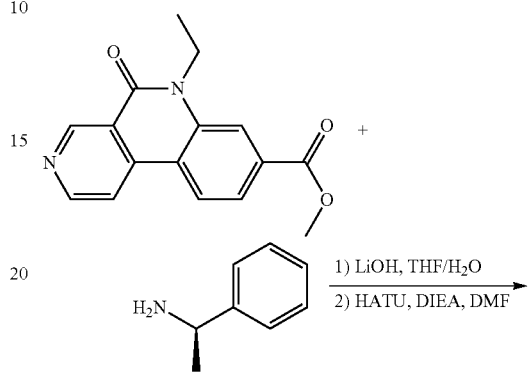

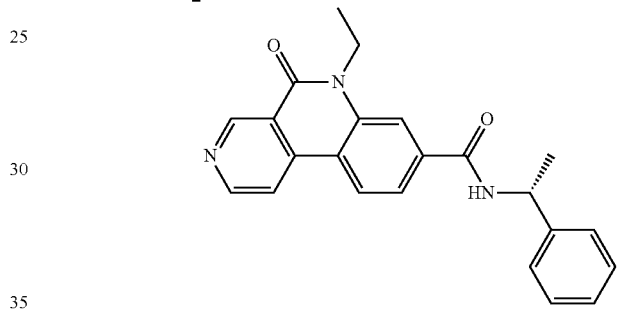

To a solution of X-5c (17 mg, 0.060 mmol) in THF (2 mL) and water (0.5 mL) was added LiOH (7.21 mg, 0.301 mmol) at rt. The reaction was stirred under argon for 1 hr. Solvent was removed to give white solid. To this solid were added (R)-1-phenylethanamine (21.68 mg, 0.179 mmol), DIEA (0.052 mL, 0.298 mmol) and HATU (34.0 mg, 0.089 mmol) at rt. The reaction was stirred under argon for 2 h. Purification by reverse phase chromatography afforded X-5 as white solid (17.4 mg, 78%). LC-MS (ESI) m/z: 372.20[M+H]+; 1H NMR (500 MHz, DMSO-d6) δ 9.52 (br. s., 1H), 9.15 (d, J=7.4 Hz, 1H), 8.97 (br. s., 1H), 8.70 (d, J=8.0 Hz, 1H), 8.52 (br. s., 1H), 8.04 (br. s., 1H), 7.95 (d, J=7.4 Hz, 1H), 7.45 (d, J=6.9 Hz, 2H), 7.37 (br. s., 2H), 7.30-7.24 (m, J=6.6 Hz, 1H), 5.32-5.21 (m, J=6.5, 6.5 Hz, 1H), 4.47 (d, J=5.8 Hz, 2H), 1.56 (d, J=6.1 Hz, 3H), 1.33 (br. s., 3H); Analytical HPLC RT E: 1.31 min, F: 1.50 min.

Compounds listed in Table XI were prepared by following procedures similar to those described for Example I-1 and Example VIII-3 using the appropriate intermediates described or purchased from commercial sources. Other coupling reagents than the one described, such as HATU, T3P, BOP, PyBop, and EDC/HOBt, could be used.

TABLE XI

| Ex. No. | Structure | Name | LCMS [M + H]+ | HPLC Method, RT (min.) | 1H NMR (δ, ppm) |
|---|---|---|---|---|---|
| XI-1 | Chiral | 2-acetamido-N-[(1R)-1-phenylethyl]-5H-chromeno[3,4-c]pyridine-8-carboxamide | 388.1 | E: 1.27 F: 1.51 | (500 MHz, DMSO-d$_6$) δ 10.46 (s, 1H), 8.97 (d, J = 7.9 Hz, 1H), 8.34 (s, 1H), 8.22 (s, 1H), 7.86 (d, J = 7.9 Hz, 1H), 7.57 (d, J = 7.9 Hz, 1H), 7.45 (s, 1H), 7.38-7.25 (m, 4H), 7.23-7.14 (m, 1H), 5.14 (s, 2H), 5.09 (t, J = 7.3 Hz, 1H), 2.10 (s, 3H), 1.44 (d, J = 7.0 Hz, 3H) |
| XI-2 | 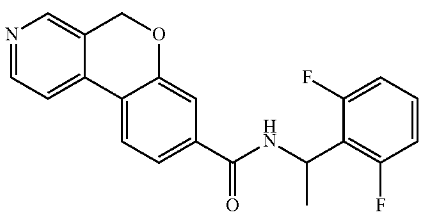 [SMILES: CC(NC(=O)c1ccc2c(c1)OCc1cnccc1-2)c1c(F)cccc1F] | N-[1-(2,6-difluorophenyl)ethyl]-5H-chromeno[3,4-c]pyridine-8-carboxamide | 367.1 | E: 1.18 F: 1.57 | (500 MHz, DMSO-d$_6$) δ 9.00 (d, J = 6.4 Hz, 1H), 8.61 (d, J = 5.0 Hz, 1H), 8.52 (s, 1H), 8.04 (d, J = 8.4 Hz, 1H), 7.86 (d, J = 5.0 Hz, 1H), 7.59 (d, J = 7.7 Hz, 1H), 7.51 (s, 1H), 7.40-7.20 (m, 1H), 7.04 (t, J = 8.1 Hz, 2H), 5.36 (t, J = 6.9 Hz, 1H), 5.26 (s, 2H), 1.56 (d, J = 7.1 Hz, 3H) |
| XI-3 | 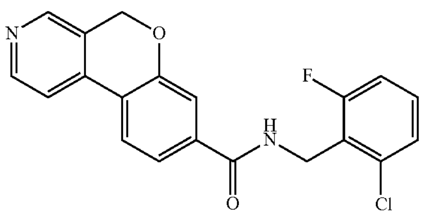 [SMILES: O=C(NCc1c(F)cccc1Cl)c1ccc2c(c1)OCc1cnccc1-2] | N-[(2-chloro-6-fluorophenyl)methyl]-5H-chromeno[3,4-c]pyridine-8-carboxamide | 369.0 | E: 1.14 F: 1.17 | (500 MHz, DMSO-d$_6$) δ 8.90 (br. s., 1H), 8.60 (d, J = 5.0 Hz, 1H), 8.52 (s, 1H), 8.04 (d, J = 8.1 Hz, 1H), 7.86 (d, J = 5.0 Hz, 1H), 7.59 (d, J = 8.1 Hz, 1H), 7.48 (s, 1H), 7.42-7.31 (m, 2H), 7.23 (t, J = 8.9 Hz, 1H), 5.25 (s, 2H), 4.58 (d, J = 4.0 Hz, 2H) |
| XI-4 | 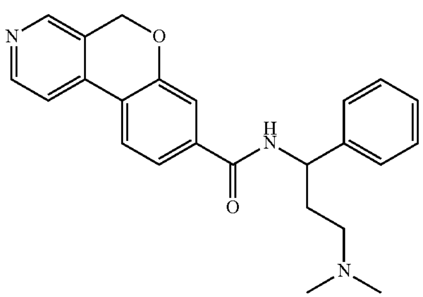 [SMILES: CN(C)CCC(NC(=O)c1ccc2c(c1)OCc1cnccc1-2)c1ccccc1] | N-[3-(dimethylamino)-1-phenylpropyl]-5H-chromeno[3,4-c]pyridine-8-carboxamide | 388.1 | E: 0.88 F: 1.11 | (500 MHz, DMSO-d$_6$) δ 9.05 (d, J = 7.6 Hz, 1H), 8.59 (br. s., 1H), 8.51 (s, 1H), 8.05 (d, J = 7.9 Hz, 1H), 7.84 (br. s., 1H), 7.58 (d, J = 7.9 Hz, 1H), 7.49 (br. s., 1H), 7.40-7.28 (m, 4H), 7.22 (br. s., 1H), 5.25 (s, 2H), 5.04 (br. s., 1H), 2.29 (br. s., 2H), 2.17 (br. s., 6H), 1.89 (m, 2H) |

TABLE XI-continued

| Ex. No. | Structure | Name | LCMS [M + H]+ | HPLC Method, RT (min.) | 1H NMR (δ, ppm) |
|---|---|---|---|---|---|
| XI-5 | 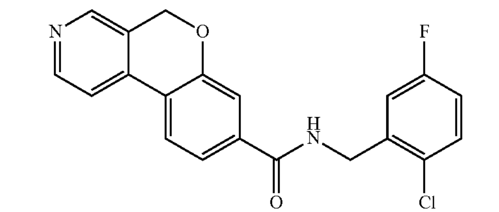 [SMILES: O=C(NCc1cc(F)ccc1Cl)c1ccc2c(c1)OCc1cnccc1-2] | N-[(2-chloro-5-fluorophenyl)methyl]-5H-chromeno[3,4-c]pyridine-8-carboxamide | 369.0 | E: 1.19 F: 1.59 | (500 MHz, DMSO-d6) δ 9.21 (t, J = 5.6 Hz, 1H), 8.67 (d, J = 5.0 Hz, 1H), 8.59 (s, 1H), 8.13 (d, J = 8.1 Hz, 1H), 7.98 (d, J = 5.0 Hz, 1H), 7.67 (d, J = 7.1 Hz, 1H), 7.62-7.43 (m, 2H), 7.22-7.09 (m, 2H), 5.30 (s, 2H), 4.52 (d, J = 5.4 Hz, 2H) |
| XI-6 | 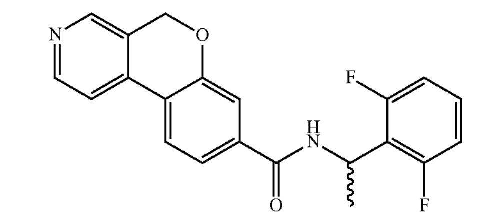 [SMILES: CC(NC(=O)c1ccc2c(c1)OCc1cnccc1-2)c1c(F)cccc1F] | N-[1-(2,6-difluorophenyl)ethyl]-5H-chromeno[3,4-c]pyridine-8-carboxamide | 367.1 | E: 1.18 F: 1.57 | (500 MHz, DMSO-d6) δ 9.04 (d, J = 6.1 Hz, 1H), 8.71 (br. s., 1H), 8.64 (br. s., 1H), 8.12 (d, J = 8.1 Hz, 1H), 8.07 (d, J = 5.4 Hz, 1H), 7.62 (d, J = 8.1 Hz, 1H), 7.54 (s, 1H), 7.37-7.27 (m, 1H), 7.04 (t, J = 8.1 Hz, 2H), 5.36 (t, J = 6.9 Hz, 1H), 5.31 (s, 2H), 1.57 (d, J = 7.1 Hz, 3H) |
| XI-7 | 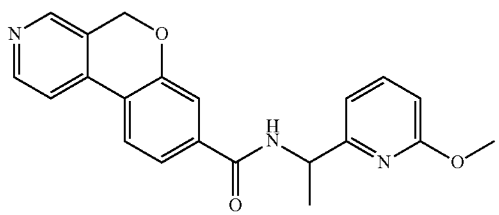 [SMILES: COc1cccc(C(C)NC(=O)c2ccc3c(c2)OCc2cnccc2-3)n1] | N-[1-(6-methoxypyridin-2-yl)ethyl]-5H-chromeno[3,4-c]pyridine-8-carboxamide | 362.1 | E: 0.95 F: 1.41 | (500 MHz, DMSO-d6) δ 8.89 (d, J = 7.7 Hz, 1H), 8.61 (d, J = 5.0 Hz, 1H), 8.53 (s, 1H), 8.08 (d, J = 8.1 Hz, 1H), 7.87 (d, J = 5.0 Hz, 1H), 7.70-7.62 (m, 2H), 7.57 (s, 1H), 6.96 (d, J = 7.1 Hz, 1H), 6.67 (d, J = 8.1 Hz, 1H), 5.27 (s, 2H), 5.09 (quin, J = 7.2 Hz, 1H), 3.86 (s, 3H), 1.51 (d, J = 7.1 Hz, 3H) |
| XI-8 | 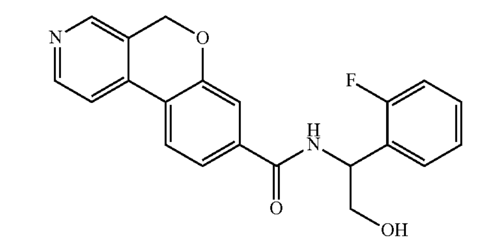 [SMILES: O=C(NC(CO)c1ccccc1F)c1ccc2c(c1)OCc1cnccc1-2] | N-[1-(2-fluorophenyl)-2-hydroxyethyl]-5H-chromeno[3,4-c]pyridine-8-carboxamide | 365.1 | E: 0.81 F: 1.12 | (500 MHz, DMSO-d6) δ 8.87 (d, J = 7.7 Hz, 1H), 8.62 (d, J = 5.0 Hz, 1H), 8.54 (s, 1H), 8.08 (d, J = 8.1 Hz, 1H), 7.89 (d, J = 5.0 Hz, 1H), 7.64 (d, J = 8.1 Hz, 1H), 7.58 (s, 1H), 7.49 (t, J = 7.1 Hz, 1H), 7.35-7.24 (m, 1H), 7.22-7.11 (m, 2H), 5.45-5.32 (m, 1H), 5.28 (s, 2H), 3.78-3.59 (m, 2H) |

TABLE XI-continued

| Ex. No. | Structure | Name | LCMS [M + H]+ | HPLC Method, RT (min.) | ¹H NMR (δ, ppm) |
|---|---|---|---|---|---|
| XI-9 | 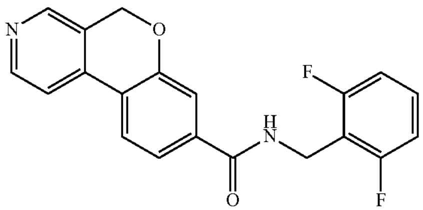 [SMILES: O=C(NCc1c(F)cccc1F)c1ccc2c(c1)OCc1cnccc1-2] | N-[(2,6-difluorophenyl)methyl]-5H-chromeno[3,4-c]pyridine-8-carboxamide | 353.0 | E: 0.96 F: 1.41 | (500 MHz, DMSO-d$_6$) δ 9.00 (br. s., 1H), 8.61 (d, J = 5.0 Hz, 1H), 8.52 (s, 1H), 8.05 (d, J = 8.1 Hz, 1H), 7.87 (d, J = 5.4 Hz, 1H), 7.59 (d, J = 8.1 Hz, 1H), 7.48 (s, 1H), 7.40 (quin, J = 7.4 Hz, 1H), 7.09 (t, J = 7.7 Hz, 2H), 5.25 (s, 2H), 4.52 (d, J = 5.0 Hz, 2H) |
| XI-10 | chiral | N-[1-(2,6-difluorophenyl)ethyl]-5H-chromeno[3,4-c]pyridine-8-carboxamide | 367.1 | E: 1.19 F: 1.57 | (500 MHz, DMSO-d$_6$) δ 8.99 (d, J = 6.4 Hz, 1H), 8.63 (d, J = 4.4 Hz, 1H), 8.55 (br. s., 1H), 8.07 (d, J = 8.4 Hz, 1H), 7.90 (d, J = 5.0 Hz, 1H), 7.60 (d, J = 8.1 Hz, 1H), 7.52 (s, 1H), 7.32 (t, J = 6.7 Hz, 1H), 7.08-6.98 (m, 2H), 5.36 (t, J = 6.9 Hz, 1H), 5.27 (s, 2H), 1.57 (d, J = 7.4 Hz, 3H) |
| XI-11 | Chiral | N-[(1S)-2-methoxy-1-phenylethyl]-5H-chromeno[3,4-c]pyridine-8-carboxamide | 361.1 | E: 1.14 F: 1.48 | (500 MHz, DMSO-d$_6$) δ 8.96 (d, J = 7.9 Hz, 1H), 8.59 (d, J = 5.2 Hz, 1H), 8.51 (s, 1H), 8.05 (d, J = 8.2 Hz, 1H), 7.84 (d, J = 5.2 Hz, 1H), 7.65-7.58 (m, 1H), 7.52 (d, J = 1.5 Hz, 2H), 7.43-7.37 (m, 2H), 7.33 (t, J = 7.6 Hz, 2H), 7.27-7.20 (m, 1H), 5.25 (s, 2H), 5.24-5.20 (m, 1H), 3.75-3.53 (m, 5H) |
| XI-12 | Chiral | 2-amino-N-[(1R)-1-(3-methoxyphenyl)ethyl]-5H-chromeno[3,4-c]pyridine-8-carboxamide | 376.1 | E: 1.24 F: 1.46 | (500 MHz, DMSO-d$_6$) δ 8.86 (d, J = 8.2 Hz, 1H), 7.88-7.78 (m, 2H), 7.57 (d, J = 7.9 Hz, 1H), 7.48 (s, 1H), 7.23 (t, J = 8.1 Hz, 1H), 6.98-6.91 (m, 2H), 6.85 (s, 1H), 6.81-6.73 (m, 1H), 5.15-5.07 (m, 1H), 5.02 (s, 2H), 3.72 (s, 3H), 1.45 (d, J = 7.0 Hz, 3H) |

TABLE XI-continued

| Ex. No. | Structure | Name | LCMS [M + H]+ | HPLC Method, RT (min.) | 1H NMR (δ, ppm) |
|---|---|---|---|---|---|
| XI-13 | 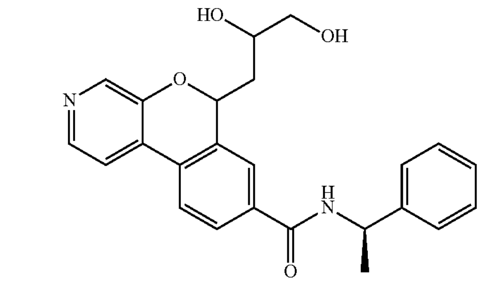 [SMILES: C[C@@H](NC(=O)c1ccc2c(c1)C(CC(O)CO)Oc1cnccc1-2)c1ccccc1] | 6-(2,3-dihydroxypropyl)-N-[(1R)-1-phenylethyl]-6H-isochromeno[3,4-c]pyridine-8-carboxamide | 405.1 | E: 1.07 F: 1.26 | (500 MHz, DMSO-d6) δ 8.92 (br. s., 1H), 8.30 (d, J = 15.7 Hz, 2H), 8.07 (br. s., 1H), 8.01-7.90 (m, 2H), 7.81 (br. s., 1H), 7.40 (br. s., 2H), 7.33 (br. s., 2H), 7.23 (br. s., 1H), 5.68-5.54 (m, 1H), 5.19 (br. s., 1H), 5.02-4.34 (m, 2H), 3.79 (br. s., 1H), 3.30-3.21 (m, 2H), 2.00-1.82 (m, 2H), 1.50 (br. s., 3H) |
| XI-14 | 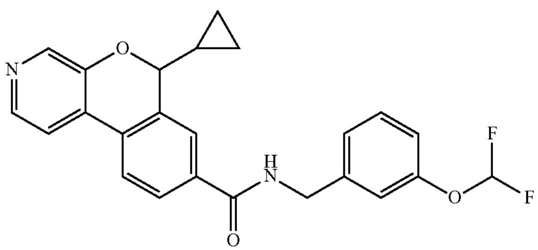 [SMILES: O=C(NCc1cccc(OC(F)F)c1)c1ccc2c(c1)C(C1CC1)Oc1cnccc1-2] | 6-cyclopropyl-N-{[3-(difluoromethoxy)phenyl]methyl}-6H-isochromeno[3,4-c]pyridine-8-carboxamide | 423.1 | E: 1.39 F: 1.81 | (500 MHz, DMSO-d6) δ 9.23 (br. s., 1H), 8.46 (br. s., 1H), 8.36 (br. s., 1H), 8.15 (d, J = 7.7 Hz, 1H), 8.07 (br. s., 1H), 8.02 (d, J = 7.7 Hz, 1H), 7.95 (br. s., 1H), 7.45-7.34 (m, 1H), 7.26-7.19 (m, 1H), 7.14 (br. s., 1H), 7.11-7.04 (m, 2H), 4.78 (d, J = 8.8 Hz, 1H), 4.53 (br. s., 2H), 1.28 (br. s., 1H), 0.62 (br. s., 2H), 0.56 (br. s., 2H) |
| XI-15 | 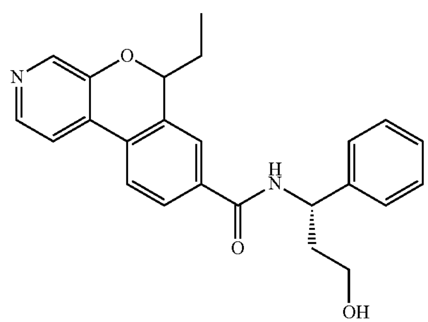 [SMILES: CCC1Oc2cnccc2-c2ccc(C(=O)N[C@@H](CCO)c3ccccc3)cc21] | 6-ethyl-N-[(1S)-3-hydroxy-1-phenylpropyl]-6H-isochromeno[3,4-c]pyridine-8-carboxamide | 389.1 | E: 1.11 F: 1.45 | (500 MHz, DMSO-d6) δ 8.85 (dd, J = 8.0, 3.0 Hz, 1H), 8.33 (s, 1H), 8.28 (d, J = 5.0 Hz, 1H), 8.07 (d, J = 8.3 Hz, 1H), 7.99-7.83 (m, 1H), 7.91 (d, J = 5.0 Hz, 1H), 7.79 (s, 1H), 7.45-7.36 (m, 2H), 7.33 (t, J = 7.6 Hz, 2H), 7.27-7.15 (m, 1H), 5.35 (dd, J = 8.3, 4.1 Hz, 1H), 5.22-5.13 (m, 1H), 4.57 (t, J = 4.8 Hz, 1H), 3.53-3.38 (m, 1H), 2.12-2.00 (m, 1H), 1.92 (dq, J = 13.4, 6.5 Hz, 1H), 1.86-1.66 (m, 2H), 0.99 (td, J = 7.2, 4.5 Hz, 3H) |

TABLE XI-continued

| Ex. No. | Structure | Name | LCMS [M + H]+ | HPLC Method, RT (min.) | 1H NMR (δ, ppm) |
|---|---|---|---|---|---|
| XI-16 | Chiral | 6-ethyl-N-[(1R)-1-(3-methoxyphenyl)ethyl]-6H-isochromeno[3,4-c]pyridine-8-carboxamide | 389.1 | A: 8.99 B: 9.93 | (400 MHz, methanol-$d_4$) δ 8.57-8.23 (br, 2H), 8.08-7.98 (m, 1H), 7.92 (dd, J = 8.1, 1.8 Hz, 2H), 7.74 (d, J = 1.8 Hz, 1H), 7.32-7.24 (m, 1H), 7.08-6.96 (m, 2H), 6.86-6.74 (m, 1H), 5.31 (dd, J = 8.8, 4.6 Hz, 1H), 5.27-5.17 (m, 1H), 3.80 (s, 3H), 2.03-1.74 (m, 2H), 1.59 (d, J = 7.0 Hz, 3H), 1.07 (t, J = 7.4 Hz, 3H) |
| XI-17 | Chiral | 6-ethyl-N-[(1R)-1-(3-methoxyphenyl)ethyl]-6H-isochromeno[3,4-c]pyridine-8-carboxamide | 389.1 | A: 9.05 B: 9.97 | (400 MHz, methanol-$d_4$) δ 8.26 (s, 1H), 8.23 (d, J = 5.1 Hz, 1H), 8.04-8.00 (m, 1H), 7.96-7.90 (m, 1H), 7.86 (d, J = 5.1 Hz, 1H), 7.74 (d, J = 1.5 Hz, 1H), 7.30-7.22 (m, 1H), 7.04-6.95 (m, 2H), 6.85-6.78 (m, 1H), 5.31 (dd, J = 8.8, 4.6 Hz, 1H), 5.24 (q, J = 7.0 Hz, 1H), 3.80 (s, 3H), 1.99-1.76 (m, 2H), 1.59 (d, J = 7.0 Hz, 3H), 1.08 (t, J = 7.4 Hz, 3H) |
| XI-18 | Chiral | 2-fluoro-N-[(1R)-1-phenylethyl]-6H-isochromeno[3,4-c]pyridine-8-carboxamide | 349.0 | E: 1.68 F: 1.69 | (500 MHz, DMSO-$d_6$) δ 8.93 (d, J = 8.0 Hz, 1H), 8.14 (d, J = 8.3 Hz, 1H), 8.01-7.96 (m, 2H), 7.86 (s, 1H), 7.79 (s, 1H), 7.46-7.38 (m, 2H), 7.33 (t, J = 7.6 Hz, 2H), 7.27-7.16 (m, 1H), 5.30 (s, 2H), 5.18 (quin, J = 7.2 Hz, 1H), 1.49 (d, J = 7.2 Hz, 3H) |

TABLE XI-continued

| Ex. No. | Structure | Name | LCMS [M + H]+ | HPLC Method, RT (min.) | 1H NMR (δ, ppm) |
|---|---|---|---|---|---|
| XI-19 | 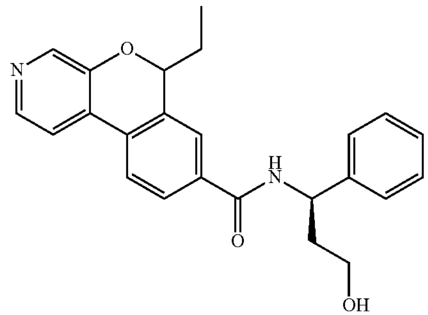 [SMILES: CCC1Oc2cnccc2-c2ccc(C(=O)N[C@H](CCO)c3ccccc3)cc21] | 6-ethyl-N-[(1R)-3-hydroxy-1-phenylpropyl]-6H-isochromeno[3,4-c]pyridine-8-carboxamide | 389.2 | E: 1.11 F: 1.45 | (500 MHz, DMSO-d$_6$) δ 8.85 (dd, J = 8.0, 2.8 Hz, 1H), 8.33 (s, 1H), 8.27 (d, J = 5.0 Hz, 1H), 8.07 (d, J = 8.3 Hz, 1H), 7.94 (d, J = 7.7 Hz, 1H), 7.90 (d, J = 5.2 Hz, 1H), 7.79 (s, 1H), 7.44-7.37 (m, 2H), 7.33 (t, J = 7.4 Hz, 2H), 7.23 (d, J = 7.2 Hz, 1H), 5.35 (dd, J = 8.4, 4.3 Hz, 1H), 5.17 (d, J = 6.3 Hz, 1H), 4.58 (t, J = 4.7 Hz, 1H), 3.51-3.39 (m, 2H), 2.11-2.00 (m, 1H), 1.97-1.88 (m, 1H), 1.85-1.67 (m, 2H), 1.04-0.94 (m, 3H) |
| XI-20 | Chiral | 6-ethyl-N-({3-[(2-hydroxy-2-methylpropyl)carbamoyl]phenyl}methyl)-6H-isochromeno[3,4-c]pyridine-8-carboxamide | 460.2 | A: 4.30 B: 4.69 | (400 MHz, DMSO-d$_6$) δ 9.18 (t, J = 5.8 Hz, 1H), 8.34 (s, 1H), 8.28 (d, J = 4.8 Hz, 1H), 8.21 (t, J = 6.1 Hz, 1H), 8.10 (d, J = 8.1 Hz, 1H), 7.98 (dd, J = 8.1, 1.5 Hz, 1H), 7.92 (d, J = 5.1 Hz, 1H), 7.84 (s, 2H), 7.76 (d, J = 7.7 Hz, 1H), 7.57-7.47 (m, 1H), 7.46-7.38 (m, 1H), 5.36 (dd, J = 8.6, 4.6 Hz, 1H), 4.56 (d, J = 5.9 Hz, 2H), 3.25 (d, J = 6.2 Hz, 3H), 1.90-1.64 (m, 2H), 1.10 (s, 6H), 0.99 (t, J = 7.3 Hz, 3H) |
| XI-21 | Chiral | 6-ethyl-N-({3-[(2-hydroxy-2-methylpropyl)carbamoyl]phenyl}methyl)-6H-isochromeno[3,4-c]pyridine-8-carboxamide | 460.2 | A: 4.11 B: 4.38 | (400 MHz, DMSO-d$_6$) δ 9.18 (t, J = 5.8 Hz, 1H), 8.46-8.25 (m, 2H), 8.20 (t, J = 6.1 Hz, 1H), 8.09 (d, J = 8.1 Hz, 1H), 7.97 (dd, J = 8.1, 1.8 Hz, 1H), 7.92 (d, J = 4.8 Hz, 1H), 7.84 (s, 2H), 7.75 (d, J = 7.7 Hz, 1H), 7.55-7.47 (m, 1H), 7.46-7.38 (m, 1H), 5.35 (dd, J = 8.6, 4.6 Hz, 1H), 4.55 (d, J = 5.9 Hz, 2H), 3.25 (d, J = 6.2 Hz, 3H), 2.02-1.65 (m, 2H), 1.10 (s, 6H), 0.99 (t, J = 7.4 Hz, 3H) |

TABLE XI-continued

| Ex. No. | Structure | Name | LCMS [M + H]+ | HPLC Method, RT (min.) | 1H NMR (δ, ppm) |
|---|---|---|---|---|---|
| XI-22 | Chiral | 6-ethyl-N-{[3-(ethylcarbamoyl)-4-fluorophenyl]methyl}-6H-isochromeno[3,4-c]pyridine-8-carboxamide | 434.2 | A: 4.69 B: 5.11 | (400 MHz, DMSO-d$_6$) δ 9.18 (t, J = 5.9 Hz, 1H), 8.33 (s, 1H), 8.28 (d, J = 5.1 Hz, 2H), 8.09 (d, J = 8.1 Hz, 1H), 7.96 (dd, J = 8.1, 1.5 Hz, 1H), 7.91 (d, J = 5.1 Hz, 1H), 7.82 (d, J = 1.3 Hz, 1H), 7.57 (dd, J = 7.0, 2.2 Hz, 1H), 7.50-7.41 (m, 1H), 7.24 (dd, J = 10.3, 8.6 Hz, 1H), 5.35 (dd, J = 8.6, 4.8 Hz, 1H), 4.50 (d, J = 5.9 Hz, 2H), 3.26 (dd, J = 7.3, 5.7 Hz, 2H), 1.87-1.68 (m, 2H), 1.10 (t, J = 7.2 Hz, 3H), 0.99 (t, J = 7.4 Hz, 3H) |
| XI-23 | Chiral | 6-ethyl-N-{[3-(ethylcarbamoyl)-4-fluorophenyl]methyl}-6H-isochromeno[3,4-c]pyridine-8-carboxamide | 434.2 | A: 4.68 B: 5.11 | (400 MHz, DMSO-d$_6$) δ 9.18 (t, J = 5.9 Hz, 1H), 8.41-8.21 (m, 3H), 8.09 (d, J = 8.1 Hz, 1H), 7.96 (dd, J = 8.0, 1.7 Hz, 1H), 7.91 (d, J = 5.1 Hz, 1H), 7.82 (d, J = 1.1 Hz, 1H), 7.57 (dd, J = 7.0, 2.2 Hz, 1H), 7.51-7.40 (m, 1H), 7.24 (dd, J = 10.3, 8.6 Hz, 1H), 5.35 (dd, J = 8.6, 4.6 Hz, 1H), 4.50 (d, J = 5.9 Hz, 2H), 3.28-3.19 (m, 2H), 1.90-1.65 (m, 2H), 1.10 (t, J = 7.2 Hz, 3H), 0.99 (t, J = 7.3 Hz, 3H) |
| XI-24 | Chiral | 6-ethyl-N-[(1R)-3-hydroxy-1-phenylpropyl]-6H-isochromeno[3,4-c]pyridine-8-carboxamide | 389.2 | A: 4.68 B: 5.07 | (400 MHz, DMSO-d$_6$) δ 8.85 (d, J = 8.1 Hz, 1H), 8.33 (s, 1H), 8.28 (d, J = 5.1 Hz, 1H), 8.07 (d, J = 8.1 Hz, 1H), 7.95 (dd, J = 8.0, 1.7 Hz, 1H), 7.91 (d, J = 5.1 Hz, 1H), 7.79 (s, 1H), 7.44-7.37 (m, 2H), 7.36-7.28 (m, 2H), 7.27-7.15 (m, 1H), 5.36 (dd, J = 8.6, 4.6 Hz, 1H), 5.24-5.10 (m, 1H), 4.57 (t, J = 4.8 Hz, 1H), 3.45 (qd, J = 11.0, 4.7 Hz, 2H), 2.14-1.99 (m, 1H), 1.92 (dq, J = 13.3, 6.6 Hz, 1H), 1.85-1.65 (m, 2H), 0.99 (t, J = 7.3 Hz, 3H) |

TABLE XI-continued

| Ex. No. | Structure | Name | LCMS [M + H]+ | HPLC Method, RT (min.) | 1H NMR (δ, ppm) |
|---|---|---|---|---|---|
| XI-25 | Chiral | 6-ethyl-N-[(1R)-3-hydroxy-1-phenylpropyl]-6H-isochromeno[3,4-c]pyridine-8-carboxamide | 389.1 | A: 4.67 B: 5.05 | (400 MHz, DMSO-d6) δ 8.84 (d, J = 8.1 Hz, 1H), 8.33 (s, 1H), 8.28 (d, J = 5.1 Hz, 1H), 8.07 (d, J = 8.4 Hz, 1H), 7.94 (dd, J = 8.1, 1.5 Hz, 1H), 7.91 (d, J = 5.1 Hz, 1H), 7.79 (s, 1H), 7.46-7.37 (m, 2H), 7.36-7.28 (m, 2H), 7.23 (d, J = 7.3 Hz, 1H), 5.35 (dd, J = 8.7, 4.7 Hz, 1H), 5.25-5.08 (m, 1H), 4.56 (t, J = 5.0 Hz, 1H), 3.55-3.38 (m, 2H), 2.13-2.00 (m, 1H), 1.98-1.86 (m, 1H), 1.85-1.68 (m, 2H), 0.99 (t, J = 7.3 Hz, 3H) |
| XI-26 | Chiral | 6,6-dimethyl-N-[(1R)-1-phenylethyl]-6H-isochromeno[3,4-c]pyridine-8-carboxamide | 359.1 | A: 5.76 B: 6.27 | (400 MHz, CD3OD) δ 8.82 (d, J = 7.3 Hz, 1H), 8.16 (br. s., 2H), 7.95 (d, J = 7.9 Hz, 1H), 7.89-7.81 (m, 2H), 7.79 (s, 1H), 7.36-7.29 (m, 2H), 7.24 (t, J = 7.7 Hz, 2H), 7.18-7.10 (m, 1H), 5.18 (t, J = 7.3 Hz, 1H), 1.62 (s, 6H), 1.50 (d, J = 7.0 Hz, 3H) |
| XI-27 | Chiral | N-[(1R)-1-(4-fluorophenyl)ethyl]-6,6-dimethyl-6H-isochromeno[3,4-c]pyridine-8-carboxamide | 377.1 | A: 5.80 B: 6.52 | (400 MHz, CD3OD) δ 8.98 (d, J = 7.3 Hz, 1H), 8.48 (s, 1H), 8.41 (d, J = 5.5 Hz, 1H), 8.36 (d, J = 5.9 Hz, 1H), 8.18 (d, J = 8.1 Hz, 1H), 8.00 (dd, J = 8.1, 1.8 Hz, 1H), 7.94 (d, J = 1.5 Hz, 1H), 7.44 (dd, J = 8.6, 5.3 Hz, 2H), 7.07 (t, J = 8.8 Hz, 2H), 5.27 (quin, J = 7.2 Hz, 1H), 1.78 (s, 6H), 1.60 (d, J = 7.0 Hz, 3H) |

TABLE XI-continued

| Ex. No. | Structure | Name | LCMS [M + H]+ | HPLC Method, RT (min.) | 1H NMR (δ, ppm) |
|---|---|---|---|---|---|
| XI-28 | Chiral | 2-amino-N-[(1R)-1-phenylethyl]-6H-isochromeno[3,4-c]pyridine-8-carboxamide | 346.1 | E: 1.22<br>F: 1.47 | (500 MHz, DMSO-d6) δ 9.01 (d, J = 7.3 Hz, 1H), 7.97 (br. s., 2H), 7.83 (br. s., 1H), 7.50-7.28 (m, 6H), 7.25-7.17 (m, 1H), 5.20 (s, 2H), 5.17-5.07 (m, 1H), 1.47 (d, J = 6.4 Hz, 3H) |
| XI-29 | Chiral | 2-acetamido-N-[(1R)-1-phenylethyl]-6H-isochromeno[3,4-c]pyridine-8-carboxamide | 388.2 | E: 1.35<br>F: 1.51 | (500 MHz, DMSO-d6) δ 10.43 (br. s., 1H), 8.95 (d, J = 7.7 Hz, 1H), 8.03-7.91 (m, 2H), 7.89-7.75 (m, 2H), 7.40 (d, J = 7.7 Hz, 2H), 7.33 (t, J = 7.4 Hz, 2H), 7.25-7.18 (m, 1H), 5.25 (s, 2H), 5.17 (t, J = 7.2 Hz, 1H), 2.12 (br. s., 3H), 1.48 (d, J = 6.7 Hz, 3H) |
| XI-30 | Chiral | 2-amino-N-[(1R)-1-(3-methoxyphenyl)ethyl]-6H-isochromeno[3,4-c]pyridine-8-carboxamide | 376.1 | E: 1.31<br>F: 1.37 | (500 MHz, DMSO-d6) δ 8.98 (d, J = 7.7 Hz, 1H), 8.05-7.96 (m, 2H), 7.87 (d, J = 14.8 Hz, 2H), 7.39 (s, 1H), 7.24 (t, J = 8.1 Hz, 1H), 7.01-6.94 (m, 2H), 6.80 (d, J = 7.4 Hz, 1H), 5.24 (s, 2H), 5.14 (t, J = 7.2 Hz, 1H), 3.74 (s, 3H), 1.47 (d, J = 7.1 Hz, 3H) |

TABLE XI-continued

| Ex. No. | Structure | Name | LCMS [M + H]+ | HPLC Method, RT (min.) | 1H NMR (δ, ppm) |
|---|---|---|---|---|---|
| XI-31 | Chiral | N-[(1S)-2-hydroxy-1-phenylethyl]-6,6-dimethyl-6H-isochromeno[3,4-c]pyridine-8-carboxamide | 375.3 | E: 0.96 F: 1.30 | (500 MHz, DMSO-d6) δ 8.87 (d, J = 8.1 Hz, 1H), 8.33-8.23 (m, 2H), 8.10 (d, J = 8.1 Hz, 1H), 7.99 (d, J = 8.1 Hz, 1H), 7.97-7.89 (m, 2H), 7.41 (d, J = 7.4 Hz, 2H), 7.34 (t, J = 7.4 Hz, 2H), 7.29-7.21 (m, 1H), 5.11 (d, J = 6.1 Hz, 1H), 5.04 (t, J = 5.6 Hz, 1H), 3.81-3.62 (m, 2H), 1.70-1.66 (m, 3H), 1.66 (s, 3H) |
| XI-32 | Chiral | 2-amino-N-[(1S)-1-(2,6-difluorophenyl)-2-hydroxyethyl]-6H-isochromeno[3,4-c]pyridine-8-carboxamide | 398.1 | E: 0.91 F: 1.22 | (500 MHz, DMSO-d6) δ 8.79 (d, J = 7.1 Hz, 1H), 7.99-7.69 (m, 4H), 7.34 (t, J = 7.1 Hz, 1H), 7.04 (t, J = 8.1 Hz, 2H), 6.92 (s, 1H), 5.37 (d, J = 6.7 Hz, 1H), 5.07 (s, 2H), 3.89 (d, J = 6.4 Hz, 1H), 3.77 (d, J = 5.4 Hz, 1H) |
| XI-33 | Chiral | 2-acetamido-N-[(1R)-1-(3-methoxyphenyl)ethyl]-6H-isochromeno[3,4-c]pyridine-8-carboxamide | 418.0 | E: 1.31 F: 1.46 | (500 MHz, DMSO-d6) δ 10.48 (s, 1H), 8.94 (d, J = 8.1 Hz, 1H), 8.50 (s, 1H), 8.10 (s, 1H), 8.00-7.93 (m, 1H), 7.91-7.80 (m, 2H), 7.25 (t, J = 7.9 Hz, 1H), 7.02-6.91 (m, 2H), 6.81 (d, J = 9.1 Hz, 1H), 5.26 (s, 2H), 5.15 (t, J = 7.2 Hz, 1H), 3.75 (s, 3H), 2.11 (s, 3H), 1.49 (d, 3H) |

TABLE XI-continued

| Ex. No. | Structure | Name | LCMS [M + H]+ | HPLC Method, RT (min.) | 1H NMR (δ, ppm) |
|---|---|---|---|---|---|
| XI-34 | Chiral | 2-(3-methylbutanamido)-N-[(1R)-1-phenylethyl]-6H-isochromeno[3,4-c]pyridine-8-carboxamide | 430.3 | E: 1.57 F: 1.78 | (500 MHz, DMSO-d6) δ 10.43 (s, 1H), 8.96 (d, J = 8.1 Hz, 1H), 8.56 (s, 1H), 8.11 (s, 1H), 7.99 (d, J = 8.1 Hz, 1H), 7.88 (d, J = 15.8 Hz, 2H), 7.45-7.38 (m, 2H), 7.34 (t, J = 7.6 Hz, 2H), 7.28-7.18 (m, 1H), 5.26 (s, 2H), 5.20 (t, J = 7.2 Hz, 1H), 2.29 (d, J = 7.1 Hz, 2H), 2.17-2.05 (m, 1H), 1.50 (d, J = 7.1 Hz, 3H), 0.95 (d, J = 6.7 Hz, 6H) |
| XI-35 | Chiral | N-[(1R)-1-phenylethyl]-2-(3-phenylpropanamido)-6H-isochromeno[3,4-c]pyridine-8-carboxamide | 478.1 | E: 1.76 F: 1.92 | (500 MHz, DMSO-d6) δ 10.51 (s, 1H), 8.97 (d, J = 8.1 Hz, 1H), 8.54 (s, 1H), 8.10 (s, 1H), 8.03-7.93 (m, 2H), 7.87 (d, J = 17.5 Hz, 2H), 7.43-7.38 (m, 2H), 7.34 (t, J = 7.6 Hz, 2H), 7.28 (m, 6H), 7.20 (d, J = 6.7 Hz, 1H), 5.26 (s, 2H), 5.19 (t, J = 7.2 Hz, 1H), 2.97-2.91 (m, 2H), 2.77-2.70 (m, 2H), 1.50 (d, J = 6.7 Hz, 3H) |
| XI-36 | Chiral | 2-[3-(morpholin-4-yl)propanamido]-N-[(1R)-1-phenylethyl]-6H-isochromeno[3,4-c]pyridine-8-carboxamide | 487.0 | E: 1.16 F: 1.51 | (500 MHz, DMSO-d6) δ 10.66 (s, 1H), 8.96 (d, J = 8.1 Hz, 1H), 8.55 (s, 1H), 8.12 (s, 1H), 8.02-7.94 (m, 1H), 7.90-7.84 (m, 2H), 7.44-7.39 (m, 2H), 7.34 (t, J = 7.6 Hz, 2H), 7.27-7.21 (m, 1H), 5.26 (s, 2H), 5.19 (t, J = 7.2 Hz, 1H), 3.59 (br. s., 4H), 2.64 (d, J = 6.4 Hz, 2H), 2.58 (d, J = 6.4 Hz, 2H), 2.43 (br. s., 4H), 1.50 (d, J = 7.1 Hz, 3H) |

EXAMPLE XI-37

Methyl N-(8-{[(1R)-1-phenylethyl]carbamoyl}-6H-isochromeno[3,4-c]pyridin-2-yl)carbamate

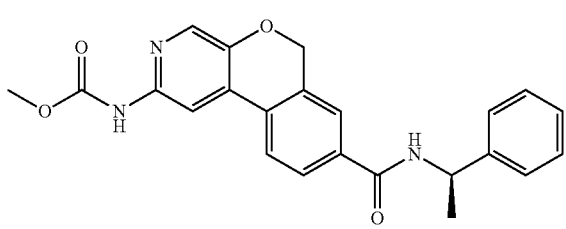 [SMILES: COC(=O)Nc1cc2c(cn1)OCc1cc(C(=O)N[C@H](C)c3ccccc3)ccc1-2]

Example XI-28 (9.3 mg, 0.020 mmol) was suspended in 2 mL of CH₂Cl₂ and was cooled in an ice bath. To this mixture was added methyl carbonochloridate (7.82 µl, 0.101 mmol) and DIEA (0.035 mL, 0.202 mmol). The mixture was stirred at 0° C. for 10 minutes. The solvent was removed. The residue was dissolved in DMF, filtered, and purified by reverse phase HPLC (2.1 mg, 25%). LC-MS (ESI) m/z: 404.1 [M+H]⁺; ¹H NMR (500 MHz, DMSO-$d_6$) δ 9.51 (s, 1H), 9.09 (d, J=7.9 Hz, 1H), 8.96 (d, J=5.2 Hz, 1H), 8.66 (d, J=8.2 Hz, 1H), 8.52 (d, J=5.8 Hz, 1H), 7.95-7.81 (m, 2H), 7.45 (dd, J=8.2, 5.8 Hz, 2H), 7.19-7.10 (m, 2H), 6.08-5.94 (m, 1H), 5.30-5.14 (m, 2H), 5.06 (d, J=15.3 Hz, 3H), 1.52 (d, J=7.0 Hz, 3H).

EXAMPLE XI-38

Propan-2-yl N-(8-{[(1R)-1-phenylethyl]carbamoyl}-6H-isochromeno[3,4-c]pyridin-2-yl)carbamate

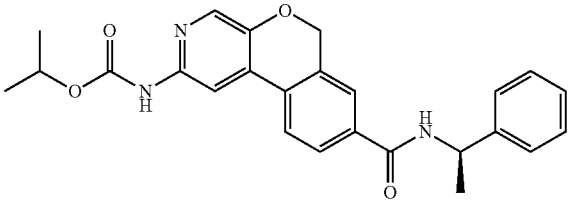 [SMILES: CC(C)OC(=O)Nc1cc2c(cn1)OCc1cc(C(=O)N[C@H](C)c3ccccc3)ccc1-2]

Example XI-38 was prepared according to the procedures described for Example XI-37. LC-MS (ESI) m/z: 432.2 [M+H]⁺; ¹H NMR (500 MHz, DMSO-$d_6$) δ 9.97 (s, 1H), 8.96 (d, J=8.1 Hz, 1H), 8.23 (s, 1H), 8.06 (s, 1H), 8.01-7.95 (m, 1H), 7.90 (d, J=8.1 Hz, 1H), 7.86 (s, 1H), 7.45-7.39 (m, 2H), 7.34 (t, J=7.6 Hz, 2H), 7.27-7.17 (m, 1H), 5.19 (t, J=7.2 Hz, 1H), 4.94 (dt, J=12.3, 6.3 Hz, 1H), 2.90 (s, 1H), 2.74 (s, 1H), 1.50 (d, J=6.7 Hz, 3H), 1.28 (d, J=6.4 Hz, 6H)

INTERMEDIATE 18

Methyl 5-oxo-5,6-dihydrobenzo[c][2,7]naphthyridine-8-carboxylate

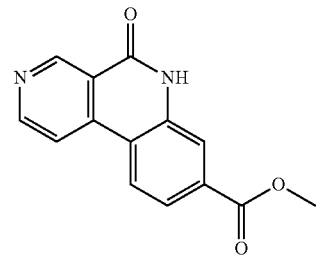 [SMILES: COC(=O)c1ccc2c(c1)[nH]c(=O)c1cnccc12]

INTERMEDIATE 18A

Methyl 4-chloronicotinate

To a suspension of 4-chloronicotinic acid (1.1 g, 7.1 mmol) in DCM (10 mL), was added oxalyl chloride (2 M in DCM) (8.9 mL, 18 mmol) followed by addition of DMF (0.25 mL), dropwise. The reaction mixture was stirred at rt for 45 min, cooled to 0° C., and was quenched with methanol. The solvent was removed. The residue was suspended in EtOAc. White precipitate was filtered, washed with hexane and EtOAc, and dried to afford Intermediate 18A (1.2 g, 98%) as off-white solid. LC-MS (ESI) m/z: 172.0 [M+H]⁺; ¹H NMR (400 MHz, DMSO-$d_6$) δ 8.97 (s, 1H), 8.70 (d, J=5.5 Hz, 1H), 7.72 (d, J=5.5 Hz, 1H), 3.91 (s, 3H).

INTERMEDIATE 18

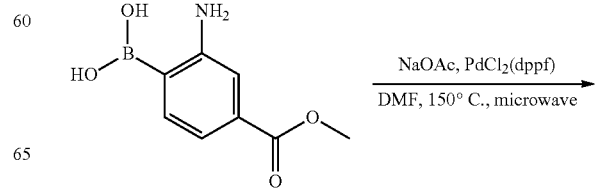

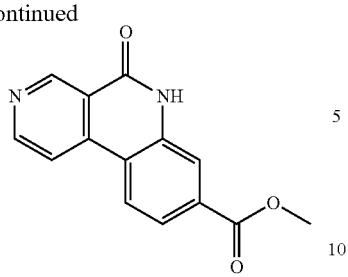

To a solution of Intermediate 18A (780 mg, 3.9 mmol) in DMF (10 mL), were added (2-amino-4-(methoxycarbonyl)phenyl)boronic acid (750 mg, 3.9 mmol), sodium acetate (1300 mg, 16 mmol), and $PdCl_2(dppf)$-$CH_2Cl_2$ adduct (250 mg, 0.31 mmol). The reaction was purged with nitrogen and then was heated in a microwave reactor at 150° C. for 10 min. The reaction mixture was cooled to rt and water (70 mL) was added. The solid formed was filtered, washed with water (3×), ether (5×), and was dried to afford Intermediate 18 (540 mg, 55%) as a tan solid. LC-MS (ESI) m/z: 255.1 [M+H]$^+$; $^1$H NMR (400 MHz, DMSO-$d_6$) δ 12.06 (br. s., 1H), 9.46 (s, 1H), 8.96 (d, J=5.3 Hz, 1H), 8.59 (d, J=8.1 Hz, 1H), 8.46 (d, J=5.5 Hz, 1H), 8.00 (s, 1H), 7.81 (d, J=8.1 Hz, 1H), 3.91 (s, 3H).

INTERMEDIATE 19

5-Oxo-5,6-dihydrobenzo[c][2,7]naphthyridine-8-carboxylic acid

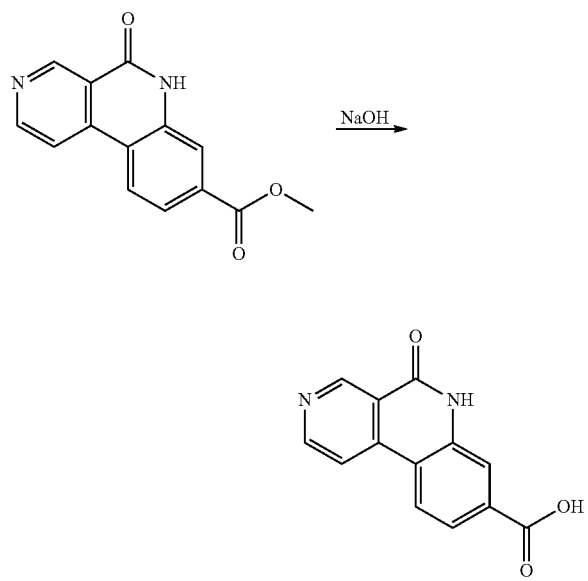

To a suspension of Intermediate 18 (40 mg, 0.13 mmol) in EtOH (1.5 mL), was added NaOH (1 N, 0.38 mL, 0.38 mmol). The reaction mixture was stirred under argon at rt for 1.5 h. To the mixture was added HCl (3.7 N, 0.07 mL, 0.25 mmol) to adjust the pH to ~8. Purification by reverse phase chromatography afforded Intermediate 19 (30 mg, 67%) as a brown solid. LC-MS (ESI) m/z: 241.1 [M+H]$^+$.

INTERMEDIATE 20

6-(2-Methoxyethyl)-5-oxo-5,6-dihydrobenzo[c][2,7]naphthyridine-8-carboxylic acid

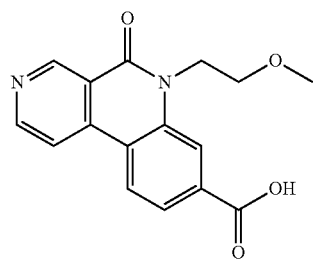 [SMILES: COCCn1c(=O)c2cnccc2c2ccc(C(=O)O)cc21]

INTERMEDIATE 20A

Methyl 6-(2-methoxyethyl)-5-oxo-5,6-dihydrobenzo[c][2,7]naphthyridine-8-carboxylate

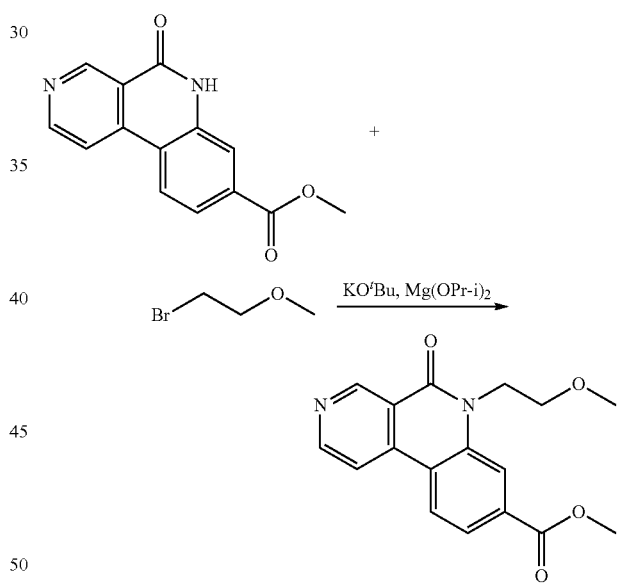

To a solution of 18 (70 mg, 0.28 mmol) and 1-bromo-2-methoxyethane (120 mg, 0.83 mmol) in THF (2.5 mL), were added potassium tert-butoxide (1 M, 0.29 mL, 0.29 mmol) and magnesium isopropyloxide (94 mg, 0.55 mmol). The reaction was stirred at rt in a sealed tube for 1 h, and then was heated at 70° C. for 6 h. The solvent was removed. The residue was purified by reverse phase chromatography to afford Intermediate 20A (35 mg, 30%) as a yellowish solid. LC-MS (ESI) m/z: 313.1 [M+H]$^+$; $^1$H NMR (400 MHz, CD$_3$OD) δ 9.61 (s, 1H), 8.94 (d, J=5.9 Hz, 1H), 8.63 (d, J=8.4 Hz, 1H), 8.57 (d, J=5.9 Hz, 1H), 8.41 (d, J=1.1 Hz, 1H), 8.02 (dd, J=8.4, 1.3 Hz, 1H), 4.69 (t, J=5.6 Hz, 2H), 4.01 (s, 3H), 3.84 (t, J=5.6 Hz, 2H), 3.37 (s, 3H).

INTERMEDIATE 20

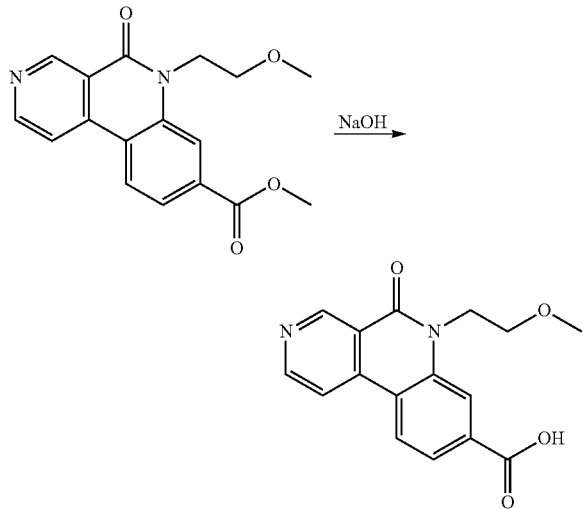

To a solution of 20A (35 mg, 0.080 mmol) in EtOH (2 mL), was added NaOH (1N, 0.49 mL, 0.49 mmol). The reaction mixture was stirred under argon at rt for 1.5 h. Aqueous HCl (3.7 N) (0.09 mL, 0.33 mmol) was added to adjust the pH to ~8. Purification by reverse chromatography afforded Intermediate 20 (31 mg, 90%) as yellow solid. LC-MS (ESI) m/z: 299.1 [M+H]$^+$.

INTERMEDIATE 21

6-Allyl-5-oxo-5,6-dihydrobenzo[c][2,7]naphthyridine-8-carboxylic acid

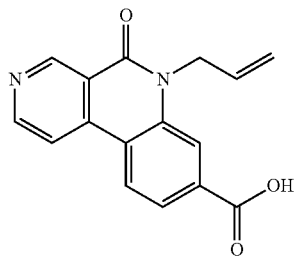 [SMILES: C=CCn1c(=O)c2cnccc2c2ccc(C(=O)O)cc21]

INTERMEDIATE 21A

Methyl 6-allyl-5-oxo-5,6-dihydrobenzo[c][2,7]naphthyridine-8-carboxylate

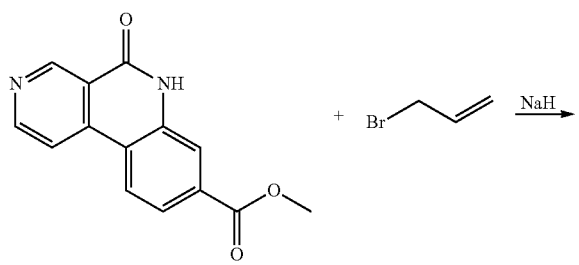

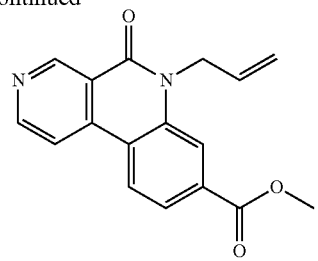

NaH (60% suspension, 320 mg, 7.9 mmol) was added to a solution of Intermediate 18 (500 mg, 1.6 mmol) in DMF (10 mL) at 0° C., portionwise. The reaction temperature was stirred at 0° C. for 10 min. Allyl bromide (1.4 mL, 16 mmol) was then added dropwise. The ice bath was removed, and the reaction mixture was allowed to warm to rt. The reaction mixture was stirred at rt for 1 h. It was cooled with an ice bath, diluted with EtOAc, and was slowly quenched with water. The organic layer was separated, washed with water and brine, dried over sodium sulfate, and concentrated. Purification by normal phase chromatography afforded Intermediate 21A (120 mg, 25%) as an orange solid. LC-MS (ESI) m/z: 295.1 [M+H]$^+$; $^1$H NMR (400 MHz, CDCl$_3$) δ 9.77 (s, 1H), 8.97 (d, J=5.5 Hz, 1H), 8.34 (d, J=8.4 Hz, 1H), 8.12 (d, J=1.3 Hz, 1H), 8.08 (d, J=5.5 Hz, 1H), 7.99 (dd, J=8.3, 1.4 Hz, 1H), 6.03 (ddt, J=17.2, 10.5, 5.1 Hz, 1H), 5.31 (dd, J=10.5, 0.8 Hz, 1H), 5.23 (dd, J=17.3, 0.8 Hz, 1H), 5.13-5.00 (m, 2H), 4.00 (s, 3H).

INTERMEDIATE 21

6-Allyl-5-oxo-5,6-dihydrobenzo[c][2,7]naphthyridine-8-carboxylic acid

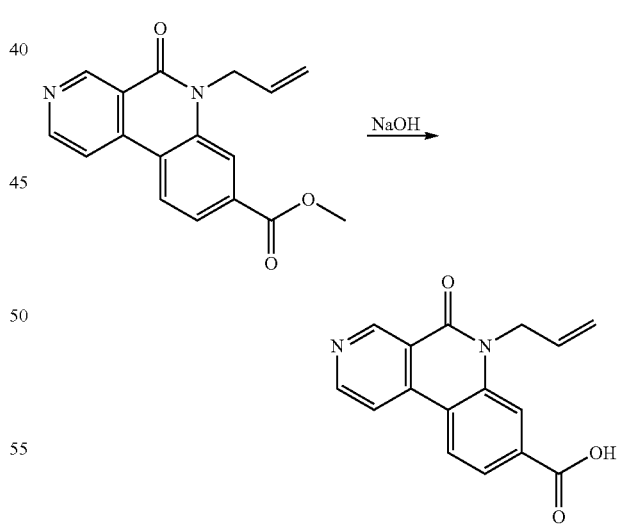

To a suspension of Intermediate 21A (150 mg, 0.50 mmol) in EtOH (3 mL), was added NaOH (1 N, 1.0 mL, 1.0 mmol). The reaction was stirred under argon at rt for 1.5 h. Aqueous HCl (3.7 N) (0.14 mL, 0.51 mmol) was added to adjust the pH to ~8. Purification by reverse chromatography afforded Intermediate 21 (120 mg, 85%) as yellow solid. LC-MS (ESI) m/z: 281.0 [M+H]$^+$; $^1$H NMR (400 MHz, DMSO-d$_6$) δ 9.52 (s, 1H), 8.98 (d, J=5.5 Hz, 1H), 8.70 (d, J=8.4 Hz, 1H), 8.51 (d, J=5.5 Hz, 1H), 8.00 (s, 1H), 7.90 (d, J=8.4 Hz, 1H), 6.14-5.97 (m, 1H), 5.20 (d, J=10.6 Hz, 1H), 5.09-4.97 (m, 3H).

EXAMPLE XII-1

(R)-6-Allyl-N-(1-(4-fluorophenyl)ethyl)-5-oxo-5,6-dihydrobenzo[c][2,7]naphthyridine-8-carboxamide

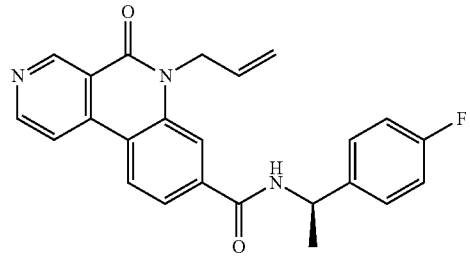

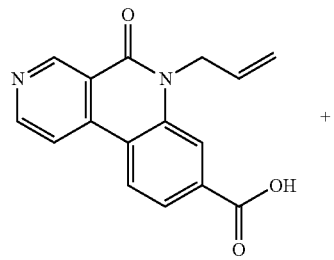

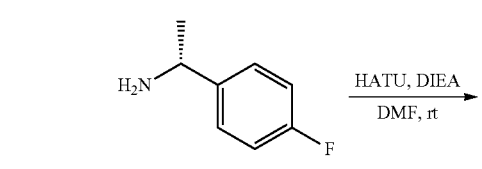

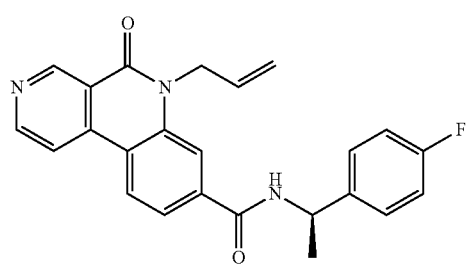

To a solution of Intermediate 21 (110 mg, 0.39 mmol) in DMF (3 mL) were added (R)-1-(4-fluorophenyl)ethanamine (110 mg, 0.78 mmol), HATU (250 mg, 0.67 mmol), and DIEA (0.34 mL, 1.9 mmol). The reaction mixture was stirred under argon at rt for 2 h. The reaction was partitioned between EtOAc and water. The organic layer was dried over sodium sulfate, and purified by normal phase chromatography to afford Example XII-1 (210 mg, 91%) as a foam. LC-MS (ESI) m/z: 402.2 [M+H]$^+$; $^1$H NMR (500 MHz, DMSO-$d_6$) δ 9.51 (s, 1H), 9.09 (d, J=7.9 Hz, 1H), 8.96 (d, J=5.2 Hz, 1H), 8.66 (d, J=8.2 Hz, 1H), 8.52 (d, J=5.8 Hz, 1H), 7.95-7.81 (m, 2H), 7.45 (dd, J=8.2, 5.8 Hz, 2H), 7.19-7.10 (m, 2H), 6.08-5.94 (m, 1H), 5.30-5.14 (m, 2H), 5.06 (d, J=15.3 Hz, 3H), 1.52 (d, J=7.0 Hz, 3H).

EXAMPLE XII-2

(R)-N-(1-(4-Fluorophenyl)ethyl)-5-oxo-6-(2-(pyrrolidin-1-yl)ethyl)-5,6-dihydrobenzo[c][2,7]naphthyridine-8-carboxamide

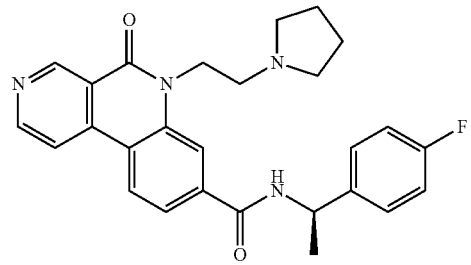 [SMILES: C[C@@H](NC(=O)c1ccc2c3ccncc3c(=O)n(CCN3CCCC3)c2c1)c1ccc(F)cc1]

INTERMEDIATE XII-2A (R)-N-(1-(4-Fluorophenyl)ethyl)-5-oxo-6-(2-oxoethyl)-5,6-dihydrobenzo[c][2,7]naphthyridine-8-carboxamide

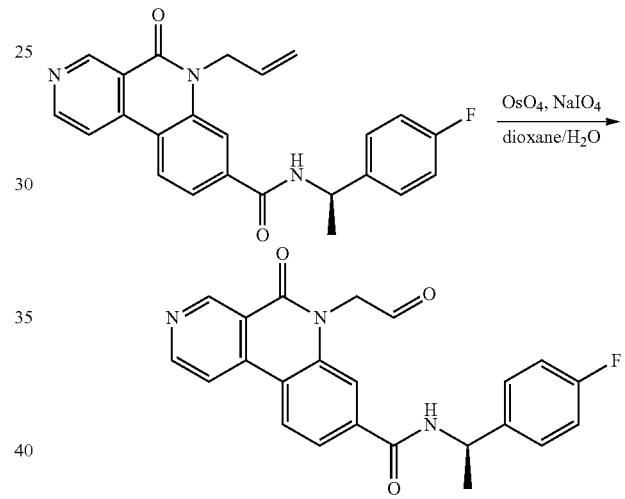

To a solution of Example XII-1 (50 mg, 0.13 mmol) in dioxane (5 mL) and water (0.5 mL), were added sodium periodate (80 mg, 0.37 mmol) and osmium tetroxide (4% in water, 0.016 mL, 2.5 μmol). The reaction was stirred under argon at rt overnight. The reaction mixture was diluted with EtOAc, washed with water and brine, dried over sodium sulfate and concentrated. Purification by normal phase chromatography afforded Intermediate XII-2A (23 mg, 46%) as film of solid. LC-MS (ESI) m/z: 404.1 [M+H]$^+$.

EXAMPLE XII-2

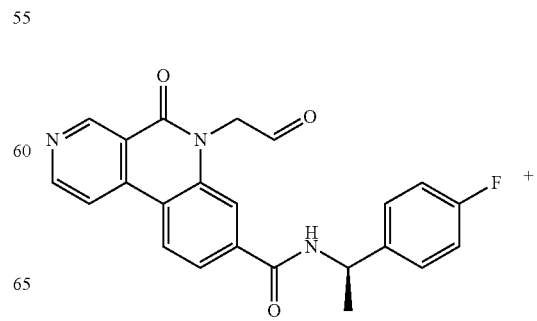

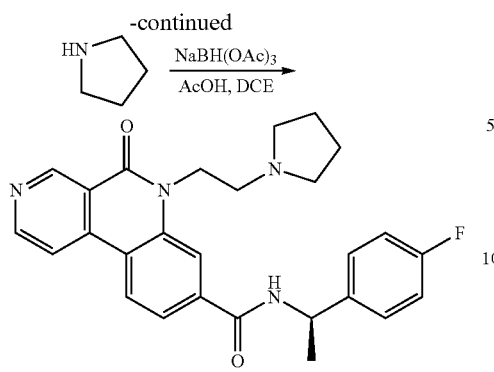

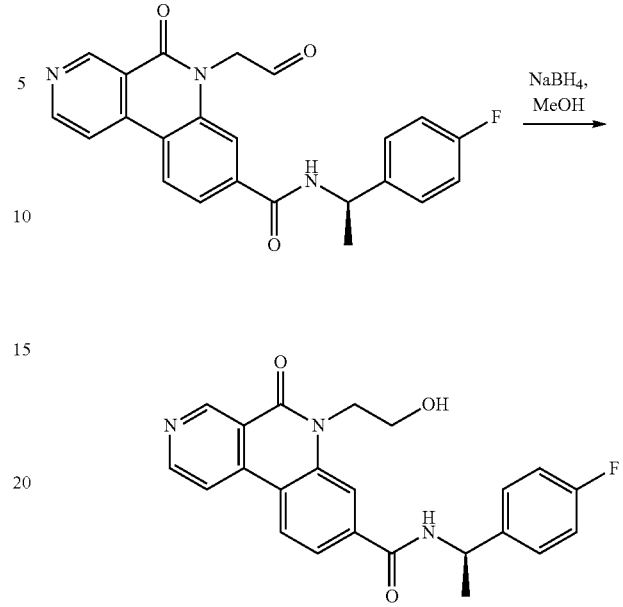

To a suspension of Intermediate XII-2A (23 mg, 0.06 mmol) in DCE (3 mL), were added pyrrolidine (20 mg, 0.28 mmol) and AcOH (0.07 mL, 1.1 mmol). The reaction mixture was stirred at rt for 20 min, and then sodium triacetoxyborohydride (85 mg, 0.40 mmol) was added in portions. The reaction was stirred under argon at rt for 30 min. The solvent was removed. The residue was dissolved in MeOH, and was purified by reverse chromatography to afford Example XII-2 (5.1 mg, 19%) as a solid. LC-MS (ESI) m/z: 459.2 [M+H]$^+$; $^1$H NMR (500 MHz, DMSO-d$_6$) δ 9.50 (br. s., 1H), 9.13 (d, J=7.3 Hz, 1H), 8.96 (d, J=4.6 Hz, 1H), 8.68 (d, J=8.2 Hz, 1H), 8.50 (d, J=4.6 Hz, 1H), 7.96-7.90 (m, 1H), 7.47 (br. s., 2H), 7.27-7.12 (m, 3H), 6.64 (br. s., 1H), 5.39-5.27 (m, 2H), 5.25-5.17 (m, 1H), 3.06 (m, 2H), 2.04-1.77 (m, 10H), 1.53 (d, J=6.7 Hz, 3H).

EXAMPLE XII-3

(R)-N-(1-(4-Fluorophenyl)ethyl)-6-(2-hydroxyethyl)-5-oxo-5,6-dihydrobenzo[c][2,7]naphthyridine-8-carboxamide

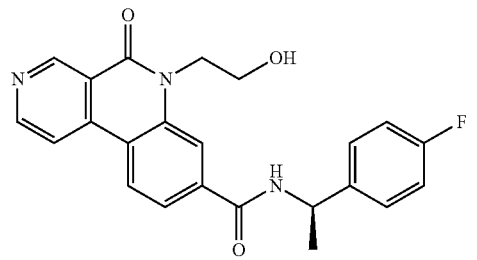

To a solution of Intermediate XII-2A (10 mg, 0.03 mmol) in MeOH (2 mL), was added NaBH$_4$ (9.4 mg, 0.25 mmol). The reaction mixture was stirred under argon at rt for 50 min. Purification by reverse phase chromatography afforded Example XII-3. LC-MS (ESI) m/z: 406.1 [M+H]]+; $^1$H NMR (500 MHz, DMSO-d$_6$) δ 9.45 (br. s., 1H), 9.13 (d, J=7.6 Hz, 1H), 8.90 (br. s., 1H), 8.57 (d, J=8.2 Hz, 1H), 8.42 (d, J=4.9 Hz, 1H), 8.10 (s, 1H), 7.84 (d, J=8.2 Hz, 1H), 7.44 (t, J=6.6 Hz, 2H), 7.14 (t, J=8.7 Hz, 2H), 5.19 (t, J=7.0 Hz, 1H), 4.47 (br. s., 2H), 3.70-3.60 (m, 3H), 1.51 (d, J=6.7 Hz, 3H).

Compounds listed in Table XII were prepared by following procedures similar to those described for Example XII-1 using the appropriate intermediates described or purchased from commercial sources. Other coupling reagents, such as HATU, T$_3$P, BOP, PyBop, and EDC/HOBt, could be instead of the one described.

TABLE XII

| Ex. No. | Structure | Name | LCMS [M + H]$^+$ | HPLC Method, RT (min.) | $^1$H NMR (δ, ppm) |
|---|---|---|---|---|---|
| XII-4 | 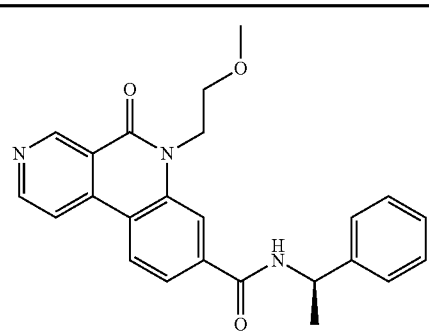 | 6-(2-methoxyethyl)-5-oxo-N-[(1R)-1-phenylethyl]-5H,6H-benzo[c]2,7-naphthyridine-8-carboxamide | 402.1 | E: 1.26 F: 1.46 | (500 MHz, DMSO-d$_6$) δ 9.50 (s, 1H), 9.10 (d, J = 7.7 Hz, 1H), 8.95 (d, J = 5.2 Hz, 1H), 8.66 (d, J = 8.3 Hz, 1H), 8.50 (d, J = 5.8 Hz, 1H), 8.13 (s, 1H), 7.90 (d, J = 8.3 Hz, 1H), 7.43 (d, J = 7.7 Hz, 2H), 7.35 (t, J = 7.6 Hz, 2H), 7.28-7.19 (m, 1H), 5.24 (t, J = 7.2 Hz, 1H), 4.63 (t, J = 5.8 Hz, 2H), 3.71 (t, J = 5.9 Hz, 2H), 3.27 (s, 3H), 1.54 (d, J = 6.9 Hz, 3H) |

TABLE XII-continued

| Ex. No. | Structure | Name | LCMS [M + H]+ | HPLC Method, RT (min.) | ¹H NMR (δ, ppm) |
|---|---|---|---|---|---|
| XII-5 | 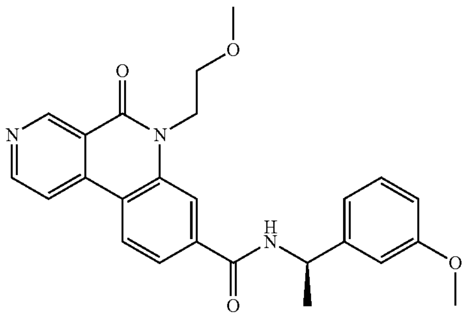 [SMILES: COCCn1c(=O)c2cnccc2c2ccc(C(=O)N[C@H](C)c3cccc(OC)c3)cc21] | 6-(2-methoxy-ethyl)-N-[(1R)-1-(3-methoxy-phenyl)ethyl]-5-oxo-5H,6H-benzo[c] 2,7-naphthyridine-8-carboxamide | 432.2 | E: 1.83 F: 2.11 | (500 MHz, DMSO-$d_6$) δ 9.50 (s, 1H), 9.08 (d, J = 8.2 Hz, 1H), 8.95 (d, J = 5.2 Hz, 1H), 8.67 (d, J = 8.5 Hz, 1H), 8.50 (d, J = 5.2 Hz, 1H), 8.12 (s, 1H), 7.89 (d, J = 7.9 Hz, 1H), 7.26 (t, J = 7.9 Hz, 1H), 6.99 (br. s., 2H), 6.82 (d, J = 7.9 Hz, 1H), 5.21 (t, J = 6.9 Hz, 1H), 4.63 (br. s., 2H), 3.75 (s, 3H), 3.71 (br. s., 2H), 3.27 (s, 3H), 1.52 (d, J = 6.7 Hz, 3H) |
| XII-6 | 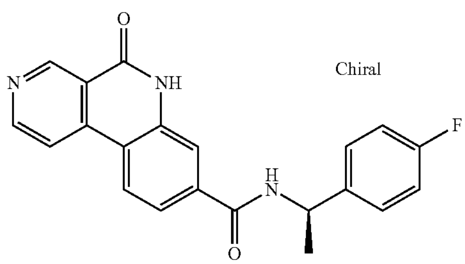 [SMILES: C[C@@H](NC(=O)c1ccc2c(c1)[nH]c(=O)c1cnccc12)c1ccc(F)cc1] | N-[(1R)-1-(4-fluorophenyl)ethyl]-5-oxo-5H,6H-benzo[c]2,7-naphthyridine-8-carboxamide | 362.2 | E: 1.12 F: 1.31 | (500 MHz, DMSO-$d_6$) δ 9.43 (s, 1H), 9.05 (d, J = 7.9 Hz, 1H), 8.93 (d, J = 5.5 Hz, 1H), 8.52 (d, J = 8.5 Hz, 1H), 8.44 (d, J = 5.5 Hz, 1H), 7.86-7.74 (m, 2H), 7.48-7.38 (m, 2H), 7.14 (t, J = 8.5 Hz, 2H), 5.29-5.05 (m, 1H), 1.48 (d, J = 7.0 Hz, 3H) |

EXAMPLE XIII-1

N-(3-Methoxybenzyl)-5-methyl-6-oxo-5,6-dihydrobenzo[c][1,7]naphthyridine-8-carboxamide

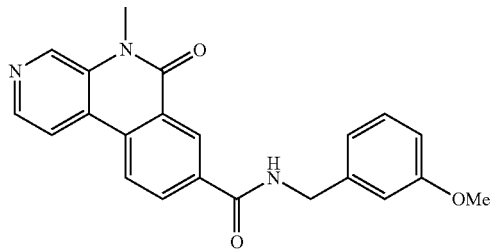 [SMILES: COc1cccc(CNC(=O)c2ccc3c(c2)c(=O)n(C)c2cnccc32)c1]

EXAMPLE XIII-1A

2-Hydroxy-5-(methoxycarbonyl)benzoic acid

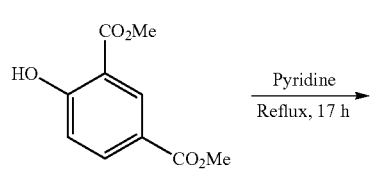

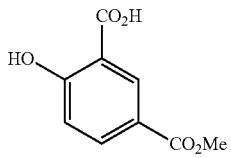

Pyridine (140 ml, 1700 mmol) was added to dimethyl 4-hydroxyisophthalate (10 g, 48 mmol) and the mixture was refluxed for 17 h. The mixture was then concentrated in vacuo, and the residue was acidified with 1.5 N HCl/H₂O (1:1) (120 mL). The resulting precipitate was collected by filtration, washed with water (3×20 mL), and dried in vacuo to give a brown solid, which was azeotroped with toluene to give Example XIII-1A as brown solid (9.0 g. 92%). LC-MS (ESI) m/z: 194.9 [M−H]⁻.

EXAMPLE XIII-1B 3-tert-Butyl 1-methyl 4-hydroxyisophthalate

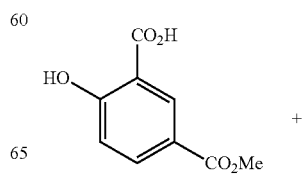

+

-continued

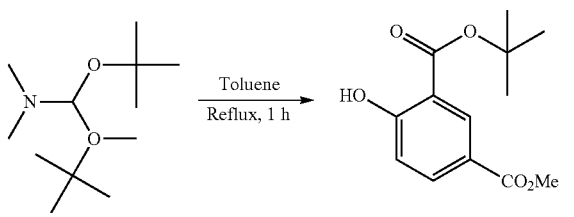

To a solution of Example XIII-1A (5.0 g, 26 mmol) in toluene (100 mL), was added 1,1-di-tert-butoxyltrimethyl-amine (25 mL, 100 mmol). The reaction was refluxed for 1.5 h. The reaction was cooled to rt, diluted with toluene (30 mL), washed with 10% percent citric acid solution (2×50 mL) and dried over $Na_2SO_4$. The solvent was evaporated under reduced pressure to give a yellow liquid, which was purified by normal phase chromatography to give Example XIII-1B as a white solid (3.2 g, 48%). LC-MS (ESI) m/z: 251.0 $[M-H]^-$.

EXAMPLE XIII-1C 3-tert-Butyl 1-methyl 4-(((trifluoromethyl)sulfonyl)oxy)isophthalate

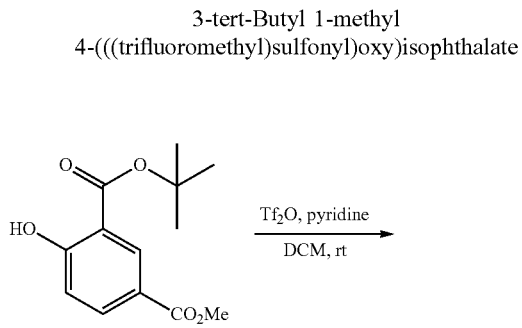

To a solution of Example XIII-1B (3.2 g, 13 mmol) and pyridine (5.2 mL, 64 mmol) in DCM (70 mL), was added $Tf_2O$ (4.3 mL, 25 mmol). The reaction mixture was stirred at rt for 2.5 h. The reaction was quenched with water (50 mL), extracted with DCM (3×50 mL). The combined DCM layers were washed with brine, dried over $Na_2SO_4$, filtered and concentrated. The crude product was purified by normal phase chromatography to give Example XIII-1C as a colorless viscous liquid (3.5 g, 70%). LC-MS (ESI) m/z: 402.0 $[M+H+NH_2]^+$.

EXAMPLE XIII-1D 3-tert-Butyl 1-methyl 4-(3-fluoropyridin-4-yl)isophthalate

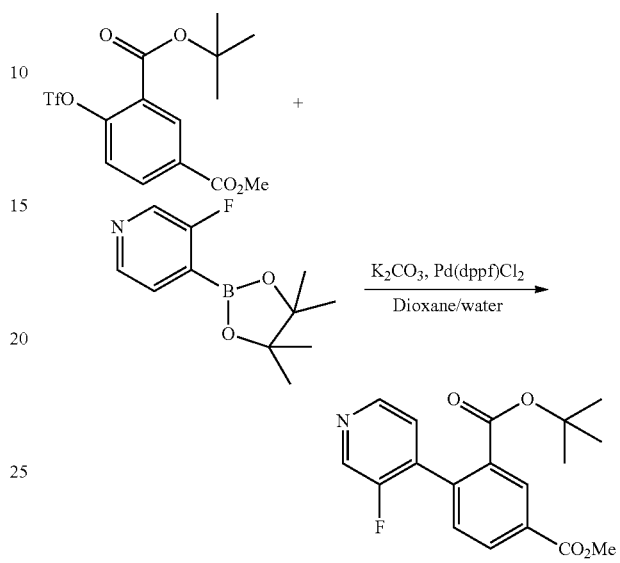

A solution of Example XIII-1C (3.5 g, 9.1 mmol), 3-fluoro-4-(4,4,5,5-tetramethyl-1,3,2-dioxaborolan-2-yl)pyridine (2.0 g, 9.1 mmol) and $K_2CO_3$ (3.8 g, 27 mmol) in dioxane (60 mL) and water (10 mL) was purged with nitrogen for 10 minutes, and then was added $PdCl_2(dppf)$ (0.40 g, 0.55 mmol). The reaction was heated at 80° C. for 2 h and then it was cooled to rt. The reaction was diluted with ethyl acetate (50 mL), washed with brine solution (2×30 mL), dried over $Na_2SO_4$, filtered and concentrated. The crude product was purified by normal phase chromatography to give Example XIII-1D as a brown solid (2.7 g, 89%). LC-MS (ESI) m/z: 332.1 $[M+I-1]^+$.

EXAMPLE XIII-1E 2-(3-Fluoropyridin-4-yl)-5-(methoxycarbonyl)benzoic acid

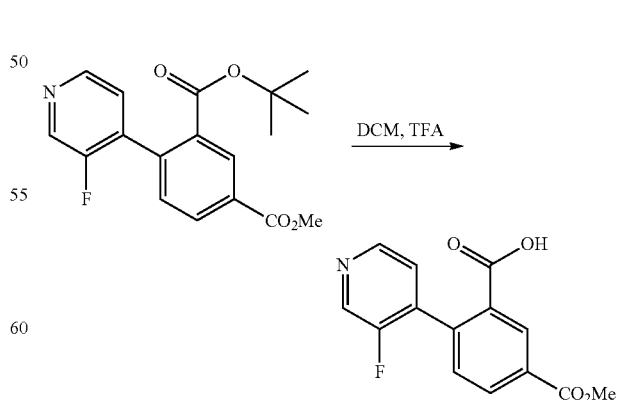

To the solution of Example XIII-1D (2.7 g, 8.2 mmol) in DCM (25 mL) was added TFA (6 mL, 78 mmol). The reaction was stirred at rt for 18 h. The solvent was removed to give brown solid. It was washed with petroleum ether (2×25 mL), diethyl ether (2×15 mL) and dried in vacuo to give Example XIII-1E as an off-white solid (2.2 g, 68%). LC-MS (ESI) m/z: 276.0 [M+H]+.

EXAMPLE XIII-1F

Methyl 4-(3-fluoropyridin-4-yl)-3-(methylcarbamoyl)benzoate

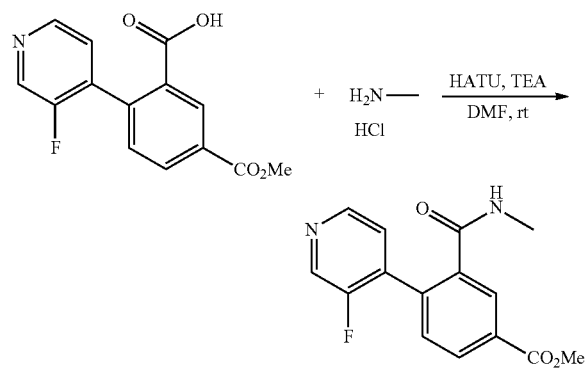

To the solution of Example XIII-1E (800 mg, 2.9 mmol) and methylamine HCl salt (290 mg, 4.4 mmol) in DMF (5 mL) at 0° C., were added TEA (2.0 mL, 15 mmol) and HATU (1100 mg, 2.9 mmol). The reaction was warmed to rt and stirred overnight. The solvent was removed to give brown solid, which was partitioned between water (15 mL) and ethyl acetate (25 mL). The organic solution was extracted with ethyl acetate (3×25 mL). The combined ethyl acetate layers were washed with brine solution, dried over Na2SO4, filtered and concentrated. Purification by normal phase chromatography gave an off-white solid. The solid was dissolved in DCM (4 mL) and reprecipitated by adding petroleum ether, and filtered to give Example XIII-1F as white solid (400 mg, 46%). LC-MS (ESI) m/z: 289.1 [M+H]+.

EXAMPLE XIII-1G

Methyl 5-methyl-6-oxo-5,6-dihydrobenzo[c][1,7]naphthyridine-8-carboxylate, and

EXAMPLE XIII-1H

5-Methyl-6-oxo-5,6-dihydrobenzo[c][1,7]naphthyridine-8-carboxylic acid

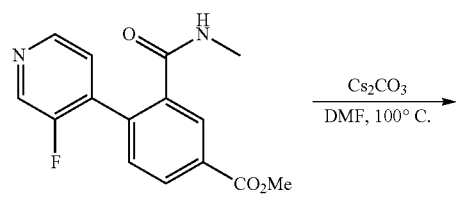

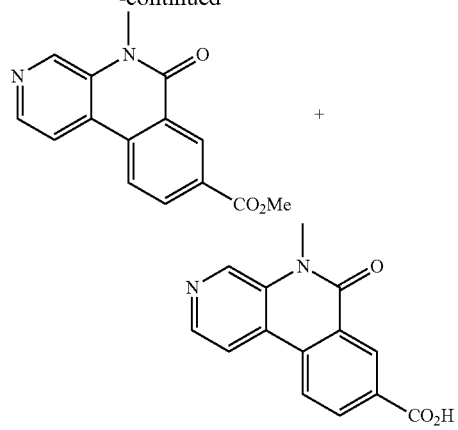

To the suspension of methyl 4-(3-fluoropyridin-4-yl)-3-(methylcarbamoyl)benzoate (440 mg, 1.5 mmol) in DMF (10 mL), was added Cs2CO3 (1200 mg, 3.8 mmol). The reaction was refluxed at 85° C. overnight. The solvent was removed to give a yellow residue, which was dissolved in ethyl acetate (40 mL) and water (15 mL). Two layers were separated. The aqueous layer was saturated with NaCl and extracted with ethyl acetate (4×20 mL). The combined ethyl acetate layers were washed with brine solution (1×5 mL), dried over Na2SO4, filtered and concentrated to give Example XIII-1G as an off-white solid (100 mg, 24%). LC-MS (ESI) m/z: 269.0 [M+H]+. The aqueous layer was acidified to pH 5 and solid was precipitated, which was filtered and dried in vacuo to give Example XIII-1H as an off-white solid (240 mg, 58%). LC-MS (ESI) m/z: 253.0 [M+H]+.

EXAMPLE XIII-1

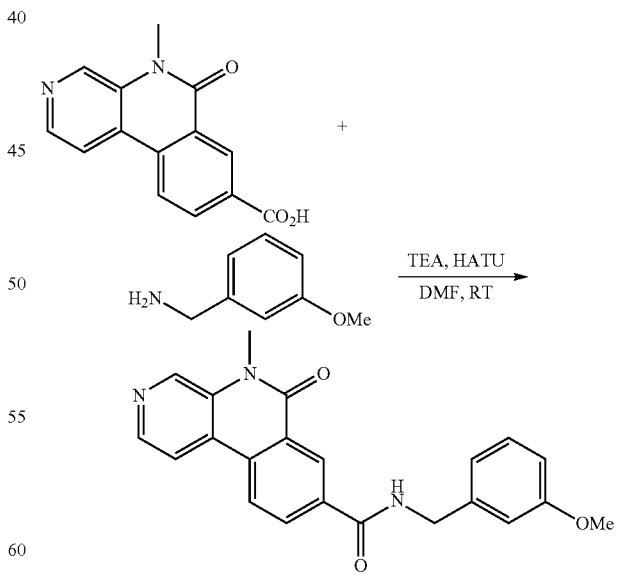

To the suspension of Example XIII-1H (120 mg, 0.47 mmol) and (3-methoxyphenyl)methanamine (65 mg, 0.47 mmol) in DMF (4 mL) were added TEA (0.33 mL, 2.4 mmol) and HATU (270 mg, 0.71 mmol). The reaction was stirred at rt for overnight. Reaction was diluted with water (40 mL), and precipitated solid was collected and further purified by normal phase chromatography to give Example XIII-1 as a white solid (25 mg, 13%). LC-MS (ESI) m/z: 374.2 [M+H]+. 1H NMR (400 MHz, DMSO-d$_6$) δ ppm 9.46 (t, J=5.96 Hz, 1 H) 8.93-9.02 (m, 2 H) 8.77 (d, J=8.47 Hz, 1 H) 8.55-8.60 (m, 1 H) 8.47 (d, J=5.21 Hz, 1 H) 8.39 (dd, J=8.44, 1.98 Hz, 1 H) 7.24-7.30 (m, 1 H) 6.92-6.97 (m, 2 H) 6.82-6.87 (m, 1 H) 4.52 (d, J=5.90 Hz, 2 H) 3.83 (s, 3 H) 3.75 (s, 3 H); Analytical HPLC RT A: 6.34 min, B: 6.39 min.

Compounds listed in Table XIII were prepared by following a similar procedure to that described for Example XIII-1.

TABLE XIII

| Ex. No. | Structure | Name | LCMS [M + H]+ | HPLC Method, RT (min.) | 1H NMR (δ, ppm) |
|---|---|---|---|---|---|
| XIII-2 | 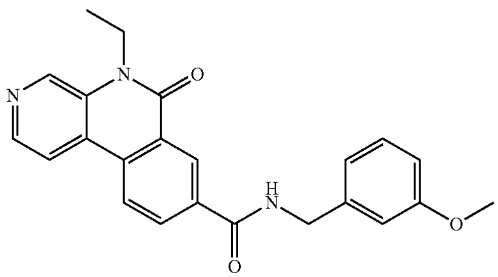 [SMILES: CCn1c(=O)c2cc(C(=O)NCc3cccc(OC)c3)ccc2c2ccncc21] | 5-ethyl-N-[(3-methoxyphenyl)methyl]-6-oxo-5H,6H-benzo[c]1,7-naphthyridine-8-carboxamide | 388.2 | A: 6.83 B: 6.93 | (400 MHz, DMSO-d$_6$) 9.46 (t, J = 6.02 Hz, 1 H) 9.04 (s, 1 H) 8.96 (d, J = 2.01 Hz, 1 H) 8.77 (d, J = 8.53 Hz, 1 H) 8.57 (d, J = 5.02 Hz, 1 H) 8.46-8.51 (m, 1 H) 8.39 (dd, J = 8.53, 2.01 Hz, 1 H) 7.24-7.30 (m, 1 H) 6.92-6.97 (m, 2 H) 6.81-6.87 (m, 1 H) 4.46-4.56 (m, 4 H) 3.75 (s, 3 H) 1.33 (t, J = 7.03 Hz, 3 H) |
| XIII-3 | 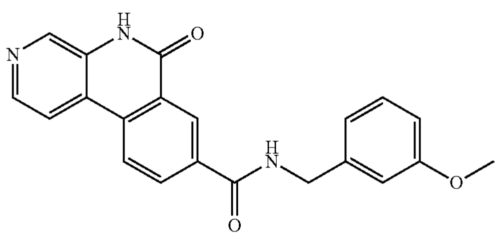 [SMILES: COc1cccc(CNC(=O)c2ccc3c(c2)c(=O)[nH]c2cnccc23)c1] | N-[(3-methoxyphenyl)methyl]-6-oxo-5H,6H-benzo[c]1,7-naphthyridine-8-carboxamide | 360.2 | A: 5.85 B: 6.09 | (400 MHz, DMSO-d$_6$) 12.02 (br. s., 1 H) 9.45 (t, J = 6.02 Hz, 1 H) 8.91 (d, J = 2.01 Hz, 1 H) 8.70-8.75 (m, 2 H) 8.44-8.47 (m, 1 H) 8.35-8.41 (m, 2 H) 7.24-7.29 (m, 1 H) 6.92-6.96 (m, 2 H) 6.81-6.86 (m, 1 H) 4.52 (d, J = 5.52 Hz, 2 H) 3.74-3.76 (s, 3 H) |
| XIII-4 | 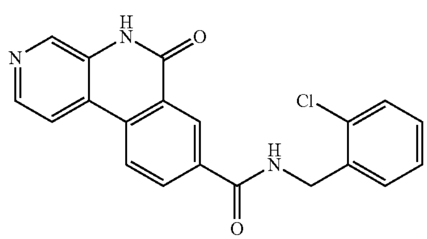 [SMILES: O=C(NCc1ccccc1Cl)c1ccc2c(c1)c(=O)[nH]c1cnccc12] | N-[(2-chlorophenyl)methyl]-6-oxo-5H,6H-benzo[c]1,7-naphthyridine-8-carboxamide | 364.0 | A: 6.46 B: 6.67 | (400 MHz, DMSO-d$_6$) 12.02 (br. s., 1 H) 9.47 (t, J = 5.77 Hz, 1 H) 8.94 (d, J = 2.01 Hz, 1 H) 8.71-8.77 (m, 2 H) 8.46 (d, J = 5.52 Hz, 1 H) 8.41 (dd, J = 8.53, 2.01 Hz, 1 H) 8.38 (d, J = 5.52 Hz, 1 H) 7.46-7.51 (m, 1 H) 7.41-7.45 (m, 1 H) 7.29-7.38 (m, 2 H) 4.62 (d, J = 5.52 Hz, 2 H) |
| XIII-5 | Chiral | 6-oxo-N-[(1R)-1-phenylethyl]-5H,6H-benzo[c]1,7-naphthyridine-8-carboxamide | 344.2 | A: 6.19 B: 6.25 | (400 MHz, DMSO-d$_6$) 9.28 (d, J = 7.97 Hz, 1 H) 8.93 (d, J = 1.76 Hz, 1 H) 8.70-8.74 (m, 2 H) 8.46 (d, J = 5.33 Hz, 1 H) 8.36-8.40 (m, 2 H) 7.42-7.47 (m, 2 H) 7.33-7.38 (m, 2 H) 7.22-7.28 (m, 1 H) 5.25 (t, J = 7.37 Hz, 1 H) 1.54 (d, J = 7.09 Hz, 3 H) |
| XIII-6 | Chiral | N-[(1R)-1-(3-methoxyphenyl)ethyl]-6-oxo-5H,6H-benzo[c]1,7-naphthyridine-8-carboxamide | 374.2 | A: 6.22 B: 6.33 | (400 MHz, DMSO-d$_6$) δ ppm 12.03 (br. s, 1 H) 9.24 (d, J = 8.09 Hz, 1 H) 8.92 (d, J = 1.82 Hz, 1 H) 8.69-8.74 (m, 2 H) 8.45 (d, J = 5.33 Hz, 1 H) 8.35-8.40 (m, 2 H) 7.24-7.29 (m, 1 H) 6.99-7.03 (m, 2 H) 6.80-6.84 (m, 1 H) 5.21 (quin, J = 7.17 Hz, 1 H) 3.76 (s, 3 H) 1.53 (d, J = 7.09 Hz, 3 H) |

TABLE XIII-continued

| Ex. No. | Structure | Name | LCMS [M + H]+ | HPLC Method, RT (min.) | 1H NMR (δ, ppm) |
|---|---|---|---|---|---|
| XIII-7 | 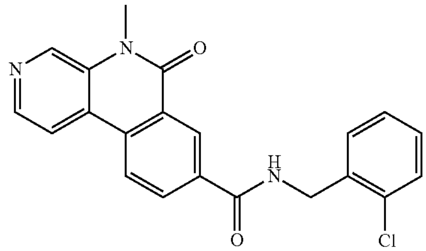 [SMILES: Cn1c(=O)c2cc(C(=O)NCc3ccccc3Cl)ccc2c2ccncc21] | N-[(2-chlorophenyl)methyl]-5-methyl-6-oxo-5H,6H-benzo[c]1,7-naphthyridine-8-carboxamide | 378.2 | A: 6.98 B: 7.00 | (400 MHz, DMSO-d$_6$) 9.48 (t, J = 5.68 Hz, 1 H) 8.97-9.01 (m, 2 H) 8.78 (d, J = 8.41 Hz, 1 H) 8.55-8.61 (m, 1 H) 8.48 (d, J = 5.15 Hz, 1 H) 8.41 (dd, J = 8.41, 1.95 Hz, 1 H) 7.47-7.51 (m, 1 H) 7.41-7.46 (m, 1 H) 7.30-7.39 (m, 2 H) 4.62 (d, J = 5.71 Hz, 2 H) 3.83 (s, 3 H) |
| XIII-8 | 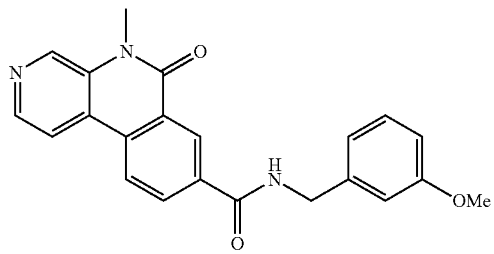 [SMILES: COc1cccc(CNC(=O)c2ccc3c(c2)c(=O)n(C)c2cnccc32)c1] | N-[(3-methoxyphenyl)methyl]-5-methyl-6-oxo-5H,6H-benzo[c]1,7-naphthyridine-8-carboxamide | 374.2. | A: 6.34 B: 6.39 | (400 MHz, DMSO-d$_6$) ppm 9.46 (t, J = 5.96 Hz, 1 H) 8.93-9.02 (m, 2 H) 8.77 (d, J = 8.47 Hz, 1H) 8.55-8.60 (m, 1 H) 8.47 (d, J = 5.21 Hz, 1 H) 8.39 (dd, J = 8.44, 1.98 Hz, 1 H) 7.24-7.30 (m, 1 H) 6.92-6.97 (m, 2 H) 6.82-6.87 (m, 1 H) 4.52 (d, J = 5.90 Hz, 2 H) 3.83 (s, 3 H) 3.75 (s, 3 H) |
| XIII-9 | Chiral | 5-ethyl-6-oxo-N-[(1R)-1-phenylethyl]-5H,6H-benzo[c]1,7-naphthyridine-8-carboxamide | 372.2 | G: 13.81 H: 18.58 | (400 MHz, DMSO-d$_6$) 9.28 (d, J = 7.97 Hz, 1 H) 9.04 (s, 1 H) 8.96 (d, J = 1.82 Hz, 1 H) 8.75 (d, J = 8.47 Hz, 1 H) 8.56 (d, J = 5.27 Hz, 1 H) 8.49 (d, J = 5.33 Hz, 1 H) 8.38 (dd, J = 8.44, 1.91 Hz, 1 H) 7.45 (d, J = 7.22 Hz, 2 H) 7.33-7.39 (m, 2 H) 7.22-7.28 (m, 1 H) 5.24 (quin, J = 7.28 Hz, 1 H) 4.50 (q, J = 7.01 Hz, 2 H) 1.54 (d, J = 7.09 Hz, 3 H) 1.33 (t, J = 7.03 Hz, 3 H) |
| XIII-10 | Chiral | 5-ethyl-[(1R)-1-(3-methoxyphenyl)ethyl]-6-oxo-5H,6H-benzo[c]1,7-naphthyridine-8-carboxamide | 402.2 | G: 13.96 H: 18.65 | (400 MHz, DMSO-d$_6$) 9.28 (d, J = 7.97 Hz, 1 H) 9.04 (s, 1 H) 8.96 (d, J = 1.82 Hz, 1 H) 8.75 (d, J = 8.47 Hz, 1 H) 8.56 (d, J = 5.27 Hz, 1 H) 8.49 (d, J = 5.33 Hz, 1 H) 8.38 (dd, J = 8.44, 1.91 Hz, 1 H) 7.45 (d, J = 7.22 Hz, 2 H) 7.33-7.39 (m, 2 H) 7.22-7.28 (m, 1 H) 5.24 (quin, J = 7.28 Hz, 1 H) 4.50 (q, J = 7.01 Hz, 2 H) 1.54 (d, J = 7.09 Hz, 3 H) 1.33 (t, J = 7.03 Hz, 3 H) |

INTERMEDIATE 22

9H-Pyrido[3,4-]indole-7-carboxylic acid

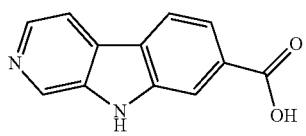 [SMILES: O=C(O)c1ccc2c(c1)[nH]c1cnccc12]

INTERMEDIATE 22A

Methyl 3-amino-4-(3-fluoropyridin-4-yl)benzoate

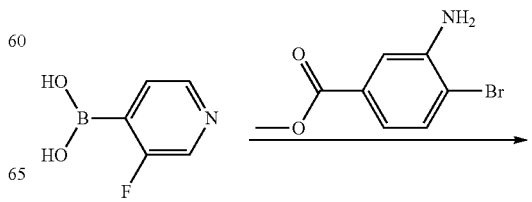

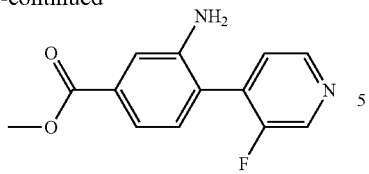

Methyl 3-amino-4-bromobenzoate (4 g, 17.39 mmol), (3-fluoropyridin-4-yl)boronic acid (5.5 g, 39.0 mmol), dioxane (10 mL), water (2 mL) and potassium carbonate (8.41 g, 60.9 mmol) were taken in a dried two neck RB (25 mL) and purged with nitrogen for 10 minutes. To this mixture was added PdCl$_2$(dppf) (1.27 g, 1.74 mmol) at 50° C. The mixture was flushed with nitrogen and heated at 80° C. for 8 h. The reaction mixture was cooled to room temperature, then was diluted with the DCM. The organic phase was washed with the water, dried over sodium sulfate. The crude compound was purified by silica gel chromatography (gradient elution, 30-65% ethyl acetate in petroleum ether) to afford 2.9 g (68%) of the title compound. LC-MS (ESI) m/z: 241.0 [M+H]$^+$; $^1$H NMR (400 MHz, chloroform-d) δ ppm 8.60 (d, J=1.57 Hz, 1 H) 8.52 (dd, J=4.86, 1.10 Hz, 1H) 7.48-7.52 (m, 2 H) 7.35-7.39 (m, 1H) 7.19 (d, J=7.78 Hz, 1H) 3.93 (s, 3 H) 3.79-3.84 (m, 2 H).

INTERMEDIATE 22

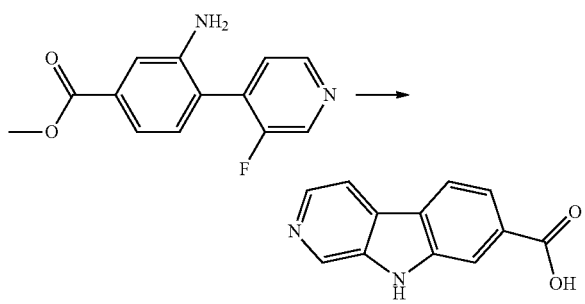

To pyridine hydrochloride (1.5 g, 12.98 mmol) at 150° C., was added Intermediate 22A (1g, 4.06 mmol) under nitrogen atmosphere. The mixture was heated to 170° C. for 2 h, then was allowed to cool to rt. The reaction mixture was quenched with aq. NaOH and stirred for 3 h. the reaction mixture was neutralized with acetic acid and concentrated under reduced pressure. The crude mass was treated with water and the solid was collected by filtration and dried to afford Intermediate 22 (450 mg, 52%). The material was used without further purification. LC-MS (ESI) m/z: 241.0 [M+H]$^+$; $^1$H NMR (400 MHz, DMSO-d$_6$) δ ppm 11.79 (bs, 1 H) 8.97 (s, 1 H) 8.37 (d, J=5.27 Hz, 1 H) 8.11-8.29 (m, 3 H) 7.83 (d, J=8.28 Hz, 1 H).

INTERMEDIATE 23

Benzofuro[2,3-c]pyridine-7-carboxylic acid, HCl salt

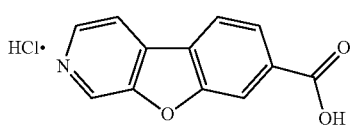 [SMILES: O=C(O)c1ccc2c(c1)oc1cnccc12]

INTERMEDIATE 23A

Methyl 4-(3-fluoropyridin-4-yl)-3-hydroxybenzoate

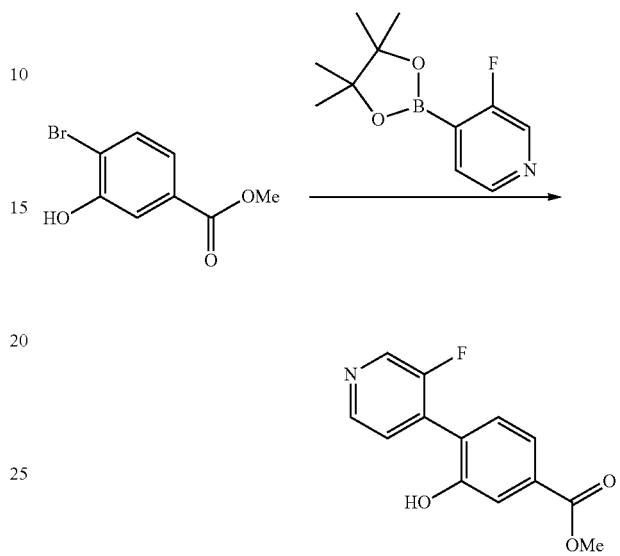

To a solution of methyl 4-bromo-3-hydroxybenzoate (1.0 g, 4.3 mmol) in dioxane (20 mL) and water (2 mL), was added K$_2$CO$_3$ (1.80 g, 13.0 mmol) and 3-fluoro-4-(4,4,5,5-tetramethyl-1,3,2-dioxaborolan-2-yl)pyridine (1.16 g, 5.19 mmol). The reaction mixture was degassed by bubbling with N$_2$ for 5 mins. PdCl$_2$(dppf) (0.317 g, 0.433 mmol) was added to the reaction, which was degassed again. The mixture was then heated to 90° C. for 6 h. The reaction mixture was diluted with water (30 mL) and was extracted with EtOAc (3×80 mL). The combined organic extracts were washed with water and brine, dried over Na$_2$SO$_4$ and concentrated to give crude product which was purified by flash chromatography (gradient elution, 0-60% EtOAc/Hex) to afford Intermediate 23A (0.65 g, 61% yield) as an off-white solid. LC-MS (ESI) m/z: 248.0 [M+H]$^+$; $^1$H NMR (400 MHz, DMSO-d$_6$) δ ppm 10.36 (s, 1 H), 8.64 (d, J=1.88 Hz, 1 H), 8.50 (dd, J=4.86, 1.10 Hz, 1 H), 7.60 (d, J=1.51 Hz, 1 H), 7.49-7.54 (m, 2 H), 7.42 (d, J=7.97 Hz, 1 H), 3.88 (s, 3 H); $^{19}$F NMR: (400 MHz, DMSO-d$_6$): −128.57.

INTERMEDIATE 23B

Methyl benzofuro[2,3-c]pyridine-7-carboxylate

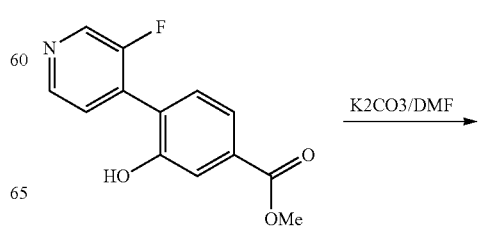

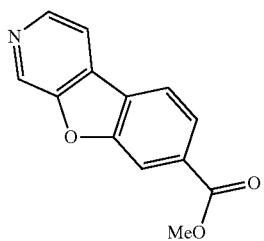

To a solution of Intermediate 23A (0.450 g, 1.820 mmol) in DMF (5 mL), was added $K_2CO_3$ (0.755 g, 5.46 mmol). The mixture was stirred at 100° C. for 2 hr. The DMF was evaporated and the mixture was diluted with water (50 mL). The obtained solid was filtered and washed with 50 ml of water and diethyl ether (10 ml) to afford Intermediate 23B (210 mg, 51%) as an off-white solid. LC-MS (ESI) m/z: 228.1 [M+H]$^+$; $^1$H NMR (400 MHz, DMSO-$d_6$) δ ppm 9.19 (s, 1 H), 8.67 (d, J=5.08 Hz, 1 H), 8.44 (d, J=8.09 Hz, 1 H), 8.34 (s, 1 H), 8.30 (d, J=5.02 Hz, 1 H), 8.10 (dd, J=8.16, 1.25 Hz, 1 H), 3.94 (s, 3 H).

INTERMEDIATE 23

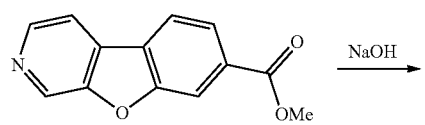

To a solution of Intermediate 23B (0.090 g, 0.40 mmol) in MeOH (3 mL) and water (1 mL), was added sodium hydroxide (0.024 g, 0.59 mmol). The reaction mixture was stirred at rt for 1 hr, then the solvent was evaporated. The crude mass was washed with diethyl ether (10 mL), and then the residue was treated with 4M HCl in dioxane for 30 min. The solvent was evaporated to give Intermediate 23 (0.10 g, 100%) as a white solid. LC-MS (ESI) m/z: 214.0 [M+H]$^+$.

INTERMEDIATE 24

9-Methyl-9H-pyrido[3,4-b]indole-7-carboxylic acid

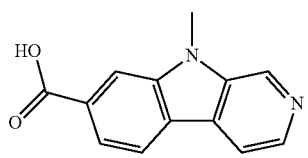 [SMILES: Cn1c2cnccc2c2ccc(C(=O)O)cc21]

INTERMEDIATE 24A

Methyl 4-bromo-3-(methylamino)benzoate

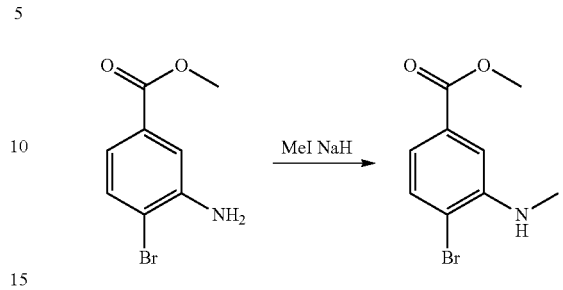

To a solution of methyl 3-amino-4-bromobenzoate (1.5 g, 6.52 mmol) in THF (30 mL) at 0° C., was added NaH (0.203 g, 8.48 mmol). The mixture was stirred for 10 min, then iodomethane (1.11 g, 7.82 mmol) was added. The reaction mixture was stirred for 5 hr, then was quenched with addition of sat. ammonium chloride solution. The mixture was extracted with DCM. The organic phase was dried over $Na_2SO_4$ and concentrated. The crude compound was purified by flash chromatography (5 to 80% gradient of ethyl acetate in pet. ether) to afford 0.75 g (47%) of Intermediate 24A. LC-MS (ESI) m/z: 244.0 [M+H]$^+$; $^1$H NMR (400 MHz, chloroform-d) δ ppm 7.48 (d, J=8.16 Hz, 1 H) 7.26-7.27 (m, 1 H) 7.24 (d, J=2.01 Hz, 1 H) 7.22 (d, J=2.01 Hz, 1 H) 3.90 (s, 3 H) 2.95 (d, J=5.21 Hz, 3 H).

INTERMEDIATE 24B

Methyl 4-(3-fluoropyridin-4-yl)-3-(methylamino)benzoate

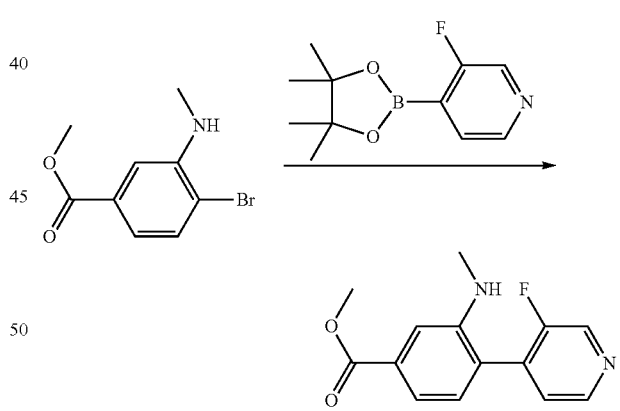

To a degassed solution of Intermediate 24A (700 mg, 2.87 mmol) in dioxane (20 mL) and water (3 mL), were added 3-fluoro-4-(4,4,5,5-tetramethyl-1,3,2-dioxaborolan-2-yl) pyridine (1.02 g, 4.59 mmol), potassium carbonate (1.39 g, 10.0 mmol) and PdCl$_2$(dppf) (210 mg, 0.287 mmol) at rt. The reaction was stirred under argon at 90° C. for 6 h. The reaction mixture was cooled to rt, then was diluted with the DCM. The organic phase was washed with the water, dried over sodium sulfate and concentrated. The crude compound was purified by silica gel chromatography (30-60% ethyl acetate gradient in pet. ether) to afford Intermediate 24B (400 mg, 51%). LC-MS (ESI) m/z: 246.0 [M+H]$^+$; $^1$H NMR (400 MHz, chloroform-d) δ ppm 8.59 (d, J=1.51 Hz, 2 H)

8.50 (dd, J=4.83, 1.00 Hz, 2 H) 7.46 (dd, J=7.81, 1.60 Hz, 2 H) 7.39 (d, J=1.51 Hz, 2 H) 7.33 (s, 1 H) 7.14 (d, J=7.78 Hz, 1 H) 3.94 (s, 3 H) 3.66-3.73 (m, 1 H) 2.89 (d, J=5.15 Hz, 3H).

INTERMEDIATE 24

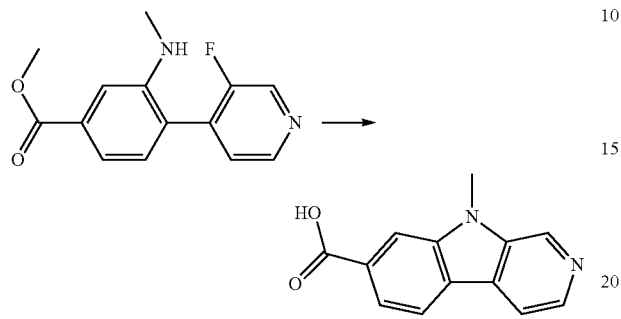

To pyridine hydrochloride (250 mg, 2.16 mmol) at 150° C., was add added Intermediate 24B (250 mg, 0.961 mmol). The mixture was heated at 175° C. for 2 h, then was cooled to rt. To the crude reaction mixture, was added 50% NaOH solution and the mixture was stirred for 2h. The reaction mixture was concentrated, then was neutralized with the addition of acetic acid. The mixture was concentrated in vacuo, then was treated with water and the solid was collected by filtration and dried to afford Intermediate 24 (90 mg, 41%). LC-MS (ESI) m/z: 227.0 [M+H]$^+$; $^1$H NMR (400 MHz, DMSO-$d_6$) δ ppm 9.13 (s, 1 H) 8.44 (d, J=5.27 Hz, 1 H) 8.38 (d, J=8.09 Hz, 1 H) 8.28 (s, 1 H) 8.21 (dd, J=5.21, 1.00 Hz, 1 H) 7.88 (dd, J=8.16, 1.32 Hz, 1 H) 4.05 (s, 3 H).

INTERMEDIATE 25

Methyl 9H-pyrido[3,4-b]indole-7-carboxylate

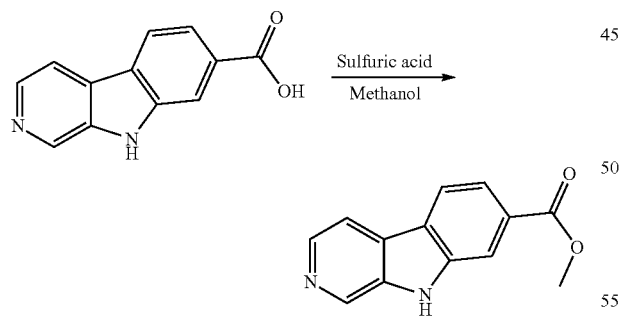

To a suspension of Intermediate 22 (3.1 g, 10.81 mmol) in methanol (75 mL), was added sulfuric acid (4.0 ml, 75 mmol). The mixture was heated at 68° C. for 3 h, then was concentrated. The crude material was basified with 10% NaHCO$_3$ solution and extracted with EtOAc (3×). The combined organic fraction was again washed with 10% NaHCO$_3$, followed by brine solution. The organic layer was dried with Na$_2$SO$_4$, filtered and concentrated to afford Intermediate 25 (0.721 g, 3.19 mmol, 29.5% yield) as a pale yellow solid. LC-MS (ESI) m/z: 227.0 [M+H]$^+$; $^1$H NMR (300 MHz, DMSO-$d_6$) δ 11.89 (s, 1H), 9.01 (s, 1H), 8.48-8.31 (m, 2H), 8.25-8.13 (m, 2H), 7.84 (dd, J=8.3, 1.5 Hz, 1H), 3.92 (s, 3H).

INTERMEDIATE 26

9-(2-Amino-2-oxoethyl)-9H-pyrido[3,4-b]indole-7-carboxylic acid compound with 9-(carboxymethyl)-9H-pyrido[3,4-b]indole-7-carboxylic acid (1:1)

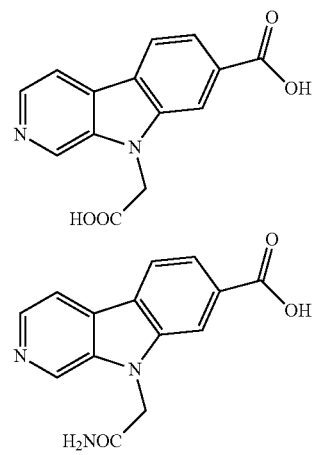

INTERMEDIATE 26A

Methyl 9-(cyanomethyl)-9H-pyrido[3,4-b]indole-7-carboxylate

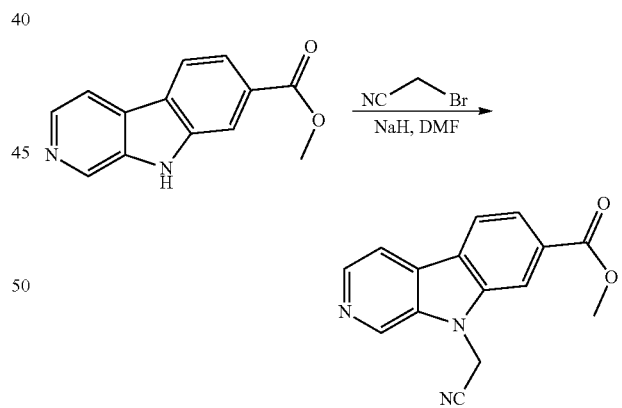

To the solution of Intermediate 25 (0.225 g, 0.995 mmol) in DMF (6 mL) at 0° C., sodium hydride (0.119 g, 2.98 mmol) was added. The mixture was stirred at rt for 15 min. 2-Bromoacetonitrile (0.139 mL, 1.989 mmol) was added to the reaction mixture and stirred at rt for 2 h. Water was added to the reaction mixture, which was then extracted with EtOAc (2×60 mL). The combined organic layers were dried with Na$_2$SO$_4$, filtered and concentrated. The crude product was purified by flash chromatography (0-4% gradient MeOH/CHCl$_3$) to afford Intermediate 26A (0.29 g) as a dark yellow solid. LC-MS (ESI) m/z: 266.0 [M+H]$^+$; $^1$H NMR (300 MHz, DMSO-d$_6$) δ 9.27 (s, 1 H), 8.59-8.43 (m, 3 H), 8.34-8.25 (m, 1 H), 7.98-7.92 (m, 1 H), 6.04-6.00 (m, 2 H), 3.96 (s, 3 H).

INTERMEDIATE 26

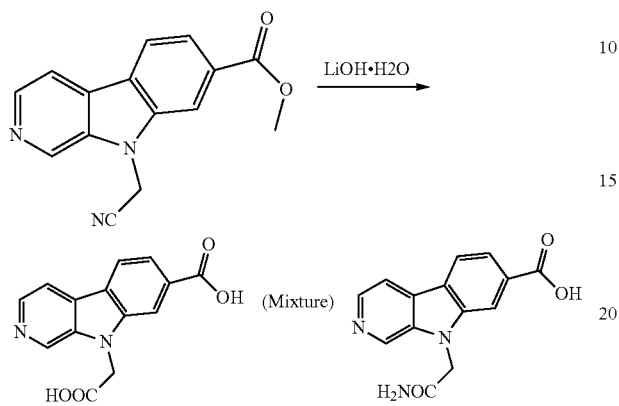

To the solution of Intermediate 26A (0.35 g, 1.32 mmol) in a mixture of MeOH (4 mL), water (4 mL) and THF (2 mL), lithium hydroxide hydrate (0.166 g, 3.96 mmol) was added and stirred at RT for 1.5 h. The reaction mixture was concentrated under reduced pressure. The crude product was acidified by slow addition of 1.5 N HCl at 0° C. The resultant precipitate was collected by filtration and the residue was washed with ether to afford the mixture of products Intermediate 26 (0.102 g) as a yellow solid. MS (ESI) m/z: 270.1 and 271.0 [M+H]$^+$.

INTERMEDIATE 27

Lithium 9-(cyclopropylmethyl)-9H-pyrido[3,4-b]indole-7-carboxylate

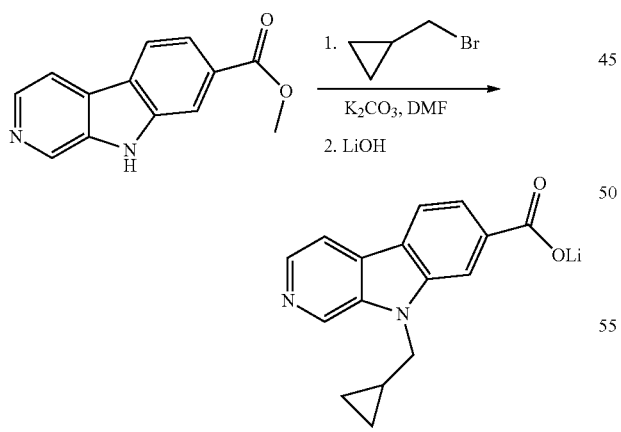

To a solution of Intermediate 25 (0.050 g, 0.22 mmol) in DMF (2 mL), were added K$_2$CO$_3$ (0.061 g, 0.44 mmol) and (bromomethyl)cyclopropane (0.060 g, 0.442 mmol). The mixture was heated at 80° C. for 3 h. Water was added to the reaction mixture, which was extracted with EtOAc (2×). The combined organic layer was dried with Na$_2$SO$_4$, filtered and concentrated. The crude product was purified by flash chromatography (0-4% MeOH gradient in CHCl$_3$) to afford 9-(cyclopropylmethyl)-9H-pyrido[3,4-b]indole-7-carboxylic acid. LC-MS (ESI) m/z: 281.1 [M+H]$^+$. The material was dissolved in THF (4 mL) and water (2 mL), then lithium hydroxide hydrate (0.040 g, 0.95 mmol) was added and the mixture was stirred at RT overnight. The reaction mixture was concentrated under reduced pressure to dryness. Then the crude was washed with ether for several times to get Intermediate 27 (0.085) as a yellow solid. MS (ESI) m/z: 267 [M+H]$^+$.

INTERMEDIATE 28

9-Ethyl-9H-pyrido[3,4-b]indole-7-carboxylic acid

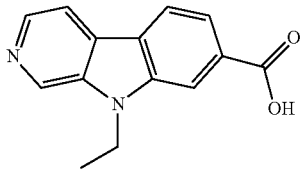 [SMILES: CCn1c2cnccc2c2ccc(C(=O)O)cc21]

INTERMEDIATE 28A

Methyl 3-(ethylamino)-4-(3-fluoropyridin-4-yl)benzoate

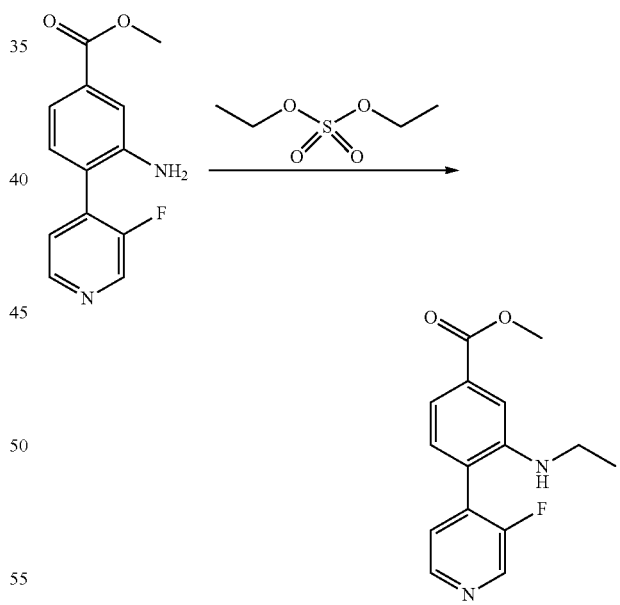

To a solution of Intermediate 22A (800 mg, 3.25 mmol) in DMF (5 mL), was added potassium carbonate (674 mg, 4.87 mmol). The mixture was stirred at 50° C. for 10 min, then was cooled to RT. To this mixture, diethyl sulfate (751 mg, 4.87 mmol) was added, then the mixture was heated for 5 h at 120° C. The reaction mixture was cooled to room temperature, diluted with the DCM, washed with water, dried over sodium sulfate and concentrated. The crude compound was purified by silica gel chromatography (30-80% gradient of ethyl acetate in pet. ether) to afford Intermediate 28A (300 mg, 34%). MS (ESI) m/z: 241.1 [M+H]+; 1H NMR (400 MHz, DMSO-d6) δ ppm 8.65 (d, J=1.63 Hz, 1 H) 8.50 (dd, J=4.86, 1.04 Hz, 1 H) 7.45 (dd, J=6.37, 4.86 Hz, 1 H) 7.22-7.27 (m, 2 H) 7.15 (d, J=7.72 Hz, 1 H) 5.13 (t, J=5.6 Hz, 1 H) 3.86 (s, 3 H) 3.13 (dd, J=6.93, 5.80 Hz, 2 H) 1.10 (t, J=7.09 Hz, 3 H).

INTERMEDIATE 28

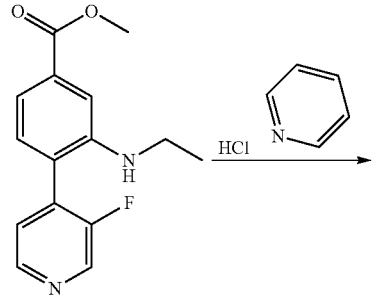

To melted pyridine hydrochloride (379 mg, 3.28 mmol) at 150° C., was added Intermediate 28A (300 mg, 1.09 mmol). The mixture was heated at 175° C. for 2 h. To the crude reaction mixture was added 50% NaOH solution to reach pH 11. The reaction mixture was stirred for 3 h, then was concentrated. The reaction mixture was neutralized with acetic acid. Excess acetic acid was evaporated and the mixture was treated with water and the solid was collected to afford Intermediate 28 (250 mg, 95%). LC-MS (ESI) m/z: 241.1 [M+H]+; 1H NMR (400 MHz, DMSO-d6) δ ppm 9.14 (s, 1 H) 8.43 (d, J=5.27 Hz, 1 H) 8.36 (d, J=8.16 Hz, 1 H) 8.27 (s, 1 H) 8.21 (dd, J=5.21, 0.88 Hz, 1 H) 7.87 (dd, J=8.19, 1.22 Hz, 1 H) 4.63 (q, J=7.13 Hz, 2 H) 1.38 (t, J=7.12 Hz, 3 H).

INTERMEDIATE 29

4-Fluoro-9H-pyrido[3,4-b]indole-7-carboxylic acid

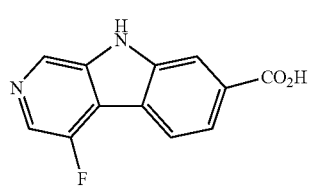 [SMILES: O=C(O)c1ccc2c(c1)[nH]c1cncc(F)c12]

INTERMEDIATE 29A

Methyl 4-(3-fluoropyridin-4-yl)-3-nitrobenzoate

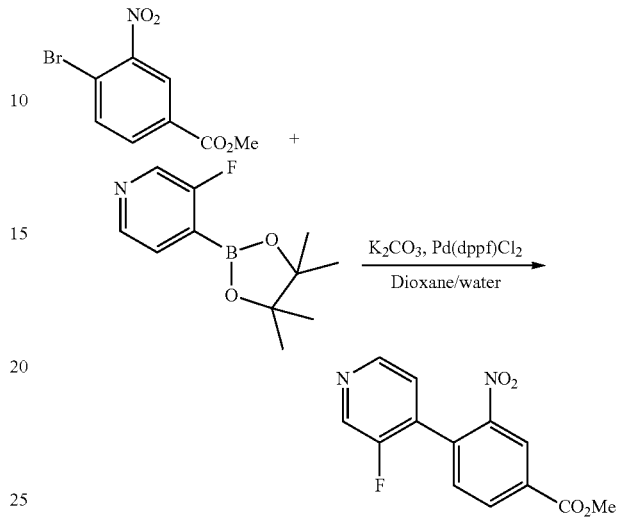

A solution of methyl 4-bromo-3-nitrobenzoate (0.8 g, 3.1 mmol) and K2CO3 (1.276 g, 9.23 mmol) in dioxane (10 mL) and water (2 mL) was bubbled with nitrogen for 10 min. To this solution was added 3-fluoro-4-(4,4,5,5-tetramethyl-1,3,2-dioxaborolan-2-yl)pyridine (0.686 g, 3.08 mmol) and PdCl2(dppf) (0.135 g, 0.185 mmol). The mixture was heated at 80° C. overnight. The mixture was diluted with ethyl acetate (30 mL), washed with brine (2×), dried over Na2SO4, filtered and concentrated. The crude product was purified by flash chromatography (gradient elution; 0-100% EtOAc/Hex) to afford Intermediate 29A (0.58 g, 68% yield). LC-MS (ESI) m/z: 277.0 [M+H]+; 1H NMR (400 MHz, DMSO-d6) δ ppm 8.71 (s, 1 H) 8.60-8.64 (m, 2 H) 8.41 (d, J=7.97 Hz, 1 H) 7.85 (d, J=7.91 Hz, 1 H) 7.67 (t, J=5.65 Hz, 1 H) 3.96 (s, 3 H).

INTERMEDIATE 29B

Methyl 4-fluoro-9H-pyrido[3,4-b]indole-7-carboxylate

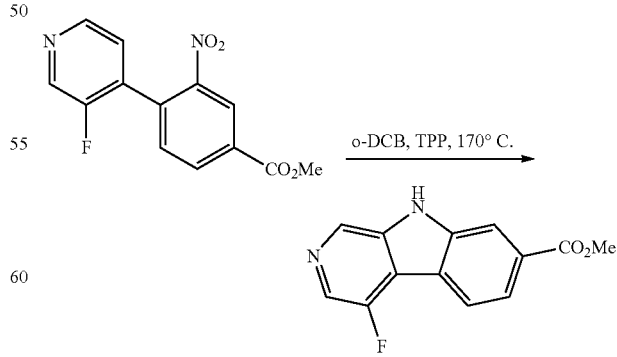

To a solution of Intermediate 29A (580 mg, 2.1 mmol) in 1,2-dichlorobenzene (6 mL) was added triphenylphosphine (1.38 g, 5.25 mmol). The mixture was heated at 170° C. for 4 h. To the cooled reaction mixture was added pet. ether (50 mL). The precipitate was filtered and washed with pet. ether (2×). The crude product was purified by flash chromatography (0-100% EtOAc/Hex). The solid was further purified by suspension in DCM (5 mL) and pet. ether (30 mL). The precipitate was collected by filtration to afford Intermediate 29B as a light brown solid (105 mg, 19%). LC-MS (ESI) m/z: 245.0 [M+H]$^+$; $^1$H NMR (400 MHz, DMSO-d$_6$) δ ppm 12.26 (s, 1 H) 8.91 (d, J=2.64 Hz, 1 H) 8.37 (d, J=1.19 Hz, 1 H) 8.26-8.30 (m, 2 H) 7.90-7.94 (m, 1 H) 3.94 (s, 3 H).

INTERMEDIATE 29

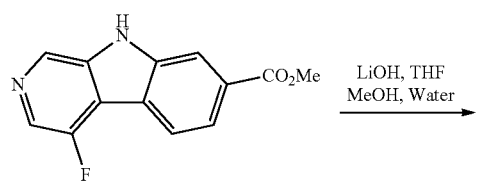
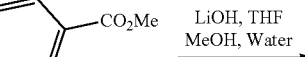

To a suspension of Intermediate 29B (105 mg, 0.430 mmol) in THF (3 mL) and water (1 mL), was added LiOH (25.7 mg, 1.08 mmol). The resultant clear yellow solution was stirred overnight. The reaction mixture was concentrated, then the residue was dissolved in THF (1.5 mL) and water (0.5 mL). To this mixture was added LiOH (25.7 mg, 1.075 mmol). The mixture was stirred overnight, then was concentrated. The residue was dissolved in water, then was acidified to pH 3 with 1.5 N HCl. The precipitated solid was collected by filtration, washed with water and hexane, and dried in vacuo to afford Intermediate 29 as a brown solid (75 mg). LC-MS (ESI) m/z: 231.0 [M+H]$^+$; $^1$H NMR (400 MHz, DMSO-d$_6$) δ ppm 12.23 (s, 1 H) 8.89 (d, J=2.64 Hz, 1 H) 8.37 (d, J=1.44 Hz, 1 H) 8.24-8.27 (m, 2 H) 7.89-7.92 (m, 1 H).

INTERMEDIATE 30

1-Fluoro-9H-pyrido[3,4-b]indole-7-carboxylic acid

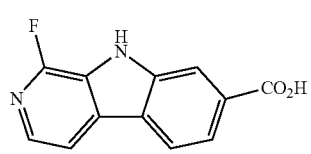 [SMILES: O=C(O)c1ccc2c(c1)[nH]c1c(F)nccc12]

INTERMEDIATE 30A

Methyl 4-(2-fluoropyridin-4-yl)-3-nitrobenzoate

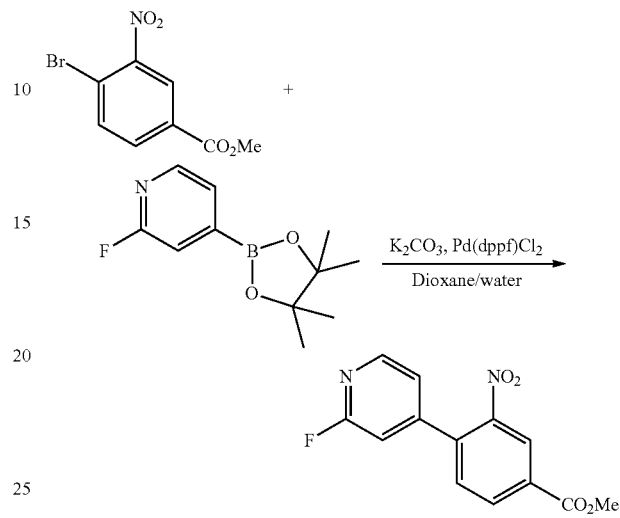

A solution of methyl 4-bromo-3-nitrobenzoate (1.0 g, 3.85 mmol), 2-fluoro-4-(4,4,5,5-tetramethyl-1,3,2-dioxaborolan-2-yl)pyridine (0.858 g, 3.85 mmol) and K$_2$CO$_3$ (1.59 g, 11.5 mmol) in dioxane (20 mL) and water (4 mL) was bubbled with nitrogen for 10 minutes. To this mixture were added 2-fluoro-4-(4,4,5,5-tetramethyl-1,3,2-dioxaborolan-2-yl)pyridine (0.858 g, 3.85 mmol) and PdCl$_2$(dppf)-CH$_2$Cl$_2$ adduct (0.188 g, 0.231 mmol). The mixture was heated at 80° C. for 4 h, then was diluted with EtOAc. The organic phase was washed with brine (2×), dried with Na$_2$SO$_4$, filtered and concentrated. The crude product was purified by flash chromatography (0-100% gradient of EtOAc/Hex.) to afford Intermediate 30A as a yellow solid (0.8 g, 73%). LC-MS (ESI) m/z: 277.0 [M+H]$^+$; $^1$H NMR (400 MHz, DMSO-d$_6$) δ ppm 8.60 (d, J=1.63 Hz, 1 H) 8.34-8.38 (m, 2 H) 7.80 (d, J=7.97 Hz, 1 H) 7.38-7.46 (m, 2 H) 3.96 (s, 3 H).

INTERMEDIATE 30B

Methyl 1-fluoro-9H-pyrido[3,4-b]indole-7-carboxylate

INTERMEDIATE 30C

Methyl 3-fluoro-9H-pyrido[3,4-b]indole-7-carboxylate

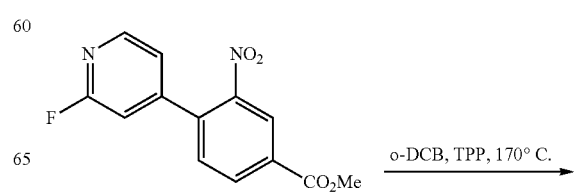

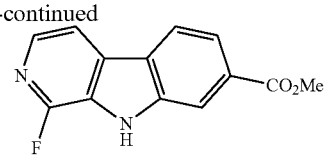

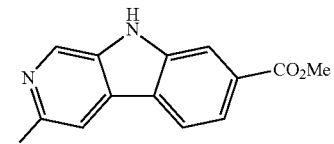

To a solution of Intermediate 30A (800 mg, 2.90 mmol) in 1,2-dichlorobenzene (8 mL), was added triphenylphosphine (1.9 g, 7.24 mmol). The mixture was heated at 170° C. overnight, then was concentrated. The crude product was purified by flash chromatography (0-100% EtOAc/Hex.) to afford Intermediate 30B (240 mg) as a yellow solid and Intermediate 30C, which was repurified by flash chromatography (0-100% EtOAc/Hex.) to afford 55 mg.

Intermediate 30B: LC-MS (ESI) m/z: 245.0 [M+H]$^+$; $^1$H NMR (400 MHz, DMSO-d$_6$) δ ppm 12.43 (s, 1 H) 8.41 (d, J=8.34 Hz, 1 H) 8.23 (dd, J=1.44, 0.69 Hz, 1 H) 8.18 (dd, J=5.36, 3.17 Hz, 1 H) 7.96 (dd, J=5.36, 1.85 Hz, 1 H) 7.89 (dd, J=8.31, 1.47 Hz, 1 H) 3.94 (s, 3 H).

Intermediate 30C: LC-MS (ESI) m/z: 245.1 [M+H]$^+$; $^1$H NMR (400 MHz, DMSO-d$_6$) δ ppm 11.88 (s, 1 H) 8.60 (dd, J=1.51, 0.94 Hz, 1 H) 8.40 (d, J=8.28 Hz, 1H) 8.21 (dd, J=1.38, 0.69 Hz, 1 H) 7.99 (d, J=2.20 Hz, 1 H) 7.83 (dd, J=8.28, 1.51 Hz, 1 H) 3.92-3.95 (m, 3 H).

INTERMEDIATE 30

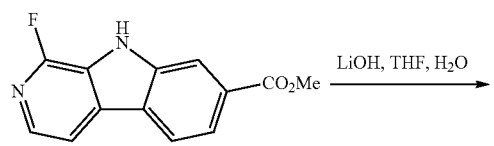

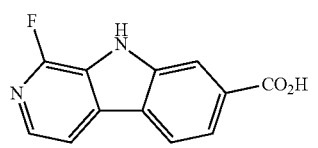

To a suspension of Intermediate 30B (230 mg, 0.942 mmol) in THF (2 mL) and water (0.5 mL), was added LiOH (67.7 mg, 2.83 mmol). The yellow solution was allowed to stir at rt overnight. The reaction mixture was concentrated to gave yellow residue, which was dissolved in water (8 mL) and acidified with 1.5 N HCl to pH 3. The precipitated solid was filtered and washed with water, hexane, and dried to afford Intermediate 30 (190 mg, 64%) as a brown solid. LC-MS (ESI) m/z: 231.0 [M+H]$^+$; $^1$H NMR (300 MHz, DMSO-d$_6$) δ ppm 13.11 (s, 1 H) 12.39 (s, 1 H) 8.38 (d, J=8.17 Hz, 1 H) 8.14-8.22 (m, 2 H) 7.94 (d, J=5.15 Hz, 1 H) 7.87 (d, J=8.26 Hz, 1 H).

INTERMEDIATE 31

3-Fluoro-9H-pyrido[3,4-b]indole-7-carboxylic acid

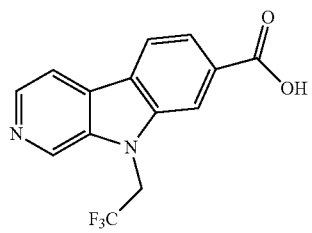 [SMILES: O=C(O)c1ccc2c3ccncc3n(CC(F)(F)F)c2c1]

To a suspension of Intermediate 30C (55 mg, 0.23 mmol) in THF (2 mL) and water (0.5 mL), was added LiOH (16.2 mg, 0.676 mmol). The resultant yellow solution was allowed to stir at rt overnight. The reaction mixture was concentrated to gave yellow residue, which was dissolved in water (8 mL) and acidified with 1.5 N HCl to pH 3. The precipitated solid was filtered and washed with water and hexane, and dried to afford Intermediate 31 (42 mg, 57%) as a brown solid. LC-MS (ESI) m/z: 231.0 [M+H]$^+$; $^1$H NMR (400 MHz, DMSO-d$_6$) δ ppm 11.86 (s, 1 H) 8.58 (s, 1 H) 8.37 (d, J=8.28 Hz, 1 H) 8.19 (d, J=0.63 Hz, 1 H) 7.97 (d, J=2.13 Hz, 1 H) 7.82 (dd, J=8.28, 1.38 Hz, 1 H).

INTERMEDIATE 32

9-(2,2,2-Trifluoroethyl)-9H-pyrido[3,4-b]indole-7-carboxylic acid

INTERMEDIATE 32A

Methyl 9-(2,2,2-trifluoroethyl)-9H-pyrido[3,4-b]indole-7-carboxylate

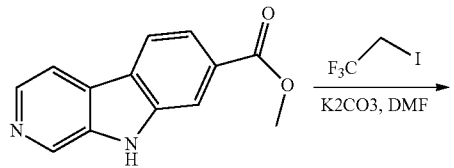

-continued

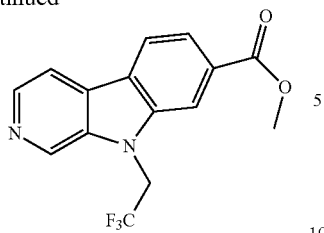

To a suspension of Intermediate 22 (0.20 g, 0.88 mmol) in DMF (5 mL), was added $K_2CO_3$ (0.611 g, 4.42 mmol), followed by the addition of 1,1,1-trifluoro-2-iodoethane (0.436 mL, 4.42 mmol). The mixture was heated at 100° C. overnight. Water was added to the reaction mixture, which was then extracted with EtOAc (2×). The combined organic phase was dried with $Na_2SO_4$, filtered and concentrated. The crude product was purified by flash chromatography (0-4% $MeOH/CHCl_3$) to afford Intermediate 32A (0.14 g, 22% yield) as yellow semi-solid. LC-MS (ESI) m/z: 309.0 $[M+H]^+$; $^1H$ NMR (400 MHz, DMSO-$d_6$) δ 9.25 (s, 1H), 8.56-8.41 (m, 3H), 8.30-8.24 (m, 1H), 7.99-7.93 (m, 1H), 5.72 (q, J=9.4 Hz, 2H), 3.95 (s, 3H).

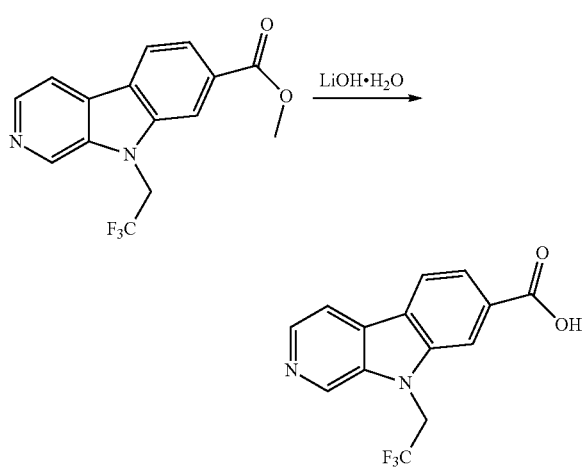

To a solution of Intermediate 32A (0.14 g, 0.45 mmol) in THF (2 mL) and water (2 mL), was added lithium hydroxide hydrate (0.076 g, 1.817 mmol). The mixture was stirred at rt overnight. The reaction mixture was concentrated under reduced pressure to dryness. Then the crude product was washed with ether several times to afford Intermediate 32 (0.161 g, 82% yield) as a yellow solid. MS (ES): m/z=295.0 $[M+H]^+$.

INTERMEDIATE 33

Sodium 4-methyl-9H-pyrido[3,4-b]indole-7-carboxylate

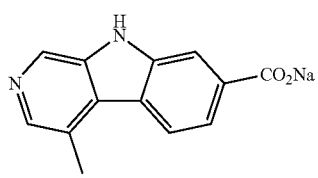

INTERMEDIATE 33A

Methyl 4-(3-methylpyridin-4-yl)-3-nitrobenzoate

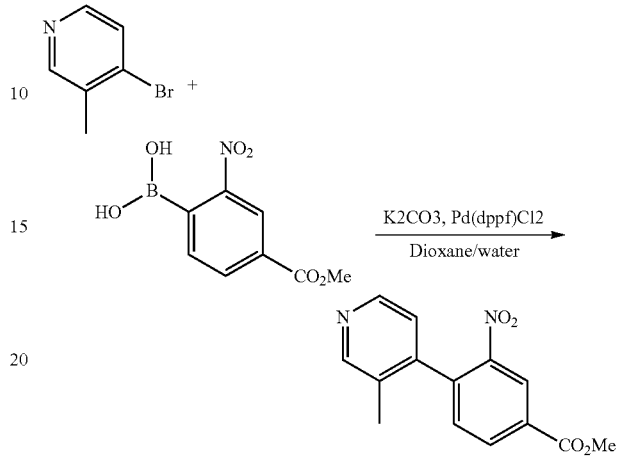

A solution of (4-(methoxycarbonyl)-2-nitrophenyl)boronic acid (0.445 g, 1.98 mmol), 4-bromo-3-methylpyridine, hydrobromide (0.50 g, 1.98 mmol) and $K_2CO_3$ (0.820 g, 5.93 mmol) in dioxane (20 mL) and water (4 mL) was bubbled nitrogen for 10 minutes. To this mixture was added $PdCl_2(dppf)$-$CH_2Cl_2$ adduct (0.097 g, 0.12 mmol). The mixture was heated at 80° C. overnight. The reaction mixture was diluted with ethyl acetate. The organic phase was washed with brine solution (2×), dried over $Na_2SO_4$, filtered and concentrated. The crude product was purified by flash chromatography (gradient elution; 0-100% EtOAc/Hex.) to afford Intermediate 33A as a yellow solid (0.100 g, 18%). MS (ES): m/z=273.8 $[M+H]^+$; $^1H$ NMR (400 MHz, DMSO-$d_6$) δ ppm 8.61-8.64 (m, 1 H) 8.57 (s, 1 H) 8.48 (d, J=4.96 Hz, 1 H) 8.35 (dd, J=7.97, 1.69 Hz, 1 H) 7.66 (d, J=7.97 Hz, 1 H) 7.23 (d, J=4.96 Hz, 1 H) 3.96 (s, 3 H) 2.05 (s, 3 H).

INTERMEDIATE 33B

Methyl 4-methyl-9H-pyrido[3,4-b]indole-7-carboxylate

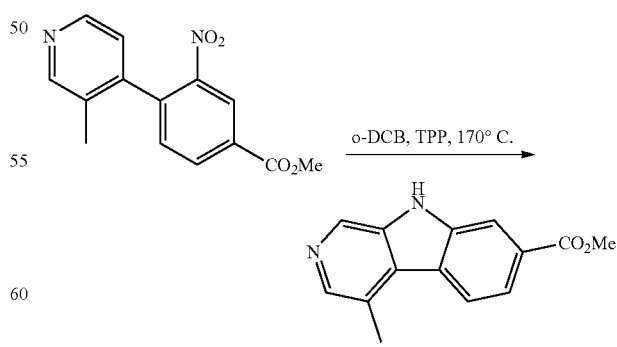

To a solution of Intermediate 33A (100 mg, 0.367 mmol) in 1,2-dichlorobenzene (3 mL), was added triphenylphosphine (241 mg, 0.918 mmol). The mixture was heated at 170° C. for 5 h. The reaction mixture was cooled to rt, then was diluted with pet. ether. The precipitate was collected by filtration. The solid was purified twice by flash chromatography (gradient elution; 0-100% EtOAc/Hex) to afford Intermediate 33B (100 mg, 29%) as a yellow solid. MS (ES): m/z=241.5 [M+H]$^+$.

INTERMEDIATE 33

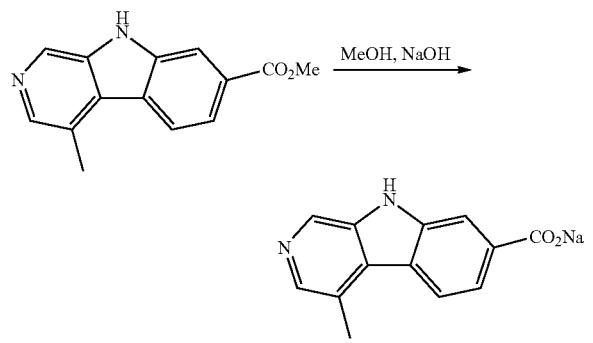

To a solution of Intermediate 33B (100 mg, 0.416 mmol) in MeOH (2 mL) and water (0.67 mL), was added NaOH (0.050 g, 1.25 mmol). The mixture was stirred at rt overnight. The solvent was evaporated, then the mixture was coevaporated with toluene to afford a 100 mg of a yellow solid that was used as without further purification. MS (ES): m/z=227.5 [M+H]$^+$; $^1$H NMR (300 MHz, DMSO-d$_6$) δ 13.20 (br. s., 1H), 9.26 (s, 1H), 8.52 (d, J=8.7 Hz, 1H), 8.48 (s, 1H), 8.41 (d, J=0.8 Hz, 1H), 7.98 (dd, J=8.3, 1.5 Hz, 1H), 2.99 (s, 3H).

INTERMEDIATE 34

1-(Difluoromethyl)benzofuro[2,3-c]pyridine-7-carboxylic acid

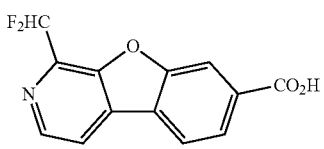 [SMILES: O=C(O)c1ccc2c(c1)oc1c(C(F)F)nccc12]

INTERMEDIATE 34A methyl 1-(difluoromethyl)benzofuro[2,3-c]pyridine-7-carboxylate

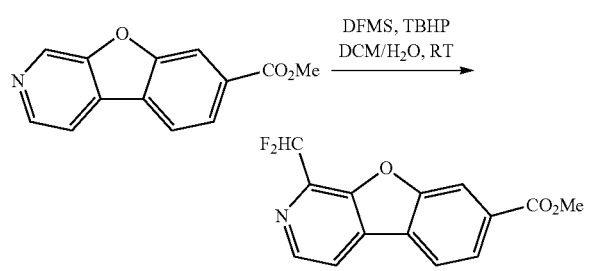

To s suspension of methyl benzofuro[2,3-c]pyridine-7-carboxylate (90 mg, 0.40 mmol) and zinc difluoromethanesulfinate (389 mg, 1.19 mmol) in DCM (5 mL) and water (2 mL) at 0° C., was added tert-butyl hydroperoxide (0.192 mL, 1.98 mmol). The reaction mixture was stirred at rt overnight, then was diluted with DCM. The phases were separated, then the aqueous phase was extracted with DCM. The combined DCM phase was washed with brine, dried over Na$_2$SO$_4$, filtered and concentrated. The crude product was purified by flash chromatography (gradient elution; 0-80% EtOAc/Hex.) to afford Intermediate 34A (70 mg, 44%) as an off-white solid. MS (ES): m/z=278.4 [M+H]$^+$; $^1$H NMR (400 MHz, DMSO-d$_6$) δ ppm 8.74 (d, J=5.02 Hz, 1 H) 8.49-8.55 (m, 2 H) 8.40 (dd, J=1.29, 0.60 Hz, 1 H) 8.15 (dd, J=8.16, 1.38 Hz, 1 H) 7.23-7.53 (t, J=56, 1 H) 3.95 (s, 3 H).

INTERMEDIATE 34

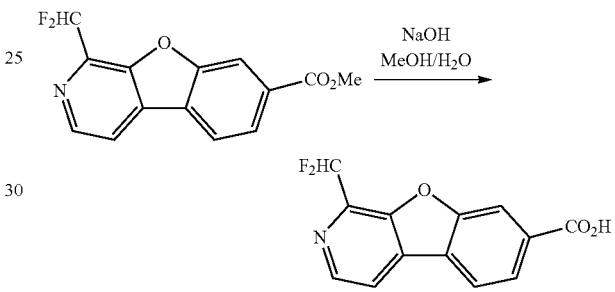

To s solution of Intermediate 34A (70 mg, 0.25 mmol) in methanol (3 mL) and water (1 mL), was added NaOH (30.3 mg, 0.758 mmol). The mixture was stirred at rt for 4 h. The solvent was evaporated, then the residue was dissolved water (15 mL) and washed with ethyl acetate (×2). The aqueous was acidified with 1.5 N HCl to pH 2 then was extracted with ethyl acetate. The combined organic phase was washed with brine, dried over Na$_2$SO$_4$, filtered and concentrated to afford Intermediate 34 (50 mg, 59% yield) as a yellow solid. MS (ES): m/z=278.4 [M+H]$^+$; $^1$H NMR (400 MHz, DMSO-d$_6$) δ ppm 8.74 (d, J=5.02 Hz, 1 H) 8.52 (d, J=5.08 Hz, 1 H) 8.48 (dd, J=8.13, 0.53 Hz, 1H) 8.36 (d, J=0.69 Hz, 1 H) 8.13 (dd, J=8.09, 1.32 Hz, 1 H) 7.25-7.53 (t, J=56.8 Hz, 1 H).

INTERMEDIATE 35

Lithium 4-fluorobenzofuro[2,3-c]pyridine-7-carboxylate

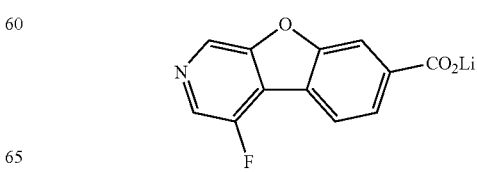

INTERMEDIATE 35A

Methyl 3-acetoxy-4-(4,4,5,5-tetramethyl-1,3,2-dioxaborolan-2-yl)benzoate

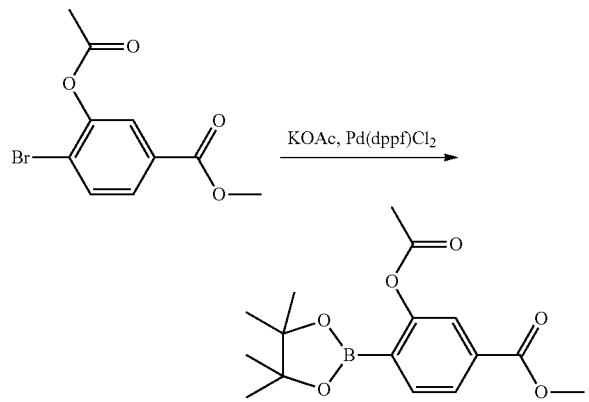

To a solution of methyl 3-acetoxy-4-bromobenzoate (540 mg, 1.98 mmol) in dioxane (20 mL), was added potassium acetate (485 mg, 4.94 mmol). The mixture was bubbled with nitrogen for 10 minutes, then bis(pinacolato)diboron (753 mg, 2.97 mmol) and PdCl$_2$(dppf) (87 mg, 0.12 mmol) were added. The mixture was bubbled with nitrogen for 5 minutes, then was heated at 100° C. overnight. The reaction mixture was cooled to rt, filtered through a CELITE® bed, rinsing with ethyl acetate. The filtrate was concentrated. The residue was purified by flash chromatography (gradient elution; 0-100% EtOAc/Hex.) to afford Intermediate 35A (450 mg, 71% yield) as a yellow gummy solid. MS (ES): m/z=239 [M+H]$^+$.

INTERMEDIATE 35B

Methyl 4-(3,5-difluoropyridin-4-yl)-3-hydroxybenzoate

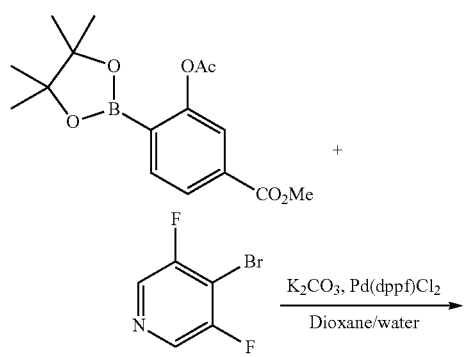

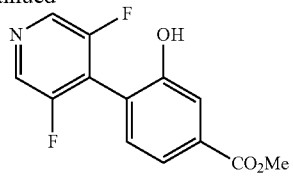

A solution of Intermediate 35A (248 mg, 0.773 mmol), 4-bromo-3,5-difluoropyridine (100 mg, 0.516 mmol) and K$_2$CO$_3$ (214 mg, 1.55 mmol) in dioxane (10 mL) and water (2 mL) was bubbled with nitrogen for 10 minutes then, PdCl$_2$(dppf)-CH$_2$Cl$_2$ Adduct (25.3 mg, 0.031 mmol) were added. The mixture was heated at 80° C. for 4 h. The mixture was diluted with ethyl acetate (30 mL), washed with brine (2×), dried over Na$_2$SO$_4$, filtered and concentrated. The residue was purified by flash chromatography (gradient elution; 0-100% EtOAc/Hex.) to afford Intermediate 35B (37 mg, 0.092 mmol, 17.93% yield) as a yellow solid. MS (ES): m/z=266.0 [M+H]$^+$; $^1$H NMR (400 MHz, DMSO-d$_6$) δ 10.49 (s, 1H), 8.62 (s, 2H), 7.60 (d, J=1.5 Hz, 1H), 7.56-7.49 (m, 1H), 7.48-7.40 (m, 1H), 3.87 (s, 3H).

INTERMEDIATE 35

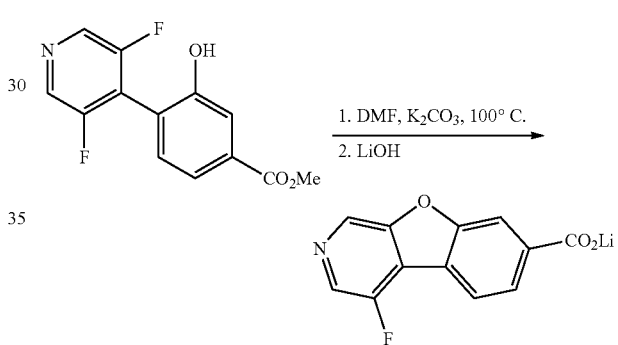

To the solution of Intermediate 35B (37 mg, 0.14 mmol) in DMF (1 mL), was added potassium carbonate (57.8 mg, 0.419 mmol). The mixture was heated at 120° C. for 4 h. The reaction mixture was cooled to rt and the solvent was evaporated to give an off-white solid. The solid was dissolved in THF (2.5 mL) and water (1 mL), then was treated with LiOH (9.77 mg, 0.408 mmol). The mixture was stirred at rt for 3 h. The mixture was concentrated, then was coevaporated with toluene (2×) to afford Intermediate 35 (45 mg) as an off-white solid, which was used as is without further purification. MS (ESI): m/z=232.0 [M+H]$^+$; $^1$H NMR (400 MHz, DMSO-d$_6$) δ ppm 8.98-9.00 (m, 1 H) 8.59 (m, 1 H) 8.15 (s, 1 H) 8.03-8.07 (m, 1 H) 7.98-8.02 (m, 1 H).

Compounds listed in Table XIV were prepared by following similar procedures to those described for Example I-1 using the appropriate intermediates described or purchased from commercial sources. Coupling reagents, such as HATU, T$_3$P, BOP, PyBop, and EDC/HOBt, could be used instead of the one described.

TABLE XIV

| Ex. No. | Structure | Name | LCMS [M + H]+ | HPLC Method, RT (min.) | 1H NMR (δ, ppm) |
|---|---|---|---|---|---|
| XIV-1 | (3-methoxyphenyl structure with pyrido-indole carboxamide) | N-[(3-methoxyphenyl)methyl]-9H-pyrido[3,4-b]indole-7-carboxamide | 332.2 | I: 5.52 J: 6.21 | 1H NMR (400 MHz, DMSO-d6) δ ppm 11.81-11.85 (m, 1 H) 9.17 (t, J = 6.27 Hz, 1 H) 8.94-8.98 (m, 1 H) 8.37-8.41 (m, 1H) 8.33 (d, J = 8.47 Hz, 1 H) 8.15-8.20 (m, 1H) 8.12-8.15 (m, 1 H) 7.79 (dd, J = 8.31, 1.47 Hz, 1 H) 7.27 (t, J = 8.13 Hz, 1 H) 6.91-6.98 (m, 2 H) 6.80-6.86 (m, 1 H) 4.52 (d, J = 6.02 Hz, 3 H) 3.75 (s, 3 H) |
| XIV-2 | (1-phenylethyl structure) | (R)-N-(1-phenylethyl)-9H-pyrido[3,4-b]indole-7-carboxamide | 316.3 | I: 5.61 J: 6.42 | 1H NMR (400 MHz, chloroform-d) δ ppm 8.96-8.97 (s, 1 H) 8.51 (d, J = 5.40 Hz, 1 H) 8.44-8.47 (s, 1 H) 8.16 (d, J = 8.16 Hz, 1 H) 8.09 (d, J = 0.75 Hz, 1 H) 7.98 (d, J = 5.21 Hz, 1 H) 7.60 (dd, J = 8.19, 1.47 Hz, 1 H) 7.37-7.46 (m, 2 H) 7.29-7.34 (m, 2 H) 7.20-7.29 (m, 1 H) 6.44 (d, J = 7.59 Hz, 1 H) 5.41 (quin, J = 6.98 Hz, 1 H) 1.67 (d, J = 6.90 Hz, 3 H) |
| XIV-3 | (2-chlorobenzyl structure) | N-(2-chlorobenzyl)-9H-pyrido[3,4-b]indole-7-carboxamide | 336.0 | I: 6.00 J: 6.64 | 1H NMR (400 MHz, DMSO-d6) δ = 12.70 (s, 1 H), 9.38-9.25 (m, 2 H), 8.78-8.71 (m, 1 H), 8.65-8.55 (m, 2 H), 8.31 (s, 1 H), 7.99-7.90 (m, 1 H), 7.53-7.40 (m, 2 H), 7.39-7.27 (m, 2 H), 4.64 (d, J = 5.6 Hz, 2 H) |
| XIV-4 | (1-(3-methoxyphenyl)ethyl structure) | (R)-N-(1-(3-methoxyphenyl)ethyl)-9H-pyrido[3,4-b]indole-7-carboxamide | 346.2 | I: 6.08 J: 6.52 | 1H NMR (400 MHz, DMSO-d6) δ = 12.71 (s, 1 H), 9.32 (s, 1 H), 9.08 (s, 1 H), 8.78 (s, 1 H), 8.64-8.54 (m, 2 H), 8.26 (s, 1 H), 7.92 (dd, J = 1.5, 8.5 Hz, 1 H), 7.30-7.22 (m, 1 H), 7.05-6.97 (m, 2 H), 6.86-6.77 (m, 1 H), 5.22 (t, J = 7.5 Hz, 1 H), 3.76 (s, 3 H), 1.53 (d, J = 7.0 Hz, 3 H) |

TABLE XIV-continued

| Ex. No. | Structure | Name | LCMS [M + H]+ | HPLC Method, RT (min.) | 1H NMR (δ, ppm) |
|---|---|---|---|---|---|
| XIV-5 | 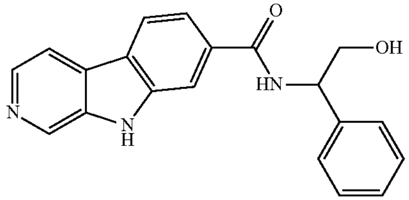 [SMILES: O=C(NC(CO)c1ccccc1)c1ccc2c(c1)[nH]c1cnccc12] | N-(2-hydroxy-1-phenylethyl)-9H-pyrido[3,4-b]indole-7-carboxamide | 332.2 | K: 8.92 L: 11.64 | 1H NMR (400 MHz, chloroform-d) δ ppm 8.95 (s, 1 H) 8.64 (br. s., 1 H) 8.50 (d, J = 5.00 Hz, 1 H) 8.07-8.18 (m, 2 H) 7.96 (d, J = 4.50 Hz, 1 H) 7.65 (d, J = 7.75 Hz, 1 H) 7.30-7.46 (m, 54 H) 7.09 (br. s., 1 H) 5.38 (br. s., 1 H) 4.09 (d, J = 3.50 Hz, 1 H) |
| XIV-6 | 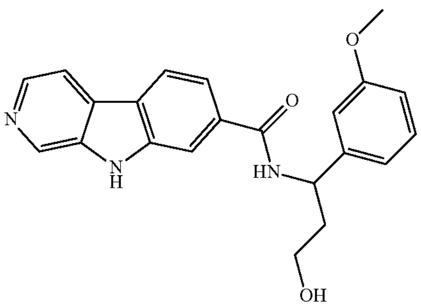 [SMILES: COc1cccc(C(CCO)NC(=O)c2ccc3c(c2)[nH]c2cnccc23)c1] | N-(3-hydroxy-1-(3-methoxyphenyl)propyl)-9H-pyrido[3,4-b]indole-7-carboxamide | 376.2 | M: 1.32 N: 1.66 | 1H NMR (400 MHz, DMSO-d6) δ ppm 11.82 (s, 1 H) 8.97 (s, 1 H) 8.91 (d, J = 8.22 Hz, 1 H) 8.39 (d, J = 5.27 Hz, 1 H) 8.33 (d, J = 8.22 Hz, 1 H) 8.18 (d, J = 5.27 Hz, 1 H) 8.09 (d, J = 0.75 Hz, 1 H) 7.76 (dd, J = 8.25, 1.47 Hz, 1 H) 7.25 (d, J = 8.16 Hz, 1 H) 7.02 (d, J = 1.63 Hz, 2 H) 6.83 (d, J = 1.76 Hz, 1 H) 5.15-5.25 (m, 1 H) 4.59 (d, J = 9.79 Hz, 1 H) 3.76 (s, 3 H) 3.41-3.55 (m, 2 H) 2.03-2.14 (m, 1 H) 1.89-1.99 (m, 1 H) |
| XIV-7 | 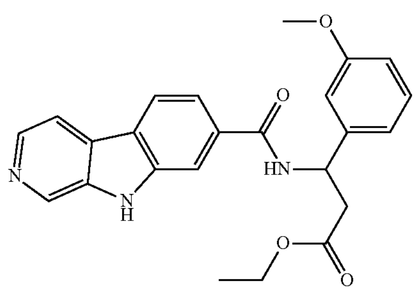 [SMILES: CCOC(=O)CC(NC(=O)c1ccc2c(c1)[nH]c1cnccc12)c1cccc(OC)c1] | ethyl 3-(3-methoxyphenyl)-3-(9H-pyrido[3,4-b]indole-7-carboxamido)propanoate | 418.2 | I: 6.20 J: 7.03 | 1H NMR (400 MHz, chloroform-d) δ ppm 9.03 (s, 1 H) 8.51 (d, J = 5.32 Hz, 1 H) 8.17-8.22 (m, 2 H) 8.02 (d, J = 5.57 Hz, 1 H) 7.76 (d, J = 8.57 Hz, 1 H) 7.72 (m, J = 1.50 Hz, 1 H) 7.28-7.31 (m, 1 H) 6.99-7.03 (m, 1 H) 6.97 (t, J = 2.00 Hz, 1 H) 6.80-6.85 (m, 1 H) 5.65-5.72 (m, 1 H) 4.11-4.12 (m, 1 H) 4.14 (q, J = 7.07 Hz, 2 H) 2.95-3.11 (m, 2 H) 1.21 (t, J = 6.8 Hz, 3 H) |

TABLE XIV-continued

| Ex. No. | Structure | Name | LCMS [M + H]+ | HPLC Method, RT (min.) | 1H NMR (δ, ppm) |
|---|---|---|---|---|---|
| XIV-8 | 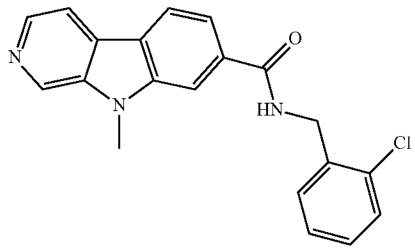 [SMILES: Cn1c2cnccc2c2ccc(C(=O)NCc3ccccc3Cl)cc21] | N-(2-chlorobenzyl)-9-methyl-9H-pyrido[3,4-b]indole-7-carboxamide | 350.2 | I: 6.16<br>J: 6.97 | 1H NMR (400 MHz, DMSO-d6) δ ppm 9.19 (m, 1 H) 9.12 (d, J = 0.88 Hz, 1 H) 8.44 (d, J = 5.21 Hz, 1 H) 8.38 (d, J = 8.16 Hz, 1 H) 8.29 (d, J = 0.69 Hz, 1 H) 8.20 (dd, J = 5.24, 1.04 Hz, 1 H) 7.86 (dd, J = 8.19, 1.41 Hz, 1 H) 7.47-7.50 (m, 1 H) 7.43-7.46 (m, 1 H) 7.34 (td, J = 7.51, 1.85 Hz, 2 H) 4.64 (d, J = 5.71 Hz, 2 H) 4.05 (s, 3 H) |
| XIV-9 | 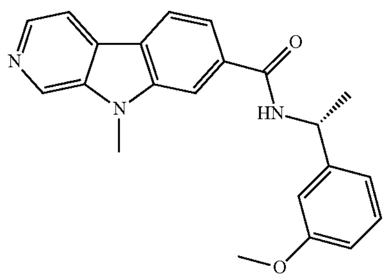 [SMILES: COc1cccc([C@@H](C)NC(=O)c2ccc3c4ccncc4n(C)c3c2)c1] | (R)-N-(1-(3-methoxyphenyl)ethyl)-9-methyl-9H-pyrido[3,4-b]indole-7-carboxamide | 360.2 | I: 6.04<br>J: 6.79 | 1H NMR (400 MHz, DMSO-d6) δ ppm 9.11 (d, J = 0.94 Hz, 1 H) 8.91 (d, J = 7.78 Hz, 1 H) 8.43 (d, J = 5.21 Hz, 1 H) 8.36 (dd, J = 8.22, 0.50 Hz, 1 H) 8.24 (d, J = 0.75 Hz, 1 H) 8.19 (dd, J = 5.21, 1.07 Hz, 1 H) 7.82 (dd, J = 8.22, 1.44 Hz, 1 H) 7.24-7.29 (m, 1 H) 7.00-7.04 (m, 2 H) 6.80-6.84 (m, 1 H) 5.22 (m, J = 7.47, 7.47 Hz, 1 H) 4.05 (s, 3 H) 3.76 (s, 3 H) 1.54 (d, J = 7.09 Hz, 3 H) |
| XIV-10 | 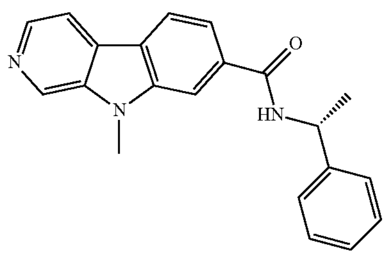 [SMILES: C[C@@H](NC(=O)c1ccc2c3ccncc3n(C)c2c1)c1ccccc1] | (R)-9-methyl-N-(1-phenylethyl)-9H-pyrido[3,4-b]indole-7-carboxamide | 330.2 | I: 5.99<br>J: 6.73 | 1H NMR (400 MHz, DMSO-d6) δ ppm 9.11 (d, J = 0.82 Hz, 1 H) 8.94 (d, J = 7.97 Hz, 1 H) 8.43 (d, J = 5.21 Hz, 1 H) 8.35 (d, J = 8.22 Hz, 1 H) 8.25 (d, J = 0.75 Hz, 1 H) 8.19 (dd, J = 5.21, 1.00 Hz, 1 H) 7.83 (dd, J = 8.22, 1.38 Hz, 1 H) 7.43-7.48 (m, 2H) 7.21-7.38 (m, 3 H) 5.22-5.31 (m, 1 H) 4.05 (s, 3 H) 1.55 (d, J = 7.03 Hz, 3 H) |

TABLE XIV-continued

| Ex. No. | Structure | Name | LCMS [M + H]+ | HPLC Method, RT (min.) | 1H NMR (δ, ppm) |
|---|---|---|---|---|---|
| XIV-11 | 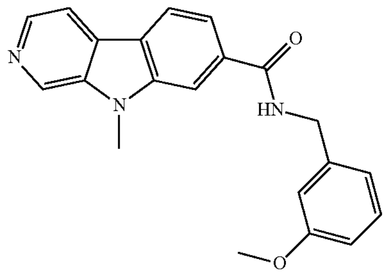 [SMILES: COc1cccc(CNC(=O)c2ccc3c4ccncc4n(C)c3c2)c1] | N-(3-methoxybenzyl)-9-methyl-9H-pyrido[3,4-b]indole-7-carboxamide | 346.2 | I: 5.82<br>J: 6.46 | 1H NMR (400 MHz, DMSO-d6) δ 9.16 (t, J = 5.8 Hz, 1H), 9.10 (s, 1H), 8.43 (d, J = 5.0 Hz, 1H), 8.36 (d, J = 8.0 Hz, 1H), 8.26 (s, 1H), 8.21-8.15 (m, 1H), 7.83 (dd, J = 8.0, 1.5 Hz, 1H), 7.26 (t, J = 8.0 Hz, 1H), 6.98-6.91 (m, 2H), 6.86-6.79 (m, 1H), 4.54 (d, J = 6.0 Hz, 2H), 4.03 (s, 3H), 3.74 (s, 3H) |
| XIV-12 | 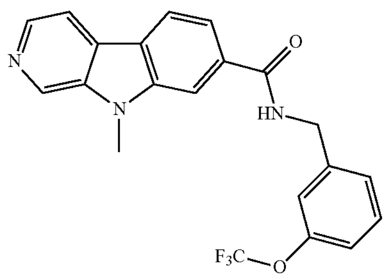 [SMILES: Cn1c2cnccc2c2ccc(C(=O)NCc3cccc(OC(F)(F)F)c3)cc21] | 9-methyl-N-(3-(trifluoromethoxy)benzyl)-9H-pyrido[3,4-b]indole-7-carboxamide | 400.2 | I: 6.89<br>J: 7.66 | 1H NMR (400 MHz, DMSO-d6) δ ppm 9.29 (1 H, s) 9.12 (1 H, s) 8.44 (1 H, d, J = 5.52 Hz) 8.38 (1 H, d, J = 8.03 Hz) 8.27 (1 H, s) 8.20 (1 H, dd, J = 5.02, 1.00 Hz) 7.84 (1 H, dd, J = 8.53, 1.51 Hz) 7.50 (1 H, d, J = 8.03 Hz) 7.44 (1 H, s) 7.36 (1 H, s) 7.25-7.30 (1 H, m) 4.62 (2 H, d, J = 6.02 Hz) 4.05 (3 H, s) |
| XIV-13 | 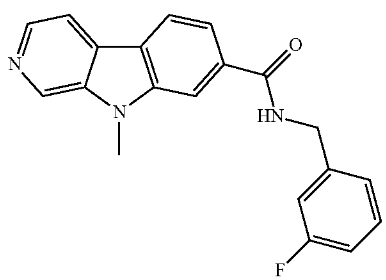 [SMILES: Cn1c2cnccc2c2ccc(C(=O)NCc3cccc(F)c3)cc21] | N-(3-fluorobenzyl)-9-methyl-9H-pyrido[3,4-b]indole-7-carboxamide | 334.2 | I: 6.00<br>J: 6.55 | 1H NMR (400 MHz, DMSO-d6) δ 9.24 (t, J = 6.3 Hz, 1H), 9.10 (s, 1H), 8.43 (d, J = 5.5 Hz, 1H), 8.37 (d, J = 8.0 Hz, 1H), 8.26 (s, 1H), 8.22-8.15 (m, 1H), 7.83 (dd, J = 8.0, 1.5 Hz, 1H), 7.40 (td, J = 8.0, 6.0 Hz, 1H), 7.25-7.15 (m, 2H), 7.13-7.03 (m, 1H), 4.58 (d, J = 5.5 Hz, 2H), 4.04 (s, 3H) |

TABLE XIV-continued

| Ex. No. | Structure | Name | LCMS [M + H]+ | HPLC Method, RT (min.) | 1H NMR (δ, ppm) |
|---|---|---|---|---|---|
| XIV-14 | (structure) | N-(2-chlorobenzyl)-9-(cyclopropylmethyl)-9H-pyrido[3,4-b]indole-7-carboxamide | 390.0 | E: 1.26<br>F: 1.76 | 1H NMR (400 MHz, DMSO-d6) δ 9.20 (t, J = 5.8 Hz, 1H), 9.16 (s, 1H), 8.43 (d, J = 5.3 Hz, 1H), 8.39 (d, J = 8.3 Hz, 1H), 8.34 (s, 1H), 8.20 (d, J = 5.3 Hz, 1H), 7.86 (dd, J = 8.3, 1.3 Hz, 1H), 7.48 (dd, J = 7.4, 1.6 Hz, 1H), 7.44 (dd, J = 7.4, 1.9 Hz, 1H), 7.33 (qd, J = 7.5, 5.6 Hz, 2H), 4.64 (d, J = 5.5 Hz, 2H), 4.48 (d, J = 6.8 Hz, 2H), 1.39 (dt, J = 13.2, 6.5 Hz, 1H), 0.50 (d, J = 6.5 Hz, 4H) |
| XIV-15 | (structure) | 9-ethyl-N-(2-hydroxy-1-phenylethyl)-9H-pyrido[3,4-b]indole-7-carboxamide | 360.3 | K: 8.09<br>L: 10.63 | 1H NMR (400 MHz, chloroform-d) δ ppm 8.93-8.97 (m, 1 H) 8.51 (d, J = 5.25 Hz, 1 H) 8.18 (d, J = 8.25 Hz, 1 H) 8.09 (d, J = 0.50 Hz, 1 H) 8.00 (dd, J = 5.25, 1.00 Hz, 1 H) 7.62 (dd, J = 8.25, 1.50 Hz, 1 H) 7.44-7.35 (m, 1 H) 6.99-7.03 (m, 1 H) 5.35-5.40 (m, 1 H) 4.50 (q, J = 7.25 Hz, 2 H) 4.09-4.12 (m, 2 H) 1.50-1.58 (t, J = 14.51 Hz, 3 H) |
| XIV-16 | (structure) | (R)-4-fluoro-N-(1-(3-methoxyphenyl)ethyl)-9H-pyrido[3,4-b]indole-7-carboxamide | 364.0 | M: 1.65<br>N: 2.11 | 1H NMR (400 MHz, DMSO-d6) δ ppm 12.19 (s, 1 H) 9.00 (d, J = 8.09 Hz, 1 H) 8.86 (d, J = 2.57 Hz, 1 H) 8.35 (d, J = 1.32 Hz, 1 H) 8.22 (d, J = 8.22 Hz, 1 H) 8.15-8.18 (m, 1 H) 7.85 (dd, J = 8.28, 1.44 Hz, 1 H) 7.23-7.29 (m, 1 H) 7.00-7.04 (m, 2 H) 6.82 (ddd, J = 8.20, 2.46, 1.00 Hz, 1 H) 5.21 (quin, J = 7.20 Hz, 1 H) 3.76 (s, 3 H) 1.52 (d, J = 7.09 Hz, 3 H) |

| Ex. No. | Structure | Name | LCMS [M + H]+ | HPLC Method, RT (min.) | 1H NMR (δ, ppm) |
|---|---|---|---|---|---|
| XIV-17 | 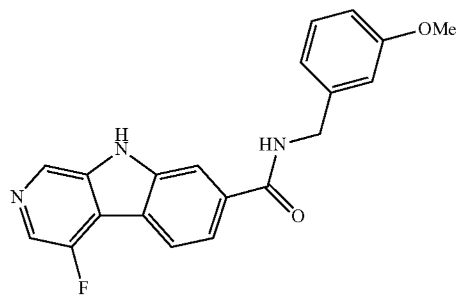 [SMILES: COc1cccc(CNC(=O)c2ccc3c(c2)[nH]c2cncc(F)c23)c1] | 4-fluoro-N-(3-methoxybenzyl)-9H-pyrido[3,4-b]indole-7-carboxamide | 350.0 | M: 1.59<br>N: 2.03 | 1H NMR (400 MHz, DMSO-d6) δ ppm 12.21 (s, 1 H) 9.23 (t, J = 6.02 Hz, 1 H) 8.86 (d, J = 2.64 Hz, 1 H) 8.35 (d, J = 1.26 Hz, 1 H) 8.18-8.25 (m, 2 H) 7.86 (dd, J = 8.28, 1.44 Hz, 1 H) 7.24-7.30 (m, 1 H) 6.92-6.97 (m, 2 H) 6.81-6.86 (m, 1 H) 4.52 (d, J = 5.90 Hz, 2 H) 3.75 (s, 3 H). |
| XIV-18 | 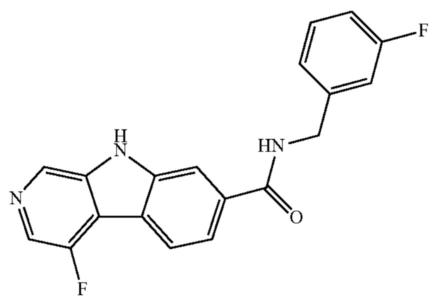 [SMILES: O=C(NCc1cccc(F)c1)c1ccc2c(c1)[nH]c1cncc(F)c12] | 4-fluoro-N-(3-fluorobenzyl)-9H-pyrido[3,4-b]indole-7-carboxamide | 338.1 | E: 1.13<br>F: 1.49 | 1H NMR (400 MHz, DMSO-d6) δ ppm 12.22 (s, 1 H) 9.29 (t, J = 5.93 Hz, 1 H) 8.86 (d, J = 2.64 Hz, 1 H) 8.35 (d, J = 1.25 Hz, 1 H) 8.19-8.25 (m, 2 H) 7.86 (dd, J = 8.28, 1.51 Hz, 1 H) 7.40 (td, J = 7.91, 6.15 Hz, 1 H) 7.15-7.24 (m, 2 H) 7.09 (td, J = 8.60, 1.88 Hz, 1 H) 4.57 (d, J = 5.90 Hz, 2 H) |
| XIV-19 | 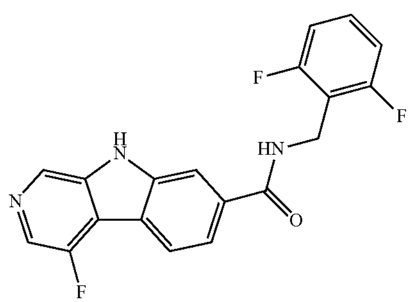 [SMILES: O=C(NCc1c(F)cccc1F)c1ccc2c(c1)[nH]c1cncc(F)c12] | N-(2,6-difluorobenzyl)-4-fluoro-9H-pyrido[3,4-b]indole-7-carboxamide | 356.2 | I: 6.41<br>J: 7.13 | 1H NMR (400 MHz, DMSO-d6) δ ppm 12.18 (s, 1 H) 9.09 (t, J = 5.11 Hz, 1 H) 8.84 (d, J = 2.64 Hz, 1 H) 8.34 (d, J = 1.25 Hz, 1 H) 8.19 (d, J = 8.28 Hz, 1 H) 8.14 (d, J = 0.63 Hz, 1 H) 7.81 (dd, J = 8.28, 1.38 Hz, 1 H) 7.42 (tt, J = 8.37, 6.66 Hz, 1 H) 7.07-7.16 (m, 2 H) 4.59 (d, J = 5.08 Hz, 2 H) |

TABLE XIV-continued

| Ex. No. | Structure | Name | LCMS [M + H]+ | HPLC Method, RT (min.) | 1H NMR (δ, ppm) |
|---|---|---|---|---|---|
| XIV-20 | 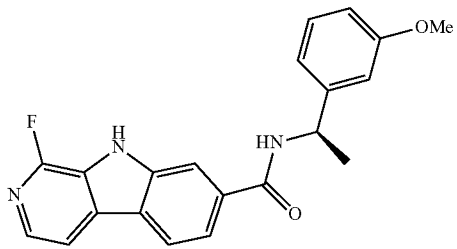 [SMILES: COc1cccc([C@@H](C)NC(=O)c2ccc3c(c2)[nH]c2c(F)nccc23)c1] | (R)-1-fluoro-N-(1-(3-methoxyphenyl)ethyl)-9H-pyrido[3,4-b]indole-7-carboxamide | 364.2 | I: 9.77  J: 9.20 | 1H NMR (400 MHz, DMSO-d6) δ ppm 12.32 (s, 1 H) 8.99 (d, J = 8.09 Hz, 1 H) 8.35 (d, J = 8.31, 0.47 Hz, 1 H) 8.10-8.17 (m, 2 H) 7.94 (dd, J = 5.36, 1.79 Hz, 1 H) 7.83 (dd, J = 8.35, 1.44 Hz, 1 H) 7.24-7.30 (m ,1 H) 6.98-7.05 (m, 2 H) 6.82 (ddd, J = 8.19, 2.42, 1.07 Hz 1 H) 5.21 (quin, J = 7.36 Hz, 1 H) 3.76 (s, 3 H) 1.53 (s, 3 H) |
| XIV-21 | 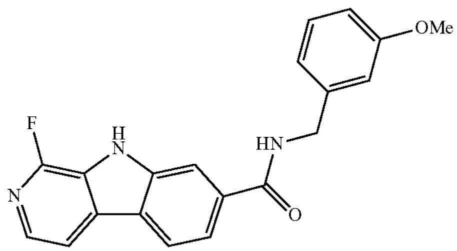 [SMILES: COc1cccc(CNC(=O)c2ccc3c(c2)[nH]c2c(F)nccc23)c1] | 1-fluoro-N-(3-methoxybenzyl)-9H-pyrido[3,4-b]indole-7-carboxamide | 350.2 | I: 9.11  J: 8.86 | 1H NMR (400 MHz, DMSO-d6) δ ppm 12.35 (s, 1 H) 9.22 (t, J = 6.02 Hz, 1 H) 8.36 (dd, J = 8.35 Hz, 1 H) 8.12-8.17 (m, 2 H) 7.94 (dd, J = 5.33, 1.76 Hz, 1 H) 7.84 (dd, J = 8.34, 1.44 Hz, 1 H) 7.23-7.30 (m, 1 H) 6.93-6.97 (m, 2 H) 6.81-6.86 (m, 1 H) 4.52 (d, J = 5.90 Hz, 2 H) 3.75 (s, 3 H) |
| XIV-22 | 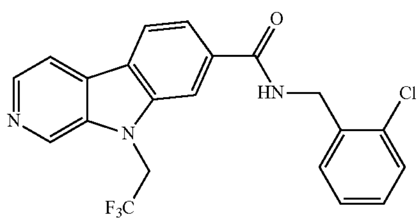 [SMILES: O=C(NCc1ccccc1Cl)c1ccc2c3ccncc3n(CC(F)(F)F)c2c1] | N-(2-chlorobenzyl)-9-(2,2,2-trifluoroethyl)-9H-pyrido[3,4-b]indole-7-carboxamide | 418.0 | M: 1.81  N: 2.35 | 1H NMR (400 MHz, DMSO-d6) δ ppm 9.22 (s, 1 H), 9.17 (t, J = 5.8 Hz, 1 H), 8.54-8.50 (m, 1 H), 8.46-8.40 (m, 2 H), 8.28-8.22 (m, 1 H) 7.95 (dd, J = 1.3, 8.3 Hz, 1 H), 7.52-7.42 (m, 2 H), 7.39-7.29 (m, 2 H), 5.68-5.57 (m, 2 H), 4.65 (d, J = 5.5 Hz, 2 H) |
| XIV-23 | 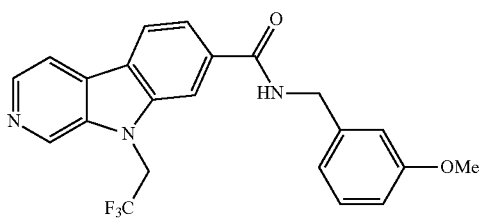 [SMILES: COc1cccc(CNC(=O)c2ccc3c4ccncc4n(CC(F)(F)F)c3c2)c1] | N-(3-methoxybenzyl)-9-(2,2,2-trifluoroethyl)-9H-pyrido[3,4-b]indole-7-carboxamide | 414.0 | M: 1.68  N: 2.19 | 1H NMR (400 MHz, DMSO-d6) δ ppm 9.21 (s, 1 H), 9.14 (t, J = 6.0 Hz, 1 H), 8.52-8.50 (m, 1 H), 8.44-8.38 (m, 2 H), 8.24 (dd, J = 1.0, 5.5 Hz, 1 H), 7.91 (dd, J = 1.3, 8.3 Hz, 1 H), 7.30-7.23 (m, 1 H), 6.98-6.93 (m, 2 H), 6.87-6.80 (m, 1 H), 5.62 (q, J = 9.5 Hz, 2 H), 4.55 (d, J = 6.0 Hz, 2 H), 3.75 (s, 3 H) |

TABLE XIV-continued

| Ex. No. | Structure | Name | LCMS [M + H]+ | HPLC Method, RT (min.) | 1H NMR (δ, ppm) |
|---|---|---|---|---|---|
| XIV-24 | 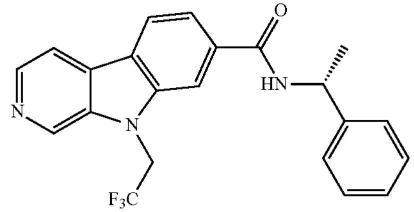 [SMILES: C[C@@H](NC(=O)c1ccc2c3ccncc3n(CC(F)(F)F)c2c1)c1ccccc1] | (R)-N-(1-phenylethyl)-9-(2,2,2-trifluoroethyl)-9H-pyrido[3,4-b]indole-7-carboxamide | 398.0 | M: 1.77 N: 2.29 | 1H NMR (400 MHz, DMSO-d6) δ = 8.25 (s, 1 H), 7.67 (d, J = 5.5 Hz, 1 H), 7.55 (d, J = 8.0 Hz, 1 H), 7.46 (s, 1 H), 7.42 (d, J = 5.5 Hz, 1 H), 7.09 (dd, J = 1.3, 8.3 Hz, 1 H), 6.69-6.64 (m, 2 H), 6.59-6.53 (m, 2 H), 6.49-6.43 (m, 1 H), 4.63-4.49 (m, 3 H), 0.84 (d, J = 7.0 Hz, 3 H) |
| XIV-25 | 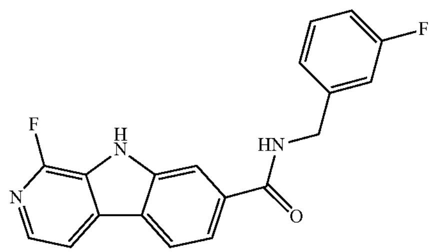 [SMILES: O=C(NCc1cccc(F)c1)c1ccc2c(c1)[nH]c1c(F)nccc12] | 1-fluoro-N-(3-fluorobenzyl)-9H-pyrido[3,4-b]indole-7-carboxamide | 338.2 | I: 9.36 J: 9.02 | 1H NMR (400 MHz, DMSO-d6) δ ppm 12.35 (s, 1 H) 9.29 (t, J = 5.96 Hz, 1 H) 8.37 (dd, J = 8.31, 0.60 Hz, 1 H) 8.13-8.18 (m, 2 H) 7.94 (dd, J = 5.36, 1.79 Hz, 1 H) 7.84 (dd, J = 8.31, 1.47 Hz, 1 H) 7.40 (td, J = 7.94, 6.15 Hz, 1 H) 7.15-7.24 (m, 2 H) 7.06-7.12 (m, 1 H) 4.56 (d, J = 5.96 Hz, 2 H). |
| XIV-26 | 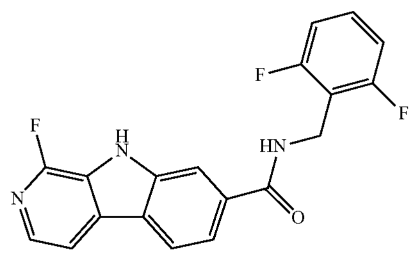 [SMILES: O=C(NCc1c(F)cccc1F)c1ccc2c(c1)[nH]c1c(F)nccc12] | N-(2,6-difluorobenzyl)-1-fluoro-9H-pyrido[3,4-b]indole-7-carboxamide | 356.2 | I: 9.30 J: 8.95 | 1H NMR (400 MHz, DMSO-d6) δ ppm 12.32 (s, 1 H) 9.09 (t, J = 5.15 Hz, 1 H) 8.33 (d, J = 8.35 Hz, 1 H) 8.08-8.15 (m, 2 H) 7.93 (dd, J = 5.33, 1.82 Hz, 1 H) 7.78 (dd, J = 8.31, 1.47 Hz, 1 H) 7.42 (tt, J = 8.39, 6.64 Hz, 1 H) 7.06-7.16 (m, 2 H) 4.59 (d, J = 5.15 Hz, 2 H) |
| XIV-27 | 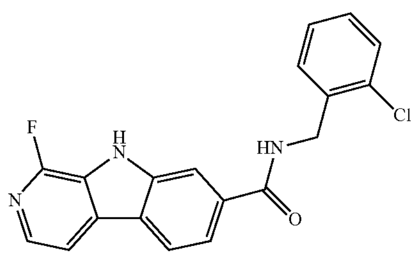 [SMILES: O=C(NCc1ccccc1Cl)c1ccc2c(c1)[nH]c1c(F)nccc12] | N-(2-chlorobenzyl)-1-fluoro-9H-pyrido[3,4-b]indole-7-carboxamide | 354.0 | I: 9.90 J: 9.44 | 1H NMR (400 MHz, DMSO-d6) δ ppm 12.37 (s, 1 H) 9.25 (t, J = 5.77 Hz, 1 H) 8.38 (d, J = 8.28 Hz, 1 H) 8.13-8.20 (m, 2 H) 7.95 (dd, J = 5.33, 1.76 Hz, 1 H) 7.87 (dd, J = 8.35, 1.44 Hz, 1 H) 7.47-7.51 (m, 1 H) 7.40-7.45 (m, 1 H) 7.29-7.38 (m, 2 H) 4.62 (d, J = 5.77 Hz, 2 H) |

TABLE XIV-continued

| Ex. No. | Structure | Name | LCMS [M + H]+ | HPLC Method, RT (min.) | 1H NMR (δ, ppm) |
|---|---|---|---|---|---|
| XIV-28 | (structure with OMe substituent) | (R)-3-fluoro-N-(1-(3-methoxyphenyl)ethyl)-9H-pyrido[3,4-b]indole-7-carboxamide | 364.2 | E: 1.53<br>F: 1.51 | 1H NMR (400 MHz, DMSO-$d_6$) δ ppm 11.80 (s, 1 H) 8.95 (d, J = 8.09 Hz, 1 H) 8.54 (dd, J = 1.41, 0.91 Hz, 1 H) 8.35 (d, J = 8.28 Hz, 1 H) 8.09 (d, J = 0.69 Hz, 1 H) 7.94 (d, J = 2.07 Hz, 1 H) 7.76 (dd, J = 8.31, 1.47 Hz, 1 H) 7.23-7.30 (m, 1 H) 6.99-7.04 (m, 2 H) 6.82 (ddd, J = 8.20, 2.49, 0.97 Hz, 1 H) 5.21 (quin, J = 7.37 Hz, 1 H) 3.76 (s, 3 H) 1.52 (d, J = 7.03 Hz, 3 H). |
| XIV-29 | (structure with F substituent) | 3-fluoro-N-(3-fluorobenzyl)-9H-pyrido[3,4-b]indole-7-carboxamide | 338.1 | E: 1.47<br>F: 1.43 | 1H NMR (400 MHz, DMSO-$d_6$) δ ppm 11.83 (s, 1 H) 9.24 (t, J = 5.90 Hz, 1 H) 8.53 (s, 1 H) 8.35 (d, J = 8.28 Hz, 1 H) 8.11 (d, J = 0.75 Hz, 1 H) 7.93 (d, J = 2.01 Hz, 1 H) 7.77 (dd, J = 8.28, 1.25 Hz, 1 H) 7.39 (td, J = 7.91, 6.02 Hz, 1 H) 7.14-7.24 (m, 2 H) 7.08 (td, J = 8.60, 1.88 Hz, 1 H) 4.55 (d, J = 5.77 Hz, 2 H) |
| XIV-30 | (structure with CN substituent) | N-(3-cyanobenzyl)-1-fluoro-9H-pyrido[3,4-b]indole-7-carboxamide | 345.1 | E: 1.33<br>F: 1.30 | 1H NMR (400 MHz, DMSO-$d_6$) δ ppm 12.37 (s, 1 H) 9.32 (t, J = 5.90 Hz, 1 H) 8.37 (d, J = 8.28 Hz, 1 H) 8.13-8.18 (m, 2 H) 7.94 (dd, J = 5.33, 1.82 Hz, 1 H) 7.80-7.86 (m, 2 H) 7.70-7.77 (m, 2 H) 7.56-7.61 (m, 1 H) 4.59 (d, J = 5.90 Hz, 2 H) |

TABLE XIV-continued

| Ex. No. | Structure | Name | LCMS [M + H]+ | HPLC Method, RT (min.) | 1H NMR (δ, ppm) |
|---|---|---|---|---|---|
| XIV-31 | (structure with 3-methoxyphenyl, ethyl, N-ethyl pyrido-indole) | (R)-9-ethyl-N-(1-(3-methoxyphenyl)ethyl)-9H-pyrido[3,4-b]indole-7-carboxamide | 374.2 | E: 1.21<br>F: 1.66 | 1H NMR (400 MHz, methanol-d4) δ ppm 9.00 (s, 1 H) 8.29-8.46 (m, 2 H) 8.11-8.24 (m, 2 H) 7.82 (dd, J = 8.22, 1.44 Hz, 1 H) 7.24-7.41 (m, 1 H) 7.01-7.13 (m, 2 H) 6.84 (ddd, J = 8.22, 2.45 , 1.00 Hz, 1 H) 5.32 (q, J = 7.03 Hz, 1 H) 4.53-4.69 (m, 2 H) 3.73-4.02 (m, 3 H) 1.64 (d, J = 7.09 Hz, 3 H) 1.51 (t, J = 7.22 Hz, 3 H) |
| XIV-32 | (structure with 3-methoxybenzyl) | 9-ethyl-N-(3-methoxybenzyl)-9H-pyrido[3,4-b]indole-7-carboxamide | 360.2 | E: 1.11<br>F: 1.50 | 1H NMR (400 MHz, methanol-d4) δ ppm 9.01 (s, 1 H) 8.31-8.46 (m, 2 H) 8.16-8.27 (m, 2 H) 7.84 (dd, J = 8.25, 1.47 Hz, 1 H) 7.20-7.36 (m, 1 H) 6.96-7.10 (m, 2 H) 6.77-6.93 (m, 1 H) 4.47-4.73 (m, 6 H) 3.82 (s, 3 H) 1.51 (t, J = 7.22 Hz, 3 H) |
| XIV-33 | (structure with 3-chlorobenzyl) | N-(3-chlorobenzyl)-9-ethyl-9H-pyrido[3,4-b]indole-7-carboxamide | 364.2 | E: 1.22<br>F: 1.64 | 1H NMR (400 MHz, DMSO-d6) δ ppm 8.96-9.34 (m, 2 H) 8.36-8.50 (m, 2 H) 8.30 (d, J = 0.69 Hz, 1H) 8.21 (dd, J = 5.21, 1.07 Hz, 1 H) 7.87 (dd, J = 8.22, 1.44 Hz, 1 H) 7.42-7.54 (m, 2 H) 7.23-7.40 (m, 2 H) 4.41-4.73 (m, 4 H) 1.42 (t, J = 7.15 Hz, 3 H) |
| XIV-34 | (structure with 3-cyanobenzyl) | N-(3-cyanobenzyl)-9-ethyl-9H-pyrido[3,4-b]indole-7-carboxamide | 355.2 | E: 1.04<br>F: 1.42 | 1H NMR (400 MHz, DMSO-d6) δ 9.47 (s, 1H), 9.37 (t, J = 5.8 Hz, 1H), 8.67 (br. s., 1H), 8.63-8.55 (m, 2H), 8.39 (s, 1H), 7.95 (dd, J = 8.3, 1.3 Hz, 1H), 7.83 (s, 1H), 7.78-7.70 (m, 2H), 7.62-7.55 (m, 1H), 4.70 (q, J = 7.5 Hz, 2H), 4.62 (d, J = 6.0 Hz, 2H), 1.44 (t, J = 7.3 Hz, 3H) |

TABLE XIV-continued

| Ex. No. | Structure | Name | LCMS [M + H]+ | HPLC Method, RT (min.) | 1H NMR (δ, ppm) |
|---|---|---|---|---|---|
| XIV-35 | (structure) | 9-ethyl-N-(2-fluorobenzyl)-9H-pyrido[3,4-b]indole-7-carboxamide | 338.2 | E: 1.15<br>F: 1.53 | 1H NMR (400 MHz, methanol-d4) δ 8.98 (s, 1H), 8.38 (d, J = 5.5 Hz, 1H), 8.36-8.30 (m, 1H), 8.22-8.15 (m, 2H), 7.81 (dd, J = 8.0, 1.5 Hz, 1H), 7.47 (td, J = 7.7, 1.8 Hz, 1H), 7.36-7.27 (m, 1H), 7.21-7.08 (m, 2H), 4.61 (q, J = 7.0 Hz, 2H), 4.56 (s, 2H), 1.49 (t, J = 7.3 Hz, 3H) |
| XIV-36 | (structure) | (R)-N-(1-(3-methoxyphenyl)ethyl)-4-methyl-9H-pyrido[3,4-b]indole-7-carboxamide | 360.2 | M: 1.66<br>N: 2.11 | 1H NMR (400 MHz, DMSO-d6) δ ppm 11.83 (s, 1 H) 8.96 (d, J = 8.16 Hz, 1H) 8.81 (s, 1H) 8.27 (d, J = 8.35 Hz, 1 H) 8.19 (d, J = 0.63 Hz, 1 H) 8.12 (d, J = 0.94 Hz, 1 H) 7.79 (dd, J = 8.31, 1.54 Hz, 1 H) 7.23-7.28 (m, 1 H) 6.99-7.04 (m, 2 H) 6.81 (ddd, J = 8.20, 2.37, 1.10 Hz, 1 H) 5.21 (quin, J = 7.34 Hz, 1 H) 3.75 (s, 3 H) 2.81 (s, 3 H) 1.52 (d, J = 7.09 Hz, 3 H) |
| XIV-37 | (structure) | N-(2-fluoro-5-methoxybenzyl)-4-methyl-9H-pyrido[3,4-b]indole-7-carboxamide | 364.2 | M: 1.62<br>N: 2.06 | 1H NMR (400 MHz, DMSO-d6) δ ppm 11.86 (s, 1 H) 9.17 (t, J = 5.87 Hz, 1 H) 8.82 (s, 1 H) 8.29 (d, J = 8.35 Hz, 1 H) 8.12-8.21 (m, 2 H) 7.81 (dd, J = 8.35, 1.51 Hz, 1 H) 7.10-7.17 (m, 1 H) 6.95 (dd, J = 6.12, 3.17 Hz, 1 H) 6.86 (dt, J = 8.85, 3.67 Hz, 1 H) 4.54 (d, J = 5.71 Hz, 2 H) 3.71 (s, 3 H) 2.82 (s, 3 H). |

Compounds listed in Table XV were prepared by following similar procedures to those described for Example I-1 using the appropriate intermediates described or purchased from commercial sources. Coupling reagents, such as HATU, T$_3$P, BOP, PyBop, and EDC/HOBt, could be used instead of the one described.

TABLE XV

| Ex. No. | Structure | Name | LCMS [M + H]$^+$ | HPLC Method, RT (min.) | $^1$H NMR (δ, ppm) |
|---|---|---|---|---|---|
| XV-1 | 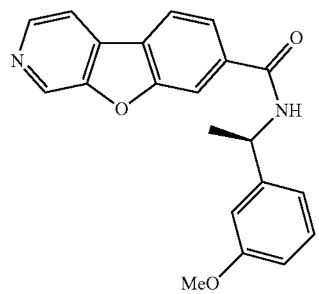 [SMILES: COc1cccc([C@@H](C)NC(=O)c2ccc3c(c2)oc2cnccc23)c1] | (R)-N-(1-(3-methoxyphenyl)ethyl)benzofuro[2,3-c]pyridine-7-carboxamide | 347.2 | I: 6.30 J: 6.45 | $^1$H NMR (400 MHz, DMSO-d$_6$) δ ppm 9.16 (d, J = 0.69 Hz, 1 H), 9.02 (d, J = 7.97 Hz, 1 H), 8.65 (d, J = 5.02 Hz, 1 H), 8.36-8.42 (m, 1 H), 8.32 (d, J = 0.82 Hz, 1 H), 8.26 (dd, J = 5.08, 1.00 Hz, 1 H), 8.04 (dd, J = 8.16, 1.38 Hz, 1 H), 7.22-7.31 (m, 1 H), 7.01 (d, J = 2.45 Hz, 2 H), 6.82 (ddd, J = 8.20, 2.49, 0.91 Hz, 1 H), 5.20 (quin, J = 7.23 Hz, 1 H), 3.76 (s, 3 H), 1.52 (d, J = 7.09 Hz, 3 H) |
| XV-2 | 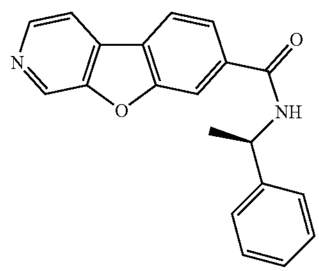 [SMILES: C[C@@H](NC(=O)c1ccc2c(c1)oc1cnccc12)c1ccccc1] | (R)-N-(1-phenylethyl)benzofuro[2,3-c]pyridine-7-carboxamide | 317.1 | I: 6.23 J: 6.35 | $^1$H NMR (400 MHz, DMSO-d$_6$) δ ppm 9.16 (d, J = 0.69 Hz, 1 H), 9.05 (d, J = 7.97 Hz, 1 H), 8.65 (d, J = 5.08 Hz, 1 H), 8.39 (dd, J = 8.13, 0.41 Hz, 1 H), 8.33 (d, J = 0.82 Hz, 1 H), 8.26 (dd, J = 5.08, 1.00 Hz, 1 H), 8.04 (dd, J = 8.16, 1.44 Hz, 1 H), 7.42-7.47 (m, 2 H), 7.32-7.38 (m, 2 H), 7.21-7.28 (m, 1 H), 5.23 (quin, J = 7.23 Hz, 1 H), 1.54 (d, J = 7.03 Hz, 3 H) |
| XV-3 | 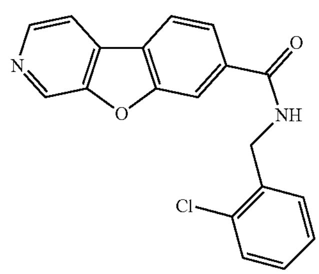 [SMILES: O=C(NCc1ccccc1Cl)c1ccc2c(c1)oc1cnccc12] | N-(2-chlorobenzyl)benzofuro[2,3-c]pyridine-7-carboxamide | 337.0 | I: 6.72 J: 6.92 | $^1$H NMR (400 MHz, DMSO-d$_6$) δ ppm 9.30 (t, J = 5.7 Hz, 1 H), 9.18 (s, 1 H), 8.66 (d, J = 5.0 Hz, 1 H), 8.42 (d, J = 8.2 Hz, 1 H), 8.36 (s, 1 H), 8.28 (dd, J = 1.0, 5.1 Hz, 1 H), 8.08 (dd, J = 1.4, 8.2 Hz, 1 H), 7.52-7.47 (m, 1 H), 7.46-7.41 (m, 1 H), 7.40-7.25 (m, 2 H), 4.63 (d, J = 5.8 Hz, 2 H) |
| XV-4 | 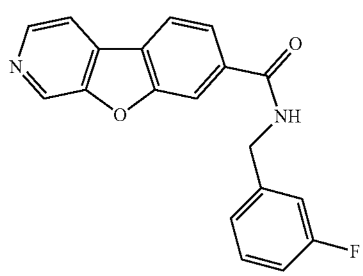 [SMILES: O=C(NCc1cccc(F)c1)c1ccc2c(c1)oc1cnccc12] | N-(3-fluorobenzyl)benzofuro[2,3-c]pyridine-7-carboxamide | 321.1 | I: 6.25 J: 6.47 | $^1$H NMR (400 MHz, DMSO-d$_6$) δ ppm 9.34 (t, J = 5.87 Hz, 1 H), 9.17 (d, J = 0.56 Hz, 1 H), 8.66 (d, J = 5.08 Hz, 1 H), 8.41 (d, J = 8.16 Hz, 1 H), 8.33 (d, J = 0.75 Hz, 1 H), 8.27 (dd, J = 5.08, 1.00 Hz, 1 H), 8.06 (dd, J = 8.16, 1.38 Hz, 1 H), 7.40 (td, J = 7.87, 6.21 Hz, 1 H), 7.16-7.25 (m, 2 H), 7.10 (td, J = 8.56, 2.26 Hz, 1 H), 4.57 (d, J = 5.96 Hz, 2 H) |
| XV-5 | 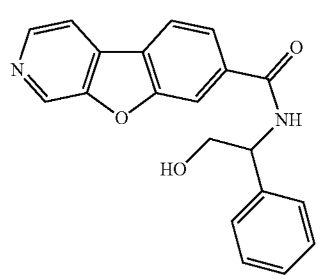 [SMILES: O=C(NC(CO)c1ccccc1)c1ccc2c(c1)oc1cnccc12] | N-(2-hydroxy-1-phenylethyl)benzofuro[2,3-c]pyridine-7-carboxamide, TFA | 333.2 | K: 9.14 L: 10.29 | $^1$H NMR (400 MHz, DMSO-d$_6$) δ ppm 9.17 (s, 1 H), 8.97 (d, J = 8.28 Hz, 1 H), 8.66 (d, J = 4.96 Hz, 1 H), 8.40 (d, J = 8.16 Hz, 1 H), 8.36 (d, J = 0.75 Hz, 1 H), 8.27 (dd, J = 5.08, 1.00 Hz, 1 H), 8.06 (dd, J = 8.16, 1.44 Hz, 1 H), 7.44 (d, J = 7.34 Hz, 2 H), 7.32-7.39 (m, 2 H), 7.23-7.29 (m, 1 H), 5.10-5.18 (m, 1 H), 5.01 (t, J = 5.84 Hz, 1 H), 3.74-3.82 (m, 1 H), 3.65-3.73 (m, 1 H) |

TABLE XV-continued

| Ex. No. | Structure | Name | LCMS [M + H]+ | HPLC Method, RT (min.) | 1H NMR (δ, ppm) |
|---|---|---|---|---|---|
| XV-6 | 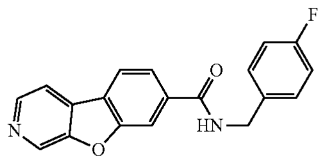 [SMILES: O=C(NCc1ccc(F)cc1)c1ccc2c(c1)oc1cnccc12] | N-(4-fluorobenzyl) benzofuro[2,3-c] pyridine-7- carboxamide, TFA | 321.2 | K: 11.64 L: 12.77 | 1H NMR (400 MHz, DMSO-d6) δ ppm 9.34 (t, J = 5.80 Hz, 1 H), 9.29 (br. s., 1 H), 8.73 (d, J = 5.02 Hz, 1 H), 8.46 (d, J = 8.16 Hz, 1 H), 8.41 (d, J = 5.21 Hz, 1 H), 8.35 (s, 1 H), 8.08 (dd, J = 8.16, 1.19 Hz, 1 H), 7.38-7.45 (m, 2 H), 7.14-7.22 (m, 2 H), 4.54 (d, J = 5.90 Hz, 2 H) |
| XV-7 | 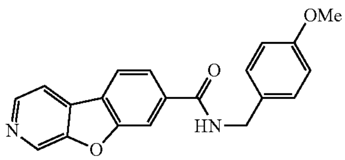 [SMILES: COc1ccc(CNC(=O)c2ccc3c(c2)oc2cnccc23)cc1] | N-(4- methoxybenzyl) benzofuro[2,3-c] pyridine-7- carboxamide | 333.2 | K: 11.18 L: 12.31 | 1H NMR (400 MHz, DMSO-d6) δ ppm 9.24 (t, J = 6.02 Hz, 1 H), 9.16 (d, J = 0.75 Hz, 1 H), 8.66 (s, 1 H), 8.39 (d, J = 8.09 Hz, 1 H), 8.31 (s, 1 H), 8.24-8.29 (m, 1 H), 8.04 (dd, J = 8.16, 1.38 Hz, 1 H), 7.27-7.33 (m, 2 H), 6.89-6.94 (m, 2 H), 4.48 (d, J = 5.90 Hz, 2 H), 3.74 (s, 3 H) |
| XV-8 | 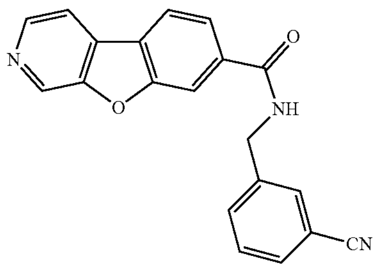 [SMILES: N#Cc1cccc(CNC(=O)c2ccc3c(c2)oc2cnccc23)c1] | N-(3- cyanobenzyl) benzofuro[2,3-c] pyridine-7- carboxamide | 328.2 | I: 5.88 J: 6.07 | 1H NMR (300MHz, DMSO-d6) δ ppm 9.37 (t, J = 6.0 Hz, 1 H), 9.17 (s, 1 H), 8.65 (t, J = 5.1 Hz, 1 H), 8.40 (d, J = 8.2 Hz, 1 H), 8.33 (s, 1 H), 8.27 (dd, J = 0.9, 5.1 Hz, 1 H), 8.05 (dd, J = 1.3, 8.2 Hz, 1 H), 7.82 (s, 1 H), 7.74 (t, J = 8.0 Hz, 2 H), 7.62-7.51 (m, 1 H), 4.59 (d, J = 5.9 Hz, 2 H) |
| XV-9 | 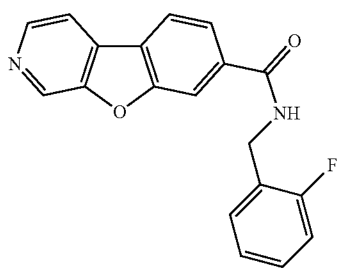 [SMILES: O=C(NCc1ccccc1F)c1ccc2c(c1)oc1cnccc12] | N-(2- fluorobenzyl) benzofuro[2,3-c] pyridine-7- carboxamide | 321.2 | I: 5.98 J: 6.74 | 1H NMR (400MHz, DMSO-d6) δ ppm 9.30 (t, J = 5.8 Hz, 1 H), 9.17 (s, 1 H), 8.66 (d, J = 5.0 Hz, 1 H), 8.41 (dd, J = 0.5, 8.2 Hz, 1 H), 8.36-8.31 (m, 1 H), 8.27 (dd, J = 1.0, 5.1 Hz, 1 H), 8.06 (dd, J = 1.4, 8.2 Hz, 1 H), 7.46-7.40 (m, 1 H), 7.39-7.30 (m, 1 H), 7.26-7.10 (m, 2 H), 4.60 (d, J = 5.7 Hz, 2 H) |
| XV-10 | 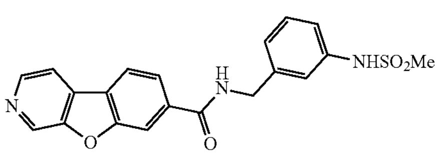 | N-(3- (methylsulfon- amido)benzyl) benzofuro[2,3- c]pyridine-7- carboxamide | 396.0 | M: 1.21 N: 1.66 | 1H NMR (400 MHz, DMSO-d6) δ ppm 9.74 (s, 1 H), 9.31 (t, J = 5.93 Hz, 1 H), 9.15 (d, J = 0.80 Hz, 1 H), 8.65 (d, J = 5.20 Hz, 1 H), 8.40 (d, J = 8.00Hz, 1 H), 8.31 (d, J = 0.80 Hz, 1 H), 8.27 (dd, J = 5.08, 1.07 Hz, 1 H), 8.05 (dd, J = 8.16, 1.44 Hz, 1 H), 7.27-7.35 (m, 1 H), 7.21-7.26 (m, 1 H), 7.01-7.15 (m, 2 H), 4.53 (d, J = 5.84 Hz, 2 H), 2.99 (s, 3 H) |
| XV-11 | 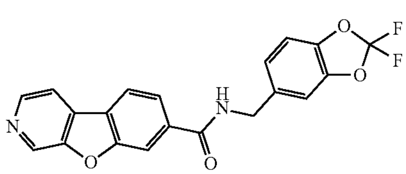 [SMILES: O=C(NCc1ccc2c(c1)OC(F)(F)O2)c1ccc2c(c1)oc1cnccc12] | N-((2,2- difluorobenzo [d][1,3]dioxol- 5-yl)methyl) benzofuro[2,3- c]pyridine-7- carboxamide | 383.0 | M: 1.79 N: 2.33 | 1H NMR (400 MHz, DMSO-d6) δ ppm 9.32 (t, J = 5.90 Hz, 1 H), 9.17 (d, J = 0.69 Hz, 1 H), 8.66 (s, 1 H), 8.40 (d, J = 8.16 Hz, 1 H), 8.32 (s, 1 H), 8.27 (dd, J = 5.08, 1.00 Hz, 1 H), 8.04 (dd, J = 8.13, 1.41 Hz, 1 H), 7.43 (d, J = 1.51 Hz, 1 H), 7.38 (d, J = 8.28 Hz, 1 H), 7.23 (dd, J = 8.31, 1.66 Hz, 1 H), 4.55 (d, J = 5.90 Hz, 2 H) |

TABLE XV-continued

| Ex. No. | Structure | Name | LCMS [M + H]+ | HPLC Method, RT (min.) | 1H NMR (δ, ppm) |
|---|---|---|---|---|---|
| XV-12 | 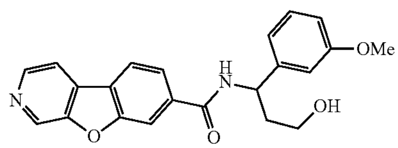 [SMILES: COc1cccc(C(CCO)NC(=O)c2ccc3c(c2)oc2cnccc23)c1] | N-(3-hydroxy-1-(3-methoxyphenyl)propyl)benzofuro[2,3-c]pyridine-7-carboxamide | 377.2 | M: 1.31 N: 1.79 | 1H NMR (400 MHz, DMSO-d6) δ ppm 9.16 (d, J = 0.80 Hz, 1 H), 9.00 (d, J = 8.16 Hz, 1 H), 8.66 (d, J = 4.80 Hz, 1 H), 8.39 (dd, J = 8.13, 0.53 Hz, 1 H), 8.22-8.33 (m, 1 H), 8.02 (dd, J = 8.16, 1.44 Hz, 1 H), 7.20-7.32 (m, 1 H), 6.95-7.04 (m, 2 H), 6.81 (ddd, J = 8.22, 2.48, 0.97 Hz, 1 H), 5.20 (td, J = 8.41, 6.21 Hz, 1 H), 3.75 (s, 3 H), 3.37-3.56 (m, 2 H), 2.02-2.15 (m, 1 H), 1.90-2.00 (m, 1 H), 1.87 (s, 2 H) |
| XV-13 | 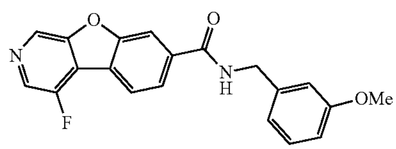 [SMILES: COc1cccc(CNC(=O)c2ccc3c(c2)oc2cncc(F)c23)c1] | 4-fluoro-N-(3-methoxybenzyl)benzofuro[2,3-c]pyridine-7-carboxamide | 351.0 | M: 2.21 N: 2.27 | 1H NMR (400 MHz, DMSO-d6) δ ppm 9.33 (t, J = 5.87 Hz, 1 H) 9.10 (dd, J = 1.98, 0.53 Hz, 1 H) 8.68 (s, 1 H) 8.38 (dd, J = 1.38, 0.56 Hz, 1 H) 8.28 (dd, J = 8.16, 0.56 Hz, 1 H) 8.10 (dd, J = 8.13, 1.41 Hz, 1 H) 7.23-7.29 (m, 1 H) 6.92-6.97 (m, 2 H) 6.81-6.86 (m, 1 H) 4.53 (d, J = 5.90 Hz, 2 H) 3.75 (s, 3 H). |
| XV-14 | 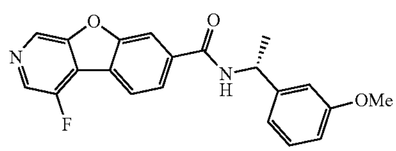 [SMILES: COc1cccc([C@@H](C)NC(=O)c2ccc3c(c2)oc2cncc(F)c23)c1] | (R)-4-fluoro-N-(1-(3-methoxyphenyl)ethyl)benzofuro[2,3-c]pyridine-7-carboxamide | 365.2 | E: 1.59 F: 166 | 1H NMR (400 MHz, DMSO-d6) δ ppm 9.05-9.12 (m, 2 H) 8.69 (s, 1 H) 8.39 (d, J = 0.75 Hz, 1 H) 8.27 (dd, J = 8.13, 0.53 Hz, 1 H) 8.10 (dd, J = 8.16, 1.44 Hz, 1 H) 7.23-7.30 (m, 1 H) 6.98-7.03 (m, 2 H) 6.82 (ddd, J = 8.22, 2.51, 0.94 Hz, 1 H) 5.16-5.25 (m, 1 H) 3.76 (s, 3 H) 1.53 (d, J = 7.09 Hz, 3 H). |
| XV-15 | 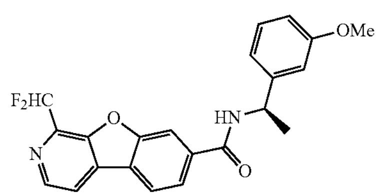 [SMILES: COc1cccc([C@@H](C)NC(=O)c2ccc3c(c2)oc2c(C(F)F)nccc23)c1] | (R)-1-(difluoromethyl)-N-(1-(3-methoxyphenyl)ethyl)benzofuro[2,3-c]pyridine-7-carboxamide | 397.2 | M: 2.59 N: 2.54 | 1H NMR (400 MHz, DMSO-d6) δ ppm 9.00 (d, J = 8.03 Hz, 1 H) 8.71 (d, J = 5.02 Hz, 1 H) 8.48 (d, J = 5.02 Hz, 1 H) 8.40-8.46 (m, 2 H) 8.06 (dd, J = 8.16, 1.38 Hz, 1 H) 7.37 (t, J = 53.6 Hz, 1 H) 7.22-7.26 (m, 1 H) 6.98-7.03 (m, 2 H) 6.81 (ddd, J = 8.19, 2.48, 0.94 Hz, 1 H) 5.19 (quin, J = 7.14 Hz, 1 H) 3.75 (s, 3 H) 1.51 (d, J = 7.09 Hz, 3 H). |
| XV-16 | 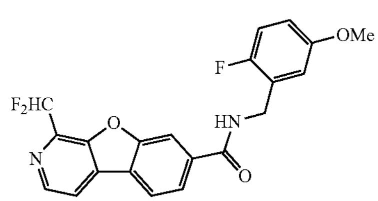 [SMILES: COc1ccc(F)c(CNC(=O)c2ccc3c(c2)oc2c(C(F)F)nccc23)c1] | 1-(difluoromethyl)-N-(2-fluoro-5-methoxybenzyl)benzofuro[2,3-c]pyridine-7-carboxamide | 401.0 | M: 2.58 N: 2.56 | 1H NMR (400 MHz, DMSO-d6) δ ppm 9.24 (t, J = 5.65 Hz, 1 H) 8.72 (d, J = 5.02 Hz, 1 H) 8.43-8.50 (m, 2 H) 8.38 (d, J = 0.75 Hz, 1 H) 8.08 (dd, J = 8.16, 1.38 Hz, 1 H) 7.37 (t, J = 52.0, 1 H) 7.14 (t, J = 9.29 Hz, 1 H) 6.96 (dd, J = 6.12, 3.17 Hz, 1 H) 6.87 (dt, J = 8.91, 3.61 Hz, 1 H) 4.55 (d, J = 5.71 Hz, 2 H) 3.72 (s, 3 H). |

EXAMPLE XVI-1

(R)-9-(Cyanomethyl)-N-(1-phenylethyl)-9H-pyrido[3,4-b]indole-7-carboxamide

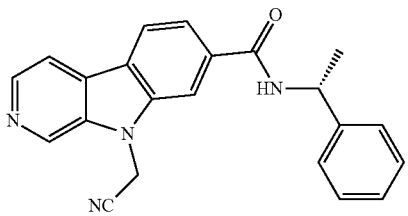 [SMILES: C[C@@H](NC(=O)c1ccc2c3ccncc3n(CC#N)c2c1)c1ccccc1]

EXAMPLE XVI-1A (R)-N-(1-Phenylethyl)-9H-pyrido[3,4-b]indole-7-carboxamide

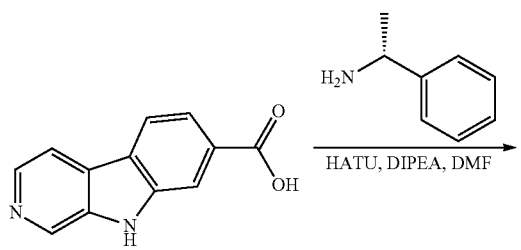

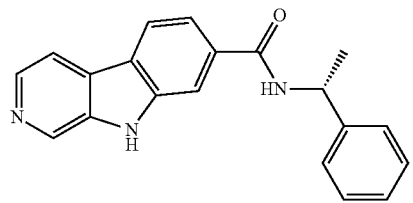

To a solution of Intermediate 22 (0.100 g, 0.471 mmol) in DMF (2 mL), HATU (0.358 g, 0.942 mmol) was added. The mixture was stirred for 20 min, then (R)-1-phenylethanamine (0.120 mL, 0.942 mmol) was added to the reaction mixture, followed by the addition of DIEA (0.247 mL, 1.41 mmol). The mixture was stirred at rt overnight. Water was added, then the reaction mixture was extracted with EtOAc (2×). The combined organic phase was dried with $Na_2SO_4$, filtered and concentrated. The product was purified by flash chromatography (gradient, 0-5% MeOH/$CHCl_3$) to afford Example XVI-1A (139 mg) as a yellow semi-solid. LC-MS (ESI) m/z: 316.1 [M+H]$^+$.

EXAMPLE XVI-1

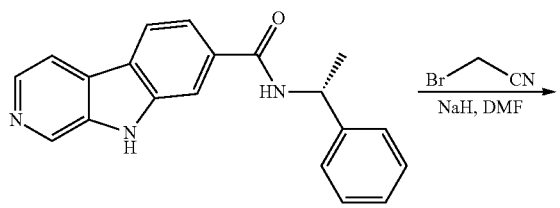

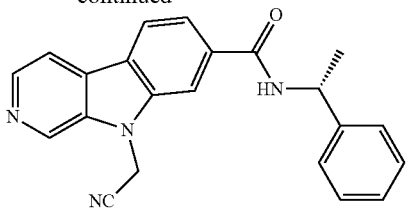

To s solution of Example XVI-1A (0.139 g, 0.295 mmol) in DMF (2 mL) at 0° C., sodium hydride (0.014 g, 0.35 mmol) was added. The mixture was stirred at RT for 15 min, then 2-bromoacetonitrile (0.031 mL, 0.44 mmol) was added. The mixture was stirred at rt for 1 h. Water was added, then the mixture was extracted with EtOAc (2×). The combined organic phase was dried over $Na_2SO_4$, filtered and concentrated. The crude product was purified by preparative HPLC (Acetonitrile/water/$NH_4OAc$) to afford Example XVI-1 (2 mg, 2% yield). MS (ESI) m/z: 355 [M+H]$^+$; $^1$H NMR (400 MHz, DMSO-$d_6$) δ=9.24 (s, 1 H), 8.97 (d, J=8.0 Hz, 1 H), 8.54 (d, J=5.0 Hz, 1 H), 8.43 (d, J=8.5 Hz, 1 H), 8.38 (s, 1 H), 8.27 (dd, J=1.0, 5.0 Hz, 1 H), 7.93 (dd, J=1.5, 8.0 Hz, 1 H), 7.49-7.44 (m, 2 H), 7.39-7.33 (m, 2 H), 7.28-7.22 (m, 1 H), 5.95 (s, 2 H), 5.28 (quin, J=7.2 Hz, 1 H), 1.56 (d, J=7.0 Hz, 3 H).

EXAMPLE XVI-2

N-(2-Chlorobenzyl)-1-methyl-9H-pyrido[3,4-b]indole-7-carboxamide

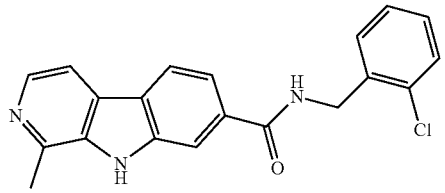 [SMILES: Cc1nccc2c1[nH]c1cc(C(=O)NCc3ccccc3Cl)ccc12]

EXAMPLE XVI-2A

Methyl 4-(2-methylpyridin-4-yl)-3-nitrobenzoate

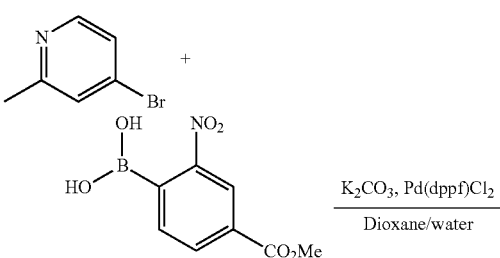

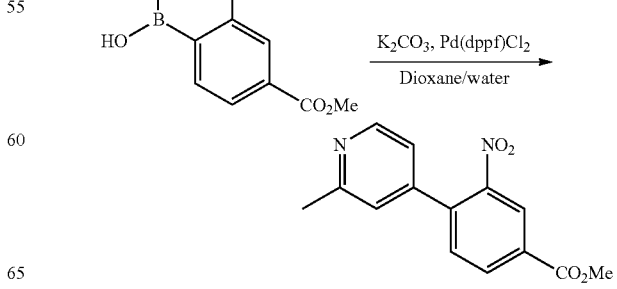

A solution of 4-bromo-2-methylpyridine (1.0 g, 5.81 mmol) and $K_2CO_3$ (2.41 g, 17.4 mmol) in dioxane (20 mL) and water (4 mL) was bubbled with nitrogen for 10 minutes. To this mixture were added (4-(methoxycarbonyl)-2-nitrophenyl)boronic acid (1.308 g, 5.81 mmol) and $PdCl_2(dppf)$-$CH_2Cl_2$ adduct (0.285 g, 0.349 mmol). The mixture was heated at 80° C. overnight. The reaction mixture was cooled to rt and diluted with EtOAc. The mixture was washed with brine solution (2×), dried with $Na_2SO_4$, filtered and concentrated. The crude product was purified by flash chromatography (gradient elution; 0-100% EtOAc/Hex.) to afford Example XVI-2A (520 mg, 30% yield) as a yellow solid. LC-MS (ESI) m/z: 273.5 $[M+H]^+$; $^1$H NMR (400 MHz, DMSO-$d_6$) δ ppm 8.51-8.56 (m, 2 H) 8.32 (dd, J=8.00, 1.73 Hz, 1 H) 7.75 (d, J=8.03 Hz, 1 H) 7.31-7.34 (m, 1 H) 7.22 (ddd, J=5.11, 1.73, 0.56 Hz, 1 H) 3.95 (s, 3 H) 2.53 (s, 3 H).

EXAMPLE XVI-2B

Methyl 1-methyl-9H-pyrido[3,4-b]indole-7-carboxylate and methyl 3-methyl-9H-pyrido[3,4-b]indole-7-carboxylate (~1:1 mixture)

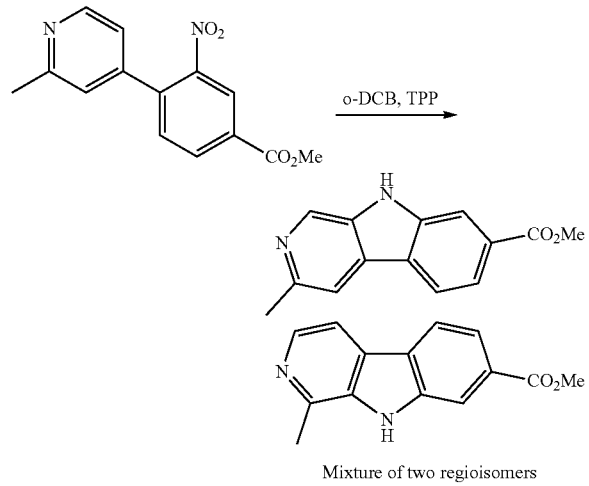

Mixture of two regioisomers

To a solution of Example XVI-2A (800 mg, 2.94 mmol) in 1,2-dichlorobenzene (8 mL), was added triphenylphosphine (1.93 g, 7.35 mmol). The mixture was heated at 170° C. for 5 h, then was cooled to rt. Pet. ether was added and the resultant precipitate was collected by filtration. The solid was purified by flash chromatography (gradient elution; 0-100% EtOAc/Hex.) to afford Example XVI-2B (690 mg) as a mixture of isomers. The mixture was contaminated with triphenylphosphine oxide and was taken onto the following step without further purification. LC-MS (ESI) m/z: 241.5 $[M+H]^+$.

EXAMPLE XVI-2C

3-Methyl-9H-pyrido[3,4-b]indole-7-carboxylic acid and 1-methyl-9H-pyrido[3,4-b]indole-7-carboxylic acid (~1:1 mixture)

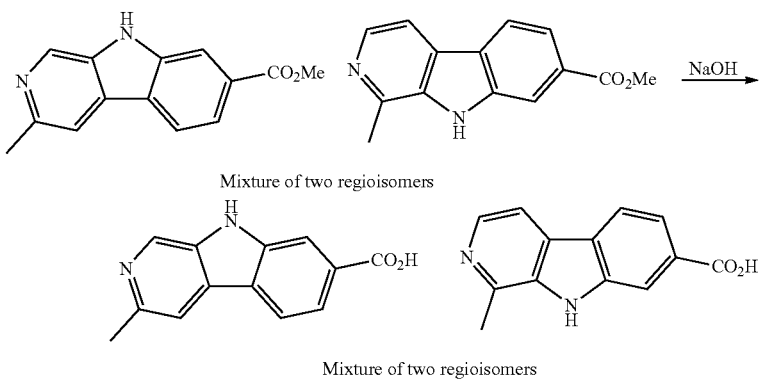

Mixture of two regioisomers

To a solution of Example XVI-2B (0.69 g, 2.87 mmol) in MeOH (6 mL) and water (2 mL), was added NaOH (0.345 g, 8.62 mmol). The mixture was stirred at rt overnight, then was concentrated. The mixture was taken up in water (10 mL) and the solid was removed by filtration. The filtrate was washed with ethyl acetate. The aqueous phase was acidified to pH 4 with 1.5N HCl and the resultant precipitated solid was collected by filtration. The solid was washed with water and pet. ether to gave Example XVI-2C (260 mg) as a yellow solid. LC-MS (ESI) m/z: 227.5 $[M+H]^+$.

EXAMPLE XVI-2

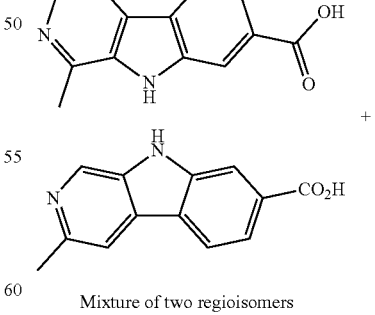

Mixture of two regioisomers

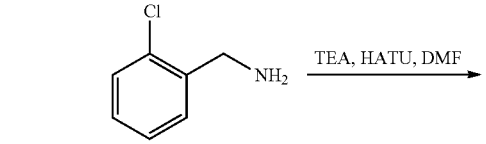

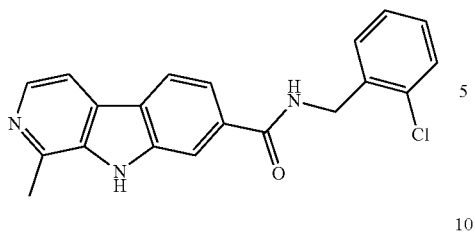

To a solution of Example XVI-2C (60 mg, 0.27 mmol) in DMF (2 mL), was added (2-chlorophenyl)methanamine (75 mg, 0.53 mmol), TEA (0.185 mL, 1.33 mmol) and HATU (111 mg, 0.292 mmol). The mixture was stirred at rt overnight. The reaction mixture was diluted with ice cold water (15 mL) and stirred for 15 minutes. The precipitate was collected by filtration, washed with water and pet. ether and dried. The material was purified by Supercritical Fluid Chromatography (SFC) to afford Example XVI-2. LC-MS (ESI) m/z: 350.2 [M+H]$^+$; $^1$H NMR (400 MHz, DMSO-d$_6$) δ ppm 11.79 (br. s., 1 H) 9.21 (t, J=5.77 Hz, 1 H) 8.28-8.33 (m, 1 H) 8.25 (d, J=5.33 Hz, 1 H) 8.14 (d, J=0.75 Hz, 1 H) 7.99 (dd, J=5.33, 0.44 Hz, 1 H) 7.80 (dd, J=8.28, 1.51 Hz, 1 H) 7.46-7.51 (m, 1 H) 7.39-7.44 (m, 1 H) 7.28-7.38 (m, 2 H) 4.61 (d, J=5.77 Hz, 2 H) 2.79 (s, 3 H).

EXAMPLE XVI-3

(R)-N-(1-(3-Methoxyphenyl)ethyl)-1-methyl-9H-pyrido[3,4-b]indole-7-carboxamide, and

EXAMPLE XVI-4

(R)-N-(1-(3-Methoxyphenyl)ethyl)-3-methyl-9H-pyrido[3,4-b]indole-7-carboxamide

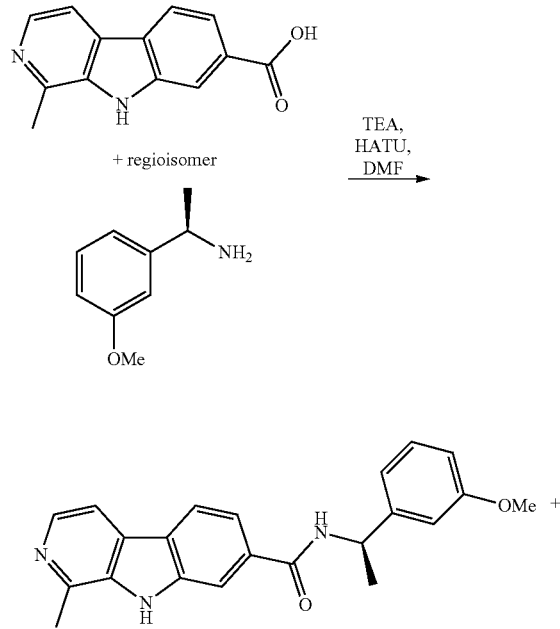

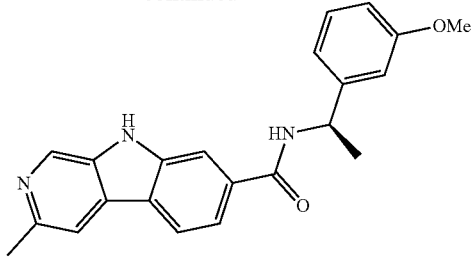

To a solution of Example XVI-2C (60 mg, 0.265 mmol) in DMF (2 mL), were added (R)-1-(3-methoxyphenyl)ethanamine (80 mg, 0.530 mmol), TEA (0.185 mL, 1.33 mmol) and HATU (111 mg, 0.292 mmol). The mixture was stirred at rt overnight. The reaction mixture was diluted with ice cold water (15 mL) and stirred for 15 minutes. The precipitate was collected by filtration, washed with water and pet. ether and dried. The material was purified by Supercritical Fluid Chromatography (Co-Solvent 0.3% DEA in methanol) to afford Example XVI-3 and Example XVI-4.

EXAMPLE XVI-3

40 mg. LC-MS (ESI) m/z: 360.2 [M+H]$^+$; $^1$H NMR (400 MHz, DMSO-d$_6$) δ ppm 11.76 (s, 1 H) 8.94 (d, J=8.22 Hz, 1 H) 8.22-8.31 (m, 2 H) 8.08 (d, J=0.69 Hz, 1 H) 7.98 (d, J=5.33 Hz, 1 H) 7.77 (dd, J=8.28, 1.44 Hz, 1 H) 7.23-7.29 (m, 1 H) 6.98-7.04 (m, 2 H) 6.78-6.84 (m, 1 H) 5.20 (quin, J=7.29 Hz, 1 H) 3.76 (s, 3 H) 2.78 (s, 3 H) 1.51 (d, J=7.09 Hz, 3 H).

EXAMPLE XVI-4

12 mg. LC-MS (ESI) m/z: 360.2 [M+H]$^+$; $^1$H NMR (400 MHz, DMSO-d$_6$) δ ppm 11.61 (s, 1 H) 8.92 (d, J=8.16 Hz, 1 H) 8.82 (d, J=1.07 Hz, 1 H) 8.26 (d, J=8.22 Hz, 1 H) 8.06 (d, J=0.75 Hz, 1 H) 7.99 (s, 1 H) 7.73 (dd, J=8.25, 1.47 Hz, 1 H) 7.22-7.29 (m, 1 H) 6.98-7.03 (m, 2 H) 6.81 (ddd, J=8.20, 2.46, 1.00 Hz, 1 H) 5.15-5.24 (quin, J=7.29 Hz, 1 H) 3.75 (s, 3 H) 2.62 (s, 3 H) 1.51 (d, J=7.03 Hz, 3 H).

EXAMPLE XVI-5

N-(2-Fluoro-5-methoxybenzyl)-1-methyl-9H-pyrido[3,4-b]indole-7-carboxamide

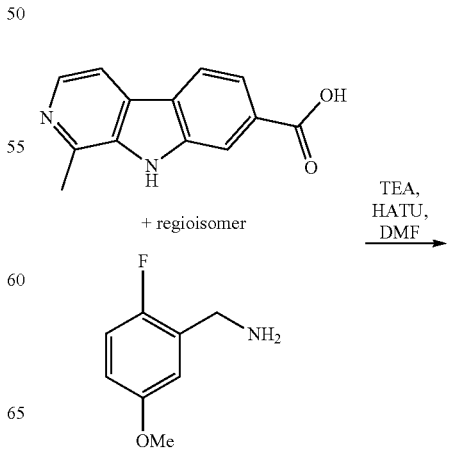

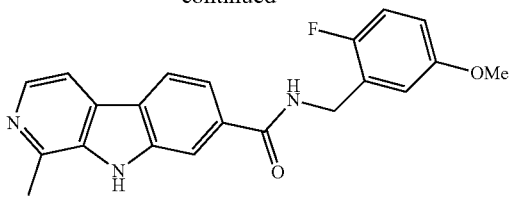

To a solution of Example XVI-2C (60 mg, 0.265 mmol) in DMF (2 mL), were added (2-fluoro-5-methoxyphenyl)methanamine (82 mg, 0.53 mmol), TEA (0.185 mL, 1.33 mmol) and HATU (111 mg, 0.292 mmol). The mixture was stirred at rt overnight. The reaction mixture was diluted with ice cold water (15 mL) and stirred for 15 minutes. The precipitate was collected by filtration, washed with water and pet. ether, and dried. The material was purified by Supercritical Fluid Chromatography (Co-Solvent 0.3% DEA in methanol) to afford 37 mg (38%) of Example XVI-5. LC-MS (ESI) m/z: 364.2 [M+H]$^+$; $^1$H NMR (400 MHz, DMSO-d$_6$) δ ppm 11.78 (s, 1 H) 9.16 (t, J=5.84 Hz, 1 H) 8.29 (dd, J=8.25, 0.47 Hz, 1 H) 8.24 (d, J=5.33 Hz, 1 H) 8.11 (d, J=0.82 Hz, 1 H) 7.99 (d, J=5.33 Hz, 1 H) 7.77 (dd, J=8.28, 1.51 Hz, 1 H) 7.14 (t, J=9.32 Hz, 1 H) 6.95 (dd, J=6.12, 3.17 Hz, 1 H) 6.86 (dt, J=8.82, 3.66 Hz, 1 H) 4.54 (d, J=5.77 Hz, 2 H) 3.71 (s, 3 H) 2.79 (s, 3 H).

EXAMPLE XVI-6

N-(3-Methoxybenzyl)-1-methyl-9H-pyrido[3,4-b]indole-7-carboxamide

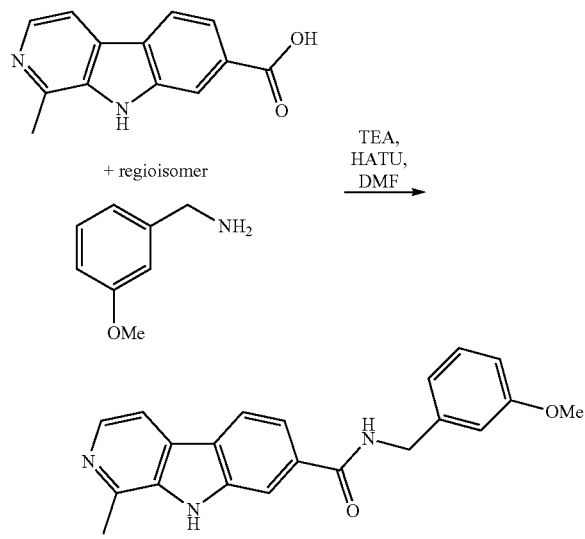

To a solution of Example XVI-2C (60 mg, 0.265 mmol) in DMF (2 mL), were added (3-methoxyphenyl)methanamine (72.8 mg, 0.530 mmol), TEA (0.185 mL, 1.33 mmol) and HATU (111 mg, 0.292 mmol). The mixture was stirred at rt overnight. The reaction mixture was diluted with ice cold water (15 mL) and stirred for 15 minutes. The precipitate was collected by filtration, washed with water and pet. ether, and dried. The material was purified by Supercritical Fluid Chromatography (Co-Solvent 0.3% DEA in methanol) to afford 34 mg (37%) of Example XVI-6. LC-MS (ESI) m/z: 346.2 [M+H]$^+$; $^1$H NMR (400 MHz, DMSO-d$_6$) δ ppm 11.76 (s, 1 H) 9.18 (t, J=5.99 Hz, 1 H) 8.29 (dd, J=8.25, 0.53 Hz, 1 H) 8.24 (d, J=5.33 Hz, 1 H) 8.12 (d, J=0.75 Hz, 1 H) 7.98 (dd, J=5.33, 0.50 Hz, 1 H) 7.77 (dd, J=8.28, 1.51 Hz, 1 H) 7.24-7.30 (m, 1 H) 6.92-6.97 (m, 2 H) 6.80-6.86 (m, 1 H) 4.52 (d, J=5.96 Hz, 2 H) 3.75 (s, 3 H) 2.79 (s, 3 H).

What is claimed is:
1. A compound of Formula (IV):

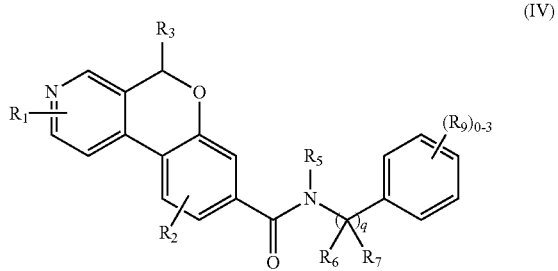

or a stereoisomer, tautomer, pharmaceutically acceptable salt thereof, wherein
$R_1$ and $R_2$ are H;
$R_3$ is independently selected from H and Me;
$R_5$ is H;
$R_6$ and $R_7$ are independently selected from H, $C_{1-4}$alkyl substituted with 0-4 $R_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, —(CH$_2$)$_r$-C$_{3-6}$ carbocyclyl substituted with 0-3 $R_e$, and —(CH$_2$)$_r$-heterocyclyl substituted with 0-3 $R_e$;
alternatively, $R_6$ and $R_7$ together with the carbon atom to which they are both attached form a cycloalkyl or heterocyclyl, each substituted with 0-5 $R_e$; alternatively, when q is 2 or 3, two adjacent $R_6$ groups form a cycloalkyl or heterocyclyl, each substituted with 0-5 $R_e$;
$R_9$ is independently selected from F, Cl, Br, $C_{1-4}$alkyl substituted with 0-5 $R_e$, $C_{2-4}$alkenyl substituted with 0-5 $R_e$, $C_{2-4}$alkynyl substituted with 0-5 $R_e$, =O, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 $R_e$;
alternatively, two adjacent $R_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 $R_e$;
$R_a$, at each occurrence, is independently selected from H, $C_{1-6}$ alkyl substituted with 0-5 $R_e$, $C_{2-6}$alkenyl substituted with 0-5 $R_e$, —(CH$_2$)$_r$-C$_{3-10}$ carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, —$(CH_2)_r$—$C_{3-10}$ carbocyclyl, —$(CH_2)_r$-heterocyclyl, F, Cl, Br, CN, $NO_2$, =O, $CO_2H$, $CO_2C_{1-6}$ alkyl, —$(CH_2)_rOC_{1-5}$ alkyl, —$(CH_2)_rOH$, —$(CH_2)_rNR_fR_f$, —$(CH_2)_rNR_fR_fC(=O)$ $C_{1-4}$alkyl, —$C(=O)NR_fR_f$, —$C(=O)R_f$, $S(O)_pNR_fR_f$, —$NR_fS(O)_pC_{1-4}$alkyl, and $S(O)_pC_{1-4}$alkyl;

$R_f$, at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from 1 and 2; and r, at each occurrence, is independently selected from zero, 1, 2, 3, and 4.

2. The compound of claim 1 or a stereoisomer, tautomer, pharmaceutically acceptable salt thereof, wherein $R_6$ and $R_7$ are independently selected from H and $C_{1-4}$alkyl substituted with 0-4 $R_e$;

$R_9$ is independently selected from F, Cl, Br, $C_{1-4}$alkyl substituted with 0-5 $R_e$, $C_{2-4}$alkenyl substituted with 0-5 $R_e$, =O, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_rOC(=O)R_b$, —$(CHR_d)_rC(=O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, $C_{1-6}$ alkyl substituted with 0-5 $R_e$, $C_{2-6}$alkenyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl (optionally substituted with F, Cl, Br, and OH), $C_{2-6}$ alkenyl, $C_{2-6}$ alkynyl, —$(CH_2)_r$—$C_{3-10}$ carbocyclyl, —$(CH_2)_r$-heterocyclyl, F, Cl, Br, CN, $NO_2$, =O, $CO_2H$, $CO_2C_{1-6}$ alkyl, —$(CH_2)_rOC_{1-5}$ alkyl, —$(CH_2)_rOH$, —$(CH_2)_rNR_fR_f$, —$(CH_2)_rNR_fR_fC(=O)$ $C_{1-4}$alkyl, —$C(=O)NR_fR_f$, —$C(=O)R_f$, $S(O)_pNR_fR_f$, —$NR_fS(O)_pC_{1-4}$alkyl, and $S(O)_pC_{1-4}$alkyl;

$R_f$, at each occurrence, is independently selected from H, F, Cl, Br, $C_{1-5}$alkyl, and $C_{3-6}$ cycloalkyl; or $R_f$ and $R_f$ together with the nitrogen atom to which they are both attached form a heterocyclic ring;

p, at each occurrence, is independently selected from zero, 1, and 2;

q, at each occurrence, is independently selected from 1 and 2; and r, at each occurrence, is independently selected from zero, 1, 2, 3, and 4.

3. A pharmaceutical composition comprising one or more compounds according to claim 1 and a pharmaceutically acceptable carrier or diluent.

4. A compound or a stereoisomer, tautomer, pharmaceutically acceptable salt thereof selected from:

(R)-N-(1-(3-Methoxyphenyl)ethyl)-5H-chromeno[3,4-c]pyridine-8-carboxamide;

N-(2-chlorobenzyl)-5H-chromeno[3,4-c]pyridine-8-carboxamide;

N-(1-phenylethyl)-5H-chromeno[3,4-c]pyridine-8-carboxamide;

N-phenethyl-5H-chromeno[3,4-c]pyridine-8-carboxamide;

N-(3-phenylpropyl)-5H-chromeno[3,4-c]pyridine-8-carboxamide;

N-(1-(2-chlorophenyl)cyclopropyl)-5H-chromeno[3,4-c]pyridine-8-carboxamide;

N-(cyclohexylmethyl)-5H-chromeno[3,4-c]pyridine-8-carboxamide;

N-((tetrahydrofuran-2-yl)methyl)-5H-chromeno[3,4-c]pyridine-8-carboxamide;

N-(2,2-diphenylethyl)-5H-chromeno[3,4-c]pyridine-8-carboxamide;

N-(2-chlorophenethyl)-5H-chromeno[3,4-c]pyridine-8-carboxamide;

N-(4-chlorophenethyl)-5H-chromeno[3,4-c]pyridine-8-carboxamide;

N-(4-methoxyphenethyl)-5H-chromeno[3,4-c]pyridine-8-carboxamide;

N-(4-hydroxyphenethyl)-5H-chromeno[3,4-c]pyridine-8-carboxamide;

N-(2-phenoxyethyl)-5H-chromeno[3,4-c]pyridine-8-carboxamide;

N-(1-benzylpyrrolidin-3-yl)-5H-chromeno[3,4-c]pyridine-8-carboxamide;

N-(4-cyanobenzyl)-5H-chromeno[3,4-c]pyridine-8-carboxamide;

N-(furan-2-ylmethyl)-5H-chromeno[3,4-c]pyridine-8-carboxamide;

N-(thiophen-2-ylmethyl)-5H-chromeno[3,4-c]pyridine-8-carboxamide;

N-(benzo[d][1,3]dioxol-5-ylmethyl)-5H-chromeno[3,4-c]pyridine-8-carboxamide;

N-(pyridin-3-ylmethyl)-5H-chromeno[3,4-c]pyridine-8-carboxamide;

N-(pyridin-4-ylmethyl)-5H-chromeno[3,4-c]pyridine-8-carboxamide;
N-benzyl-5H-chromeno[3,4-c]pyridine-8-carboxamide;
N-(2-methoxybenzyl)-5H-chromeno[3,4-c]pyridine-8-carboxamide;
N-(2-methylbenzyl)-5H-chromeno[3,4-c]pyridine-8-carboxamide;
N-(3-fluorobenzyl)-5H-chromeno[3,4-c]pyridine-8-carboxamide;
N-(3,4-dichlorobenzyl)-5H-chromeno[3,4-c]pyridine-8-carboxamide;
N-(3-methoxybenzyl)-5H-chromeno[3,4-c]pyridine-8-carboxamide;
N-(4-fluorobenzyl)-5H-chromeno[3,4-c]pyridine-8-carboxamide;
N-(4-methoxybenzyl)-5H-chromeno[3,4-c]pyridine-8-carboxamide;
N-(4-methylbenzyl)-5H-chromeno[3,4-c]pyridine-8-carboxamide;
N-(4-(trifluoromethyl)benzyl)-5H-chromeno[3,4-c]pyridine-8-carboxamide;
N-(3-nitrobenzyl)-5H-chromeno[3,4-c]pyridine-8-carboxamide;
N-(4-nitrobenzyl)-5H-chromeno[3,4-c]pyridine-8-carboxamide;
N-(2,3-dimethoxybenzyl)-5H-chromeno[3,4-c]pyridine-8-carboxamide;
N-(3-(trifluoromethoxy)benzyl)-5H-chromeno[3,4-c]pyridine-8-carboxamide;
N-(2-(trifluoromethoxy)benzyl)-5H-chromeno[3,4-c]pyridine-8-carboxamide;
N-(4-chloro-3-(trifluoromethyl)benzyl)-5H-chromeno[3,4-c]pyridine-8-carboxamide;
N-(biphenyl-2-ylmethyl)-5H-chromeno[3,4-c]pyridine-8-carboxamide;
N-(biphenyl-3-ylmethyl)-5H-chromeno[3,4-c]pyridine-8-carboxamide;
N-benzyl-N-methyl-5H-chromeno[3,4-c]pyridine-8-carboxamide;
N-(2-fluorobenzyl)-5H-chromeno[3,4-c]pyridine-8-carboxamide;
N-(4-sulfamoylbenzyl)-5H-chromeno[3,4-c]pyridine-8-carboxamide;
N-(4-aminobenzyl)-5H-chromeno[3,4-c]pyridine-8-carboxamide;
N-(pyridin-2-ylmethyl)-5H-chromeno[3,4-c]pyridine-8-carboxamide;
N-(4-fluorophenethyl)-5H-chromeno[3,4-c]pyridine-8-carboxamide;
N-(2-(phenylamino)ethyl)-5H-chromeno[3,4-c]pyridine-8-carboxamide;
N-(2-(thiophen-2-yl)ethyl)-5H-chromeno[3,4-c]pyridine-8-carboxamide;
N-methyl-N-phenethyl-5H-chromeno[3,4-c]pyridine-8-carboxamide;
N-(benzo[d]thiazol-2-ylmethyl)-5H-chromeno[3,4-c]pyridine-8-carboxamide;
N-(4-hydroxybenzyl)-5H-chromeno[3,4-c]pyridine-8-carboxamide;
(R)—N-(1-phenylethyl)-5H-chromeno[3,4-c]pyridine-8-carboxamide;
(S)-N-(1-phenylethyl)-5H-chromeno[3,4-c]pyridine-8-carboxamide;
(S)-N-(1-(2-chlorophenyl)ethyl)-5H-chromeno[3,4-c]pyridine-8-carboxamide;
N-(3,5-dichlorobenzyl)-5H-chromeno[3,4-c]pyridine-8-carboxamide;
N-(4-bromobenzyl)-5H-chromeno[3,4-c]pyridine-8-carboxamide;
N-(3-chlorobenzyl)-5H-chromeno[3,4-c]pyridine-8-carboxamide;
N-(3,4-dichlorobenzyl)-N-methyl-5H-chromeno[3,4-c]pyridine-8-carboxamide;
N-(2-(trifluoromethyl)benzyl)-5H-chromeno[3,4-c]pyridine-8-carboxamide;
N-(4-chlorobenzyl)-5H-chromeno[3,4-c]pyridine-8-carboxamide;
N-(3-methylbenzyl)-5H-chromeno[3,4-c]pyridine-8-carboxamide;
N-(3-(trifluoromethyl)benzyl)-5H-chromeno[3,4-c]pyridine-8-carboxamide;
N-(2,4-dimethoxybenzyl)-5H-chromeno[3,4-c]pyridine-8-carboxamide;
N-(2,3-dichlorobenzyl)-5H-chromeno[3,4-c]pyridine-8-carboxamide;
N-(3,4-dimethoxybenzyl)-5H-chromeno[3,4-c]pyridine-8-carboxamide;
N-(2,4-dichlorobenzyl)-5H-chromeno[3,4-c]pyridine-8-carboxamide;
N-(3-chlorophenethyl)-5H-chromeno[3,4-c]pyridine-8-carboxamide;
N-(2-phenylpropan-2-yl)-5H-chromeno[3,4-c]pyridine-8-carboxamide;
N-(2-aminobenzyl)-5H-chromeno[3,4-c]pyridine-8-carboxamide;
N-(2-hydroxybenzyl)-5H-chromeno[3,4-c]pyridine-8-carboxamide;
N-(3-hydroxybenzyl)-5H-chromeno[3,4-c]pyridine-8-carboxamide;
(R)-N-(1-(2-chlorophenyl)ethyl)-5H-chromeno[3,4-c]pyridine-8-carboxamide;
(S)-N-(1-(3-methoxyphenyl)ethyl)-5H-chromeno[3,4-c]pyridine-8-carboxamide;
N-(5-methoxy-2-oxoindolin-3-yl)-5H-chromeno[3,4-c]pyridine-8-carboxamide;
N-(3-ethoxybenzyl)-5H-chromeno[3,4-c]pyridine-8-carboxamide;
N-(3-(2-methoxyethoxy)benzyl)-5H-chromeno[3,4-c]pyridine-8-carboxamide;
N-(3-isopropoxybenzyl)-5H-chromeno[3,4-c]pyridine-8-carboxamide;
N-(3-phenoxybenzyl)-5H-chromeno[3,4-c]pyridine-8-carboxamide;
(S)-N-(1-(3-methoxyphenyl)propyl)-5H-chromeno[3,4-c]pyridine-8-carboxamide;
N-(1-(3-methoxyphenyl)cyclohexyl)-5H-chromeno[3,4-c]pyridine-8-carboxamide;
N-(2-(3-methoxyphenyl)propan-2-yl)-5H-chromeno[3,4-c]pyridine-8-carboxamide;
N-(2-chloro-3-methoxybenzyl)-5H-chromeno[3,4-c]pyridine-8-carboxamide;
N-(1-(3-ethoxyphenyl)-4-methylcyclohexyl)-5H-chromeno[3,4-c]pyridine-8-carboxamide;
N-(1-(3-ethoxyphenyl)ethyl)-5H-chromeno[3,4-c]pyridine-8-carboxamide;
N-(3-sulfamoylbenzyl)-5H-chromeno[3,4-c]pyridine-8-carboxamide;
N-(3-(N-ethylsulfamoyl)benzyl)-5H-chromeno[3,4-c]pyridine-8-carboxamide;
N-(2-oxo-2-o-tolylethyl)-5H-chromeno[3,4-c]pyridine-8-carboxamide;
N-((5-phenylisoxazol-3-yl)methyl)-5H-chromeno[3,4-c]pyridine-8-carboxamide;

N-((5-cyclopropyl-1H-pyrazol-3-yl)methyl)-5H-chromeno[3,4-c]pyridine-8-carboxamide;
N-((5-isopropyl-1,2,4-oxadiazol-3-yl)methyl)-5H-chromeno[3,4-c]pyridine-8-carboxamide;
N-((5-methylthiophen-3-yl)methyl)-5H-chromeno[3,4-c]pyridine-8-carboxamide;
N-(2-(4-fluorophenyl)-2-oxoethyl)-5H-chromeno[3,4-c]pyridine-8-carboxamide;
N-(2-oxo-2-phenylethyl)-5H-chromeno[3,4-c]pyridine-8-carboxamide;
N-((1H-benzo[d]imidazol-2-yl)methyl)-5H-chromeno[3,4-c]pyridine-8-carboxamide;
N-(2-(4-methoxyphenyl)-2-oxoethyl)-5H-chromeno[3,4-c]pyridine-8-carboxamide;
N-(thiophen-3-ylmethyl)-5H-chromeno[3,4-c]pyridine-8-carboxamide;
N-((1-methyl-1H-pyrazol-4-yl)methyl)-5H-chromeno[3,4-c]pyridine-8-carboxamide;
N-((3-phenyl-1H-pyrazol-4-yl)methyl)-5H-chromeno[3,4-c]pyridine-8-carboxamide;
N-(2-(3-nitrophenyl)-2-oxoethyl)-5H-chromeno[3,4-c]pyridine-8-carboxamide;
N-(2-(4-bromophenyl)-2-oxoethyl)-5H-chromeno[3,4-c]pyridine-8-carboxamide;
N-((5-methylisoxazol-3-yl)methyl)-5H-chromeno[3,4-c]pyridine-8-carboxamide;
N-((5-phenyl-1H-imidazol-2-yl)methyl)-5H-chromeno[3,4-c]pyridine-8-carboxamide;
N-(2-oxo-2-(pyridin-3-yl)ethyl)-5H-chromeno[3,4-c]pyridine-8-carboxamide;
N-(2-(4-chlorophenyl)-2-oxoethyl)-5H-chromeno[3,4-c]pyridine-8-carboxamide;
N-(2-(4-nitrophenyl)-2-oxoethyl)-5H-chromeno[3,4-c]pyridine-8-carboxamide;
N-(3-(methylsulfonyl)benzyl)-5H-chromeno[3,4-c]pyridine-8-carboxamide;
N-(1-(3,5-difluorophenyl)ethyl)-5H-chromeno[3,4-c]pyridine-8-carboxamide;
N-(3-(morpholine-4-carbonyl)benzyl)-5H-chromeno[3,4-c]pyridine-8-carboxamide;
N-(2-chloro-4-fluorobenzyl)-5H-chromeno[3,4-c]pyridine-8-carboxamide;
N-(2,4-difluoro-3-methoxybenzyl)-5H-chromeno[3,4-c]pyridine-8-carboxamide;
N-(2,6-difluoro-3-methoxybenzyl)-5H-chromeno[3,4-c]pyridine-8-carboxamide;
(R)-N-(1-(3-ethoxyphenyl)ethyl)-5H-chromeno[3,4-c]pyridine-8-carboxamide;
(S)-N-(1-(3-ethoxyphenyl)ethyl)-5H-chromeno[3,4-c]pyridine-8-carboxamide;
N-((1H-1,2,4-triazol-3-yl)methyl)-5H-chromeno[3,4-c]pyridine-8-carboxamide;
N-(thiazol-2-ylmethyl)-5H-chromeno[3,4-c]pyridine-8-carboxamide;
3-((5H-chromeno[3,4-c]pyridine-8-carboxamido)methyl)-5-tent-butylfuran-2-carboxylic acid;
N-((1H-imidazol-2-yl)methyl)-5H-chromeno[3,4-c]pyridine-8-carboxamide;
N-(oxazol-2-ylmethyl)-5H-chromeno[3,4-c]pyridine-8-carboxamide;
N-((2-bromothiophen-3-yl)methyl)-5H-chromeno[3,4-c]pyridine-8-carboxamide;
N-((3,5-dimethylisoxazol-4-yl)methyl)-5H-chromeno[3,4-c]pyridine-8-carboxamide;
N-((6-oxo-1,6-dihydropyridin-3-yl)methyl)-5H-chromeno[3,4-c]pyridine-8-carboxamide;
N-(2-(3-fluorophenyl)-2-oxoethyl)-5H-chromeno[3,4-c]pyridine-8-carboxamide;
N-((5-phenyl-1,3,4-oxadiazol-2-yl)methyl)-5H-chromeno[3,4-c]pyridine-8-carboxamide;
N-((1,2,4-oxadiazol-3-yl)methyl)-5H-chromeno[3,4-c]pyridine-8-carboxamide;
N-(1-(3-fluorophenyl)ethyl)-5H-chromeno[3,4-c]pyridine-8-carboxamide;
N-(2-fluoro-5-methoxybenzyl)-5H-chromeno[3,4-c]pyridine-8-carboxamide;
N-(5-fluoro-2-methylbenzyl)-5H-chromeno[3,4-c]pyridine-8-carboxamide;
N-(2,5-difluorobenzyl)-5H-chromeno[3,4-c]pyridine-8-carboxamide;
N-(3,5-difluorobenzyl)-5H-chromeno[3,4-c]pyridine-8-carboxamide;
N-((5-methyl-1H-pyrazol-4-yl)methyl)-5H-chromeno[3,4-c]pyridine-8-carboxamide;
N-(furan-3-ylmethyl)-5H-chromeno[3,4-c]pyridine-8-carboxamide;
N-((1H-indazol-3-yl)methyl)-5H-chromeno[3,4-c]pyridine-8-carboxamide;
N-((5-methyl-1,3,4-oxadiazol-2-yl)methyl)-5H-chromeno[3,4-c]pyridine-8-carboxamide;
N-((4,5,6,7-tetrahydro-1H-indazol-3-yl)methyl)-5H-chromeno[3,4-c]pyridine-8-carboxamide;
N-((5-(2-fluorophenyl)-1,3,4-oxadiazol-2-yl)methyl)-5H-chromeno[3,4-c]pyridine-8-carboxamide;
N-(imidazo[1,2-a]pyridine-6-ylmethyl)-5H-chromeno[3,4-c]pyridine-8-carboxamide;
N-((5-ethyl-1,3,4-oxadiazol-2-yl)methyl)-5H-chromeno[3,4-c]pyridine-8-carboxamide;
N-((5-cyclopropylisoxazol-3-yl)methyl)-5H-chromeno[3,4-c]pyridine-8-carboxamide;
N-((4-bromothiazol-2-yl)methyl)-5H-chromeno[3,4-c]pyridine-8-carboxamide;
N-(benzo[c][1,2,5]thiadiazol-4-ylmethyl)-5H-chromeno[3,4-c]pyridine-8-carboxamide;
N-((1H-pyrazol-4-yl)methyl)-5H-chromeno[3,4-c]pyridine-8-carboxamide;
N-((5-(furan-2-yl)isoxazol-3-yl)methyl)-5H-chromeno[3,4-c]pyridine-8-carboxamide;
N-((3-(methoxymethyl)-1,2,4-oxadiazol-5-yl)methyl)-5H-chromeno[3,4-c]pyridine-8-carboxamide;
N-((1-methyl-1H-pyrazol-3-yl)methyl)-5H-chromeno[3,4-c]pyridine-8-carboxamide;
N-((1,5-dimethyl-1H-pyrazol-3-yl)methyl)-5H-chromeno[3,4-c]pyridine-8-carboxamide;
4-((5H-chromeno[3,4-c]pyridine-8-carboxamido)methyl)-2,5-dimethylfuran-3-carboxylic acid;
N-(benzo[b]thiophen-3-ylmethyl)-5H-chromeno[3,4-c]pyridine-8-carboxamide;
N-(2-(3-chlorothiophen-2-yl)-2-oxoethyl)-5H-chromeno[3,4-c]pyridine-8-carboxamide;
N-((5-chlorobenzo[b]thiophen-3-yl)methyl)-5H-chromeno[3,4-c]pyridine-8-carboxamide;
N-((4-bromo-1-ethyl-1H-pyrazol-3-yl)methyl)-5H-chromeno[3,4-c]pyridine-8-carboxamide;
N-((4-bromo-1-methyl-1H-pyrazol-3-yl)methyl)-5H-chromeno[3,4-c]pyridine-8-carboxamide;
N-(benzo[d]oxazol-2-ylmethyl)-5H-chromeno[3,4-c]pyridine-8-carboxamide;
N-((5-methyl-4H-1,2,4-triazol-3-yl)methyl)-5H-chromeno[3,4-c]pyridine-8-carboxamide;
N-(pyrazolo[1,5-a]pyridin-2-ylmethyl)-5H-chromeno[3,4-c]pyridine-8-carboxamide;

N-((1H-indol-3-yl)methyl)-5H-chromeno[3,4-c]pyridine-8-carboxamide;
N-((5-amino-1H-1,2,4-triazol-3-yl)methyl)-5H-chromeno[3,4-c]pyridine-8-carboxamide;
N-((5-phenyl-1H-imidazol-2-yl)methyl)-5H-chromeno[3,4-c]pyridine-8-carboxamide;
N((2,5-dimethylfuran-3-yl)methyl)-5H-chromeno[3,4-c]pyridine-8-carboxamide;
(R)-N-(1-(3,5-difluorophenyl)ethyl)-5H-chromeno[3,4-c]pyridine-8-carboxamide;
(S)-N-(1-(3,5-difluorophenyl)ethyl)-5H-chromeno[3,4-c]pyridine-8-carboxamide;
(R)-N-(1-(3-fluorophenyl)ethyl)-5H-chromeno[3,4-c]pyridine-8-carboxamide;
(S)-N-(1-(3-fluorophenyl)ethyl)-5H-chromeno[3,4-c]pyridine-8-carboxamide;
(R)-N-(1-(4-fluorophenyl)ethyl)-5H-chromeno[3,4-c]pyridine-8-carboxamide;
N-(3-(methylsulfonamido)benzyl)-5H-chromeno[3,4-c]pyridine-8-carboxamide;
N-(3-hydroxy-1-phenylpropyl)-5H-chromeno[3,4-c]pyridine-8-carboxamide;
N-(3-hydroxy-1-phenylpropyl)-5H-chromeno[3,4-c]pyridine-8-carboxamide;
N-(3-hydroxy-1-phenylpropyl)-5H-chromeno[3,4-c]pyridine-8-carboxamide;
(S)-Methyl 2-(2-chlorophenyl)-2-(5H-chromeno[3,4-c]pyridine-8-carboxamido)acetate;
(S)-2-(2-Chlorophenyl)-2-(5H-chromeno[3,4-c]pyridine-8-carboxamido)acetic acid;
(S)-N-(1-(2-Chlorophenyl)-2-(methylamino)-2-oxoethyl)-5H-chromeno[3,4-c]pyridine-8-carboxamide;
(S)-methyl 2-(5H-chromeno[3,4-c]pyridine-8-carboxamido)-2-phenylacetate;
(S)-tent-butyl 2-(5H-chromeno[3,4-c]pyridine-8-carboxamido)-3-phenylpropanoate;
(R)-2-(5H-chromeno[3,4-c]pyridine-8-carboxamido)-3-phenylpropanoic acid;
(S)-2-(5H-chromeno[3,4-c]pyridine-8-carboxamido)-2-phenylacetic acid;
(R)-tert-butyl 2-(5H-chromeno[3,4-c]pyridine-8-carboxamido)-3-phenylpropanoate;
(S)-N-(2-amino-2-oxo-1-phenylethyl)-5H-chromeno[3,4-c]pyridine-8-carboxamide;
(R)-methyl 2-(5H-chromeno[3,4-c]pyridine-8-carboxamido)-4-phenylbutanoate;
(R)-N-(1-amino-1-oxo-3-phenylpropan-2-yl)-5H-chromeno[3,4-c]pyridine-8-carboxamide;
(S)-2-(5H-chromeno[3,4-c]pyridine-8-carboxamido)-3-phenylpropanoic acid;
(S)-N-(1-(2-chlorophenyl)-2-(dimethylamino)-2-oxoethyl)-5H-chromeno[3,4-c]pyridine-8-carboxamide;
(S)-N-(2-amino-1-(2-chlorophenyl)-2-oxoethyl)-5H-chromeno[3,4-c]pyridine-8-carboxamide;
(R)-methyl 2-(2-chlorophenyl)-2-(5H-chromeno[3,4-c]pyridine-8-carboxamido)acetate;
(R)-2-(2-chlorophenyl)-2-(5H-chromeno[3,4-c]pyridine-8-carboxamido)acetic acid;
Methyl 3-((5H-chromeno[3,4-c]pyridine-8-carboxamido)methyl)benzoate;
3-((5H-Chromeno[3,4-c]pyridine-8-carboxamido)methyl)benzoic acid;
N-(3-(Methylcarbamoyl)benzyl)-5H-chromeno[3,4-c]pyridine-8-carboxamide;
N-(3-carbamoylbenzyl)-5H-chromeno[3,4-c]pyridine-8-carboxamide;
N-(3-(ethylcarbamoyl)benzyl)-5H-chromeno[3,4-c]pyridine-8-carboxamide;
N-(3-(dimethylcarbamoyl)benzyl)-5H-chromeno[3,4-c]pyridine-8-carboxamide;
N-(3-(pyrrolidine-1-carbonyl)benzyl)-5H-chromeno[3,4-c]pyridine-8-carboxamide;
N-(3-(azetidine-1-carbonyl)benzyl)-5H-chromeno[3,4-c]pyridine-8-carboxamide;
N-(3-(ethyl(methyl)carbamoyl)benzyl)-5H-chromeno[3,4-c]pyridine-8-carboxamide;
N-(3-((2-methoxyethyl)(methyl)carbamoyl)benzyl)-5H-chromeno[3,4-c]pyridine-8-carboxamide;
N-(3-(piperidine-1-carbonyl)benzyl)-5H-chromeno[3,4-c]pyridine-8-carboxamide;
N-(3-(morpholine-4-carbonyl)benzyl)-5H-chromeno[3,4-c]pyridine-8-carboxamide;
N-(3-(cyclopropylcarbamoyl)benzyl)-5H-chromeno[3,4-c]pyridine-8-carboxamide;
N-(3-(3-methoxyazetidine-1-carbonyl)benzyl)-5H-chromeno[3,4-c]pyridine-8-carboxamide;
(R)-N-(3-(3-hydroxypyrrolidine-1-carbonyl)benzyl)-5H-chromeno[3,4-c]pyridine-8-carboxamide;
(S)-N-(3-(3-hydroxypyrrolidine-1-carbonyl)benzyl)-5H-chromeno[3,4-c]pyridine-8-carboxamide;
(R)-N-(3-(3-methoxypyrrolidine-1-carbonyl)benzyl)-5H-chromeno[3,4-c]pyridine-8-carboxamide;
N-(3-(3-fluoroazetidine-1-carbonyl)benzyl)-5H-chromeno[3,4-c]pyridine-8-carboxamide;
N-(3-(3,3-difluoroazetidine-1-carbonyl)benzyl)-5H-chromeno[3,4-c]pyridine-8-carboxamide;
Ethyl 2-(3-((5H-chromeno[3,4-c]pyridine-8-carboxamido)methyl)phenyl)thiazole-4-carboxylate;
2-(3-((5H-Chromeno[3,4-c]pyridine-8-carboxamido)methyl)phenyl)thiazole-4-carboxylic acid;
N-(3-(1-methyl-1H-pyrazol-5-yl)benzyl)-5H-chromeno[3,4-c]pyridine-8-carboxamide;
N-(3-(2-(azetidin-1-yl)pyrimidin-5-yl)benzyl)-5H-chromeno[3,4-c]pyridine-8-carboxamide;
N-(3-(1-methyl-1H-pyrazol-4-yl)benzyl)-5H-chromeno[3,4-c]pyridine-8-carboxamide;
N-(3-(1H-imidazol-4-yl)benzyl)-5H-chromeno[3,4-c]pyridine-8-carboxamide;
N-(3-(1-methyl-1H-imidazol-4-yl)benzyl)-5H-chromeno[3,4-c]pyridine-8-carboxamide;
methyl 3-(3-((5H-chromeno[3,4-c]pyridine-8-carboxamido)methyl)phenyl)furan-2-carboxylate;
N-(3-(1-methyl-1H-imidazol-5-yl)benzyl)-5H-chromeno[3,4-c]pyridine-8-carboxamide;
N-(3-(2-methylimidazo[1,2-a]pyridin-3-yl)benzyl)-5H-chromeno[3,4-c]pyridine-8-carboxamide;
N-(3-(2-methoxythiazol-4-yl)benzyl)-5H-chromeno[3,4-c]pyridine-8-carboxamide;
N-(3-(imidazo[1,2-a]pyrimidin-3-yl)benzyl)-5H-chromeno[3,4-c]pyridine-8-carboxamide;
N-(3-(imidazo[1,2-a]pyridin-3-yl)benzyl)-5H-chromeno[3,4-c]pyridine-8-carboxamide;
N-(3-(2-(methyl sulfonyl)pyrimidin-5-yl)benzyl)-5H-chromeno[3,4-c]pyridine-8-carboxamide;
ethyl 2-(3-((5H-chromeno[3,4-c]pyridine-8-carboxamido)methyl)phenyl)-5-(trifluoromethyl)-1H-imidazole-4-carboxylate;
tert-butyl 3-(3-((5H-chromeno[3,4-c]pyridine-8-carboxamido)methyl)phenyl)-5,6-dihydroimidazo[1,2-a]pyrazine-7(8H)-carboxylate;
N-(3-(1,4-dimethyl-1H-imidazol-2-yl)benzyl)-5H-chromeno[3,4-c]pyridine-8-carboxamide;

N-(3-(5,6,7,8-tetrahydroimidazo[1,2-a]pyrazin-3-yl)benzyl)-5H-chromeno[3,4-c]pyridine-8-carboxamide;
ethyl 2-(3-((5H-chromeno[3,4-c]pyridine-8-carboxamido)methyl)phenyl)oxazole-4-carboxylate;
Methyl 3-((5-methyl-5H-chromeno[3,4-c]pyridine-8-carboxamido)methyl)benzoate;
3-((5-Methyl-5H-chromeno[3,4-c]pyridine-8-carboxamido)methyl)benzoic acid;
N-(3-(2-Hydroxy-2-methylpropylcarbamoyl)benzyl)-5-methyl-5H-chromeno[3,4-c]pyridine-8-carboxamide;
N-(1-(3,5-difluorophenyl)ethyl)-5-methyl-5H-chromeno[3,4-c]pyridine-8-carboxamide;
N-((R)-1-(3-methoxyphenyl)ethyl)-5-methyl-5H-chromeno[3,4-c]pyridine-8-carboxamide;
N-(3-(cyclopropylcarbamoyl)benzyl)-5-methyl-5H-chromeno[3,4-c]pyridine-8-carboxamide;
N-(3-(ethylcarbamoyl)benzyl)-5-methyl-5H-chromeno[3,4-c]pyridine-8-carboxamide;
N-(3-carbamoylbenzyl)-5-methyl-5H-chromeno[3,4-c]pyridine-8-carboxamide;
N-(3-(cyclopropylmethylcarbamoyl)benzyl)-5-methyl-5H-chromeno[3,4-c]pyridine-8-carboxamide;
5-methyl-N-(3-(methylcarbamoyl)benzyl)-5H-chromeno[3,4-c]pyridine-8-carboxamide;
5-methyl-N-(3-(1-methyl cyclopropylcarbamoyl)benzyl)-5H-chromeno[3,4-c]pyridine-8-carboxamide; and
5-methyl-N-(3-(((R)-tetrahydrofuran-2-yl)methylcarbamoyl)benzyl)-5H-chromeno[3,4-c]pyridine-8-carboxamide.

* * * * *